US012680108B2

(12) United States Patent
Banks et al.

(10) Patent No.: US 12,680,108 B2
(45) Date of Patent: Jul. 14, 2026

(54) MINIATURIZED DYSTROPHINS AND USES THEREOF

(71) Applicant: BRISTOL-MYERS SQUIBB COMPANY, Princeton, NJ (US)

(72) Inventors: Glen Banks, Yardley, PA (US); Jonathan Harry Davis, Madison, WI (US); Paul Charles Levesque, Yardley, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 1039 days.

(21) Appl. No.: 17/288,029

(22) PCT Filed: Oct. 24, 2019

(86) PCT No.: PCT/US2019/057855

§ 371 (c)(1),
(2) Date: Apr. 23, 2021

(87) PCT Pub. No.: WO2020/086844

PCT Pub. Date: Apr. 30, 2020

(65) Prior Publication Data

US 2021/0403947 A1 Dec. 30, 2021

Related U.S. Application Data

(60) Provisional application No. 62/749,982, filed on Oct. 24, 2018.

(51) Int. Cl.

| | |
|---|---|
| ***C12N 15/62*** | (2006.01) |
| ***C07K 14/78*** | (2006.01) |
| ***C12N 15/86*** | (2006.01) |
| *A61K 48/00* | (2006.01) |
| *C12N 15/864* | (2006.01) |

(52) U.S. Cl.

CPC .............. *C12N 15/86* (2013.01); *C07K 14/78* (2013.01); *C12N 15/62* (2013.01); *C12N 2750/14143* (2013.01)

(58) Field of Classification Search

None

See application file for complete search history.

(56) References Cited

U.S. PATENT DOCUMENTS

| | | | | |
|---|---|---|---|---|
| 6,869,777 | B2 | 3/2005 | Chamberlain et al. | |
| 7,001,761 | B2 | 2/2006 | Xiao | |
| 7,241,447 | B1 | 7/2007 | Engelhardt et al. | |
| 7,282,199 | B2 | 10/2007 | Gao et al. | |
| 7,510,867 | B2 | 3/2009 | Xiao et al. | |
| 7,655,467 | B2 | 2/2010 | Chamberlain et al. | |
| 7,790,449 | B2 | 9/2010 | Gao et al. | |
| 7,803,622 | B2 | 9/2010 | Engelhardt et al. | |
| 7,892,824 | B2 | 2/2011 | Duan et al. | |
| 8,236,557 | B2 | 8/2012 | Dongsheng et al. | |
| 8,318,480 | B2 | 11/2012 | Gao et al. | |
| 8,501,920 | B2 | 8/2013 | Chamberlain et al. | |
| 8,846,030 | B2 | 9/2014 | Engelhardt et al. | |
| 8,962,330 | B2 | 2/2015 | Gao et al. | |
| 9,624,282 | B2 | 4/2017 | Lai et al. | |
| 9,862,945 | B2 | 1/2018 | Flanigan et al. | |
| 10,166,272 | B2 | 1/2019 | Dickson et al. | |
| 10,351,611 | B2 | 7/2019 | Lai et al. | |
| 10,479,821 | B2 | 11/2019 | Chamberlain et al. | |
| 10,543,260 | B2 | 1/2020 | Steinman | |
| 10,590,435 | B2 | 3/2020 | Gao et al. | |
| 10,647,751 | B2 | 5/2020 | Dickson | |
| 10,786,546 | B2 | 9/2020 | Dickson et al. | |
| 2003/0017131 | A1 | 1/2003 | Park et al. | |
| 2013/0091326 | A1 | 4/2013 | Choi et al. | |
| 2014/0234255 | A1* | 8/2014 | Lai | C07K 14/4708 435/320.1 |
| 2015/0196670 | A1 | 7/2015 | Popplewell et al. | |
| 2015/0214960 | A1 | 7/2015 | Kim et al. | |
| 2015/0321416 | A1 | 11/2015 | Patel et al. | |
| 2016/0207893 | A1 | 7/2016 | Kelly et al. | |
| 2016/0214960 | A1 | 7/2016 | Kuduk et al. | |
| 2016/0311236 | A1 | 10/2016 | Kozuma et al. | |
| 2017/0021000 | A1 | 1/2017 | Steinman et al. | |
| 2017/0157213 | A1 | 6/2017 | Dickson et al. | |
| 2017/0349640 | A1 | 12/2017 | Lai et al. | |
| 2017/0368198 | A1 | 12/2017 | Xiao et al. | |
| 2018/0148488 | A1 | 5/2018 | Chamberlain et al. | |
| 2018/0271069 | A1 | 9/2018 | Min et al. | |
| 2018/0346533 | A1 | 12/2018 | Dickson | |
| 2019/0184033 | A1 | 6/2019 | Duan et al. | |
| 2020/0031890 | A1 | 1/2020 | Chamberlain et al. | |

(Continued)

FOREIGN PATENT DOCUMENTS

| | | | |
|---|---|---|---|
| JP | 14213498 | A | 5/1998 |
| WO | 198706844 | A1 | 11/1987 |

(Continued)

OTHER PUBLICATIONS

Amit C. Nathwani, “Advances in Gene Therapy for Hemophilia”, Human Gene Therapy, 2017, vol. 28, 11-1004-1012.

Andrew K.M. Cheung, et al, “Integration of the Adeno-Associated Virus Genome into Cellular DNA in Latently Infected Human Detroit 6 Cells”, Journal of Virology, 1980, 739-748.

Atchison, R.W., et al., “Adenovirus-Associated Defective Virus Particles”, Science, ’1965, 149(3685), 754-755.

Catherine A. Laughlin, et al., “Cloning of infectious adeno-associated virus genomes in bacterial plasmids”, Gene., 1983, 65-73.

Christopher D. Saudek, et al., “A Preliminary Trial of the Programmable Implantable Medication System for Insulin Delivery”, The New England Journal of Medicine, 1989, 321, 574-579.

(Continued)

*Primary Examiner* — Maria Marvich
(74) *Attorney, Agent, or Firm* — Melissa Wenk

(57) ABSTRACT

Disclosed herein are nucleic acid molecules, polypeptides, cells, vectors, and pharmaceutical compositions relating to miniaturized dystrophin. Methods of production and methods of therapeutic use of the miniaturized dystrophin are also disclosed.

27 Claims, 25 Drawing Sheets

Specification includes a Sequence Listing.

(56) References Cited

U.S. PATENT DOCUMENTS

2020/0078473 A1 3/2020 Lochmuller
2020/0095298 A1 3/2020 Chamberlain et al.
2020/0168938 A1 5/2020 Fleck et al.
2020/0376141 A1 12/2020 Xiao et al.

FOREIGN PATENT DOCUMENTS

WO 2020183695 A2 11/2001
WO 200229056 A2 4/2002
WO 2003052051 A2 6/2003
WO 2005049850 A2 6/2005
WO 2005099763 A2 10/2005
WO 2008088895 A2 7/2008
WO 2014009567 A1 1/2014
WO 2014172669 A1 10/2014
WO 2015197232 A1 12/2015
WO 2015197869 A1 12/2015
WO 2016109596 A1 7/2016
WO 2016115543 A2 7/2016
WO 2016177911 A1 11/2016
WO 2017181011 A1 10/2017
WO 2017181014 A1 10/2017
WO 2017181015 A1 10/2017
WO 2017221145 A1 12/2017
WO 2017223128 A1 12/2017
WO 2018022608 A2 2/2018
WO 2018170408 A1 9/2018
WO 2019012336 A2 1/2019
WO 2019078916 A1 4/2019
WO 2019118806 A1 6/2019
WO 2019195362 A1 10/2019
WO 2019245973 A1 12/2019
WO 2019246480 A1 12/2019
WO 2020086844 A1 4/2020

OTHER PUBLICATIONS

Dan Wang, et al., "Adeno-associated virus vector as a platform for gene therapy delivery", Nature, 2019, vol. 18, 358-378.
Elizabeth M. McNally, et al., "Contemporary Cardiac Issues in Duchenne Muscular Dystrophy", HHS Public Access, 2015, 131(18), 1590-1598.
Faber, R.M., et al, "Myofiber branching rather than myofiber hyperplasia contributes to muscle hypertrophy in mdx mice", Skeletal Muscle, 2014, vol. 4:10, 1-11.
Glen B. Banks, et al., "Muscle Structure Influences Utrophin Expression in mdx Mice", PLOS Genetics, 2014, 10(6), e1004431.
Glen B. Banks, et al., The Polyproline Site in Hinge 2 Influences the Functional Capacity of Truncated Dystrophins, Open Acess, 2010, 6(5), e1000958.
Gottlieb, John, "In Vitro Excision of Adeno-Associated Virus DNA from Recombinant Plasmids: Isolation of an Enzyme Fraction from Hela Cells That Cleaves DNA at Poly(G) Sequences", Molecular and Cellular Biology, 1988, 6(8), 2513-2522.
Henry Buchwald, M.D., et al., "Long-term, continuous intravenous heparin administration by an implantable infusion bump in ambulatory patients with recurrent venous thrombosis", Surgery, 1980, 88(4), 507-16.
J. Sambrook, et al., "Molecular Cloning", a Laboratory Manual, Second Edition, Synthetic Oligonucleotide Probes, 1989, 11.1-11.61.
James A. Rose, "Evidence for a single-stranded adenovirus-associated virus genome: Formation of a DNA Density Hybrid on Release of Viral DNA", Natl Institute of Allergy and Infectious Diseases, National Institute of Health, 1969, 863-869.
Jerry R. Mendell, et al, "Gene Therapy for Muscular Dystrophy: Lessons Learned and Path Forward", NIH Public Access; 2012, 527(2), 90-99.
Jerry R. Mendell, MD, et al, "Molecular Therapeutic Strategies Targeting Duchenne Muscular Dystrophy", 2010, 25(9), 1145-1148.
Jorge L. Santiego-Ortiz, et al.,, "Adeno-Associated Virus (AAV) Vectors in Cancer Gene Therapy", HHS Public Access, Author Manuscript, J Control Release, 2016, 240, 287-301.
Keeler, AM, et al., "Gene Therapy 2017:Progress and Future Directions", Clinical Transl Sci, 2017, 10, 242-248.
Kutmeier G., et al., "Assembly of Humanized Antibody Genes from Synthetic Oligonucleotides Using a Single-Round PCR", Biotechniques. 1994, 17:242-6.
Louise R. Rodino-Klapac, et al., "Update on the Treatment of Duchenne Muscular Dystrophy", HHS Public Access, 2013, 13(3),332, 1-11.
Manuel AFV Goncalves, "Adeno-associated virus: from defective virus to effective vector", Virology Journal, 2005, 2:(43), 1-17.
Matthew J. During, MD, et al., "Controlled Release of Dopamine from a Polymeric Brain Implant: In Vivo Characterization", Ann. Neurol., 1989—25:351-356.
McRae W. Williams, et al., Extensive but Coordinated Reorganization of the Membrane Skeleton in Myofibers of Dystrophic (mdx) Mice, The Journal of Cell Biology, 1999, vol. 144, 6, 1259-1270.
Michael V. Sefton, "Implantable Pumps—Characteristics of the Ideal Implantable Pump", CRC Critical Reviews in Biomedical Engineering, 1987, vol. 14, Issue 3, 201-240.
Nathalie Vincent, et al., Long-term correction of mouse dystrophic degeneration by adenovirus-mediated transfer of a minidystrophin gene, Nature Genetics, 1993, 5, 130-134.
Paul L. Hermonat, et al, "Use of adeno-associated virus as a mammalian DNA cloning vector: Transduction of heomycin resistance into mammalian tissue culture cells", Proc. Natl. Acad. Sci., 81(20), pp. 6466-6470, 1984.
Paul N. Valdmanis, et al., "Future of rAAV Gene Therapy: Platform for RNAi, Gene Editing, and Beyond", Human Gene Therapy, 2017, vol. 28, 4, 361-374.
Periannan Senapathy, et al., "Replication of Adeno-associated Virus DNA", J. Mol. Biol., 1984, 178, 179, 1-20.
Ramzi J. Khairallah, et al., "Microtubules Underlie Dysfunction in Duchenne Muscular Dystrophy", Physiology, 2012, 5 (236), 1-12.
Richard J. Samulski, et al., Rescue of Adeno-Associated Virus from Recombinant Plasmids: Gene Correction within the Terminal Repeats of AAV, Cell, 1983, vol. 33, 135-143.
Richard Jude Samulski, et al., "A Recombinant Plasmid from Which an Infectious Adeno-Associated Virus Genome Can be Excised In Vitro and Its Use to Study Viral Replication", Journal of Virology, 61(10), 1987, 3096-3101.
Robert J. Levy, "Ocelli: A Celestial Compass in the Desert Ant Cataglyphis", 1985, Science, 190-192.
Robert Langer, "New Methods of Drug Delivery", Science, 1990, 249, 1527-33.
Scott Q. Harper, "Molecular dissection of dystrophin identifies the docking site for nNOS", PNAS, 2013, 110, 2, 387-388.
Scott Q. Harper, et al., Modular flexibility of dystrophin: Implications for gene therapy of Duchenne muscular dystrophy, Nature Medicine, 2002, 8, 3, 253-261.
T. Matsushita, et al., "Adeno-associated virus vectors can be efficiently produced without helper virus", Gene Therapy, 1998, 5, 938-945.
Xiao Xiao, et al., "Production of High-titer Recombinant Adeno-Associated Virus Vectors in the Absence of Helper Adenovirus", Journal of Virology, 1998, vol. 72, 3, 2224-2232.
Lai, et al., Edited by Louis M. Kunkel, "Alpha 2 and Alpha3 helices of dystrophin R16 and R17 frame a microdomain in the Alpha1 helix of dystrophin R17 for neuronal NOS binding", PNAS, 2013, 110, 2, 525-530.
Yutaka Takebe, et al., "SR Alpha Promoter: an Efficient and Versatile Mammalian cDNA Expression System Composed of the Simian Virus 40 Early Promoter and the R-U5 Segment of Human T-Cell Leukemia Virus Type 1 Long Terminal Repeat", Molecular and Cellular Biology, Jan. 1988, p. 466-472.
LeRumeur, et al., Dystrophin: More than just the sum of its parts, Biochimica ET Biophysica ACTA (BBA), Proteins and Proteomics, ElSevier, Netherlands, 1804(9), 2010, 1713-1722.
Yi Lai, et al., Edited by Louis M. Kunkel, "Dystrophins carrying spectrin-like repeats 16 and 17 anchor nNOS to the sarcolemma and enhance exercise performance in a mouse of muscular dystrophy", J. Clin Invest., 2009, 119(3), 624-635.

(56) References Cited

OTHER PUBLICATIONS

Duan, D., "Systemic AAV Micro-dystrophin Gene Therapy for Duchenne Muscular Dystrophy" vol. 26 (10), pp. 2337-2356 (2018).

* cited by examiner

Original Junction 10

Junction10 Version3

MINIATURIZED DYSTROPHINS AND USES THEREOF

REFERENCE TO RELATED APPLICATIONS

This application claims the priority benefit of U.S. Provisional Application No. 62/749,982, filed Oct. 24, 2018, which is incorporated herein by reference in its entirety.

1. FIELD

The presently disclosed subject matter generally relates to polynucleotides, polypeptides, cells, vectors, uses, and kits relating to miniaturized dystrophin.

2. BACKGROUND OF THE DISCLOSURE

Duchenne muscular dystrophy (DMD) is a recessively-inherited muscle wasting disorder afflicting approximately 1 in 3,500 males. DMD is caused by mutations in the dystrophin gene, which is located on the X chromosome. Mutations in this gene lead to aberrant or absent expression of the dystrophin protein.

Dystrophin is a key component of a protein complex that is responsible for regulating muscle cell integrity and function. DMD patients typically lose the ability to physically support themselves during childhood and become progressively weaker over time. This progressive wasting of skeletal muscles and cardiac dysfunction typically leads to loss of ambulation and premature death, primarily due to cardiac or respiratory failure.

Some attempts have been made in the past to treat DMD. However, the available treatment options were significantly limited due to the large size of the wild type dystrophin cDNA (approximately 13.9 kb) which cannot be administered to and expressed in DMD patients using standard viral vectors, including Adeno-associated virus (AAV), which cannot transfer more than approximately 4.9 kb of heterologous DNA. Therefore, there is a need to develop a recombinant dystrophin gene that can be efficiently packaged into a vector for gene therapy.

Adeno-associated viral (AAV) vectors have been shown to be useful in gene therapeutic approaches aimed at correcting genetic deficiencies that result in reduced or completely abolished levels of protein expression (Nathwani et al to A. M Keeler et al.), and are potentially useful for gene knockdown, genome editing or modification, and non-coding RNA modulation (Valdmanis et al., 2017).

Packaging the entire cDNA of the muscle-specific isoform of dystrophin into a single rAAV capsid cannot be achieved easily because of the large size of the dystrophin cDNA. Previous studies have focused on the development of smaller genetic constructs that express only particular domains of dystrophin. See U.S. Pat. Nos. 6,869,777 and 8,501,920, each of which is incorporated by reference. However, these approaches have had only limited success.

There remains a need for more precise and efficient gene therapy tools for treating patients with mutations in the dystrophin gene, and, in particular, a need to develop a recombinant dystrophin gene that can be efficiently packaged into a vector for gene therapy.

3. SUMMARY OF THE DISCLOSURE

The present disclosure provides a nucleic acid molecule comprising a nucleotide sequence, which encodes a miniaturized dystrophin polypeptide comprising from N terminus to C terminus hinge 1 (H1) domain, spectrin repeat 1 (R1) domain, spectrin repeat 3 (R3) domain, hinge 2 (H2) domain, spectrin repeat 16 (R16) domain, spectrin repeat 17 (R17) domain, spectrin repeat 24 (R24) domain, and hinge 4 (H4) domain of dystrophin, wherein the miniaturized dystrophin polypeptide does not comprise spectrin repeat 2 of dystrophin. In some embodiments, the miniaturized dystrophin polypeptide does not comprise spectrin repeat 2 (R2) domain, spectrin repeat 4 (R4) domain, spectrin repeat 5 (R5) domain, spectrin repeat 6 (R6) domain, spectrin repeat 7 (R7) domain, spectrin repeat 8 (R8) domain, spectrin repeat 9 (R9) domain, spectrin repeat 10 (R10) domain, spectrin repeat 11 (R11) domain, spectrin repeat 12 (R12) domain, spectrin repeat 13 (R13) domain, spectrin repeat 14 (R14) domain, spectrin repeat 15 (R15) domain, spectrin repeat 18 (R18) domain, spectrin repeat 19 (R19) domain, spectrin repeat 20 (R20) domain, spectrin repeat 21 (R21) domain, spectrin repeat 22 (R22) domain, or spectrin repeat 23 (R23) domain, or any combination thereof. In some embodiments, the R1 domain is directly fused to R3 domain by a peptide bond. In some embodiments, the R1 domain and the R3 domain are fused by amino acids ARG-VAL (RV). In some embodiments, the H2 domain and the R16 domain are fused by a linker.

In some embodiments, the linker comprises an amino acid sequence at least about 80%, at least about 90%, at least about 95%, at least about 96%, at least about 97%, at least about 98%, at least about 99%, or about 100% identical to SEQ ID NO: 75 (IHTVREE TMMMTEDMP LEI), wherein the amino acid sequence is capable of improving nNOS signaling.

In some embodiments, disclosed herein is a nucleic acid molecule comprising a nucleotide sequence which encodes an amino acid sequence comprising SEQ ID NO: 75 (IHTVREE TMMMTEDMP LEI), wherein the nucleic acid molecule is at least about 80%, at least about 90%, at least about 95%, at least about 96%, at least about 97%, at least about 98%, at least about 99%, or about 100% identical to SEQ ID NO: 100 (ATCCACACCGTGCGGGAAGAGACAATGATGGTCATGACAGAGGAC ATGCCCCTGGAAATC), wherein the amino acid sequence is capable of improving nNOS signaling. In some embodiments, the amino acid sequence is a linker connecting a first domain of dystrophin to a second domain of dystrophin. In some embodiments, the first domain of dystrophin is a H2 domain and the second domain of dystrophin is an R16 domain. In some embodiments, the amino acid sequence further comprises the sequence of SEQ ID NO: 74 at the N terminus.

In some embodiments, the nucleic acid molecule encodes a miniaturized dystrophin polypeptide. In some embodiments, the miniaturized dystrophin polypeptide comprises from N terminus to C terminus hinge 1 (H1) domain, spectrin repeat 1 (R1) domain, spectrin repeat 3 (R3) domain, hinge 2 (H2) domain, spectrin repeat 16 (R16) domain, spectrin repeat 17 (R17) domain, spectrin repeat 24 (R24) domain, and hinge 4 (H4) domain of dystrophin. In some embodiments, the R1 domain and the R3 domain are fused by amino acids ARG-VAL (RV) and wherein the H2 domain and the R16 domain are fused by the amino acid sequence set forth in SEQ ID NOs: 74-75 in combination. In some embodiments, (i) the H1 domain and the R1 domain are fused directly, (ii) the R3 domain and the H2 domain are fused directly, (iii) the R16 and R17 domains are fused directly, (iv) the R17 and R24 domains are fused directly, or (v) the R24 and H4 domains are fused directly, or (vi) any combination thereof. In some embodiments, the miniaturized dystrophin polypeptide further comprises ABD1 domain and/or CR domain. In some embodiments, the miniaturized dystrophin polypeptide consists essentially of or consists of, from N terminus to C terminus, the ABD1 domain, the H1 domain, the R1 domain, amino acids RV, the R3 domain, the H2 domain, the amino acid sequence as set forth in SEQ ID NOs: 74-75, the R16 domain, the R17 domain, the R24 domain, the H4 domain, and the CR domain of dystrophin.

In some embodiments, the H1 domain is an amino acid sequence at least about 80%, at least about 85%, at least about 90%, at least about 95%, at least about 96%, at least about 97%, at least about 98%, at least about 99%, or about 100% identical to SEQ ID NO: 69. In some embodiments, the R1 domain is an amino acid sequence at least about 80%, at least about 85%, at least about 90%, at least about 95%, at least about 96%, at least about 97%, at least about 98%, at least about 99%, or about 100% identical to SEQ ID NO: 70. In some embodiments, the R3 domain is an amino acid sequence at least about 80%, at least about 85%, at least about 90%, at least about 95%, at least about 96%, at least about 97%, at least about 98%, at least about 99%, or about 100% identical to SEQ ID NO: 72. In some embodiments, the H2 domain is an amino acid sequence at least about 80%, at least about 85%, at least about 90%, at least about 95%, at least about 96%, at least about 97%, at least about 98%, at least about 99%, or about 100% identical to SEQ ID NO: 73. In some embodiments, the R16 domain is an amino acid sequence at least about 80%, at least about 85%, at least about 90%, at least about 95%, at least about 96%, at least about 97%, at least about 98%, at least about 99%, or about 100% identical to SEQ ID NO: 76. In some embodiments, the R17 domain is an amino acid sequence at least about 80%, at least about 85%, at least about 90%, at least about 95%, at least about 96%, at least about 97%, at least about 98%, at least about 99%, or about 100% identical to SEQ ID NO: 77. In some embodiments, the R24 domain is an amino acid sequence at least about 80%, at least about 85%, at least about 90%, at least about 95%, at least about 96%, at least about 97%, at least about 98%, at least about 99%, or about 100% identical to SEQ ID NO: 78. In some embodiments, the H4 domain is an amino acid sequence at least about 80%, at least about 85%, at least about 90%, at least about 95%, at least about 96%, at least about 97%, at least about 98%, at least about 99%, or about 100% identical to SEQ ID NO: 79. In some embodiments, the miniaturized dystrophin polypeptide further comprises at the N terminus an amino acid sequence at least about 80%, at least about 85%, at least about 90%, at least about 95%, at least about 96%, at least about 97%, at least about 98%, at least about 99%, or about 100% identical to SEQ ID NO: 68. In some embodiments, the miniaturized dystrophin polypeptide further comprises at the C terminus an amino acid sequence at least about 80%, at least about 85%, at least about 90%, at least about 95%, at least about 96%, at least about 97%, at least about 98%, at least about 99%, or about 100% identical to SEQ ID NO: 80. In some embodiments, the miniaturized dystrophin polypeptide comprises an amino acid sequence at least about 80%, at least about 85%, at least about 90%, at least about 95%, at least about 96%, at least about 97%, at least about 98%, at least about 99%, or about 100% identical to SEQ ID NO: 118. In some embodiments, the nucleotide sequence comprises a sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% identical to the nucleotide sequence of SEQ ID NO: 133.

In some embodiments, the miniaturized dystrophin polypeptide exhibits one or more properties selected from the group consisting of (i) having a lower CD4 proliferation compared to BXA-027741, (ii) having a lower CD8 proliferation compared to BXA-027741, (iii) having a higher expression of the miniaturized dystrophin polypeptide than BXA-027741, and (iv) any combination thereof.

In some embodiments, the nucleic acid molecule comprises a nucleotide sequence, which encodes a miniaturized dystrophin polypeptide comprising spectrin repeat 1 (R1) domain and spectrin 16 (R16) domain, wherein the R1 domain and the R16 domain are fused by a linker comprising the amino acid sequence set forth in SEQ ID NO: 84 (IHTVREETMMVMTEDMPLEI).

In some embodiments, the nucleic acid molecule comprises a nucleotide sequence, which encodes a miniaturized dystrophin polypeptide comprising from N terminus to C terminus a hinge 1 (H1) domain, spectrin repeat 1 (R1) domain, spectrin repeat 16 (R16) domain, spectrin repeat 17 (R17) domain, a hinge 3 (H3) domain, spectrin repeat 23 (R23) domain, spectrin repeat 24 (R24) domain, and hinge 4 (H4) domain of dystrophin, wherein the R1 domain and the R16 domain are fused by the amino acid sequence set forth in SEQ ID NO: 84 (IHTVREETMMVMTEDMPLEI).

In some embodiments, (i) the H1 domain and the R1 domain are fused directly, (ii) the R16 and R17 domains are fused directly, (iii) the R17 and the H3 domains are fused directly, (iv) the R23 and R24 domains are fused directly, or (v) the R24 and H4 domains are fused directly, or (vi) any combination thereof.

In some embodiments, the miniaturized dystrophin polypeptide does not comprise a spectrin repeat 2 (R2) domain, spectrin repeat 3 (R3) domain, spectrin repeat 4 (R4) domain, spectrin repeat 5 (R5) domain, spectrin repeat 6 (R6) domain, spectrin repeat 7 (R7) domain, spectrin repeat 8 (R8) domain, spectrin repeat 9 (R9) domain, spectrin repeat 10 (R10) domain, spectrin repeat 11 (R11) domain, spectrin repeat 12 (R12) domain, spectrin repeat 13 (R13) domain, spectrin repeat 14 (R14) domain, spectrin repeat 15 (R15) domain, spectrin repeat 18 (R18) domain, spectrin repeat 19 (R19) domain, spectrin repeat 20 (R20) domain, spectrin repeat 21 (R21) domain, and/or spectrin repeat 22 (R22) domain. In some embodiments, the miniaturized dystrophin polypeptide further comprises an ABD1 domain and/or a CR domain. In some embodiments, the miniaturized dystrophin polypeptide consists essentially of or consists of, from N terminus to C terminus, the ABD1 domain, the H1 domain, the R1 domain, the amino acid sequence set forth in SEQ ID NO: 84, the R16 domain, the R17 domain, the H3 domain, the R23 domain, the R24 domain, the H4 domain, and the CR domain of dystrophin. In some embodiments, the H1 domain is an amino acid sequence at least about 80%, at least about 85%, at least about 90%, at least about 95%, at least about 96%, at least about 97%, at least about 98%, at least about 99%, or about 100% identical to SEQ ID NO: 82. In some embodiments, the R1 domain is an amino acid sequence at least about 80%, at least about 85%, at least about 90%, at least about 95%, at least about 96%, at least about 97%, at least about 98%, at least about 99%, or about 100% identical to SEQ ID NO: 83. In some embodiments, the R16 domain is an amino acid sequence at least about 80%, at least about 85%, at least about 90%, at least about 95%, at least about 96%, at least about 97%, at least about 98%, at least about 99%, or about 100% identical to SEQ ID NO: 85. In some embodiments, the R17 domain is an amino acid sequence at least about 80%, at least about 85%, at least about 90%, at least about 95%, at least about 96%, at least about 97%, at least about 98%, at least about 99%, or about 100% identical to SEQ ID NO: 86. In some embodiments, the H3 domain is an amino acid sequence at least about 80%, at least about 85%, at least about 90%, at least about 95%, at least about 96%, at least about 97%, at least about 98%, at least about 99%, or about 100% identical to SEQ ID NO: 87. In some embodiments, the R23 domain is an amino acid sequence at least about 80%, at least about 85%, at least about 90%, at least about 95%, at least about 96%, at least about 97%, at least about 98%, at least about 99%, or about 100% identical to SEQ ID NO: 88. In some embodiments, the R24 domain is an amino acid sequence at least about 80%, at least about 85%, at least about 90%, at least about 95%, at least about 96%, at least about 97%, at least about 98%, at least about 99%, or about 100% identical to SEQ ID NO: 89. In some embodiments, the H4 domain is an amino acid sequence at least about 80%, at least about 85%, at least about 90%, at least about 95%, at least about 96%, at least about 97%, at least about 98%, at least about 99%, or about 100% identical to SEQ ID NO: 90.

In some embodiments, the miniaturized dystrophin polypeptide further comprises at the N terminus an amino acid sequence at least about 80%, at least about 85%, at least about 90%, at least about 95%, at least about 96%, at least about 97%, at least about 98%, at least about 99%, or about 100% identical to SEQ ID NO: 81. In some embodiments, the miniaturized dystrophin polypeptide further comprises at the C terminus an amino acid sequence at least about 80%, at least about 85%, at least about 90%, at least about 95%, at least about 96%, at least about 97%, at least about 98%, at least about 99%, or about 100% identical to SEQ ID NO: 91. In some embodiments, the miniaturized dystrophin polypeptide comprises an amino acid sequence at least about 80%, at least about 85%, at least about 90%, at least about 95%, at least about 96%, at least about 97%, at least about 98%, at least about 99%, or about 100% identical to SEQ ID NO: 132, or to SEQ ID NO: 132 wherein the C-terminal domain is deleted. In some embodiments, the nucleotide sequence comprises a sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% identical to the nucleotide sequence of SEQ ID NO: 147 or SEQ ID NO: 148 or SEQ ID NO: 149.

In some embodiments, the miniaturized dystrophin polypeptide exhibits a higher expression of the miniaturized dystrophin polypeptide than BXA-196481.

In some embodiments, the miniaturized dystrophin polypeptide expression is at least about 1.5 fold, at least about 1.6 fold, at least about 1.7 fold, at least about 1.8 fold, at least about 1.9 fold, at least about 2 fold, at least about 2.1 fold, at least about 2.2 fold, at least about 2.3 fold, at least about 2.4 fold, at least about 2.5 fold, at least about 2.6 fold, at least about 2.7 fold, at least about 2.8 fold, at least about 2.9 fold or at least about 3 fold higher than the BXA-196481 polypeptide expression.

In some embodiments, the nucleic acid molecule further comprises a promoter. In some embodiments, the promoter is a tissue-specific promoter. In some embodiments, the promoter drives expression of the therapeutic protein in hepatocytes, muscle cells, endothelial cells, neuronal cells, sinusoidal cells, or any combination thereof. In some embodiments, the promoter is selected from the group consisting of a mouse thyretin promoter (mTTR), an endogenous human factor VIII promoter (F8), a human alpha-1-antitrypsin promoter (hAAT), a human albumin minimal promoter, a mouse albumin promoter, a tristetraprolin (TTP) promoter, a CASI promoter, a synapsin 1 gene promoter, a CAG promoter, a cytomegalovirus (CMV) promoter, α1-antitrypsin (AAT), muscle creatine kinase (MCK), myosin heavy chain alpha (αMHC), myoglobin (MB), desmin (DES), SPc5-12, 2R5Sc5-12, dMCK, tMCK, and a phosphoglycerate kinase (PGK) promoter.

In some embodiments, the nucleic acid molecule further comprises an intronic sequence. In some embodiments, the intronic sequence is positioned 5' to the nucleotide sequence encoding the miniaturized dystrophin polypeptide. In some embodiments, the intronic sequence is positioned 3' to the promoter. In some embodiments, the intronic sequence comprises a synthetic intronic sequence.

In some embodiments, the nucleic acid molecule further comprises a post-transcriptional regulatory element. In some embodiments, the post-transcriptional regulatory element is positioned 3' to the nucleotide sequence encoding the miniaturized dystrophin polypeptide. In some embodiments, the post-transcriptional regulatory element comprises a mutated woodchuck hepatitis virus post-transcriptional regulatory element (WPRE), a microRNA binding site, or a DNA nuclear targeting sequence, or any combination thereof.

In some embodiments, the nucleic acid molecule further comprises a 3'UTR poly(A) tail sequence. In some embodiments, the 3'UTR poly(A) tail sequence is selected from the group consisting of bGH poly(A), actin poly(A), hemoglobin poly(A), and any combination thereof. In some embodiments, the 3'UTR poly(A) tail sequence comprises bGH poly(A). In some embodiments, the nucleic acid molecule further comprises an enhancer sequence. In some embodiments, the nucleic acid molecule further comprises a first ITR and/or a second ITR. In some embodiments, the first ITR and the second ITR are identical. In some embodiments, the first ITR and/or the second ITR are derived from adeno-associated virus. In some embodiments, the nucleic acid molecule comprises a heterologous moiety. In some embodiments, the heterologous moiety is selected from the group consisting of albumin or a fragment thereof, an immunoglobulin Fc region, the C-terminal peptide (CTP) of the β subunit of human chorionic gonadotropin, a PAS sequence, a HAP sequence, a transferrin or a fragment thereof, an albumin-binding moiety or a derivative thereof, and any combination thereof.

In some embodiments, provided is a vector comprising a nucleic acid molecule disclosed herein. In some embodiments, the vector is selected from the group consisting of a adenoviral vector, a retroviral vector, poxvirus vector, a baculovirus vector, a herpes viral vector. In some embodiments, the vector is an adeno-associated virus (AAV) vector. In some embodiments, the AAV vector is selected from AAV1, AAV2, AAV3, AAV4, AAV5, AAV6, AAV7, AAV8, AAV9, AAV10, and AAV11. In some embodiments, the AAV vector is AAV9.

In some embodiments, the nucleic acid molecule or vector disclosed herein is formulated with a delivery agent. In some embodiments, the delivery agent comprises a lipid nanoparticle. In some embodiments, the delivery agent is selected from the group consisting of liposomes, non-lipid polymeric molecules, endosomes, and any combination thereof.

In some embodiments, the nucleic acid molecule or the vector disclosed herein is formulated for intravenous, transdermal, intradermal, subcutaneous, pulmonary, or oral delivery, or any combination thereof. In some embodiments, the nucleic acid molecule or vector disclosed herein is formulated for intravenous delivery.

In some embodiments, provided is a polypeptide encoded by the nucleic acid molecule or vector disclosed herein.

In some embodiments, provided is a host cell comprising the nucleic acid molecule disclosed herein. In some embodiments, the cell is a CHO cell, a HEK293 cell, a HBK cell, a COS cell, a NSO cell, or a HT1080 cell.

In some embodiments, provided is a pharmaceutical composition comprising (a) the nucleic acid disclosed herein, the vector disclosed herein, the polypeptide disclosed herein, or the host cell disclosed herein; and (b) a pharmaceutically acceptable excipient.

In some embodiments, provided is a kit, comprising the nucleic acid disclosed herein, the vector disclosed herein, the polypeptide disclosed herein, the host cell disclosed herein, or the pharmaceutical composition disclosed herein, and instructions for administering the nucleic acid molecule to a subject in need thereof.

In some embodiments, provided is a method of producing a miniaturized dystrophin polypeptide, comprising: culturing the host cell disclosed herein under suitable conditions and recovering the miniaturized dystrophin polypeptide.

In some embodiments, provided is a method of expressing a miniaturized dystrophin polypeptide in a subject in need thereof, comprising administering to the subject the nucleic acid disclosed herein, the vector disclosed herein, the host cell disclosed herein, or the pharmaceutical composition disclosed herein.

In some embodiments, provided is a method of treating a subject having a disease or condition comprising administering to the subject the nucleic acid disclosed herein, the vector disclosed herein, the polypeptide disclosed herein, the host cell disclosed herein, or the pharmaceutical composition disclosed herein. In some embodiments, the disease or condition is a disease caused by dystrophin deficiency. In some embodiments, the disease is Sarcopenia, a heart disease, cachexia, Duchenne muscular dystrophy (DMD), Becker muscular dystrophy (BMD), X-linked dilated cardiomyopathy (XLDC), facioscapulohumeral muscular dystrophy, myotonic muscular dystrophy, limb-girdle muscular dystrophy, oculopharyngeal muscular dystrophy, Emery-Dreifuss muscular dystrophy, distal muscular dystrophy, and/or congenital muscular dystrophy. In some embodiments, the nucleic acid molecule, the vector, the polypeptide, the host cell, or the pharmaceutical composition of the invention is administered intravenously, transdermally, intradermally, subcutaneously, orally, or pulmonarily, or any combination thereof. In some embodiments, the nucleic acid molecule, the vector, the polypeptide, the host cell, or the pharmaceutical composition is administered intravenously, transdermally, intradermally, subcutaneously, orally, or pulmonarily, or any combination thereof.

In some embodiments, the method further comprises administering to the subject a second agent.

In some embodiments, the subject is a human. In some embodiments, the administration of the nucleic acid molecule, the vector, the polypeptide, the host cell, or the pharmaceutical composition to the subject results in increased dystrophin protein expression, relative to dystrophin protein expression in the subject prior to the administration, wherein the dystrophin protein expression is increased by at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 20-fold, at least about 25-fold, at least about 30-fold, at least about 35-fold, at least about 40-fold, at least about 50-fold, at least about 60-fold, at least about 70-fold, at least about 80-fold, at least about 90-fold, or at least about 100-fold.

In some embodiments, disclosed herein is a nucleic acid molecule comprising a nucleotide sequence, which encodes a miniaturized dystrophin polypeptide comprising hinge 2 (H2) domain and spectrin 16 (R16) domain, wherein the H2 domain and the R16 domain are fused by a linker comprising the amino acid sequence set forth in SEQ ID NO: 84 (IHTVREETMMVMTEDMPLEI).

4. BRIEF DESCRIPTION OF THE DRAWINGS

FIG. 1 shows a schematic diagram of the full length human Dystrophin protein. ABD1: actin-binding domain-1; H # (e.g., H1): hinge region; R # (e.g., R1): spectrin-like repeat domains; ABD2: actin-binding domain-2; CR: cysteine-rich domain; C-term: C-terminal domain of the protein.

FIG. 2 shows schematic diagrams of miniaturized dystrophin polypeptides BXA-027741, BXA-027742, BXA-027743, BXA-027744, BXA-196480 and BXA-196481, as well as, as a point of reference, the full length human Dystrophin protein of FIG. 1.

FIG. 3 shows the ratio of miniaturized dystrophin polypeptide expression to miniaturized dystrophin mRNA expression in human isogenic induced-pluripotent stem cell (iPSC)-derived cardiac myocytes (iCMs) (carrying an E2035X premature stop codon in the dystrophin gene that prevented endogenous dystrophin expression) after transfection of plasmids expressing the indicated miniaturized dystrophin polypeptides.

Figure 6A:
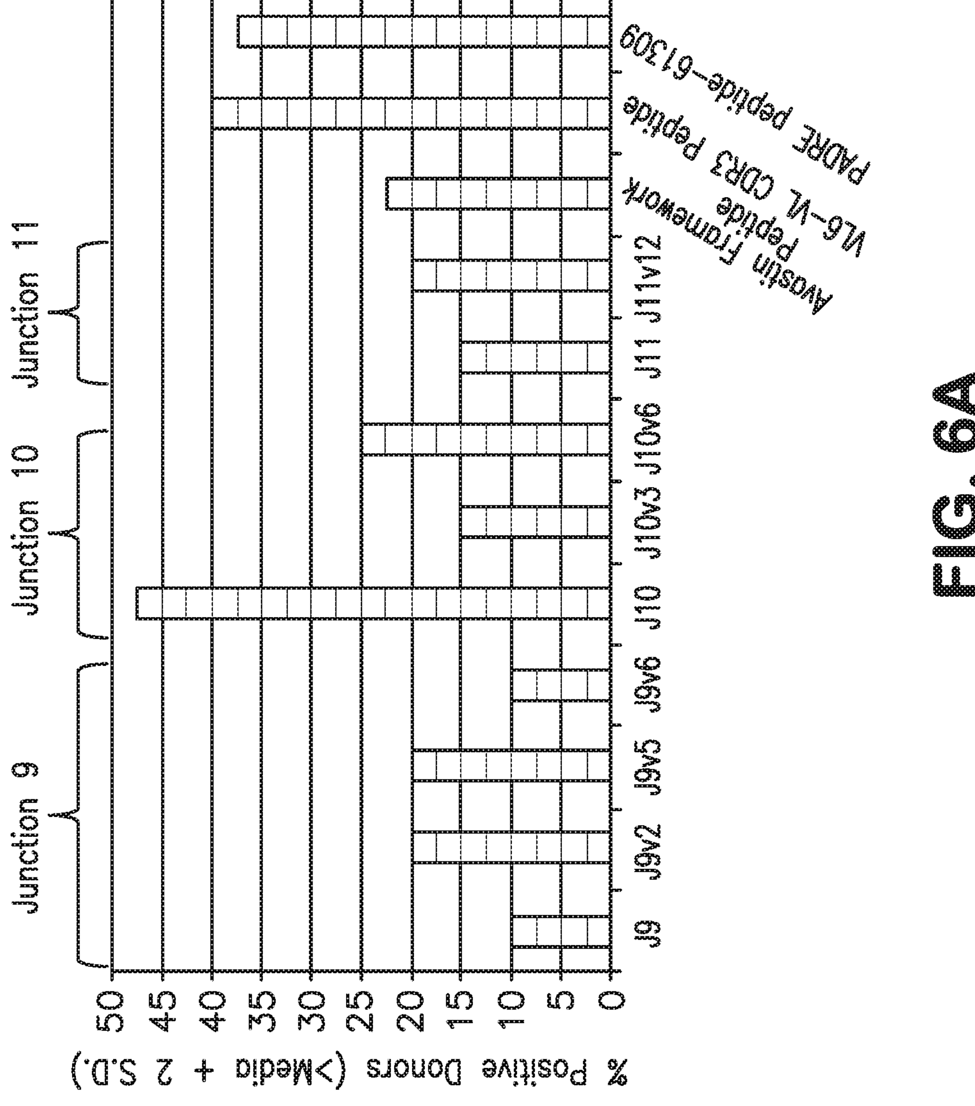
Figure 6B:
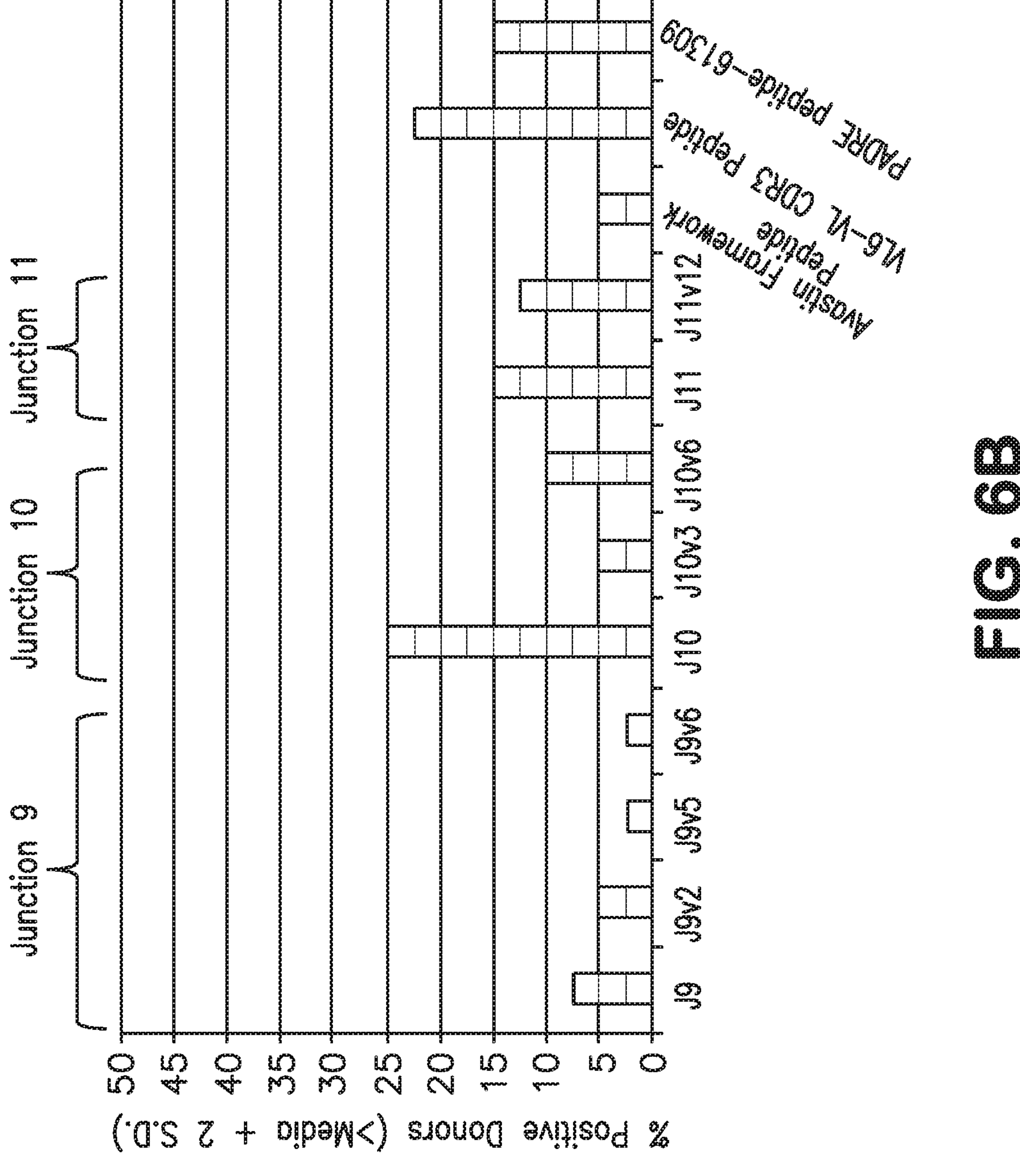

FIG. 6A shows a histogram indicating the proportion of samples, among the 40-samples cell panel tested, that were pulsed with various junction peptides as indicated and had CD4+ proliferating cells (each colored square represents one patient sample). FIG. 6B shows a histogram indicating the proportion of samples, among the 40-samples cell panel tested, that were pulsed with various junction peptides as indicated and had CD8+ proliferating cells (each colored square represents one patient sample).

Figure 7:
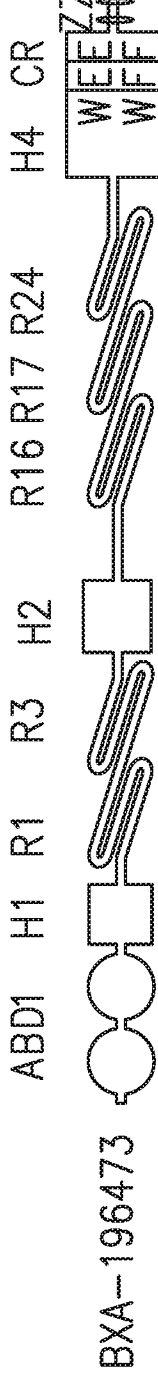

FIG. 7 shows a schematic diagram of the miniaturized dystrophin polypeptide of BXA-196473 (SEQ ID NO:119).

Figure 8A:
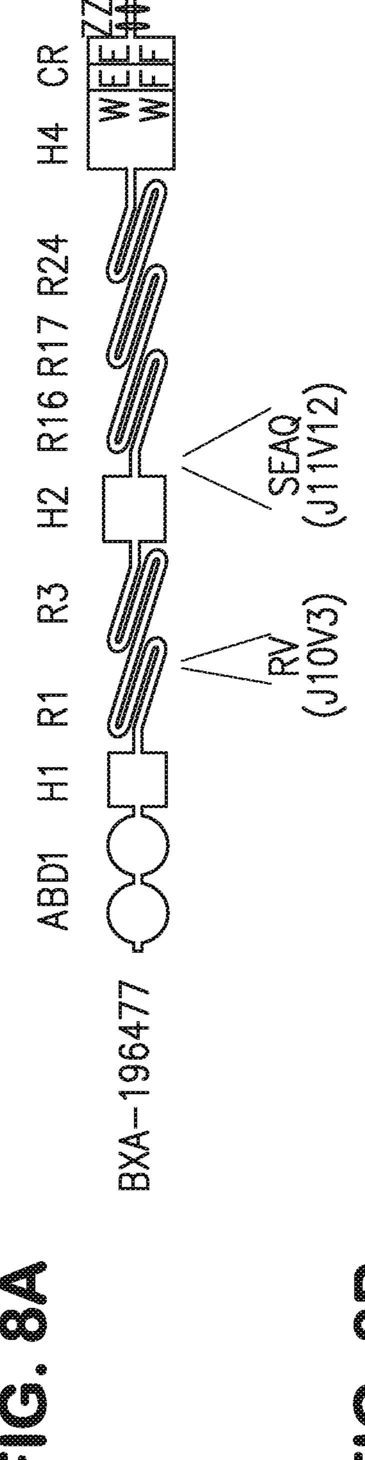
Figure 8B:
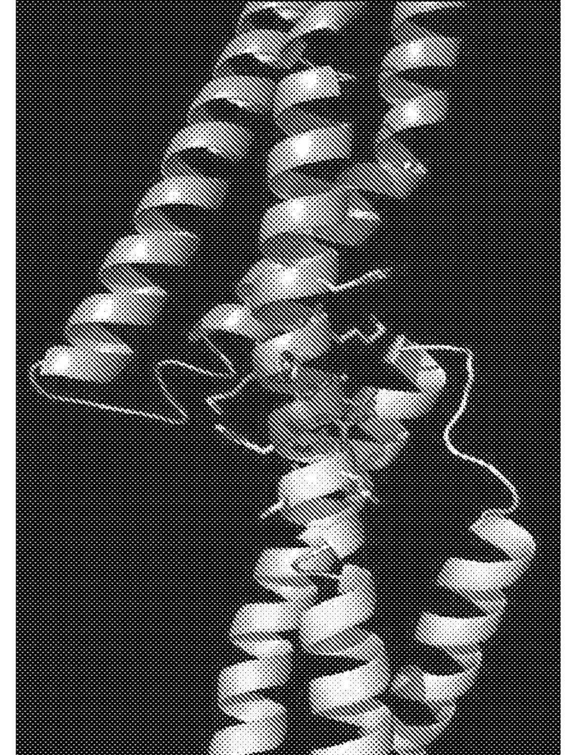
Figure 8B:
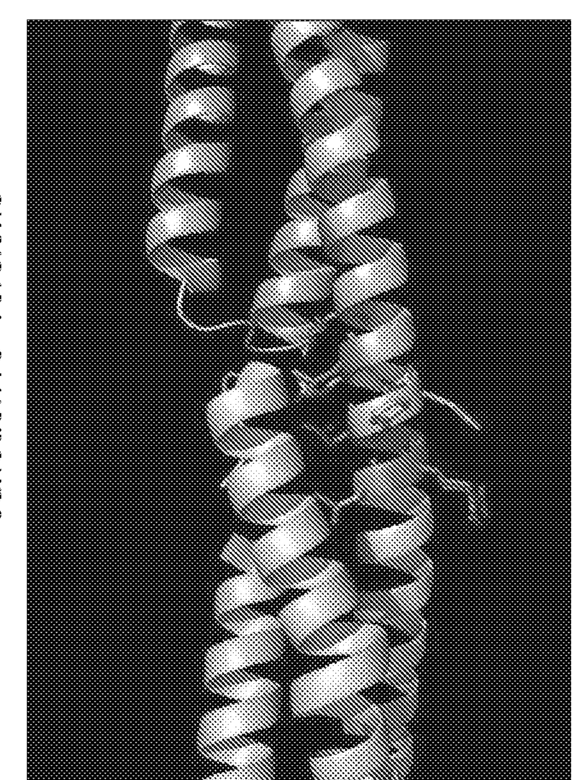

FIG. 8A shows a schematic diagram of the miniaturized dystrophin polypeptide of BXA-196477 (SEQ ID NO:118). RV: arginine-valine dipeptide between R1 and R3; SEAQ: serine-glutamic acid-alanine-glutamine peptide. FIG. 8B shows the three-dimensional folding around original junction 10 between R1 and R3 of miniaturized dystrophin polypeptide BXA-027741 (SEQ ID NO: 129) (left), and the three-dimensional folding around version 3 of the junction 10 of miniaturized dystrophin polypeptide BXA-196477 (SEQ ID NO: 118) (right).

Figure 9:
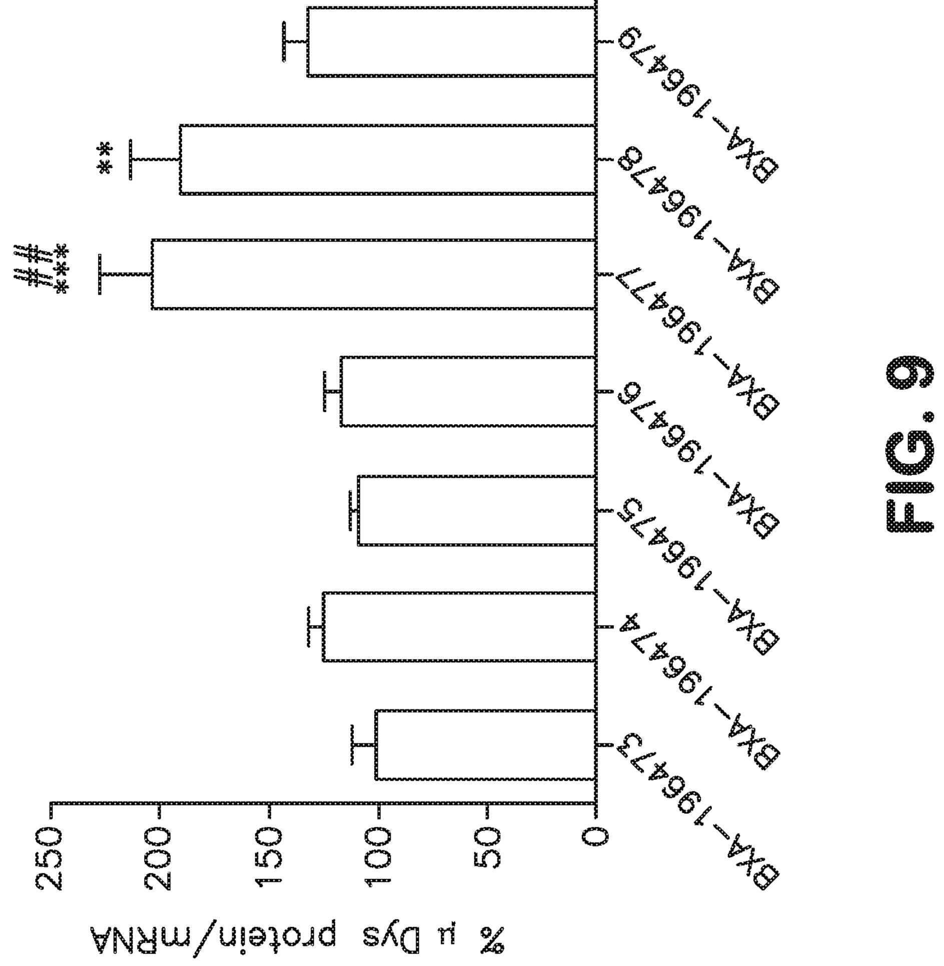

FIG. 9 shows the ratio of miniaturized dystrophin polypeptide expression to miniaturized dystrophin mRNA in human isogenic induced-pluripotent stem cell (iPSC)-derived cardiac myocytes (iCMs) (carrying an E2035X premature stop codon in the dystrophin gene that prevented endogenous dystrophin expression) after transfection of plasmids expressing the indicated miniaturized dystrophin polypeptides.

Figure 10:
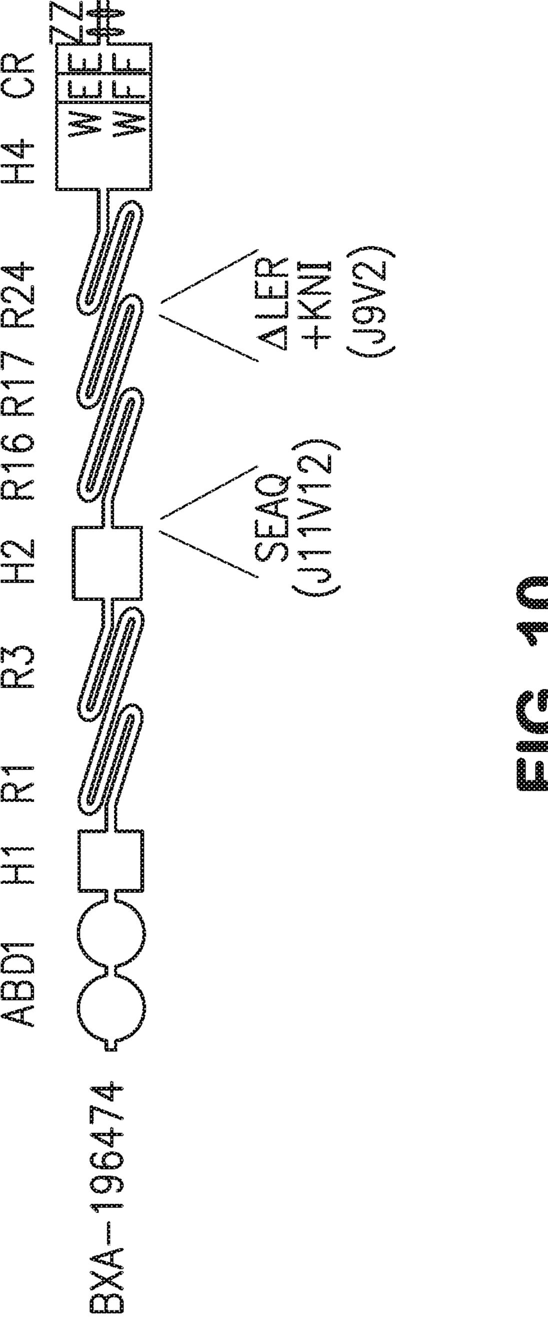

FIG. 10 shows a schematic diagram of the miniaturized dystrophin polypeptide of BXA-196474 (SEQ ID NO:120).

Figure 11:
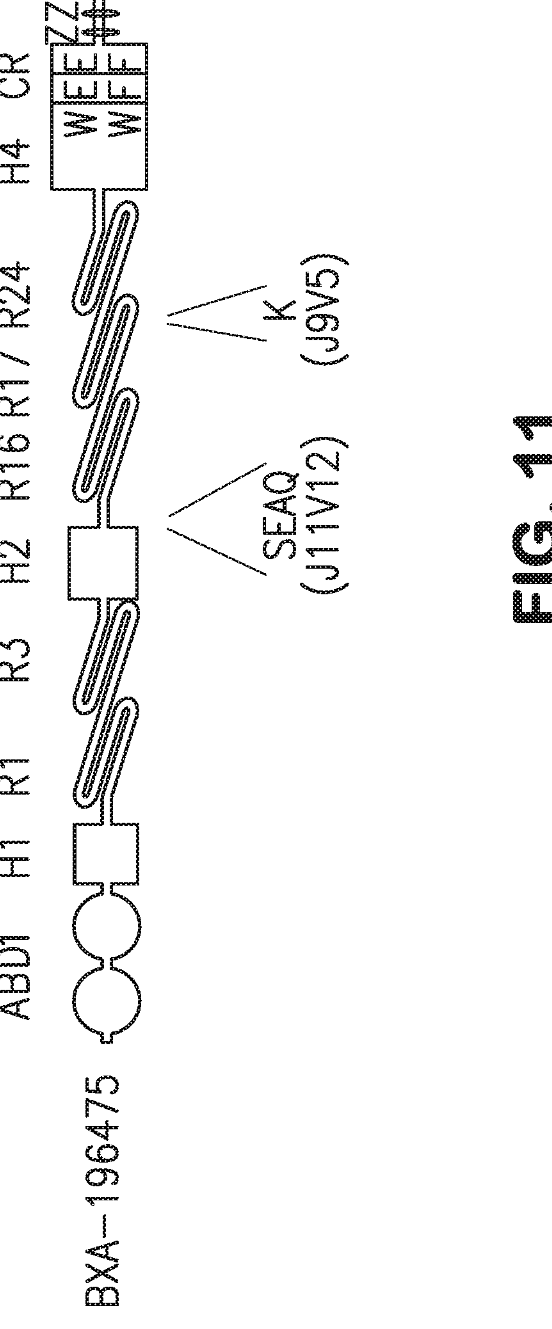

FIG. 11 shows a schematic diagram of the miniaturized dystrophin polypeptide of BXA-196475 (SEQ ID NO:121).

Figure 12:
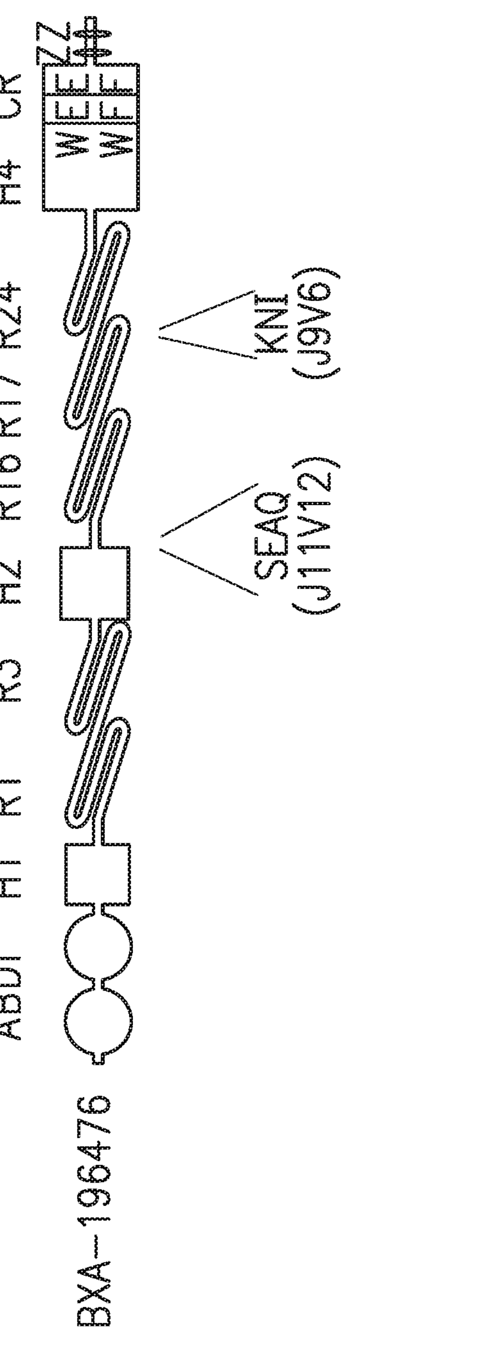

FIG. 12 shows a schematic diagram of the miniaturized dystrophin polypeptide of BXA-196476 (SEQ ID NO:122).

Figure 13:
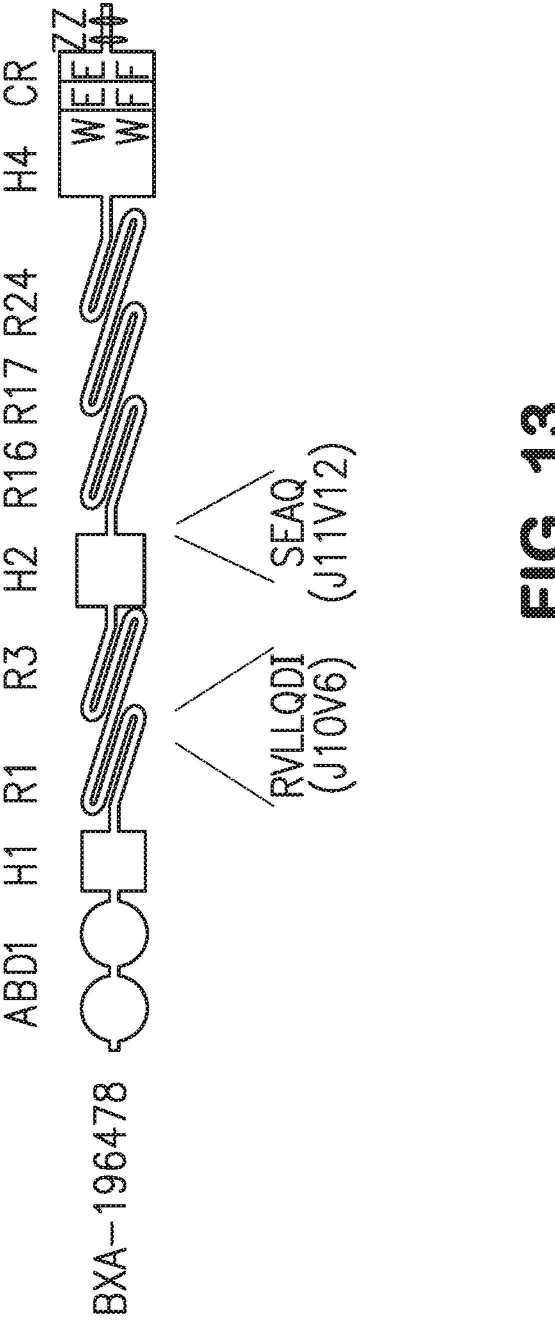

FIG. 13 shows a schematic diagram of the miniaturized dystrophin polypeptide of BXA-196478 (SEQ ID NO:124).

Figure 14:
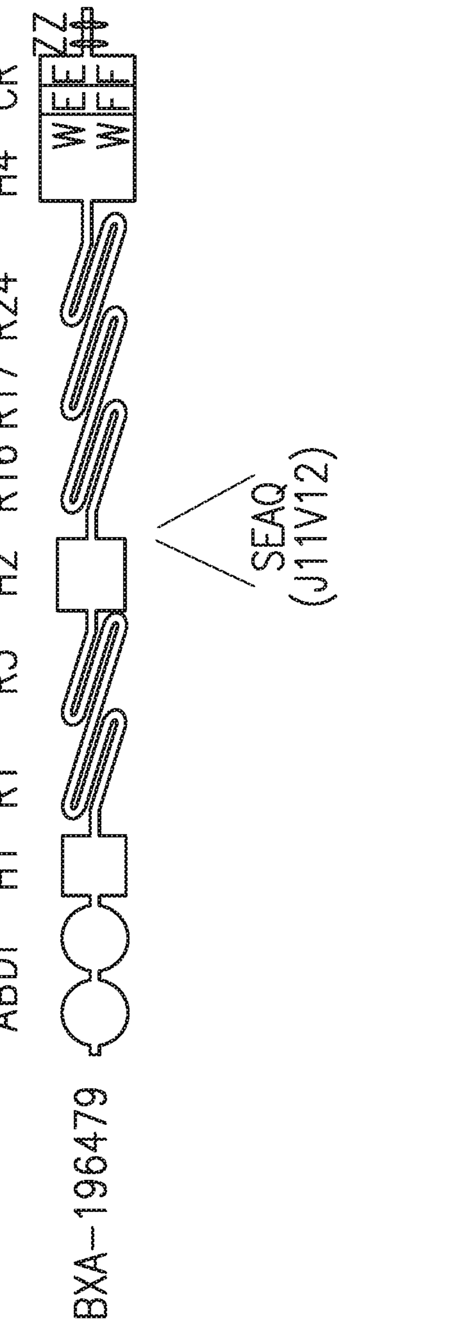

FIG. 14 shows a schematic diagram of the miniaturized dystrophin polypeptide of BXA-196479 (SEQ ID NO:125).

Figures 15A, 15B, 15C:
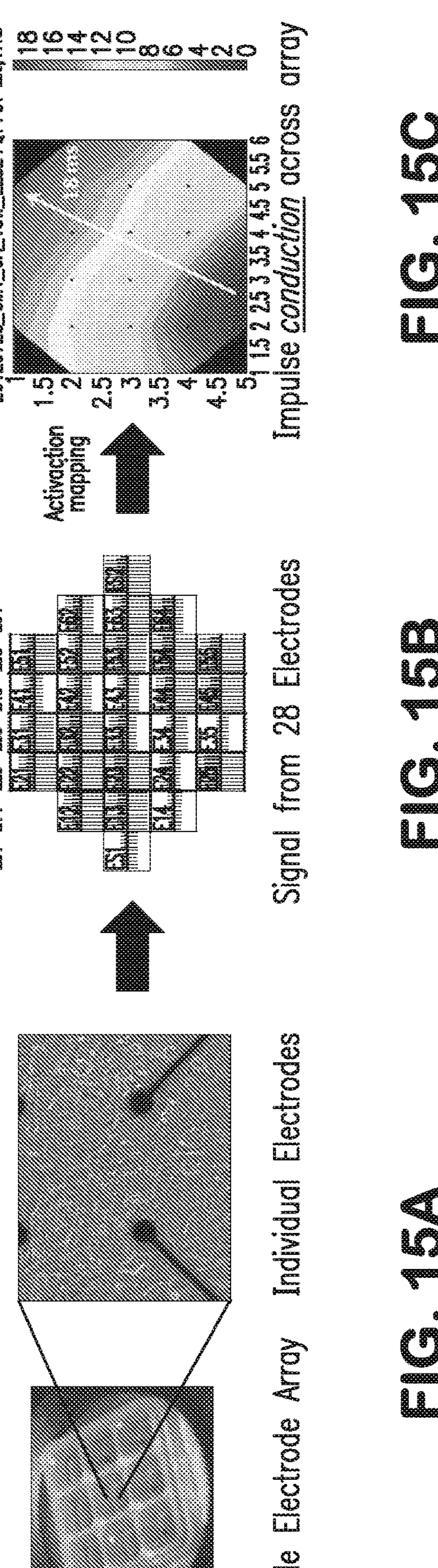
Figures 15D, 15E, 15F:
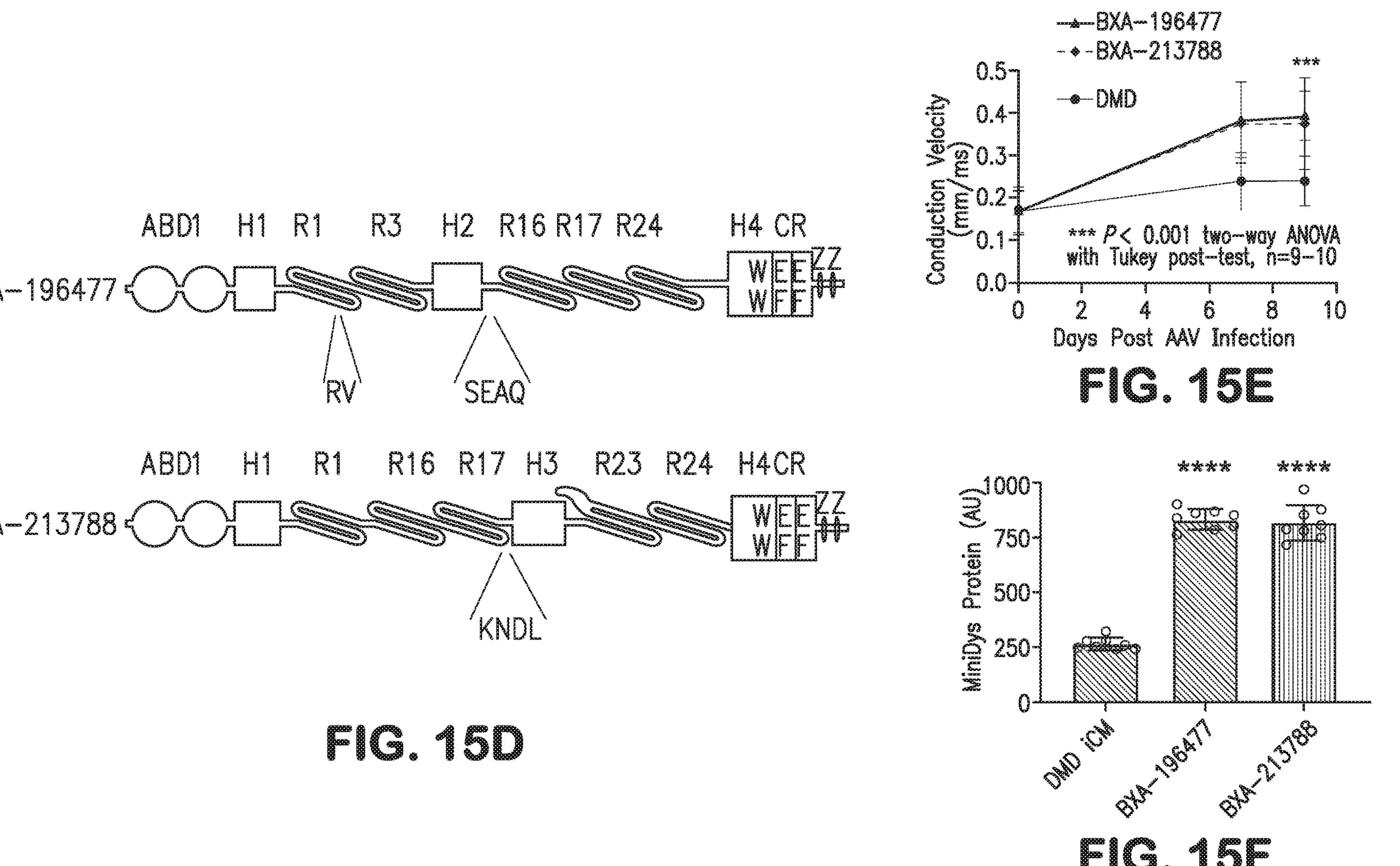

FIG. 15 Conduction velocity in human DMD hiPSC CMs infected with AAV9-constructs expressing miniaturized dystrophin polypeptides of BXA-196477 and BXA-213788. FIG. 15A shows a photograph of a Multiple Electrode Array (MEA) used in the experiments (left) and a photograph of individual electrodes of the MEA (right). FIG. 15B shows the signal from the 28 electrodes of the MEA under experimental conditions. FIG. 15C shows a graphic illustrating impulse conduction across the array. FIG. 15D shows schematic diagrams of the miniaturized dystrophin polypeptides of BXA-196477 (SEQ ID NO: 118) and BXA-213788 (SEQ ID NO:152). The linker between H2 and R16 of BXA-196477 is SEQ ID NO:173 and the linker between R17 and H3 of BXA-213788 is SEQ ID NO:174. FIG. 15E shows a graphic wherein the conduction velocity of human DMD hiPSC CMs expressing miniaturized dystrophin polypeptides of BXA-196477 (SEQ ID NO: 118) and BXA-213788 is plotted as a function of time post transfection. FIG. 15F shows a histogram indicating the expression of miniaturized dystrophin polypeptides in cells in which conduction velocity was measured.

Figure 16:
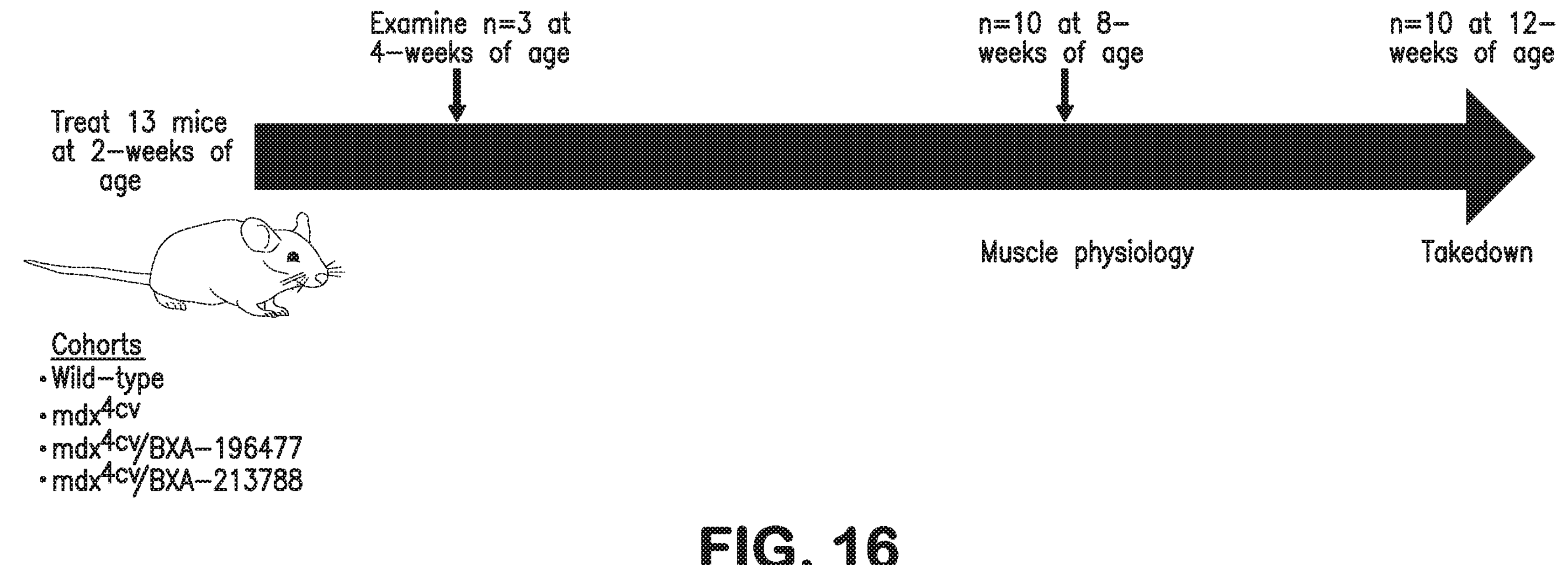

FIG. 16 shows a schematic summarizing the experimental set-up of in vivo studies that were conducted.

Figure 17B:
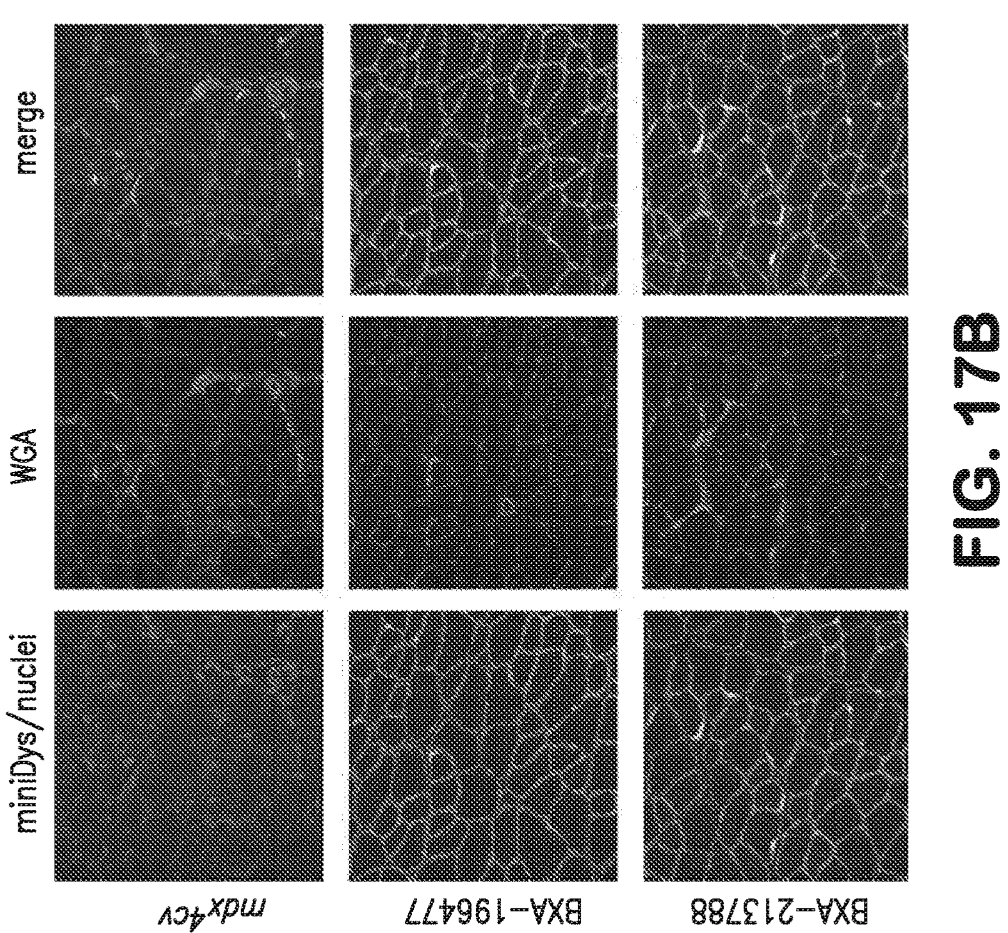
Figure 17A:
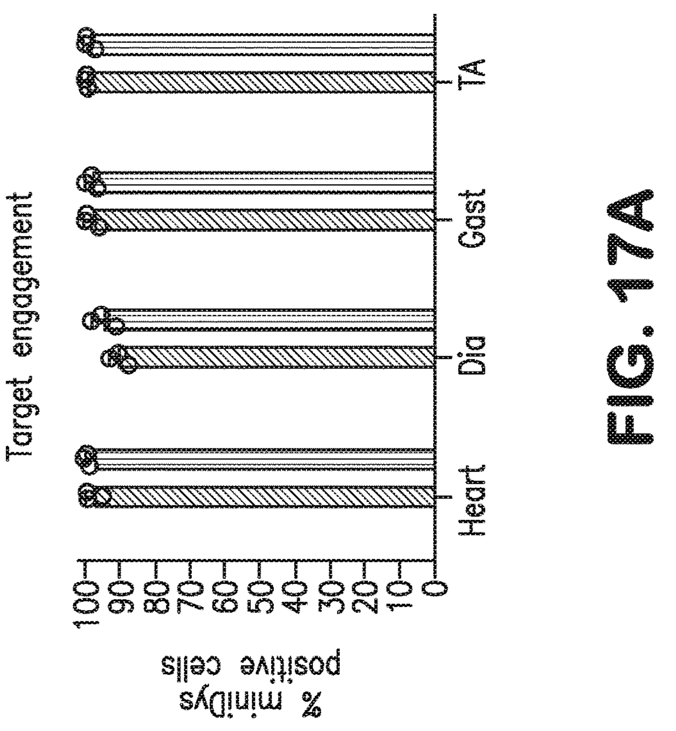

FIG. 17 Target engagement of AAV9-BXA-196477 or AAV9-BXA-213788. FIG. 17B shows immuno-fluorescence visualization of expression of miniaturized dystrophin polypeptides and wheat germ-agglutinin (WGA) in muscle tissue of mice treated with AAV9-BXA-196477 or AAV9-BXA-213788. FIG. 17A shows histograms indicating the relative number of cells in various muscles positive for miniaturized dystrophin. Bars with diagonal pattern=% BXA-196477 miniaturized Dystrophin positive cells as a proportion of WGA positive cells; bars with longitudinal pattern=% BXA-213788 miniaturized Dystrophin as a proportion of WGA positive cells.

Figures 18A, 18B, 18C, 18D:
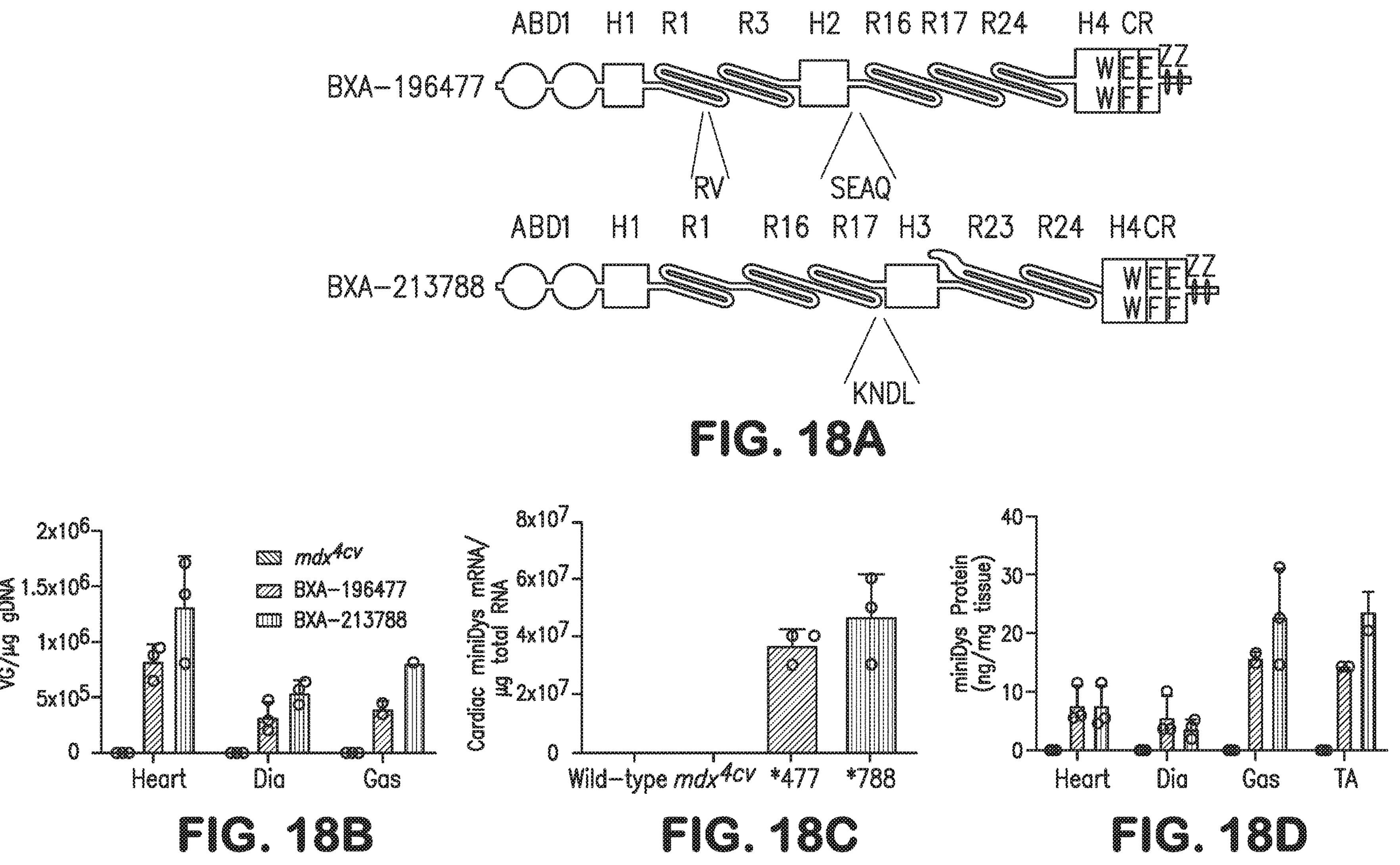

FIG. 18 Target engagement of AAV9-BXA-196477 or AAV9-BXA-213788 determined in $mdx^{4cv}$ mice at 4-weeks of age. FIG. 18A shows schematic diagrams of the miniaturized dystrophin polypeptides of BXA-196477 (SEQ ID NO: 118) and BXA-213788 (SEQ ID NO:152). The linker between H2 and R16 of BXA-196477 is SEQ ID NO:173 and the linker between R17 and H3 of BXA-213788 is SEQ ID NO: 174. FIG. 18B shows a histogram indicating the relative amount of viral genomes in muscle tissue of $mdx^{4cv}$ mice treated with AAV9-BXA-196477 or AAV9-BXA-213788. FIG. 18C shows a histogram indicating the relative amount of miniaturized dystrophin mRNA in the heart of $mdx^{4cv}$ mice treated with AAV9-BXA-196477 or AAV9-BXA-213788. FIG. 18D shows a histogram indicating the relative amount of miniaturized dystrophin protein in muscle tissue of mice treated with AAV9-BXA-196477 or AAV9-BXA-213788. Dia=diaphragm; Gas=gastrocnemius; TA=tibialis anterior. Treated mice were compared to wildtype and $mdx^{4cv}$ non-treated mice.

Figures 19A, 19B:
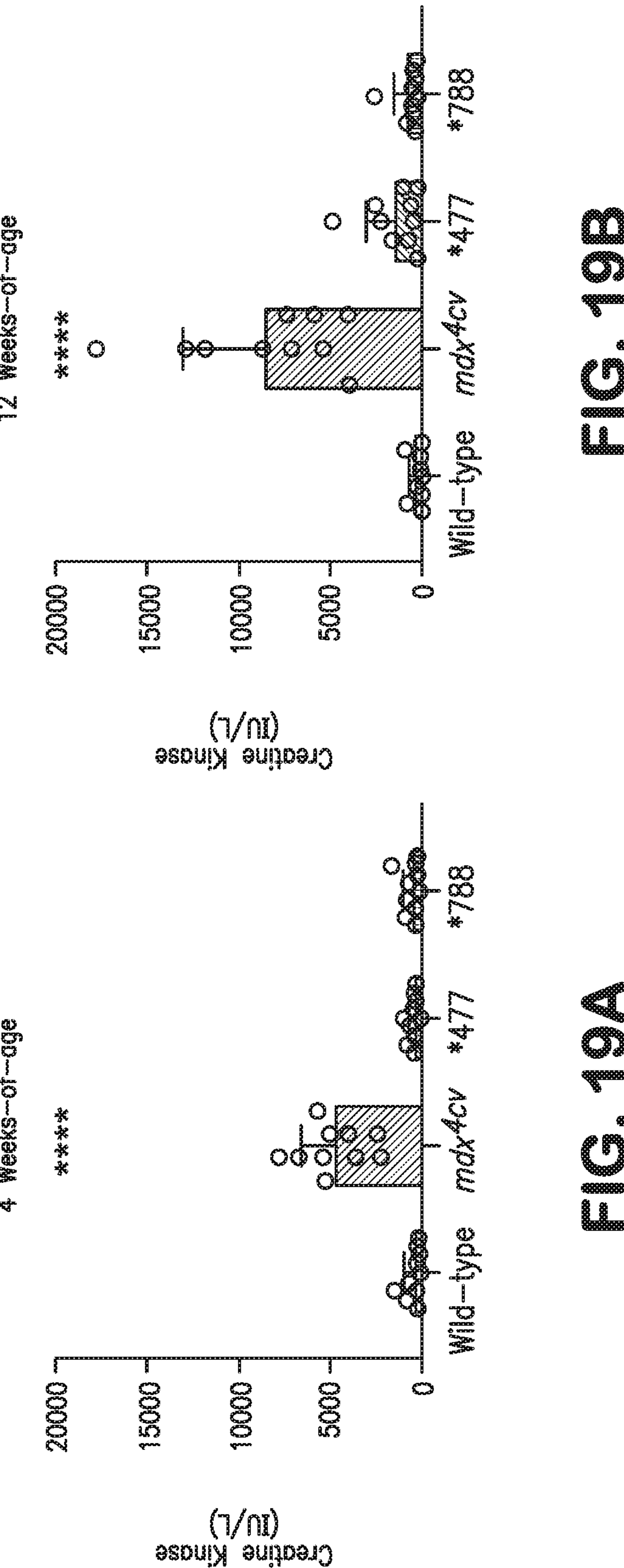
Figure 20A:
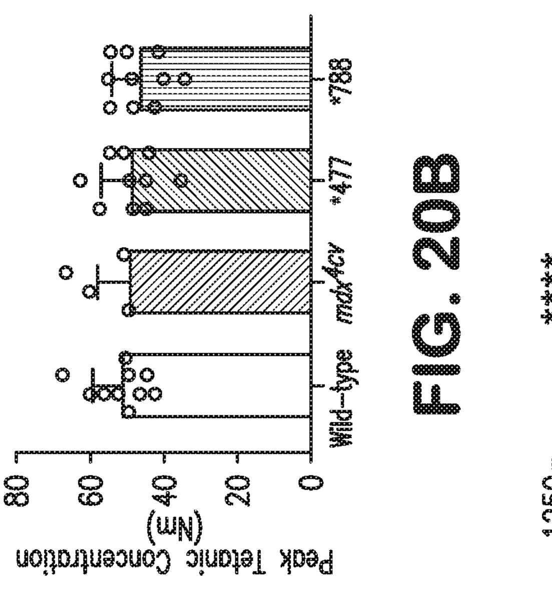
Figure 20B:
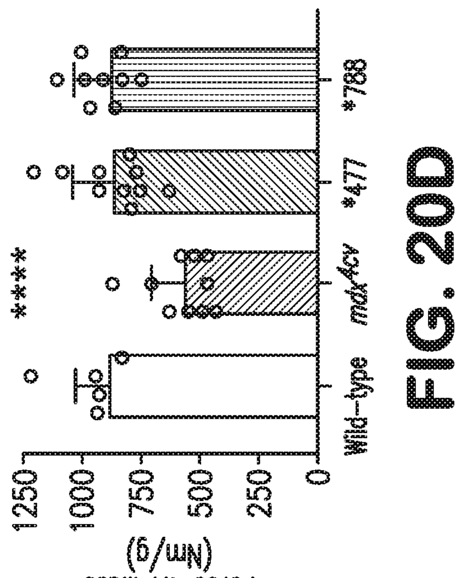
Figure 20C:
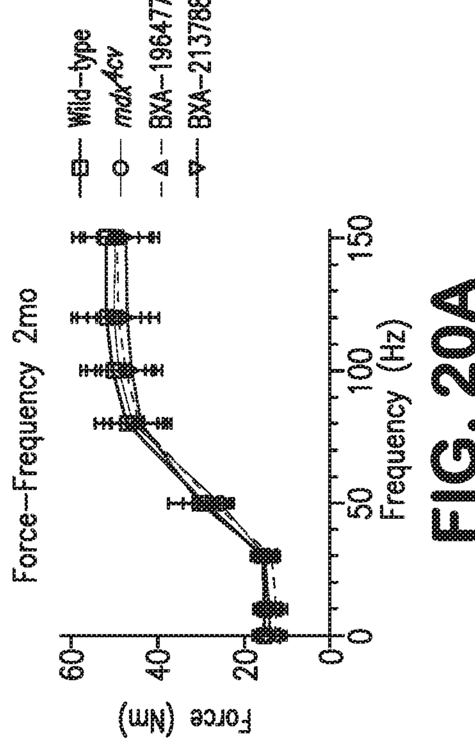
Figure 20D:
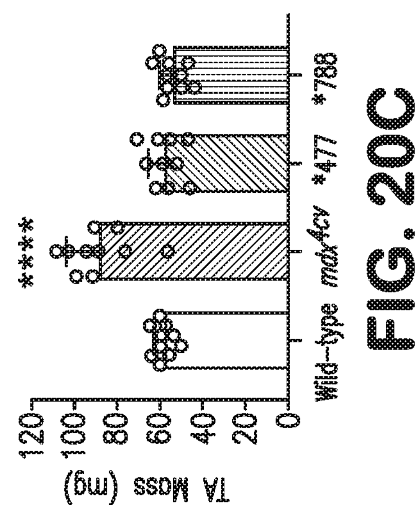

FIG. 19A shows a histogram indicating the amount of creatine kinase in the serum of $mdx^{4cv}$ mice (4-weeks) treated with AAV9-BXA-196477 or AAV9-BXA-213788. FIG. 19B shows a histogram indicating the amount of creatine kinase in the serum of $mdx^{4cv}$ mice (12-weeks) treated with AAV9-BXA-196477 or AAV9-BXA-213788. Treated mice were compared to wildtype and $mdx^{4cv}$ non-treated mice.

FIG. 20 Peak tetanic contraction at 2-months of age. FIG. 20A shows a graph indicating contractile properties (Force in Newton meters; Nm) in mice $mdx^{4cv}$ treated with AAV9-BXA-196477 or AAV9-BXA-213788. FIG. 20B shows a histogram indicating peak tetanic contraction in treated mice. FIG. 20C shows a histogram indicating TA mass in treated mice. FIG. 20D shows a histogram indicating force/TA mass in treated mice. Treated mice were compared to wildtype and $mdx^{4cv}$ non-treated mice.

Figure 21B:
Figure 21A:
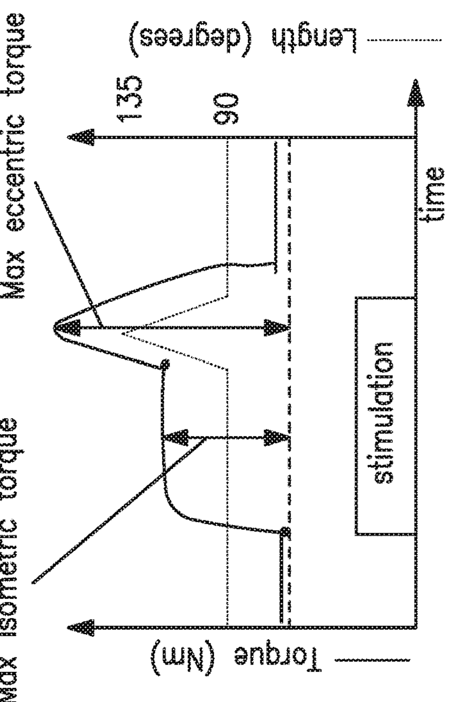

FIG. 21 Protection from contraction-induced injury. FIG. 21A shows a graphic outlining the experimental setup. FIG. 21B shows a graph indicating contractile properties (maximum isometric torque) of muscles in mice treated with AAV9-BXA-196477 or AAV9-BXA-213788. Treated mice were compared to wildtype and $mdx^{4cv}$ non-treated mice.

Figures 22A, 22B:
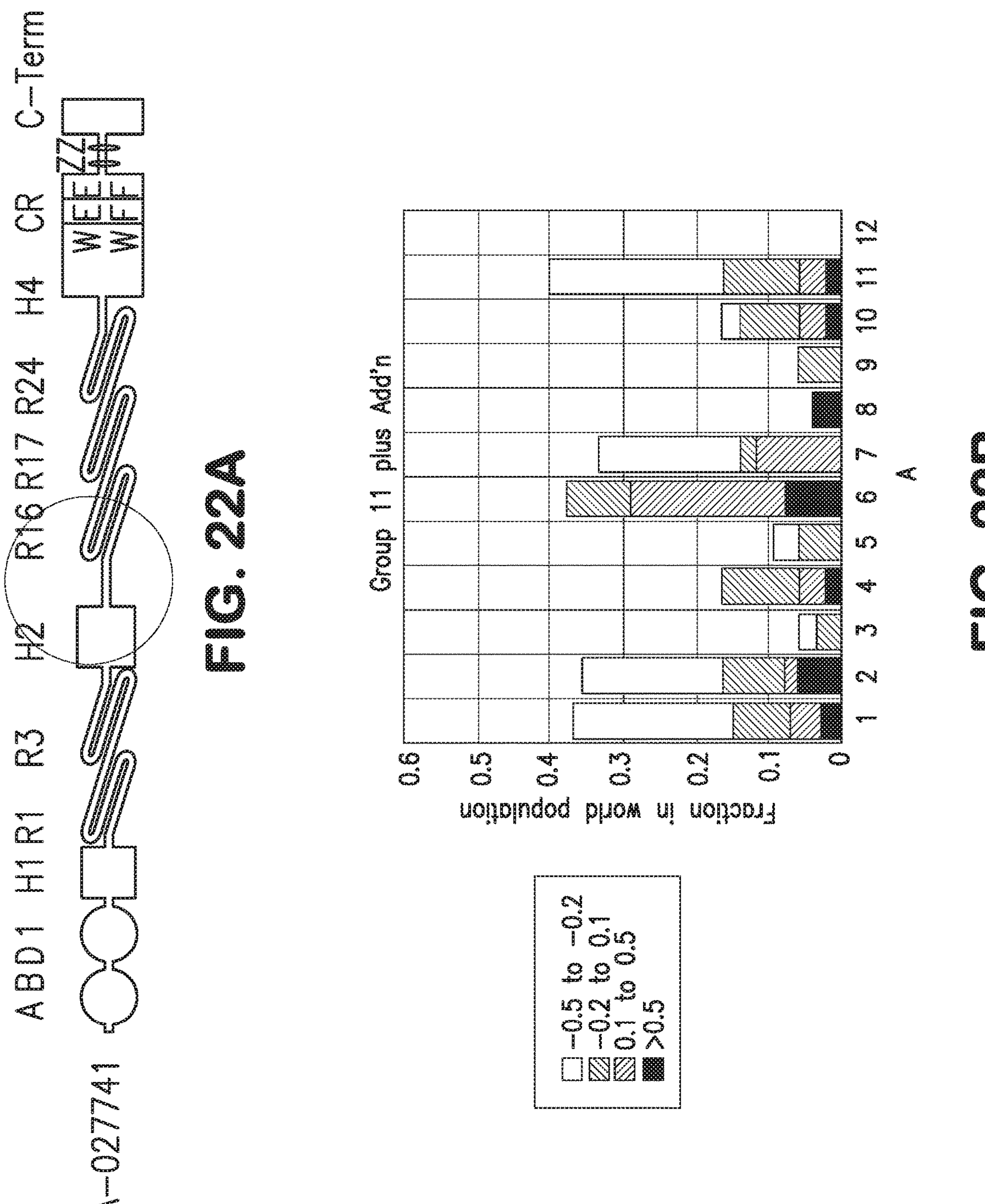

FIG. 22A shows a schematic diagram of the miniaturized dystrophin polypeptides of BXA-027741 (SEQ ID NO: SEQ ID NO: 129). FIG. 22B shows a histogram indicating immunogenicity of junction peptides 1 to 12.

Figure 23A:
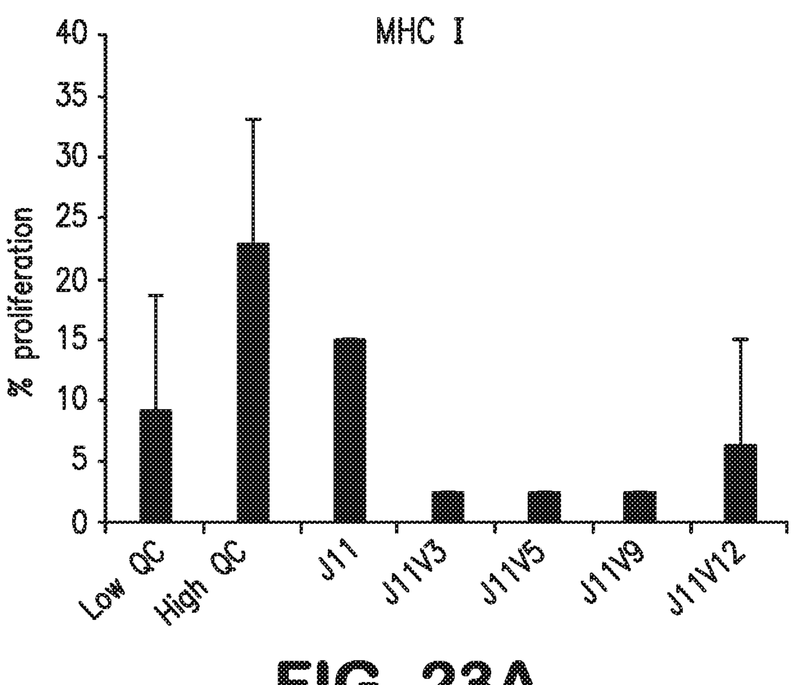

FIG. 23A shows a histogram indicating the MHC I/CD8+ immune response to junction peptides. Peptide J11v3 her is the same peptide as peptide no. 3 in FIG. 22B.

Figure 23B:
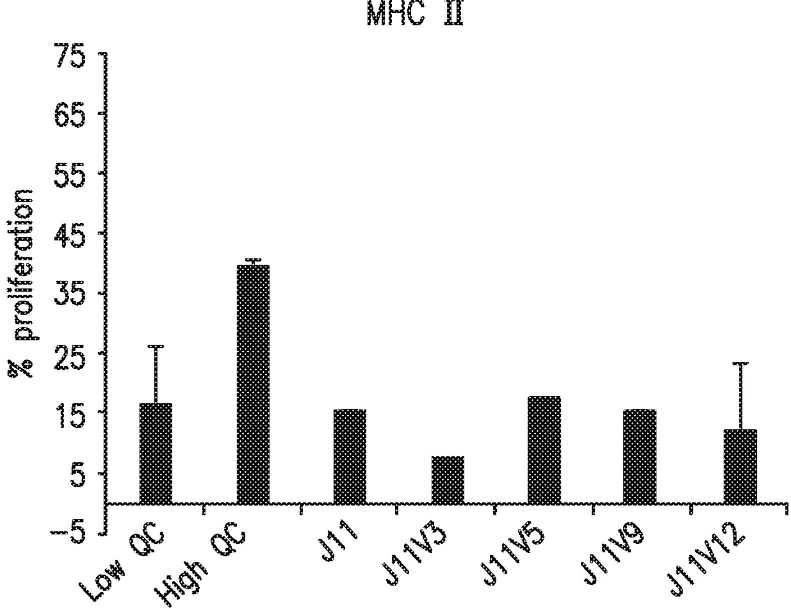

FIG. 23B shows a histogram indicating the MHC II/CD4+ immune response to junction peptides. Peptide J11v3 here is the same peptide as peptide no. 3 in FIG. 22B.

5. DETAILED DESCRIPTION OF THE DISCLOSURE

5.1 Overview

The present disclosure relates to novel miniaturized dystrophins or the genes encoding the same. The miniaturized dystrophins can be operatively linked to a regulatory cassette. The present disclosure also relates to methods of treating a subject having muscular dystrophy, sarcopenia, heart failure, or cachexia. Further, the present disclosure relates to methods of prophylactically treating a subject at risk of developing muscular dystrophy, sarcopenia, heart failure, or cachexia. The methods for treating a subject having, or at risk of developing, muscular dystrophy, sarcopenia, heart failure, or cachexia can comprise administering a pharmaceutical composition including a miniaturized dystrophin gene and a delivery vehicle to the subject.

5.2 Definitions

In order that the present disclosure can be more readily understood, certain terms are first defined. As used in this application, except as otherwise expressly provided herein, each of the following terms shall have the meaning set forth below. Additional definitions are set forth throughout the application.

The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as “A, B, and/or C” is intended to encompass each of the following aspects: A, B, and C; A, B, or C; A or C; A or B; B or C; A and C; A and B; B and C; A (alone); B (alone); and C (alone). It is understood that wherever aspects are described herein with the language “comprising,” otherwise analogous aspects described in terms of “consisting of” and/or “consisting essentially of” are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Systeme International de Unites (SI) accepted form. Numeric ranges are inclusive of the numbers defining the range. The headings provided herein are not limitations of the various aspects of the disclosure, which can be had by reference to the specification as a whole. Accordingly, the terms defined immediately below are more fully defined by reference to the specification in its entirety. Dystrophin (DMD) is a large human X-linked gene that encodes Dystrophin. The protein Dystrophin is a 427 kDa cytoskeletal protein that localizes to the cytoplasmic face of the sarcolemma and is enriched at costameres in muscle fibers. The Dystrophin protein has four main functional domains: an actin-binding amino-terminal domain (ABD1); a central rod domain comprising a series of rods, called “spectrin repeat domains” and hinges; a cysteine-rich domain; and a carboxyl-terminus.

As used herein, the term “miniaturized dystrophin polypeptide” or “miniaturized dystrophin peptide” refers to a polypeptide that is smaller in size than the full-length wild-type dystrophin polypeptide. In some embodiments, the miniaturized dystrophin polypeptide is capable of altering (increasing or decreasing, as the case may be) a measurable value of muscle physiology or anatomy in a DMD animal model by at least approximately 10 or 20% of the wild type value, such that the value is closer to the wild-type value (e.g., a mdx mouse has a measurable value of muscle physiology or anatomy that is 50% of the wild-type value, and this value is increased to at least 60% of the wild-type value; or a mdx mouse has a measurable value of muscle physiology or anatomy that is 150% of the wild-type value, and this value is decreased to at most 140% of the wild-type value). In certain embodiments, the miniaturized dystrophin polypeptide is capable of altering a measurable value of muscle physiology or anatomy in a DMD animal model by at least approximately 30% of the wild type value. In some embodiments, the miniaturized dystrophin polypeptide is capable of altering a measurable value of muscle physiology or anatomy in a DMD animal model to a level similar to the wild-type value (e.g., ±4%).

As used herein, the term “spectrin repeats” or “spectrin-like repeats” refers to peptides composed of approximately 100 amino acids that are responsible for the rod-like shape of many structural proteins including, but not limited to, dystrophin, wherein the spectrin repeats are typically present in multiple copies. Spectrin repeats can include mutations of the natural peptide sequences, such as conservative and/or non-conservative changes in amino acid sequence, as well as the addition or deletion of up to 1, 2, 3, 4, 5, 6, 7, 8, 9, or 10 amino acids to/from the end of a spectrin repeat or within the spectrin repeat. In some embodiments, each spectrin repeat (each of R1 to R24) has at least 70%, at least 75%, at least 80%, at least 85%, at least 90%, at least 95%, at least 96%, at least 97%, at least 98%, at least 99%, or 100% sequence identity to the naturally occurring spectrin repeat (each of the naturally occurring R1 to R24).

As used herein, the term “spectrin repeat encoding sequences” refers to nucleic acid sequences encoding spectrin repeat peptides. This term includes natural and synthetic nucleic acid sequences encoding the spectrin repeats (e.g., both the naturally occurring and mutated spectrin repeat peptides).

As used herein, the term “spectrin repeat domain” refers to the region in a miniaturized dystrophin polypeptide that contains the spectrin repeats of the miniaturized dystrophin polypeptide.

The term “fused” refers to a first amino acid sequence that is linked in frame to a second amino acid sequence with which it is not normally linked in nature, forming a “fusion” protein/polypeptide. These fused amino acid sequences which normally exist in separate proteins can be brought together in the fusion polypeptide, or the amino acid sequences which normally exist in the same protein can be placed in a new arrangement in the fusion polypeptide. A fusion protein is created, for example, by chemical peptide synthesis, or by recombinant DNA technology whereby a polynucleotide is created, and then translated, in which the peptide regions are encoded in the desired relationship. A fusion protein can also comprise a second amino acid sequence associated with the first amino acid sequence by a covalent, non-peptide bond or by a non-covalent bond. In some embodiments, “fusion” between two polypeptides is achieved by a linker. Linkers can be amino acids or other chemical structures. In some embodiments, linkers can be synthetic.

In some embodiments, “fusion” between two polypeptides is a direct fusion, i.e., without intervening linker. The term “fused directly” or “direct fusion” refers to a linkage between two polypeptide chains by a peptide bond. For example, a first amino acid is “fused directly” to a second amino acid when the first amino acid is “fused” to a second amino acid by a peptide bond.

“Heterologous” and “heterologous moiety” in reference to a polypeptide moiety or polynucleotide moiety that is part of a larger polypeptide or polynucleotide, respectively, describes a polypeptide or polynucleotide that originates from a different polypeptide or polynucleotide than the remaining part of the polypeptide or polynucleotide molecule. The additional heterologous component of the polypeptide or polynucleotide can originate from the same organism as the remaining polypeptide or polynucleotide, respectively, described herein, or the additional components can be from a different organism. For instance, a heterologous polypeptide can be synthetic, or derived from a different species, different cell type of an individual, or the same or different type of cell of distinct individuals. In one aspect, a heterologous moiety is a polypeptide fused to another polypeptide to produce a polypeptide. In another aspect, a heterologous moiety is a non-polypeptide such as PEG conjugated to a polypeptide or protein.

As used herein, the terms “muscle cell” refers to a cell derived from muscle tissue, including, but not limited to, cells derived from skeletal muscle, smooth muscle (e.g. from the digestive tract, urinary bladder, and blood vessels), and cardiac muscle. The term includes muscle cells in vitro, ex vivo, and in vivo. Thus, for example, an isolated cardiomyocyte would constitute a muscle cell, as would a cell as it exists in muscle tissue present in a subject in vivo. This term also encompasses both terminally differentiated and nondifferentiated muscle cells, such as myocytes, myotubes, myoblasts, cardiomyocytes, and cardiomyoblasts.

As used herein, the term "muscle-specific" in reference to a gene regulatory element (e.g., enhancer sequence, promoter sequence) means that the regulatory element drives transcriptional activity primarily in muscle cells or tissue (e.g., 20:1) compared to the transcriptional activity driven by the regulatory element in other tissues. Assays to determine the muscle-specificity of a regulatory element are known in the art (e.g., in vitro assay using murine muscle cells and liver cells transfected with an expression vector comprising the regulatory element to be tested driving expression of a beta-galactoside reporter).

As used herein, the term "adeno-associated virus" or "AAV" includes but is not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, snake AAV, avian AAV, bovine AAV, canine AAV, equine AAV, ovine AAV, goat AAV, shrimp AAV, primate AAV, non-primate AAV, and ovine AAV, those AAV serotypes and clades disclosed by Gao et al. (J. Virol. 78:6381 (2004)) and Moris et al. (Virol. 33:375 (2004)), and any other AAV now known or later discovered. See, e.g., Fields et al. VIROLOGY, volume 2, chapter 69 (4th ed., Lippincott-Raven Publishers). AAV refers to a Dependoparvovirus within the Parvoviridae family of viruses. For example, the AAV can be an AAV derived from a naturally occurring "wild-type" virus, an AAV derived from a recombinant AAV (rAAV) genome packaged into a capsid derived from capsid proteins encoded by a naturally occurring cap gene and/or a rAAV genome packaged into a capsid derived from capsid proteins encoded by a non-natural capsid cap gene. As used herein, "AAV" can be used to refer to the virus itself or derivatives thereof. The term covers all subtypes and both naturally occurring and recombinant forms, except where expressly indicated otherwise. "Primate AAV" refers to AAV that infect primates, "non-primate AAV" refers to AAV that infects animals other than primates, "bovine AAV" refers to AAV that infect bovine mammals, etc. See, e.g., BERNARD N FIELDS et al. VIROLOGY, volume 2, chapter 69 (3 d ed., Lippincott-Raven Publishers) The term "rAAV" refers to a "recombinant AAV." In some embodiments, a recombinant AAV has an AAV genome in which part or all of the rep and cap genes have been replaced with heterologous polynucleotide sequences.

An "AAV vector" or "adeno-associated virus vector" as used herein refers to an rAAV comprising a polynucleotide sequence not of AAV origin (i.e., a polynucleotide heterologous to AAV), typically a sequence of interest for the genetic transformation of a cell. In general, the heterologous polynucleotide is flanked by at least one, and generally by two, AAV inverted terminal repeat sequences (ITRs).

A "capsid-free" or "capsid-less" (or variations thereof) viral (e.g., AAV) genome or nucleic acid molecule refers to a genome or nucleic acid molecule free from a capsid. In some embodiments, the capsid-less genome or nucleic acid molecule does not contain sequences encoding, for example, an AAV Rep protein.

An "AAV" or "AAV viral particle" or "AAV vector" or "rAAV vector particle" refers to a viral particle composed of at least one AAV capsid protein (typically of all of the capsid proteins of a wild-type AAV) and an encapsidated polynucleotide. If the particle comprises a heterologous polynucleotide (i.e. a polynucleotide other than a wild-type AAV genome, such as a transgene to be delivered to a mammalian cell), it is typically referred to as an "rAAV vector particle" or simply an "AAV vector."

A "helper virus" for AAV refers to a virus that allows AAV (e.g., wild-type AAV) to be replicated and packaged by a mammalian cell. A variety of such helper viruses for AAV are known in the art, including adenoviruses, herpesviruses and poxviruses such as vaccinia. The adenoviruses encompass a number of different subgroups, although Adenovirus type 5 of subgroup C is most commonly used. Numerous adenoviruses of human, non-human mammalian and avian origin are known and available from depositories such as the ATCC. Viruses of the herpes family include, for example, herpes simplex viruses (HSV) and Epstein-Barr viruses (EBV), as well as cytomegaloviruses (CMV) and pseudorabies viruses (PRV), all of which are also available from depositories such as ATCC.

As used herein, the term "inverted terminal repeat" (or "ITR") refers to a single stranded sequence of nucleotides followed downstream by its reverse complement. The intervening sequence of nucleotides between the initial sequence and the reverse complement can be any length including zero. The AAV genome typically comprises inverted terminal repeats (ITRs) at both ends, wherein each end typically is palindromic and can form a hairpin. The terms "polynucleotide" and "nucleic acid" are used interchangeably herein and refer to a biopolymer composed of a plurality of nucleotide monomers covalently bonded in a chain The term "tropism" as used herein refers to a virus's (e.g., AAV's) ability to infect only one or more particular cell types and its ability to interact only with specific cell surface moieties to achieve cell entry, optionally and preferably followed by expression (e.g., transcription and, optionally, translation) of sequences carried by the virus (e.g., AAV) into the cell (e.g., for a recombinant virus, expression of the heterologous nucleotide sequence(s)).

As used herein, the term "transduction" refers to the entry of the virus (e.g., AAV) into the cell and the transfer of genetic material contained within the virus into the cell to obtain expression from the virus genome. Typically, a virus (e.g., AAV) enters cells in accordance with its tropism.

"Administering" refers to the physical introduction of a therapeutic agent to a subject, using any of the various methods and delivery systems known to those skilled in the art. Exemplary routes of administration, e.g., for an AAV therapy, include intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural, intrasterna, oral, rectal, topical, epidermal, mucosal, intranasal, vaginal, rectal, and sublingual administration. Administering can also be performed, for example, once, a plurality of times, and/or over one or more extended periods.

"Treatment" or "therapy" of a subject refers to any type of intervention or process performed on, or the administration of an active agent to, a subject with the objective of reversing, alleviating, ameliorating, inhibiting, slowing down, or preventing the onset, progression, development, severity, or recurrence of a symptom, complication, condition, or biochemical indicia associated with a disease.

A "therapeutically effective amount," "therapeutic dose," "effective dose," or "effective dosage," as used herein, means an amount or a dose that achieves a therapeutic goal, as described herein. One of ordinary skill in the art will further understand that a therapeutically effective amount etc. can be administered in a single dose, or can be achieved by administration of multiple doses (i.e., 1, 2, 3, 4, 5, 6, 7, 8, 9, 10 or more doses). The ability of a therapeutic agent to promote disease regression or inhibit the development or recurrence of the disease can be evaluated using a variety of methods known to the skilled practitioner, such as in human subjects during clinical trials, in animal model systems predictive of efficacy in humans, or by assaying the activity of the agent in in vitro assays.

A "subject" includes any human or non-human animal. The term "nonhuman animal" includes, but is not limited to, vertebrates such as nonhuman primates, sheep, dogs, and rodents such as mice, rats, and guinea pigs. In some embodiments, the subject is a human. The terms "subject" and "patient" are used interchangeably herein.

As used herein, the terms "ug" and "uM" are used interchangeably with "µg" and "µM," respectively.

The use of the alternative (e.g., "or") should be understood to mean either one, both, or any combination thereof of the alternatives. As used herein, the indefinite articles "a" or "an" should be understood to refer to "one or more" of any recited or enumerated component or entity.

Approximately or about: As used herein, the term "approximately" or "about," as applied to one or more values of interest, refers to a value that is similar to a stated reference value and within a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). When the term "approximately" or "about" is applied herein to a particular value, the value without the term "approximately" or "about is also disclosed herein.

As described herein, any concentration range, percentage range, ratio range, or integer range is to be understood to include the value of any integer within the recited range and, when appropriate, fractions thereof (such as one tenth and one hundredth of an integer), unless otherwise indicated.

Various aspects of the disclosure are described in further detail in the following subsections.

5.3 Polynucleotides and Polypeptides

5.3.1 Miniaturized Dystrophin

The present disclosure is directed to a nucleic acid molecule comprising a nucleotide sequence, which encodes a miniaturized dystrophin polypeptide. In some embodiments, the miniaturized dystrophin polypeptide comprises at least three hinge domains of dystrophin and at least five Spectrin repeat domains.

Dystrophin is a rod-shaped cytoplasmic protein that connects the cytoskeleton of a muscle fiber to the surrounding extracellular matrix through the cell membrane. This protein is located primarily in muscles used for movement (skeletal muscles) and in heart (cardiac) muscle. Small amounts of dystrophin are present in nerve cells in the brain. In skeletal and cardiac muscles, dystrophin is part of a group of proteins (a protein complex) that work together to strengthen muscle fibers and protect them from injury as muscles contract and relax. The dystrophin complex acts as an anchor, connecting each muscle cell's structural framework (cytoskeleton) with the lattice of proteins and other molecules outside the cell (extracellular matrix). The dystrophin complex can also play a role in cell signaling by interacting with proteins that send and receive chemical signals.

The DMD gene, encoding the full length dystrophin protein, is one of the longest human genes known, covering 2.3 megabases (0.08% of the human genome) at locus Xp21. The primary transcript in muscle measures about 2,100 kilobases and takes 16 hours to transcribe; the mature mRNA measures 14.0 kilobases. The 79-exon muscle transcript codes for a protein of 3685 amino acid residues.

Disclosed herein are amino acid and nucleotide sequences for dystrophin. The amino acid sequence constituting human wild type dystrophin, isoform Dp427m, is known as UniProt identifier No. NP 003997.1 and shown in Table 1.

TABLE 1

| Amino Acids sequence of full-length Dystrophin Protein (NP 003997.1). |
|---|
| SEQ ID NO: 1 |
| MLWWEEVEDCYEREDVQKKTFTKWVNAQFSKFGKQHIENLFSDLQDGRRL |
| LDLLEGLTGQKLPKEKGSTRVHALNNVNKALRVLQNNNVDLVNIGSTDIV |
| DGNHKLTLGLIWNIILHWQVKNVMKNIMAGLQQTNSEKILLSWVRQSTRN |
| YPQVNVINFTTSWSDGLALNALIHSHRPDLFDWNSVVCQQSATQRLEHAF |
| NIARYQLGIEKLLDPEDVDTTYPDKKSILMYITSLFQVLPQQVSIEAIQE |
| VEMLPRPPKVTKEEHFQLHHQMHYSQQITVSLAQGYERTSSPKPRFKSYA |
| YTQAAYVTTSDPTRSPFPSQHLEAPEDKSFGSSLMESEVNLDRYQTALEE |
| VLSWLLSAEDTLQAQGEISNDVEVVKDQFHTHEGYMMDLTAHQGRVGNIL |
| QLGSKLIGTGKLSEDEETEVQEQMNLLNSRWECLRVASMEKQSNLHRVLM |
| DLQNQKLKELNDWLTKTEERTRKMEEEPLGPDLEDLKRQVQQHKVLQEDL |
| EQEQVRVNSLTHMVVVVDESSGDHATAALEEQLKVLGDRWANICRWTEDR |
| WVLLQDILLKWQRLTEEQCLFSAWLSEKEDAVNKIHTTGFKDQNEMLSSL |
| QKLAVLKADLEKKKQSMGKLYSLKQDLLSTLKNKSVTQKTEAWLDNFARC |
| WDNLVQKLEKSTAQISQAVTTTQPSLTQTTVMETVTTVTTREQILVKHAQ |
| EELPPPPPQKKRQITVDSEIRKRLDVDITELHSWITRSEAVLQSPEFAIF |
| RKEGNFSDLKEKVNAIEREKAEKFRKLQDASRSAQALVEQMVNEGVNADS |
| IKQASEQLNSRWIEFCQLLSERLNWLEYQNNIIAFYNQLQQLEQMTTTAE |
| NWLKIQPTTPSEPTAIKSQLKICKDEVNRLSGLQPQIERLKIQSIALKEK |
| GQGPMFLDADFVAFTNHFKQVFSDVQAREKELQTIFDTLPPMRYQETMSA |
| IRTWVQQSETKLSIPQLSVTDYEIMEQRLGELQALQSSLQEQQSGLYYLS |
| TTVKEMSKKAPSEISRKYQSEFEEIEGRWKKLSSQLVEHCQKLEEQMNKL |
| RKIQNHIQTLKKWMAEVDVFLKEEWPALGDSEILKKQLKQCRLLVSDIQT |
| IQPSLNSVNEGGQKIKNEAEPEFASRLETELKELNTQWDHMCQQVYARKE |
| ALKGGLEKTVSLQKDLSEMHEWMTQAEEEYLERDFEYKTPDELQKAVEEM |
| KRAKEEAQQKEAKVKLLTESVNSVIAQAPPVAQEALKKELETLTTNYQWL |
| CTRLNGKCKTLEEVWACWHELLSYLEKANKWLNEVEFKLKTTENIPGGAE |
| EISEVLDSLENLMRHSEDNPNQIRILAQTLTDGGVMDELINEELETFNSR |
| WRELHEEAVRRQKLLEQSIQSAQETEKSLHLIQESLTFIDKQLAAYIADK |
| VDAAQMPQEAQKIQSDLTSHEISLEEMKKHNQGKEAAQRVLSQIDVAQKK |
| LQDVSMKFRLFQKPANFEQRLQESKMILDEVKMHLPALETKSVEQEVVQS |
| QLNHCVNLYKSLSEVKSEVEMVIKTGRQIVQKKQTENPKELDERVTALKL |

TABLE 1-continued

| Amino Acids sequence of full-length Dystrophin Protein (NP 003997.1). |
|---|
| HYNELGAKVTERKQQLEKCLKLSRKMRKEMNVLTEWLAATDMELTKRSAV |
| EGMPSNLDSEVAWGKATQKEIEKQKVHLKSITEVGEALKTVLGKKETLVE |
| DKLSLLNSNWIAVTSRAEEWLNLLLEYQKHMETFDQNVDHITKWIIQADT |
| LLDESEKKKPQQKEDVLKRLKAELNDIRPKVDSTRDQAANLMANRGDHCR |
| KLVEPQISELNHRFAAISHRIKTGKASIPLKELEQFNSDIQKLLEPLEAE |
| IQQGVNLKEEDFNKDMNEDNEGTVKELLQRGDNLQQRITDERKREEIKIK |
| QQLLQTKHNALKDLRSQRRKKALEISHQWYQYKRQADDLLKCLDDIEKKL |
| ASLPEPRDERKIKEIDRELQKKKEELNAVRRQAEGLSEDGAAMAVEPTQI |
| QLSKRWREIESKFAQFRRLNFAQIHTVREETMMVMTEDMPLEISYVPSTY |
| LTEITHVSQALLEVEQLLNAPDLCAKDFEDLFKQEESLKNIKDSLQQSSG |
| RIDIIHSKKTAALQSATPVERVKLQEALSQLDFQWEKVNKMYKDRQGRFD |
| RSVEKWRRFHYDIKIFNQWLTEAEQFLRKTQIPENWEHAKYKWYLKELQD |
| GIGQRQTVVRTLNATGEEIIQQSSKTDASILQEKLGSLNLRWQEVCKQLS |
| DRKKRLEEQKNILSEFQRDLNEFVLWLEEADNIASIPLEPGKEQQLKEKL |
| EQVKLLVEELPLRQGILKQLNETGGPVLVSAPISPEEQDKLENKLKQTNL |
| QWIKVSRALPEKQGEIEAQIKDLGQLEKKLEDLEEQLNHLLLWLSPIRNQ |
| LEIYNQPNQEGPFDVQETEIAVQAKQPDVEEILSKGQHLYKEKPATQPVK |
| RKLEDLSSEWKAVNRLLQELRAKQPDLAPGLTTIGASPTQTVTLVTQPVV |
| TKETAISKLEMPSSLMLEVPALADFNRAWTELTDWLSLLDQVIKSQRVMV |
| GDLEDINEMIIKQKATMQDLEQRRPQLEELITAAQNLKNKTSNQEARTII |
| TDRIERIQNQWDEVQEHLQNRRQQLNEMLKDSTQWLEAKEEAEQVLGQAR |
| AKLESWKEGPYTVDAIQKKITETKQLAKDLRQWQTNVDVANDLALKLLRD |
| YSADDTRKVHMITENINASWRSIHKRVSEREAALEETHRLLQQFPLDLEK |
| FLAWLTEAETTANVLQDATRKERLLEDSKGVKELMKQWQDLQGEIEAHTD |
| VYHNLDENSQKILRSLEGSDDAVLLQRRLDNMNFKWSELRKKSLNIRSHL |
| EASSDQWKRLHLSLQELLVWLQLKDDELSRQAPIGGDFPAVQKQNDVHRA |
| FKRELKTKEPVIMSTLETVRIFLTEQPLEGLEKLYQEPRELPPEERAQNV |
| TRLLRKQAEEVNTEWEKLNLHSADWQRKIDETLERLQELQEATDELDLKL |
| RQAEVIKGSWQPVGDLLIDSLQDHLEKVKALRGEIAPLKENVSHVNDLAR |
| QLTTLGIQLSPYNLSTLEDLNTRWKLLQVAVEDRVRQLHEAHRDFGPASQ |
| HFLSTSVQGPWERAISPNKVPYYINHETQTTCWDHPKMTELYQSLADLNN |
| VRFSAYRTAMKLRRLQKALCLDLLSLSAACDALDQHNLKQNDQPMDILQI |
| INCLTTIYDRLEQEHNNLVNVPLCVDMCLNWLLNVYDTGRTGRIRVLSFK |
| TGIISLCKAHLEDKYRYLFKQVASSTGFCDQRRLGLLLHDSIQIPRQLGE |
| VASFGGSNIEPSVRSCFQFANNKPEIEAALFLDWMRLEPQSMVWLPVLHR |
| VAAAETAKHQAKCNICKECPIIGFRYRSLKHFNYDICQSCFFSGRVAKGH |
| KMHYPMVEYCTPTTSGEDVRDFAKVLKNKFRTKRYFAKHPRMGYLPVQTV |
| LEGDNMETPVTLINFWPVDSAPASSPQLSHDDTHSRIEHYASRLAEMENS |
| NGSYLNDSISPNESIDDEHLLIQHYCQSLNQDSPLSQPRSPAQILISLES |
| EERGELERILADLEEENRNLQAEYDRLKQQHEHKGLSPLPSPPEMMPTSP |
| QSPRDAELIAEAKLLRQHKGRLEARMQILEDHNKQLESQLHRLRQLLEQP |
| QAEAKVNGTTVSSPSTSLQRSDSSQPMLLRVVGSQTSDSMGEEDLLSPPQ |
| DTSTGLEEVMEQLNNSFPSSRGRNTPGKPMREDTM |

Various other dystrophin isoforms are known in the art that result from alternative splicing. In some embodiments, the constructs comprise the nucleotide sequences recited in Table 2.

Also disclosed herein is a nucleotide sequence encoding the full-length dystrophin protein.

TABLE 2

| Nucleotide sequence of full-length Dystrophin Protein (isoform Dp427m). |
|---|
| SEQ ID NO: 2<br>GGGATTCCCTCACTTTCCCCCTACAGGACTCAGATCTGGGAGGCAATTACCTTCGG |
| AGAAAAACGAATAGGAAAAACTGAAGTGTTACTTTTTTTAAAGCTGCTGAAGTTT |
| GTTGGTTTCTCATTGTTTTTAAGCCTACTGGAGCAATAAAGTTTGAAGAACTTTTA |
| CCAGGTTTTTTTTATCGCTGCCTTGATATACACTTTTCAAAATGCTTTGGTGGGAAG |
| AAGTAGAGGACTGTTATGAAAGAGAAGATGTTCAAAAGAAAACATTCACAAAAT |
| GGGTAAATGCACAATTTTCTAAGTTTGGGAAGCAGCATATTGAGAACCTCTTCAGT |
| GACCTACAGGATGGGAGGCGCCTCCTAGACCTCCTCGAAGGCCTGACAGGGCAAA |
| AACTGCCAAAAGAAAAAGGATCCACAAGAGTTCATGCCCTGAACAATGTCAACA |
| AGGCACTGCGGGTTTTGCAGAACAATAATGTTGATTTAGTGAATATTGGAAGTAC |
| TGACATCGTAGATGGAAATCATAAACTGACTCTTGGTTTGATTTGGAATATAATCC |
| TCCACTGGCAGGTCAAAAATGTAATGAAAAATATCATGGCTGGATTGCAACAAAC |

TABLE 2-continued

Nucleotide sequence of full-length Dystrophin Protein (isoform Dp427m).

CAACAGTGAAAAGATTCTCCTGAGCTGGGTCCGACAATCAACTCGTAATTATCCA

CAGGTTAATGTAATCAACTTCACCACCAGCTGGTCTGATGGCCTGGCTTTGAATGC

TCTCATCCATAGTCATAGGCCAGACCTATTTGACTGGAATAGTGTGGTTTGCCAGC

AGTCAGCCACACAACGACTGGAACATGCATTCAACATCGCCAGATATCAATTAGG

CATAGAGAAACTACTCGATCCTGAAGATGTTGATACCACCTATCCAGATAAGAAG

TCCATCTTAATGTACATCACATCACTCTTCCAAGTTTTGCCTCAACAAGTGAGCAT

TGAAGCCATCCAGGAAGT

GGAAATGTTGCCAAGGCCACCTAAAGTGACTAAAGAAGAACATTTTCAGTTACAT

CATCA

AATGCACTATTCTCAACAGATCACGGTCAGTCTAGCACAGGGATATGAGAGAACT

TCTTC

CCCTAAGCCTCGATTCAAGAGCTATGCCTACACACAGGCTGCTTATGTCACCACCT

CTGA

CCCTACACGGAGCCCATTTCCTTCACAGCATTTGGAAGCTCCTGAAGACAAGTCAT

TTGG

CAGTTCATTGATGGAGAGTGAAGTAAACCTGGACCGTTATCAAACAGCTTTAGAA

GAAGT

ATTATCGTGGCTTCTTTCTGCTGAGGACACATTGCAAGCACAAGGAGAGATTTCTA

ATGA

TGTGGAAGTGGTGAAAGACCAGTTTCATACTCATGAGGGGTACATGATGGATTTG

ACAGC

CCATCAGGGCCGGGTTGGTAATATTCTACAATTGGGAAGTAAGCTGATTGGAACA

GGAAA

ATTATCAGAAGATGAAGAAACTGAAGTACAAGAGCAGATGAATCTCCTAAATTCA

AGATG

GGAATGCCTCAGGGTAGCTAGCATGGAAAAACAAAGCAATTTACATAGAGTTTTA

ATGGA

TCTCCAGAATCAGAAACTGAAAGAGTTGAATGACTGGCTAACAAAAACAGAAGA

AAGAAC

AAGGAAAATGGAGGAAGAGCCTCTTGGACCTGATCTTGAAGACCTAAAACGCCA

AGTACA

ACAACATAAGGTGCTTCAAGAAGATCTAGAACAAGAACAAGTCAGGGTCAATTCT

CTCAC

TCACATGGTGGTGGTAGTTGATGAATCTAGTGGAGATCACGCAACTGCTGCTTTGG

AAGA

ACAACTTAAGGTATTGGGAGATCGATGGGCAAACATCTGTAGATGGACAGAAGAC

CGCTG

GGTTCTTTTACAAGACATCCTTCTCAAATGGCAACGTCTTACTGAAGAACAGTGCCTTTT

TABLE 2-continued

| Nucleotide sequence of full-length Dystrophin Protein (isoform Dp427m). |
|---|
| TAGTGCATGGCTTTCAGAAAAAGAAGATGCAGTGAACAAGATTCACACAACTGGC |
| TTTAA |
| AGATCAAAATGAAATGTTATCAAGTCTTCAAAAACTGGCCGTTTTAAAAGCGGAT |
| CTAGA |
| AAAGAAAAAGCAATCCATGGGCAAACTGTATTCACTCAAACAAGATCTTCTTTCA |
| ACACT |
| GAAGAATAAGTCAGTGACCCAGAAGACGGAAGCATGGCTGGATAACTTTGCCCG |
| GTGTTG |
| GGATAATTTAGTCCAAAAACTTGAAAAGAGTACAGCACAGATTTCACAGGCTGTC |
| ACCAC |
| CACTCAGCCATCACTAACACAGACAACTGTAATGGAAACAGTAACTACGGTGACC |
| ACAAG |
| GGAACAGATCCTGGTAAAGCATGCTCAAGAGGAACTTCCACCACCACCTCCCCAA |
| AAGAA |
| GAGGCAGATTACTGTGGATTCTGAAATTAGGAAAAGGTTGGATGTTGATATAACT |
| GAACT |
| TCACAGCTGGATTACTCGCTCAGAAGCTGTGTTGCAGAGTCCTGAATTTGCAATCT |
| TTCG |
| GAAGGAAGGCAACTTCTCAGACTTAAAAGAAAAAGTCAATGCCATAGAGCGAGAAAAAGC |
| TGAGAAGTTCAGAAAACTGCAAGATGCCAGCAGATCAGCTCAGGCCCTGGTGGAA |
| CAGAT |
| GGTGAATGAGGGTGTTAATGCAGATAGCATCAAACAAGCCTCAGAACAACTGAAC |
| AGCCG |
| GTGGATCGAATTCTGCCAGTTGCTAAGTGAGAGACTTAACTGGCTGGAGTATCAG |
| AACAA |
| CATCATCGCTTTCTATAATCAGCTACAACAATTGGAGCAGATGACAACTACTGCTG |
| AAAA |
| CTGGTTGAAAATCCAACCCACCACCCCATCAGAGCCAACAGCAATTAAAAGTCAG |
| TTAAA |
| AATTTGTAAGGATGAAGTCAACCGGCTATCAGGTCTTCAACCTCAAATTGAACGA |
| TTAAA |
| AATTCAAAGCATAGCCCTGAAAGAGAAAGGACAAGGACCCATGTTCCTGGATGCA |
| GACTT |
| TGTGGCCTTTACAAATCATTTTAAGCAAGTCTTTTCTGATGTGCAGGCCAGAGAGAAAGA |
| GCTACAGACAATTTTTGACACTTTGCCACCAATGCGCTATCAGGAGACCATGAGT |
| GCCAT |
| CAGGACATGGGTCCAGCAGTCAGAAACCAAACTCTCCATACCTCAACTTAGTGTC |
| ACCGA |
| CTATGAAATCATGGAGCAGAGACTCGGGGAATTGCAGGCTTTACAAAGTTCTCTG |

TABLE 2-continued

| Nucleotide sequence of full-length Dystrophin Protein (isoform Dp427m). |
|---|
| CAAGA |
| GCAACAAAGTGGCCTATACTATCTCAGCACCACTGTGAAAGAGATGTCGAAGAAA |
| GCGCC |
| CTCTGAAATTAGCCGGAAATATCAATCAGAATTTGAAGAAATTGAGGGACGCTGG |
| AAGAA |
| GCTCTCCTCCCAGCTGGTTGAGCATTGTCAAAAGCTAGAGGAGCAAATGAATAAA |
| CTCCG |
| AAAAATTCAGAATCACATACAAACCCTGAAGAAATGGATGGCTGAAGTTGATGTT |
| TTTCT |
| GAAGGAGGAATGGCCTGCCCTTGGGGATTCAGAAATTCTAAAAAAGCAGCTGAA |
| ACAGTG |
| CAGACTTTTAGTCAGTGATATTCAGACAATTCAGCCCAGTCTAAACAGTGTCAATGAAGG |
| TGGGCAGAAGATAAAGAATGAAGCAGAGCCAGAGTTTGCTTCGAGACTTGAGAC |
| AGAACT |
| CAAAGAACTTAACACTCAGTGGGATCACATGTGCCAACAGGTCTATGCCAGAAAG |
| GAGGC |
| CTTGAAGGGAGGTTTGGAGAAAACTGTAAGCCTCCAGAAAGATCTATCAGAGATG |
| CACGA |
| ATGGATGACACAAGCTGAAGAAGAGTATCTTGAGAGAGATTTTGAATATAAAACT |
| CCAGA |
| TGAATTACAGAAAGCAGTTGAAGAGATGAAGAGAGCTAAAGAAGAGGCCCAACA |
| AAAAGA |
| AGCGAAAGTGAAACTCCTTACTGAGTCTGTAAATAGTGTCATAGCTCAAGCTCCA |
| CCTGT |
| AGCACAAGAGGCCTTAAAAAAGGAACTTGAAACTCTAACCACCAACTACCAGTGG |
| CTCTG |
| CACTAGGCTGAATGGGAAATGCAAGACTTTGGAAGAAGTTTGGGCATGTTGGCAT |
| GAGTT |
| ATTGTCATACTTGGAGAAAGCAAACAAGTGGCTAAATGAAGTAGAATTTAAACTT |
| AAAAC |
| CACTGAAAACATTCCTGGCGGAGCTGAGGAAATCTCTGAGGTGCTAGATTCACTT |
| GAAAA |
| TTTGATGCGACATTCAGAGGATAACCCAAATCAGATTCGCATATTGGCACAGACC |
| CTAAC |
| AGATGGCGGAGTCATGGATGAGCTAATCAATGAGGAACTTGAGACATTTAATTCT |
| CGTTG |
| GAGGGAACTACATGAAGAGGCTGTAAGGAGGCAAAAGTTGCTTGAACAGAGCAT |
| CCAGTC |

TABLE 2-continued

| Nucleotide sequence of full-length Dystrophin Protein (isoform Dp427m). |
|---|
| TGCCCAGGAGACTGAAAAATCCTTACACTTAATCCAGGAGTCCCTCACATTCATTGACAA |
| GCAGTTGGCAGCTTATATTGCAGACAAGGTGGACGCAGCTCAAATGCCTCAGGAA |
| GCCCA |
| GAAAATCCAATCTGATTTGACAAGTCATGAGATCAGTTTAGAAGAAATGAAGAAA |
| CATAA |
| TCAGGGGAAGGAGGCTGCCCAAAGAGTCCTGTCTCAGATTGATGTTGCACAGAAA |
| AAATT |
| ACAAGATGTCTCCATGAAGTTTCGATTATTCCAGAAACCAGCCAATTTTGAGCTGCGTCT |
| ACAAGAAAGTAAGATGATTTTAGATGAAGTGAAGATGCACTTGCCTGCATTGGAA |
| ACAAA |
| GAGTGTGGAACAGGAAGTAGTACAGTCACAGCTAAATCATTGTGTGAACTTGTAT |
| AAAAG |
| TCTGAGTGAAGTGAAGTCTGAAGTGGAAATGGTGATAAAGACTGGACGTCAGATT |
| GTACA |
| GAAAAAGCAGACGGAAAATCCCAAAGAACTTGATGAAAGAGTAACAGCTTTGAA |
| ATTGCA |
| TTATAATGAGCTGGGAGCAAAGGTAACAGAAAGAAAGCAACAGTTGGAGAAATG |
| CTTGAA |
| ATTGTCCCGTAAGATGCGAAAGGAAATGAATGTCTTGACAGAATGGCTGGCAGCT |
| ACAGA |
| TATGGAATTGACAAAGAGATCAGCAGTTGAAGGAATGCCTAGTAATTTGGATTCT |
| GAAGT |
| TGCCTGGGGAAAGGCTACTCAAAAAGAGATTGAGAAACAGAAGGTGCACCTGAA |
| GAGTAT |
| CACAGAGGTAGGAGAGGCCTTGAAAACAGTTTTGGGCAAGAAGGAGACGTTGGT |
| GGAAGA |
| TAAACTCAGTCTTCTGAATAGTAACTGGATAGCTGTCACCTCCCGAGCAGAAGAG |
| TGGTT |
| AAATCTTTTGTTGGAATACCAGAAACACATGGAAACTTTTGACCAGAATGTGGAC |
| CACAT |
| CACAAAGTGGATCATTCAGGCTGACACACTTTTGGATGAATCAGAGAAAAAGAAA |
| CCCCA |
| GCAAAAAGAAGACGTGCTTAAGCGTTTAAAGGCAGAACTGAATGACATACGCCC |
| AAAGGT |
| GGACTCTACACGTGACCAAGCAGCAAACTTGATGGCAAACCGCGGTGACCACTGC |
| AGGAA |
| ATTAGTAGAGCCCCAAATCTCAGAGCTCAACCATCGATTTGCAGCCATTTCACACAGAAT |
| TAAGACTGGAAAGGCCTCCATTCCTTTGAAGGAATTGGAGCAGTTTAACTCAGAT |
| ATACA |

TABLE 2-continued

| Nucleotide sequence of full-length Dystrophin Protein (isoform Dp427m). |
|---|

AAAATTGCTTGAACCACTGGAGGCTGAAATTCAGCAGGGGGTGAATCTGAAAGAG

GAAGA

CTTCAATAAAGATATGAATGAAGACAATGAGGGTACTGTAAAAGAATTGTTGCAA

AGAGG

AGACAACTTACAACAAAGAATCACAGATGAGAGAAAGAGAGAGGAAATAAAGAT

AAAACA

GCAGCTGTTACAGACAAAACATAATGCTCTCAAGGATTTGAGGTCTCAAAGAAGA

AAAAA

GGCTCTAGAAATTTCTCATCAGTGGTATCAGTACAAGAGGCAGGCTGATGATCTC

CTGAA

ATGCTTGGATGACATTGAAAAAAAATTAGCCAGCCTACCTGAGCCCAGAGATGAA

AGGAA

AATAAAGGAAATTGATCGGGAATTGCAGAAGAAGAAAGAGGAGCTGAATGCAGT

GCGTAG

GCAAGCTGAGGGCTTGTCTGAGGATGGGGCCGCAATGGCAGTGGAGCCAACTCAG

ATCCA

GCTCAGCAAGCGCTGGCGGGAAATTGAGAGCAAATTTGCTCAGTTTCGAAGACTC

AACTT

TGCACAAATTCACACTGTCCGTGAAGAAACGATGATGGTGATGACTGAAGACATG

CCTTT

GGAAATTTCTTATGTGCCTTCTACTTATTTGACTGAAATCACTCATGTCTCACAAGCCCT

ATTAGAAGTGGAACAACTTCTCAATGCTCCTGACCTCTGTGCTAAGGACTTTGAAG

ATCT

CTTTAAGCAAGAGGAGTCTCTGAAGAATATAAAAGATAGTCTACAACAAAGCTCA

GGTCG

GATTGACATTATTCATAGCAAGAAGACAGCAGCATTGCAAAGTGCAACGCCTGTG

GAAAG

GGTGAAGCTACAGGAAGCTCTCTCCCAGCTTGATTTCCAATGGGAAAAAGTTAAC

AAAAT

GTACAAGGACCGACAAGGGCGATTTGACAGATCTGTTGAGAAATGGCGGCGTTTT

CATTA

TGATATAAAGATATTTAATCAGTGGCTAACAGAAGCTGAACAGTTTCTCAGAAAG

ACACA

AATTCCTGAGAATTGGGAACATGCTAAATACAAATGGTATCTTAAGGAACTCCAG

GATGG

CATTGGGCAGCGGCAAACTGTTGTCAGAACATTGAATGCAACTGGGGAAGAAATA

ATTCA

GCAATCCTCAAAAACAGATGCCAGTATTCTACAGGAAAAATTGGGAAGCCTGAAT

TABLE 2-continued

| Nucleotide sequence of full-length Dystrophin Protein (isoform Dp427m). |
|---|
| CTGCG |
| GTGGCAGGAGGTCTGCAAACAGCTGTCAGACAGAAAAAAGAGGCTAGAAGAACA |
| AAAGAA |
| TATCTTGTCAGAATTTCAAAGAGATTTAAATGAATTTGTTTTATGGTTGGAGGAAGCAGA |
| TAACATTGCTAGTATCCCACTTGAACCTGGAAAAGAGCAGCAACTAAAAGAAAAG |
| CTTGA |
| GCAAGTCAAGTTACTGGTGGAAGAGTTGCCCCTGCGCCAGGGAATTCTCAAACAA |
| TTAAA |
| TGAAACTGGAGGACCCGTGCTTGTAAGTGCTCCCATAAGCCCAGAAGAGCAAGAT |
| AAACT |
| TGAAAATAAGCTCAAGCAGACAAATCTCCAGTGGATAAAGGTTTCCAGAGCTTTA |
| CCTGA |
| GAAACAAGGAGAAATTGAAGCTCAAATAAAAGACCTTGGGCAGCTTGAAAAAAA |
| GCTTGA |
| AGACCTTGAAGAGCAGTTAAATCATCTGCTGCTGTGGTTATCTCCTATTAGGAATC |
| AGTT |
| GGAAATTTATAACCAACCAAACCAAGAAGGACCATTTGACGTTCAGGAAACTGAA |
| ATAGC |
| AGTTCAAGCTAAACAACCGGATGTGGAAGAGATTTTGTCTAAAGGGCAGCATTTG |
| TACAA |
| GGAAAAACCAGCCACTCAGCCAGTGAAGAGGAAGTTAGAAGATCTGAGCTCTGA |
| GTGGAA |
| GGCGGTAAACCGTTTACTTCAAGAGCTGAGGGCAAAGCAGCCTGACCTAGCTCCT |
| GGACT |
| GACCACTATTGGAGCCTCTCCTACTCAGACTGTTACTCTGGTGACACAACCTGTGG |
| TTAC |
| TAAGGAAACTGCCATCTCCAAACTAGAAATGCCATCTTCCTTGATGTTGGAGGTAC |
| CTGC |
| TCTGGCAGATTTCAACCGGGCTTGGACAGAACTTACCGACTGGCTTTCTCTGCTTGATCA |
| AGTTATAAAATCACAGAGGGTGATGGTGGGTGACCTTGAGGATATCAACGAGATG |
| ATCAT |
| CAAGCAGAAGGCAACAATGCAGGATTTGGAACAGAGGCGTCCCCAGTTGGAAGA |
| ACTCAT |
| TACCGCTGCCCAAAATTTGAAAAACAAGACCAGCAATCAAGAGGCTAGAACAATC |
| ATTAC |
| GGATCGAATTGAAAGAATTCAGAATCAGTGGGATGAAGTACAAGAACACCTTCAG |
| AACCG |
| GAGGCAACAGTTGAATGAAATGTTAAAGGATTCAACACAATGGCTGGAAGCTAA |
| GGAAGA |

TABLE 2-continued

| Nucleotide sequence of full-length Dystrophin Protein (isoform Dp427m). |
|---|
| AGCTGAGCAGGTCTTAGGACAGGCCAGAGCCAAGCTTGAGTCATGGAAGGAGGG |
| TCCCTA |
| TACAGTAGATGCAATCCAAAAGAAAATCACAGAAACCAAGCAGTTGGCCAAAGA |
| CCTCCG |
| CCAGTGGCAGACAAATGTAGATGTGGCAAATGACTTGGCCCTGAAACTTCTCCGG |
| GATTA |
| TTCTGCAGATGATACCAGAAAAGTCCACATGATAACAGAGAATATCAATGCCTCT |
| TGGAG |
| AAGCATTCATAAAAGGGTGAGTGAGCGAGAGGCTGCTTTGGAAGAAACTCATAG |
| ATTACT |
| GCAACAGTTCCCCCTGGACCTGGAAAAGTTTCTTGCCTGGCTTACAGAAGCTGAA |
| ACAAC |
| TGCCAATGTCCTACAGGATGCTACCCGTAAGGAAAGGCTCCTAGAAGACTCCAAG |
| GGAGT |
| AAAAGAGCTGATGAAACAATGGCAAGACCTCCAAGGTGAAATTGAAGCTCACAC |
| AGATGT |
| TTATCACAACCTGGATGAAAACAGCCAAAAAATCCTGAGATCCCTGGAAGGTTCC |
| GATGA |
| TGCAGTCCTGTTACAAAGACGTTTGGATAACATGAACTTCAAGTGGAGTGAACTT |
| CGGAA |
| AAAGTCTCTCAACATTAGGTCCCATTTGGAAGCCAGTTCTGACCAGTGGAAGCGT |
| CTGCA |
| CCTTTCTCTGCAGGAACTTCTGGTGTGGCTACAGCTGAAAGATGATGAATTAAGCC |
| GGCA |
| GGCACCTATTGGAGGCGACTTTCCAGCAGTTCAGAAGCAGAACGATGTACATAGG |
| GCCTT |
| CAAGAGGGAATTGAAAACTAAAGAACCTGTAATCATGAGTACTCTTGAGACTGTA |
| CGAAT |
| ATTTCTGACAGAGCAGCCTTTGGAAGGACTAGAGAAACTCTACCAGGAGCCCAGA |
| GAGCT |
| GCCTCCTGAGGAGAGAGCCCAGAATGTCACTCGGCTTCTACGAAAGCAGGCTGAG |
| GAGGT |
| CAATACTGAGTGGGAAAAATTGAACCTGCACTCCGCTGACTGGCAGAGAAAAATA |
| GATGA |
| GACCCTTGAAAGACTCCAGGAACTTCAAGAGGCCACGGATGAGCTGGACCTCAAG |
| CTGCG |
| CCAAGCTGAGGTGATCAAGGGATCCTGGCAGCCCGTGGGCGATCTCCTCATTGAC |
| TCTCT |

TABLE 2-continued

| Nucleotide sequence of full-length Dystrophin Protein (isoform Dp427m). |
|---|
| CCAAGATCACCTCGAGAAAGTCAAGGCACTTCGAGGAGAAATTGCGCCTCTGAAA |
| GAGAA |
| CGTGAGCCACGTCAATGACCTTGCTCGCCAGCTTACCACTTTGGGCATTCAGCTCTCACC |
| GTATAACCTCAGCACTCTGGAAGACCTGAACACCAGATGGAAGCTTCTGCAGGTG |
| GCCGT |
| CGAGGACCGAGTCAGGCAGCTGCATGAAGCCCACAGGGACTTTGGTCCAGCATCT |
| CAGCA |
| CTTTCTTTCCACGTCTGTCCAGGGTCCCTGGGAGAGAGCCATCTCGCCAAACAAAG |
| TGCC |
| CTACTATATCAACCACGAGACTCAAACAACTTGCTGGGACCATCCCAAAATGACA |
| GAGCT |
| CTACCAGTCTTTAGCTGACCTGAATAATGTCAGATTCTCAGCTTATAGGACTGCCA |
| TGAA |
| ACTCCGAAGACTGCAGAAGGCCCTTTGCTTGGATCTCTTGAGCCTGTCAGCTGCAT |
| GTGA |
| TGCCTTGGACCAGCACAACCTCAAGCAAAATGACCAGCCCATGGATATCCTGCAG |
| ATTAT |
| TAATTGTTTGACCACTATTTATGACCGCCTGGAGCAAGAGCACAACAATTTGGTCA |
| ACGT |
| CCCTCTCTGCGTGGATATGTGTCTGAACTGGCTGCTGAATGTTTATGATACGGGAC |
| GAAC |
| AGGGAGGATCCGTGTCCTGTCTTTTAAAACTGGCATCATTTCCCTGTGTAAAGCAC |
| ATTT |
| GGAAGACAAGTACAGATACCTTTTCAAGCAAGTGGCAAGTTCAACAGGATTTTGT |
| GACCA |
| GCGCAGGCTGGGCCTCCTTCTGCATGATTCTATCCAAATTCCAAGACAGTTGGGTG |
| AAGT |
| TGCATCCTTTGGGGGCAGTAACATTGAGCCAAGTGTCCGGAGCTGCTTCCAATTTG |
| CTAA |
| TAATAAGCCAGAGATCGAAGCGGCCCTCTTCCTAGACTGGATGAGACTGGAACCC |
| CAGTC |
| CATGGTGTGGCTGCCCGTCCTGCACAGAGTGGCTGCTGCAGAAACTGCCAAGCAT |
| CAGGC |
| CAAATGTAACATCTGCAAAGAGTGTCCAATCATTGGATTCAGGTACAGGAGTCTA |
| AAGCA |
| CTTTAATTATGACATCTGCCAAAGCTGCTTTTTTTCTGGTCGAGTTGCAAAAGGCCATAA |
| AATGCACTATCCCATGGTGGAATATTGCACTCCGACTACATCAGGAGAAGATGTT |
| CGAGA |
| CTTTGCCAAGGTACTAAAAAACAAATTTCGAACCAAAAGGTATTTTGCGAAGCAT |

TABLE 2-continued

Nucleotide sequence of full-length Dystrophin Protein (isoform Dp427m).

CCCCG

AATGGGCTACCTGCCAGTGCAGACTGTCTTAGAGGGGGACAACATGGAAACTCCC

GTTAC

TCTGATCAACTTCTGGCCAGTAGATTCTGCGCCTGCCTCGTCCCCTCAGCTTTCAC

ACGA

TGATACTCATTCACGCATTGAACATTATGCTAGCAGGCTAGCAGAAATGGAAAAC

AGCAA

TGGATCTTATCTAAATGATAGCATCTCTCCTAATGAGAGCATAGATGATGAACATT

TGTT

AATCCAGCATTACTGCCAAAGTTTGAACCAGGACTCCCCCCTGAGCCAGCCTCGT

AGTCC

TGCCCAGATCTTGATTTCCTTAGAGAGTGAGGAAAGAGGGGAGCTAGAGAGAATC

CTAGC

AGATCTTGAGGAAGAAAACAGGAATCTGCAAGCAGAATATGACCGTCTAAAGCA

GCAGCA

CGAACATAAAGGCCTGTCCCCACTGCCGTCCCCTCCTGAAATGATGCCCACCTCTC

CCCA

GAGTCCCCGGGATGCTGAGCTCATTGCTGAGGCCAAGCTACTGCGTCAACACAAA

GGCCG

CCTGGAAGCCAGGATGCAAATCCTGGAAGACCACAATAAACAGCTGGAGTCACA

GTTACA

CAGGCTAAGGCAGCTGCTGGAGCAACCCCAGGCAGAGGCCAAAGTGAATGGCACAACGGT

GTCCTCTCCTTCTACCTCTCTACAGAGGTCCGACAGCAGTCAGCCTATGCTGCTCCGAGT

GGTTGGCAGTCAAACTTCGGACTCCATGGGTGAGGAAGATCTTCTCAGTCCTCCCC

AGGA

CACAAGCACAGGGTTAGAGGAGGTGATGGAGCAACTCAACAACTCCTTCCCTAGT

TCAAG

AGGAAGAAATACCCCTGGAAAGCCAATGAGAGAGGACACAATGTAGGAAGTCTT

TTCCAC

ATGGCAGATGATTTGGGCAGAGCGATGGAGTCCTTAGTATCAGTCATGACAGATG

AAGAA

GGAGCAGAATAAATGTTTTACAACTCCTGATTCCCGCATGGTTTTTATAATATTCA

TACA

ACAAAGAGGATTAGACAGTAAGAGTTTACAAGAAATAAATCTATATTTTTGTGAA

GGGTA

GTGGTATTATACTGTAGATTTCAGTAGTTTCTAAGTCTGTTATTGTTTTGTTAACAA

TGG

CAGGTTTTACACGTCTATGCAATTGTACAAAAAAGTTATAAGAAAACTACATGTA

TABLE 2-continued

| Nucleotide sequence of full-length Dystrophin Protein (isoform Dp427m). |
|---|
| AAATC |
| TTGATAGCTAAATAACTTGCCATTTCTTTATATGGAACGCATTTTGGGTTGTTTAA |
| AAAT |
| TTATAACAGTTATAAAGAAAGATTGTAAACTAAAGTGTGCTTTATAAAAAAAAGT |
| TGTTT |
| ATAAAAACCCCTAAAAACAAAACAAACACACACACACACACATACACACACACA |
| CACAAA |
| ACTTTGAGGCAGCGCATTGTTTTGCATCCTTTTGGCGTGATATCCATATGAAATTC |
| ATGG |
| CTTTTTCTTTTTTTGCATATTAAAGATAAGACTTCCTCTACCACCACACCAAATGACTAC |
| TACACACTGCTCATTTGAGAACTGTCAGCTGAGTGGGGCAGGCTTGAGTTTTCATT |
| TCAT |
| ATATCTATATGTCTATAAGTATATAAATACTATAGTTATATAGATAAAGAGATACG |
| AATT |
| TCTATAGACTGACTTTTTCCATTTTTTAAATGTTCATGTCACATCCTAATAGAAAGA |
| AAT |
| TACTTCTAGTCAGTCATCCAGGCTTACCTGCTTGGTCTAGAATGGATTTTTCCCGG |
| AGCC |
| GGAAGCCAGGAGGAAACTACACCACACTAAAACATTGTCTACAGCTCCAGATGTT |
| TCTCA |
| TTTTAAACAACTTTCCACTGACAACGAAAGTAAAGTAAAGTATTGGATTTTTTTAA |
| AGGG |
| AACATGTGAATGAATACACAGGACTTATTATATCAGAGTGAGTAATCGGTTGGTT |
| GGTTG |
| ATTGATTGATTGATTGATACATTCAGCTTCCTGCTGCTAGCAATGCCACGATTTAGATTT |
| AATGATGCTTCAGTGGAAATCAATCAGAAGGTATTCTGACCTTGTGAACATCAGA |
| AGGTA |
| TTTTTTAACTCCCAAGCAGTAGCAGGACGATGATAGGGCTGGAGGGCTATGGATT |
| CCCAG |
| CCCATCCCTGTGAAGGAGTAGGCCACTCTTTAAGTGAAGGATTGGATGATTGTTCA |
| TAAT |
| ACATAAAGTTCTCTGTAATTACAACTAAATTATTATGCCCTCTTCTCACAGTCAAA |
| AGGA |
| ACTGGGTGGTTTGGTTTTTGTTGCTTTTTTAGATTTATTGTCCCATGTGGGATGAGTTTT |
| TAAATGCCACAAGACATAATTTAAAATAAATAAACTTTGGGAAAAGGTGTAAGAC |
| AGTAG |
| CCCCATCACATTTGTGATACTGACAGGTATCAACCCAGAAGCCCATGAACTGTGTT |
| TCCA |
| TCCTTTGCATTTCTCTGCGAGTAGTTCCACACAGGTTTGTAAGTAAGTAAGAAAGA |

TABLE 2-continued

| Nucleotide sequence of full-length Dystrophin Protein (isoform Dp427m). |
|---|
| AGGC |
| AAATTGATTCAAATGTTACAAAAAAACCCTTCTTGGTGGATTAGACAGGTTAAAT |
| ATATAAACAAACAAACAAAAATTGCTCAAAAAAGAGGAGAAAAGCTCAAGAGGAAAAGCTAAGGA |
| CTGGTAGGAAAAAGCTTTACTCTTTCATGCCATTTTATTTCTTTTTGATTTTTAAAT |
| CAT |
| TCATTCAATAGATACCACCGTGTGACCTATAATTTTGCAAATCTGTTACCTCTGAC |
| ATCA |
| AGTGTAATTAGCTTTTGGAGAGTGGGCTGACATCAAGTGTAATTAGCTTTTGGAGA |
| GTGG |
| GTTTTGTCCATTATTAATAATTAATTAATTAACATCAAACACGGCTTCTCATGCTAT |
| TTC |
| TACCTCACTTTGGTTTTGGGGTGTTCCTGATAATTGTGCACACCTGAGTTCACAGC |
| TTCA |
| CCACTTGTCCATTGCGTTATTTTCTTTTTCCTTTATAATTCTTTCTTTTTCCTTCATA |
| AT |
| TTTCAAAAGAAAACCCAAAGCTCTAAGGTAACAAATTACCAAATTACATGAAGAT |
| TTGGT |
| TTTTGTCTTGCATTTTTTTCCTTTATGTGACGCTGGACCTTTTCTTTACCCAAGGATTTT |
| TAAAACTCAGATTTAAAACAAGGGGTTACTTTACATCCTACTAAGAAGTTTAAGT |
| AAGTA |
| AGTTTCATTCTAAAATCAGAGGTAAATAGAGTGCATAAATAATTTTGTTTTAATCT |
| TTTT |
| GTTTTTCTTTTAGACACATTAGCTCTGGAGTGAGTCTGTCATAATATTTGAACAAA |
| AATT |
| GAGAGCTTTATTGCTGCATTTTAAGCATAATTAATTTGGACATTATTTCGTGTTGTG |
| TTC |
| TTTATAACCACCGAGTATTAAACTGTAAATCATAATGTAACTGAAGCATAAACATCACAT |
| GGCATGTTTTGTCATTGTTTTCAGGTACTGAGTTCTTACTTGAGTATCATAATATAT |
| TGT |
| GTTTTAACACCAACACTGTAACATTTACGAATTATTTTTTTAAACTTCAGTTTTACTGCA |
| TTTTCACAACATATCAGACTTCACCAAATATATGCCTTACTATTGTATTATAGTACTGCT |
| TTACTGTGTATCTCAATAAAGCACGCAGTTATGTTAC |

The wild type, full length dystrophin protein (isoform Dp427m) contains 24 spectrin like repeats, at least four hinge regions, actin binding domain (ABD1), Cysteine rich domain (CR), and C terminal Domain (C-term.). The polypeptide sequence of each domain is shown in Table 3, and the nucleotide sequence of each domain is shown in Table 4.

TABLE 3

Amino Acid Sequences of Dystrophin Domains

| Description and Sequence Identifier | Sequence |
|---|---|
| ABD1 (SEQ ID NO: 3) | MLWWEEVEDCYEREDVQKKTFTKWVNAQFSKFGKQHIENLFSDLQDG RRLLDLLEGLTGQKLPKEKGSTR VHALNNVNKALRVLQNNNVDLVNIGSTDIVDGNHKLTLGLIWNIILHW QVKNVMKNIMAGLQQTNSEKIL LSWVRQSTRNYPQVNVINFTTSWSDGLALNALIHSHRPDLFDWNSVVC QQSATQRLEHAFNIARYQLGIE KLLDPEDVDTTYPDKKSILMYITSLFQVLPQQVSIEAIQEVE |
| Hinge 1 (SEQ ID NO: 4) | MLPRPPKVTKEEHFQLHHQMHYSQQITVSLAQGYERTSSPKPRFKSYAY TQAAYVTTSDPTRSPFPSQHL EAPEDKSFGSSLMES |
| Spectrin repeat 1 (SEQ ID NO: 5) | EVNLDRYQTALEEVLSWLLSAEDTLQAQGEISNDVEVVKDQFHTHEGY MMDLTAHQGRVGNILQLGSKLI GTGKLSEDEETEVQEQMNLLNSRWECLRVASMEKQSNLH |
| Spectrin repeat 2 (SEQ ID NO: 6) | RVLMDLQNQKLKELNDWLTKTEERTRKMEEEPLGPDLEDLKRQVQQH KVLQEDLEQEQVRVNSLTHMVVV VDESSGDHATAALEEQLKVLGDRWANICRWTEDRWVLLQDI |
| Spectrin repeat 3 (SEQ ID NO: 7) | LLKWQRLTEEQCLFSAWLSEKEDAVNKIHTTGFKDQNEMLSSLQKLAV LKADLEKKKQSMGKLYSLKQDL LSTLKNKSVTQKTEAWLDNFARCWDNLVQKLEKSTAQISQA |
| Hinge 2 (SEQ ID NO: 8) | VTTTQPSLTQTTVMETVTTVTTREQILVKHAQEELPPPPPQKKRQITVD |
| Spectrin repeat 4 (SEQ ID NO: 9) | SEIRKRLDVDITELHSWITRSEAVLQSPEFAIFRKEGNFSDLKEKVNAIER EKAEKFRKLQDASRSAQAL VEQMVNEGVNADSIKQASEQLNSRWIEFCQLLSERLNWLEY |
| Spectrin repeat 5 (SEQ ID NO: 10) | QNNIIAFYNQLQQLEQMTTTAENWLKIQPTTPSEPTAIKSQLKICKDEVN RLSGLQPQIERLKIQSIALK EKGQGPMFLDADFVAFTNHFKQVFSDVQAREKELQTIFD |
| Spectrin repeat 6 (SEQ ID NO: 11) | TLPPMRYQETMSAIRTWVQQSETKLSIPQLSVTDYEIMEQRLGELQALQ SSLQEQQSGLYYLSTTVKEMS KKAPSEISRKYQSEFEEIEGRWKKLSSQLVEHCQKLEEQ |
| Spectrin repeat 7 (SEQ ID NO: 12) | MNKLRKIQNHIQTLKKWMAEVDVFLKEEWPALGDSEILKKQLKQCRLL VSDIQTIQPSLNSVNEGGQKIK NEAEPEFASRLETELKELNTQWDHMCQQVYARKEALKGG |
| Spectrin repeat 8 (SEQ ID NO: 13) | LEKTVSLQKDLSEMHEWMTQAEEEYLERDFEYKTPDELQKAVEEMKR AKEEAQQKEAKVKLLTESVNSVI AQAPPVAQEALKKELETLTTNYQWLCTRLNGKCKTLEEV |
| Spectrin repeat 9 (SEQ ID NO: 14) | WACWHELLSYLEKANKWLNEVEFKLKTTENIPGGAEEISEVLDSLENL MRHSEDNPNQIRILAQTLTDGG VMDELINEELETFNSRWRELHEEAVRRQKLLEQS |
| Spectrin repeat 10 (SEQ ID NO: 15) | IQSAQETEKSLHLIQESLTFIDKQLAAYIADKVDAAQMPQEAQKIQSDLT SHEISLEEMKKHNQGKEAAQ RVLSQIDVAQKKLQDVSMKFRL |
| Spectrin repeat 11 (SEQ ID NO: 16) | FQKPANFEQRLQESKMILDEVKMHLPALETKSVEQEVVQSQLNHCVNL YKSLSEVKSEVEMVIKTGRQIV QKKQTENPKELDERVTALKLHYNELGAKVTERKQQLEKC |
| Spectrin repeat 12 (SEQ ID NO: 17) | LKLSRKMRKEMNVLTEWLAATDMELTKRSAVEGMPSNLDSEVAWGK ATQKEIEKQKVHLKSITEVGEALK TVLGKKETLVEDKLSLLNSNWIAVTSRAEEWLNLLLEY |
| Spectrin repeat 13 (SEQ ID NO: 18) | QKHMETFDQNVDHITKWITQADTLLDESEKKKPQQKEDVLKRLKAELN DIRPKVDSTRDQAANLMANRGD HCRKLVEPQISELNHRFAAISHRIKTGKASIPLK |
| Spectrin repeat 14 | ELEQFNSDIQKLLEPLEAEIQQGVNLKEEDFNKDMNEDNEGTVKELLQR GDNLQQRITDERKREEIKIKQ |

TABLE 3-continued

| Amino Acid Sequences of Dystrophin Domains | |
|---|---|
| Description and Sequence Identifier | Sequence |
| (SEQ ID NO: 19) | QLLQTKHNALKDLRSQRRKKALEI |
| Spectrin repeat 15 (SEQ ID NO: 20) | SHQWYQYKRQADDLLKCLDDIEKKLASLPEPRDERKIKEIDRELQKKKE ELNAVRRQAEGLSEDGAAMAV EPTQIQLSKRWREIESKFAQFRRLNFAQ |
| L3 20-mer linker) (SEQ ID NO: 21) | IHTVREETMMVMTEDMPLEI |
| Spectrin repeat 16 (SEQ ID NO: 22) | SYVPSTYLTEITHVSQALLEVEQLLNAPDLCAKDFEDLFKQEESLKNIKD SLQQSSGRIDIIHSKKTAAL QSATPVERVKLQEALSQLDFQWEKVNKMYKDRQGRFDRS |
| Spectrin repeat 17 (SEQ ID NO: 23) | VEKWRRFHYDIKIFNQWLTEAEQFLRKTQIPENWEHAKYKWYLKELQ DGIGQRQTVVRTLNATGEEIIQQ SSKTDASILQEKLGSLNLRWQEVCKQLSDRKKRLEEQ |
| Spectrin repeat 18 (SEQ ID NO: 24) | KNILSEFQRDLNEFVLWLEEADNIASIPLEPGKEQQLKEKLEQVKLLVEE LPLRQGILKQLNETGGPVLV SAPISPEEQDKLENKLKQTNLQWIKVSRALPEKQGEIEAQIKDLGQL |
| Spectrin repeat 19 (SEQ ID NO: 25) | EKKLEDLEEQLNHLLLWLSPIRNQLEIYNQPNQEGPFDVQETEIAVQAK QPDVEEILSKGQHLYKEKPAT QPVKRKLEDLSSEWKAVNRLLQELRAKQPDL |
| Hinge 3 (SEQ ID NO: 26) | APGLTTIGASPTQTVTLVTQPVVTKETAISKLEMPSSLMLE |
| Spectrin repeat 20 (SEQ ID NO: 27) | VPALADFNRAWTELTDWLSLLDQVIKSQRVMVGDLEDINEMIIKQKAT MQDLEQRRPQLEELITAAQNLK NKTSNQEARTIITDRIERIQNQWDEVQEHLQNRRQQLNEM |
| Spectrin repeat 21 (SEQ ID NO: 28) | LKDSTQWLEAKEEAEQVLGQARAKLESWKEGPYTVDAIQKKITETKQL AKDLRQWQTNVDVANDLALKLL RDYSADDTRKVHMITENINASWRSIHKRVSEREAALEET |
| Spectrin repeat 22 (SEQ ID NO: 29) | HRLLQQFPLDLEKFLAWLTEAETTANVLQDATRKERLLEDSKGVKELM KQWQDLQGEIEAHTDVYHNLDE NSQKILRSLEGSDDAVLLQRRLDNMNFKWSELRKKSLNIRSHLEAS |
| Spectrin repeat 23 (SEQ ID NO: 30) | SDQWKRLHLSLQELLVWLQLKDDELSRQAPIGGDFPAVQKQNDVHRA FKRELKTKEPVIMSTLETVRIFL TEQPLEGLEKLYQEPRELPPEERAQNVTRLLRKQAEEVNTEWEKLNLHS ADWQRKIDET |
| Spectrin repeat 24 (SEQ ID NO: 31) | LERLQELQEATDELDLKLRQAEVIKGSWQPVGDLLIDSLQDHLEKVKA LRGEIAPLKENVSHVNDLARQL TTLGIQLSPYNLSTLEDLNTRWKLLQVAVEDRVRQLHE |
| Hinge 4 (SEQ ID NO: 32) | AHRDFGPASQHFLSTSVQGPWERAISPNKVPYYINHETQTTCWDHPKM TELYQSLADLNNVRFSAYRTAM KL |
| CR (SEQ ID NO: 33) | RRLQKALCLDLLSLSAACDALDQHNLKQNDQPMDILQIINCLTTIYDRL EQEHNNLVNVPLCVDMCLNWL LNVYDTGRTGRIRVLSFKTGIISLCKAHLEDKYRYLFKQVASSTGFCDQ RRLGLLLHDSIQIPRQLGEVA SFGGSNIEPSVRSCFQFANNKPEIEAALFLDWMRLEPQSMVWLPVLHRV AAAETAKHQAKCNICKECPII GFRYRSLKHFNYDICQSCFFSGRVAKGHKMHYPMVEYCTPTTSGEDVR DFAKVLKNKFRTKRYFAKHPRM GYLPVQTVLEGDNMET |

TABLE 3-continued

| Amino Acid Sequences of Dystrophin Domains | |
|---|---|
| Description and Sequence Identifier | Sequence |
| C-term (SEQ ID NO: 34) | PVTLINFWPVDSAPASSPQLSHDDTHSRIEHYASRLAEMENSNGSYLND SISPNESIDDEHLLIQHYCQS LNQDSPLSQPRSPAQILISLESEERGELERILADLEEENRNLQAEYDRLKQ QHEHKGLSPLPSPPEMMPT SPQSPRDAELIAEAKLLRQHKGRLEARMQILEDHNKQLESQLHRLRQLL EQPQAEAKVNGTTVSSPSTSL QRSDSSQPMLLRVVGSQTSDSMGEEDLLSPPQDTSTGLEEVMEQLNNSF PSSRGRNTPGKPMREDTM |

TABLE 4

| Nucleotide Sequences of Dystrophin Domains | |
|---|---|
| Description and Sequence Identifier | Sequence |
| 5' untranslated region (SEQ ID NO: 35) | ggattccct cactttcccc ctacaggact cagatctggg aggcaattac cttcggagaa 60<br>aaacgaatag gaaaaactga agtgttactt tttttaaagc tgctgaagtt tgttggtttc 120<br>tcattgtttt taagcctact ggagcaataa agtttgaaga acttttacca ggtttttttt 180<br>atcgctgcct tgatatacac ttttcaaa 208 |
| ABD1 (SEQ ID NO: 36) | atgctttggt gggaagaagt agaggactgt tatgaaagag aagatgttca aaagaaaaca 60<br>ttcacaaaat gggtaaatgc acaattttct aagtttggga agcagcatat tgagaacctc 120<br>ttcagtgacc tacaggatgg gaggcgcctc ctagacctcc tcgaaggcct gacagggcaa 180<br>aaactgccaa aagaaaaagg atccacaaga gttcatgccc tgaacaatgt caacaaggca 240<br>ctgcgggttt tgcagaacaa taatgttgat ttagtgaata ttggaagtac tgacatcgta 300<br>gatggaaatc ataaactgac tcttggtttg atttggaata taatcctcca ctggcaggtc 360<br>aaaaatgtaa tgaaaaatat catggctgga ttgcaacaaa ccaacagtga aaagattctc 420<br>ctgagctggg tccgacaatc aactcgtaat tatccacagg ttaatgtaat caacttcacc 480<br>accagctggt ctgatggcct ggctttgaat gctctcatcc atagtcatag gccagaccta 540<br>tttgactgga atagtgtggt ttgccagcag tcagccacac aacgactgga acatgcattc 600<br>aacatcgcca gatatcaatt aggcatagag aaactactcg atcctgaaga tgttgatacc 660<br>acctatccag ataagaagtc catcttaatg tacatcacat cactcttcca agttttgcct 720<br>caacaagtga gcattgaagc catccaggaa gtggaa 756 |
| Hinge 1 (SEQ ID NO: 37) | atgttgccaa ggccacctaa agtgactaaa gaagaacatt ttcagttaca tcatcaaatg 60<br>cactattctc aacagatcac ggtcagtcta gcacagggat atgagagaac ttcttcccct 120<br>aagcctcgat tcaagagcta tgcctacaca caggctgctt atgtcaccac ctctgaccct 180<br>acacggagcc catttccttc acagcatttg gaagctcctg aagacaagtc atttggcagt 240<br>tcattgatgg agagt 255 |
| Spectrin repeat 1 (SEQ ID NO: 38) | gaagtaaacc tggaccgtta tcaaacagct ttagaagaag tattatcgtg gcttcttct 60<br>gctgaggaca cattgcaagc acaaggagag atttctaatg atgtggaagt ggtgaaagac 120<br>cagtttcata ctcatgaggg gtacatgatg gatttgacag cccatcaggg ccgggttggt 180<br>aatattctac aattgggaag taagctgatt ggaacaggaa aattatcaga agatgaagaa 240<br>actgaagtac aagagcagat gaatctccta aattcaagat gggaatgcct cagggtagct 300<br>agcatggaaa aacaaagcaa tttacat 327 |
| Spectrin repeat 2 (SEQ ID NO: 39) | agagttttaa tggatctcca gaatcagaaa ctgaaagagt tgaatgactg gctaacaaaa 60<br>acagaagaaa gaacaaggaa aatggaggaa gagcctcttg gacctgatct tgaagaccta 120<br>aaacgccaag tacaacaaca taaggtgctt caagaagatc tagaacaaga acaagtcagg 180<br>gtcaattctc tcactcacat ggtggtggta gttgatgaat ctagtggaga tcacgcaact 240<br>gctgctttgg aagaacaact taaggtattg ggagatcgat gggcaaacat ctgtagatgg 300<br>acagaagacc gctgggttct tttacaagac atc 333 |
| Spectrin repeat 3 (SEQ ID NO: 40) | cttctcaaat ggcaacgtct tactgaagaa cagtgccttt ttagtgcatg gctttcagaa 60<br>aaagaagatg cagtgaacaa gattcacaca actggcttta aagatcaaaa tgaaatgtta 120<br>tcaagtcttc aaaaactggc cgttttaaaa gcggatctag aaaagaaaaa gcaatccatg 180<br>ggcaaactgt attcactcaa acaagatctt ctttcaacac tgaagaataa gtcagtgacc 240<br>cagaagacgg aagcatggct ggataacttt gcccggtgtt gggataattt agtccaaaaa 300<br>cttgaaaaga gtacagcaca gatttcacag gct 333 |
| Hinge 2 (SEQ ID NO: 41) | gtcaccacca ctcagccatc actaacacag acaactgtaa tggaaacagt aactacggtg 60<br>accacaaggg aacagatcct ggtaaagcat gctcaagagg aacttccacc accacctccc 120<br>caaaagaaga ggcagattac tgtggat 147 |
| Spectrin repeat 4 (SEQ ID | tctgaaatta ggaaaaggtt ggatgttgat ataactgaac ttcacagctg gattactcgc 60<br>tcagaagctg tgttgcagag tcctgaattt gcaatctttc ggaaggaagg caacttctca 120<br>gacttaaaag aaaaagtcaa tgccatagag cgagaaaaag ctgagaagtt cagaaaactg 180 |

TABLE 4-continued

| Nucleotide Sequences of Dystrophin Domains | |
|---|---|
| Description and Sequence Identifier | Sequence |
| NO: 42) | caagatgcca gcagatcagc tcaggccctg gtggaacaga tggtgaatga gggtgttaat 240<br>gcagatagca tcaaacaagc ctcagaacaa ctgaacagcc ggtggatcga attctgccag 300<br>ttgctaagtg agagacttaa ctggctggag tat 333 |
| Spectrin repeat 5 (SEQ ID NO: 43) | cagaacaaca tcatcgcttt ctataatcag ctacaacaat tggagcagat gacaactact 60<br>gctgaaaact ggttgaaaat ccaacccacc accccatcag agccaacagc aattaaaagt 120<br>cagttaaaaa tttgtaagga tgaagtcaac cggctatcag gtcttcaacc tcaaattgaa 180<br>cgattaaaaa ttcaaagcat agccctgaaa gagaaaggac aaggacccat gttcctggat 240<br>gcagactttg tggcctttac aaatcatttt aagcaagtct tttctgatgt gcaggccaga 300<br>gagaaagagc tacagacaat tttgac 327 |
| Spectrin repeat 6 (SEQ ID NO: 44) | actttgccac caatgcgcta tcaggagacc atgagtgcca tcaggacatg ggtccagcag 60<br>tcagaaacca aactctccat acctcaactt agtgtcaccg actatgaaat catggagcag 120<br>agactcgggg aattgcaggc tttacaaagt tctctgcaag agcaacaaag tggcctatac 180<br>tatctcagca ccactgtgaa agagatgtcg aagaaagcgc cctctgaaat tagccggaaa 240<br>tatcaatcag aatttgaaga aattgaggga cgctggaaga agctctcctc ccagctggtt 300<br>gagcattgtc aaaagctaga ggagcaa 327 |
| Spectrin repeat 7 (SEQ ID NO: 45) | atgaataaac tccgaaaaat tcagaatcac atacaaaccc tgaagaaatg gatggctgaa 60<br>gttgatgttt ttctgaagga ggaatggcct gcccttgggg attcagaaat tctaaaaaag 120<br>cagctgaaac agtgcagact tttagtcagt gatattcaga caattcagcc cagtctaaac 180<br>agtgtcaatg aaggtgggca gaagataaag aatgaagcag agccagagtt tgcttcgaga 240<br>cttgagacag aactcaaaga acttaacact cagtgggatc acatgtgcca acaggtctat 300<br>gccagaaagg aggccttgaa gggaggt 327 |
| Spectrin repeat 8 (SEQ ID NO: 46) | ttggagaaaa ctgtaagcct ccagaaagat ctatcagaga tgcacgaatg gatgacacaa 60<br>gctgaagaag agtatcttga gagagatttt gaatataaaa ctccagatga attacagaaa 120<br>gcagttgaag agatgaagag agctaaagaa gaggcccaac aaaaagaagc gaaagtgaaa 180<br>ctccttactg agtctgtaaa tagtgtcata gctcaagctc cacctgtagc acaagaggcc 240<br>ttaaaaaagg aacttgaaac tctaaccacc aactaccagt ggctctgcac taggctgaat 300<br>gggaaatgca agactttgga agaagtt 327 |
| Spectrin repeat 9 (SEQ ID NO: 47) | tgggcatgtt ggcatgagtt attgtcatac ttggagaaag caaacaagtg gctaaatgaa 60<br>gtagaattta aacttaaaac cactgaaaac attcctggcg gagctgagga aatctctgag 120<br>gtgctagatt cacttgaaaa tttgatgcga cattcagagg ataacccaaa tcagattcgc 180<br>atattggcac agaccctaac agatggcgga gtcatggatg agctaatcaa tgaggaactt 240<br>gagacattta attctcgttg gagggaacta catgaagagg ctgtaaggag gcaaaagttg 300<br>cttgaacaga gc 312 |
| Spectrin Repeat 10 (SEQ ID NO: 48) | atccagtctg cccaggagac tgaaaaatcc ttacacttaa tccaggagtc cctcacattc 60<br>attgacaagc agttggcagc ttatattgca gacaaggtgg acgcagctca aatgcctcag 120<br>gaagcccaga aaatccaatc tgatttgaca agtcatgaga tcagtttaga agaaatgaag 180<br>aaacataatc aggggaagga ggctgcccaa agagtcctgt ctcagattga tgttgcacag 240<br>aaaaaattac aagatgtctc catgaagttt cgatta 276 |
| Spectrin repeat 11 (SEQ ID NO: 49) | ttccagaaac cagccaattt tgagctgcgt ctacaagaaa gtaagatgat tttagatgaa 60<br>gtgaagatgc acttgcctgc attggaaaca aagagtgtgg aacaggaagt agtacagtca 120<br>cagctaaatc attgtgtgaa cttgtataaa agtctgagtg aagtgaagtc tgaagtggaa 180<br>atggtgataa agactggacg tcagattgta cagaaaaagc agacggaaaa tcccaaagaa 240<br>cttgatgaaa gagtaacagc tttgaaattg cattataatg agctgggagc aaaggtaaca 300<br>gaaagaaagc aacagttgga gaaatgc 327 |
| Spectrin repeat 12 (SEQ ID NO: 50) | ttgaaattgt cccgtaagat gcgaaaggaa atgaatgtct tgacagaatg gctggcagct 60<br>acagatatgg aattgacaaa gagatcagca gttgaaggaa tgcctagtaa tttggattct 120<br>gaagttgcct ggggaaaggc tactcaaaaa gagattgaga aacagaaggt gcacctgaag 180<br>agtatcacag aggtaggaga ggccttgaaa acagttttgg gcaagaagga gacgttggtg 240<br>gaagataaac tcagtcttct gaatagtaac tggatagctg tcacctcccg agcagaagag 300<br>tggttaaatc ttttgttgga atac 324 |
| Spectrin repeat 13 (SEQ ID NO: 51) | cagaaacaca tggaaacttt tgaccagaat gtggaccaca tcacaaagtg gatcattcag 60<br>gctgacacac ttttggatga atcagagaaa aagaaacccc agcaaaaaga agacgtgctt 120<br>aagcgtttaa aggcagaact gaatgacata cgcccaaagg tggactctac acgtgaccaa 180<br>gcagcaaact tgatggcaaa ccgcggtgac cactgcagga aattagtaga gccccaaatc 240<br>tcagagctca accatcgatt tgcagccatt tcacacagaa ttaagactgg aaaggcctcc 300<br>attcctttga ag 312 |
| Spectrin repeat 14 (SEQ ID NO: 52) | gaattggagc agtttaactc agatatacaa aaattgcttg aaccactgga ggctgaaatt 60<br>cagcaggggg tgaatctgaa agaggaagac ttcaataaag atatgaatga agacaatgag 120<br>ggtactgtaa aagaattgtt gcaaagagga gacaacttac aacaaagaat cacagatgag 180<br>agaaagagag aggaaataaa gataaaacag cagctgttac agacaaaaca taatgctctc 240<br>aaggatttga ggtctcaaag aagaaaaaag gctctagaaa tt 282 |
| Spectrin repeat 15 | tctcatcagt ggtatcagta caagaggcag gctgatgatc tcctgaaatg cttggatgac 60<br>attgaaaaaa aattagccag cctacctgag cccagagatg aaaggaaaat aaaggaaatt 120 |

TABLE 4-continued

Nucleotide Sequences of Dystrophin Domains

| Description and Sequence Identifier | Sequence |
|---|---|
| (SEQ ID NO: 53) | gatcgggaat tgcagaagaa gaaagaggag ctgaatgcag tgcgtaggca agctgagggc 180<br>ttgtctgagg atggggccgc aatggcagtg gagccaactc agatccagct cagcaagcgc 240<br>tggcgggaaa ttgagagcaa atttgctcag tttcgaagac tcaactttgc acaa 294 |
| L3 (20-mer linker) (SEQ ID NO: 54) | attcacactg tccgtgaaga aacgatgatg gtgatgactg aagacatgcc tttggaaatt 60 |
| Spectrin repeat 16 (SEQ ID NO: 55) | tcttatgtgc cttctactta tttgactgaa atcactcatg tctcacaagc cctattagaa 60<br>gtggaacaac ttctcaatgc tcctgacctc tgtgctaagg actttgaaga tctctttaag 120<br>caagaggagt ctctgaagaa tataaaagat agtctacaac aaagctcagg tcggattgac 180<br>attattcata gcaagaagac agcagcattg caaagtgcaa cgcctgtgga aagggtgaag 240<br>ctacaggaag ctctctccca gcttgatttc caatgggaaa aagttaacaa aatgtacaag 300<br>gaccgacaag ggcgatttga cagatct 327 |
| Spectrin repeat 17 (SEQ ID NO: 56) | gttgagaaat ggcggcgttt tcattatgat ataaagatat ttaatcagtg gctaacagaa 60<br>gctgaacagt ttctcagaaa gacacaaatt cctgagaatt gggaacatgc taaatacaaa 120<br>tggtatctta aggaactcca ggatggcatt gggcagcggc aaactgttgt cagaacattg 180<br>aatgcaactg gggaagaaat aattcagcaa tcctcaaaaa cagatgccag tattctacag 240<br>gaaaaattgg gaagcctgaa tctgcggtgg caggaggtct gcaaacagct gtcagacaga 300<br>aaaaagaggc tagaagaaca a 321 |
| Spectrin repeat 18 (SEQ ID NO: 57) | aagaatatct tgtcagaatt tcaaagagat ttaaatgaat ttgttttatg gttggaggaa 60<br>gcagataaca ttgctagtat cccacttgaa cctggaaaag agcagcaact aaaagaaaag 120<br>cttgagcaag tcaagttact ggtggaagag ttgcccctgc gccagggaat tctcaaacaa 180<br>ttaaatgaaa ctggaggacc cgtgcttgta agtgctccca taagcccaga agagcaagat 240<br>aaacttgaaa ataagctcaa gcagacaaat ctccagtgga taaaggtttc cagagcttta 300<br>cctgagaaac aaggagaaat tgaagctcaa ataaaagacc ttgggcagct t 351 |
| Spectrin repeat 19 (SEQ ID NO: 58) | gaaaaaaagc ttgaagacct tgaagagcag ttaaatcatc tgctgctgtg gttatctcct 60<br>attaggaatc agttggaaat ttataaccaa ccaaaccaag aaggaccatt tgacgttcag 120<br>gaaactgaaa tagcagttca agctaaacaa ccggatgtgg aagagatttt gtctaaaggg 180<br>cagcatttgt acaaggaaaa accagccact cagccagtga agaggaagtt agaagatctg 240<br>agctctgagt ggaaggcggt aaaccgttta cttcaagagc tgagggcaaa gcagcctgac 300<br>cta 303 |
| Hinge 3 (SEQ ID NO: 59) | gctcctggac tgaccactat tggagcctct cctactcaga ctgttactct ggtgacacaa 60<br>cctgtggtta ctaaggaaac tgccatctcc aaactagaaa tgccatcttc cttgatgttg 120<br>gag 123 |
| Spectrin repeat 20 (SEQ ID NO: 60) | gtacctgctc tggcagattt caaccgggct tggacagaac ttaccgactg gctttctctg 60<br>cttgatcaag ttataaaatc acagagggtg atggtgggtg accttgagga tatcaacgag 120<br>atgatcatca agcagaaggc aacaatgcag gatttggaac agaggcgtcc ccagttggaa 180<br>gaactcatta ccgctgccca aaatttgaaa aacaagacca gcaatcaaga ggctagaaca 240<br>atcattacgg atcgaattga aagaattcag aatcagtggg atgaagtaca agaacacctt 300<br>cagaaccgga ggcaacagtt gaatgaaatg 330 |
| Spectrin repeat 21 (SEQ ID NO: 61) | ttaaaggatt caacacaatg gctggaagct aaggaagaag ctgagcaggt cttaggacag 60<br>gccagagcca agcttgagtc atggaaggag ggtccctata cagtagatgc aatccaaaag 120<br>aaaatcacag aaaccaagca gttggccaaa gacctccgcc agtggcagac aaatgtagat 180<br>gtggcaaatg acttggccct gaaacttctc cgggattatt ctgcagatga taccagaaaa 240<br>gtccacatga taacagagaa tatcaatgcc tcttggagaa gcattcataa aagggtgagt 300<br>gagcgagagg ctgctttgga agaaact 327 |
| Spectrin repeat 22 (SEQ ID NO: 62) | catagattac tgcaacagtt ccccctggac ctggaaaagt ttcttgcctg gcttacagaa 60<br>gctgaaacaa ctgccaatgt cctacaggat gctacccgta aggaaaggct cctagaagac 120<br>tccaagggag taaaagagct gatgaaacaa tggcaagacc tccaaggtga aattgaagct 180<br>cacacagatg tttatcacaa cctggatgaa aacagccaaa aaatcctgag atccctggaa 240<br>ggttccgatg atgcagtcct gttacaaaga cgtttggata acatgaactt caagtggagt 300<br>gaacttcgga aaaagtctct caacattagg tcccatttgg aagccagt 348 |
| Spectrin repeat 23 (SEQ ID NO: 63) | tctgaccagt ggaagcgtct gcacctttct ctgcaggaac ttctggtgtg gctacagctg 60<br>aaagatgatg aattaagccg gcaggcacct attggaggcg actttccagc agttcagaag 120<br>cagaacgatg tacatagggc cttcaagagg gaattgaaaa ctaaagaacc tgtaatcatg 180<br>agtactcttg agactgtacg aatatttctg acagagcagc ctttggaagg actagagaaa 240<br>ctctaccagg agcccagaga gctgcctcct gaggagagag cccagaatgt cactcggctt 300<br>ctacgaaagc aggctgagga ggtcaatact gagtgggaaa aattgaacct gcactccgct 360<br>gactggcaga gaaaaataga tgagacc 387 |
| Spectrin repeat 24 (SEQ ID NO: 64) | cttgaaagac tccaggaact tcaagaggcc acggatgagc tggacctcaa gctgcgccaa 60<br>gctgaggtga tcaagggatc ctggcagccc gtgggcgatc tcctcattga ctctctccaa 120<br>gatcacctcg agaaagtcaa ggcacttcga ggagaaattg cgcctctgaa agagaacgtg 180<br>agccacgtca atgaccttgc tcgccagctt accactttgg gcattcagct ctcaccgtat 240 |

TABLE 4-continued

Nucleotide Sequences of Dystrophin Domains

| Description and Sequence Identifier | Sequence |
|---|---|
| | aacctcagca ctctggaaga cctgaacacc agatggaagc ttctgcaggt ggccgtcgag 300<br>gaccgagtca ggcagctgca tgaa 324 |
| Hinge 4 (SEQ ID NO: 65) | gcccacaggg actttggtcc agcatctcag cactttcttt ccacgtctgt ccagggtccc 60<br>tgggagagag ccatctcgcc aaacaaagtg ccctactata tcaaccacga gactcaaaca 120<br>acttgctggg accatcccaa aatgacagag ctctaccagt ctttagctga cctgaataat 180<br>gtcagattct cagcttatag gactgccatg aaactc 216 |
| CR (SEQ ID NO: 66) | cgaagactgc agaaggccct ttgcttggat ctcttgagcc tgtcagctgc atgtgatgcc 60<br>ttggaccagc acaacctcaa gcaaaatgac cagcccatgg atatcctgca gattattaat 120<br>tgtttgacca ctatttatga ccgcctggag caagagcaca acaatttggt caacgtccct 180<br>ctctgcgtgg atatgtgtct gaactggctg ctgaatgttt atgatacggg acgaacaggg 240<br>aggatccgtg tcctgtcttt taaaactggc atcatttccc tgtgtaaagc acatttggaa 300<br>gacaagtaca gataccttt caagcaagtg gcaagttcaa caggattttg tgaccagcgc 360<br>aggctgggcc tccttctgca tgattctatc caaattccaa gacagttggg tgaagttgca 420<br>tcctttgggg gcagtaacat tgagccaagt gtccggagct gcttccaatt tgctaataat 480<br>aagccagaga tcgaagcggc cctcttccta gactggatga gactggaacc ccagtccatg 540<br>gtgtggctgc ccgtcctgca cagagtggct gctgcagaaa ctgccaagca tcaggccaaa 600<br>tgtaacatct gcaaagagtg tccaatcatt ggattcaggt acaggagtct aaagcacttt 660<br>aattatgaca tctgccaaag ctgctttttt tctggtcgag ttgcaaaagg ccataaaatg 720<br>cactatccca tggtggaata ttgcactccg actacatcag gagaagatgt tcgagacttt 780<br>gccaaggtac taaaaaacaa atttcgaacc aaaaggtatt ttgcgaagca tccccgaatg 840<br>ggctacctgc cagtgcagac tgtcttagag gggacaaca tggaaact |
| C-term (SEQ ID NO: 67) | cccgttactc tgatcaactt ctggccagta gattctgcgc ctgcctcgtc ccctcagctt 60<br>tcacacgatg atactcattc acgcattgaa cattatgcta gcaggctagc agaaatggaa 120<br>aacagcaatg gatcttatct aaatgatagc atctctccta atgagagcat agatgatgaa 180<br>catttgttaa tccagcatta ctgccaaagt ttgaaccagg actcccccct gagccagcct 240<br>cgtagtcctg cccagatctt gatttcctta gagagtgagg aaagagggga gctagagaga 300<br>atcctagcag atcttgagga agaaaacagg aatctgcaag cagaatatga ccgtctaaag 360<br>cagcagcacg aacataaagg cctgtcccca ctgccgtccc ctcctgaaat gatgcccacc 420<br>tctccccaga gtccccggga tgctgagctc attgctgagg ccaagctact gcgtcaacac 480<br>aaaggccgcc tggaagccag gatgcaaatc ctggaagacc acaataaaca gctggagtca 540<br>cagttacaca ggctaaggca gctgctggag caaccccagg cagaggccaa Agtgaatggc 600<br>acaacggtgt cctctccttc tacctctcta cagaggtccg acagcagtca gcctatgctg 660<br>ctccgagtgg ttggcagtca aacttcggac tccatgggtg aggaagatct tctcagtcct 720<br>ccccaggaca caagcacagg gttagaggag gtgatggagc aactcaacaa ctccttccct 780<br>agttcaagag gaagaaatac ccctggaaag ccaatgagag aggacacaat gtag |

The present disclosure is directed to a miniaturized dystrophin polypeptide that is smaller than the full-length dystrophin protein, i.e., isoform Dp427m, and that is not identical to the naturally occurring dystrophin protein isoforms, or a nucleic acid molecule comprising a nucleotide sequence encoding the miniaturized dystrophin polypeptide. When the present disclosure discloses miniaturized dystrophin polypeptides, the present disclosure also discloses nucleic acid molecule comprising a nucleotide sequence encoding the corresponding disclosed miniaturized dystrophin polypeptide, and vice versa. In some embodiments, the nucleic acid molecule encoding the miniaturized dystrophin polypeptide is suitable for gene therapy. Accordingly, the nucleic acid molecule encoding the miniaturized dystrophin polypeptide is constructed not only to fit into a gene therapy vector, e.g., AAV vector, or to be suitable for recombinant expression, but also to reduce any unwanted immune response (e.g., humoral immune response and/or cellular immune response, e.g., CD4 and/or CD8) against the miniaturized dystrophin polypeptide when administered or expressed in vivo. In some embodiments, the miniaturized dystrophin polypeptide of the present disclosure comprises from N terminus to C terminus hinge 1 (H1) domain, spectrin repeat 1 (R1) domain, spectrin repeat 3 (R3) domain, hinge 2 (H2) domain, spectrin repeat 16 (R16) domain, spectrin repeat 17 (R17) domain, spectrin repeat 24 (R24) domain, and hinge 4 (H4) domain of dystrophin. In some embodiments, the miniaturized dystrophin polypeptide does not comprise spectrin repeat 2 (R2) domain of dystrophin. In other embodiments, the miniaturized dystrophin polypeptide does not comprise spectrin repeat 2 (R2) domain and (1) spectrin repeat 4 (R4) domain, (2) spectrin repeat 5 (R5) domain, (3) spectrin repeat 6 (R6) domain, (4) spectrin repeat 7 (R7) domain, (5) spectrin repeat 8 (R8) domain, (6) spectrin repeat 9 (R9) domain, (7) spectrin repeat 10 (R10) domain, (8) spectrin repeat 11 (R11) domain, (9) spectrin repeat 12 (R12) domain, (10) spectrin repeat 13 (R13) domain, (11) spectrin repeat 14 (R14) domain, (12) spectrin repeat 15 (R15) domain, (13) spectrin repeat 18 (R18) domain, (14) spectrin repeat 19 (R19) domain, (15) spectrin repeat 20 (R20) domain, (16) spectrin repeat 21 (R21) domain, (17) spectrin repeat 22 (R22) domain, or (18) spectrin repeat 23 (R23) domain, or (19) any combination thereof. In some embodiments, the miniaturized dystrophin polypeptide does not comprise spectrin repeat 2 (R2) domain, spectrin repeat 4 (R4) domain, spectrin repeat 5 (R5) domain, spectrin repeat 6 (R6) domain, spectrin repeat 7 (R7) domain, spectrin repeat 8 (R8) domain, spectrin repeat 9 (R9) domain, spectrin repeat 10 (R10) domain, spectrin repeat 11 (R11) domain, spectrin repeat 12 (R12) domain, spectrin repeat 13 (R13) domain, spectrin repeat 14 (R14) domain, spectrin repeat 15 (R15)

domain, spectrin repeat 18 (R18) domain, spectrin repeat 19 (R19) domain, spectrin repeat 20 (R20) domain, spectrin repeat 21 (R21) domain, spectrin repeat 22 (R22) domain, and spectrin repeat 23 (R23) domain.

In certain embodiments, the miniaturized dystrophin polypeptide of the present disclosure comprises from N terminus to C terminus hinge 1 (H1) domain, spectrin repeat 1 (R1) domain, spectrin repeat 3 (R3) domain, hinge 2 (H2) domain, spectrin repeat 16 (R16) domain, spectrin repeat 17 (R17) domain, spectrin repeat 24 (R24) domain, and hinge 4 (H4) domain of dystrophin, wherein the R1 domain is directly fused to R3 domain by a peptide bond, e.g., See miniaturized dystrophin polypeptide BXA-027741.

In some embodiments, the miniaturized dystrophin polypeptide of the present disclosure comprises from N terminus to C terminus hinge 1 (H1) domain, spectrin repeat 1 (R1) domain, spectrin repeat 3 (R3) domain, hinge 2 (H2) domain, spectrin repeat 16 (R16) domain, spectrin repeat 17 (R17) domain, spectrin repeat 24 (R24) domain, and hinge 4 (H4) domain of dystrophin, wherein the R1 domain and the R3 domain are fused by amino acids ARG-VAL (RV).

In some embodiments, the miniaturized dystrophin polypeptide of the present disclosure comprises from N terminus to C terminus hinge 1 (H1) domain, spectrin repeat 1 (R1) domain, spectrin repeat 3 (R3) domain, hinge 2 (H2) domain, spectrin repeat 16 (R16) domain, spectrin repeat 17 (R17) domain, spectrin repeat 24 (R24) domain, and hinge 4 (H4) domain of dystrophin, wherein the H2 domain and the R16 domain are fused by a linker. The linker can be any linker known in the art. In other embodiments, the linker can be selected from any linker disclosed herein. In other embodiments, the linker can be a linker in Section 5.3.2. In some embodiments, the linker can comprise an amino acid sequence at least about 80%, at least about 90%, at least about 95%, at least about 96%, at least about 97%, at least about 98%, at least about 99%, or about 100% identical to SEQ ID NO: 75 (IHTVREE TMMVMTEDMP LEI).

In some embodiments, the miniaturized dystrophin polypeptide of the present disclosure comprises from N terminus to C terminus hinge 1 (H1) domain, spectrin repeat 1 (R1) domain, spectrin repeat 3 (R3) domain, hinge 2 (H2) domain, spectrin repeat 16 (R16) domain, spectrin repeat 17 (R17) domain, spectrin repeat 24 (R24) domain, and hinge 4 (H4) domain of dystrophin, wherein the H2 domain and the R16 domain are fused by a linker. In some embodiments, the linker can comprise an amino acid sequence at least about 80%, at least about 90%, at least about 95%, at least about 96%, at least about 97%, at least about 98%, at least about 99%, or about 100% identical to SEQ ID NOs: 74-75 in combination (SEAQ IHTVREE TMMVMTEDMP LEI).

In some embodiments, the miniaturized dystrophin polypeptide of the present disclosure comprises from N terminus to C terminus hinge 1 (H1) domain, spectrin repeat 1 (R1) domain, spectrin repeat 3 (R3) domain, hinge 2 (H2) domain, spectrin repeat 16 (R16) domain, spectrin repeat 17 (R17) domain, spectrin repeat 24 (R24) domain, and hinge 4 (H4) domain of dystrophin, wherein the H2 domain and the R16 domain are fused by a linker. In some embodiments, the linker can comprise an amino acid sequence at least about 80%, at least about 90%, at least about 95%, at least about 96%, at least about 97%, at least about 98%, at least about 99%, or about 100% identical to SEQ ID NO: 74 (SEAQ). In other embodiments, the miniaturized dystrophin polypeptide of the present disclosure comprises from N terminus to C terminus hinge 1 (H1) domain, spectrin repeat 1 (R1) domain, spectrin repeat 3 (R3) domain, hinge 2 (H2) domain, spectrin repeat 16 (R16) domain, spectrin repeat 17 (R17) domain, spectrin repeat 24 (R24) domain, and hinge 4 (H4) domain of dystrophin, wherein the R1 domain and the R3 domain are fused by amino acids ARG-VAL and wherein the H2 domain and the R16 domain are fused by a linker, e.g., SEQ ID NOs: 74-75 in combination.

In some embodiments, the miniaturized dystrophin polypeptide of the present disclosure comprises from N terminus to C terminus hinge 1 (H1) domain, spectrin repeat 1 (R1) domain, spectrin repeat 3 (R3) domain, hinge 2 (H2) domain, spectrin repeat 16 (R16) domain, spectrin repeat 17 (R17) domain, spectrin repeat 24 (R24) domain, and hinge 4 (H4) domain of dystrophin, wherein the R1 domain and the R3 domain are fused by amino acids ARG-VAL, wherein the H2 domain and the R16 domain are fused by a linker, e.g., SEQ ID NOs: 74-75 in combination, and wherein (i) the H1 domain and the R1 domain are fused directly, (ii) the R3 domain and the H2 domain are fused directly, (iii) the R16 and R17 domains are fused directly, (iv) the R17 and R24 domains are fused directly, or (v) the R24 and H4 domains are fused directly, or (vi) any combination thereof. In some embodiments, the miniaturized dystrophin polypeptide useful for the present disclosure comprises from N terminus to C terminus: hinge 1 (H1) domain, spectrin repeat 1 (R1) domain, spectrin repeat 3 (R3) domain, hinge 2 (H2) domain, spectrin repeat 16 (R16) domain, spectrin repeat 17 (R17) domain, spectrin repeat 24 (R24) domain, and hinge 4 (H4) domain of dystrophin, wherein the R1 domain and the R3 domain are fused by amino acids ARG-VAL, wherein the H2 domain and the R16 domain are fused by a linker, e.g., SEQ ID NOs: 74-75 in combination, and wherein (i) the H1 domain and the R1 domain are fused directly, (ii) the R3 domain and the H2 domain are fused directly, (iii) the R16 and R17 domains are fused directly, (iv) the R17 and R24 domains are fused directly, and (v) the R24 and H4 domains are fused directly. In some embodiments, the miniaturized dystrophin polypeptide useful for the present disclosure further comprises an ABD1 domain (optionally at the N terminus) and/or a CR domain (optionally at the N terminus). In some embodiments, the miniaturized dystrophin polypeptide consists essentially of or consists of, from N terminus to C terminus, an ABD1 domain, a H1 domain, an R1 domain, amino acids RV, an R3 domain, an H2 domain, the amino acid sequence as set forth in SEQ ID NOs: 74-75 in combination, an R16 domain, an R17 domain, an R24 domain, an H4 domain, and a CR domain of dystrophin.

Each domain in the miniaturized dystrophin polypeptides can have one or more changes from the corresponding wild-type domain.

For example, the miniaturized dystrophin BXA-196477 consists of the following protein domains in order:

TABLE 5A

Amino acid sequence and domain structure of miniaturized dystrophin polypeptide BXA-196477.

| SEQ ID NO: | Description | Sequence |
|---|---|---|
| 68 | ABD1 | MLWWEEVEDCYEREDVQKKTFTKWVNAQFSKFGKQHIEN LFSDLQDGRRLLDLLEGLTGQKLPKEKGSTRVHALNNVNK ALRVLQNNNVDLVNIGSTDIVDGNHKLTLGLIWNIILHWQV KNVMKNIMAGLQQTNSEKILLSWVRQSTRNYPQVNVINFT TSWSDGLALNALIHSHRPDLFDWNSVVCQQSATQRLEHAF NIARYQLGIEKLLDPEDVDTTYPDKKSILMYITSLFQVLPQQ VSIEAIQEVE |
| 69 | Hinge 1 | MLPRPPKVTKEEHFQLHHQMHYSQQITVSLAQGYERTSSP KPRFKSYAYTQAAYVTTSDPTRSPFPSQHLEAPEDKSFGSSL MES |
| 70 | Spectrin-1 | EVNLDRYQTALEEVLSWLLSAEDTLQAQGEISNDVEVVKD QFHTHEGYMMDLTAHQGRVGNILQLGSKLIGTGKLSEDEE TEVQEQMNLLNSRWECLRVASMEKQSNLH |
| 71 | L1 (RV-Linker) | RV |
| 72 | Spectrin-3 | LLKWQRLTEEQCLFSAWLSEKEDAVNKIHTTGFKDQNEML SSLQKLAVLKADLEKKKQSMGKLYSLKQDLLSTLKNKSVT QKTEAWLDNFARCWDNLVQKLEKSTAQISQA |
| 73 | Hinge 2 | VTTTQPSLTQTTVMETVTTVTTREQILVKHAQEELPPPPPQK KRQITVD |
| 74 | L2 (SEAQ linker) | SEAQ |
| 75 | L3 (20-mer linker) | IHTVREETMMVMTEDMPLEI |
| 76 | Spectrin-16 | SYVPSTYLTEITHVSQALLEVEQLLNAPDLCAKDFEDLFKQ EESLKNIKDSLQQSSGRIDIIHSKKTAALQSATPVERVKLQE ALSQLDFQWEKVNKMYKDRQGRFDRS |
| 77 | Spectrin-17 | VEKWRRFHYDIKIFNQWLTEAEQFLRKTQIPENWEHAKYK WYLKELQDGIGQRQTVVRTLNATGEEIIQQSSKTDASILQE KLGSLNLRWQEVCKQLSDRKKRLEEQ |
| 78 | Spectrin-24 | LERLQELQEATDELDLKLRQAEVIKGSWQPVGDLLIDSLQD HLEKVKALRGEIAPLKENVSHVNDLARQLTTLGIQLSPYNL STLEDLNTRWKLLQVAVEDRVRQLHE |
| 79 | Hinge 4 | AHRDFGPASQHFLSTSVQGPWERAISPNKVPYYINHETQTT CWDHPKMTELYQSLADLNNVRFSAYRTAMKL |
| 80 | CR | RRLQKALCLDLLSLSAACDALDQHNLKQNDQPMDILQIINC LTTIYDRLEQEHNNLVNVPLCVDMCLNWLLNVYDTGRTG RIRVLSFKTGIISLCKAHLEDKYRYLFKQVASSTGFCDQRRL GLLLHDSIQIPRQLGEVASFGGSNIEPSVRSCFQFANNKPEIE AALFLDWMRLEPQSMVWLPVLHRVAAAETAKHQAKCNIC KECPIIGFRYRSLKHFNYDICQSCFFSGRVAKGHKMHYPMV EYCTPTTSGEDVRDFAKVLKNKFRTKRYFAKHPRMGYLPV QTVLEGDNMETDTM |

In some embodiments, the H1 domain in the miniaturized dystrophin polypeptide is an amino acid sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 69. In some embodiments, the R1 domain is an amino acid sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 70. In some embodiments, the R3 domain is an amino acid sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 72. In some embodiments, the H2 domain is an amino acid sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 73. In some embodiments, the R16 domain is an amino acid sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 76. In some embodiments, the R17 domain is an amino acid sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 77. In some embodiments, the R24 domain is an amino acid sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 78. In some embodiments, the H4 domain is an amino acid sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 79. In some embodiments, the miniaturized dystrophin polypeptide further comprises at the N terminus a polypeptide sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 68. In some embodiments, the miniaturized dystrophin polypeptide further comprises at the C terminus a polypeptide sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 80.

TABLE 5B

Amino acid sequence and domain structure of miniaturized dystrophin polypeptide BXA-027743.

| SEQ ID NO: | Description | Sequence |
|---|---|---|
| 81 | ABD1 | MLWWEEVEDCYEREDVQKKTFTKWVNAQFSKFGKQHIEN LFSDLQDGRRLLDLLEGLTGQKLPKEKGSTRVHALNNVNK ALRVLQNNNVDLVNIGSTDIVDGNHKLTLGLIWNIILHWQV KNVMKNIMAGLQQTNSEKILLSWVRQSTRNYPQVNVINFT TSWSDGLALNALIHSHRPDLFDWNSVVCQQSATQRLEHAF NIARYQLGIEKLLDPEDVDTTYPDKKSILMYITSLFQVLPQQ VSIEAIQEVE |
| 82 | Hinge 1 | MLPRPPKVTKEEHFQLHHQMHYSQQITVSLAQGYERTSSP KPRFKSYAYTQAAYVTTSDPTRSPFPSQHLEAPEDKSFGSSL MES |
| 83 | Spectrin-1 | EVNLDRYQTALEEVLSWLLSAEDTLQAQGEISNDVEVVKD QFHTHEGYMMDLTAHQGRVGNILQLGSKLIGTGKLSEDEE TEVQEQMNLLNSRWECLRVASMEKQSNLH |
| 84 | L1 | IHTVREETMMVMTEDMPLEI |
| 85 | Spectrin-16 | SYVPSTYLTEITHVSQALLEVEQLLNAPDLCAKDFEDLFKQ EESLKNIKDSLQQSSGRIDIIHSKKTAALQSATPVERVKLQE ALSQLDFQWEKVNKMYKDRQGRFDRS |
| 86 | Spectrin-17 | VEKWRRFHYDIKIFNQWLTEAEQFLRKTQIPENWEHAKYK WYLKELQDGIGQRQTVVRTLNATGEEIIQQSSKTDASILQE KLGSLNLRWQEVCKQLSDRKKRLEEQ |
| 87 | Hinge 3 | APGLTTIGASPTQTVTLVTQPVVTKETAISKLEMPSSLMLE |
| 88 | Spectrin-23 | SDQWKRLHLSLQELLVWLQLKDDELSRQAPIGGDFPAVQK QNDVHRAFKRELKTKEPVIMSTLETVRIFLTEQPLEGLEKL YQEPRELPPEERAQNVTRLLRKQAEEVNTEWEKLNLHSAD WQRKIDET |
| 89 | Spectrin-24 | LERLQELQEATDELDLKLRQAEVIKGSWQPVGDLLIDSLQD HLEKVKALRGEIAPLKENVSHVNDLARQLTTLGIQLSPYNL STLEDLNTRWKLLQVAVEDRVRQLHE |
| 90 | Hinge 4 | AHRDFGPASQHFLSTSVQGPWERAISPNKVPYYINHETQTT CWDHPKMTELYQSLADLNNVRFSAYRTAMKL |
| 91 | CR/C-term | RRLQKALCLDLLSLSAACDALDQHNLKQNDQPMDILQIINC LTTIYDRLEQEHNNLVNVPLCVDMCLNWLLNVYDTGRTG RIRVLSFKTGIISLCKAHLEDKYRYLFKQVASSTGFCDQRRL GLLLHDSIQIPRQLGEVASFGGSNIEPSVRSCFQFANNKPEIE AALFLDWMRLEPQSMVWLPVLHRVAAAETAKHQAKCNIC KECPIIGFRYRSLKHFNYDICQSCFFSGRVAKGHKMHYPMV EYCTPTTSGEDVRDFAKVLKNKFRTKRYFAKHPRMGYLPV QTVLEGDNMETPAQILISLESEERGELERILADLEEENRNLQ AEYDRLKQQHEHKGLSPLPSPPDTM |

In some embodiments, the present disclosure provides a miniaturized dystrophin polypeptide comprising spectrin repeat 1 (R1) domain and spectrin 16 (R16) domain, wherein the R1 domain and the R16 domain are fused by a linker comprising the amino acid sequence set forth in SEQ ID NO: 84 (IHTVREETMMVMTEDMPLEI). In some embodiments, the present disclosure provides a miniaturized dystrophin polypeptide comprising from N terminus to C terminus a hinge 1 (H1) domain, spectrin repeat 1 (R1) domain, spectrin repeat 16 (R16) domain, spectrin repeat 17 (R17) domain, a hinge 3 (H3) domain, spectrin repeat 23 (R23) domain, spectrin repeat 24 (R24) domain, and hinge 4 (H4) domain of dystrophin, wherein the R1 domain and the R16 domain are fused by the amino acid sequence set forth in SEQ ID NO: 84 (IHTVREETMMVMTEDMPLEI).

In some embodiments, the present disclosure includes a nucleic acid molecule comprising a nucleotide sequence, which encodes a miniaturized dystrophin polypeptide comprising spectrin repeat 1 (R1) domain and spectrin 16 (R16) domain, wherein the R1 domain and the R16 domain are fused by a linker comprising the amino acid sequence set forth in SEQ ID NO: 84 (IHTVREETMMVMTEDMPLEI). In some embodiments, the present disclosure provides a nucleic acid molecule comprising a nucleotide sequence, which encodes a miniaturized dystrophin polypeptide comprising from N terminus to C terminus a hinge 1 (H1) domain, spectrin repeat 1 (R1) domain, spectrin repeat 16 (R16) domain, spectrin repeat 17 (R17) domain, a hinge 3 (H3) domain, spectrin repeat 23 (R23) domain, spectrin repeat 24 (R24) domain, and hinge 4 (H4) domain of dystrophin, wherein the R1 domain and the R16 domain are fused by the amino acid sequence set forth in SEQ ID NO: 84 (IHTVREETMMVMTEDMPLEI).

In some embodiments, the miniaturized dystrophin polypeptide of the present disclosure has the following characteristics: (i) the H1 domain and the R1 domain are fused directly, (ii) the R16 and R17 domains are fused directly, (iii) the R17 and the H3 domains are fused directly, (iv) the R23 and R24 domains are fused directly, or (v) the R24 and H4 domains are fused directly, or (vi) any combination thereof. In some embodiments, the miniaturized dystrophin polypeptide for the present disclosure does not comprise a spectrin repeat 2 (R2) domain, spectrin repeat 3 (R3) domain, spectrin repeat 4 (R4) domain, spectrin repeat 5 (R5) domain, spectrin repeat 6 (R6) domain, spectrin repeat 7 (R7) domain, spectrin repeat 8 (R8) domain, spectrin repeat 9 (R9) domain, spectrin repeat 10 (R10) domain, spectrin repeat 11 (R11) domain, spectrin repeat 12 (R12) domain, spectrin repeat 13 (R13) domain, spectrin repeat 14 (R14) domain, spectrin repeat 15 (R15) domain, spectrin repeat 18 (R18) domain, spectrin repeat 19 (R19) domain, spectrin repeat 20 (R20) domain, spectrin repeat 21 (R21) domain, and/or spectrin repeat 22 (R22) domain. In some embodiments, the miniaturized dystrophin polypeptide further comprises an ABD1 domain and/or a CR domain.

In some embodiments, the miniaturized dystrophin polypeptide comprises, consists essentially of, or consists of, from N terminus to C terminus, the ABD1 domain, the H1 domain, the R1 domain, the amino acid sequence set forth in SEQ ID NO: 84 (IHTVREETMMVMTEDMPLEI), the R16 domain, the R17 domain, the H3 domain, the R23 domain, the R24 domain, the H4 domain, and the CR domain of dystrophin.

In some embodiments, the H1 domain useful for the miniaturized dystrophin polypeptide comprises an amino acid sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 82. In other embodiments, the R1 domain useful for the miniaturized dystrophin polypeptide comprises an amino acid sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 83.

In some embodiments, the R16 domain useful for the miniaturized dystrophin polypeptide comprises an amino acid sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 85.

In some embodiments, the R17 domain useful for the miniaturized dystrophin polypeptide comprises an amino acid sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 86.

In other embodiments, the H3 domain useful for the miniaturized dystrophin polypeptide comprises an amino acid sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 87.

In some embodiments, the R23 domain useful for the miniaturized dystrophin polypeptide comprises an amino acid sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 88.

In other embodiments, the R24 domain useful for the miniaturized dystrophin polypeptide comprises an amino acid sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 89.

In some embodiments, the H4 domain useful for the miniaturized dystrophin polypeptide comprises an amino acid sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 90.

In some embodiments, the miniaturized dystrophin polypeptide further comprises at the N terminus an amino acid sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 81. In some embodiments, the miniaturized dystrophin polypeptide further comprises at the C terminus an amino acid sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 91. In some embodiments, a nucleic acid sequence encoding each domain can be the following:

TABLE 6A

Nucleotide sequence (and domain structure) encoding miniaturized dystrophin polypeptide BXA-196477.

| SEQ ID NO: | Description | Nucleotide Sequence |
|---|---|---|
| 92 | 5' UTR | CCGCCTTCGGCACCATTCCTCACGACACCCAAATATGGCACG GGTGAGGAATGGTGGGGAGTTATTTTAGAGCGGTGAGGAAG GTGGGCAGGCAGCAGGTGTTGGCGCTCTAAAAATAACTCCCG GGAGTTATTTTAGAGCGGAGGAATGGTGGACACCCAAATAGG CGACGGTTCCTCACCCGTCGCCATATTTGGGTGTCCGCCCTCG GCCGGGGCCGCATTCCTGGGGCCGGGCGGTGCTCCCGCCCGC CTCGATAAAAGGCTCCGGGGCCGGCGGCGGCCCACGAGCTAC CCGGAGGAGCGGGAGGCTCTAGACCACC |
| 93 | ABD1 | ATGCTGTGGTGGGAGGAAGTGGAAGATTGCTACGAGCGCGA GGACGTGCAGAAGAAAACCTTCACCAAATGGGTGAACGCCC AGTTCAGCAAGTTCGGCAAGCAGCACATCGAGAACCTGTTCA GCGACCTGCAGGACGGCAGACGGCTGCTGGACCTGCTGGAA GGCCTGACCGGCCAGAAGCTGCCCAAAGAGAAGGGCAGCAC CAGAGTGCACGCCCTGAACAACGTGAACAAGGCCCTGCGGGT GCTGCAGAACAACAACGTGGACCTGGTGAACATCGGCAGCA CCGACATCGTGGACGGCAACCACAAGCTGACCCTGGGCCTGA TCTGGAACATCATCCTGCACTGGCAGGTCAAAAACGTGATGA AGAACATCATGGCCGGCCTGCAGCAGACCAACAGCGAGAAG ATCCTGCTGAGCTGGGTGCGCCAGAGCACCCGGAACTACCCC CAGGTCAACGTGATCAACTTCACCACCTCTTGGAGCGACGGC CTGGCCCTGAACGCCCTGATCCACAGCCACCGGCCCGACCTG TTCGACTGGAACAGCGTGGTCTGCCAGCAGAGCGCCACCCAG CGGCTGGAACACGCCTTCAATATCGCCAGATACCAGCTGGGC ATCGAGAAGCTGCTGGATCCCGAGGACGTGGACACCACCTAC CCCGACAAGAAATCCATCCTGATGTATATCACCAGCCTGTTC CAGGTGCTGCCCCAGCAGGTGTCCATCGAGGCCATCCAGGAA GTGGAA |
| 94 | Hinge 1 | ATGCTGCCCAGACCCCCCAAAGTGACCAAAGAGGAACACTTC CAGCTGCACCACCAGATGCACTACAGCCAGCAGATCACCGTG TCCCTGGCCCAGGGCTACGAGAGAACCAGCAGCCCCAAGCCC CGGTTCAAGAGCTACGCCTATACCCAGGCCGCCTACGTGACC ACCAGCGACCCTACCAGAAGCCCATTCCCCAGCCAGCATCTG GAAGCCCCCGAGGACAAGAGCTTCGGCAGCAGCCTGATGGA AAGC |
| 95 | Spectrin-1 | GAAGTGAACCTGGACAGATACCAGACCGCCCTGGAAGAGGT GCTGAGCTGGCTGCTGAGCGCCGAGGATACACTGCAGGCTCA GGGCGAGATCAGCAACGACGTGGAAGTCGTGAAGGACCAGT TCCACACCCACGAGGGCTACATGATGGACCTGACAGCCCACC AGGGCAGAGTGGGCAACATCCTGCAGCTGGGCTCCAAGCTGA TCGGCACCGGCAAGCTGAGCGAGGACGAAGAGACAGAGGTG CAGGAACAGATGAACCTGCTGAACAGCAGATGGGAGTGCCT GCGGGTGGCCAGCATGGAAAAGCAGAGCAACCTGCAT |
| 96 | L1(RV-Linker) | AGGGTC |
| 97 | Spectrin-3 | CTGCTGAAGTGGCAGCGGCTGACCGAGGAACAGTGCCTGTTT AGCGCCTGGCTGTCCGAGAAAGAGGACGCCGTGAACAAGAT CCACACCACCGGCTTCAAGGACCAGAACGAGATGCTGAGCA GCCTGCAGAAACTGGCCGTGCTGAAGGCCGACCTGGAAAAG AAAAAGCAGTCCATGGGCAAGCTGTACTCCCTGAAGCAGGAC CTGCTGTCCACCCTGAAGAACAAGAGCGTGACCCAGAAAACC GAGGCCTGGCTGGACAACTTCGCCCGGTGCTGGGACAACCTG GTGCAGAAGCTGGAAAAGTCCACCGCCCAGATCTCCCAGGCC |
| 98 | Hinge 2 | GTGACCACAACACAGCCCAGCCTGACCCAGACCACCGTGATG GAAACCGTGACAACAGTGACCACCCGGGAACAGATCCTCGTG AAGCACGCCCAGGAAGAACTGCCCCCTCCACCCCCCCAGAAG AAACGGCAGATCACAGTGGAC |
| 99 | L2 (SEAQ linker) | AGTGAAGCTCAG |
| 100 | L3 (20-mer linker) | ATCCACACCGTGCGGGAAGAGACAATGATGGTCATGACAGA GGACATGCCCCTGGAAATC |
| 101 | Spectrin-16 | AGCTACGTGCCCAGCACCTACCTGACCGAGATCACCCATGTG TCCCAGGCCCTGCTGGAAGTGGAACAGCTGCTGAACGCCCCC GACCTGTGCGCCAAGGATTTCGAGGACCTGTTCAAGCAGGAA GAGAGCCTGAAGAATATCAAGGATAGCCTGCAGCAGAGCAG CGGCCGGATCGACATCATCCACAGCAAGAAAACAGCCGCCCT |

TABLE 6A-continued

Nucleotide sequence (and domain structure) encoding miniaturized dystrophin polypeptide BXA-196477.

| SEQ ID NO: | Description | Nucleotide Sequence |
|---|---|---|
| | | GCAGAGCGCCACCCCCGTGGAAAGAGTGAAACTGCAGGAAG CCCTGTCCCAGCTGGACTTCCAGTGGGAGAAAGTGAACAAAA TGTACAAGGACCGGCAGGGCAGATTCGACCGCAGC |
| 102 | Spectrin-17 | GTGGAAAAGTGGCGGCGGTTCCACTACGACATCAAGATCTTC AACCAGTGGCTGACAGAGGCCGAGCAGTTCCTGAGAAAGAC CCAGATCCCCGAGAACTGGGAGCACGCCAAGTACAAGTGGT ATCTGAAAGAGCTGCAGGACGGCATCGGCCAGAGACAGACA GTCGTGCGGACCCTGAATGCCACCGGCGAGGAAATCATCCAG CAGTCCAGCAAGACCGACGCCAGCATTCTGCAGGAAAAGCTG GGCAGCCTGAACCTGCGGTGGCAGGAAGTGTGCAAGCAGCT GTCCGACCGGAAGAAGCGGCTGGAAGAACAG |
| 103 | Spectrin-24 | CTGGAACGGCTGCAGGAACTGCAGGAGGCCACCGACGAGCT GGACCTGAAACTGAGACAGGCCGAAGTGATCAAGGGCAGCT GGCAGCCAGTGGGCGACCTGCTGATCGACTCCCTGCAGGACC ATCTGGAAAAAGTGAAGGCCCTGAGAGGCGAGATCGCCCCC CTGAAAGAAAACGTGTCCCACGTGAACGACCTGGCCCGGCAG CTGACAACACTGGGCATTCAGCTGAGCCCCTACAACCTGAGC ACACTGGAAGATCTGAACACCCGGTGGAAGCTGCTGCAGGTG GCCGTGGAAGATAGAGTGCGGCAGCTGCACGAG |
| 104 | Hinge 4 | GCCCACAGAGATTTTGGCCCTGCCTCCCAGCACTTCCTGAGC ACCAGTGTGCAGGGCCCTTGGGAGAGAGCCATCTCCCCTAAC AAGGTGCCCTACTACATCAACCACGAGACACAGACCACCTGT TGGGACCACCCCAAGATGACCGAGCTGTACCAGAGCCTGGCT GACCTGAACAACGTGCGGTTCAGGCCTACCGGACCGCCATGA AGCTG |
| 105 | CR/C -term | CGGAGACTGCAGAAAGCTCTGTGCCTGGATCTGCTGTCCCTG TCCGCCGCCTGTGATGCCCTGGACCAGCACAATCTGAAGCAG AACGACCAGCCCATGGATATCCTGCAGATCATCAACTGCCTG ACCACCATCTACGACCGGCTGGAACAGGAACACAACAATCTC GTGAACGTGCCCCTGTGCGTGGACATGTGCCTGAATTGGCTG CTGAATGTGTACGACACCGGCCGGACAGGCCGGATCAGAGTG CTGTCCTTCAAGACCGGCATCATCAGCCTGTGCAAAGCCCAC CTGGAAGATAAGTACCGGTATCTGTTCAAACAGGTGGCCTCT AGCACCGGCTTTTGCGACCAGAGAAGGCTGGGCCTGCTGCTG CACGACAGCATCCAGATCCCTAGACAGCTGGGCGAAGTGGCC AGCTTTGGCGGCAGCAACATCGAGCCTAGCGTGCGGAGCTGC TTCCAGTTCGCCAACAACAAGCCCGAGATCGAGGCCGCCCTG TTCCTGGACTGGATGAGACTGGAACCCCAGAGCATGGTGTGG CTGCCCGTGCTGCATAGAGTGGCCGCTGCCGAGACAGCCAAG CACCAGGCCAAGTGCAACATCTGCAAAGAGTGCCCCATCATC GGCTTCCGGTACAGAAGCCTGAAGCACTTCAACTACGATATC TGCCAGAGCTGTTTCTTCAGCGGCAGGGTGGCCAAGGGCCAC AAAATGCACTACCCCATGGTGGAATACTGCACCCCCACCACA AGCGGCGAGGATGTGCGGGATTTCGCCAAGGTGCTGAAAAA CAAGTTCCGGACCAAGCGGTACTTCGCCAAACACCCCCGGAT GGGCTACCTGCCTGTGCAGACAGTGCTGGAAGGCGACAACAT GGAAACCGACACCATGTGATGATGATTTGGGCAGAGCGATGG AGTCCTTAGTATCAGTCATGACAGATGAAGAAGGAGCAGAAT AAATGTTTTACAACTCCTGATTCCCGCATGCGGCCAGCTTATC GATACCGTCGAAATAAAAGATCCTTATTTTCATTGGATCTGTG TGTTGGTTTTTTGTGTG |

In some embodiments, a nucleic acid sequence encoding the H1 domain in the miniaturized dystrophin polypeptide is a sequence at least about 60%, at least about 70%, at least about 80%, at least about 85%, at least about 90%, at least about 95%, at least about 96%, at least about 97%, at least about 98%, at least about 99%, or about 100% identical to SEQ ID NO: 94. In some embodiments, a nucleic acid sequence encoding the R1 domain is a sequence at least about 60%, at least about 70%, at least about 80%, at least about 85%, at least about 90%, at least about 95%, at least about 96%, at least about 97%, at least about 98%, at least about 99%, or about 100% identical to SEQ ID NO: 95. In some embodiments, a nucleic acid sequence encoding the R3 domain is a sequence at least about 60%, at least about 70%, at least about 80%, at least about 85%, at least about 90%, at least about 95%, at least about 96%, at least about 97%, at least about 98%, at least about 99%, or about 100% identical to SEQ ID NO: 97. In some embodiments, a nucleic acid sequence encoding the H2 domain is a sequence at least about 60%, at least about 70%, at least about 80%, at least about 85%, at least about 90%, at least about 95%, at least about 96%, at least about 97%, at least about 98%, at least about 99%, or about 100% identical to SEQ ID NO: 98. In some embodiments, a nucleic acid sequence encoding the R16 domain is a sequence at least about 60%, at least about 70%, at least about 80%, at least about 85%, at least about 90%, at least about 95%, at least about 96%, at least about 97%, at least about 98%, at least about 99%, or about 100% identical to SEQ ID NO: 101. In some embodiments, a nucleic acid sequence encoding the R17 domain is a sequence at least about 60%, at least about 70%, at least about 80%, at least about 85%, at least about 90%, at least about 95%, at least about 96%, at least about 97%, at least about 98%, at least about 99%, or about 100% identical to SEQ ID NO: 102. In some embodiments, a nucleic acid sequence encoding the R24 domain is a sequence at least about 60%, at least about 70%, at least about 80%, at least about 85%, at least about 90%, at least about 95%, at least about 96%, at least about 97%, at least about 98%, at least about 99%, or about 100% identical to SEQ ID NO: 103. In some embodiments, a nucleic acid sequence encoding the H4 domain is a sequence at least about 60%, at least about 70%, at least about 80%, at least about 85%, at least about 90%, at least about 95%, at least about 96%, at least about 97%, at least about 98%, at least about 99%, or about 100% identical to SEQ ID NO: 104. In some embodiments, a nucleic acid sequence encoding the ABD1 domain in the miniaturized dystrophin polypeptide is a sequence at least about 60%, at least about 70%, at least about 80%, at least about 85%, at least about 90%, at least about 95%, at least about 96%, at least about 97%, at least about 98%, at least about 99%, or about 100% identical to SEQ ID NO: 93. In some embodiments, a nucleic acid sequence encoding the CR/C-term. polypeptide is a sequence at least about 60%, at least about 70%, at least about 80%, at least about 85%, at least about 90%, at least about 95%, at least about 96%, at least about 97%, at least about 98%, at least about 99%, or about 100% identical to SEQ ID NO: 105.

TABLE 6B

Nucleotide sequence (and domain structure) encoding miniaturized dystrophin polypeptide BXA-027743.

| SEQ ID NO: | Description | Nucleotide Sequence |
|---|---|---|
| 106 | 5' UTR | CCTGCGGCCGCCTTCGGCACCATTCCTCACGACACCCAAATA TGGCGACGGGTGAGGAATGGTGGGGAGTTATTTTTAGAGCGG TGAGGAAGGTGGGCAGGCAGCAGGTGTTGGCGCTCTAAAAA TAACTCCCGGGAGTTATTTTTAGAGCGGAGGAATGGTGGACA CCCAAATATGGCGACGGTTCCTCACCCGTCGCCATATTTGGGT GTCCGCCCTCGGCCGGGGCCGCATTCCTGGGGGCCGGGCGGT GCTCCCGCCCGCCTCGATAAAAGGCTCCGGGGCCGGCGGCGG CCCACGAGCTACCCGGAGGAGCGGGAGGCTCTAGACCACC |
| 107 | ABD1 | ATGCTGTGGTGGGAGGAAGTGGAAGATTGCTACGAGCGCGA GGACGTGCAGAAGAAAACCTTCACCAAATGGGTGAACGCCC AGTTCAGCAAGTTCGGCAAGCAGCACATCGAGAACCTGTTCA GCGACCTGCAGGACGGCAGACGGCTGCTGGACCTGCTGGAA GGCCTGACCGGCCAGAAGCTGCCCAAAGAGAAGGGCAGCAC CAGAGTGCACGCCCTGAACAACGTGAACAAGGCCCTGCGGGT GCTGCAGAACAACAACGTGGACCTGGTGAACATCGGCAGCA CCGACATCGTGGACGGCAACCACAAGCTGACCCTGGGCCTGA TCTGGAACATCATCCTGCACTGGCAGGTCAAAAACGTGATGA AGAACATCATGGCCGGCCTGCAGCAGACCAACAGCGAGAAG ATCCTGCTGAGCTGGGTGCGCCAGAGCACCCGGAACTACCCC CAGGTCAACGTGATCAACTTCACCACCTCTTGGAGCGACGGC CTGGCCCTGAACGCCCTGATCCACAGCCACCGGCCCGACCTG TTCGACTGGAACAGCGTGGTCTGCCAGCAGAGCGCCACCCAG CGGCTGGAACACGCCTTCAATATCGCCAGATACCAGCTGGGC ATCGAGAAGCTGCTGGATCCCGAGGACGTGGACACCACCTAC CCCGACAAGAAATCCATCCTGATGTATATCACCAGCCTGTTC CAGGTGCTGCCCCAGCAGGTGTCCATCGAGGCCATCCAGGAA GTGGAA |
| 108 | Hinge 1 | ATGCTGCCCAGACCCCCCAAAGTGACCAAAGAGGAACACTTC CAGCTGCACCACCAGATGCACTACAGCCAGCAGATCACCGTG TCCCTGGCTCAGGGCTACGAGCGGACCAGCAGCCCCAAGCCC CGGTTCAAGAGCTACGCCTACACCCAGGCCGCCTACGTGACC ACCAGCGACCCCACCAGAAGCCCATTCCCCAGCCAGCATCTG GAAGCCCCCGAGGACAAGAGCTTCGGCAGCAGCCTGATGGA AAGC |
| 108 | Spectrin-1 | GAAGTGAACCTGGACAGATACCAGACCGCCCTGGAAGAGGT GCTGTCCTGGCTGCTGAGCGCCGAGGATACACTGCAGGCCCA GGGCGAGATCAGCAACGACGTGGAAGTGGTGAAAGACCAGT TCCACACCCACGAGGGCTACATGATGGACCTGACCGCCCACC AGGGCAGAGTGGGCAACATCCTGCAGCTGGGCAGCAAGCTG ATCGGCACCGGCAAGCTGAGCGAGGACGAAGAGACAGAGGT GCAGGAACAGATGAACCTGCTGAACAGCAGATGGGAGTGCC TGCGGGTGGCCAGCATGGAAAAGCAGAGCAACCTGCAC |
| 110 | L1 | ATCCACACCGTGCGGGAAGAGACAATGATGGTGATGACCGA GGACATGCCCCTGGAAATC |
| 111 | Spectrin-16 | AGCTACGTGCCCAGCACCTACCTGACCGAGATCACCCACGTG TCCCAGGCTCTGCTGGAAGTGGAACAGCTGCTGAACGCCCCC GACCTGTGCGCCAAGGACTTCGAGGATCTGTTCAAGCAGGAA GAGAGCCTGAAGAATATCAAGGACTCCCTGCAGCAGTCCAGC GGCCGGATCGACATCATCCACAGCAAGAAAACAGCCGCCCTG |

TABLE 6B-continued

Nucleotide sequence (and domain structure) encoding miniaturized dystrophin polypeptide BXA-027743.

| SEQ ID NO: | Description | Nucleotide Sequence |
|---|---|---|
| | | CAGTCCGCCACCCCCGTGGAAAGAGTGAAGCTGCAGGAAGC CCTGAGCCAGCTGGACTTCCAGTGGGAGAAAGTGAACAAGAT GTACAAGGACCGGCAGGGCAGATTCGACCGCAGC |
| 112 | Spectrin-17 | GTGGAAAAGTGGCGGCGGTTCCACTACGACATCAAGATCTTC AACCAGTGGCTGACCGAGGCCGAGCAGTTCCTGAGAAAGAC CCAGATCCCCGAGAACTGGGAGCACGCCAAGTACAAGTGGT ATCTGAAAGAACTGCAGGATGGCATCGGCCAGCGGCAGACC GTGGTGCGCACACTGAATGCCACCGGCGAGGAAATCATCCAG CAGAGCAGCAAGACCGACGCCAGCATCCTGCAGGAAAAGCT GGGCTCCCTGAACCTGCGGTGGCAGGAAGTGTGCAAGCAGCT GAGCGACCGGAAGAAGAGGCTGGAAGAACAG |
| 113 | Hinge 3 | GCCCCTGGCCTGACCACCATCGGCGCCAGCCCTACCCAGACC GTGACCCTGGTGACACAGCCCGTGGTGACAAAAGAGACAGC CATCTCCAAGCTGGAAATGCCCAGCTCCCTGATGCTGGAA |
| 114 | Spectrin-23 | TCTGACCAGTGGAAGCGTCTGCACCTTTCTCTGCAGGAACTTC TGGTGTGGCTACAGCTGAAAGATGATGAATTAAGCCGGCAGG CACCTATTGGAGGCGACTTTCCAGCAGTTCAGAAGCAGAACG ATGTACATAGGGCCTTCAAGAGGGAATTGAAAACTAAAGAA CCTGTAATCATGAGTACTCTTGAGACTGTACGAATATTTCTGA CAGAGCAGCCTTTGGAAGGACTAGAGAAACTCTACCAGGAG CCCAGAGAGCTGCCTCCTGAGGAGAGAGCCCAGAATGTCACT CGGCTTCTACGAAAGCAGGCTGAGGAGGTCAATACTGAGTGG GAAAAATTGAACCTGCACTCCGCTGACTGGCAGAGAAAAATA GATGAGACC |
| 115 | Spectrin-24 | CTGGAAAGGCTGCAGGAACTGCAGGAGGCCACCGACGAGCT GGACCTGAAGCTGCGGCAGGCCGAAGTGATCAAGGGCAGCT GGCAGCCCGTGGGCGACCTGCTGATCGACAGCCTGCAGGACC ACCTGGAAAAAGTGAAGGCCCTGAGAGGCGAGATCGCCCCC CTGAAAGAAAACGTGTCCCACGTGAACGACCTGGCCCGGCAG CTGACCACCCTGGGCATCCAGCTGAGCCCCTACAACCTGAGC ACCCTGGAAGATCTGAACACCCGGTGGAAGCTGCTGCAGGTG GCCGTGGAAGATAGAGTGCGGCAGCTGCACGAG |
| 116 | Hinge 4 | GCCCACAGAGACTTTGGCCCTGCCAGCCAGCACTTCCTGAGC ACCTCTGTGCAGGGACCCTGGGAGAGAGCCATCAGCCCCAAC AAGGTGCCCTACTACATCAACCACGAGACACAGACCACCTGT TGGGACCACCCCAAGATGACCGAGCTGTACCAGAGCCTGGCC GACCTGAACAATGTGCGGTTCAGCGCCTACCGGACCGCCATG AAGCTG |
| 117 | CR/C-term | AGGCGGCTGCAGAAAGCTCTGTGCCTGGATCTGCTGAGCCTG AGCGCCGCCTGCGACGCCCTGGACCAGCACAACCTGAAGCAG AACGACCAGCCCATGGATATCCTGCAGATCATCAACTGCCTG ACCACAATCTACGACAGGCTGGAACAGGAACACAACAATCT GGTCAACGTGCCCCTGTGCGTGGACATGTGCCTGAATTGGCT GCTGAATGTGTACGACACCGGCCGGACCGGCAGAATCCGGGT GCTGAGCTTCAAGACCGGCATCATCAGCCTGTGCAAGGCCCA CCTGGAAGATAAGTACCGCTACCTGTTCAAACAGGTGGCCAG CTCCACCGGCTTTTGCGACCAGCGGAGACTGGGCCTGCTGCT GCACGACAGCATCCAGATCCCCAGACAGCTGGGCGAGGTGG CCTCCTTCGGCGGCAGCAACATTGAGCCCAGCGTGCGGAGCT GCTTCCAGTTCGCCAACAACAAGCCCGAGATCGAGGCCGCCC TGTTCCTGGACTGGATGAGACTGGAACCCCAGAGCATGGTGT GGCTGCCCGTGCTGCATCGGGTGGCCGCTGCCGAGACAGCCA AGCACCAGGCCAAGTGCAACATCTGCAAAGAGTGCCCCATCA TCGGCTTCCGGTACAGAAGCCTGAAGCACTTCAACTACGATA TCTGCCAGAGCTGCTTCTTCAGCGGCAGAGTGGCCAAGGGCC ACAAAATGCACTACCCCATGGTGGAATACTGCACCCCCACCA CCAGCGGCGAGGATGTGCGGGACTTCGCCAAGGTGCTGAAA AACAAGTTCCGGACCAAGCGGTACTTTGCCAAGCACCCCCGG ATGGGCTACCTGCCCGTGCAGACAGTGCTGGAAGGCGACAAC ATGGAAACCCCTGCCCAGATCCTGATCAGCCTGGAAAGCGAG GAACGGGGCGAGCTGGAACGGATCCTGGCCGATCTGGAAGA GGAAAACCGGAACCTGCAGGCCGAGTACGACCGGCTGAAGC AGCAGCACGAGCACAAGGGCCTGAGCCCCCTGCCTAGCCCCC CTGACACCATGTGA |

The various miniaturized dystrophin polypeptides of the present disclosure are shown in Table 7.

TABLE 7

Amino Acid Sequences of miniaturized dystrophin constructs.

| SEQ ID NO and Description | Sequence |
|---|---|
| SEQ ID NO: 118-BXA-196477 | MLWWEEVEDCYEREDVQKKTFTKWVNAQFSKFGKQHIENLFSDLQDG<br>RRLLDLLEGLTGQKLPKEKGSTRVHALNNVNKALRVLQNNNVDLVNIG<br>STDIVDGNHKLTLGLIWNIILHWQVKNVMKNIMAGLQQTNSEKILLSWV<br>RQSTRNYPQVNVINETTSWSDGLALNALIHSHRPDLEDWNSVVCQQSAT<br>QRLEHAFNIARYQLGIEKLLDPEDVDTTYPDKKSILMYITSLFQVLPQQV<br>SIEAIQEVEMLPRPPKVTKEEHEQLHHQMHYSQQITVSLAQGYERTSSPK<br>PRFKSYAYTQAAYVTTSDPTRSPFPSQHLEAPEDKSFGSSLMESEVNLDR<br>YQTALEEVLSWLLSAEDTLQAQGEISNDVEVVKDQFHTHEGYMMDLTA<br>HQGRVGNILQLGSKLIGTGKLSEDEETEVQEQMNLLNSRWECLRVASM<br>EKQSNLHRVLLKWQRLTEEQCLFSAWLSEKEDAVNKIHTTGEKDQNEM<br>LSSLQKLAVLKADLEKKKQSMGKLYSLKQDLLSTLKNKSVTQKTEAWL<br>DNFARCWDNLVQKLEKSTAQISQAVTTTQPSLTQTTVMETVTTVTTREQ<br>ILVKHAQEELPPPPPQKKRQITVDSEAQIHTVREETMMVMTEDMPLEISY<br>VPSTYLTEITHVSQALLEVEQLLNAPDLCAKDFEDLFKQEESLKNIKDSL<br>QQSSGRIDIIHSKKTAALQSATPVERVKLQEALSQLDFQWEKVNKMYKD<br>RQGREDRSVEKWRREHYDIKIENQWLTEAEQFLRKTQIPENWEHAKYK<br>WYLKELQDGIGQRQTVVRTLNATGEEIIQQSSKTDASILQEKLGSLNLR<br>WQEVCKQLSDRKKRLEEQLERLQELQEATDELDLKLRQAEVIKGSWQP<br>VGDLLIDSLQDHLEKVKALRGEIAPLKENVSHVNDLARQLTTLGIQLSPY<br>NLSTLEDLNTRWKLLQVAVEDRVRQLHEAHRDFGPASQHFLSTSVQGP<br>WERAISPNKVPYYINHETQTTCWDHPKMTELYQSLADLNNVRFSAYRT<br>AMKLRRLQKALCLDLLSLSAACDALDQHNLKQNDQPMDILQIINCLTTI<br>YDRLEQEHNNLVNVPLCVDMCLNWLLNVYDTGRTGRIRVLSEKTGIISL<br>CKAHLEDKYRYLFKQVASSTGECDQRRLGLLLHDSIQIPRQLGEVASFG<br>GSNIEPSVRSCFQFANNKPEIEAALFLDWMRLEPQSMVWLPVLHRVAAA<br>ETAKHQAKCNICKECPIIGERYRSLKHFNYDICQSCEFSGRVAKGHKMH<br>YPMVEYCTPTTSGEDVRDFAKVLKNKFRTKRYFAKHPRMGYLPVQTVL<br>EGDNMETDTM |
| SEQ ID NO: 119-BXA-196473 | MLWWEEVEDCYEREDVQKKTFTKWVNAQFSKFGKQHIENLFSDLQDG<br>RRLLDLLEGLTGQKLPKEKGSTRVHALNNVNKALRVLQNNNVDLVNIG<br>STDIVDGNHKLTLGLIWNIILHWQVKNVMKNIMAGLQQTNSEKILLSWV<br>RQSTRNYPQVNVINETTSWSDGLALNALIHSHRPDLEDWNSVVCQQSAT<br>QRLEHAFNIARYQLGIEKLLDPEDVDTTYPDKKSILMYITSLFQVLPQQV<br>SIEAIQEVEMLPRPPKVTKEEHFQLHHQMHYSQQITVSLAQGYERTSSPK<br>PRFKSYAYTQAAYVTTSDPTRSPFPSQHLEAPEDKSFGSSLMESEVNLDR<br>YQTALEEVLSWLLSAEDTLQAQGEISNDVEVVKDQFHTHEGYMMDLTA<br>HQGRVGNILQLGSKLIGTGKLSEDEETEVQEQMNLLNSRWECLRVASM<br>EKQSNLHLLKWQRLTEEQCLFSAWLSEKEDAVNKIHTTGFKDQNEMLS<br>SLQKLAVLKADLEKKKQSMGKLYSLKQDLLSTLKNKSVTQKTEAWLD<br>NEARCWDNLVQKLEKSTAQISQAVTTTQPSLTQTTVMETVTTVTTREQI<br>LVKHAQEELPPPPPQKKRQITVDIHTVREETMMVMTEDMPLEISYVPSTY<br>LTEITHVSQALLEVEQLLNAPDLCAKDFEDLFKQEESLKNIKDSLQQSSG<br>RIDIIHSKKTAALQSATPVERVKLQEALSQLDFQWEKVNKMYKDRQGRF<br>DRSVEKWRRFHYDIKIFNQWLTEAEQFLRKTQIPENWEHAKYKWYLKE<br>LQDGIGQRQTVVRTLNATGEEIIQQSSKTDASILQEKLGSLNLRWQEVCK<br>QLSDRKKRLEEQLERLQELQEATDELDLKLRQAEVIKGSWQPVGDLLID<br>SLQDHLEKVKALRGEIAPLKENVSHVNDLARQLTTLGIQLSPYNLSTLED<br>LNTRWKLLQVAVEDRVRQLHEAHRDFGPASQHFLSTSVQGPWERAISP<br>NKVPYYINHETQTTCWDHPKMTELYQSLADLNNVRFSAYRTAMKLRRL<br>QKALCLDLLSLSAACDALDQHNLKQNDQPMDILQIINCLTTIYDRLEQEH<br>NNLVNVPLCVDMCLNWLLNVYDTGRTGRIRVLSFKTGIISLCKAHLEDK<br>YRYLFKQVASSTGFCDQRRLGLLLHDSIQIPRQLGEVASFGGSNIEPSVRS<br>CFQFANNKPEIEAALFLDWMRLEPQSMVWLPVLHRVAAAETAKHQAK<br>CNICKECPIIGFRYRSLKHFNYDICQSCFFSGRVAKGHKMHYPMVEYCTP<br>TTSGEDVRDFAKVLKNKFRTKRYFAKHPRMGYLPVQTVLEGDNMETDT<br>M |
| SEQ ID NO: 120-BXA-196474 | MLWWEEVEDCYEREDVQKKTFTKWVNAQFSKFGKQHIENLFSDLQDG<br>RRLLDLLEGLTGQKLPKEKGSTRVHALNNVNKALRVLQNNNVDLVNIG<br>STDIVDGNHKLTLGLIWNIILHWQVKNVMKNIMAGLQQTNSEKILLSWV<br>RQSTRNYPQVNVINFTTSWSDGLALNALIHSHRPDLFDWNSVVCQQSAT<br>QRLEHAFNIARYQLGIEKLLDPEDVDTTYPDKKSILMYITSLFQVLPQQV<br>SIEAIQEVEMLPRPPKVTKEEHFQLHHQMHYSQQITVSLAQGYERTSSPK<br>PRFKSYAYTQAAYVTTSDPTRSPFPSQHLEAPEDKSFGSSLMESEVNLDR<br>YQTALEEVLSWLLSAEDTLQAQGEISNDVEVVKDQFHTHEGYMMDLTA<br>HQGRVGNILQLGSKLIGTGKLSEDEETEVQEQMNLLNSRWECLRVASM<br>EKQSNLHLLKWQRLTEEQCLFSAWLSEKEDAVNKIHTTGFKDQNEMLS<br>SLQKLAVLKADLEKKKQSMGKLYSLKQDLLSTLKNKSVTQKTEAWLD<br>NEARCWDNLVQKLEKSTAQISQAVTTTQPSLTQTTVMETVTTVTTREQI<br>LVKHAQEELPPPPPQKKRQITVDSEAQIHTVREETMMVMTEDMPLEISY<br>VPSTYLTEITHVSQALLEVEQLLNAPDLCAKDFEDLFKQEESLKNIKDSL<br>QQSSGRIDIIHSKKTAALQSATPVERVKLQEALSQLDFQWEKVNKMYKD<br>RQGRFDRSVEKWRRFHYDIKIFNQWLTEAEQFLRKTQIPENWEHAKYK |

TABLE 7-continued

Amino Acid Sequences of miniaturized dystrophin constructs.

| SEQ ID NO and Description | Sequence |
|---|---|
| | WYLKELQDGIGQRQTVVRTLNATGEEIIQQSSKTDASILQEKLGSLNLR<br>WQEVCKQLSDRKKRLEEQKNILQELQEATDELDLKLRQAEVIKGSWQP<br>VGDLLIDSLQDHLEKVKALRGEIAPLKENVSHVNDLARQLTTLGIQLSPY<br>NLSTLEDLNTRWKLLQVAVEDRVRQLHEAHRDFGPASQHFLSTSVQGP<br>WERAISPNKVPYYINHETQTTCWDHPKMTELYQSLADLNNVRFSAYRT<br>AMKLRRLQKALCLDLLSLSAACDALDQHNLKQNDQPMDILQIINCLTTI<br>YDRLEQEHNNLVNVPLCVDMCLNWLLNVYDTGRTGRIRVLSFKTGIISL<br>CKAHLEDKYRYLFKQVASSTGFCDQRRLGLLLHDSIQIPRQLGEVASFG<br>GSNIEPSVRSCFQFANNKPEIEAALFLDWMRLEPQSMVWLPVLHRVAAA<br>ETAKHQAKCNICKECPIIGFRYRSLKHFNYDICQSCFFSGRVAKGHKMH<br>YPMVEYCTPTTSGEDVRDFAKVLKNKFRTKRYFAKHPRMGYLPVQTVL<br>EGDNMETTPCDDDLGRAMESLVSVMTDEEGAE |
| SEQ ID NO: 121-BXA-196475 | MLWWEEVEDCYEREDVQKKTFTKWVNAQFSKFGKQHIENLFSDLQDG<br>RRLLDLLEGLTGQKLPKEKGSTRVHALNNVNKALRVLQNNNVDLVNIG<br>STDIVDGNHKLTLGLIWNIILHWQVKNVMKNIMAGLQQTNSEKILLSWV<br>RQSTRNYPQVNVINFTTSWSDGLALNALIHSHRPDLFDWNSVVCQQSAT<br>QRLEHAFNIARYQLGIEKLLDPEDVDTTYPDKKSILMYITSLFQVLPQQV<br>SIEAIQEVEMLPRPPKVTKEEHFQLHHQMHYSQQITVSLAQGYERTSSPK<br>PRFKSYAYTQAAYVTTSDPTRSPFPSQHLEAPEDKSFGSSLMESEVNLDR<br>YQTALEEVLSWLLSAEDTLQAQGEISNDVEVVKDQFHTHEGYMMDLTA<br>HQGRVGNILQLGSKLIGTGKLSEDEETEVQEQMNLLNSRWECLRVASM<br>EKQSNLHLLKWQRLTEEQCLFSAWLSEKEDAVNKIHTTGFKDQNEMLS<br>SLQKLAVLKADLEKKKQSMGKLYSLKQDLLSTLKNKSVTQKTEAWLD<br>NFARCWDNLVQKLEKSTAQISQAVTTTQPSLTQTTVMETVTTVTTREQI<br>LVKHAQEELPPPPPQKKRQITVDSEAQIHTVREETMMVMTEDMPLEISY<br>VPSTYLTEITHVSQALLEVEQLLNAPDLCAKDFEDLFKQEESLKNIKDSL<br>QQSSGRIDIIHSKKTAALQSATPVERVKLQEALSQLDFQWEKVNKMYKD<br>RQGRFDRSVEKWRRFHYDIKIFNQWLTEAEQFLRKTQIPENWEHAKYK<br>WYLKELQDGIGQRQTVVRTLNATGEEIIQQSSKTDASILQEKLGSLNLR<br>WQEVCKQLSDRKKRLEEQKLERLQELQEATDELDLKLRQAEVIKGSWQ<br>PVGDLLIDSLQDHLEKVKALRGEIAPLKENVSHVNDLARQLTTLGIQLSP<br>YNLSTLEDLNTRWKLLQVAVEDRVRQLHEAHRDFGPASQHFLSTSVQG<br>PWERAISPNKVPYYINHETQTTCWDHPKMTELYQSLADLNNVRFSAYRT<br>AMKLRRLQKALCLDLLSLSAACDALDQHNLKQNDQPMDILQIINCLTTI<br>YDRLEQEHNNLVNVPLCVDMCLNWLLNVYDTGRTGRIRVLSFKTGIISL<br>CKAHLEDKYRYLFKQVASSTGFCDQRRLGLLLHDSIQIPRQLGEVASFG<br>GSNIEPSVRSCFQFANNKPEIEAALFLDWMRLEPQSMVWLPVLHRVAAA<br>ETAKHQAKCNICKECPIIGFRYRSLKHFNYDICQSCFFSGRVAKGHKMH<br>YPMVEYCTPTTSGEDVRDFAKVLKNKFRTKRYFAKHPRMGYLPVQTVL<br>EGDNMETDTM |
| SEQ ID NO: 122-BXA-196476 | MLWWEEVEDCYEREDVQKKTFTKWVNAQFSKFGKQHIENLFSDLQDG<br>RRLLDLLEGLTGQKLPKEKGSTRVHALNNVNKALRVLQNNNVDLVNIG<br>STDIVDGNHKLTLGLIWNIILHWQVKNVMKNIMAGLQQTNSEKILLSWV<br>RQSTRNYPQVNVINFTTSWSDGLALNALIHSHRPDLFDWNSVVCQQSAT<br>QRLEHAFNIARYQLGIEKLLDPEDVDTTYPDKKSILMYITSLFQVLPQQV<br>SIEAIQEVEMLPRPPKVTKEEHFQLHHQMHYSQQITVSLAQGYERTSSPK<br>PRFKSYAYTQAAYVTTSDPTRSPFPSQHLEAPEDKSFGSSLMESEVNLDR<br>YQTALEEVLSWLLSAEDTLQAQGEISNDVEVVKDQFHTHEGYMMDLTA<br>HQGRVGNILQLGSKLIGTGKLSEDEETEVQEQMNLLNSRWECLRVASM<br>EKQSNLHLLKWQRLTEEQCLFSAWLSEKEDAVNKIHTTGFKDQNEMLS<br>SLQKLAVLKADLEKKKQSMGKLYSLKQDLLSTLKNKSVTQKTEAWLD<br>NEARCWDNLVQKLEKSTAQISQAVTTTQPSLTQTTVMETVTTVTTREQI<br>LVKHAQEELPPPPPQKKRQITVDSEAQIHTVREETMMVMTEDMPLEISY<br>VPSTYLTEITHVSQALLEVEQLLNAPDLCAKDFEDLFKQEESLKNIKDSL<br>QQSSGRIDIIHSKKTAALQSATPVERVKLQEALSQLDFQWEKVNKMYKD<br>RQGRFDRSVEKWRRFHYDIKIFNQWLTEAEQFLRKTQIPENWEHAKYK<br>WYLKELQDGIGQRQTVVRTLNATGEEIIQQSSKTDASILQEKLGSLNLR<br>WQEVCKQLSDRKKRLEEQKNILERLQELQEATDELDLKLRQAEVIKGS<br>WQPVGDLLIDSLQDHLEKVKALRGEIAPLKENVSHVNDLARQLTTLGIQ<br>LSPYNLSTLEDLNTRWKLLQVAVEDRVRQLHEAHRDFGPASQHFLSTSV<br>QGPWERAISPNKVPYYINHETQTTCWDHPKMTELYQSLADLNNVRFSA<br>YRTAMKLRRLQKALCLDLLSLSAACDALDQHNLKQNDQPMDILQIINCL<br>TTIYDRLEQEHNNLVNVPLCVDMCLNWLLNVYDTGRTGRIRVLSFKTGI<br>ISLCKAHLEDKYRYLFKQVASSTGFCDQRRLGLLLHDSIQIPRQLGEVAS<br>FGGSNIEPSVRSCFQFANNKPEIEAALFLDWMRLEPQSMVWLPVLHRVA<br>AAETAKHQAKCNICKECPIIGFRYRSLKHFNYDICQSCFFSGRVAKGHK<br>MHYPMVEYCTPTTSGEDVRDFAKVLKNKFRTKRYFAKHPRMGYLPVQ<br>TVLEGDNMETDTM |
| SEQ ID NO: 123-BXA- | MLWWEEVEDCYEREDVQKKTFTKWVNAQFSKFGKQHIENLFSDLQDG<br>RRLLDLLEGLTGQKLPKEKGSTRVHALNNVNKALRVLQNNNVDLVNIG<br>STDIVDGNHKLTLGLIWNIILHWQVKNVMKNIMAGLQQTNSEKILLSWV |

TABLE 7-continued

| Amino Acid Sequences of miniaturized dystrophin constructs. | |
|---|---|
| SEQ ID NO and Description | Sequence |
| 196477-Q | RQSTRNYPQVNVINFTTSWSDGLALNALIHSHRPDLFDWNSVVCQQSAT QRLEHAFNIARYQLGIEKLLDPEDVDTTYPDKKSILMYITSLFQVLPQQV SIEAIQEVEMLPRPPKVTKEEHFQLHHQMHYSQQITVSLAQGYERTSSPK PRFKSYAYTQAAYVTTSDPTRSPFPSQHLEAPEDKSFGSSLMESEVNLDR YQTALEEVLSWLLSAEDTLQAQGEISNDVEVVKDQFHTHEGYMMDLTA HQGRVGNILQLGSKLIGTGKLSEDEETEVQEQMNLLNSRWECLRVASM EKQSNLHRVLLKWQRLTEEQCLFSAWLSEKEDAVNKIHTTGFKDQNEM LSSLQKLAVLKADLEKKKQSMGKLYSLKQDLLSTLKNKSVTQKTEAWL DNFARCWDNLVQKLEKSTAQISQAVTTTQPSLTQTTVMETVTTVTTREQ ILVKHAQEELPPPPPQKKRQITVDSEAQIHTVREETMMVMTEDMPLEISY VPSTYLTEITHVSQALLEVEQLLNAPDLCAKDFEDLFKQEESLKNIKDSL QQSSGRIDIIHSKKTAALQSATPVERVKLQEALSQLDFQWEKVNKMYKD RQGRFDRSVEKWRRFHYDIKIFNQWLTEAEQFLRKTQIPENWEHAKYK WYLKELQDGIGQRQTVVRTLNATGEEIIQQSSKTDASILQEKLGSLNLR WQEVCKQLSDRKKRLEEQLERLQELQEATDELDLKLRQAEVIKGSWQP VGDLLIDSLQDHLEKVKALRGEIAPLKENVSHVNDLARQLTTLGIQLSPY NLSTLEDLNTRWKLLQVAVEDRVRQLHEAHRDFGPASQHFLSTSVQGP WERAISPNKVPYYINHETQTTCWDHPKMTELYQSLADLNNVRFSAYRT AMKLRRLQKALCLDLLSLSAACDALDQHNLKQNDQPMDILQIINCLTTI YDRLEQEHNNLVNVPLCVDMCLNWLLNVYDTGRTGRIRVLSFKTGIISL CKAHLEDKYRYLFKQVASSTGFCDQRRLGLLLHDSIQIPRQLGEVASFG GSNIEPSVRSCFQFANNKPEIEAALFLDWMRLEPQSMVWLPVLHRVAAA ETAKHQAKCNICKECPIIGFRYRSLKHFNYDICQSCFFSGRVAKGHKMH YPMVEYCTPTTSGEDVRDFAKVLKNKFRTKRYFAKHPRMGYLPVQTVL EGDNMETDTM |
| SEQ ID NO: 124-BXA-196478 | MLWWEEVEDCYEREDVQKKTFTKWVNAQFSKFGKQHIENLFSDLQDG RRLLDLLEGLTGQKLPKEKGSTRVHALNNVNKALRVLQNNNVDLVNIG STDIVDGNHKLTLGLIWNIILHWQVKNVMKNIMAGLQQTNSEKILLSWV RQSTRNYPQVNVINFTTSWSDGLALNALIHSHRPDLFDWNSVVCQQSAT QRLEHAFNIARYQLGIEKLLDPEDVDTTYPDKKSILMYITSLFQVLPQQV SIEAIQEVEMLPRPPKVTKEEHFQLHHQMHYSQQITVSLAQGYERTSSPK PRFKSYAYTQAAYVTTSDPTRSPFPSQHLEAPEDKSFGSSLMESEVNLDR YQTALEEVLSWLLSAEDTLQAQGEISNDVEVVKDQFHTHEGYMMDLTA HQGRVGNILQLGSKLIGTGKLSEDEETEVQEQMNLLNSRWECLRVASM EKQSNLHRVLLQDILLKWQRLTEEQCLFSAWLSEKEDAVNKIHTTGFKD QNEMLSSLQKLAVLKADLEKKKQSMGKLYSLKQDLLSTLKNKSVTQKT EAWLDNFARCWDNLVQKLEKSTAQISQAVTTTQPSLTQTTVMETVTTV TTREQILVKHAQEELPPPPPQKKRQITVDSEAQIHTVREETMMVMTEDM PLEISYVPSTYLTEITHVSQALLEVEQLLNAPDLCAKDFEDLFKQEESLKN IKDSLQQSSGRIDIIHSKKTAALQSATPVERVKLQEALSQLDFQWEKVNK MYKDRQGRFDRSVEKWRRFHYDIKIFNQWLTEAEQFLRKTQIPENWEH AKYKWYLKELQDGIGQRQTVVRTLNATGEEIIQQSSKTDASILQEKLGSL NLRWQEVCKQLSDRKKRLEEQLERLQELQEATDELDLKLRQAEVIKGS WQPVGDLLIDSLQDHLEKVKALRGEIAPLKENVSHVNDLARQLTTLGIQ LSPYNLSTLEDLNTRWKLLQVAVEDRVRQLHEAHRDFGPASQHFLSTSV QGPWERAISPNKVPYYINHETQTTCWDHPKMTELYQSLADLNNVRFSA YRTAMKLRRLQKALCLDLLSLSAACDALDQHNLKQNDQPMDILQIINCL TTIYDRLEQEHNNLVNVPLCVDMCLNWLLNVYDTGRTGRIRVLSFKTGI ISLCKAHLEDKYRYLFKQVASSTGFCDQRRLGLLLHDSIQIPRQLGEVAS FGGSNIEPSVRSCFQFANNKPEIEAALFLDWMRLEPQSMVWLPVLHRVA AAETAKHQAKCNICKECPIIGFRYRSLKHFNYDICQSCFFSGRVAKGHK MHYPMVEYCTPTTSGEDVRDFAKVLKNKFRTKRYFAKHPRMGYLPVQ TVLEGDNMETDTM |
| SEQ ID NO: 125-BXA-196479 | MLWWEEVEDCYEREDVQKKTFTKWVNAQFSKFGKQHIENLFSDLQDG RRLLDLLEGLTGQKLPKEKGSTRVHALNNVNKALRVLQNNNVDLVNIG STDIVDGNHKLTLGLIWNIILHWQVKNVMKNIMAGLQQTNSEKILLSWV RQSTRNYPQVNVINFTTSWSDGLALNALIHSHRPDLFDWNSVVCQQSAT QRLEHAFNIARYQLGIEKLLDPEDVDTTYPDKKSILMYITSLFQVLPQQV SIEAIQEVEMLPRPPKVTKEEHFQLHHQMHYSQQITVSLAQGYERTSSPK PRFKSYAYTQAAYVTTSDPTRSPFPSQHLEAPEDKSFGSSLMESEVNLDR YQTALEEVLSWLLSAEDTLQAQGEISNDVEVVKDQFHTHEGYMMDLTA HQGRVGNILQLGSKLIGTGKLSEDEETEVQEQMNLLNSRWECLRVASM EKQSNLHLLKWQRLTEEQCLFSAWLSEKEDAVNKIHTTGFKDQNEMLS SLQKLAVLKADLEKKKQSMGKLYSLKQDLLSTLKNKSVTQKTEAWLD NFARCWDNLVQKLEKSTAQISQAVTTTQPSLTQTTVMETVTTVTTREQI LVKHAQEELPPPPPQKKRQITVDSEAQIHTVREETMMVMTEDMPLEISY VPSTYLTEITHVSQALLEVEQLLNAPDLCAKDFEDLFKQEESLKNIKDSL QQSSGRIDIIHSKKTAALQSATPVERVKLQEALSQLDFQWEKVNKMYKD RQGRFDRSVEKWRRFHYDIKIFNQWLTEAEQFLRKTQIPENWEHAKYK WYLKELQDGIGQRQTVVRTLNATGEEIIQQSSKTDASILQEKLGSLNLR WQEVCKQLSDRKKRLEEQLERLQELQEATDELDLKLRQAEVIKGSWQP VGDLLIDSLQDHLEKVKALRGEIAPLKENVSHVNDLARQLTTLGIQLSPY |

TABLE 7-continued

Amino Acid Sequences of miniaturized dystrophin constructs.

| SEQ ID NO and Description | Sequence |
|---|---|
| | NLSTLEDLNTRWKLLQVAVEDRVRQLHEAHRDFGPASQHFLSTSVQGP WERAISPNKVPYYINHETQTTCWDHPKMTELYQSLADLNNVRFSAYRT AMKLRRLQKALCLDLLSLSAACDALDQHNLKQNDQPMDILQIINCLTTI YDRLEQEHNNLVNVPLCVDMCLNWLLNVYDTGRTGRIRVLSFKTGIISL CKAHLEDKYRYLFKQVASSTGFCDQRRLGLLLHDSIQIPRQLGEVASFG GSNIEPSVRSCFQFANNKPEIEAALFLDWMRLEPQSMVWLPVLHRVAAA ETAKHQAKCNICKECPIIGFRYRSLKHFNYDICQSCFFSGRVAKGHKMH YPMVEYCTPTTSGEDVRDFAKVLKNKFRTKRYFAKHPRMGYLPVQTVL EGDNMETDTM |
| SEQ ID NO: 126- BXA- 196480 | MLWWEEVEDCYEREDVQKKTFTKWVNAQFSKFGKQHIENLFSDLQDG RRLLDLLEGLTGQKLPKEKGSTRVHALNNVNKALRVLQNNNVDLVNIG STDIVDGNHKLTLGLIWNIILHWQVKNVMKNIMAGLQQTNSEKILLSWV RQSTRNYPQVNVINFTTSWSDGLALNALIHSHRPDLFDWNSVVCQQSAT QRLEHAFNIARYQLGIEKLLDPEDVDTTYPDKKSILMYITSLFQVLPQQV SIEAIQEVEMLPRPPKVTKEEHFQLHHQMHYSQQITVSLAQGYERTSSPK PRFKSYAYTQAAYVTTSDPTRSPFPSQHLEAPEDKSFGSSLMESEVNLDR YQTALEEVLSWLLSAEDTLQAQGEISNDVEVVKDQFHTHEGYMMDLTA HQGRVGNILQLGSKLIGTGKLSEDEETEVQEQMNLLNSRWECLRVASM EKQSNLHIHTVREETMMVMTEDMPLEISYVPSTYLTEITHVSQALLEVEQ LLNAPDLCAKDFEDLFKQEESLKNIKDSLQQSSGRIDIIHSKKTAALQSAT PVERVKLQEALSQLDFQWEKVNKMYKDRQGRFDRSVEKWRRFHYDIKI FNQWLTEAEQFLRKTQIPENWEHAKYKWYLKELQDGIGQRQTVVRTLN ATGEEIIQQSSKTDASILQEKLGSLNLRWQEVCKQLSDRKKRLEEQAPGL TTIGASPTQTVTLVTQPVVTKETAISKLEMPSSLMLELERLQELQEATDE LDLKLRQAEVIKGSWQPVGDLLIDSLQDHLEKVKALRGEIAPLKENVSH VNDLARQLTTLGIQLSPYNLSTLEDLNTRWKLLQVAVEDRVRQLHEAH RDFGPASQHFLSTSVQGPWERAISPNKVPYYINHETQTTCWDHPKMTEL YQSLADLNNVRFSAYRTAMKLRRLQKALCLDLLSLSAACDALDQHNLK QNDQPMDILQIINCLTTIYDRLEQEHNNLVNVPLCVDMCLNWLLNVYDT GRTGRIRVLSFKTGIISLCKAHLEDKYRYLFKQVASSTGFCDQRRLGLLL HDSIQIPRQLGEVASFGGSNIEPSVRSCFQFANNKPEIEAALFLDWMRLEP QSMVWLPVLHRVAAAETAKHQAKCNICKECPIIGFRYRSLKHFNYDICQ SCFFSGRVAKGHKMHYPMVEYCTPTTSGEDVRDFAKVLKNKFRTKRYF AKHPRMGYLPVQTVLEGDNMETPAQILISLESEERGELERILADLEEENR NLQAEYDRLKQQHEHKGLSPLPSPPDTM |
| SEQ ID NO: 127- BXA- 196480- Variant | MLWWEEVEDCYEREDVQKKTFTKWVNAQFSKFGKQHIENLFSDLQDG RRLLDLLEGLTGQKLPKEKGSTRVHALNNVNKALRVLQNNNVDLVNIG STDIVDGNHKLTLGLIWNIILHWQVKNVMKNIMAGLQQTNSEKILLSWV RQSTRNYPQVNVINFTTSWSDGLALNALIHSHRPDLFDWNSVVCQQSAT QRLEHAFNIARYQLGIEKLLDPEDVDTTYPDKKSILMYITSLFQVLPQQV SIEAIQEVEMLPRPPKVTKEEHFQLHHQMHYSQQITVSLAQGYERTSSPK PRFKSYAYTQAAYVTTSDPTRSPFPSQHLEAPEDKSFGSSLMESEVNLDR YQTALEEVLSWLLSAEDTLQAQGEISNDVEVVKDQFHTHEGYMMDLTA HQGRVGNILQLGSKLIGTGKLSEDEETEVQEQMNLLNSRWECLRVASM EKQSNLHRVLIHTVREETMMVMTEDMPLEISYVPSTYLTEITHVSQALLE VEQLLNAPDLCAKDFEDLFKQEESLKNIKDSLQQSSGRIDIIHSKKTAAL QSATPVERVKLQEALSQLDFQWEKVNKMYKDRQGRFDRSVEKWRRFH YDIKIFNQWLTEAEQFLRKTQIPENWEHAKYKWYLKELQDGIGQRQTV VRTLNATGEEIIQQSSKTDASILQEKLGSLNLRWQEVCKQLSDRKKRLEE QKNDLAPGLTTIGASPTQTVTLVTQPVVTKETAISKLEMPSSLMLEVERL QELQEATDELDLKLRQAEVIKGSWQPVGDLLIDSLQDHLEKVKALRGEI APLKENVSHVNDLARQLTTLGIQLSPYNLSTLEDLNTRWKLLQVAVEDR VRQLHEAHRDFGPASQHFLSTSVQGPWERAISPNKVPYYINHETQTTCW DHPKMTELYQSLADLNNVRFSAYRTAMKLRRLQKALCLDLLSLSAACD ALDQHNLKQNDQPMDILQIINCLTTIYDRLEQEHNNLVNVPLCVDMCLN WLLNVYDTGRTGRIRVLSFKTGIISLCKAHLEDKYRYLFKQVASSTGFCD QRRLGLLLHDSIQIPRQLGEVASFGGSNIEPSVRSCFQFANNKPEIEAALF LDWMRLEPQSMVWLPVLHRVAAAETAKHQAKCNICKECPIIGFRYRSL KHFNYDICQSCFFSGRVAKGHKMHYPMVEYCTPTTSGEDVRDFAKVLK NKFRTKRYFAKHPRMGYLPVQTVLEGDNMETPAQILISLESEERGELERI LADLEEENRNLQAEYDRLKQQHEHKGLSPLPSPPDTM |
| SEQ ID NO: 128- BXA- 196481 | MLWWEEVEDCYEREDVQKKTFTKWVNAQFSKFGKQHIENLFSDLQDG RRLLDLLEGLTGQKLPKEKGSTRVHALNNVNKALRVLQNNNVDLVNIG STDIVDGNHKLTLGLIWNIILHWQVKNVMKNIMAGLQQTNSEKILLSWV RQSTRNYPQVNVINFTTSWSDGLALNALIHSHRPDLFDWNSVVCQQSAT QRLEHAFNIARYQLGIEKLLDPEDVDTTYPDKKSILMYITSLFQVLPQQV SIEAIQEVEMLPRPPKVTKEEHFQLHHQMHYSQQITVSLAQGYERTSSPK PRFKSYAYTQAAYVTTSDPTRSPFPSQHLEAPEDKSFGSSLMESEVNLDR YQTALEEVLSWLLSAEDTLQAQGEISNDVEVVKDQFHTHEGYMMDLTA HQGRVGNILQLGSKLIGTGKLSEDEETEVQEQMNLLNSRWECLRVASM EKQSNLHSYVPSTYLTEITHVSQALLEVEQLLNAPDLCAKDFEDLFKQEE |

TABLE 7-continued

Amino Acid Sequences of miniaturized dystrophin constructs.

| SEQ ID NO and Description | Sequence |
|---|---|
| | SLKNIKDSLQQSSGRIDIIHSKKTAALQSATPVERVKLQEALSQLDFQWE KVNKMYKDRQGREDRSVEKWRREHYDIKIENQWLTEAEQFLRKTQIPE NWEHAKYKWYLKELQDGIGQRQTVVRTLNATGEEIIQQSSKTDASILQE KLGSLNLRWQEVCKQLSDRKKRLEEQLEGLEKLYQEPRELPPEERAQNV TRLLRKQAEEVNTEWEKLNLHSADWQRKIDETLERLQELQEATDELDL KLRQAEVIKGSWQPVGDLLIDSLQDHLEKVKALRGEIAPLKENVSHVND LARQLTTLGIQLSPYNLSTLEDLNTRWKLLQVAVEDRVRQLHEAHRDFG PASQHFLSTSVQGPWERAISPNKVPYYINHETQTTCWDHPKMTELYQSL ADLNNVRFSAYRTAMKLRRLQKALCLDLLSLSAACDALDQHNLKQND QPMDILQIINCLTTIYDRLEQEHNNLVNVPLCVDMCLNWLLNVYDTGRT GRIRVLSFKTGIISLCKAHLEDKYRYLFKQVASSTGFCDQRRLGLLLHDSI QIPRQLGEVASFGGSNIEPSVRSCFQFANNKPEIEAALFLDWMRLEPQSM VWLPVLHRVAAAETAKHQAKCNICKECPIIGFRYRSLKHFNYDICQSCFF SGRVAKGHKMHYPMVEYCTPTTSGEDVRDFAKVLKNKFRTKRYFAKH PRMGYLPVQTVLEGDNMETPAQILISLESEERGELERILADLEEENRNLQ AEYDRLKQQHEHKGLSPLPSPPDTM |
| SEQ ID NO: 129-BXA-027741 | MLWWEEVEDCYEREDVQKKTFTKWVNAQFSKFGKQHIENLFSDLQDG RRLLDLLEGLTGQKLPKEKGSTRVHALNNVNKALRVLQNNNVDLVNIG STDIVDGNHKLTLGLIWNIILHWQVKNVMKNIMAGLQQTNSEKILLSWV RQSTRNYPQVNVINFTTSWSDGLALNALIHSHRPDLFDWNSVVCQQSAT QRLEHAFNIARYQLGIEKLLDPEDVDTTYPDKKSILMYITSLFQVLPQQV SIEAIQEVEMLPRPPKVTKEEHFQLHHQMHYSQQITVSLAQGYERTSSPK PRFKSYAYTQAAYVTTSDPTRSPFPSQHLEAPEDKSFGSSLMESEVNLDR YQTALEEVLSWLLSAEDTLQAQGEISNDVEVVKDQFHTHEGYMMDLTA HQGRVGNILQLGSKLIGTGKLSEDEETEVQEQMNLLNSRWECLRVASM EKQSNLHLLKWQRLTEEQCLFSAWLSEKEDAVNKIHTTGFKDQNEMLS SLQKLAVLKADLEKKKQSMGKLYSLKQDLLSTLKNKSVTQKTEAWLD NEARCWDNLVQKLEKSTAQISQAVTTTQPSLTQTTVMETVTTVTTREQI LVKHAQEELPPPPPQKKRQITVDIHTVREETMMVMTEDMPLEISYVPSTY LTEITHVSQALLEVEQLLNAPDLCAKDFEDLFKQEESLKNIKDSLQQSSG RIDIIHSKKTAALQSATPVERVKLQEALSQLDFQWEKVNKMYKDRQGRF DRSVEKWRREHYDIKIENQWLTEAEQFLRKTQIPENWEHAKYKWYLKE LQDGIGQRQTVVRTLNATGEEIIQQSSKTDASILQEKLGSLNLRWQEVCK QLSDRKKRLEEQLERLQELQEATDELDLKLRQAEVIKGSWQPVGDLLID SLQDHLEKVKALRGEIAPLKENVSHVNDLARQLTTLGIQLSPYNLSTLED LNTRWKLLQVAVEDRVRQLHEAHRDFGPASQHFLSTSVQGPWERAISP NKVPYYINHETQTTCWDHPKMTELYQSLADLNNVRFSAYRTAMKLRRL QKALCLDLLSLSAACDALDQHNLKQNDQPMDILQIINCLTTIYDRLEQEH NNLVNVPLCVDMCLNWLLNVYDTGRTGRIRVLSFKTGIISLCKAHLEDK YRYLFKQVASSTGFCDQRRLGLLLHDSIQIPRQLGEVASFGGSNIEPSVRS CFQFANNKPEIEAALFLDWMRLEPQSMVWLPVLHRVAAAETAKHQAK CNICKECPIIGFRYRSLKHFNYDICQSCFFSGRVAKGHKMHYPMVEYCTP TTSGEDVRDFAKVLKNKFRTKRYFAKHPRMGYLPVQTVLEGDNMETPA QILISLESEERGELERILADLEEENRNLQAEYDRLKQQHEHKGLSPLPSPP DTM |
| SEQ ID NO: 130-BXA-027744 | MLWWEEVEDCYEREDVQKKTFTKWVNAQFSKFGKQHIENLFSDLQDG RRLLDLLEGLTGQKLPKEKGSTRVHALNNVNKALRVLQNNNVDLVNIG STDIVDGNHKLTLGLIWNIILHWQVKNVMKNIMAGLQQTNSEKILLSWV RQSTRNYPQVNVINFTTSWSDGLALNALIHSHRPDLFDWNSVVCQQSAT QRLEHAFNIARYQLGIEKLLDPEDVDTTYPDKKSILMYITSLFQVLPQQV SIEAIQEVEMLPRPPKVTKEEHFQLHHQMHYSQQITVSLAQGYERTSSPK PRFKSYAYTQAAYVTTSDPTRSPFPSQHLEAPEDKSFGSSLMESEVNLDR YQTALEEVLSWLLSAEDTLQAQGEISNDVEVVKDQFHTHEGYMMDLTA HQGRVGNILQLGSKLIGTGKLSEDEETEVQEQMNLLNSRWECLRVASM EKQSNLHIHTVREETMMVMTEDMPLEISYVPSTYLTEITHVSQALLEVEQ LLNAPDLCAKDFEDLFKQEESLKNIKDSLQQSSGRIDIIHSKKTAALQSAT PVERVKLQEALSQLDFQWEKVNKMYKDRQGRFDRSVEKWRRFHYDIKI FNQWLTEAEQFLRKTQIPENWEHAKYKWYLKELQDGIGQRQTVVRTLN ATGEEIIQQSSKTDASILQEKLGSLNLRWQEVCKQLSDRKKRLEEQAPGL TTIGASPTQTVTLVTQPVVTKETAISKLEMPSSLMLEVPALADFNRAWTE LTDWLSLLDQVIKSQRVMVGDLEDINEMIIKQKATMQDLEQRRPQLEEL ITAAQNLKNKTSNQEARTIITDRIERIQNQWDEVQEHLQNRRQQLNEML ERLQELQEATDELDLKLRQAEVIKGSWQPVGDLLIDSLQDHLEKVKALR GEIAPLKENVSHVNDLARQLTTLGIQLSPYNLSTLEDLNTRWKLLQVAV EDRVRQLHEAHRDFGPASQHFLSTSVQGPWERAISPNKVPYYINHETQT TCWDHPKMTELYQSLADLNNVRFSAYRTAMKLRRLQKALCLDLLSLSA ACDALDQHNLKQNDQPMDILQIINCLTTIYDRLEQEHNNLVNVPLCVDM CLNWLLNVYDTGRTGRIRVLSFKTGIISLCKAHLEDKYRYLFKQVASST GFCDQRRLGLLLHDSIQIPRQLGEVASFGGSNIEPSVRSCFQFANNKPEIE AALFLDWMRLEPQSMVWLPVLHRVAAAETAKHQAKCNICKECPIIGFR YRSLKHFNYDICQSCFFSGRVAKGHKMHYPMVEYCTPTTSGEDVRDFA |

TABLE 7-continued

Amino Acid Sequences of miniaturized dystrophin constructs.

| SEQ ID NO and Description | Sequence |
|---|---|
| | KVLKNKFRTKRYFAKHPRMGYLPVQTVLEGDNMETPAQILISLESEERG<br>ELERILADLEEENRNLQAEYDRLKQQHEHKGLSPLPSPPDTM |
| SEQ ID NO: 131-BXA-027742 | MLWWEEVEDCYEREDVQKKTFTKWVNAQFSKFGKQHIENLFSDLQDG<br>RRLLDLLEGLTGQKLPKEKGSTRVHALNNVNKALRVLQNNNVDLVNIG<br>STDIVDGNHKLTLGLIWNIILHWQVKNVMKNIMAGLQQTNSEKILLSWV<br>RQSTRNYPQVNVINFTTSWSDGLALNALIHSHRPDLFDWNSVVCQQSAT<br>QRLEHAFNIARYQLGIEKLLDPEDVDTTYPDKKSILMYITSLFQVLPQQV<br>SIEAIQEVEMLPRPPKVTKEEHFQLHHQMHYSQQITVSLAQGYERTSSPK<br>PRFKSYAYTQAAYVTTSDPTRSPFPSQHLEAPEDKSFGSSLMESEVNLDR<br>YQTALEEVLSWLLSAEDTLQAQGEISNDVEVVKDQFHTHEGYMMDLTA<br>HQGRVGNILQLGSKLIGTGKLSEDEETEVQEQMNLLNSRWECLRVASM<br>EKQSNLHRVLMDLQNQKLKELNDWLTKTEERTRKMEEEPLGPDLEDLK<br>RQVQQHKVLQEDLEQEQVRVNSLTHMVVVVDESSGDHATAALEEQLK<br>VLGDRWANICRWTEDRWVLLQDILLKWQRLTEEQCLFSAWLSEKEDA<br>VNKIHTTGFKDQNEMLSSLQKLAVLKADLEKKKQSMGKLYSLKQDLLS<br>TLKNKSVTQKTEAWLDNFARCWDNLVQKLEKSTAQISQAIHTVREETM<br>MVMTEDMPLEISYVPSTYLTEITHVSQALLEVEQLLNAPDLCAKDFEDLF<br>KQEESLKNIKDSLQQSSGRIDIIHSKKTAALQSATPVERVKLQEALSQLDF<br>QWEKVNKMYKDRQGREDRSVEKWRREHYDIKIENQWLTEAEQFLRKT<br>QIPENWEHAKYKWYLKELQDGIGQRQTVVRTLNATGEEIIQQSSKTDAS<br>ILQEKLGSLNLRWQEVCKQLSDRKKRLEEQLERLQELQEATDELDLKLR<br>QAEVIKGSWQPVGDLLIDSLQDHLEKVKALRGEIAPLKENVSHVNDLAR<br>QLTTLGIQLSPYNLSTLEDLNTRWKLLQVAVEDRVRQLHEAHRDFGPAS<br>QHFLSTSVQGPWERAISPNKVPYYINHETQTTCWDHPKMTELYQSLADL<br>NNVRFSAYRTAMKLRRLQKALCLDLLSLSAACDALDQHNLKQNDQPM<br>DILQIINCLTTIYDRLEQEHNNLVNVPLCVDMCLNWLLNVYDTGRTGRIR<br>VLSFKTGIISLCKAHLEDKYRYLFKQVASSTGFCDQRRLGLLLHDSIQIPR<br>QLGEVASFGGSNIEPSVRSCFQFANNKPEIEAALFLDWMRLEPQSMVWL<br>PVLHRVAAAETAKHQAKCNICKECPIIGFRYRSLKHFNYDICQSCFFSGR<br>VAKGHKMHYPMVEYCTPTTSGEDVRDFAKVLKNKFRTKRYFAKHPRM<br>GYLPVQTVLEGDNMETDTM |
| SEQ ID NO: 132-BXA-027743 | MLWWEEVEDCYEREDVQKKTFTKWVNAQFSKFGKQHIENLFSDLQDG<br>RRLLDLLEGLTGQKLPKEKGSTRVHALNNVNKALRVLQNNNVDLVNIG<br>STDIVDGNHKLTLGLIWNIILHWQVKNVMKNIMAGLQQTNSEKILLSWV<br>RQSTRNYPQVNVINFTTSWSDGLALNALIHSHRPDLFDWNSVVCQQSAT<br>QRLEHAFNIARYQLGIEKLLDPEDVDTTYPDKKSILMYITSLFQVLPQQV<br>SIEAIQEVEMLPRPPKVTKEEHF'QLHHQMHYSQQITVSLAQGYERTSSPK<br>PRFKSYAYTQAAYVTTSDPTRSPFPSQHLEAPEDKSFGSSLMESEVNLDR<br>YQTALEEVLSWLLSAEDTLQAQGEISNDVEVVKDQFHTHEGYMMDLTA<br>HQGRVGNILQLGSKLIGTGKLSEDEETEVQEQMNLLNSRWECLRVASM<br>EKQSNLHIHTVREETMMVMTEDMPLEISYVPSTYLTEITHVSQALLEVEQ<br>LLNAPDLCAKDFEDLFKQEESLKNIKDSLQQSSGRIDIIHSKKTAALQSAT<br>PVERVKLQEALSQLDFQWEKVNKMYKDRQGRFDRSVEKWRRFHYDIKI<br>FNQWLTEAEQFLRKTQIPENWEHAKYKWYLKELQDGIGQRQTVVRTLN<br>ATGEEIIQQSSKTDASILQEKLGSLNLRWQEVCKQLSDRKKRLEEQAPGL<br>TTIGASPTQTVTLVTQPVVTKETAISKLEMPSSLMLESDQWKRLHLSLQE<br>LLVWLQLKDDELSRQAPIGGDEPAVQKQNDVHRAFKRELKTKEPVEVIST<br>LETVRIFLTEQPLEGLEKLYQEPRELPPEERAQNVTRLLRKQAEEVNTEW<br>EKLNLHSADWQRKIDETLERLQELQEATDELDLKLRQAEVIKGSWQPV<br>GDLLIDSLQDHLEKVKALRGEIAPLKENVSHVNDLARQLTTLGIQLSPYN<br>LSTLEDLNTRWKLLQVAVEDRVRQLHEAHRDFGPASQHFLSTSVQGPW<br>ERAISPNKVPYYINHETQTTCWDHPKMTELYQSLADLNNVRFSAYRTA<br>MKLRRLQKALCLDLLSLSAACDALDQHNLKQNDQPMDILQIINCLTTIY<br>DRLEQEHNNLVNVPLCVDMCLNWLLNVYDTGRTGRIRVLSFKTGIISLC<br>KAHLEDKYRYLFKQVASSTGFCDQRRLGLLLHDSIQIPRQLGEVASFGGS<br>NIEPSVRSCFQFANNKPEIEAALFLDWMRLEPQSMVWLPVLHRVAAAET<br>AKHQAKCNICKECPIIGFRYRSLKHFNYDICQSCFFSGRVAKGHKMHYP<br>MVEYCTPTTSGEDVRDFAKVLKNKFRTKRYFAKHPRMGYLPVQTVLEG<br>DNMETPAQILISLESEERGELERILADLEEENRNLQAEYDRLKQQHEHKG<br>LSPLPSPPDTM |

In some embodiments, the miniaturized dystrophin polypeptide comprises an amino acid sequence at least about 70%, at least about 75%, at least about 80%, at least about 85%, at least about 90%, at least about 95%, at least about 96%, at least about 97%, at least about 98%, at least about 99%, or about 100% identical to SEQ ID NOs: 118-132, wherein the amino acid sequence when expressed has at least one dystrophin activity. In some embodiments, the miniaturized dystrophin polypeptide comprises an amino acid sequence at least about 70%, at least about 75%, at least about 80%, at least about 85%, at least about 90%, at least about 95%, at least about 96%, at least about 97%, at least about 98%, at least about 99%, or about 100% identical to one of SEQ ID NO: 118 (BXA-196477), SEQ ID NO:119 (BXA-196473), SEQ ID NO: 120 (BXA-196474), SEQ ID NO: 121 (BXA-196475), SEQ ID NO: 122 (BXA-196476), SEQ ID NO: 124 (BXA-196478), or SEQ ID NO: 125 (BXA-196479). In some embodiments, the miniaturized dystrophin polypeptide comprises an amino acid sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 118, wherein the amino acid sequence when expressed has at least one dystrophin activity. In some embodiments, the miniaturized dystrophin polypeptide comprises an amino acid sequence at least about 60%, at least about 70%, at least about 80%, at least about 85%, at least about 90%, at least about 95%, at least about 96%, at least about 97%, at least about 98%, at least about 99%, or about 100% identical to SEQ ID NO: 119, wherein the amino acid sequence when expressed has at least one dystrophin activity. In some embodiments, the miniaturized dystrophin polypeptide comprises an amino acid sequence at least about 60%, at least about 70%, at least about 80%, at least about 85%, at least about 90%, at least about 95%, at least about 96%, at least about 97%, at least about 98%, at least about 99%, or about 100% identical to SEQ ID NO: 120, wherein the amino acid sequence when expressed has at least one dystrophin activity. In some embodiments, the miniaturized dystrophin polypeptide comprises an amino acid sequence at least about 60%, at least about 70%, at least about 80%, at least about 85%, at least about 90%, at least about 95%, at least about 96%, at least about 97%, at least about 98%, at least about 99%, or about 100% identical to SEQ ID NO: 121, wherein the amino acid sequence when expressed has at least one dystrophin activity. In some embodiments, the miniaturized dystrophin polypeptide comprises an amino acid sequence at least about 60%, at least about 70%, at least about 80%, at least about 85%, at least about 90%, at least about 95%, at least about 96%, at least about 97%, at least about 98%, at least about 99%, or about 100% identical to SEQ ID NO: 122, wherein the amino acid sequence when expressed has at least one dystrophin activity. In some embodiments, the miniaturized dystrophin polypeptide comprises an amino acid sequence at least about 60%, at least about 70%, at least about 80%, at least about 85%, at least about 90%, at least about 95%, at least about 96%, at least about 97%, at least about 98%, at least about 99%, or about 100% identical to SEQ ID NO: 123, wherein the amino acid sequence when expressed has at least one dystrophin activity. In some embodiments, the miniaturized dystrophin polypeptide comprises an amino acid sequence at least about 60%, at least about 70%, at least about 80%, at least about 85%, at least about 90%, at least about 95%, at least about 96%, at least about 97%, at least about 98%, at least about 99%, or about 100% identical to SEQ ID NO: 124, wherein the amino acid sequence when expressed has at least one dystrophin activity. In some embodiments, the miniaturized dystrophin polypeptide comprises an amino acid sequence at least about 60%, at least about 70%, at least about 80%, at least about 85%, at least about 90%, at least about 95%, at least about 96%, at least about 97%, at least about 98%, at least about 99%, or about 100% identical to SEQ ID NO: 125, wherein the amino acid sequence when expressed has at least one dystrophin activity.

In certain embodiments, the miniaturized dystrophin polypeptide comprises an amino acid sequence at least about 60%, at least about 70%, at least about 80%, at least about 85%, at least about 90%, at least about 95%, at least about 96%, at least about 97%, at least about 98%, at least about 99%, or about 100% identical to SEQ ID NO: 126, wherein the amino acid sequence when expressed has at least one dystrophin activity. In certain embodiments, the miniaturized dystrophin polypeptide comprises an amino acid sequence at least about 60%, at least about 70%, at least about 80%, at least about 85%, at least about 90%, at least about 95%, at least about 96%, at least about 97%, at least about 98%, at least about 99%, or about 100% identical to SEQ ID NO: 127, wherein the amino acid sequence when expressed has at least one dystrophin activity. In certain embodiments, the miniaturized dystrophin polypeptide comprises an amino acid sequence at least about 60%, at least about 70%, at least about 80%, at least about 85%, at least about 90%, at least about 95%, at least about 96%, at least about 97%, at least about 98%, at least about 99%, or about 100% identical to SEQ ID NO: 128, wherein the amino acid sequence when expressed has at least one dystrophin activity. In certain embodiments, the miniaturized dystrophin polypeptide comprises an amino acid sequence at least about 60%, at least about 70%, at least about 80%, at least about 85%, at least about 90%, at least about 95%, at least about 96%, at least about 97%, at least about 98%, at least about 99%, or about 100% identical to SEQ ID NO: 129, wherein the amino acid sequence when expressed has at least one dystrophin activity. In certain embodiments, the miniaturized dystrophin polypeptide comprises an amino acid sequence at least about 60%, at least about 70%, at least about 80%, at least about 85%, at least about 90%, at least about 95%, at least about 96%, at least about 97%, at least about 98%, at least about 99%, or about 100% identical to SEQ ID NO: 130, wherein the amino acid sequence when expressed has at least one dystrophin activity. In certain embodiments, the miniaturized dystrophin polypeptide comprises an amino acid sequence at least about 60%, at least about 70%, at least about 80%, at least about 85%, at least about 90%, at least about 95%, at least about 96%, at least about 97%, at least about 98%, at least about 99%, or about 100% identical to SEQ ID NO: 131, wherein the amino acid sequence when expressed has at least one dystrophin activity. In certain embodiments, the miniaturized dystrophin polypeptide comprises an amino acid sequence at least about 60%, at least about 70%, at least about 80%, at least about 85%, at least about 90%, at least about 95%, at least about 96%, at least about 97%, at least about 98%, at least about 99%, or about 100% identical to SEQ ID NO: 132, wherein the amino acid sequence when expressed has at least one dystrophin activity.

In some embodiments, the miniaturized dystrophin polypeptide encoded by the nucleic acid molecule has formula (I):

H1-R1-L1-R3-H2-L2-L3-R16-R17-R24-H4 (I)

wherein: H1 is a hinge 1 domain of dystrophin; R1 is a spectrin repeat 1 domain of dystrophin; L1 is amino acids Arg-Val (RV); R3 is a spectrin repeat 3 domain of dystrophin; H2 is a hinge 2 domain of dystrophin; L2 is the amino acid sequence set forth in SEQ ID NO:74 (SEAQ); L3 is the amino acid sequence set forth in SEQ ID NO:75 (IHTVREE TMMVMTEDMP LEI); R16 is a spectrin repeat 16 of dystrophin; R17 is a spectrin repeat 17 of dystrophin; R24 is a spectrin repeat 24 of dystrophin; H4 is a hinge 4 domain of dystrophin; and (-) is a peptide bond.

In some embodiments, the miniaturized dystrophin polypeptide encoded by the nucleic acid molecule exhibits one or more properties selected from the group consisting of (i) having a lower CD4 proliferation compared to BXA-027741, (ii) having a lower CD8 proliferation compared to BXA-027741, and (iv) any combination thereof.

In some embodiments, the miniaturized dystrophin polypeptide encoded by the nucleic acid molecule has formula (II):

H1-R1-L-R16-R17-H3-R23-R24-H4 (II)

wherein: H1 is a hinge 1 domain of dystrophin; R1 is a spectrin repeat 1 domain of dystrophin; L is amino acids SEQ ID NO:84 (IHTVREETMMVMTEDMPLEI); R16 is a spectrin repeat 16 of dystrophin; R17 is a spectrin repeat 17 of dystrophin; H3 is a hinge 3 domain of dystrophin; R23 is a spectrin repeat 23 of dystrophin; R24 is a spectrin repeat 24 of dystrophin; H4 is a hinge 4 domain of dystrophin; and (-) is a peptide bond.

In some embodiments, the miniaturized dystrophin polypeptide encoded by the nucleic acid molecule comprises an amino acid sequence at least about 60%, at least about 70%, at least about 80%, at least about 85%, at least about 90%, at least about 95%, at least about 96%, at least about 97%, at least about 98%, at least about 99%, or about 100% identical to SEQ ID NO: 132.

In some embodiments, the nucleotide sequence comprises a sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% identical to the nucleotide sequence of SEQ ID NO: 147.

In some embodiments, the miniaturized dystrophin polypeptide exhibits a higher expression of the miniaturized dystrophin polypeptide than BXA-196481. In some other embodiments, the miniaturized dystrophin polypeptide expression is at least about 1.5 fold, at least about 1.6 fold, at least about 1.7 fold, at least about 1.8 fold, at least about 1.9 fold, at least about 2 fold, at least about 2.1 fold, at least about 2.2 fold, at least about 2.3 fold, at least about 2.4 fold, at least about 2.5 fold, at least about 2.6 fold, at least about 2.7 fold, at least about 2.8 fold, at least about 2.9 fold or at least about 3 fold higher than the BXA-196481 polypeptide expression.

In some embodiments, the miniaturized dystrophin polypeptides can be encoded by nucleotide sequences. Some examples of the nucleotide sequences are shown in Table 8.

TABLE 8

Nucleotide Sequences of Dystrophin constructs.

| SEQ ID NO and Description | Sequence |
|---|---|
| SEQ ID NO: 133-BXA-196477 | ATGCTGTGGTGGGAGGAAGTGGAAGATTGCTACGAGCGCGAGGACG TGCAGAAGAAAACCTTCACCAAATGGGTGAACGCCCAGTTCAGCAA GTTCGGCAAGCAGCACATCGAGAACCTGTTCAGCGACCTGCAGGACG GCAGACGGCTGCTGGACCTGCTGGAAGGCCTGACCGGCCAGAAGCT GCCCAAAGAGAAGGGCAGCACCAGAGTGCACGCCCTGAACAACGTG AACAAGGCCCTGCGGGTGCTGCAGAACAACAACGTGGACCTGGTGA ACATCGGCAGCACCGACATCGTGGACGGCAACCACAAGCTGACCCTG GGCCTGATCTGGAACATCATCCTGCACTGGCAGGTCAAAAACGTGAT GAAGAACATCATGGCCGGCCTGCAGCAGACCAACAGCGAGAAGATC CTGCTGAGCTGGGTGCGCCAGAGCACCCGGAACTACCCCCAGGTCAA CGTGATCAACTTCACCACCTCTTGGAGCGACGGCCTGGCCCTGAACG CCCTGATCCACAGCCACCGGCCCGACCTGTTCGACTGGAACAGCGTG GTCTGCCAGCAGAGCGCCACCCAGCGGCTGGAACACGCCTTCAATAT CGCCAGATACCAGCTGGGCATCGAGAAGCTGCTGGATCCCGAGGAC GTGGACACCACCTACCCCGACAAGAAATCCATCCTGATGTATATCAC CAGCCTGTTCCAGGTGCTGCCCCAGCAGGTGTCCATCGAGGCCATCC AGGAAGTGGAAATGCTGCCCAGACCCCCCAAAGTGACCAAAGAGGA ACACTTCCAGCTGCACCACCAGATGCACTACAGCCAGCAGATCACCG TGTCCCTGGCCCAGGGCTACGAGAGAACCAGCAGCCCCAAGCCCCGG TTCAAGAGCTACGCCTATACCCAGGCCGCCTACGTGACCACCAGCGA CCCTACCAGAAGCCCATTCCCCAGCCAGCATCTGGAAGCCCCCGAGG ACAAGAGCTTCGGCAGCAGCCTGATGGAAAGCGAAGTGAACCTGGA CAGATACCAGACCGCCCTGGAAGAGGTGCTGAGCTGGCTGCTGAGCG CCGAGGATACACTGCAGGCTCAGGGCGAGATCAGCAACGACGTGGA AGTCGTGAAGGACCAGTTCCACACCCACGAGGGCTACATGATGGACC TGACAGCCCACCAGGGCAGAGTGGGCAACATCCTGCAGCTGGGCTCC AAGCTGATCGGCACCGGCAAGCTGAGCGAGGACGAAGAGACAGAGG TGCAGGAACAGATGAACCTGCTGAACAGCAGATGGGAGTGCCTGCG GGTGGCCAGCATGGAAAAGCAGAGCAACCTGCATAGGGTCCTGCTG AAGTGGCAGCGGCTGACCGAGGAACAGTGCCTGTTTAGCGCCTGGCT GTCCGAGAAAGAGGACGCCGTGAACAAGATCCACACCACCGGCTTC AAGGACCAGAACGAGATGCTGAGCAGCCTGCAGAAACTGGCCGTGC TGAAGGCCGACCTGGAAAAGAAAAAGCAGTCCATGGGCAAGCTGTA CTCCCTGAAGCAGGACCTGCTGTCCACCCTGAAGAACAAGAGCGTGA CCCAGAAAACCGAGGCCTGGCTGGACAACTTCGCCCGGTGCTGGGAC AACCTGGTGCAGAAGCTGGAAAAGTCCACCGCCCAGATCTCCCAGGC CGTGACCACAACACAGCCCAGCCTGACCCAGACCACCGTGATGGAA ACCGTGACAACAGTGACCACCCGGGAACAGATCCTCGTGAAGCACG CCCAGGAAGAACTGCCCCCTCCACCCCCCCAGAAGAAACGGCAGATC ACAGTGGACAGTGAAGCTCAGATCCACACCGTGCGGGAAGAGACAA TGATGGTCATGACAGAGGACATGCCCCTGGAAATCAGCTACGTGCCC AGCACCTACCTGACCGAGATCACCCATGTGTCCCAGGCCCTGCTGGA AGTGGAACAGCTGCTGAACGCCCCCGACCTGTGCGCCAAGGATTTCG AGGACCTGTTCAAGCAGGAAGAGAGCCTGAAGAATATCAAGGATAG CCTGCAGCAGAGCAGCGGCCGGATCGACATCATCCACAGCAAGAAA ACAGCCGCCCTGCAGAGCGCCACCCCCGTGGAAAGAGTGAAACTGC |

TABLE 8-continued

| Nucleotide Sequences of Dystrophin constructs. | |
|---|---|
| SEQ ID NO and Description | Sequence |
| | AGGAAGCCCTGTCCCAGCTGGACTTCCAGTGGGAGAAAGTGAACAA AATGTACAAGGACCGGCAGGGCAGATTCGACCGCAGCGTGGAAAAG TGGCGGCGGTTCCACTACGACATCAAGATCTTCAACCAGTGGCTGAC AGAGGCCGAGCAGTTCCTGAGAAAGACCCAGATCCCCGAGAACTGG GAGCACGCCAAGTACAAGTGGTATCTGAAAGAGCTGCAGGACGGCA TCGGCCAGAGACAGACAGTCGTGCGGACCCTGAATGCCACCGGCGA GGAAATCATCCAGCAGTCCAGCAAGACCGACGCCAGCATTCTGCAGG AAAAGCTGGGCAGCCTGAACCTGCGGTGGCAGGAAGTGTGCAAGCA GCTGTCCGACCGGAAGAAGCGGCTGGAAGAACAGCTGGAACGGCTG CAGGAACTGCAGGAGGCCACCGACGAGCTGGACCTGAAACTGAGAC AGGCCGAAGTGATCAAGGGCAGCTGGCAGCCAGTGGGCGACCTGCT GATCGACTCCCTGCAGGACCATCTGGAAAAAGTGAAGGCCCTGAGA GGCGAGATCGCCCCCCTGAAAGAAAACGTGTCCCACGTGAACGACCT GGCCCGGCAGCTGACAACACTGGGCATTCAGCTGAGCCCCTACAACC TGAGCACACTGGAAGATCTGAACACCCGGTGGAAGCTGCTGCAGGTG GCCGTGGAAGATAGAGTGCGGCAGCTGCACGAGGCCCACAGAGATT TTGGCCCTGCCTCCCAGCACTTCCTGAGCACCAGTGTGCAGGGCCCTT GGGAGAGAGCCATCTCCCCTAACAAGGTGCCCTACTACATCAACCAC GAGACACAGACCACCTGTTGGGACCACCCCAAGATGACCGAGCTGTA CCAGAGCCTGGCTGACCTGAACAACGTGCGGTTCAGCGCCTACCGGA CCGCCATGAAGCTGCGGAGACTGCAGAAAGCTCTGTGCCTGGATCTG CTGTCCCTGTCCGCCGCCTGTGATGCCCTGGACCAGCACAATCTGAA GCAGAACGACCAGCCCATGGATATCCTGCAGATCATCAACTGCCTGA CCACCATCTACGACCGGCTGGAACAGGAACACAACAATCTCGTGAAC GTGCCCCTGTGCGTGGACATGTGCCTGAATTGGCTGCTGAATGTGTA CGACACCGGCCGGACAGGCCGGATCAGAGTGCTGTCCTTCAAGACCG GCATCATCAGCCTGTGCAAAGCCCACCTGGAAGATAAGTACCGGTAT CTGTTCAAACAGGTGGCCTCTAGCACCGGCTTTTGCGACCAGAGAAG GCTGGGCCTGCTGCTGCACGACAGCATCCAGATCCCTAGACAGCTGG GCGAAGTGGCCAGCTTTGGCGGCAGCAACATCGAGCCTAGCGTGCGG AGCTGCTTCCAGTTCGCCAACAACAAGCCCGAGATCGAGGCCGCCCT GTTCCTGGACTGGATGAGACTGGAACCCCAGAGCATGGTGTGGCTGC CCGTGCTGCATAGAGTGGCCGCTGCCGAGACAGCCAAGCACCAGGCC AAGTGCAACATCTGCAAAGAGTGCCCCATCATCGGCTTCCGGTACAG AAGCCTGAAGCACTTCAACTACGATATCTGCCAGAGCTGTTTCTTCA GCGGCAGGGTGGCCAAGGGCCACAAAATGCACTACCCCATGGTGGA ATACTGCACCCCCACCACAAGCGGCGAGGATGTGCGGGATTTCGCCA AGGTGCTGAAAAACAAGTTCCGGACCAAGCGGTACTTCGCCAAACAC CCCCGGATGGGCTACCTGCCTGTGCAGACAGTGCTGGAAGGCGACAA CATGGAAACCGACACCATGTGATGATGATTTGGGCAGAGCGATGGA GTCCTTAGTATCAGTCATGACAGATGAAGAAGGAGCAGAATAAATGT TTTACAACTCCTGATTCCCGCATGCGGCCAGCTTATCGATACCGTCGA AATAAAAGATCCTTATTTTCATTGGATCTGTGTGTTGGTTTTTTGTGT G |
| SEQ ID NO: 134-BXA-196473 | ATGCTGTGGTGGGAGGAAGTGGAAGATTGCTACGAGCGCGAGGACG TGCAGAAGAAAACCTTCACCAAATGGGTGAACGCCCAGTTCAGCAA GTTCGGCAAGCAGCACATCGAGAACCTGTTCAGCGACCTGCAGGACG GCAGACGGCTGCTGGACCTGCTGGAAGGCCTGACCGGCCAGAAGCT GCCCAAAGAGAAGGGCAGCACCAGAGTGCACGCCCTGAACAACGTG AACAAGGCCCTGCGGGTGCTGCAGAACAACAACGTGGACCTGGTGA ACATCGGCAGCACCGACATCGTGGACGGCAACCACAAGCTGACCCTG GGCCTGATCTGGAACATCATCCTGCACTGGCAGGTCAAAAACGTGAT GAAGAACATCATGGCCGGCCTGCAGCAGACCAACAGCGAGAAGATC CTGCTGAGCTGGGTGCGCCAGAGCACCCGGAACTACCCCCAGGTCAA CGTGATCAACTTCACCACCTCTTGGAGCGACGGCCTGGCCCTGAACG CCCTGATCCACAGCCACCGGCCCGACCTGTTCGACTGGAACAGCGTG GTCTGCCAGCAGAGCGCCACCCAGCGGCTGGAACACGCCTTCAATAT CGCCAGATACCAGCTGGGCATCGAGAAGCTGCTGGATCCCGAGGAC GTGGACACCACCTACCCCGACAAGAAATCCATCCTGATGTATATCAC CAGCCTGTTCCAGGTGCTGCCCCAGCAGGTGTCCATCGAGGCCATCC AGGAAGTGGAAATGCTGCCCAGACCCCCCAAAGTGACCAAAGAGGA ACACTTCCAGCTGCACCACCAGATGCACTACAGCCAGCAGATCACCG TGTCCCTGGCCCAGGGCTACGAGAGAACCAGCAGCCCCAAGCCCCGG TTCAAGAGCTACGCCTATACCCAGGCCGCCTACGTGACCACCAGCGA CCCTACCAGAAGCCCATTCCCCAGCCAGCATCTGGAAGCCCCCGAGG ACAAGAGCTTCGGCAGCAGCCTGATGGAAAGCGAAGTGAACCTGGA CAGATACCAGACCGCCCTGGAAGAGGTGCTGAGCTGGCTGCTGAGCG CCGAGGATACACTGCAGGCTCAGGGCGAGATCAGCAACGACGTGGA AGTCGTGAAGGACCAGTTCCACACCCACGAGGGCTACATGATGGACC TGACAGCCCACCAGGGCAGAGTGGGCAACATCCTGCAGCTGGGCTCC AAGCTGATCGGCACCGGCAAGCTGAGCGAGGACGAAGAGACAGAGG TGCAGGAACAGATGAACCTGCTGAACAGCAGATGGGAGTGCCTGCG GGTGGCCAGCATGGAAAAGCAGAGCAACCTGCATCTGCTGAAGTGG |

TABLE 8-continued

| Nucleotide Sequences of Dystrophin constructs. | |
|---|---|
| SEQ ID NO and Description | Sequence |
| | CAGCGGCTGACCGAGGAACAGTGCCTGTTTAGCGCCTGGCTGTCCGA<br>GAAAGAGGACGCCGTGAACAAGATCCACACCACCGGCTTCAAGGAC<br>CAGAACGAGATGCTGAGCAGCCTGCAGAAACTGGCCGTGCTGAAGG<br>CCGACCTGGAAAAGAAAAAGCAGTCCATGGGCAAGCTGTACTCCCTG<br>AAGCAGGACCTGCTGTCCACCCTGAAGAACAAGAGCGTGACCCAGA<br>AAACCGAGGCCTGGCTGGACAACTTCGCCCGGTGCTGGGACAACCTG<br>GTGCAGAAGCTGGAAAAGTCCACCGCCCAGATCTCCCAGGCCGTGAC<br>CACAACACAGCCCAGCCTGACCCAGACCACCGTGATGGAAACCGTG<br>ACAACAGTGACCACCCGGGAACAGATCCTCGTGAAGCACGCCCAGG<br>AAGAACTGCCCCCTCCACCCCCCCAGAAGAAACGGCAGATCACAGTG<br>GACATCCACACCGTGCGGGAAGAGACAATGATGGTCATGACAGAGG<br>ACATGCCCCTGGAAATCAGCTACGTGCCCAGCACCTACCTGACCGAG<br>ATCACCCATGTGTCCCAGGCCCTGCTGGAAGTGGAACAGCTGCTGAA<br>CGCCCCCGACCTGTGCGCCAAGGATTTCGAGGACCTGTTCAAGCAGG<br>AAGAGAGCCTGAAGAATATCAAGGATAGCCTGCAGCAGAGCAGCGG<br>CCGGATCGACATCATCCACAGCAAGAAAACAGCCGCCCTGCAGAGC<br>GCCACCCCCGTGGAAAGAGTGAAACTGCAGGAAGCCCTGTCCCAGCT<br>GGACTTCCAGTGGGAGAAAGTGAACAAAATGTACAAGGACCGGCAG<br>GGCAGATTCGACCGCAGCGTGGAAAAGTGGCGGCGGTTCCACTACG<br>ACATCAAGATCTTCAACCAGTGGCTGACAGAGGCCGAGCAGTTCCTG<br>AGAAAGACCCAGATCCCCGAGAACTGGGAGCACGCCAAGTACAAGT<br>GGTATCTGAAAGAGCTGCAGGACGGCATCGGCCAGAGACAGACAGT<br>CGTGCGGACCCTGAATGCCACCGGCGAGGAAATCATCCAGCAGTCCA<br>GCAAGACCGACGCCAGCATTCTGCAGGAAAAGCTGGGCAGCCTGAA<br>CCTGCGGTGGCAGGAAGTGTGCAAGCAGCTGTCCGACCGGAAGAAG<br>CGGCTGGAAGAACAGCTGGAACGGCTGCAGGAACTGCAGGAGGCCA<br>CCGACGAGCTGGACCTGAAACTGAGACAGGCCGAAGTGATCAAGGG<br>CAGCTGGCAGCCAGTGGGCGACCTGCTGATCGACTCCCTGCAGGACC<br>ATCTGGAAAAAGTGAAGGCCCTGAGAGGCGAGATCGCCCCCCTGAA<br>AGAAAACGTGTCCCACGTGAACGACCTGGCCCGGCAGCTGACAACA<br>CTGGGCATTCAGCTGAGCCCCTACAACCTGAGCACACTGGAAGATCT<br>GAACACCCGGTGGAAGCTGCTGCAGGTGGCCGTGGAAGATAGAGTG<br>CGGCAGCTGCACGAGGCCCACAGAGATTTTGGCCCTGCCTCCCAGCA<br>CTTCCTGAGCACCAGTGTGCAGGGCCCTTGGGAGAGAGCCATCTCCC<br>CTAACAAGGTGCCCTACTACATCAACCACGAGACACAGACCACCTGT<br>TGGGACCACCCCAAGATGACCGAGCTGTACCAGAGCCTGGCTGACCT<br>GAACAACGTGCGGTTCAGCGCCTACCGGACCGCCATGAAGCTGCGGA<br>GACTGCAGAAAGCTCTGTGCCTGGATCTGCTGTCCCTGTCCGCCGCCT<br>GTGATGCCCTGGACCAGCACAATCTGAAGCAGAACGACCAGCCCATG<br>GATATCCTGCAGATCATCAACTGCCTGACCACCATCTACGACCGGCT<br>GGAACAGGAACACAACAATCTCGTGAACGTGCCCCTGTGCGTGGACA<br>TGTGCCTGAATTGGCTGCTGAATGTGTACGACACCGGCCGGACAGGC<br>CGGATCAGAGTGCTGTCCTTCAAGACCGGCATCATCAGCCTGTGCAA<br>AGCCCACCTGGAAGATAAGTACCGGTATCTGTTCAAACAGGTGGCCT<br>CTAGCACCGGCTTTTGCGACCAGAGAAGGCTGGGCCTGCTGCTGCAC<br>GACAGCATCCAGATCCCTAGACAGCTGGGCGAAGTGGCCAGCTTTGG<br>CGGCAGCAACATCGAGCCTAGCGTGCGGAGCTGCTTCCAGTTCGCCA<br>ACAACAAGCCCGAGATCGAGGCCGCCCTGTTCCTGGACTGGATGAGA<br>CTGGAACCCCAGAGCATGGTGTGGCTGCCCGTGCTGCATAGAGTGGC<br>CGCTGCCGAGACAGCCAAGCACCAGGCCAAGTGCAACATCTGCAAA<br>GAGTGCCCCATCATCGGCTTCCGGTACAGAAGCCTGAAGCACTTCAA<br>CTACGATATCTGCCAGAGCTGTTTCTTCAGCGGCAGGGTGGCCAAGG<br>GCCACAAAATGCACTACCCCATGGTGGAATACTGCACCCCCACCACA<br>AGCGGCGAGGATGTGCGGGATTTCGCCAAGGTGCTGAAAAACAAGT<br>TCCGGACCAAGCGGTACTTCGCCAAACACCCCCGGATGGGCTACCTG<br>CCTGTGCAGACAGTGCTGGAAGGCGACAACATGGAAACCGACACCA<br>TGTGATGATGATTTGGGCAGAGCGATGGAGTCCTTAGTATCAGTCAT<br>GACAGATGAAGAAGGAGCAGAATAAATGTTTTACAACTCCTGATTCC<br>CGCATGCGGCCAGCTTATCGATACCGTCGAAATAAAAGATCCTTATT<br>TTCATTGGATCTGTGTGTTGGTTTTTTGTGTG |
| SEQ ID NO: 135-BXA-196474 | ATGCTGTGGTGGGAGGAAGTGGAAGATTGCTACGAGCGCGAGGACG<br>TGCAGAAGAAAACCTTCACCAAATGGGTGAACGCCCAGTTCAGCAA<br>GTTCGGCAAGCAGCACATCGAGAACCTGTTCAGCGACCTGCAGGACG<br>GCAGACGGCTGCTGGACCTGCTGGAAGGCCTGACCGGCCAGAAGCT<br>GCCCAAAGAGAAGGGCAGCACCAGAGTGCACGCCCTGAACAACGTG<br>AACAAGGCCCTGCGGGTGCTGCAGAACAACAACGTGGACCTGGTGA<br>ACATCGGCAGCACCGACATCGTGGACGGCAACCACAAGCTGACCCTG<br>GGCCTGATCTGGAACATCATCCTGCACTGGCAGGTCAAAAACGTGAT<br>GAAGAACATCATGGCCGGCCTGCAGCAGACCAACAGCGAGAAGATC<br>CTGCTGAGCTGGGTGCGCCAGAGCACCCGGAACTACCCCCAGGTCAA<br>CGTGATCAACTTCACCACCTCTTGGAGCGACGGCCTGGCCCTGAACG<br>CCCTGATCCACAGCCACCGGCCCGACCTGTTCGACTGGAACAGCGTG<br>GTCTGCCAGCAGAGCGCCACCCAGCGGCTGGAACACGCCTTCAATAT |

TABLE 8-continued

Nucleotide Sequences of Dystrophin constructs.

| SEQ ID NO and Description | Sequence |
|---|---|
| | CGCCAGATACCAGCTGGGCATCGAGAAGCTGCTGGATCCCGAGGAC |
| | GTGGACACCACCTACCCCGACAAGAAATCCATCCTGATGTATATCAC |
| | CAGCCTGTTCCAGGTGCTGCCCCAGCAGGTGTCCATCGAGGCCATCC |
| | AGGAAGTGGAAATGCTGCCCAGACCCCCCAAAGTGACCAAAGAGGA |
| | ACACTTCCAGCTGCACCACCAGATGCACTACAGCCAGCAGATCACCG |
| | TGTCCCTGGCCCAGGGCTACGAGAGAACCAGCAGCCCCAAGCCCCGG |
| | TTCAAGAGCTACGCCTATACCCAGGCCGCCTACGTGACCACCAGCGA |
| | CCCTACCAGAAGCCCATTCCCCAGCCAGCATCTGGAAGCCCCCGAGG |
| | ACAAGAGCTTCGGCAGCAGCCTGATGGAAAGCGAAGTGAACCTGGA |
| | CAGATACCAGACCGCCCTGGAAGAGGTGCTGAGCTGGCTGCTGAGCG |
| | CCGAGGATACACTGCAGGCTCAGGGCGAGATCAGCAACGACGTGGA |
| | AGTCGTGAAGGACCAGTTCCACACCCACGAGGGCTACATGATGGACC |
| | TGACAGCCCACCAGGGCAGAGTGGGCAACATCCTGCAGCTGGGCTCC |
| | AAGCTGATCGGCACCGGCAAGCTGAGCGAGGACGAAGAGACAGAGG |
| | TGCAGGAACAGATGAACCTGCTGAACAGCAGATGGGAGTGCCTGCG |
| | GGTGGCCAGCATGGAAAAGCAGAGCAACCTGCATCTGCTGAAGTGG |
| | CAGCGGCTGACCGAGGAACAGTGCCTGTTTAGCGCCTGGCTGTCCGA |
| | GAAAGAGGACGCCGTGAACAAGATCCACACCACCGGCTTCAAGGAC |
| | CAGAACGAGATGCTGAGCAGCCTGCAGAAACTGGCCGTGCTGAAGG |
| | CCGACCTGGAAAAGAAAAAGCAGTCCATGGGCAAGCTGTACTCCCTG |
| | AAGCAGGACCTGCTGTCCACCCTGAAGAACAAGAGCGTGACCCAGA |
| | AAACCGAGGCCTGGCTGGACAACTTCGCCCGGTGCTGGGACAACCTG |
| | GTGCAGAAGCTGGAAAAGTCCACCGCCCAGATCTCCCAGGCCGTGAC |
| | CACAACACAGCCCAGCCTGACCCAGACCACCGTGATGGAAACCGTG |
| | ACAACAGTGACCACCCGGGAACAGATCCTCGTGAAGCACGCCCAGG |
| | AAGAACTGCCCCCTCCACCCCCCCAGAAGAAACGGCAGATCACAGTG |
| | GACAGTGAAGCTCAGATCCACACCGTGCGGGAAGAGACAATGATGG |
| | TCATGACAGAGGACATGCCCCTGGAAATCAGCTACGTGCCCAGCACC |
| | TACCTGACCGAGATCACCCATGTGTCCCAGGCCCTGCTGGAAGTGGA |
| | ACAGCTGCTGAACGCCCCCGACCTGTGCGCCAAGGATTTCGAGGACC |
| | TGTTCAAGCAGGAAGAGAGCCTGAAGAATATCAAGGATAGCCTGCA |
| | GCAGAGCAGCGGCCGGATCGACATCATCCACAGCAAGAAAACAGCC |
| | GCCCTGCAGAGCGCCACCCCCGTGGAAAGAGTGAAACTGCAGGAAG |
| | CCCTGTCCCAGCTGGACTTCCAGTGGGAGAAAGTGAACAAAATGTAC |
| | AAGGACCGGCAGGGCAGATTCGACCGCAGCGTGGAAAAGTGGCGGC |
| | GGTTCCACTACGACATCAAGATCTTCAACCAGTGGCTGACAGAGGCC |
| | GAGCAGTTCCTGAGAAAGACCCAGATCCCCGAGAACTGGGAGCACG |
| | CCAAGTACAAGTGGTATCTGAAAGAGCTGCAGGACGGCATCGGCCA |
| | GAGACAGACAGTCGTGCGGACCCTGAATGCCACCGGCGAGGAAATC |
| | ATCCAGCAGTCCAGCAAGACCGACGCCAGCATTCTGCAGGAAAAGCT |
| | GGGCAGCCTGAACCTGCGGTGGCAGGAAGTGTGCAAGCAGCTGTCC |
| | GACCGGAAGAAGCGGCTGGAAGAACAGAAGAACATCCTGCAGGAAC |
| | TGCAGGAGGCCACCGACGAGCTGGACCTGAAACTGAGACAGGCCGA |
| | AGTGATCAAGGGCAGCTGGCAGCCAGTGGGCGACCTGCTGATCGACT |
| | CCCTGCAGGACCATCTGGAAAAAGTGAAGGCCCTGAGAGGCGAGAT |
| | CGCCCCCCTGAAAGAAAACGTGTCCCACGTGAACGACCTGGCCCGGC |
| | AGCTGACAACACTGGGCATTCAGCTGAGCCCCTACAACCTGAGCACA |
| | CTGGAAGATCTGAACACCCGGTGGAAGCTGCTGCAGGTGGCCGTGGA |
| | AGATAGAGTGCGGCAGCTGCACGAGGCCCACAGAGATTTTGGCCCTG |
| | CCTCCCAGCACTTCCTGAGCACCAGTGTGCAGGGCCCTTGGGAGAGA |
| | GCCATCTCCCCTAACAAGGTGCCCTACTACATCAACCACGAGACACA |
| | GACCACCTGTTGGGACCACCCCAAGATGACCGAGCTGTACCAGAGCC |
| | TGGCTGACCTGAACAACGTGCGGTTCAGCGCCTACCGGACCGCCATG |
| | AAGCTGCGGAGACTGCAGAAAGCTCTGTGCCTGGATCTGCTGTCCCT |
| | GTCCGCCGCCTGTGATGCCCTGGACCAGCACAATCTGAAGCAGAACG |
| | ACCAGCCCATGGATATCCTGCAGATCATCAACTGCCTGACCACCATC |
| | TACGACCGGCTGGAACAGGAACACAACAATCTCGTGAACGTGCCCCT |
| | GTGCGTGGACATGTGCCTGAATTGGCTGCTGAATGTGTACGACACCG |
| | GCCGGACAGGCCGGATCAGAGTGCTGTCCTTCAAGACCGGCATCATC |
| | AGCCTGTGCAAAGCCCACCTGGAAGATAAGTACCGGTATCTGTTCAA |
| | ACAGGTGGCCTCTAGCACCGGCTTTTGCGACCAGAGAAGGCTGGGCC |
| | TGCTGCTGCACGACAGCATCCAGATCCCTAGACAGCTGGGCGAAGTG |
| | GCCAGCTTTGGCGGCAGCAACATCGAGCCTAGCGTGCGGAGCTGCTT |
| | CCAGTTCGCCAACAACAAGCCCGAGATCGAGGCCGCCCTGTTCCTGG |
| | ACTGGATGAGACTGGAACCCCAGAGCATGGTGTGGCTGCCCGTGCTG |
| | CATAGAGTGGCCGCTGCCGAGACAGCCAAGCACCAGGCCAAGTGCA |
| | ACATCTGCAAAGAGTGCCCCATCATCGGCTTCCGGTACAGAAGCCTG |
| | AAGCACTTCAACTACGATATCTGCCAGAGCTGTTTCTTCAGCGGCAG |
| | GGTGGCCAAGGGCCACAAAATGCACTACCCCATGGTGGAATACTGCA |
| | CCCCCACCACAAGCGGCGAGGATGTGCGGGATTTCGCCAAGGTGCTG |
| | AAAAACAAGTTCCGGACCAAGCGGTACTTCGCCAAACACCCCCGGAT |
| | GGGCTACCTGCCTGTGCAGACAGTGCTGGAAGGCGACAACATGGAA |
| | ACCACACCATGTGATGATGATTTGGGCAGAGCGATGGAGTCCTTAGT |
| | ATCAGTCATGACAGATGAAGAAGGAGCAGAATAAATGTTTTACAACT |

TABLE 8-continued

| Nucleotide Sequences of Dystrophin constructs. | |
|---|---|
| SEQ ID NO and Description | Sequence |
| | CCTGATTCCCGCATGCGGCCAGCTTATCGATACCGTCGAAATAAAAG ATCCTTATTTTCATTGGATCTGTGTGTTGGTTTTTTGTGTG |
| SEQ ID NO: 136- BXA- 196475 | ATGCTGTGGTGGGAGGAAGTGGAAGATTGCTACGAGCGCGAGGACG TGCAGAAGAAAACCTTCACCAAATGGGTGAACGCCCAGTTCAGCAA GTTCGGCAAGCAGCACATCGAGAACCTGTTCAGCGACCTGCAGGACG GCAGACGGCTGCTGGACCTGCTGGAAGGCCTGACCGGCCAGAAGCT GCCCAAAGAGAAGGGCAGCACCAGAGTGCACGCCCTGAACAACGTG AACAAGGCCCTGCGGGTGCTGCAGAACAACAACGTGGACCTGGTGA ACATCGGCAGCACCGACATCGTGGACGGCAACCACAAGCTGACCCTG GGCCTGATCTGGAACATCATCCTGCACTGGCAGGTCAAAAACGTGAT GAAGAACATCATGGCCGGCCTGCAGCAGACCAACAGCGAGAAGATC CTGCTGAGCTGGGTGCGCCAGAGCACCCGGAACTACCCCCAGGTCAA CGTGATCAACTTCACCACCTCTTGGAGCGACGGCCTGGCCCTGAACG CCCTGATCCACAGCCACCGGCCCGACCTGTTCGACTGGAACAGCGTG GTCTGCCAGCAGAGCGCCACCCAGCGGCTGGAACACGCCTTCAATAT CGCCAGATACCAGCTGGGCATCGAGAAGCTGCTGGATCCCGAGGAC GTGGACACCACCTACCCCGACAAGAAATCCATCCTGATGTATATCAC CAGCCTGTTCCAGGTGCTGCCCCAGCAGGTGTCCATCGAGGCCATCC AGGAAGTGGAAATGCTGCCCAGACCCCCCAAAGTGACCAAAGAGGA ACACTTCCAGCTGCACCACCAGATGCACTACAGCCAGCAGATCACCG TGTCCCTGGCCCAGGGCTACGAGAGAACCAGCAGCCCCAAGCCCCGG TTCAAGAGCTACGCCTATACCCAGGCCGCCTACGTGACCACCAGCGA CCCTACCAGAAGCCCATTCCCCAGCCAGCATCTGGAAGCCCCCGAGG ACAAGAGCTTCGGCAGCAGCCTGATGGAAAGCGAAGTGAACCTGGA CAGATACCAGACCGCCCTGGAAGAGGTGCTGAGCTGGCTGCTGAGCG CCGAGGATACACTGCAGGCTCAGGGCGAGATCAGCAACGACGTGGA AGTCGTGAAGGACCAGTTCCACACCCACGAGGGCTACATGATGGACC TGACAGCCCACCAGGGCAGAGTGGGCAACATCCTGCAGCTGGGCTCC AAGCTGATCGGCACCGGCAAGCTGAGCGAGGACGAAGAGACAGAGG TGCAGGAACAGATGAACCTGCTGAACAGCAGATGGGAGTGCCTGCG GGTGGCCAGCATGGAAAAGCAGAGCAACCTGCATCTGCTGAAGTGG CAGCGGCTGACCGAGGAACAGTGCCTGTTTAGCGCCTGGCTGTCCGA GAAAGAGGACGCCGTGAACAAGATCCACACCACCGGCTTCAAGGAC CAGAACGAGATGCTGAGCAGCCTGCAGAAACTGGCCGTGCTGAAGG CCGACCTGGAAAAGAAAAAGCAGTCCATGGGCAAGCTGTACTCCCTG AAGCAGGACCTGCTGTCCACCCTGAAGAACAAGAGCGTGACCCAGA AAACCGAGGCCTGGCTGGACAACTTCGCCCGGTGCTGGGACAACCTG GTGCAGAAGCTGGAAAAGTCCACCGCCCAGATCTCCCAGGCCGTGAC CACAACACAGCCCAGCCTGACCCAGACCACCGTGATGGAAACCGTG ACAACAGTGACCACCCGGGAACAGATCCTCGTGAAGCACGCCCAGG AAGAACTGCCCCCTCCACCCCCCCAGAAGAAACGGCAGATCACAGTG GACAGTGAAGCTCAGATCCACACCGTGCGGGAAGAGACAATGATGG TCATGACAGAGGACATGCCCCTGGAAATCAGCTACGTGCCCAGCACC TACCTGACCGAGATCACCCATGTGTCCCAGGCCCTGCTGGAAGTGGA ACAGCTGCTGAACGCCCCCGACCTGTGCGCCAAGGATTTCGAGGACC TGTTCAAGCAGGAAGAGAGCCTGAAGAATATCAAGGATAGCCTGCA GCAGAGCAGCGGCCGGATCGACATCATCCACAGCAAGAAAACAGCC GCCCTGCAGAGCGCCACCCCCGTGGAAAGAGTGAAACTGCAGGAAG CCCTGTCCCAGCTGGACTTCCAGTGGGAGAAAGTGAACAAAATGTAC AAGGACCGGCAGGGCAGATTCGACCGCAGCGTGGAAAAGTGGCGGC GGTTCCACTACGACATCAAGATCTTCAACCAGTGGCTGACAGAGGCC GAGCAGTTCCTGAGAAAGACCCAGATCCCCGAGAACTGGGAGCACG CCAAGTACAAGTGGTATCTGAAAGAGCTGCAGGACGGCATCGGCCA GAGACAGACAGTCGTGCGGACCCTGAATGCCACCGGCGAGGAAATC ATCCAGCAGTCCAGCAAGACCGACGCCAGCATTCTGCAGGAAAAGCT GGGCAGCCTGAACCTGCGGTGGCAGGAAGTGTGCAAGCAGCTGTCC GACCGGAAGAAGCGGCTGGAAGAACAGAAGCTGGAACGGCTGCAGG AACTGCAGGAGGCCACCGACGAGCTGGACCTGAAACTGAGACAGGC CGAAGTGATCAAGGGCAGCTGGCAGCCAGTGGGCGACCTGCTGATC GACTCCCTGCAGGACCATCTGGAAAAAGTGAAGGCCCTGAGAGGCG AGATCGCCCCCCTGAAAGAAAACGTGTCCCACGTGAACGACCTGGCC CGGCAGCTGACAACACTGGGCATTCAGCTGAGCCCCTACAACCTGAG CACACTGGAAGATCTGAACACCCGGTGGAAGCTGCTGCAGGTGGCCG TGGAAGATAGAGTGCGGCAGCTGCACGAGGCCCACAGAGATTTTGG CCCTGCCTCCCAGCACTTCCTGAGCACCAGTGTGCAGGGCCCTTGGG AGAGAGCCATCTCCCCTAACAAGGTGCCCTACTACATCAACCACGAG ACACAGACCACCTGTTGGGACCACCCCAAGATGACCGAGCTGTACCA GAGCCTGGCTGACCTGAACAACGTGCGGTTCAGCGCCTACCGGACCG CCATGAAGCTGCGGAGACTGCAGAAAGCTCTGTGCCTGGATCTGCTG TCCCTGTCCGCCGCCTGTGATGCCCTGGACCAGCACAATCTGAAGCA GAACGACCAGCCCATGGATATCCTGCAGATCATCAACTGCCTGACCA CCATCTACGACCGGCTGGAACAGGAACACAACAATCTCGTGAACGTG CCCCTGTGCGTGGACATGTGCCTGAATTGGCTGCTGAATGTGTACGA |

TABLE 8-continued

| Nucleotide Sequences of Dystrophin constructs. | |
|---|---|
| SEQ ID NO and Description | Sequence |
| | CACCGGCCGGACAGGCCGGATCAGAGTGCTGTCCTTCAAGACCGGCA TCATCAGCCTGTGCAAAGCCCACCTGGAAGATAAGTACCGGTATCTG TTCAAACAGGTGGCCTCTAGCACCGGCTTTTGCGACCAGAGAAGGCT GGGCCTGCTGCTGCACGACAGCATCCAGATCCCTAGACAGCTGGGCG AAGTGGCCAGCTTTGGCGGCAGCAACATCGAGCCTAGCGTGCGGAGC TGCTTCCAGTTCGCCAACAACAAGCCCGAGATCGAGGCCGCCCTGTT CCTGGACTGGATGAGACTGGAACCCCAGAGCATGGTGTGGCTGCCCG TGCTGCATAGAGTGGCCGCTGCCGAGACAGCCAAGCACCAGGCCAA GTGCAACATCTGCAAAGAGTGCCCCATCATCGGCTTCCGGTACAGAA GCCTGAAGCACTTCAACTACGATATCTGCCAGAGCTGTTTCTTCAGCG GCAGGGTGGCCAAGGGCCACAAAATGCACTACCCCATGGTGGAATA CTGCACCCCCACCACAAGCGGCGAGGATGTGCGGGATTTCGCCAAGG TGCTGAAAAACAAGTTCCGGACCAAGCGGTACTTCGCCAAACACCCC CGGATGGGCTACCTGCCTGTGCAGACAGTGCTGGAAGGCGACAACAT GGAAACCGACACCATGTGATGATGATTTGGGCAGAGCGATGGAGTCC TTAGTATCAGTCATGACAGATGAAGAAGGAGCAGAATAAATGTTTTA CAACTCCTGATTCCCGCATGCGGCCAGCTTATCGATACCGTCGAAAT AAAAGATCCTTATTTTCATTGGATCTGTGTGTTGGTTTTTTGTGTG |
| SEQ ID NO: 137-BXA-196476 | ATGCTGTGGTGGGAGGAAGTGGAAGATTGCTACGAGCGCGAGGACG TGCAGAAGAAAACCTTCACCAAATGGGTGAACGCCCAGTTCAGCAA GTTCGGCAAGCAGCACATCGAGAACCTGTTCAGCGACCTGCAGGACG GCAGACGGCTGCTGGACCTGCTGGAAGGCCTGACCGGCCAGAAGCT GCCCAAAGAGAAGGGCAGCACCAGAGTGCACGCCCTGAACAACGTG AACAAGGCCCTGCGGGTGCTGCAGAACAACAACGTGGACCTGGTGA ACATCGGCAGCACCGACATCGTGGACGGCAACCACAAGCTGACCCTG GGCCTGATCTGGAACATCATCCTGCACTGGCAGGTCAAAAACGTGAT GAAGAACATCATGGCCGGCCTGCAGCAGACCAACAGCGAGAAGATC CTGCTGAGCTGGGTGCGCCAGAGCACCCGGAACTACCCCCAGGTCAA CGTGATCAACTTCACCACCTCTTGGAGCGACGGCCTGGCCCTGAACG CCCTGATCCACAGCCACCGGCCCGACCTGTTCGACTGGAACAGCGTG GTCTGCCAGCAGAGCGCCACCCAGCGGCTGGAACACGCCTTCAATAT CGCCAGATACCAGCTGGGCATCGAGAAGCTGCTGGATCCCGAGGAC GTGGACACCACCTACCCCGACAAGAAATCCATCCTGATGTATATCAC CAGCCTGTTCCAGGTGCTGCCCCAGCAGGTGTCCATCGAGGCCATCC AGGAAGTGGAAATGCTGCCCAGACCCCCCAAAGTGACCAAAGAGGA ACACTTCCAGCTGCACCACCAGATGCACTACAGCCAGCAGATCACCG TGTCCCTGGCCCAGGGCTACGAGAGAACCAGCAGCCCCAAGCCCCGG TTCAAGAGCTACGCCTATACCCAGGCCGCCTACGTGACCACCAGCGA CCCTACCAGAAGCCCATTCCCCAGCCAGCATCTGGAAGCCCCCGAGG ACAAGAGCTTCGGCAGCAGCCTGATGGAAAGCGAAGTGAACCTGGA CAGATACCAGACCGCCCTGGAAGAGGTGCTGAGCTGGCTGCTGAGCG CCGAGGATACACTGCAGGCTCAGGGCGAGATCAGCAACGACGTGGA AGTCGTGAAGGACCAGTTCCACACCCACGAGGGCTACATGATGGACC TGACAGCCCACCAGGGCAGAGTGGGCAACATCCTGCAGCTGGGCTCC AAGCTGATCGGCACCGGCAAGCTGAGCGAGGACGAAGAGACAGAGG TGCAGGAACAGATGAACCTGCTGAACAGCAGATGGGAGTGCCTGCG GGTGGCCAGCATGGAAAAGCAGAGCAACCTGCATCTGCTGAAGTGG CAGCGGCTGACCGAGGAACAGTGCCTGTTTAGCGCCTGGCTGTCCGA GAAAGAGGACGCCGTGAACAAGATCCACACCACCGGCTTCAAGGAC CAGAACGAGATGCTGAGCAGCCTGCAGAAACTGGCCGTGCTGAAGG CCGACCTGGAAAAGAAAAAGCAGTCCATGGGCAAGCTGTACTCCCTG AAGCAGGACCTGCTGTCCACCCTGAAGAACAAGAGCGTGACCCAGA AAACCGAGGCCTGGCTGGACAACTTCGCCCGGTGCTGGGACAACCTG GTGCAGAAGCTGGAAAAGTCCACCGCCCAGATCTCCCAGGCCGTGAC CACAACACAGCCCAGCCTGACCCAGACCACCGTGATGGAAACCGTG ACAACAGTGACCACCCGGGAACAGATCCTCGTGAAGCACGCCCAGG AAGAACTGCCCCCTCCACCCCCCCAGAAGAAACGGCAGATCACAGTG GACAGTGAAGCTCAGATCCACACCGTGCGGGAAGAGACAATGATGG TCATGACAGAGGACATGCCCCTGGAAATCAGCTACGTGCCCAGCACC TACCTGACCGAGATCACCCATGTGTCCCAGGCCCTGCTGGAAGTGGA ACAGCTGCTGAACGCCCCCGACCTGTGCGCCAAGGATTTCGAGGACC TGTTCAAGCAGGAAGAGAGCCTGAAGAATATCAAGGATAGCCTGCA GCAGAGCAGCGGCCGGATCGACATCATCCACAGCAAGAAAACAGCC GCCCTGCAGAGCGCCACCCCCGTGGAAAGAGTGAAACTGCAGGAAG CCCTGTCCCAGCTGGACTTCCAGTGGGAGAAAGTGAACAAAATGTAC AAGGACCGGCAGGGCAGATTCGACCGCAGCGTGGAAAAGTGGCGGC GGTTCCACTACGACATCAAGATCTTCAACCAGTGGCTGACAGAGGCC GAGCAGTTCCTGAGAAAGACCCAGATCCCCGAGAACTGGGAGCACG CCAAGTACAAGTGGTATCTGAAAGAGCTGCAGGACGGCATCGGCCA GAGACAGACAGTCGTGCGGACCCTGAATGCCACCGGCGAGGAAATC ATCCAGCAGTCCAGCAAGACCGACGCCAGCATTCTGCAGGAAAAGCT GGGCAGCCTGAACCTGCGGTGGCAGGAAGTGTGCAAGCAGCTGTCC GACCGGAAGAAGCGGCTGGAAGAACAGAAGAACATCCTGGAACGGC |

TABLE 8-continued

Nucleotide Sequences of Dystrophin constructs.

| SEQ ID NO and Description | Sequence |
|---|---|
| | TGCAGGAACTGCAGGAGGCCACCGACGAGCTGGACCTGAAACTGAG ACAGGCCGAAGTGATCAAGGGCAGCTGGCAGCCAGTGGGCGACCTG CTGATCGACTCCCTGCAGGACCATCTGGAAAAAGTGAAGGCCCTGAG AGGCGAGATCGCCCCCCTGAAAGAAAACGTGTCCCACGTGAACGAC CTGGCCCGGCAGCTGACAACACTGGGCATTCAGCTGAGCCCCTACAA CCTGAGCACACTGGAAGATCTGAACACCCGGTGGAAGCTGCTGCAGG TGGCCGTGGAAGATAGAGTGCGGCAGCTGCACGAGGCCCACAGAGA TTTTGGCCCTGCCTCCCAGCACTTCCTGAGCACCAGTGTGCAGGGCCC TTGGGAGAGAGCCATCTCCCCTAACAAGGTGCCCTACTACATCAACC ACGAGACACAGACCACCTGTTGGGACCACCCCAAGATGACCGAGCT GTACCAGAGCCTGGCTGACCTGAACAACGTGCGGTTCAGCGCCTACC GGACCGCCATGAAGCTGCGGAGACTGCAGAAAGCTCTGTGCCTGGAT CTGCTGTCCCTGTCCGCCGCCTGTGATGCCCTGGACCAGCACAATCTG AAGCAGAACGACCAGCCCATGGATATCCTGCAGATCATCAACTGCCT GACCACCATCTACGACCGGCTGGAACAGGAACACAACAATCTCGTGA ACGTGCCCCTGTGCGTGGACATGTGCCTGAATTGGCTGCTGAATGTG TACGACACCGGCCGGACAGGCCGGATCAGAGTGCTGTCCTTCAAGAC CGGCATCATCAGCCTGTGCAAAGCCCACCTGGAAGATAAGTACCGGT ATCTGTTCAAACAGGTGGCCTCTAGCACCGGCTTTTGCGACCAGAGA AGGCTGGGCCTGCTGCTGCACGACAGCATCCAGATCCCTAGACAGCT GGGCGAAGTGGCCAGCTTTGGCGGCAGCAACATCGAGCCTAGCGTGC GGAGCTGCTTCCAGTTCGCCAACAACAAGCCCGAGATCGAGGCCGCC CTGTTCCTGGACTGGATGAGACTGGAACCCCAGAGCATGGTGTGGCT GCCCGTGCTGCATAGAGTGGCCGCTGCCGAGACAGCCAAGCACCAG GCCAAGTGCAACATCTGCAAAGAGTGCCCCATCATCGGCTTCCGGTA CAGAAGCCTGAAGCACTTCAACTACGATATCTGCCAGAGCTGTTTCT TCAGCGGCAGGGTGGCCAAGGGCCACAAAATGCACTACCCCATGGT GGAATACTGCACCCCCACCACAAGCGGCGAGGATGTGCGGGATTTCG CCAAGGTGCTGAAAAACAAGTTCCGGACCAAGCGGTACTTCGCCAAA CACCCCCGGATGGGCTACCTGCCTGTGCAGACAGTGCTGGAAGGCGA CAACATGGAAACCGACACCATGTGATGATGATTTGGGCAGAGCGATG GAGTCCTTAGTATCAGTCATGACAGATGAAGAAGGAGCAGAATAAA TGTTTTACAACTCCTGATTCCCGCATGCGGCCAGCTTATCGATACCGT CGAAATAAAAGATCCTTATTTTCATTGGATCTGTGTGTTGGTTTTTTG TGTG |
| SEQ ID NO: 138-BXA-196477-Q | ATGCTGTGGTGGGAGGAAGTGGAAGATTGCTACGAGCGCGAGGACG TGCAGAAGAAAACCTTCACCAAATGGGTGAACGCCCAGTTCAGCAA GTTCGGCAAGCAGCACATCGAGAACCTGTTCAGCGACCTGCAGGACG GCAGACGGCTGCTGGACCTGCTGGAAGGCCTGACCGGCCAGAAGCT GCCCAAAGAGAAGGGCAGCACCAGAGTGCACGCCCTGAACAACGTG AACAAGGCCCTGCGGGTGCTGCAGAACAACAACGTGGACCTGGTGA ACATCGGCAGCACCGACATCGTGGACGGCAACCACAAGCTGACCCTG GGCCTGATCTGGAACATCATCCTGCACTGGCAGGTCAAAAACGTGAT GAAGAACATCATGGCCGGCCTGCAGCAGACCAACAGCGAGAAGATC CTGCTGAGCTGGGTGCGCCAGAGCACCCGGAACTACCCCCAGGTCAA CGTGATCAACTTCACCACCTCTTGGAGCGACGGCCTGGCCCTGAACG CCCTGATCCACAGCCACCGGCCCGACCTGTTCGACTGGAACAGCGTG GTCTGCCAGCAGAGCGCCACCCAGCGGCTGGAACACGCCTTCAATAT CGCCAGATACCAGCTGGGCATCGAGAAGCTGCTGGATCCCGAGGAC GTGGACACCACCTACCCCGACAAGAAATCCATCCTGATGTATATCAC CAGCCTGTTCCAGGTGCTGCCCCAGCAGGTGTCCATCGAGGCCATCC AGGAAGTGGAAATGCTGCCCAGACCCCCCAAAGTGACCAAAGAGGA ACACTTCCAGCTGCACCACCAGATGCACTACAGCCAGCAGATCACCG TGTCCCTGGCCCAGGGCTACGAGAGAACCAGCAGCCCCAAGCCCCGG TTCAAGAGCTACGCCTATACCCAGGCCGCCTACGTGACCACCAGCGA CCCTACCAGAAGCCCATTCCCCAGCCAGCATCTGGAAGCCCCCGAGG ACAAGAGCTTCGGCAGCAGCCTGATGGAAAGCGAAGTGAACCTGGA CAGATACCAGACCGCCCTGGAAGAGGTGCTGAGCTGGCTGCTGAGCG CCGAGGATACACTGCAGGCTCAGGGCGAGATCAGCAACGACGTGGA AGTCGTGAAGGACCAGTTCCACACCCACGAGGGCTACATGATGGACC TGACAGCCCACCAGGGCAGAGTGGGCAACATCCTGCAGCTGGGCTCC AAGCTGATCGGCACCGGCAAGCTGAGCGAGGACGAAGAGACAGAGG TGCAGGAACAGATGAACCTGCTGAACAGCAGATGGGAGTGCCTGCG GGTGGCCAGCATGGAAAAGCAGAGCAACCTGCATAGGGTCCTGCTG AAGTGGCAGCGGCTGACCGAGGAACAGTGCCTGTTTAGCGCCTGGCT GTCCGAGAAAGAGGACGCCGTGAACAAGATCCACACCACCGGCTTC AAGGACCAGAACGAGATGCTGAGCAGCCTGCAGAAACTGGCCGTGC TGAAGGCCGACCTGGAAAAGAAAAAGCAGTCCATGGGCAAGCTGTA CTCCCTGAAGCAGGACCTGCTGTCCACCCTGAAGAACAAGAGCGTGA CCCAGAAAACCGAGGCCTGGCTGGACAACTTCGCCCGGTGCTGGGAC AACCTGGTGCAGAAGCTGGAAAAGTCCACCGCCCAGATCTCCCAGGC CGTGACCACAACACAGCCCAGCCTGACCCAGACCACCGTGATGGAA ACCGTGACAACAGTGACCACCCGGGAACAGATCCTCGTGAAGCACG |

TABLE 8-continued

Nucleotide Sequences of Dystrophin constructs.

| SEQ ID NO and Description | Sequence |
|---|---|
| | CCCAGGAAGAACTGCCCCCTCCACCCCCCCAGAAGAAACGGCAGATC ACAGTGGACAGTGAAGCTCAGATCCACACCGTGCGGGAAGAGACAA TGATGGTCATGACAGAGGACATGCCCCTGGAAATCAGCTACGTGCCC AGCACCTACCTGACCGAGATCACCCATGTGTCCCAGGCCCTGCTGGA AGTGGAACAGCTGCTGAACGCCCCCGACCTGTGCGCCAAGGATTTCG AGGACCTGTTCAAGCAGGAAGAGAGCCTGAAGAATATCAAGGATAG CCTGCAGCAGAGCAGCGGCCGGATCGACATCATCCACAGCAAGAAA ACAGCCGCCCTGCAGAGCGCCACCCCCGTGGAAAGAGTGAAACTGC AGGAAGCCCTGTCCCAGCTGGACTTCCAGTGGGAGAAAGTGAACAA AATGTACAAGGACCGGCAGGGCAGATTCGACCGCAGCGTGGAAAAG TGGCGGCGGTTCCACTACGACATCAAGATCTTCAACCAGTGGCTGAC AGAGGCCGAGCAGTTCCTGAGAAAGACCCAGATCCCCGAGAACTGG GAGCACGCCAAGTACAAGTGGTATCTGAAAGAGCTGCAGGACGGCA TCGGCCAGAGACAGACAGTCGTGCGGACCCTGAATGCCACCGGCGA GGAAATCATCCAGCAGTCCAGCAAGACCGACGCCAGCATTCTGCAGG AAAAGCTGGGCAGCCTGAACCTGCGGTGGCAGGAAGTGTGCAAGCA GCTGTCCGACCGGAAGAAGCGGCTGGAAGAACAGCTGGAACGGCTG CAGGAACTGCAGGAGGCCACCGACGAGCTGGACCTGAAACTGAGAC AGGCCGAAGTGATCAAGGGCAGCTGGCAGCCAGTGGGCGACCTGCT GATCGACTCCCTGCAGGACCATCTGGAAAAAGTGAAGGCCCTGAGA GGCGAGATCGCCCCCCTGAAAGAAAACGTGTCCCACGTGAACGACCT GGCCCGGCAGCTGACAACACTGGGCATTCAGCTGAGCCCCTACAACC TGAGCACACTGGAAGATCTGAACACCCGGTGGAAGCTGCTGCAGGTG GCCGTGGAAGATAGAGTGCGGCAGCTGCACGAGGCCCACAGAGATT TTGGCCCTGCCTCCCAGCACTTCCTGAGCACCAGTGTGCAGGGCCCTT GGGAGAGAGCCATCTCCCCTAACAAGGTGCCCTACTACATCAACCAC GAGACACAGACCACCTGTTGGGACCACCCCAAGATGACCGAGCTGTA CCAGAGCCTGGCTGACCTGAACAACGTGCGGTTCAGCGCCTACCGGA CCGCCATGAAGCTGCGGAGACTGCAGAAAGCTCTGTGCCTGGATCTG CTGTCCCTGTCCGCCGCCTGTGATGCCCTGGACCAGCACAATCTGAA GCAGAACGACCAGCCCATGGATATCCTGCAGATCATCAACTGCCTGA CCACCATCTACGACCGGCTGGAACAGGAACACAACAATCTCGTGAAC GTGCCCCTGTGCGTGGACATGTGCCTGAATTGGCTGCTGAATGTGTA CGACACCGGCCGGACAGGCCGGATCAGAGTGCTGTCCTTCAAGACCG GCATCATCAGCCTGTGCAAAGCCCACCTGGAAGATAAGTACCGGTAT CTGTTCAAACAGGTGGCCTCTAGCACCGGCTTTTGCGACCAGAGAAG GCTGGGCCTGCTGCTGCACGACAGCATCCAGATCCCTAGACAGCTGG GCGAAGTGGCCAGCTTTGGCGGCAGCAACATCGAGCCTAGCGTGCGG AGCTGCTTCCAGTTCGCCAACAACAAGCCCGAGATCGAGGCCGCCCT GTTCCTGGACTGGATGAGACTGGAACCCCAGAGCATGGTGTGGCTGC CCGTGCTGCATAGAGTGGCCGCTGCCGAGACAGCCAAGCACCAGGCC AAGTGCAACATCTGCAAAGAGTGCCCCATCATCGGCTTCCGGTACAG AAGCCTGAAGCACTTCAACTACGATATCTGCCAGAGCTGTTTCTTCA GCGGCAGGGTGGCCAAGGGCCACAAAATGCACTACCCCATGGTGGA ATACTGCACCCCCACCACAAGCGGCGAGGATGTGCGGGATTTCGCCA AGGTGCTGAAAAACAAGTTCCGGACCAAGCGGTACTTCGCCAAACAC CCCCGGATGGGCTACCTGCCTGTGCAGACAGTGCTGGAAGGCGACAA CATGGAAACCGACACCATGTGATGATGATTTGGGCAGAGCGATGGA GTCCTTAGTATCAGTCATGACAGATGAAGAAGGAGCAGAATAAATGT TTTACAACTCCTGATTCCCGCATGCGGCCAGCTTATCGATACCGTCGA AATAAAAGATCCTTATTTTCATTGGATCTGTGTGTTGGTTTTTTGTGT G |
| SEQ ID NO: 139-BXA-196478 | ATGCTGTGGTGGGAGGAAGTGGAAGATTGCTACGAGCGCGAGGACG TGCAGAAGAAAACCTTCACCAAATGGGTGAACGCCCAGTTCAGCAA GTTCGGCAAGCAGCACATCGAGAACCTGTTCAGCGACCTGCAGGACG GCAGACGGCTGCTGGACCTGCTGGAAGGCCTGACCGGCCAGAAGCT GCCCAAAGAGAAGGGCAGCACCAGAGTGCACGCCCTGAACAACGTG AACAAGGCCCTGCGGGTGCTGCAGAACAACAACGTGGACCTGGTGA ACATCGGCAGCACCGACATCGTGGACGGCAACCACAAGCTGACCCTG GGCCTGATCTGGAACATCATCCTGCACTGGCAGGTCAAAAACGTGAT GAAGAACATCATGGCCGGCCTGCAGCAGACCAACAGCGAGAAGATC CTGCTGAGCTGGGTGCGCCAGAGCACCCGGAACTACCCCCAGGTCAA CGTGATCAACTTCACCACCTCTTGGAGCGACGGCCTGGCCCTGAACG CCCTGATCCACAGCCACCGGCCCGACCTGTTCGACTGGAACAGCGTG GTCTGCCAGCAGAGCGCCACCCAGCGGCTGGAACACGCCTTCAATAT CGCCAGATACCAGCTGGGCATCGAGAAGCTGCTGGATCCCGAGGAC GTGGACACCACCTACCCCGACAAGAAATCCATCCTGATGTATATCAC CAGCCTGTTCCAGGTGCTGCCCCAGCAGGTGTCCATCGAGGCCATCC AGGAAGTGGAAATGCTGCCCAGACCCCCCAAAGTGACCAAAGAGGA ACACTTCCAGCTGCACCACCAGATGCACTACAGCCAGCAGATCACCG TGTCCCTGGCCCAGGGCTACGAGAGAACCAGCAGCCCCAAGCCCCGG TTCAAGAGCTACGCCTATACCCAGGCCGCCTACGTGACCACCAGCGA CCCTACCAGAAGCCCATTCCCCAGCCAGCATCTGGAAGCCCCCGAGG |

TABLE 8-continued

Nucleotide Sequences of Dystrophin constructs.

| SEQ ID NO and Description | Sequence |
|---|---|
| | ACAAGAGCTTCGGCAGCAGCCTGATGGAAAGCGAAGTGAACCTGGA CAGATACCAGACCGCCCTGGAAGAGGTGCTGAGCTGGCTGCTGAGCG CCGAGGATACACTGCAGGCTCAGGGCGAGATCAGCAACGACGTGGA AGTCGTGAAGGACCAGTTCCACACCCACGAGGGCTACATGATGGACC TGACAGCCCACCAGGGCAGAGTGGGCAACATCCTGCAGCTGGGCTCC AAGCTGATCGGCACCGGCAAGCTGAGCGAGGACGAAGAGACAGAGG TGCAGGAACAGATGAACCTGCTGAACAGCAGATGGGAGTGCCTGCG GGTGGCCAGCATGGAAAAGCAGAGCAACCTGCATAGAGTACTGCTC CAAGACATCCTGCTGAAGTGGCAGCGGCTGACCGAGGAACAGTGCCT GTTTAGCGCCTGGCTGTCCGAGAAAGAGGACGCCGTGAACAAGATCC ACACCACCGGCTTCAAGGACCAGAACGAGATGCTGAGCAGCCTGCA GAAACTGGCCGTGCTGAAGGCCGACCTGGAAAAGAAAAAGCAGTCC ATGGGCAAGCTGTACTCCCTGAAGCAGGACCTGCTGTCCACCCTGAA GAACAAGAGCGTGACCCAGAAAACCGAGGCCTGGCTGGACAACTTC GCCCGGTGCTGGGACAACCTGGTGCAGAAGCTGGAAAAGTCCACCG CCCAGATCTCCCAGGCCGTGACCACAACACAGCCCAGCCTGACCCAG ACCACCGTGATGGAAACCGTGACAACAGTGACCACCCGGGAACAGA TCCTCGTGAAGCACGCCCAGGAAGAACTGCCCCCTCCACCCCCCCAG AAGAAACGGCAGATCACAGTGGACAGTGAAGCTCAGATCCACACCG TGCGGGAAGAGACAATGATGGTCATGACAGAGGACATGCCCCTGGA AATCAGCTACGTGCCCAGCACCTACCTGACCGAGATCACCCATGTGT CCCAGGCCCTGCTGGAAGTGGAACAGCTGCTGAACGCCCCCGACCTG TGCGCCAAGGATTTCGAGGACCTGTTCAAGCAGGAAGAGAGCCTGA AGAATATCAAGGATAGCCTGCAGCAGAGCAGCGGCCGGATCGACAT CATCCACAGCAAGAAAACAGCCGCCCTGCAGAGCGCCACCCCCGTG GAAAGAGTGAAACTGCAGGAAGCCCTGTCCCAGCTGGACTTCCAGTG GGAGAAAGTGAACAAAATGTACAAGGACCGGCAGGGCAGATTCGAC CGCAGCGTGGAAAAGTGGCGGCGGTTCCACTACGACATCAAGATCTT CAACCAGTGGCTGACAGAGGCCGAGCAGTTCCTGAGAAAGACCCAG ATCCCCGAGAACTGGGAGCACGCCAAGTACAAGTGGTATCTGAAAG AGCTGCAGGACGGCATCGGCCAGAGACAGACAGTCGTGCGGACCCT GAATGCCACCGGCGAGGAAATCATCCAGCAGTCCAGCAAGACCGAC GCCAGCATTCTGCAGGAAAAGCTGGGCAGCCTGAACCTGCGGTGGCA GGAAGTGTGCAAGCAGCTGTCCGACCGGAAGAAGCGGCTGGAAGAA CAGCTGGAACGGCTGCAGGAACTGCAGGAGGCCACCGACGAGCTGG ACCTGAAACTGAGACAGGCCGAAGTGATCAAGGGCAGCTGGCAGCC AGTGGGCGACCTGCTGATCGACTCCCTGCAGGACCATCTGGAAAAAG TGAAGGCCCTGAGAGGCGAGATCGCCCCCCTGAAAGAAAACGTGTC CCACGTGAACGACCTGGCCCGGCAGCTGACAACACTGGGCATTCAGC TGAGCCCCTACAACCTGAGCACACTGGAAGATCTGAACACCCGGTGG AAGCTGCTGCAGGTGGCCGTGGAAGATAGAGTGCGGCAGCTGCACG AGGCCCACAGAGATTTTGGCCCTGCCTCCCAGCACTTCCTGAGCACC AGTGTGCAGGGCCCTTGGGAGAGAGCCATCTCCCCTAACAAGGTGCC CTACTACATCAACCACGAGACACAGACCACCTGTTGGGACCACCCCA AGATGACCGAGCTGTACCAGAGCCTGGCTGACCTGAACAACGTGCGG TTCAGCGCCTACCGGACCGCCATGAAGCTGCGGAGACTGCAGAAAGC TCTGTGCCTGGATCTGCTGTCCCTGTCCGCCGCCTGTGATGCCCTGGA CCAGCACAATCTGAAGCAGAACGACCAGCCCATGGATATCCTGCAGA TCATCAACTGCCTGACCACCATCTACGACCGGCTGGAACAGGAACAC AACAATCTCGTGAACGTGCCCCTGTGCGTGGACATGTGCCTGAATTG GCTGCTGAATGTGTACGACACCGGCCGGACAGGCCGGATCAGAGTGC TGTCCTTCAAGACCGGCATCATCAGCCTGTGCAAAGCCCACCTGGAA GATAAGTACCGGTATCTGTTCAAACAGGTGGCCTCTAGCACCGGCTT TTGCGACCAGAGAAGGCTGGGCCTGCTGCTGCACGACAGCATCCAGA TCCCTAGACAGCTGGGCGAAGTGGCCAGCTTTGGCGGCAGCAACATC GAGCCTAGCGTGCGGAGCTGCTTCCAGTTCGCCAACAACAAGCCCGA GATCGAGGCCGCCCTGTTCCTGGACTGGATGAGACTGGAACCCCAGA GCATGGTGTGGCTGCCCGTGCTGCATAGAGTGGCCGCTGCCGAGACA GCCAAGCACCAGGCCAAGTGCAACATCTGCAAAGAGTGCCCCATCAT CGGCTTCCGGTACAGAAGCCTGAAGCACTTCAACTACGATATCTGCC AGAGCTGTTTCTTCAGCGGCAGGGTGGCCAAGGGCCACAAAATGCAC TACCCCATGGTGGAATACTGCACCCCCACCACAAGCGGCGAGGATGT GCGGGATTTCGCCAAGGTGCTGAAAAACAAGTTCCGGACCAAGCGGT ACTTCGCCAAACACCCCCGGATGGGCTACCTGCCTGTGCAGACAGTG CTGGAAGGCGACAACATGGAAACCGACACCATGTGATGATGATTTGG GCAGAGCGATGGAGTCCTTAGTATCAGTCATGACAGATGAAGAAGG AGCAGAATAAATGTTTTACAACTCCTGATTCCCGCATGCGGCCAGCT TATCGATACCGTCGAAATAAAAGATCCTTATTTTCATTGGATCTGTGT GTTGGTTTTTTGTGTG |
| SEQ ID NO: 140- BXA- 196479 | ATGCTGTGGTGGGAGGAAGTGGAAGATTGCTACGAGCGCGAGGACG TGCAGAAGAAAACCTTCACCAAATGGGTGAACGCCCAGTTCAGCAA GTTCGGCAAGCAGCACATCGAGAACCTGTTCAGCGACCTGCAGGACG GCAGACGGCTGCTGGACCTGCTGGAAGGCCTGACCGGCCAGAAGCT |

TABLE 8-continued

Nucleotide Sequences of Dystrophin constructs.

| SEQ ID NO and Description | Sequence |
|---|---|
| | GCCCAAAGAGAAGGGCAGCACCAGAGTGCACGCCCTGAACAACGTG<br>AACAAGGCCCTGCGGGTGCTGCAGAACAACAACGTGGACCTGGTGA<br>ACATCGGCAGCACCGACATCGTGGACGGCAACCACAAGCTGACCCTG<br>GGCCTGATCTGGAACATCATCCTGCACTGGCAGGTCAAAAACGTGAT<br>GAAGAACATCATGGCCGGCCTGCAGCAGACCAACAGCGAGAAGATC<br>CTGCTGAGCTGGGTGCGCCAGAGCACCCGGAACTACCCCCAGGTCAA<br>CGTGATCAACTTCACCACCTCTTGGAGCGACGGCCTGGCCCTGAACG<br>CCCTGATCCACAGCCACCGGCCCGACCTGTTCGACTGGAACAGCGTG<br>GTCTGCCAGCAGAGCGCCACCCAGCGGCTGGAACACGCCTTCAATAT<br>CGCCAGATACCAGCTGGGCATCGAGAAGCTGCTGGATCCCGAGGAC<br>GTGGACACCACCTACCCCGACAAGAAATCCATCCTGATGTATATCAC<br>CAGCCTGTTCCAGGTGCTGCCCCAGCAGGTGTCCATCGAGGCCATCC<br>AGGAAGTGGAAATGCTGCCCAGACCCCCCAAAGTGACCAAAGAGGA<br>ACACTTCCAGCTGCACCACCAGATGCACTACAGCCAGCAGATCACCG<br>TGTCCCTGGCCCAGGGCTACGAGAGAACCAGCAGCCCCAAGCCCCGG<br>TTCAAGAGCTACGCCTATACCCAGGCCGCCTACGTGACCACCAGCGA<br>CCCTACCAGAAGCCCATTCCCCAGCCAGCATCTGGAAGCCCCCGAGG<br>ACAAGAGCTTCGGCAGCAGCCTGATGGAAAGCGAAGTGAACCTGGA<br>CAGATACCAGACCGCCCTGGAAGAGGTGCTGAGCTGGCTGCTGAGCG<br>CCGAGGATACACTGCAGGCTCAGGGCGAGATCAGCAACGACGTGGA<br>AGTCGTGAAGGACCAGTTCCACACCCACGAGGGCTACATGATGGACC<br>TGACAGCCCACCAGGGCAGAGTGGGCAACATCCTGCAGCTGGGCTCC<br>AAGCTGATCGGCACCGGCAAGCTGAGCGAGGACGAAGAGACAGAGG<br>TGCAGGAACAGATGAACCTGCTGAACAGCAGATGGGAGTGCCTGCG<br>GGTGGCCAGCATGGAAAAGCAGAGCAACCTGCATCTGCTGAAGTGG<br>CAGCGGCTGACCGAGGAACAGTGCCTGTTTAGCGCCTGGCTGTCCGA<br>GAAAGAGGACGCCGTGAACAAGATCCACACCACCGGCTTCAAGGAC<br>CAGAACGAGATGCTGAGCAGCCTGCAGAAACTGGCCGTGCTGAAGG<br>CCGACCTGGAAAAGAAAAAGCAGTCCATGGGCAAGCTGTACTCCCTG<br>AAGCAGGACCTGCTGTCCACCCTGAAGAACAAGAGCGTGACCCAGA<br>AAACCGAGGCCTGGCTGGACAACTTCGCCCGGTGCTGGGACAACCTG<br>GTGCAGAAGCTGGAAAAGTCCACCGCCCAGATCTCCCAGGCCGTGAC<br>CACAACACAGCCCAGCCTGACCCAGACCACCGTGATGGAAACCGTG<br>ACAACAGTGACCACCCGGGAACAGATCCTCGTGAAGCACGCCCAGG<br>AAGAACTGCCCCCTCCACCCCCCCAGAAGAAACGGCAGATCACAGTG<br>GACAGTGAAGCTCAGATCCACACCGTGCGGGAAGAGACAATGATGG<br>TCATGACAGAGGACATGCCCCTGGAAATCAGCTACGTGCCCAGCACC<br>TACCTGACCGAGATCACCCATGTGTCCCAGGCCCTGCTGGAAGTGGA<br>ACAGCTGCTGAACGCCCCCGACCTGTGCGCCAAGGATTTCGAGGACC<br>TGTTCAAGCAGGAAGAGAGCCTGAAGAATATCAAGGATAGCCTGCA<br>GCAGAGCAGCGGCCGGATCGACATCATCCACAGCAAGAAAACAGCC<br>GCCCTGCAGAGCGCCACCCCCGTGGAAAGAGTGAAACTGCAGGAAG<br>CCCTGTCCCAGCTGGACTTCCAGTGGGAGAAAGTGAACAAAATGTAC<br>AAGGACCGGCAGGGCAGATTCGACCGCAGCGTGGAAAAGTGGCGGC<br>GGTTCCACTACGACATCAAGATCTTCAACCAGTGGCTGACAGAGGCC<br>GAGCAGTTCCTGAGAAAGACCCAGATCCCCGAGAACTGGGAGCACG<br>CCAAGTACAAGTGGTATCTGAAAGAGCTGCAGGACGGCATCGGCCA<br>GAGACAGACAGTCGTGCGGACCCTGAATGCCACCGGCGAGGAAATC<br>ATCCAGCAGTCCAGCAAGACCGACGCCAGCATTCTGCAGGAAAAGCT<br>GGGCAGCCTGAACCTGCGGTGGCAGGAAGTGTGCAAGCAGCTGTCC<br>GACCGGAAGAAGCGGCTGGAAGAACAGCTGGAACGGCTGCAGGAAC<br>TGCAGGAGGCCACCGACGAGCTGGACCTGAAACTGAGACAGGCCGA<br>AGTGATCAAGGGCAGCTGGCAGCCAGTGGGCGACCTGCTGATCGACT<br>CCCTGCAGGACCATCTGGAAAAAGTGAAGGCCCTGAGAGGCGAGAT<br>CGCCCCCCTGAAAGAAAACGTGTCCCACGTGAACGACCTGGCCCGGC<br>AGCTGACAACACTGGGCATTCAGCTGAGCCCCTACAACCTGAGCACA<br>CTGGAAGATCTGAACACCCGGTGGAAGCTGCTGCAGGTGGCCGTGGA<br>AGATAGAGTGCGGCAGCTGCACGAGGCCCACAGAGATTTTGGCCCTG<br>CCTCCCAGCACTTCCTGAGCACCAGTGTGCAGGGCCCTTGGGAGAGA<br>GCCATCTCCCCTAACAAGGTGCCCTACTACATCAACCACGAGACACA<br>GACCACCTGTTGGGACCACCCCAAGATGACCGAGCTGTACCAGAGCC<br>TGGCTGACCTGAACAACGTGCGGTTCAGCGCCTACCGGACCGCCATG<br>AAGCTGCGGAGACTGCAGAAAGCTCTGTGCCTGGATCTGCTGTCCCT<br>GTCCGCCGCCTGTGATGCCCTGGACCAGCACAATCTGAAGCAGAACG<br>ACCAGCCCATGGATATCCTGCAGATCATCAACTGCCTGACCACCATC<br>TACGACCGGCTGGAACAGGAACACAACAATCTCGTGAACGTGCCCCT<br>GTGCGTGGACATGTGCCTGAATTGGCTGCTGAATGTGTACGACACCG<br>GCCGGACAGGCCGGATCAGAGTGCTGTCCTTCAAGACCGGCATCATC<br>AGCCTGTGCAAAGCCCACCTGGAAGATAAGTACCGGTATCTGTTCAA<br>ACAGGTGGCCTCTAGCACCGGCTTTTGCGACCAGAGAAGGCTGGGCC<br>TGCTGCTGCACGACAGCATCCAGATCCCTAGACAGCTGGGCGAAGTG<br>GCCAGCTTTGGCGGCAGCAACATCGAGCCTAGCGTGCGGAGCTGCTT<br>CCAGTTCGCCAACAACAAGCCCGAGATCGAGGCCGCCCTGTTCCTGG<br>ACTGGATGAGACTGGAACCCCAGAGCATGGTGTGGCTGCCCGTGCTG |

TABLE 8-continued

Nucleotide Sequences of Dystrophin constructs.

| SEQ ID NO and Description | Sequence |
|---|---|
| | CATAGAGTGGCCGCTGCCGAGACAGCCAAGCACCAGGCCAAGTGCA<br>ACATCTGCAAAGAGTGCCCCATCATCGGCTTCCGGTACAGAAGCCTG<br>AAGCACTTCAACTACGATATCTGCCAGAGCTGTTTCTTCAGCGGCAG<br>GGTGGCCAAGGGCCACAAAATGCACTACCCCATGGTGGAATACTGCA<br>CCCCCACCACAAGCGGCGAGGATGTGCGGGATTTCGCCAAGGTGCTG<br>AAAAACAAGTTCCGGACCAAGCGGTACTTCGCCAAACACCCCCGGAT<br>GGGCTACCTGCCTGTGCAGACAGTGCTGGAAGGCGACAACATGGAA<br>ACCGACACCATGTGATGATGATTTGGGCAGAGCGATGGAGTCCTTAG<br>TATCAGTCATGACAGATGAAGAAGGAGCAGAATAAATGTTTTACAAC<br>TCCTGATTCCCGCATGCGGCCAGCTTATCGATACCGTCGAAATAAAA<br>GATCCTTATTTTCATTGGATCTGTGTGTTGGTTTTTTGTGTG |
| SEQ ID NO: 141-BXA-196480 | ATGCTGTGGTGGGAGGAAGTGGAAGATTGCTACGAGCGCGAGGACG<br>TGCAGAAGAAAACCTTCACCAAATGGGTGAACGCCCAGTTCAGCAA<br>GTTCGGCAAGCAGCACATCGAGAACCTGTTCAGCGACCTGCAGGACG<br>GCAGACGGCTGCTGGACCTGCTGGAAGGCCTGACCGGCCAGAAGCT<br>GCCCAAAGAGAAGGGCAGCACCAGAGTGCACGCCCTGAACAACGTG<br>AACAAGGCCCTGCGGGTGCTGCAGAACAACAACGTGGACCTGGTGA<br>ACATCGGCAGCACCGACATCGTGGACGGCAACCACAAGCTGACCCTG<br>GGCCTGATCTGGAACATCATCCTGCACTGGCAGGTCAAAAACGTGAT<br>GAAGAACATCATGGCCGGCCTGCAGCAGACCAACAGCGAGAAGATC<br>CTGCTGAGCTGGGTGCGCCAGAGCACCCGGAACTACCCCCAGGTCAA<br>CGTGATCAACTTCACCACCTCTTGGAGCGACGGCCTGGCCCTGAACG<br>CCCTGATCCACAGCCACCGGCCCGACCTGTTCGACTGGAACAGCGTG<br>GTCTGCCAGCAGAGCGCCACCCAGCGGCTGGAACACGCCTTCAATAT<br>CGCCAGATACCAGCTGGGCATCGAGAAGCTGCTGGATCCCGAGGAC<br>GTGGACACCACCTACCCCGACAAGAAATCCATCCTGATGTATATCAC<br>CAGCCTGTTCCAGGTGCTGCCCCAGCAGGTGTCCATCGAGGCCATCC<br>AGGAAGTGGAAATGCTGCCCAGACCCCCCAAAGTGACCAAAGAGGA<br>ACACTTCCAGCTGCACCACCAGATGCACTACAGCCAGCAGATCACCG<br>TGTCCCTGGCTCAGGGCTACGAGCGGACCAGCAGCCCCAAGCCCCGG<br>TTCAAGAGCTACGCCTACACCCAGGCCGCCTACGTGACCACCAGCGA<br>CCCCACCAGAAGCCCATTCCCCAGCCAGCATCTGGAAGCCCCCGAGG<br>ACAAGAGCTTCGGCAGCAGCCTGATGGAAAGCGAAGTGAACCTGGA<br>CAGATACCAGACCGCCCTGGAAGAGGTGCTGTCCTGGCTGCTGAGCG<br>CCGAGGATACACTGCAGGCCCAGGGCGAGATCAGCAACGACGTGGA<br>AGTGGTGAAAGACCAGTTCCACACCCACGAGGGCTACATGATGGACC<br>TGACCGCCCACCAGGGCAGAGTGGGCAACATCCTGCAGCTGGGCAG<br>CAAGCTGATCGGCACCGGCAAGCTGAGCGAGGACGAAGAGACAGAG<br>GTGCAGGAACAGATGAACCTGCTGAACAGCAGATGGGAGTGCCTGC<br>GGGTGGCCAGCATGGAAAAGCAGAGCAACCTGCACATCCACACCGT<br>GCGGGAAGAGACAATGATGGTGATGACCGAGGACATGCCCCTGGAA<br>ATCAGCTACGTGCCCAGCACCTACCTGACCGAGATCACCCACGTGTC<br>CCAGGCTCTGCTGGAAGTGGAACAGCTGCTGAACGCCCCCGACCTGT<br>GCGCCAAGGACTTCGAGGATCTGTTCAAGCAGGAAGAGAGCCTGAA<br>GAATATCAAGGACTCCCTGCAGCAGTCCAGCGGCCGGATCGACATCA<br>TCCACAGCAAGAAAACAGCCGCCCTGCAGTCCGCCACCCCCGTGGAA<br>AGAGTGAAGCTGCAGGAAGCCCTGAGCCAGCTGGACTTCCAGTGGG<br>AGAAAGTGAACAAGATGTACAAGGACCGGCAGGGCAGATTCGACCG<br>CAGCGTGGAAAAGTGGCGGCGGTTCCACTACGACATCAAGATCTTCA<br>ACCAGTGGCTGACCGAGGCCGAGCAGTTCCTGAGAAAGACCCAGAT<br>CCCCGAGAACTGGGAGCACGCCAAGTACAAGTGGTATCTGAAAGAA<br>CTGCAGGATGGCATCGGCCAGCGGCAGACCGTGGTGCGCACACTGA<br>ATGCCACCGGCGAGGAAATCATCCAGCAGAGCAGCAAGACCGACGC<br>CAGCATCCTGCAGGAAAAGCTGGGCTCCCTGAACCTGCGGTGGCAGG<br>AAGTGTGCAAGCAGCTGAGCGACCGGAAGAAGAGGCTGGAAGAACA<br>GGCCCCTGGCCTGACCACCATCGGCGCCAGCCCTACCCAGACCGTGA<br>CCCTGGTGACACAGCCCGTGGTGACAAAAGAGACAGCCATCTCCAAG<br>CTGGAAATGCCCAGCTCCCTGATGCTGGAACTGGAAAGGCTGCAGGA<br>ACTGCAGGAGGCCACCGACGAGCTGGACCTGAAGCTGCGGCAGGCC<br>GAAGTGATCAAGGGCAGCTGGCAGCCCGTGGGCGACCTGCTGATCG<br>ACAGCCTGCAGGACCACCTGGAAAAAGTGAAGGCCCTGAGAGGCGA<br>GATCGCCCCCCTGAAAGAAAACGTGTCCCACGTGAACGACCTGGCCC<br>GGCAGCTGACCACCCTGGGCATCCAGCTGAGCCCCTACAACCTGAGC<br>ACCCTGGAAGATCTGAACACCCGGTGGAAGCTGCTGCAGGTGGCCGT<br>GGAAGATAGAGTGCGGCAGCTGCACGAGGCCCACAGAGACTTTGGC<br>CCTGCCAGCCAGCACTTCCTGAGCACCTCTGTGCAGGGACCCTGGGA<br>GAGAGCCATCAGCCCCAACAAGGTGCCCTACTACATCAACCACGAGA<br>CACAGACCACCTGTTGGGACCACCCCAAGATGACCGAGCTGTACCAG<br>AGCCTGGCCGACCTGAACAATGTGCGGTTCAGCGCCTACCGGACCGC<br>CATGAAGCTGAGGCGGCTGCAGAAAGCTCTGTGCCTGGATCTGCTGA<br>GCCTGAGCGCCGCCTGCGACGCCCTGGACCAGCACAACCTGAAGCAG<br>AACGACCAGCCCATGGATATCCTGCAGATCATCAACTGCCTGACCAC<br>AATCTACGACAGGCTGGAACAGGAACACAACAATCTGGTCAACGTG |

TABLE 8-continued

Nucleotide Sequences of Dystrophin constructs.

| SEQ ID NO and Description | Sequence |
|---|---|
| | CCCCTGTGCGTGGACATGTGCCTGAATTGGCTGCTGAATGTGTACGA CACCGGCCGGACCGGCAGAATCCGGGTGCTGAGCTTCAAGACCGGC ATCATCAGCCTGTGCAAGGCCCACCTGGAAGATAAGTACCGCTACCT GTTCAAACAGGTGGCCAGCTCCACCGGCTTTTGCGACCAGCGGAGAC TGGGCCTGCTGCTGCACGACAGCATCCAGATCCCCAGACAGCTGGGC GAGGTGGCCTCCTTCGGCGGCAGCAACATTGAGCCCAGCGTGCGGAG CTGCTTCCAGTTCGCCAACAACAAGCCCGAGATCGAGGCCGCCCTGT TCCTGGACTGGATGAGACTGGAACCCCAGAGCATGGTGTGGCTGCCC GTGCTGCATCGGGTGGCCGCTGCCGAGACAGCCAAGCACCAGGCCA AGTGCAACATCTGCAAAGAGTGCCCCATCATCGGCTTCCGGTACAGA AGCCTGAAGCACTTCAACTACGATATCTGCCAGAGCTGCTTCTTCAG CGGCAGAGTGGCCAAGGGCCACAAAATGCACTACCCCATGGTGGAA TACTGCACCCCCACCACCAGCGGCGAGGATGTGCGGGACTTCGCCAA GGTGCTGAAAAACAAGTTCCGGACCAAGCGGTACTTTGCCAAGCACC CCCGGATGGGCTACCTGCCCGTGCAGACAGTGCTGGAAGGCGACAAC ATGGAAACCCCTGCCCAGATCCTGATCAGCCTGGAAAGCGAGGAAC GGGGCGAGCTGGAACGGATCCTGGCCGATCTGGAAGAGGAAAACCG GAACCTGCAGGCCGAGTACGACCGGCTGAAGCAGCAGCACGAGCAC AAGGGCCTGAGCCCCCTGCCTAGCCCCCCTGACACCATGTGATGATG ATTTGGGCAGAGCGATGGAGTCCTTAGTATCAGTCATGACAGATGAA GAAGGAGCAGAATAAATGTTTTACAACTCCTGATTCCCGCATGCGGC CAGCTTATCGATACCGTCGAAATAAAAGATCCTTATTTTCATTGGATC TGTGTGTTGGTTTTTTGTGTG |
| SEQ ID NO: 142-BXA-196480-Variant | ATGCTGTGGTGGGAGGAAGTGGAAGATTGCTACGAGCGCGAGGACG TGCAGAAGAAAACCTTCACCAAATGGGTGAACGCCCAGTTCAGCAA GTTCGGCAAGCAGCACATCGAGAACCTGTTCAGCGACCTGCAGGACG GCAGACGGCTGCTGGACCTGCTGGAAGGCCTGACCGGCCAGAAGCT GCCCAAAGAGAAGGGCAGCACCAGAGTGCACGCCCTGAACAACGTG AACAAGGCCCTGCGGGTGCTGCAGAACAACAACGTGGACCTGGTGA ACATCGGCAGCACCGACATCGTGGACGGCAACCACAAGCTGACCCTG GGCCTGATCTGGAACATCATCCTGCACTGGCAGGTCAAAAACGTGAT GAAGAACATCATGGCCGGCCTGCAGCAGACCAACAGCGAGAAGATC CTGCTGAGCTGGGTGCGCCAGAGCACCCGGAACTACCCCCAGGTCAA CGTGATCAACTTCACCACCTCTTGGAGCGACGGCCTGGCCCTGAACG CCCTGATCCACAGCCACCGGCCCGACCTGTTCGACTGGAACAGCGTG GTCTGCCAGCAGAGCGCCACCCAGCGGCTGGAACACGCCTTCAATAT CGCCAGATACCAGCTGGGCATCGAGAAGCTGCTGGATCCCGAGGAC GTGGACACCACCTACCCCGACAAGAAATCCATCCTGATGTATATCAC CAGCCTGTTCCAGGTGCTGCCCCAGCAGGTGTCCATCGAGGCCATCC AGGAAGTGGAAATGCTGCCCAGACCCCCCAAAGTGACCAAAGAGGA ACACTTCCAGCTGCACCACCAGATGCACTACAGCCAGCAGATCACCG TGTCCCTGGCTCAGGGCTACGAGCGGACCAGCAGCCCCAAGCCCCGG TTCAAGAGCTACGCCTACACCCAGGCCGCCTACGTGACCACCAGCGA CCCCACCAGAAGCCCATTCCCCAGCCAGCATCTGGAAGCCCCCGAGG ACAAGAGCTTCGGCAGCAGCCTGATGGAAAGCGAAGTGAACCTGGA CAGATACCAGACCGCCCTGGAAGAGGTGCTGTCCTGGCTGCTGAGCG CCGAGGATACACTGCAGGCCCAGGGCGAGATCAGCAACGACGTGGA AGTGGTGAAAGACCAGTTCCACACCCACGAGGGCTACATGATGGACC TGACCGCCCACCAGGGCAGAGTGGGCAACATCCTGCAGCTGGGCAG CAAGCTGATCGGCACCGGCAAGCTGAGCGAGGACGAAGAGACAGAG GTGCAGGAACAGATGAACCTGCTGAACAGCAGATGGGAGTGCCTGC GGGTGGCCAGCATGGAAAAGCAGAGCAACCTGCACCGGGTGCTGAT CCACACCGTGCGGGAAGAGACAATGATGGTGATGACCGAGGACATG CCCCTGGAAATCAGCTACGTGCCCAGCACCTACCTGACCGAGATCAC CCACGTGTCCCAGGCTCTGCTGGAAGTGGAACAGCTGCTGAACGCCC CCGACCTGTGCGCCAAGGACTTCGAGGATCTGTTCAAGCAGGAAGAG AGCCTGAAGAATATCAAGGACTCCCTGCAGCAGTCCAGCGGCCGGAT CGACATCATCCACAGCAAGAAAACAGCCGCCCTGCAGTCCGCCACCC CCGTGGAAAGAGTGAAGCTGCAGGAAGCCCTGAGCCAGCTGGACTT CCAGTGGGAGAAAGTGAACAAGATGTACAAGGACCGGCAGGGCAGA TTCGACCGCAGCGTGGAAAAGTGGCGGCGGTTCCACTACGACATCAA GATCTTCAACCAGTGGCTGACCGAGGCCGAGCAGTTCCTGAGAAAGA CCCAGATCCCCGAGAACTGGGAGCACGCCAAGTACAAGTGGTATCTG AAAGAACTGCAGGATGGCATCGGCCAGCGGCAGACCGTGGTGCGCA CACTGAATGCCACCGGCGAGGAAATCATCCAGCAGAGCAGCAAGAC CGACGCCAGCATCCTGCAGGAAAAGCTGGGCTCCCTGAACCTGCGGT GGCAGGAAGTGTGCAAGCAGCTGAGCGACCGGAAGAAGAGGCTGGA AGAACAGAAGAACGACCTGGCCCCTGGCCTGACCACCATCGGCGCC AGCCCTACCCAGACCGTGACCCTGGTGACACAGCCCGTGGTGACAAA AGAGACAGCCATCTCCAAGCTGGAAATGCCCAGCTCCCTGATGCTGG AAGTGGAAAGGCTGCAGGAACTGCAGGAGGCCACCGACGAGCTGGA CCTGAAGCTGCGGCAGGCCGAAGTGATCAAGGGCAGCTGGCAGCCC GTGGGCGACCTGCTGATCGACAGCCTGCAGGACCACCTGGAAAAAGT |

TABLE 8-continued

Nucleotide Sequences of Dystrophin constructs.

| SEQ ID NO and Description | Sequence |
|---|---|
| | GAAGGCCCTGAGAGGCGAGATCGCCCCCCTGAAAGAAAACGTGTCC CACGTGAACGACCTGGCCCGGCAGCTGACCACCCTGGGCATCCAGCT GAGCCCCTACAACCTGAGCACCCTGGAAGATCTGAACACCCGGTGGA AGCTGCTGCAGGTGGCCGTGGAAGATAGAGTGCGGCAGCTGCACGA GGCCCACAGAGACTTTGGCCCTGCCAGCCAGCACTTCCTGAGCACCT CTGTGCAGGGACCCTGGGAGAGAGCCATCAGCCCCAACAAGGTGCC CTACTACATCAACCACGAGACACAGACCACCTGTTGGGACCACCCCA AGATGACCGAGCTGTACCAGAGCCTGGCCGACCTGAACAATGTGCGG TTCAGCGCCTACCGGACCGCCATGAAGCTGAGGCGGCTGCAGAAAGC TCTGTGCCTGGATCTGCTGAGCCTGAGCGCCGCCTGCGACGCCCTGG ACCAGCACAACCTGAAGCAGAACGACCAGCCCATGGATATCCTGCA GATCATCAACTGCCTGACCACAATCTACGACAGGCTGGAACAGGAAC ACAACAATCTGGTCAACGTGCCCCTGTGCGTGGACATGTGCCTGAAT TGGCTGCTGAATGTGTACGACACCGGCCGGACCGGCAGAATCCGGGT GCTGAGCTTCAAGACCGGCATCATCAGCCTGTGCAAGGCCCACCTGG AAGATAAGTACCGCTACCTGTTCAAACAGGTGGCCAGCTCCACCGGC TTTTGCGACCAGCGGAGACTGGGCCTGCTGCTGCACGACAGCATCCA GATCCCCAGACAGCTGGGCGAGGTGGCCTCCTTCGGCGGCAGCAACA TTGAGCCCAGCGTGCGGAGCTGCTTCCAGTTCGCCAACAACAAGCCC GAGATCGAGGCCGCCCTGTTCCTGGACTGGATGAGACTGGAACCCCA GAGCATGGTGTGGCTGCCCGTGCTGCATCGGGTGGCCGCTGCCGAGA CAGCCAAGCACCAGGCCAAGTGCAACATCTGCAAAGAGTGCCCCATC ATCGGCTTCCGGTACAGAAGCCTGAAGCACTTCAACTACGATATCTG CCAGAGCTGCTTCTTCAGCGGCAGAGTGGCCAAGGGCCACAAAATGC ACTACCCCATGGTGGAATACTGCACCCCCACCACCAGCGGCGAGGAT GTGCGGGACTTCGCCAAGGTGCTGAAAAACAAGTTCCGGACCAAGC GGTACTTTGCCAAGCACCCCCGGATGGGCTACCTGCCCGTGCAGACA GTGCTGGAAGGCGACAACATGGAAACCCCTGCCCAGATCCTGATCAG CCTGGAAAGCGAGGAACGGGGCGAGCTGGAACGGATCCTGGCCGAT CTGGAAGAGGAAAACCGGAACCTGCAGGCCGAGTACGACCGGCTGA AGCAGCAGCACGAGCACAAGGGCCTGAGCCCCCTGCCTAGCCCCCCT GACACCATGTGATGATGATTTGGGCAGAGCGATGGAGTCCTTAGTAT CAGTCATGACAGATGAAGAAGGAGCAGAATAAATGTTTTACAACTCC TGATTCCCGCATGCGGCCAGCTTATCGATACCGTCGAAATAAAAGAT CCTTATTTTCATTGGATCTGTGTGTTGGTTTTTTGTGTG |
| SEQ ID NO: 143-BXA-196481 | ATGCTGTGGTGGGAGGAAGTGGAAGATTGCTACGAGCGCGAGGACG TGCAGAAGAAAACCTTCACCAAATGGGTGAACGCCCAGTTCAGCAA GTTCGGCAAGCAGCACATCGAGAACCTGTTCAGCGACCTGCAGGACG GCAGACGGCTGCTGGACCTGCTGGAAGGCCTGACCGGCCAGAAGCT GCCCAAAGAGAAGGGCAGCACCAGAGTGCACGCCCTGAACAACGTG AACAAGGCCCTGCGGGTGCTGCAGAACAACAACGTGGACCTGGTGA ACATCGGCAGCACCGACATCGTGGACGGCAACCACAAGCTGACCCTG GGCCTGATCTGGAACATCATCCTGCACTGGCAGGTCAAAAACGTGAT GAAGAACATCATGGCCGGCCTGCAGCAGACCAACAGCGAGAAGATC CTGCTGAGCTGGGTGCGCCAGAGCACCCGGAACTACCCCCAGGTCAA CGTGATCAACTTCACCACCTCTTGGAGCGACGGCCTGGCCCTGAACG CCCTGATCCACAGCCACCGGCCCGACCTGTTCGACTGGAACAGCGTG GTCTGCCAGCAGAGCGCCACCCAGCGGCTGGAACACGCCTTCAATAT CGCCAGATACCAGCTGGGCATCGAGAAGCTGCTGGATCCCGAGGAC GTGGACACCACCTACCCCGACAAGAAATCCATCCTGATGTATATCAC CAGCCTGTTCCAGGTGCTGCCCCAGCAGGTGTCCATCGAGGCCATCC AGGAAGTGGAAATGCTGCCCAGACCCCCCAAAGTGACCAAAGAGGA ACACTTCCAGCTGCACCACCAGATGCACTACAGCCAGCAGATCACCG TGTCCCTGGCTCAGGGCTACGAGCGGACCAGCAGCCCCAAGCCCCGG TTCAAGAGCTACGCCTACACCCAGGCCGCCTACGTGACCACCAGCGA CCCCACCAGAAGCCCATTCCCCAGCCAGCATCTGGAAGCCCCCGAGG ACAAGAGCTTCGGCAGCAGCCTGATGGAAAGCGAAGTGAACCTGGA CAGATACCAGACCGCCCTGGAAGAGGTGCTGTCCTGGCTGCTGAGCG CCGAGGATACACTGCAGGCCCAGGGCGAGATCAGCAACGACGTGGA AGTGGTGAAAGACCAGTTCCACACCCACGAGGGCTACATGATGGACC TGACCGCCCACCAGGGCAGAGTGGGCAACATCCTGCAGCTGGGCAG CAAGCTGATCGGCACCGGCAAGCTGAGCGAGGACGAAGAGACAGAG GTGCAGGAACAGATGAACCTGCTGAACAGCAGATGGGAGTGCCTGC GGGTGGCCAGCATGGAAAAGCAGAGCAACCTGCACAGCTACGTGCC CAGCACCTACCTGACCGAGATCACCCACGTGTCCCAGGCTCTGCTGG AAGTGGAACAGCTGCTGAACGCCCCCGACCTGTGCGCCAAGGACTTC GAGGATCTGTTCAAGCAGGAAGAGAGCCTGAAGAATATCAAGGACT CCCTGCAGCAGTCCAGCGGCCGGATCGACATCATCCACAGCAAGAAA ACAGCCGCCCTGCAGTCCGCCACCCCCGTGGAAAGAGTGAAGCTGCA GGAAGCCCTGAGCCAGCTGGACTTCCAGTGGGAGAAAGTGAACAAG ATGTACAAGGACCGGCAGGGCAGATTCGACCGCAGCGTGGAAAAGT GGCGGCGGTTCCACTACGACATCAAGATCTTCAACCAGTGGCTGACC GAGGCCGAGCAGTTCCTGAGAAAGACCCAGATCCCCGAGAACTGGG |

TABLE 8-continued

Nucleotide Sequences of Dystrophin constructs.

| SEQ ID NO and Description | Sequence |
|---|---|
| | AGCACGCCAAGTACAAGTGGTATCTGAAAGAACTGCAGGATGGCAT<br>CGGCCAGCGGCAGACCGTGGTGCGCACACTGAATGCCACCGGCGAG<br>GAAATCATCCAGCAGAGCAGCAAGACCGACGCCAGCATCCTGCAGG<br>AAAAGCTGGGCTCCCTGAACCTGCGGTGGCAGGAAGTGTGCAAGCA<br>GCTGAGCGACCGGAAGAAGAGGCTGGAAGAACAGCTGGAAGGACTG<br>GAAAAGCTGTACCAGGAACCCAGAGAGCTGCCCCCCGAGGAACGGG<br>CCCAGAACGTGACCCGGCTGCTGCGGAAACAGGCCGAAGAGGTGAA<br>CACCGAGTGGGAGAAGCTGAACCTGCACTCCGCCGACTGGCAGCGG<br>AAGATCGACGAGACACTGGAAAGGCTGCAGGAACTGCAGGAGGCCA<br>CCGACGAGCTGGACCTGAAGCTGCGGCAGGCCGAAGTGATCAAGGG<br>CAGCTGGCAGCCCGTGGGCGACCTGCTGATCGACAGCCTGCAGGACC<br>ACCTGGAAAAAGTGAAGGCCCTGAGAGGCGAGATCGCCCCCCTGAA<br>AGAAAACGTGTCCCACGTGAACGACCTGGCCCGGCAGCTGACCACCC<br>TGGGCATCCAGCTGAGCCCCTACAACCTGAGCACCCTGGAAGATCTG<br>AACACCCGGTGGAAGCTGCTGCAGGTGGCCGTGGAAGATAGAGTGC<br>GGCAGCTGCACGAGGCCCACAGAGACTTTGGCCCTGCCAGCCAGCAC<br>TTCCTGAGCACCTCTGTGCAGGGACCCTGGGAGAGAGCCATCAGCCC<br>CAACAAGGTGCCCTACTACATCAACCACGAGACACAGACCACCTGTT<br>GGGACCACCCCAAGATGACCGAGCTGTACCAGAGCCTGGCCGACCTG<br>AACAATGTGCGGTTCAGCGCCTACCGGACCGCCATGAAGCTGAGGCG<br>GCTGCAGAAAGCTCTGTGCCTGGATCTGCTGAGCCTGAGCGCCGCCT<br>GCGACGCCCTGGACCAGCACAACCTGAAGCAGAACGACCAGCCCAT<br>GGATATCCTGCAGATCATCAACTGCCTGACCACAATCTACGACAGGC<br>TGGAACAGGAACACAACAATCTGGTCAACGTGCCCCTGTGCGTGGAC<br>ATGTGCCTGAATTGGCTGCTGAATGTGTACGACACCGGCCGGACCGG<br>CAGAATCCGGGTGCTGAGCTTCAAGACCGGCATCATCAGCCTGTGCA<br>AGGCCCACCTGGAAGATAAGTACCGCTACCTGTTCAAACAGGTGGCC<br>AGCTCCACCGGCTTTTGCGACCAGCGGAGACTGGGCCTGCTGCTGCA<br>CGACAGCATCCAGATCCCCAGACAGCTGGGCGAGGTGGCCTCCTTCG<br>GCGGCAGCAACATTGAGCCCAGCGTGCGGAGCTGCTTCCAGTTCGCC<br>AACAACAAGCCCGAGATCGAGGCCGCCCTGTTCCTGGACTGGATGAG<br>ACTGGAACCCCAGAGCATGGTGTGGCTGCCCGTGCTGCATCGGGTGG<br>CCGCTGCCGAGACAGCCAAGCACCAGGCCAAGTGCAACATCTGCAA<br>AGAGTGCCCCATCATCGGCTTCCGGTACAGAAGCCTGAAGCACTTCA<br>ACTACGATATCTGCCAGAGCTGCTTCTTCAGCGGCAGAGTGGCCAAG<br>GGCCACAAAATGCACTACCCCATGGTGGAATACTGCACCCCCACCAC<br>CAGCGGCGAGGATGTGCGGGACTTCGCCAAGGTGCTGAAAAACAAG<br>TTCCGGACCAAGCGGTACTTTGCCAAGCACCCCCGGATGGGCTACCT<br>GCCCGTGCAGACAGTGCTGGAAGGCGACAACATGGAAACCCCTGCC<br>CAGATCCTGATCAGCCTGGAAAGCGAGGAACGGGGCGAGCTGGAAC<br>GGATCCTGGCCGATCTGGAAGAGGAAAACCGGAACCTGCAGGCCGA<br>GTACGACCGGCTGAAGCAGCAGCACGAGCACAAGGGCCTGAGCCCC<br>CTGCCTAGCCCCCCTGACACCATGTGATGATGATTTGGGCAGAGCGA<br>TGGAGTCCTTAGTATCAGTCATGACAGATGAAGAAGGAGCAGAATA<br>AATGTTTTACAACTCCTGATTCCCGCATGCGGCCAGCTTATCGATACC<br>GTCGAAATAAAAGATCCTTATTTTCATTGGATCTGTGTGTTGGTTTTT<br>TGTGTG |
| SEQ ID NO: 144-BXA-027741 | ATGCTGTGGTGGGAGGAAGTGGAAGATTGCTACGAGCGCGAGGACG<br>TGCAGAAGAAAACCTTCACCAAATGGGTGAACGCCCAGTTCAGCAA<br>GTTCGGCAAGCAGCACATCGAGAACCTGTTCAGCGACCTGCAGGACG<br>GCAGACGGCTGCTGGACCTGCTGGAAGGCCTGACCGGCCAGAAGCT<br>GCCCAAAGAGAAGGGCAGCACCAGAGTGCACGCCCTGAACAACGTG<br>AACAAGGCCCTGCGGGTGCTGCAGAACAACAACGTGGACCTGGTGA<br>ACATCGGCAGCACCGACATCGTGGACGGCAACCACAAGCTGACCCTG<br>GGCCTGATCTGGAACATCATCCTGCACTGGCAGGTCAAAAACGTGAT<br>GAAGAACATCATGGCCGGCCTGCAGCAGACCAACAGCGAGAAGATC<br>CTGCTGAGCTGGGTGCGCCAGAGCACCCGGAACTACCCCCAGGTCAA<br>CGTGATCAACTTCACCACCTCTTGGAGCGACGGCCTGGCCCTGAACG<br>CCCTGATCCACAGCCACCGGCCCGACCTGTTCGACTGGAACAGCGTG<br>GTCTGCCAGCAGAGCGCCACCCAGCGGCTGGAACACGCCTTCAATAT<br>CGCCAGATACCAGCTGGGCATCGAGAAGCTGCTGGATCCCGAGGAC<br>GTGGACACCACCTACCCCGACAAGAAATCCATCCTGATGTATATCAC<br>CAGCCTGTTCCAGGTGCTGCCCCAGCAGGTGTCCATCGAGGCCATCC<br>AGGAAGTGGAAATGCTGCCCAGACCCCCCAAAGTGACCAAAGAGGA<br>ACACTTCCAGCTGCACCACCAGATGCACTACAGCCAGCAGATCACCG<br>TGTCCCTGGCCCAGGGCTACGAGAGAACCAGCAGCCCCAAGCCCCGG<br>TTCAAGAGCTACGCCTATACCCAGGCCGCCTACGTGACCACCAGCGA<br>CCCTACCAGAAGCCCATTCCCCAGCCAGCATCTGGAAGCCCCCGAGG<br>ACAAGAGCTTCGGCAGCAGCCTGATGGAAAGCGAAGTGAACCTGGA<br>CAGATACCAGACCGCCCTGGAAGAGGTGCTGAGCTGGCTGCTGAGCG<br>CCGAGGATACACTGCAGGCTCAGGGCGAGATCAGCAACGACGTGGA<br>AGTCGTGAAGGACCAGTTCCACACCCACGAGGGCTACATGATGGACC<br>TGACAGCCCACCAGGGCAGAGTGGGCAACATCCTGCAGCTGGGCTCC |

TABLE 8-continued

Nucleotide Sequences of Dystrophin constructs.

| SEQ ID NO and Description | Sequence |
| --- | --- |
| | AAGCTGATCGGCACCGGCAAGCTGAGCGAGGACGAAGAGACAGAGG<br>TGCAGGAACAGATGAACCTGCTGAACAGCAGATGGGAGTGCCTGCG<br>GGTGGCCAGCATGGAAAAGCAGAGCAACCTGCATCTGCTGAAGTGG<br>CAGCGGCTGACCGAGGAACAGTGCCTGTTTAGCGCCTGGCTGTCCGA<br>GAAAGAGGACGCCGTGAACAAGATCCACACCACCGGCTTCAAGGAC<br>CAGAACGAGATGCTGAGCAGCCTGCAGAAACTGGCCGTGCTGAAGG<br>CCGACCTGGAAAAGAAAAAGCAGTCCATGGGCAAGCTGTACTCCCTG<br>AAGCAGGACCTGCTGTCCACCCTGAAGAACAAGAGCGTGACCCAGA<br>AAACCGAGGCCTGGCTGGACAACTTCGCCCGGTGCTGGGACAACCTG<br>GTGCAGAAGCTGGAAAAGTCCACCGCCCAGATCTCCCAGGCCGTGAC<br>CACAACACAGCCCAGCCTGACCCAGACCACCGTGATGGAAACCGTG<br>ACAACAGTGACCACCCGGGAACAGATCCTCGTGAAGCACGCCCAGG<br>AAGAACTGCCCCCTCCACCCCCCCAGAAGAAACGGCAGATCACAGTG<br>GACATCCACACCGTGCGGGAAGAGACAATGATGGTCATGACAGAGG<br>ACATGCCCCTGGAAATCAGCTACGTGCCCAGCACCTACCTGACCGAG<br>ATCACCCATGTGTCCCAGGCCCTGCTGGAAGTGGAACAGCTGCTGAA<br>CGCCCCCGACCTGTGCGCCAAGGATTTCGAGGACCTGTTCAAGCAGG<br>AAGAGAGCCTGAAGAATATCAAGGATAGCCTGCAGCAGAGCAGCGG<br>CCGGATCGACATCATCCACAGCAAGAAAACAGCCGCCCTGCAGAGC<br>GCCACCCCCGTGGAAAGAGTGAAACTGCAGGAAGCCCTGTCCCAGCT<br>GGACTTCCAGTGGGAGAAAGTGAACAAAATGTACAAGGACCGGCAG<br>GGCAGATTCGACCGCAGCGTGGAAAAGTGGCGGCGGTTCCACTACG<br>ACATCAAGATCTTCAACCAGTGGCTGACAGAGGCCGAGCAGTTCCTG<br>AGAAAGACCCAGATCCCCGAGAACTGGGAGCACGCCAAGTACAAGT<br>GGTATCTGAAAGAGCTGCAGGACGGCATCGGCCAGAGACAGACAGT<br>CGTGCGGACCCTGAATGCCACCGGCGAGGAAATCATCCAGCAGTCCA<br>GCAAGACCGACGCCAGCATTCTGCAGGAAAAGCTGGGCAGCCTGAA<br>CCTGCGGTGGCAGGAAGTGTGCAAGCAGCTGTCCGACCGGAAGAAG<br>CGGCTGGAAGAACAGCTGGAACGGCTGCAGGAACTGCAGGAGGCCA<br>CCGACGAGCTGGACCTGAAACTGAGACAGGCCGAAGTGATCAAGGG<br>CAGCTGGCAGCCAGTGGGCGACCTGCTGATCGACTCCCTGCAGGACC<br>ATCTGGAAAAAGTGAAGGCCCTGAGAGGCGAGATCGCCCCCCTGAA<br>AGAAAACGTGTCCCACGTGAACGACCTGGCCCGGCAGCTGACAACA<br>CTGGGCATTCAGCTGAGCCCCTACAACCTGAGCACACTGGAAGATCT<br>GAACACCCGGTGGAAGCTGCTGCAGGTGGCCGTGGAAGATAGAGTG<br>CGGCAGCTGCACGAGGCCCACAGAGATTTTGGCCCTGCCTCCCAGCA<br>CTTCCTGAGCACCAGTGTGCAGGGCCCTTGGGAGAGAGCCATCTCCC<br>CTAACAAGGTGCCCTACTACATCAACCACGAGACACAGACCACCTGT<br>TGGGACCACCCCAAGATGACCGAGCTGTACCAGAGCCTGGCTGACCT<br>GAACAACGTGCGGTTCAGCGCCTACCGGACCGCCATGAAGCTGCGGA<br>GACTGCAGAAAGCTCTGTGCCTGGATCTGCTGTCCCTGTCCGCCGCCT<br>GTGATGCCCTGGACCAGCACAATCTGAAGCAGAACGACCAGCCCATG<br>GATATCCTGCAGATCATCAACTGCCTGACCACCATCTACGACCGGCT<br>GGAACAGGAACACAACAATCTCGTGAACGTGCCCCTGTGCGTGGACA<br>TGTGCCTGAATTGGCTGCTGAATGTGTACGACACCGGCCGGACAGGC<br>CGGATCAGAGTGCTGTCCTTCAAGACCGGCATCATCAGCCTGTGCAA<br>AGCCCACCTGGAAGATAAGTACCGGTATCTGTTCAAACAGGTGGCCT<br>CTAGCACCGGCTTTTGCGACCAGAGAAGGCTGGGCCTGCTGCTGCAC<br>GACAGCATCCAGATCCCTAGACAGCTGGGCGAAGTGGCCAGCTTTGG<br>CGGCAGCAACATCGAGCCTAGCGTGCGGAGCTGCTTCCAGTTCGCCA<br>ACAACAAGCCCGAGATCGAGGCCGCCCTGTTCCTGGACTGGATGAGA<br>CTGGAACCCCAGAGCATGGTGTGGCTGCCCGTGCTGCATAGAGTGGC<br>CGCTGCCGAGACAGCCAAGCACCAGGCCAAGTGCAACATCTGCAAA<br>GAGTGCCCCATCATCGGCTTCCGGTACAGAAGCCTGAAGCACTTCAA<br>CTACGATATCTGCCAGAGCTGTTTCTTCAGCGGCAGGGTGGCCAAGG<br>GCCACAAAATGCACTACCCCATGGTGGAATACTGCACCCCCACCACA<br>AGCGGCGAGGATGTGCGGGATTTCGCCAAGGTGCTGAAAAACAAGT<br>TCCGGACCAAGCGGTACTTCGCCAAACACCCCCGGATGGGCTACCTG<br>CCTGTGCAGACAGTGCTGGAAGGCGACAACATGGAAACCCCTGCCCA<br>GATCCTGATCAGCCTGGAATCCGAGGAACGGGGCGAGCTGGAACGG<br>ATCCTGGCCGATCTGGAAGAGGAAAACCGGAACCTGCAGGCCGAGT<br>ACGACCGGCTGAAGCAGCAGCACGAGCACAAGGGCCTGAGCCCCCT<br>GCCTAGCCCCCCTGACACCATGTGATGATGATTTGGGCAGAGCGATG<br>GAGTCCTTAGTATCAGTCATGACAGATGAAGAAGGAGCAGAATAAA<br>TGTTTTACAACTCCTGATTCCCGCATGCGGCCAGCTTATCGATACCGT<br>CGA |
| SEQ ID NO: 145-BXA-027744 | ATGCTGTGGTGGGAGGAAGTGGAAGATTGCTACGAGCGCGAGGACG<br>TGCAGAAGAAAACCTTCACCAAATGGGTGAACGCCCAGTTCAGCAA<br>GTTCGGCAAGCAGCACATCGAGAACCTGTTCAGCGACCTGCAGGACG<br>GCAGACGGCTGCTGGACCTGCTGGAAGGCCTGACCGGCCAGAAGCT<br>GCCCAAAGAGAAGGGCAGCACCAGAGTGCACGCCCTGAACAACGTG<br>AACAAGGCCCTGCGGGTGCTGCAGAACAACAACGTGGACCTGGTGA<br>ACATCGGCAGCACCGACATCGTGGACGGCAACCACAAGCTGACCCTG |

TABLE 8-continued

Nucleotide Sequences of Dystrophin constructs.

| SEQ ID NO and Description | Sequence |
|---|---|
| | GGCCTGATCTGGAACATCATCCTGCACTGGCAGGTCAAAAACGTGAT<br>GAAGAACATCATGGCCGGCCTGCAGCAGACCAACAGCGAGAAGATC<br>CTGCTGAGCTGGGTGCGCCAGAGCACCCGGAACTACCCCCAGGTCAA<br>CGTGATCAACTTCACCACCTCTTGGAGCGACGGCCTGGCCCTGAACG<br>CCCTGATCCACAGCCACCGGCCCGACCTGTTCGACTGGAACAGCGTG<br>GTCTGCCAGCAGAGCGCCACCCAGCGGCTGGAACACGCCTTCAATAT<br>CGCCAGATACCAGCTGGGCATCGAGAAGCTGCTGGATCCCGAGGAC<br>GTGGACACCACCTACCCCGACAAGAAATCCATCCTGATGTATATCAC<br>CAGCCTGTTCCAGGTGCTGCCCCAGCAGGTGTCCATCGAGGCCATCC<br>AGGAAGTGGAAATGCTGCCCAGACCCCCCAAAGTGACCAAAGAGGA<br>ACACTTCCAGCTGCACCACCAGATGCACTACAGCCAGCAGATCACCG<br>TGTCCCTGGCTCAGGGCTACGAGCGGACCAGCAGCCCCAAGCCCCGG<br>TTCAAGAGCTACGCCTACACCCAGGCCGCCTACGTGACCACCAGCGA<br>CCCCACCAGAAGCCCATTCCCCAGCCAGCATCTGGAAGCCCCCGAGG<br>ACAAGAGCTTCGGCAGCAGCCTGATGGAAAGCGAAGTGAACCTGGA<br>CAGATACCAGACCGCCCTGGAAGAGGTGCTGTCCTGGCTGCTGAGCG<br>CCGAGGATACACTGCAGGCCCAGGGCGAGATCAGCAACGACGTGGA<br>AGTGGTGAAAGACCAGTTCCACACCCACGAGGGCTACATGATGGACC<br>TGACCGCCCACCAGGGCAGAGTGGGCAACATCCTGCAGCTGGGCAG<br>CAAGCTGATCGGCACCGGCAAGCTGAGCGAGGACGAAGAGACAGAG<br>GTGCAGGAACAGATGAACCTGCTGAACAGCAGATGGGAGTGCCTGC<br>GGGTGGCCAGCATGGAAAAGCAGAGCAACCTGCACATCCACACCGT<br>GCGGGAAGAGACAATGATGGTGATGACCGAGGACATGCCCCTGGAA<br>ATCAGCTACGTGCCCAGCACCTACCTGACCGAGATCACCCACGTGTC<br>CCAGGCTCTGCTGGAAGTGGAACAGCTGCTGAACGCCCCCGACCTGT<br>GCGCCAAGGACTTCGAGGATCTGTTCAAGCAGGAAGAGAGCCTGAA<br>GAATATCAAGGACTCCCTGCAGCAGTCCAGCGGCCGGATCGACATCA<br>TCCACAGCAAGAAAACAGCCGCCCTGCAGTCCGCCACCCCCGTGGAA<br>AGAGTGAAGCTGCAGGAAGCCCTGAGCCAGCTGGACTTCCAGTGGG<br>AGAAAGTGAACAAGATGTACAAGGACCGGCAGGGCAGATTCGACCG<br>CAGCGTGGAAAAGTGGCGGCGGTTCCACTACGACATCAAGATCTTCA<br>ACCAGTGGCTGACCGAGGCCGAGCAGTTCCTGAGAAAGACCCAGAT<br>CCCCGAGAACTGGGAGCACGCCAAGTACAAGTGGTATCTGAAAGAA<br>CTGCAGGATGGCATCGGCCAGCGGCAGACCGTGGTGCGCACACTGA<br>ATGCCACCGGCGAGGAAATCATCCAGCAGAGCAGCAAGACCGACGC<br>CAGCATCCTGCAGGAAAAGCTGGGCTCCCTGAACCTGCGGTGGCAGG<br>AAGTGTGCAAGCAGCTGAGCGACCGGAAGAAGAGGCTGGAAGAACA<br>GGCCCCTGGCCTGACCACCATCGGCGCCAGCCCTACCCAGACCGTGA<br>CCCTGGTGACACAGCCCGTGGTGACAAAAGAGACAGCCATCTCCAAG<br>CTGGAAATGCCCAGCTCCCTGATGCTGGAAGTACCTGCTCTGGCAGA<br>TTTCAACCGGGCTTGGACAGAACTTACCGACTGGCTTTCTCTGCTTGA<br>TCAAGTTATAAAATCACAGAGGGTGATGGTGGGTGACCTTGAGGATA<br>TCAACGAGATGATCATCAAGCAGAAGGCAACAATGCAGGATTTGGA<br>ACAGAGGCGTCCCCAGTTGGAAGAACTCATTACCGCTGCCCAAAATT<br>TGAAAAACAAGACCAGCAATCAAGAGGCTAGAACAATCATTACGGA<br>TCGAATTGAAAGAATTCAGAATCAGTGGGATGAAGTACAAGAACAC<br>CTTCAGAACCGGAGGCAACAGTTGAATGAAATGCTGGAAAGGCTGC<br>AGGAACTGCAGGAGGCCACCGACGAGCTGGACCTGAAGCTGCGGCA<br>GGCCGAAGTGATCAAGGGCAGCTGGCAGCCCGTGGGCGACCTGCTG<br>ATCGACAGCCTGCAGGACCACCTGGAAAAAGTGAAGGCCCTGAGAG<br>GCGAGATCGCCCCCCTGAAAGAAAACGTGTCCCACGTGAACGACCTG<br>GCCCGGCAGCTGACCACCCTGGGCATCCAGCTGAGCCCCTACAACCT<br>GAGCACCCTGGAAGATCTGAACACCCGGTGGAAGCTGCTGCAGGTG<br>GCCGTGGAAGATAGAGTGCGGCAGCTGCACGAGGCCCACAGAGACT<br>TTGGCCCTGCCAGCCAGCACTTCCTGAGCACCTCTGTGCAGGGACCC<br>TGGGAGAGAGCCATCAGCCCCAACAAGGTGCCCTACTACATCAACCA<br>CGAGACACAGACCACCTGTTGGGACCACCCCAAGATGACCGAGCTGT<br>ACCAGAGCCTGGCCGACCTGAACAATGTGCGGTTCAGCGCCTACCGG<br>ACCGCCATGAAGCTGAGGCGGCTGCAGAAAGCTCTGTGCCTGGATCT<br>GCTGAGCCTGAGCGCCGCCTGCGACGCCCTGGACCAGCACAACCTGA<br>AGCAGAACGACCAGCCCATGGATATCCTGCAGATCATCAACTGCCTG<br>ACCACAATCTACGACAGGCTGGAACAGGAACACAACAATCTGGTCA<br>ACGTGCCCCTGTGCGTGGACATGTGCCTGAATTGGCTGCTGAATGTG<br>TACGACACCGGCCGGACCGGCAGAATCCGGGTGCTGAGCTTCAAGAC<br>CGGCATCATCAGCCTGTGCAAGGCCCACCTGGAAGATAAGTACCGCT<br>ACCTGTTCAAACAGGTGGCCAGCTCCACCGGCTTTTGCGACCAGCGG<br>AGACTGGGCCTGCTGCTGCACGACAGCATCCAGATCCCCAGACAGCT<br>GGGCGAGGTGGCCTCCTTCGGCGGCAGCAACATTGAGCCCAGCGTGC<br>GGAGCTGCTTCCAGTTCGCCAACAACAAGCCCGAGATCGAGGCCGCC<br>CTGTTCCTGGACTGGATGAGACTGGAACCCCAGAGCATGGTGTGGCT<br>GCCCGTGCTGCATCGGGTGGCCGCTGCCGAGACAGCCAAGCACCAGG<br>CCAAGTGCAACATCTGCAAAGAGTGCCCCATCATCGGCTTCCGGTAC<br>AGAAGCCTGAAGCACTTCAACTACGATATCTGCCAGAGCTGCTTCTT<br>CAGCGGCAGAGTGGCCAAGGGCCACAAAATGCACTACCCCATGGTG |

TABLE 8-continued

| Nucleotide Sequences of Dystrophin constructs. | |
|---|---|
| SEQ ID NO and Description | Sequence |
| | GAATACTGCACCCCCACCACCAGCGGCGAGGATGTGCGGGACTTCGC CAAGGTGCTGAAAAACAAGTTCCGGACCAAGCGGTACTTTGCCAAGC ACCCCCGGATGGGCTACCTGCCCGTGCAGACAGTGCTGGAAGGCGAC AACATGGAAACCCCTGCCCAGATCCTGATCAGCCTGGAAAGCGAGG AACGGGGCGAGCTGGAACGGATCCTGGCCGATCTGGAAGAGGAAAA CCGGAACCTGCAGGCCGAGTACGACCGGCTGAAGCAGCAGCACGAG CACAAGGGCCTGAGCCCCCTGCCTAGCCCCCCTGACACCATGTGATG ATGATTTGGGCAGAGCGATGGAGTCCTTAGTATCAGTCATGACAGAT GAAGAAGGAGCAGAATAAATGTTTTACAACTCCTGATTCCCGCATGC GGCCAGCTTATCGATACCGTCGAAATAAAAGATCCTTATTTTCATTGG ATCTGTGTGTTGGTTTTTTGTGTG |
| SEQ ID NO: 146-BXA-027742 | ATGCTGTGGTGGGAGGAAGTGGAAGATTGCTACGAGCGCGAGGACG TGCAGAAGAAAACCTTCACCAAATGGGTCAACGCCCAGTTCAGCAAG TTCGGCAAGCAGCACATCGAGAACCTGTTCAGCGACCTGCAGGACGG CAGACGGCTGCTGGATCTGCTGGAAGGCCTGACCGGACAGAAGCTGC CCAAAGAGAAGGGCAGCACCAGAGTGCACGCCCTGAACAACGTGAA CAAGGCCCTGCGGGTGCTGCAGAACAACAACGTGGACCTCGTGAAC ATCGGCAGCACCGACATCGTGGACGGCAACCACAAGCTGACCCTGG GCCTGATCTGGAACATCATCCTGCACTGGCAAGTGAAGAACGTGATG AAGAACATCATGGCCGGCCTGCAGCAGACCAACAGCGAGAAGATCC TGCTGAGCTGGGTGCGCCAGAGCACCAGAAACTACCCCCAAGTGAAC GTGATCAACTTCACCACCTCTTGGAGCGACGGCCTGGCCCTGAATGC CCTGATCCACAGCCACAGACCCGACCTGTTCGACTGGAACAGCGTCG TGTGTCAGCAGAGCGCCACCCAGAGGCTGGAACACGCCTTCAATATC GCCAGATACCAGCTGGGCATCGAGAAGCTGCTGGACCCCGAGGATGT GGACACCACCTACCCCGACAAGAAATCCATCCTGATGTATATCACCA GCCTGTTCCAGGTGCTGCCTCAGCAGGTGTCCATCGAGGCCATCCAG GAAGTGGAAATGCTGCCCAGACCCCCCAAAGTGACCAAAGAGGAAC ACTTCCAGCTGCACCACCAGATGCACTACTCTCAGCAGATCACCGTG TCCCTGGCCCAGGGCTACGAGAGAACCAGCAGCCCCAAGCCCCGGTT CAAGAGCTACGCCTATACCCAGGCCGCCTACGTGACCACCAGCGACC CTACCAGAAGCCCATTCCCCAGCCAGCATCTGGAAGCCCCCGAGGAC AAGAGCTTCGGCAGCAGCCTGATGGAAAGCGAAGTGAACCTGGATA GATACCAGACCGCCCTGGAAGAGGTGCTGTCCTGGCTGCTGAGCGCC GAGGATACACTGCAGGCTCAGGGCGAGATCAGCAACGACGTGGAAG TCGTGAAGGACCAGTTCCACACCCACGAGGGCTACATGATGGACCTG ACAGCCCACCAGGGCAGAGTGGGCAACATTCTGCAGCTGGGCTCCAA GCTGATCGGCACCGGCAAGCTGAGCGAGGACGAAGAGACAGAGGTG CAGGAACAGATGAACCTGCTGAACAGCAGATGGGAGTGCCTGAGAG TGGCCAGCATGGAAAAGCAGAGCAACCTGCACCGGGTGCTGATGGA TCTGCAGAACCAGAAGCTGAAAGAGCTGAACGACTGGCTGACCAAG ACCGAGGAACGGACCCGGAAGATGGAAGAGGAACCCCTGGGACCAG ACCTGGAAGATCTGAAAAGACAGGTGCAGCAGCACAAAGTGCTGCA GGAAGATCTGGAACAGGAACAGGTGCGCGTGAACAGCCTGACCCAC ATGGTCGTGGTGGTGGACGAGAGCAGCGGCGATCATGCCACAGCCG CTCTGGAAGAACAGCTGAAGGTGCTGGGCGACAGATGGGCCAACAT CTGCCGGTGGACCGAGGATAGATGGGTGCTGCTGCAGGACATCCTGC TGAAGTGGCAGCGGCTGACAGAGGAACAGTGCCTGTTCTCCGCCTGG CTGTCCGAGAAAGAGGACGCCGTGAACAAAATCCACACCACCGGCTT CAAGGACCAGAACGAGATGCTGAGCAGCCTGCAGAAACTGGCCGTG CTGAAGGCCGACCTGGAAAAGAAAAAGCAGTCCATGGGCAAGCTGT ACTCCCTGAAGCAGGACCTGCTGTCCACCCTGAAGAACAAGAGCGTG ACCCAGAAAACCGAGGCCTGGCTGGACAACTTCGCCCGGTGCTGGGA CAACCTGGTGCAGAAGCTGGAAAAGTCCACCGCCCAGATCTCCCAGG CCATTCACACCGTGCGGGAAGAGACAATGATGGTCATGACTGAGGAC ATGCCCCTGGAAATCAGCTACGTGCCCTCCACCTACCTGACCGAGAT CACCCATGTGTCCCAGGCCCTGCTGGAAGTGGAACAGCTGCTGAACG CCCCCGATCTGTGCGCCAAGGACTTCGAGGATCTGTTCAAGCAGGAA GAGAGCCTGAAGAATATCAAGGACTCTCTGCAGCAGTCCAGCGGCA GAATCGACATCATCCACAGCAAGAAAACAGCCGCCCTGCAGTCCGCC ACCCCCGTGGAAAGAGTGAAACTGCAGGAAGCCCTGTCCCAGCTGG ACTTCCAGTGGGAGAAAGTGAACAAGATGTACAAGGACCGGCAGGG CAGATTCGACCGCAGCGTGGAAAAGTGGCGGCGGTTCCACTACGACA TCAAGATCTTCAACCAGTGGCTGACCGAGGCCGAACAGTTCCTGAGA AAGACCCAGATCCCCGAGAACTGGGAGCACGCCAAGTACAAGTGGT ATCTGAAAGAACTGCAGGATGGCATCGGCCAGAGACAGACCGTCGT GCGGACACTGAATGCCACCGGCGAGGAAATCATCCAGCAGAGCAGC AAGACCGACGCCAGCATCCTGCAGGAAAAGCTGGGCAGCCTGAACC TGAGATGGCAGGAAGTGTGCAAGCAGCTGTCCGACCGGAAGAAGCG GCTGGAAGAACAGCTGGAACGGCTGCAGGAACTGCAGGAGGCCACC GACGAGCTGGACCTGAAACTGAGACAGGCCGAAGTGATCAAGGGCA GCTGGCAGCCAGTGGGCGACCTGCTGATCGATTCTCTGCAGGACCAC CTGGAAAAAGTGAAGGCCCTGAGAGGCGAGATCGCCCCCCTGAAAG |

TABLE 8-continued

Nucleotide Sequences of Dystrophin constructs.

| SEQ ID NO and Description | Sequence |
|---|---|
| | AAAACGTGTCCCACGTGAACGACCTGGCCCGGCAGCTGACAACACTG GGCATCCAGCTGAGCCCCTACAACCTGAGCACACTGGAAGATCTGAA CACCCGGTGGAAGCTGCTGCAGGTGGCCGTGGAAGATAGAGTGCGG CAGCTGCACGAGGCCCACAGAGATTTTGGCCCTGCCTCCCAGCACTT CCTGAGCACCTCAGTGCAGGGCCCTTGGGAGAGAGCCATCTCCCCTA ACAAGGTGCCCTACTACATCAACCACGAGACACAGACCACCTGTTGG GACCACCCCAAGATGACCGAGCTGTACCAGAGCCTGGCCGACCTGAA CAATGTGCGGTTCAGCGCCTACCGGACCGCCATGAAGCTGCGGAGAC TGCAGAAAGCTCTGTGCCTGGATCTGCTGTCCCTGAGCGCCGCCTGT GATGCCCTGGACCAGCACAATCTGAAGCAGAACGACCAGCCCATGG ATATCCTGCAGATCATTAACTGCCTGACCACCATCTACGACCGGCTG GAACAGGAACACAACAACCTCGTGAACGTGCCCCTGTGCGTGGACAT GTGCCTGAATTGGCTGCTGAATGTGTACGACACCGGCCGGACAGGCC GGATCAGAGTGCTGAGCTTCAAGACCGGCATCATCAGCCTGTGCAAA GCCCATCTGGAAGATAAGTACCGCTACCTGTTCAAACAGGTGGCCAG CTCTACCGGCTTCTGCGATCAGAGAAGGCTGGGCCTGCTGCTGCATG ACTCCATCCAGATCCCCAGACAGCTGGGCGAGGTGGCCTCTTTCGGC GGCAGCAATATCGAGCCTAGCGTGCGGAGCTGCTTCCAGTTCGCCAA CAACAAGCCCGAGATCGAGGCCGCCCTGTTTCTGGACTGGATGAGAC TGGAACCCCAGAGCATGGTGTGGCTGCCCGTGCTGCATAGAGTGGCC GCTGCCGAGACAGCCAAGCACCAGGCCAAGTGCAATATCTGCAAAG AGTGCCCCATCATCGGCTTCCGGTACAGAAGCCTGAAGCACTTCAAC TACGATATCTGCCAGAGCTGTTTCTTCAGCGGCAGGGTGGCCAAGGG CCACAAAATGCACTACCCCATGGTGGAATACTGCACCCCCACCACAA GCGGAGAGGATGTGCGGGACTTCGCCAAGGTGCTGAAAAACAAGTT CCGGACCAAGCGGTATTTCGCCAAACACCCCCGGATGGGCTACCTGC CTGTGCAGACAGTGCTGGAAGGCGACAACATGGAAACCGACACCAT GTGATGATGATTTGGGCAGAGCGATGGAGTCCTTAGTATCAGTCATG ACAGATGAAGAAGGAGCAGAATAAATGTTTTACAACTCCTGATTCCC GCATGCGGCCAGCTTATCGATACCGTCGAAATAAAAGATCCTTATTT TCATTGGATCTGTGTGTTGGTTTTTTGTGTG |
| SEQ ID NO: 147-BXA-027743 | ATGCTGTGGTGGGAGGAAGTGGAAGATTGCTACGAGCGCGAGGACG TGCAGAAGAAAACCTTCACCAAATGGGTGAACGCCCAGTTCAGCAA GTTCGGCAAGCAGCACATCGAGAACCTGTTCAGCGACCTGCAGGACG GCAGACGGCTGCTGGACCTGCTGGAAGGCCTGACCGGCCAGAAGCT GCCCAAAGAGAAGGGCAGCACCAGAGTGCACGCCCTGAACAACGTG AACAAGGC CCTGCGGGTGCTGCAGAACAACAACGTGGACCTGGTGAACATCGGCA GCACCGACATCGTGGACGGCAAC CACAAGCTGACCCTGGGCCTGATCTGGAACATCATCCTGCACTGGCA GGTCAAAAACGTGATGAAGAACA TCATGGCCGGCCTGCAGCAGACCAACAGCGAGAAGATCCTGCTGAGC TGGGTGCGCCAGAGCACCCGGAA CTACCCCCAGGTCAACGTGATCAACTTCACCACCTCTTGGAGCGACG GCCTGGCCCTGAACGCCCTGATC CACAGCCACCGGCCCGACCTGTTCGACTGGAACAGCGTGGTCTGCCA GCAGAGCGCCACCCAGCGGCTGG AACACGCCTTCAATATCGCCAGATACCAGCTGGGCATCGAGAAGCTG CTGGATCCCGAGGACGTGGACAC CACCTACCCCGACAAGAAATCCATCCTGATGTATATCACCAGCCTGT TCCAGGTGCTGCCCCAGCAGGTG TCCATCGAGGCCATCCAGGAAGTGGAAATGCTGCCCAGACCCCCCAA AGTGACCAAAGAGGAACACTTCC AGCTGCACCACCAGATGCACTACAGCCAGCAGATCACCGTGTCCCTG GCTCAGGGCTACGAGCGGACCAG CAGCCCCAAGCCCCGGTTCAAGAGCTACGCCTACACCCAGGCCGCCT ACGTGACCACCAGCGACCCCACC AGAAGCCCATTCCCCAGCCAGCATCTGGAAGCCCCCGAGGACAAGA GCTTCGGCAGCAGCCTGATGGAAA GCGAAGTGAACCTGGACAGATACCAGACCGCCCTGGAAGAGGTGCT GTCCTGGCTGCTGAGCGCCGAGGA TACACTGCAGGCCCAGGGCGAGATCAGCAACGACGTGGAAGTGGTG AAAGACCAGTTCCACACCCACGAG GGCTACATGATGGACCTGACCGCCCACCAGGGCAGAGTGGGCAACA TCCTGCAGCTGGGCAGCAAGCTGA TCGGCACCGGCAAGCTGAGCGAGGACGAAGAGACAGAGGTGCAGGA ACAGATGAACCTGCTGAACAGCAG ATGGGAGTGCCTGCGGGTGGCCAGCATGGAAAAGCAGAGCAACCTG CACATCCACACCGTGCGGGAAGAG ACAATGATGGTGATGACCGAGGACATGCCCCTGGAAATCAGCTACGT GCCCAGCACCTACCTGACCGAGA TCACCCACGTGTCCCAGGCTCTGCTGGAAGTGGAACAGCTGCTGAAC GCCCCCGACCTGTGCGCCAAGGA |

TABLE 8-continued

Nucleotide Sequences of Dystrophin constructs.

| SEQ ID NO and Description | Sequence |
| --- | --- |
| | CTTCGAGGATCTGTTCAAGCAGGAAGAGAGCCTGAAGAATATCAAG GACTCCCTGCAGCAGTCCAGCGGC CGGATCGACATCATCCACAGCAAGAAAACAGCCGCCCTGCAGTCCGC CACCCCCGTGGAAAGAGTGAAGC TGCAGGAAGCCCTGAGCCAGCTGGACTTCCAGTGGGAGAAAGTGAA CAAGATGTACAAGGACCGGCAGGG CAGATTCGACCGCAGCGTGGAAAAGTGGCGGCGGTTCCACTACGACA TCAAGATCTTCAACCAGTGGCTG ACCGAGGCCGAGCAGTTCCTGAGAAAGACCCAGATCCCCGAGAACT GGGAGCACGCCAAGTACAAGTGGT ATCTGAAAGAACTGCAGGATGGCATCGGCCAGCGGCAGACCGTGGT GCGCACACTGAATGCCACCGGCGA GGAAATCATCCAGCAGAGCAGCAAGACCGACGCCAGCATCCTGCAG GAAAAGCTGGGCTCCCTGAACCTG CGGTGGCAGGAAGTGTGCAAGCAGCTGAGCGACCGGAAGAAGAGGC TGGAAGAACAGGCCCCTGGCCTGA CCACCATCGGCGCCAGCCCTACCCAGACCGTGACCCTGGTGACACAG CCCGTGGTGACAAAAGAGACAGC CATCTCCAAGCTGGAAATGCCCAGCTCCCTGATGCTGGAATCTGACC AGTGGAAGCGTCTGCACCTTTCT CTGCAGGAACTTCTGGTGTGGCTACAGCTGAAAGATGATGAATTAAG CCGGCAGGCACCTATTGGAGGCG ACTTTCCAGCAGTTCAGAAGCAGAACGATGTACATAGGGCCTTCAAG AGGGAATTGAAAACTAAAGAACC TGTAATCATGAGTACTCTTGAGACTGTACGAATATTTCTGACAGAGC AGCCTTTGGAAGGACTAGAGAAA CTCTACCAGGAGCCCAGAGAGCTGCCTCCTGAGGAGAGAGCCCAGA ATGTCACTCGGCTTCTACGAAAGC AGGCTGAGGAGGTCAATACTGAGTGGGAAAAATTGAACCTGCACTCC GCTGACTGGCAGAGAAAAATAGA TGAGACCCTGGAAAGGCTGCAGGAACTGCAGGAGGCCACCGACGAG CTGGACCTGAAGCTGCGGCAGGCC GAAGTGATCAAGGGCAGCTGGCAGCCCGTGGGCGACCTGCTGATCG ACAGCCTGCAGGACCACCTGGAAA AAGTGAAGGCCCTGAGAGGCGAGATCGCCCCCCTGAAAGAAAACGT GTCCCACGTGAACGACCTGGCCCG GCAGCTGACCACCCTGGGCATCCAGCTGAGCCCCTACAACCTGAGCA CCCTGGAAGATCTGAACACCCGG TGGAAGCTGCTGCAGGTGGCCGTGGAAGATAGAGTGCGGCAGCTGC ACGAGGCCCACAGAGACTTTGGCC CTGCCAGCCAGCACTTCCTGAGCACCTCTGTGCAGGGACCCTGGGAG AGAGCCATCAGCCCCAACAAGGT GCCCTACTACATCAACCACGAGACACAGACCACCTGTTGGGACCACC CCAAGATGACCGAGCTGTACCAG AGCCTGGCCGACCTGAACAATGTGCGGTTCAGCGCCTACCGGACCGC CATGAAGCTGAGGCGGCTGCAGA AAGCTCTGTGCCTGGATCTGCTGAGCCTGAGCGCCGCCTGCGACGCC CTGGACCAGCACAACCTGAAGCA GAACGACCAGCCCATGGATATCCTGCAGATCATCAACTGCCTGACCA CAATCTACGACAGGCTGGAACAG GAACACAACAATCTGGTCAACGTGCCCCTGTGCGTGGACATGTGCCT GAATTGGCTGCTGAATGTGTACG ACACCGGCCGGACCGGCAGAATCCGGGTGCTGAGCTTCAAGACCGG CATCATCAGCCTGTGCAAGGCCCA CCTGGAAGATAAGTACCGCTACCTGTTCAAACAGGTGGCCAGCTCCA CCGGCTTTTGCGACCAGCGGAGA CTGGGCCTGCTGCTGCACGACAGCATCCAGATCCCCAGACAGCTGGG CGAGGTGGCCTCCTTCGGCGGCA GCAACATTGAGCCCAGCGTGCGGAGCTGCTTCCAGTTCGCCAACAAC AAGCCCGAGATCGAGGCCGCCCT GTTCCTGGACTGGATGAGACTGGAACCCCAGAGCATGGTGTGGCTGC CCGTGCTGCATCGGGTGGCCGCT GCCGAGACAGCCAAGCACCAGGCCAAGTGCAACATCTGCAAAGAGT GCCCCATCATCGGCTTCCGGTACA GAAGCCTGAAGCACTTCAACTACGATATCTGCCAGAGCTGCTTCTTC AGCGGCAGAGTGGCCAAGGGCCA CAAAATGCACTACCCCATGGTGGAATACTGCACCCCCACCACCAGCG GCGAGGATGTGCGGGACTTCGCC AAGGTGCTGAAAAACAAGTTCCGGACCAAGCGGTACTTTGCCAAGCA CCCCCGGATGGGCTACCTGCCCG TGCAGACAGTGCTGGAAGGCGACAACATGGAAACCCCTGCCCAGAT CCTGATCAGCCTGGAAAGCGAGGA ACGGGGCGAGCTGGAACGGATCCTGGCCGATCTGGAAGAGGAAAAC CGGAACCTGCAGGCCGAGTACGAC |

TABLE 8-continued

| Nucleotide Sequences of Dystrophin constructs. | |
|---|---|
| SEQ ID NO and Description | Sequence |
| | CGGCTGAAGCAGCAGCACGAGCACAAGGGCCTGAGCCCCCTGCCTA GCCCCCCTGACACCATGTGATGAT GATTTGGGCAGAGCGATGGAGTCCTTAGTATCAGTCATGACAGATGA AGAAGGAGCAGAATAAATGTTTT ACAACTCCTGATTCCCGCATGCGGCCAGCTTATCGATACCGTCGAAA TAAAAGATCCTTATTTTCATTGG ATCTGTGTGTTGGTTTTTTGTGTG |
| SEQ ID NO: 148-BXA-212371 | ATGCTGTGGTGGGAGGAAGTGGAAGATTGCTACGAGCGCGAGGACG TGCAGAAGAAAACCTTCACCAAATGGGTGAACGCCCAGTTCAGCAA GTTCGGCAAGCAGCACATCGAGAACCTGTTCAGCGACCTGCAGGACG GCAGACGGCTGCTGGACCTGCTGGAAGGCCTGACCGGCCAGAAGCT GCCCAAAGAGAAGGGCAGCACCAGAGTGCACGCCCTGAACAACGTG AACAAGGCCCTGCGGGTGCTGCAGAACAACAACGTGGACCTGGTGA ACATCGGCAGCACCGACATCGTGGACGGCAACCACAAGCTGACCCTG GGCCTGATCTGGAACATCATCCTGCACTGGCAGGTCAAAAACGTGAT GAAGAACATCATGGCCGGCCTGCAGCAGACCAACAGCGAGAAGATC CTGCTGAGCTGGGTGCGCCAGAGCACCCGGAACTACCCCCAGGTCAA CGTGATCAACTTCACCACCTCTTGGAGCGACGGCCTGGCCCTGAACG CCCTGATCCACAGCCACCGGCCCGACCTGTTCGACTGGAACAGCGTG GTCTGCCAGCAGAGCGCCACCCAGCGGCTGGAACACGCCTTCAATAT CGCCAGATACCAGCTGGGCATCGAGAAGCTGCTGGATCCCGAGGAC GTGGACACCACCTACCCCGACAAGAAATCCATCCTGATGTATATCAC CAGCCTGTTCCAGGTGCTGCCCCAGCAGGTGTCCATCGAGGCCATCC AGGAAGTGGAAATGCTGCCCAGACCCCCCAAAGTGACCAAAGAGGA ACACTTCCAGCTGCACCACCAGATGCACTACAGCCAGCAGATCACCG TGTCCCTGGCTCAGGGCTACGAGCGGACCAGCAGCCCCAAGCCCCGG TTCAAGAGCTACGCCTACACCCAGGCCGCCTACGTGACCACCAGCGA CCCCACCAGAAGCCCATTCCCCAGCCAGCATCTGGAAGCCCCCGAGG ACAAGAGCTTCGGCAGCAGCCTGATGGAAAGCGAAGTGAACCTGGA CAGATACCAGACCGCCCTGGAAGAGGTGCTGTCCTGGCTGCTGAGCG CCGAGGATACACTGCAGGCCCAGGGCGAGATCAGCAACGACGTGGA AGTGGTGAAAGACCAGTTCCACACCCACGAGGGCTACATGATGGACC TGACCGCCCACCAGGGCAGAGTGGGCAACATCCTGCAGCTGGGCAG CAAGCTGATCGGCACCGGCAAGCTGAGCGAGGACGAAGAGACAGAG GTGCAGGAACAGATGAACCTGCTGAACAGCAGATGGGAGTGCCTGC GGGTGGCCAGCATGGAAAAGCAGAGCAACCTGCACATCCACACCGT GCGGGAAGAGACAATGATGGTGATGACCGAGGACATGCCCCTGGAA ATCAGCTACGTGCCCAGCACCTACCTGACCGAGATCACCCACGTGTC CCAGGCTCTGCTGGAAGTGGAACAGCTGCTGAACGCCCCCGACCTGT GCGCCAAGGACTTCGAGGATCTGTTCAAGCAGGAAGAGAGCCTGAA GAATATCAAGGACTCCCTGCAGCAGTCCAGCGGCCGGATCGACATCA TCCACAGCAAGAAAACAGCCGCCCTGCAGTCCGCCACCCCCGTGGAA AGAGTGAAGCTGCAGGAAGCCCTGAGCCAGCTGGACTTCCAGTGGG AGAAAGTGAACAAGATGTACAAGGACCGGCAGGGCAGATTCGACCG CAGCGTGGAAAAGTGGCGGCGGTTCCACTACGACATCAAGATCTTCA ACCAGTGGCTGACCGAGGCCGAGCAGTTCCTGAGAAAGACCCAGAT CCCCGAGAACTGGGAGCACGCCAAGTACAAGTGGTATCTGAAAGAG CTGCAGGACGGCATCGGCCAGCGGCAGACAGTGGTCCGCACCCTGA ATGCCACCGGCGAGGAAATCATCCAGCAGAGCAGCAAGACCGACGC CAGCATCCTGCAGGAAAAGCTGGGCAGCCTGAACCTGCGGTGGCAG GAAGTGTGCAAGCAGCTGAGCGACCGGAAGAAGCGGCTGGAAGAAC AGGCCCCTGGCCTGACCACAATCGGCGCCAGCCCTACCCAGACCGTG ACCCTGGTGACACAGCCCGTGGTGACAAAAGAGACAGCCATCAGCA AGCTGGAAATGCCCAGCAGCCTGATGCTGGAAAGCGACCAGTGGAA GCGGCTGCACCTGAGCCTGCAGGAACTGCTGGTCTGGCTGCAGCTGA AGGACGACGAGCTGAGCAGACAGGCCCCCATCGGCGGCGATTTCCCC GCCGTGCAGAAACAGAACGACGTGCACCGGGCCTTCAAGCGCGAGC TGAAAACAAAAGAACCCGTGATCATGAGCACCCTGGAAACCGTGCG GATCTTCCTGACCGAGCAGCCCCTGGAAGGCCTGGAAAAGCTGTACC AGGAACCCAGAGAGCTGCCCCCCGAGGAACGGGCCCAGAACGTGAC CAGACTGCTGCGGAAGCAGGCCGAAGAGGTCAACACCGAGTGGGAG AAGCTGAACCTGCACAGCGCCGACTGGCAGCGGAAGATCGACGAGA CACTGGAACGGCTGCAGGAACTGCAGGAGGCCACCGACGAGCTGGA CCTGAAGCTGAGACAGGCCGAAGTGATCAAGGGCAGCTGGCAGCCC GTGGGCGACCTGCTGATCGACTCCCTGCAGGACCACCTGGAAAAAGT GAAGGCCCTGCGGGGCGAGATCGCCCCCCTGAAAGAAAACGTGTCC CACGTGAACGACCTGGCCCGGCAGCTGACCACCCTGGGCATCCAGCT GAGCCCCTACAACCTGTCCACCCTGGAAGATCTGAACACCCGGTGGA AGCTGCTGCAGGTGGCCGTGGAAGATAGAGTGCGGCAGCTGCACGA GGCCCACAGAGACTTTGGCCCTGCCAGCCAGCACTTCCTGAGCACCT CTGTGCAGGGACCCTGGGAGAGAGCCATCAGCCCCAACAAGGTGCC CTACTACATCAACCACGAGACACAGACCACCTGTTGGGACCACCCCA AGATGACCGAGCTGTACCAGAGCCTGGCCGACCTGAACAATGTGCGG |

TABLE 8-continued

Nucleotide Sequences of Dystrophin constructs.

| SEQ ID NO and Description | Sequence |
|---|---|
| | TTCAGCGCCTACCGGACCGCCATGAAGCTGAGGCGGCTGCAGAAAGC<br>TCTGTGCCTGGATCTGCTGAGCCTGAGCGCCGCCTGCGACGCCCTGG<br>ACCAGCACAACCTGAAGCAGAACGACCAGCCCATGGATATCCTGCA<br>GATCATCAACTGCCTGACCACAATCTACGACAGGCTGGAACAGGAAC<br>ACAACAATCTGGTCAACGTGCCCCTGTGCGTGGACATGTGCCTGAAT<br>TGGCTGCTGAATGTGTACGACACCGGCCGGACCGGCAGAATCCGGGT<br>GCTGAGCTTCAAGACCGGCATCATCAGCCTGTGCAAGGCCCACCTGG<br>AAGATAAGTACCGCTACCTGTTCAAACAGGTGGCCAGCTCCACCGGC<br>TTTTGCGACCAGCGGAGACTGGGCCTGCTGCTGCACGACAGCATCCA<br>GATCCCCAGACAGCTGGGCGAGGTGGCCTCCTTCGGCGGCAGCAACA<br>TTGAGCCCAGCGTGCGGAGCTGCTTCCAGTTCGCCAACAACAAGCCC<br>GAGATCGAGGCCGCCCTGTTCCTGGACTGGATGAGACTGGAACCCCA<br>GAGCATGGTGTGGCTGCCCGTGCTGCATCGGGTGGCCGCTGCCGAGA<br>CAGCCAAGCACCAGGCCAAGTGCAACATCTGCAAAGAGTGCCCCATC<br>ATCGGCTTCCGGTACAGAAGCCTGAAGCACTTCAACTACGATATCTG<br>CCAGAGCTGCTTCTTCAGCGGCAGAGTGGCCAAGGGCCACAAAATGC<br>ACTACCCCATGGTGGAATACTGCACCCCCACCACCAGCGGCGAGGAT<br>GTGCGGGACTTCGCCAAGGTGCTGAAAAACAAGTTCCGGACCAAGC<br>GGTACTTTGCCAAGCACCCCCGGATGGGCTACCTGCCCGTGCAGACA<br>GTGCTGGAAGGCGACAACATGGAAACCGACACCATGTGATGATGATT<br>TGGGCAGAGCGATGGAGTCCTTAGTATCAGTCATGACAGATGAAGAA<br>GGAGCAGAATAAATGTTTTACAACTCCTGATTCCCGCATGCGGCCAG<br>CTTATCGATACCGTCGAAATAAAAGATCCTTATTTTCATTGGATCTGT<br>GTGTTGGTTTTTTGTGTG |
| SEQ ID NO: 149-BXA-212372 | ATGCTGTGGTGGGAGGAAGTGGAAGATTGCTACGAGCGCGAGGACG<br>TGCAGAAGAAAACCTTCACCAAATGGGTGAACGCCCAGTTCAGCAA<br>GTTCGGCAAGCAGCACATCGAGAACCTGTTCAGCGACCTGCAGGACG<br>GCAGACGGCTGCTGGACCTGCTGGAAGGCCTGACCGGCCAGAAGCT<br>GCCCAAAGAGAAGGGCAGCACCAGAGTGCACGCCCTGAACAACGTG<br>AACAAGGCCCTGCGGGTGCTGCAGAACAACAACGTGGACCTGGTGA<br>ACATCGGCAGCACCGACATCGTGGACGGCAACCACAAGCTGACCCTG<br>GGCCTGATCTGGAACATCATCCTGCACTGGCAGGTCAAAAACGTGAT<br>GAAGAACATCATGGCCGGCCTGCAGCAGACCAACAGCGAGAAGATC<br>CTGCTGAGCTGGGTGCGCCAGAGCACCCGGAACTACCCCCAGGTCAA<br>CGTGATCAACTTCACCACCTCTTGGAGCGACGGCCTGGCCCTGAACG<br>CCCTGATCCACAGCCACCGGCCCGACCTGTTCGACTGGAACAGCGTG<br>GTCTGCCAGCAGAGCGCCACCCAGCGGCTGGAACACGCCTTCAATAT<br>CGCCAGATACCAGCTGGGCATCGAGAAGCTGCTGGATCCCGAGGAC<br>GTGGACACCACCTACCCCGACAAGAAATCCATCCTGATGTATATCAC<br>CAGCCTGTTCCAGGTGCTGCCCCAGCAGGTGTCCATCGAGGCCATCC<br>AGGAAGTGGAAATGCTGCCCAGACCCCCCAAAGTGACCAAAGAGGA<br>ACACTTCCAGCTGCACCACCAGATGCACTACAGCCAGCAGATCACCG<br>TGTCCCTGGCTCAGGGCTACGAGCGGACCAGCAGCCCCAAGCCCCGG<br>TTCAAGAGCTACGCCTACACCCAGGCCGCCTACGTGACCACCAGCGA<br>CCCCACCAGAAGCCCATTCCCCAGCCAGCATCTGGAAGCCCCCGAGG<br>ACAAGAGCTTCGGCAGCAGCCTGATGGAAAGCGAAGTGAACCTGGA<br>CAGATACCAGACCGCCCTGGAAGAGGTGCTGTCCTGGCTGCTGAGCG<br>CCGAGGATACACTGCAGGCCCAGGGCGAGATCAGCAACGACGTGGA<br>AGTGGTGAAAGACCAGTTCCACACCCACGAGGGCTACATGATGGACC<br>TGACCGCCCACCAGGGCAGAGTGGGCAACATCCTGCAGCTGGGCAG<br>CAAGCTGATCGGCACCGGCAAGCTGAGCGAGGACGAAGAGACAGAG<br>GTGCAGGAACAGATGAACCTGCTGAACAGCAGATGGGAGTGCCTGC<br>GGGTGGCCAGCATGGAAAAGCAGAGCAACCTGCACATCCACACCGT<br>GCGGGAAGAGACAATGATGGTGATGACCGAGGACATGCCCCTGGAA<br>ATCAGCTACGTGCCCAGCACCTACCTGACCGAGATCACCCACGTGTC<br>CCAGGCTCTGCTGGAAGTGGAACAGCTGCTGAACGCCCCCGACCTGT<br>GCGCCAAGGACTTCGAGGATCTGTTCAAGCAGGAAGAGAGCCTGAA<br>GAATATCAAGGACTCCCTGCAGCAGTCCAGCGGCCGGATCGACATCA<br>TCCACAGCAAGAAAACAGCCGCCCTGCAGTCCGCCACCCCCGTGGAA<br>AGAGTGAAGCTGCAGGAAGCCCTGAGCCAGCTGGACTTCCAGTGGG<br>AGAAAGTGAACAAGATGTACAAGGACCGGCAGGGCAGATTCGACCG<br>CAGCGTGGAAAAGTGGCGGCGGTTCCACTACGACATCAAGATCTTCA<br>ACCAGTGGCTGACCGAGGCCGAGCAGTTCCTGAGAAAGACCCAGAT<br>CCCCGAGAACTGGGAGCACGCCAAGTACAAGTGGTATCTGAAAGAG<br>CTGCAGGACGGCATCGGCCAGCGGCAGACAGTGGTCCGCACCCTGA<br>ATGCCACCGGCGAGGAAATCATCCAGCAGAGCAGCAAGACCGACGC<br>CAGCATCCTGCAGGAAAAGCTGGGCAGCCTGAACCTGCGGTGGCAG<br>GAAGTGTGCAAGCAGCTGAGCGACCGGAAGAAGCGGCTGGAAGAAC<br>AGGCCCCTGGCCTGACCACAATCGGCGCCAGCCCTACCCAGACCGTG<br>ACCCTGGTGACACAGCCCGTGGTGACAAAAGAGACAGCCATCAGCA<br>AGCTGGAAATGCCCAGCAGCCTGATGCTGGAAAGCGACCAGTGGAA<br>GCGGCTGCACCTGAGCCTGCAGGAACTGCTGGTCTGGCTGCAGCTGA<br>AGGACGACGAGCTGAGCAGACAGGCCCCCATCGGCGGCGATTTCCCC |

TABLE 8-continued

| Nucleotide Sequences of Dystrophin constructs. | |
|---|---|
| SEQ ID NO and Description | Sequence |
| | GCCGTGCAGAAACAGAACGACGTGCACCGGGCCTTCAAGCGCGAGC<br>TGAAAACAAAAGAACCCGTGATCATGAGCACCCTGGAAACCGTGCG<br>GATCTTCCTGACCGAGCAGCCCCTGGAAGGCCTGGAAAAGCTGTACC<br>AGGAACCCAGAGAGCTGCCCCCCGAGGAACGGGCCCAGAACGTGAC<br>CAGACTGCTGCGGAAGCAGGCCGAAGAGGTCAACACCGAGTGGGAG<br>AAGCTGAACCTGCACAGCGCCGACTGGCAGCGGAAGATCGACGAGA<br>CACTGGAACGGCTGCAGGAACTGCAGGAGGCCACCGACGAGCTGGA<br>CCTGAAGCTGAGACAGGCCGAAGTGATCAAGGGCAGCTGGCAGCCC<br>GTGGGCGACCTGCTGATCGACTCCCTGCAGGACCACCTGGAAAAAGT<br>GAAGGCCCTGCGGGGCGAGATCGCCCCCCTGAAAGAAAACGTGTCC<br>CACGTGAACGACCTGGCCCGGCAGCTGACCACCCTGGGCATCCAGCT<br>GAGCCCCTACAACCTGTCCACCCTGGAAGATCTGAACACCCGGTGGA<br>AGCTGCTGCAGGTGGCCGTGGAAGATAGAGTGCGGCAGCTGCACGA<br>GGCCCACAGAGACTTTGGCCCTGCCAGCCAGCACTTCCTGAGCACCT<br>CTGTGCAGGGACCCTGGGAGAGAGCCATCAGCCCCAACAAGGTGCC<br>CTACTACATCAACCACGAGACACAGACCACCTGTTGGGACCACCCCA<br>AGATGACCGAGCTGTACCAGAGCCTGGCCGACCTGAACAATGTGCGG<br>TTCAGCGCCTACCGGACCGCCATGAAGCTGAGGCGGCTGCAGAAAGC<br>TCTGTGCCTGGATCTGCTGAGCCTGAGCGCCGCCTGCGACGCCCTGG<br>ACCAGCACAACCTGAAGCAGAACGACCAGCCCATGGATATCCTGCA<br>GATCATCAACTGCCTGACCACAATCTACGACAGGCTGGAACAGGAAC<br>ACAACAATCTGGTCAACGTGCCCCTGTGCGTGGACATGTGCCTGAAT<br>TGGCTGCTGAATGTGTACGACACCGGCCGGACCGGCAGAATCCGGGT<br>GCTGAGCTTCAAGACCGGCATCATCAGCCTGTGCAAGGCCCACCTGG<br>AAGATAAGTACCGCTACCTGTTCAAACAGGTGGCCAGCTCCACCGGC<br>TTTTGCGACCAGCGGAGACTGGGCCTGCTGCTGCACGACAGCATCCA<br>GATCCCCAGACAGCTGGGCGAGGTGGCCTCCTTCGGCGGCAGCAACA<br>TTGAGCCCAGCGTGCGGAGCTGCTTCCAGTTCGCCAACAACAAGCCC<br>GAGATCGAGGCCGCCCTGTTCCTGGACTGGATGAGACTGGAACCCCA<br>GAGCATGGTGTGGCTGCCCGTGCTGCATCGGGTGGCCGCTGCCGAGA<br>CAGCCAAGCACCAGGCCAAGTGCAACATCTGCAAAGAGTGCCCCATC<br>ATCGGCTTCCGGTACAGAAGCCTGAAGCACTTCAACTACGATATCTG<br>CCAGAGCTGCTTCTTCAGCGGCAGAGTGGCCAAGGGCCACAAAATGC<br>ACTACCCCATGGTGGAATACTGCACCCCCACCACCAGCGGCGAGGAT<br>GTGCGGGACTTCGCCAAGGTGCTGAAAAACAAGTTCCGGACCAAGC<br>GGTACTTTGCCAAGCACCCCCGGATGGGCTACCTGCCCGTGCAGACA<br>GTGCTGGAAGGCGACAACATGGAAACCGACACCATGTGATGATGAG<br>AAGTCTTTTCCACATGGCAGATGAAATAAAAGATCCTTATTTTCATTG<br>GATCTGTGTGTTGGTTTTTTGTGTG |

SEQ ID NO:148 encodes construct BXA-212371, which is the same as construct BXA-027743, except that the C-terminus is deleted.

SEQ ID NO:149 encodes construct BXA-212372, which is the same as BXA-212371, but with a shorter 3'UTR.

In some embodiments, the miniaturized dystrophin polypeptide comprises or is the construct shown in Table 9.

TABLE 9

| Amino acid sequence of miniaturized dystrophin polypeptide BXA-213788. | |
|---|---|
| SEQ ID NO: | Sequence |
| 152 | MLWWEEVEDCYEREDVQKKTFTKWVNAQFSKFGKQHIENLFSDLQ<br>DGRRLLDLLEGLTGQKLPKEKGSTRVHALNNVNKALRVLQNNNVD<br>LVNIGSTDIVDGNHKLTLGLIWNIILHWQVKNVMKNIMAGLQQTN<br>SEKILLSWVRQSTRNYPQVNVINFTTSWSDGLALNALIHSHRPDL<br>FDWNSVVCQQSATQRLEHAFNIARYQLGIEKLLDPEDVDTTYPDK<br>KSILMYITSLFQVLPQQVSIEAIQEVEMLPRPPKVTKEEHFQLHH<br>QMHYSQQITVSLAQGYERTSSPKPRFKSYAYTQAAYVTTSDPTRS |

TABLE 9-continued

| Amino acid sequence of miniaturized dystrophin polypeptide BXA-213788. | |
|---|---|
| SEQ ID NO: | Sequence |
| | PFPSQHLEAPEDKSFGSSLMESEVNLDRYQTALEEVLSWLLSAED<br>TLQAQGEISNDVEVVKDQFHTHEGYMMDLTAHQGRVGNILQLGSK<br>LIGTGKLSEDEETEVQEQMNLLNSRWECLRVASMEKQSNLHIHTV<br>REETMMVMTEDMPLEISYVPSTYLTEITHVSQALLEVEQLLNAPD<br>LCAKDFEDLFKQEESLKNIKDSLQQSSGRIDIIHSKKTAALQSAT<br>PVERVKLQEALSQLDFQWEKVNKMYKDRQGRFDRSVEKWRRFHYD<br>IKIFNQWLTEAEQFLRKTQIPENWEHAKYKWYLKELQDGIGQRQT<br>VVRTLNATGEEIIQQSSKTDASILQEKLGSLNLRWQEVCKQLSDR<br>KKRLEEQKNDLAPGLTTIGASPTQTVTLVTQPVVTKETAISKLEM<br>PSSLMLESDQWKRLHLSLQELLVWLQLKDDELSRQAPIGGDFPAV<br>QKQNDVHRAFKRELKTKEPVIMSTLETVRIFLTEQPLEGLEKLYQ |

TABLE 9-continued

| Amino acid sequence of miniaturized dystrophin polypeptide BXA-213788. | |
|---|---|
| SEQ ID NO: | Sequence |
| | EPRELPPEERAQNVTRLLRKQAEEVNTEWEKLNLHSADWQRKIDE |
| | TLERLQELQEATDELDLKLRQAEVIKGSWQPVGDLLIDSLQDHLE |
| | KVKALRGEIAPLKENVSHVNDLARQLTTLGIQLSPYNLSTLEDLN |
| | TRWKLLQVAVEDRVRQLHEAHRDFGPASQHFLSTSVQGPWERAIS |
| | PNKVPYYINHETQTTCWDHPKMTELYQSLADLNNVRFSAYRTAMK |
| | LRRLQKALCLDLLSLSAACDALDQHNLKQNDQPMDILQIINCLTT |
| | IYDRLEQEHNNLVNVPLCVDMCLNWLLNVYDTGRTGRIRVLSFKT |
| | GIISLCKAHLEDKYRYLFKQVASSTGFCDQRRLGLLLHDSIQIPR |
| | QLGEVASFGGSNIEPSVRSCFQFANNKPEIEAALFLDWMRLEPQS |
| | MVWLPVLHRVAAAETAKHQAKCNICKECPIIGFRYRSLKHFNYDI |
| | CQSCFFSGRVAKGHKMHYPMVEYCTPTTSGEDVRDFAKVLKNKFR |
| | TKRYFAKHPRMGYLPVQTVLEGDNMET |

In some embodiments, the miniaturized dystrophin polypeptide comprises an amino acid sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 152, wherein the amino acid sequence when expressed has at least one dystrophin activity.

In some embodiments, the miniaturized dystrophin polypeptide comprises or is the construct shown in Table 10.

TABLE 10

| Amino acid sequence of miniaturized dystrophin polypeptide BXA-213780J11V3. | |
|---|---|
| SEQ ID NO: | Sequence |
| 153 | MLWWEEVEDCYEREDVQKKTFTKWVNAQFSKFGKQHIENLFSDLQ |
| | DGRRLLDLLEGLTGQKLPKEKGSTRVHALNNVNKALRVLQNNNVD |
| | LVNIGSTDIVDGNHKLTLGLIWNIILHWQVKNVMKNIMAGLQQTN |
| | SEKILLSWVRQSTRNYPQVNVINFTTSWSDGLALNALIHSHRPDL |
| | FDWNSVVCQQSATQRLEHAFNIARYQLGIEKLLDPEDVDTTYPDK |
| | KSILMYITSLFQVLPQQVSIEAIQEVEMLPRPPKVTKEEHFQLHH |
| | QMHYSQQITVSLAQGYERTSSPKPRFKSYAYTQAAYVTTSDPTRS |
| | PFPSQHLEAPEDKSFGSSLMESEVNLDRYQTALEEVLSWLLSAED |
| | TLQAQGEISNDVEVVKDQFHTHEGYMMDLTAHQGRVGNILQLGSK |
| | LIGTGKLSEDEETEVQEQMNLLNSRWECLRVASMEKQSNLHRVLL |
| | KWQRLTEEQCLFSAWLSEKEDAVNKIHTTGFKDQNEMLSSLQKLA |
| | VLKADLEKKKQSMGKLYSLKQDLLSTLKNKSVTQKTEAWLDNFAR |

TABLE 10-continued

| Amino acid sequence of miniaturized dystrophin polypeptide BXA-213780J11V3. | |
|---|---|
| SEQ ID NO: | Sequence |
| | CWDNLVQKLEKSTAQISQAVTTTQPSLTQTTVMETVTTVTTREQI |
| | LVKHAQEELPPPPPQKKRQITVDSEIHTVREETMMVMTEDMPLEI |
| | SYVPSTYLTEITHVSQALLEVEQLLNAPDLCAKDFEDLFKQEESL |
| | KNIKDSLQQSSGRIDIIHSKKTAALQSATPVERVKLQEALSQLDF |
| | QWEKVNKMYKDRQGRFDRSVEKWRRFHYDIKIFNQWLTEAEQFLR |
| | KTQIPENWEHAKYKWYLKELQDGIGQRQTVVRTLNATGEEIIQQS |
| | SKTDASILQEKLGSLNLRWQEVCKQLSDRKKRLEEQLERLQELQE |
| | ATDELDLKLRQAEVIKGSWQPVGDLLIDSLQDHLEKVKALRGEIA |
| | PLKENVSHVNDLARQLTTLGIQLSPYNLSTLEDLNTRWKLLQVAV |
| | EDRVRQLHEAHRDFGPASQHFLSTSVQGPWERAISPNKVPYYINH |
| | ETQTTCWDHPKMTELYQSLADLNNVRFSAYRTAMKLRRLQKALCL |
| | DLLSLSAACDALDQHNLKQNDQPMDILQIINCLTTIYDRLEQEHN |
| | NLVNVPLCVDMCLNWLLNVYDTGRTGRIRVLSFKTGIISLCKAHL |
| | EDKYRYLFKQVASSTGFCDQRRLGLLLHDSIQIPRQLGEVASFGG |
| | SNIEPSVRSCFQFANNKPEIEAALFLDWMRLEPQSMVWLPVLHRV |
| | AAAETAKHQAKCNICKECPIIGFRYRSLKHFNYDICQSCFFSGRV |
| | AKGHKMHYPMVEYCTPTTSGEDVRDFAKVLKNKFRTKRYFAKHPR |
| | MGYLPVQTVLEGDNMET |

SEQ ID NO:153 encodes construct BXA-213780J11V3, which is the same as construct BXA-196477, except that amino acids A and Q of the internal SEAQ linker (SEQ ID NO. 74), as well as the last three amino acids at the C-terminus, are deleted in BXA-213780J11V3.

In some embodiments, the miniaturized dystrophin polypeptide comprises an amino acid sequence at least about 70%, at least about 75%, at least about 80%, at least about 85%, at least about 90%, at least about 95%, at least about 96%, at least about 97%, at least about 98%, at least about 99%, or about 100% identical to SEQ ID NO: 153, wherein the amino acid sequence when expressed has at least one dystrophin activity.

In some embodiments, the miniaturized dystrophin BXA-213780J11V3 can be encoded by the nucleotide sequence shown in Table 11.

TABLE 11

Nucleotide sequence of miniaturized dystrophin polypeptide BXA-213780J11V3.

| SEQ ID NO: | Sequence |
|---|---|
| 154 | atgctgtggtgggaggaagtggaagattgctacgagcgcgaggacgtgcagaagaaaaccttcaccaaatgggt |
| | gaacgcccagttcagcaagttcggcaagcagcacatcgagaacctgttcagcgacctgcaggacggcagacgg |
| | ctgctggacctgctggaaggcctgaccggccagaagctgcccaaagagaagggcagcaccagagtgcacgcc |
| | ctgaacaacgtgaacaaggccctgcgggtgctgcagaacaacaacgtggacctggtgaacatcggcagcaccg |
| | acatcgtggacggcaaccacaagctgaccctgggcctgatctggaacatcatcctgcactggcaggtcaaaaacg |
| | tgatgaagaacatcatggccggcctgcagcagaccaacagcgagaagatcctgctgagctgggtgcgccagag |
| | cacccggaactacccccaggtcaacgtgatcaacttcaccacctcttggagcgacggcctggccctgaacgccct |
| | gatccacagccaccggcccgacctgttcgactggaacagcgtggtctgccagcagagcgccacccagcggctg |
| | gaacacgccttcaatatcgccagataccagctgggcatcgagaagctgctggatcccgaggacgtggacaccac |
| | ctaccccgacaagaaatccatcctgatgtatatcaccagcctgttccaggtgctgccccagcaggtgtccatcgag |
| | gccatccaggaagtggaaatgctgcccagacccccaaagtgaccaaagaggaacacttccagctgcaccaccag |
| | atgcactacagccagcagatcaccgtgtccctggcccagggctacgagagaaccagcagccccaagccccggtt |
| | caagagctacgcctatacccaggccgcctacgtgaccaccagcgaccctaccagaagcccattccccagccagc |
| | atctggaagcccccgaggacaagagcttcggcagcagcctgatggaaagcgaagtgaacctggacagatacca |
| | gaccgccctggaagaggtgctgagctggctgctgagcgccgaggatacactgcaggctcagggcgagatcagc |
| | aacgacgtggaagtcgtgaaggaccagttccacacccacgagggctacatgatggacctgacagcccaccagg |
| | gcagagtgggcaacatcctgcagctgggctccaagctgatcggcaccggcaagctgagcgaggacgaagaga |
| | cagaggtgcaggaacagatgaacctgctgaacagcagatgggagtgcctgcgggtggccagcatggaaaagca |
| | gagcaacctgcatagggtcctgctgaagtggcagcggctgaccgaggaacagtgcctgtttagcgcctggctgtc |
| | cgagaaagaggacgccgtgaacaagatccacaccaccggcttcaaggaccagaacgagatgctgagcagcctg |
| | cagaaactggccgtgctgaaggccgacctggaaaagaaaaagcagtccatgggcaagctgtactccctgaagca |
| | ggacctgctgtccaccctgaagaacaagagcgtgacccagaaaaccgaggcctggctggacaacttcgcccggt |
| | gctgggacaacctggtgcagaagctggaaaagtccaccgcccagatctcccaggccgtgaccacaacacagcc |
| | cagcctgacccagaccaccgtgatggaaaccgtgacaacagtgaccacccgggaacagatcctcgtgaagcac |
| | gcccaggaagaactgcccccctccacccccccagaagaaacggcagatcacagtggacagtgaaatccacaccg |
| | tgcgggaagagacaatgatggtcatgacagaggacatgcccctggaaatcagctacgtgcccagcacctacctg |
| | accgagatcacccatgtgtcccaggccctgctggaagtggaacagctgctgaacgcccccgacctgtgcgccaa |
| | ggatttcgaggacctgttcaagcaggaagagagcctgaagaatatcaaggatagcctgcagcagagcagcggcc |
| | ggatcgacatcatccacagcaagaaaacagccgccctgcagagcgccaccccccgtggaaagagtgaaactgca |
| | ggaagccctgtcccagctggacttccagtgggagaaagtgaacaaaatgtacaaggaccggcagggcagattcg |
| | accgcagcgtggaaaagtggcggcggttccactacgacatcaagatcttcaaccagtggctgacagaggccgag |
| | cagttcctgagaaagacccagatccccgagaactgggagcacgccaagtacaagtggtatctgaaagagctgca |
| | ggacggcatcggccagagacagacagtcgtgcggaccctgaatgccaccggcgaggaaatcatccagcagtcc |
| | agcaagaccgacgccagcattctgcaggaaaagctgggcagcctgaacctgcggtggcaggaagtgtgcaagc |
| | agctgtccgaccggaagaagcggctggaagaacagctggaacggctgcaggaactgcaggaggccaccgac |
| | gagctggacctgaaactgagacaggccgaagtgatcaagggcagctggcagccagtgggcgacctgctgatcg |
| | actccctgcaggaccatctggaaaaagtgaaggccctgagaggcgagatcgccccctgaaagaaaacgtgtcc |
| | cacgtgaacgacctggcccggcagctgacaacactgggcattcagctgagcccctacaacctgagcacactgga |

TABLE 11-continued

| Nucleotide sequence of miniaturized dystrophin polypeptide BXA-213780J11V3. | |
|---|---|
| SEQ ID NO: | Sequence |
| | agatctgaacacccggtggaagctgctgcaggtggccgtggaagatagagtgcggcagctgcacgaggcccac |
| | agagattttggccctgcctcccagcacttcctgagcaccagtgtgcagggcccttgggagagagccatctcccta |
| | acaaggtgccctactacatcaaccacgagacacagaccacctgttgggaccaccccaagatgaccgagctgtacc |
| | agagcctggctgacctgaacaacgtgcggttcagcgcctaccggaccgccatgaagctgcggagactgcagaa |
| | agctctgtgcctggatctgctgtccctgtccgccgcctgtgatgccctggaccagcacaatctgaagcagaacgac |
| | cagcccatggatatcctgcagatcatcaactgcctgaccaccatctacgaccggctggaacaggaacacaacaat |
| | ctcgtgaacgtgcccctgtgcgtggacatgtgcctgaattggctgctgaatgtgtacgacaccggccggacaggc |
| | cggatcagagtgctgtccttcaagaccggcatcatcagcctgtgcaaagcccacctggaagataagtaccggtatc |
| | tgttcaaacaggtggcctctagcaccggcttttgcgaccagagaaggctgggcctgctgctgcacgacagcatcc |
| | agatccctagacagctgggcgaagtggccagctttggcggcagcaacatcgagcctagcgtgcggagctgatc |
| | cagttcgccaacaacaagcccgagatcgaggccgccctgttcctggactggatgagactggaaccccagagcat |
| | ggtgtggctgcccgtgctgcatagagtggccgctgccgagacagccaagcaccaggccaagtgcaacatctgca |
| | aagagtgccccatcatcggcttccggtacagaagcctgaagcacttcaactacgatatctgccagagctgtttctt |
| | cagcggcagggtggccaagggccacaaaatgcactaccccatggtggaatactgcacccccaccacaagcggcga |
| | ggatgtgcgggatttcgccaaggtgctgaaaaacaagttccggaccaagcggtacttcgccaaacacccccggat |
| | gggctacctgcctgtgcagacagtgctggaaggcgacaacatggaaacctgaGAAGTCTTTTCCAC |
| | ATGGCAGATGAAATAAAAGATCCTTATTTTCATTGGATCTGTGTGTTGGTTTTTTGTGTG |

In some embodiments, the miniaturized dystrophin polypeptide has a junction between hinge 2 (H2) domain and R16 spectrin repeat 16 (R16) domain that comprises an amino acid sequence listed in Table 12.

TABLE 12

| Amino Acid Sequences of Junctions | |
|---|---|
| SEQ ID NO | Sequence |
| SEQ ID NO: 155 | LPPPPPQKKRQITVDIHTVREETMMVMTEDMPLEI |
| SEQ ID NO: 156 | LPPPPPQKKRQITVDSIHTVREETMMVMTEDMPLEI |
| SEQ ID NO: 157 | LPPPPPQKKRQITVDSEIHTVREETMMVMTEDMPLEI |
| SEQ ID NO: 158 | LPPPPPQKKRQITVDQIHTVREETMMVMTEDMPLEI |
| SEQ ID NO: 159 | LPPPPPQKKRQITVDAQIHTVREETMMVMTEDMPLEI |
| SEQ ID NO: 160 | LPPPPPQKKRQITVIHTVREETMMVMTEDMPLEI |
| SEQ ID NO: 161 | LPPPPPQKKRQITVDHTVREETMMVMTEDMPLEI |
| SEQ ID NO: 162 | LPPPPPQKKRQITVHTVREETMMVMTEDMPLEI |

TABLE 12-continued

| Amino Acid Sequences of Junctions | |
|---|---|
| SEQ ID NO | Sequence |
| SEQ ID NO: 163 | LPPPPPQKKRQITVDSQIHTVREETMMVMTEDMPLEI |
| SEQ ID NO: 164 | LPPPPPQKKRQITVDSHTVREETMMVMTEDMPLEI |
| SEQ ID NO: 165 | LPPPPPQKKRQITVQIHTVREETMMVMTEDMPLEI |
| SEQ ID NO: 166 | QKKRQITVDSEAQIHTVREETMMV |

In other embodiments, a nucleotide sequence encoding the miniaturized dystrophin polypeptide comprises a nucleic acid sequence at least about 80%, at least about 85%, at least about 90%, at least about 95%, at least about 96%, at least about 97%, at least about 98%, at least about 99%, or about 100% identical to SEQ ID NOs: 133-149, wherein the miniaturized dystrophin polypeptide when expressed from the nucleotide sequence has at least one dystrophin activity. In other embodiments, a nucleotide sequence encoding the miniaturized dystrophin polypeptide comprises a nucleic acid sequence at least about 80%, at least about 85%, at least about 90%, at least about 95%, at least about 96%, at least about 97%, at least about 98%, at least about 99%, or about 100% identical to SEQ ID NO:133 (BXA-196477), SEQ ID NO:134 (BXA-196473), SEQ ID NO:135 (BXA-196474), SEQ ID NO: 136 (BXA-196475), SEQ ID NO: 137 (BXA-196476), SEQ ID NO: 139 (BXA-196478), SEQ ID NO: 140 (BXA-196479), SEQ ID NO:148 (BXA-212371), or SEQ ID NO:149 (BXA-212372). In some embodiments, a nucleotide sequence encoding the miniaturized dystrophin polypeptide comprises a nucleic acid sequence at least about 60%, at least about 70%, at least about 80%, at least about 85%, at least about 90%, at least about 95%, at least about 96%, at least about 97%, at least about 98%, at least about 99%, or about 100% identical to SEQ ID NO: 133, wherein the miniaturized dystrophin polypeptide when expressed from the nucleotide sequence has at least one dystrophin activity. In some embodiments, a nucleotide sequence encoding the miniaturized dystrophin polypeptide comprises a nucleic acid sequence at least about 60%, at least about 70%, at least about 80%, at least about 85%, at least about 90%, at least about 95%, at least about 96%, at least about 97%, at least about 98%, at least about 99%, or about 100% identical to SEQ ID NO: 134, wherein the miniaturized dystrophin polypeptide when expressed from the nucleotide sequence has at least one dystrophin activity. In some embodiments, a nucleotide sequence encoding the miniaturized dystrophin polypeptide comprises a nucleic acid sequence at least about 60%, at least about 70%, at least about 80%, at least about 85%, at least about 90%, at least about 95%, at least about 96%, at least about 97%, at least about 98%, at least about 99%, or about 100% identical to SEQ ID NO: 135. In certain embodiments, a nucleotide sequence encoding the miniaturized dystrophin polypeptide comprises a nucleic acid sequence at least about 60%, at least about 70%, at least about 80%, at least about 85%, at least about 90%, at least about 95%, at least about 96%, at least about 97%, at least about 98%, at least about 99%, or about 100% identical to SEQ ID NO: 136. In certain embodiments, a nucleotide sequence encoding the miniaturized dystrophin polypeptide comprises a nucleic acid sequence at least about 60%, at least about 70%, at least about 80%, at least about 85%, at least about 90%, at least about 95%, at least about 96%, at least about 97%, at least about 98%, at least about 99%, or about 100% identical to SEQ ID NO: 137. In certain embodiments, a nucleotide sequence encoding the miniaturized dystrophin polypeptide comprises a nucleic acid sequence at least about 60%, at least about 70%, at least about 80%, at least about 85%, at least about 90%, at least about 95%, at least about 96%, at least about 97%, at least about 98%, at least about 99%, or about 100% identical to SEQ ID NO: 138, wherein the miniaturized dystrophin polypeptide when expressed from the nucleotide sequence has at least one dystrophin activity. In certain embodiments, a nucleotide sequence encoding the miniaturized dystrophin polypeptide comprises a nucleic acid sequence at least about 60%, at least about 70%, at least about 80%, at least about 85%, at least about 90%, at least about 95%, at least about 96%, at least about 97%, at least about 98%, at least about 99%, or about 100% identical to SEQ ID NO: 139, wherein the miniaturized dystrophin polypeptide when expressed from the nucleotide sequence has at least one dystrophin activity. In certain embodiments, a nucleotide sequence encoding the miniaturized dystrophin polypeptide comprises a nucleic acid sequence at least about 60%, at least about 70%, at least about 80%, at least about 85%, at least about 90%, at least about 95%, at least about 96%, at least about 97%, at least about 98%, at least about 99%, or about 100% identical to SEQ ID NO: 140, wherein the miniaturized dystrophin polypeptide when expressed from the nucleotide sequence has at least one dystrophin activity. In certain embodiments, a nucleotide sequence encoding the miniaturized dystrophin polypeptide comprises a nucleic acid sequence at least about 60%, at least about 70%, at least about 80%, at least about 85%, at least about 90%, at least about 95%, at least about 96%, at least about 97%, at least about 98%, at least about 99%, or about 100% identical to SEQ ID NO: 141, wherein the miniaturized dystrophin polypeptide when expressed from the nucleotide sequence has at least one dystrophin activity. In certain embodiments, a nucleotide sequence encoding the miniaturized dystrophin polypeptide comprises a nucleic acid sequence at least about 60%, at least about 70%, at least about 80%, at least about 85%, at least about 90%, at least about 95%, at least about 96%, at least about 97%, at least about 98%, at least about 99%, or about 100% identical to SEQ ID NO: 142, wherein the miniaturized dystrophin polypeptide when expressed from the nucleotide sequence has at least one dystrophin activity. In certain embodiments, a nucleotide sequence encoding the miniaturized dystrophin polypeptide comprises a nucleic acid sequence at least about 60%, at least about 70%, at least about 80%, at least about 85%, at least about 90%, at least about 95%, at least about 96%, at least about 97%, at least about 98%, at least about 99%, or about 100% identical to SEQ ID NO: 143, wherein the miniaturized dystrophin polypeptide when expressed from the nucleotide sequence has at least one dystrophin activity. In certain embodiments, a nucleotide sequence encoding the miniaturized dystrophin polypeptide comprises a nucleic acid sequence at least about 60%, at least about 70%, at least about 80%, at least about 85%, at least about 90%, at least about 95%, at least about 96%, at least about 97%, at least about 98%, at least about 99%, or about 100% identical to SEQ ID NO: 144, wherein the miniaturized dystrophin polypeptide when expressed from the nucleotide sequence has at least one dystrophin activity. In certain embodiments, a nucleotide sequence encoding the miniaturized dystrophin polypeptide comprises a nucleic acid sequence at least about 60%, at least about 70%, at least about 80%, at least about 85%, at least about 90%, at least about 95%, at least about 96%, at least about 97%, at least about 98%, at least about 99%, or about 100% identical to SEQ ID NO: 145, wherein the miniaturized dystrophin polypeptide when expressed from the nucleotide sequence has at least one dystrophin activity. In certain embodiments, a nucleotide sequence encoding the miniaturized dystrophin polypeptide comprises a nucleic acid sequence at least about 60%, at least about 70%, at least about 80%, at least about 85%, at least about 90%, at least about 95%, at least about 96%, at least about 97%, at least about 98%, at least about 99%, or about 100% identical to SEQ ID NO: 146, wherein the miniaturized dystrophin polypeptide when expressed from the nucleotide sequence has at least one dystrophin activity. In certain embodiments, a nucleotide sequence encoding the miniaturized dystrophin polypeptide comprises a nucleic acid sequence at least about 60%, at least about 70%, at least about 80%, at least about 85%, at least about 90%, at least about 95%, at least about 96%, at least about 97%, at least about 98%, at least about 99%, or about 100% identical to SEQ ID NO: 147, wherein the miniaturized dystrophin polypeptide when expressed from the nucleotide sequence has at least one dystrophin activity. In certain embodiments, a nucleotide sequence encoding the miniaturized dystrophin polypeptide comprises a nucleic acid sequence at least about 60%, at least about 70%, at least about 80%, at least about 85%, at least about 90%, at least about 95%, at least about 96%, at least about 97%, at least about 98%, at least about 99%, or about 100% identical to SEQ ID NO: 148, wherein the miniaturized dystrophin polypeptide when expressed from the nucleotide sequence has at least one dystrophin activity. In certain embodiments, a nucleotide sequence encoding the miniaturized dystrophin polypeptide comprises a nucleic acid sequence at least about 60%, at least about 70%, at least about 80%, at least about 85%, at least about 90%, at least about 95%, at least about 96%, at least about 97%, at least about 98%, at least about 99%, or about 100% identical to SEQ ID NO: 149, wherein the miniaturized dystrophin polypeptide when expressed from the nucleotide sequence has at least one dystrophin activity.

5.3.2 Linker

Also provided herein is an amino acid sequence or a nucleotide sequence encoding the amino acid sequence. In some embodiments, the present disclosure is directed to an amino acid sequence encoded by a nucleotide sequence at least about 60%, at least about 70%, at least about 80%, at least about 85%, at least about 90%, at least about 95%, at least about 96%, at least about 97%, at least about 98%, at least about 99%, or about 100% identical to SEQ ID NO: 100, wherein the amino acid sequence comprises SEQ ID NO:75 (IHTVREE TMMVMTEDMP LEI). In some embodiments, the present disclosure is directed to an amino acid sequence encoded by a sequence at least about 60%, at least about 70%, at least about 80%, at least about 85%, at least about 90%, at least about 95%, at least about 96%, at least about 97%, at least about 98%, at least about 99%, or about 100% identical to SEQ ID NOs: 99-100 in combination, wherein the amino acid sequence comprises SEQ ID NOs: 74-75 in combination (SEAQIHTVREE TMMVMTEDMP LEI). In some embodiments, a nucleic acid molecule comprises a nucleotide sequence which encodes an amino acid sequence comprising SEQ ID NO: 75 (IHTVREE TMMVMTEDMP LEI), wherein the nucleic acid molecule is at least about 80%, at least about 90%, at least about 95%, at least about 96%, at least about 97%, at least about 98%, at least about 99%, or about 100% identical to SEQ ID NO: 100 (ATCCACACCGTGCGGGAAGAGACAATGATGGTCATGACAGAGGACATGCCC CTGGAAATC).

In some embodiments, the amino acid sequence can be used as a linker connecting one or more domains of dystrophin. In some embodiments, the linker connects a first domain of dystrophin and a second domain of dystrophin. In some embodiments, the first domain and the second domain of dystrophin that can be connected are an R1 domain and an R16 domain. In other embodiments, the first domain and the second domain of dystrophin that can be connected are an R3 domain and an R16 domain. In other embodiments, the first domain and the second domain of dystrophin that can be connected are an H2 domain and an R16 domain.

In some embodiments, the disclosure includes a nucleic acid molecule comprising a nucleotide sequence which is at least about 60%, at least 70%, at least about 80%, at least about 85%, at least about 90%, at least about 95%, at least about 96%, at least about 97%, at least about 98%, at least about 99%, or about 100% identical to SEQ ID No. 99 (AGTGAAGCTCAG).

In some embodiments, the disclosure includes a nucleic acid molecule comprising a nucleotide sequence which is at least about 60%, at least 70%, at least about 80%, at least about 85%, at least about 90%, at least about 95%, at least about 96%, at least about 97%, at least about 98%, at least about 99%, or about 100% identical to SEQ ID No. 100 (ATCCACACCGTGCGGGAAGAGACAATGATGGTCATGACAGAGGACATGCCC CTGGAAATC).

In some embodiments, the disclosure includes a nucleic acid molecule comprising a nucleotide sequence which encodes an amino acid sequence that is at least 70%, at least about 80%, at least about 85%, at least about 90%, at least about 95%, at least about 96%, at least about 97%, at least about 98%, at least about 99%, or about 100% identical to SEQ ID Nos. 99 and 100 in combination, (AGTGAAGCTCAGATCCACACCGTGCGGGAAGAGACAATGATGGTCATGACA GAGGACATGCCCCTGGAAATC).

In some embodiments, the linker is placed in a miniaturized dystrophin polypeptide disclosed herein by connecting two domains of the miniaturized dystrophin polypeptide (e.g., H2 and R16 domains). In some embodiments, the linker is located between H2 and R16 domains in the miniaturized dystrophin polypeptide comprising ABD1-H1-R1-R3-H2-L-R16-R17-R24-H4-CR-C term, wherein ABD1 is actin binding domain 1, H1 is a hinge 1 domain, R1 is a spectrin repeat 1 domain, R3 is a spectrin repeat 3 domain, H2 is a hinge 2 domain, L is the linker, e.g., SEQ ID NO: 74 or SEQ ID NO: 75 (or both in combination) (or a sequence that is at least about 60%, at least about 70%, at least about 80%, at least about 85%, at least about 90%, at least about 95%, at least about 96%, at least about 97%, at least about 98%, at least about 99%, or about 100% identical to these sequences), R16 is a spectrin repeat 16 domain, R17 is a spectrin repeat 17 domain, R24 is a spectrin 24 domain, H4 is a hinge 4 domain, CR is a cysteine rich domain, and C-term is an optional C-terminal domain (or portion thereof).

The present disclosure also provides a linker comprising IHTVREETMMVMTEDMPLEI (SEQ ID NO: 84). In some embodiments, the linker comprising the sequence set forth in SEQ ID NO: 75 (IHTVREETMMVMTEDMPLEI) (or a sequence that is at least about 60%, at least about 70%, at least about 80%, at least about 85%, at least about 90%, at least about 95%, at least about 96%, at least about 97%, at least about 98%, at least about 99%, or about 100% identical to the sequence set forth in SEQ ID NO: 84 (IHTVREETMMVMTEDMPLEI)) is placed in a miniaturized dystrophin polypeptide disclosed herein by connecting two domains of the miniaturized dystrophin polypeptide (e.g., R1 and R16 domains). In some embodiments, the linker is located between R1 and R16 domains in the miniaturized dystrophin polypeptide comprising ABD1-H1-R1-L-R16-R17-H3-R23-R24-H4-CR-C term, wherein ABD1 is actin binding domain 1, H1 is a hinge 1 domain, R1 is a spectrin repeat 1 domain, L is the linker, e.g., SEQ ID NO: 84, R16 is a spectrin repeat 16 domain, R17 is a spectrin repeat 17 domain, H3 is a hinge 3 domain, R 23 is a spectrin 23 domain, R24 is a spectrin 24 domain, H4 is a hinge 4 domain, CR is a cysteine rich domain, and C-term is a C-terminal domain (or portion thereof).

5.3.3 Non-Coding Polynucleotides

In some aspects, provided herein are nucleic acid molecules, e.g., DNA or RNA, comprising a nucleotide sequence encoding a miniaturized dystrophin polypeptide.

In some embodiments, the nucleic acid molecules disclosed herein comprise non-coding components. In some embodiments, the nucleic acid molecules disclosed herein comprise promoters. Certain exemplary regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences can be used, such as the ubiquitin promoter or 3-globin promoter. Still further, regulatory elements composed of sequences from different sources may be used, such as the SRa promoter system, which contains sequences from the SV40 early promoter and the long terminal repeat of human T cell leukemia virus type 1 (Takebe, Y. et al. (1988) *Mol. Cell. Biol.* 8:466-472). In certain embodiments, the regulatory sequence comprises a tissue specific promoter. In some embodiments, the tissue specific promoter drives expression of the gene of interest in a tissue selected from the group consisting of heart, liver, lungs, eyes, nervous system, lymphatic system, central nervous system, neuronal cells, muscle and stem cells.

In some embodiments, the promoters disclosed herein are tissue-specific promoters. In some embodiments, the promoter drives expression of the therapeutic protein in hepatocytes, muscle cells, endothelial cells, sinusoidal cells, or neuronal cells, or any combination thereof. In some embodiments, the promoter is selected from the group consisting of a synapsin 1 gene promoter, a mouse thyretin promoter (mTTR), an endogenous human factor VIII promoter (F8), a human alpha-1-antitrypsin promoter (hAAT), a human albumin minimal promoter, a mouse albumin promoter, a tristetraprolin (TTP) promoter, a CASI promoter, a CAG promoter, a cytomegalovirus (CMV) promoter, an α1-antitrypsin (AAT) promoter, a muscle creatine kinase (MCK) promoter, a myosin heavy chain alpha (αMHC) promoter, a myoglobin (MB) promoter, a desmin (DES) promoter, a SPc5-12 promoter, a 2R5Sc5-12 promoter, a dMCK promoter, a tMCK promoter, an α-synuclein promoter and a phosphoglycerate kinase (PGK) promoter.

In some embodiments, the nucleic acid molecules disclosed herein comprise an intronic sequence. In some embodiments, the intronic sequence is positioned 5' to the nucleotide sequence encoding the miniaturized dystrophin polypeptide. In some embodiments, the intronic sequence is positioned 3' to the promoter. In some embodiments, the intronic sequence comprises a synthetic intronic sequence.

In some embodiments, the nucleic acid molecules disclosed herein comprise a post-transcriptional regulatory element. In some embodiments, the post-transcriptional regulatory element is positioned 3' to the nucleotide sequence encoding the miniaturized dystrophin polypeptide. In some embodiments, the post-transcriptional regulatory element comprises a mutated woodchuck hepatitis virus post-transcriptional regulatory element (WPRE), a microRNA binding site, or a DNA nuclear targeting sequence, or any combination thereof.

In some embodiments, the nucleic acid molecules disclosed herein comprise a 3'UTR poly(A) tail sequence. In some embodiments, the 3'UTR poly(A) tail sequence is selected from the group consisting of bGH poly(A), actin poly(A), hemoglobin poly(A), and any combination thereof. In some embodiments, the 3'UTR poly(A) tail sequence comprises bGH poly(A).

In some embodiments, the nucleic acid molecules disclosed herein comprise an enhancer sequence. In some embodiments, the nucleic acid molecules disclosed herein comprise a first inverted terminal repeat (ITR) and/or a second ITR. In some embodiments, the first ITR and the second ITR are identical. In some embodiments, the first ITR and/or the second ITR are derived from adeno-associated virus. In some embodiments, the first ITR is derived from adeno-associated virus, and the second ITR is derived from adeno-associated virus. It is further recognized that the nucleic acid molecule can comprise additional elements that aid in the translation of the polypeptide. Such sequences include, for example, Kozak sequences attached to the 5' end of the polynucleotide encoding polypeptide. The Kozak consensus sequence is a sequence which occurs on eukaryotic mRNA that plays a role in the initiation of the translation process and has the consensus (gee)gccRccAUGG (SEQ ID NO:150); wherein (1) a lower case letter denotes the most common base at a position where the base can nevertheless vary; (2) upper case letters indicate highly-conserved bases, i.e. the 'AUGG' sequence is constant or rarely, if ever, changes, with the exception being the IUPAC ambiguity code 'R' which indicates that a purine (adenine or guanine) is normally observed at this position; and (3) the sequence in brackets ((gee)) is of uncertain significance.

In one non-limiting embodiment, the nucleic acid molecule comprises a functional variant or fragment thereof of a Kozak sequence. A functional variant or fragment thereof of a Kozak sequence will retain the ability to increase translation of the protein when compared to the level of translation from a sequence lacking the leader. Such a functional fragment can comprise at least 5, 6, 7, 8, 9, 10, 11, 12, 13, 14, 15, 16, 17, 18, 19, 20, 30, 40 continuous nucleotides of a Kozak sequence or the sequence set forth in SEQ ID NO:150 or SEQ ID NO:151 (gccaccATGG). Alternatively, a functional variant can comprise at least 80%, 85%, 90%, 91%, 92%, 93%, 94%, 95%, 96%, 97%, 98%, or 99% sequence identity to the Kozak sequence or the sequence set forth in SEQ ID NO:150 or SEQ ID NO:151.

5.3.4 Heterologous Moieties

In some embodiments, the polypeptides of the present disclosure can further comprise an additional element, e.g., heterologous moiety. Such elements can aid in the expression of the polypeptide, aid in the secretion of the polypeptide, improve the stability of the polypeptide, allow for more efficient purification of the polypeptide, and/or modulate the activity of the polypeptide. In some embodiments, the heterologous moiety is a polypeptide moiety. In other embodiments, the heterologous moiety is a non-polypeptide moiety.

In some embodiments, the polypeptide comprises a heterologous moiety fused to the polypeptide.

In some embodiments, the polypeptide disclosed herein comprises one or more additional heterologous moieties. In some embodiments, the heterologous moieties are half-life extending moieties. In some embodiments, the heterologous moiety comprises albumin or a fragment thereof, an immunoglobulin Fc region, the C-terminal peptide (CTP) of the subunit of human chorionic gonadotropin, a PAS sequence, a HAP sequence, a transferrin or a fragment thereof, or an albumin-binding moiety or a derivative thereof, or any combination thereof.

In some embodiments, the polypeptides disclosed herein comprise one or more additional heterologous moieties. In some embodiments, the heterologous moieties are half-life extending moieties. In some embodiments, the heterologous moiety comprises albumin, an immunoglobulin constant region or a portion thereof, an immunoglobulin-binding polypeptide, an immunoglobulin G (IgG), albumin-binding polypeptide (ABP), a PASylation moiety, a HESylation moiety, XTEN, a PEGylation moiety, or an Fc region, or any combination thereof.

5.4 Cells

In certain aspects, provided herein are cells (e.g., host cells) expressing (e.g., recombinantly) proteins described herein and expression vectors comprising nucleotides that encode proteins described herein.

In some embodiments, the host cell comprises the nucleic acid molecules described herein.

In some embodiments, the host cell comprises the vectors described herein.

In some embodiments, the host cell is a eukaryotic cell. In some embodiments, the host cell is selected from the group consisting of a mammalian cell, an insect cell, a yeast cell, a transgenic mammalian cell, and a plant cell. In some embodiments, the host cell is a prokaryotic cell. In some embodiments, the prokaryotic cell is a bacterial cell.

In some embodiments, the host cell is a mammalian cell. Such mammalian host cells include but are not limited to CHO, VERO, BHK, Hela, MDCK, HEK 293, NIH 3T3, W138, BT483, Hs578T, HTB2, BT2O and T47D, NSO (a murine myeloma cell line that does not endogenously produce any immunoglobulin chains), CRL7O3O, COS (e.g., COS1 or COS), PER.C6, VERO, HsS78Bst, HEK-293T, HepG2, SP210, R1.1, B-W, L-M, BSC1, BSC40, YB/20, BMT10, HBK, NSO, HT1080 and HsS78Bst cells.

5.5 Vectors

5.5.1 Adeno-Associate Virus (AAV)

5.5.1.1 Overview

Provided herein are vectors (e.g., expression vectors) comprising nucleic acid molecules comprising nucleotide sequences encoding a miniaturized dystrophin protein for recombinant expression in host cells and cells targeted for therapeutic intervention. The term "vector," as used herein, is intended to refer to a nucleic acid molecule capable of transporting another nucleic acid to which it has been linked; or an entity comprising such a nucleic acid molecule capable of transporting another nucleic acid. One type of vector is a "plasmid," which refers to a circular double stranded DNA loop into which additional DNA segments can be ligated. Another type of vector is a viral vector, wherein additional DNA segments can be ligated into the viral genome. Certain vectors, or polynucleotides that are part of vectors, are capable of autonomous replication in a host cell into which they are introduced (e.g., bacterial vectors having a bacterial origin of replication, and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" can sometimes be used interchangeably, depending on the context, as the plasmid is the most commonly used form of vector. However, also disclosed herein are other forms of expression vectors, such as viral vectors (e.g., replication defective retroviruses, adenoviruses and adeno-associated viruses), which serve equivalent functions.

In some embodiments, the polynucleotides disclosed herein are expressed using an adeno-associated virus (AAV). AAV is a nonenveloped, single-stranded DNA virus of the Parvoviridae family. In contrast to most other members of the Parvoviridae family, AAV is replication defective and is only able to replicate efficiently in the presence of a helper virus such as adenovirus or herpes virus.

AAV was first discovered in the mid 1960's as a contaminant of viral preparations of adenovirus. See Atchison R W, Casto B C, HAMMON W M. *Science.* 149(3685), 754-756 (1965). Since then, progressively safer and more effective methods to use AAV as a recombinant DNA vector have been developed. See, e.g., Hermonat P. L. and Muzyczka N. *Proc Natl Acad Sci USA.* 81(20), 6466-6470 (1984). 3. Laughlin C. A., et al. *Gene,* 23(1), 65-73 (1983). Matsushita T., et al. *Gene Ther.* 5(7), 938-945 (1998). Xiao X., et al. *Journal of Virology.* 72(3), 2224-2232 (1998). Low numbers of AAV genomes have been shown to integrate into the host chromosome. See Cheung A K, Hoggan M D, Hauswirth W W, et al. Integration of the adeno-associated virus genome into cellular DNA in latently infected human detroit 6 cells. J Virol 1980; 33:739-748. AAV is immunologically distinct from any known adenovirus antigen. The AAV capsid contains a single-stranded DNA (ssDNA) genome. See Rose J A, Berns K I, Hoggan M D, et al. Proc Natl Acad Sci USA 1969; 64:863-869.

AAV has a single stranded, 4.7 kb DNA genome encoding a replication (rep) gene and a capsid (cap) genes flanked by two inverted terminal repeats (ITRs). It is predominantly non-integrating, and forms stable episomes in non-dividing tissue. In spite of its high seroprevalence in the adult human population, AAV has not been associated with any human disease. See Gonsalves, M. *Virol. J.* 2, 43 (2005). AAV's stable expression in tissues, its lack of pathogenicity, and its ease of high titer production have made it a very attractive vector and popular gene transfer platform.

A recombinant AAV (rAAV) is a genetically manipulated AAV in which typically part or all of the rep and cap genes have been replaced with heterologous transgene sequences. Recombinant AAVs too can trigger long-term transgene expression in postmitotic cells, most likely because the recombinant AAV genome persist as largely circular episomes within the nucleus. rAAVs' only DNA cis-element required for the production of rAAVs is the AAV inverted terminal repeats (ITRs), whereas rep, cap, and adenoviral helper genes can be provided in trans. Thus, in some embodiments disclosed herein, rAAVs contain only heterologous transgene DNA flanked by the ITRs, and this genome is encapsidated within a serotype-specific AAV capsid.

AAV possesses unique features that make it attractive as a vector system for delivering foreign DNA into cells. AAV infection of cells in culture has generally been noncytopathic, and natural infection of humans and other animals is silent and asymptomatic. Moreover, AAV infects many different types of mammalian cells allowing the possibility of targeting many different tissues in vivo. AAV also possesses additional advantages that make it a particularly attractive viral system for gene delivery, including the promotion of an immune response that is relatively mild compared to other forms of gene delivery, and persistent expression in both dividing and quiescent cells based on non-integrating, episomal vector DNA. Also, AAV withstands the conditions used to inactivate adenovirus (56° to 65° C. for several hours), making cold preservation of rAAV-based vaccines less critical.

Replication of the viral DNA is not required for integration into the host-cell genome, and thus helper virus is not required for this process. The AAV proviral genome is infectious as cloned DNA in plasmids which makes construction of recombinant genomes feasible. Furthermore, because the signals directing AAV replication, genome encapsidation and integration are contained within the ITRs of the AAV genome, the internal approximately 4.7 kb of the genome (encoding the replication and structural capsid proteins, rep-cap) can thus be replaced with foreign DNA such as a gene cassette containing a promoter, a DNA of interest and a polyadenylation signal.

AAV vectors can include additional elements that function in cis or in trans. In particular embodiments, an AAV vector that includes a vector genome also has one or more inverted terminal repeat (ITR) sequences that flank the 5' or 3' terminus of the donor sequence; an expression control element that drives transcription (e.g., a promoter or enhancer) of the donor sequence, such as a constitutive or regulatable control element, or tissue-specific expression control element; an intron sequence, a stuffer or filler polynucleotide sequence; and/or a poly-Adenine sequence located 3' of the donor sequence.

In some embodiments, AAV replicates using a helper virus. A variety of such helper viruses for AAV are known in the art, including adenoviruses, herpesviruses and poxviruses such as vaccinia. The adenoviruses encompass a number of different subgroups, although Adenovirus type 5 of subgroup C is most commonly used. Numerous adenoviruses of human, non-human mammalian and avian origin are known and available from depositories such as the ATCC. Viruses of the herpes family include, for example, herpes simplex viruses (HSV) and Epstein-Barr viruses (EBV), as well as cytomegaloviruses (CMV) and pseudorabies viruses (PRV); which are also available from depositories such as ATCC. Exemplary AAV vectors include capsid sequences of any of AAV1, AAV2, AAV3, AAV4, AAV5, AAV6, AAV7, AAV8, AAV9, AAV10, AAV11, Rh10, Rh74 or AAV-2i8, or a capsid variant of AAV1, AAV2, AAV3, AAV4, AAV5, AAV6, AAV7, AAV8, AAV9, AAV10, AAV11, Rh10, Rh74 or AAV-2i8. Recombinant AAV vectors of the invention also include AAV1, AAV2, AAV3, AAV4, AAV5, AAV6, AAV7, AAV8, AAV9, AAV10, AAV11, Rh10, Rh74 or AAV-2i8, and variants thereof. Particular capsid variants include capsid variants of AAV1, AAV2, AAV3, AAV4, AAV5, AAV6, AAV7, AAV8, AAV9, AAV10, AAV11, Rh10, Rh74 or AAV-2i8, such as a capsid sequence with an amino acid substitution, deletion or insertion/addition. In one embodiment, the AAV vector is AAV9.

In some aspects the disclosure relates to AAVs having distinct tissue targeting capabilities (e.g., tissue tropisms). In some embodiments, the variant AAV capsid polypeptides further exhibit increased transduction or tropism in one or more human stem cell types as compared to non-variant parent capsid polypeptides. In some embodiments, the human stem cell types include but are not limited to embryonic stem cells, adult tissue stem cells (i.e., somatic stem cells), bone marrow stem cells, progenitor cells, induced pluripotent stem cells, and reprogrammed stem cells. In some embodiments, adult stem cells can include organoid stem cells (i.e., stem cells derived from any organ or organ system of interest within the body). In some embodiments, the target tissue of an AAV is gonad, diaphragm, heart, stomach, liver, spleen, pancreas, muscle or kidney. In some embodiments, the AAV targets organs of the body that include, but are not limited to, skin, hair, nails, sense receptors, sweat gland, oil glands, bones, muscles, brain, spinal cord, nerve, pituitary gland, pineal gland, hypothalamus, thyroid gland, parathyroid, thymus, adrenals, pancreas (islet tissue), heart, blood vessels, lymph nodes, lymph vessels, thymus, spleen, tonsils, nose, pharynx, larynx, trachea, bronchi, lungs, mouth, pharynx, esophagus, stomach, small intestine, large intestine, rectum, anal canal, teeth, salivary glands, tongue, liver, gallbladder, pancreas, appendix, kidneys, ureters, urinary bladder, urethra, testes, ductus (vas) deferens, urethra, prostate, penis, scrotum, ovaries, uterus, uterine (fallopian) tubes, vagina, vulva, and mammary glands (breasts). Organ systems of the body include but are not limited to the integumentary system, skeletal system, muscular system, nervous system, endocrine system, cardiovascular system, lymphatic system, respiratory system, digestive system, urinary system, and reproductive system. In some embodiments, transduction and/or tropism of an AAV with variant capsid polypeptides is increased by about 5%, about 10%, about 15%, about 20%, about 25%, about 30%, about 35%, about 40%, about 45%, about 50%, about 55%, about 60%, 65%, about 70%%, about 75%, about 80%, about 85%, about 90%, about 95%, about 99%, or about 100%, by comparison to an AAV having non-variant capsid polypeptides. In some embodiments, transduction and/or tropism is increased by about 5% to about 80%, about 10% to about 70%, about 20% to about 60% or about 30% to about 60%.

5.5.1.2 Replication, Capsid, and Assembly AAV Genes

The single-stranded genome of AAV comprises three genes, rep (Replication), cap (Capsid), and aap (Assembly). These three genes give rise to at least nine gene products through the use of three promoters, alternative translation start sites, and differential splicing.

The rep gene encodes four proteins (Rep78, Rep68, Rep52, and Rep40), which are required for viral genome replication and packaging.

Cap gene expression gives rise to the viral capsid proteins (VP1; VP2; VP3), which form the outer capsid shell that protects the viral genome, as well as being actively involved in cell binding and internalization. It is estimated that the viral coat is comprised of 60 proteins arranged into an icosahedral structure.

The aap gene encodes the assembly-activating protein (AAP) in an alternate reading frame overlapping the cap gene. This nuclear protein is thought to provide a scaffolding function for capsid assembly and plays a role in nucleolar localization of VP proteins in some AAV serotypes.

In some embodiments, one or more of the rep, cap, or aap genes are naturally occurring, e.g. the rep, cap, or app genes comprise all or a portion of parvovirus rep, cap, or aap genes. In some embodiments, the one or more of the rep, cap, or aap genes comprise a synthetic sequence.

In one embodiment, the rep gene comprises a synthetic sequence. In one embodiment, the cap gene comprises a synthetic sequence. In one embodiment, the aap gene comprises a synthetic sequence. In one embodiment, the rep and cap genes comprise a synthetic sequence. In one embodiment, the rep and aap genes comprise a synthetic sequence. In one embodiment, the cap and aap genes comprise a synthetic sequence. In one embodiment, the rep, cap, and aap genes comprise a synthetic sequence.

In some embodiments, rep is from an AAV genome selected from AAV1, AAV2, AAV3, AAV4, AAV5, AAV6, AAV7, AAV8, AAV9, AAV10, AAV11, and any combination thereof. In a particular embodiment, rep is from the AAV1 genome. In a particular embodiment, rep is from the AAV2 genome. In a particular embodiment, rep is from the AAV3 genome. In a particular embodiment, rep is from the AAV4 genome. In a particular embodiment, rep is from the AAV5 genome. In a particular embodiment, rep is from the AAV6 genome. In a particular embodiment, rep is from the AAV7 genome. In a particular embodiment, rep is from the AAV8 genome. In a particular embodiment, rep is from the AAV9 genome. In a particular embodiment, rep is from the AAV10 genome. In a particular embodiment, rep is from the AAV11 genome.

In some embodiments, cap is from an AAV genome selected from AAV1, AAV2, AAV3, AAV4, AAV5, AAV6, AAV7, AAV8, AAV9, AAV10, AAV11, and any combination thereof. In a particular embodiment, cap is from the AAV1 genome. In a particular embodiment, cap is from the AAV2 genome. In a particular embodiment, cap is from the AAV3 genome. In a particular embodiment, cap is from the AAV4 genome. In a particular embodiment, cap is from the AAV5 genome. In a particular embodiment, cap is from the AAV6 genome. In a particular embodiment, cap is from the AAV7 genome. In a particular embodiment, cap is from the AAV8 genome. In a particular embodiment, cap is from the AAV9 genome. In a particular embodiment, cap is from the AAV10 genome. In a particular embodiment, cap is from the AAV11 genome.

In some embodiments, aap is from an AAV genome selected from AAV1, AAV2, AAV3, AAV4, AAV5, AAV6, AAV7, AAV8, AAV9, AAV10, AAV11, and any combination thereof. In a particular embodiment, aap is from the AAV1 genome. In a particular embodiment, aap is from the AAV2 genome. In a particular embodiment, aap is from the AAV3 genome. In a particular embodiment, aap is from the AAV4 genome. In a particular embodiment, aap is from the AAV5 genome. In a particular embodiment, aap is from the AAV6 genome. In a particular embodiment, aap is from the AAV7 genome. In a particular embodiment, aap is from the AAV8 genome. In a particular embodiment, aap is from the AAV9 genome. In a particular embodiment, aap is from the AAV10 genome. In a particular embodiment, aap is from the AAV11 genome.

It is to be understood that a particular AAV genome described herein could have genes derived from different AAV genomes (e.g., genomes from AAV1, AAV2, AAV3, AAV4, AAV5, AAV6, AAV7, AAV8, AAV9, AAV10, and AAV11). Thus, disclosed herein are AAVs that comprise any possible permutation/combination of rep, cap, or aap.

In some embodiments disclosed herein, the AAV is recombinant AAV (rAAV). In some embodiments, the rAAV lacks one or more of the rep gene, the cap gene, and the aap gene. In some embodiments, the rAAV lacks a rep gene. In some embodiments, the rAAV lacks a cap gene. In some embodiments, the rAAV lacks an aap gene. In some embodiments, the rAAV lacks a rep gene and lacks a cap gene. In some embodiments, the rAAV lacks a rep gene and lacks an aap gene. In some embodiments, the rAAV lacks a cap gene and lacks an aap gene. In some embodiments, the rAAV lacks a rep gene, a cap gene, and an aap gene.

In some embodiments disclosed herein, the rAAV is modified so that one or more of the rep gene, the cap gene, and the aap gene is mutated so that expression of one or more of the AAV genes is modified. In some embodiments, the rep gene is mutated. In some embodiments, the cap gene is mutated. In some embodiments, the aap gene is mutated. In some embodiments, the rep gene and the cap gene are mutated. In some embodiments, the rep gene and the aap gene are mutated. In some embodiments, the cap gene and the aap gene are mutated. In some embodiments, the cap gene, the rep gene, and the aap gene are mutated.

5.5.1.3 Inverted Terminal Repeats

In certain embodiments, the AAV comprises a first ITR, e.g., a 5' ITR, and second ITR, e.g., a 3' ITR. Typically, ITRs are involved in parvovirus (e.g., AAV) DNA replication and rescue, or excision, from prokaryotic plasmids (Samulski et al., 1983, 1987; Senapathy et al., 1984; Gottlieb and Muzyczka, 1988). In addition, ITRs have been reported to be the minimum sequences required for AAV proviral integration and for packaging of AAV DNA into virions (McLaughlin et al., 1988; Samulski et al., 1989). These elements are essential for efficient multiplication of a parvovirus genome.

In some embodiments, the ITR comprises a naturally occurring ITR, e.g., the ITR comprises all or a portion of a parvovirus ITR. In some embodiments, the ITR comprises a synthetic sequence. In one embodiment, the first ITR or the second ITR comprises a synthetic sequence. In another embodiment, each of the first ITR and the second ITR comprises a synthetic sequence. In some embodiments, the first ITR or the second ITR comprises a naturally occurring sequence. In another embodiment, each of the first ITR and the second ITR comprises a naturally occurring sequence.

In some embodiments, the ITR comprises an ITR from an AAV genome. In some embodiments, the ITR is an ITR of an AAV genome selected from AAV1, AAV2, AAV3, AAV4, AAV5, AAV6, AAV7, AAV8, AAV9, AAV10, AAV11, and any combination thereof. In a particular embodiment, the ITR is an ITR of the AAV2 genome. In another embodiment, the ITR is a synthetic sequence genetically engineered to include at its 5' and 3' ends ITRs derived from one or more of AAV genomes. In some embodiments, the ITRs are derived from the same genome, e.g., from the genome of the same virus, or from different genomes, e.g., from the genomes of two or more different AAV genomes. In certain embodiments, the ITRs are derived from the same AAV genome. In a specific embodiment, the two ITRs present in the nucleic acid molecule of the invention are the same, and can in particular be AAV2 ITRs. In one particular embodiment, the first ITR and the second ITR are identical.

In some embodiments, the ITRs form hairpin loop structures. In one embodiment, the first ITR forms a hairpin structure. In another embodiment, the second ITR forms a hairpin structure. Still in another embodiment, both the first ITR and the second ITR form hairpin structures.

In some embodiments, an ITR in a nucleic acid molecule described herein is a transcriptionally activated ITR. A transcriptionally-activated ITR can comprise all or a portion of a wild-type ITR that has been transcriptionally activated by inclusion of at least one transcriptionally active element. Various types of transcriptionally active elements are suitable for use in this context. In some embodiments, the transcriptionally active element is a constitutive transcriptionally active element. Constitutive transcriptionally active elements provide an ongoing level of gene transcription, and can be used when it is desired that the transgene be expressed on an ongoing basis. In other embodiments, the transcriptionally active element is an inducible transcriptionally active element. Inducible transcriptionally active elements generally exhibit low activity in the absence of an inducer (or inducing condition), and are up-regulated in the presence of the inducer (or switch to an inducing condition). Inducible transcriptionally active elements can be used when expression is desired only at certain times or at certain locations, or when it is desirable to titrate the level of expression using an inducing agent. Transcriptionally active elements can also be tissue-specific; that is, they exhibit activity only in certain tissues or cell types. Transcriptionally active elements, can be incorporated into an ITR in a variety of ways. In some embodiments, a transcriptionally active element is incorporated 5' to any portion of an ITR or 3' to any portion of an ITR. In other embodiments, a transcriptionally active element of a transcriptionally-activated ITR lies between two ITR sequences. If the transcriptionally active element comprises two or more elements which must be spaced apart, those elements can alternate with portions of the ITR. In some embodiments, a hairpin structure of an ITR is deleted and replaced with inverted repeats of a transcriptional element. This latter arrangement would create a hairpin mimicking the deleted portion in structure. Multiple tandem transcriptionally active elements can also be present in a transcriptionally-activated ITR, and these can be adjacent or spaced apart. In addition, protein binding sites (e.g., Rep binding sites) can be introduced into transcriptionally active elements of the transcriptionally-activated ITRs. A transcriptionally active element can comprise any sequence enabling the controlled transcription of DNA by RNA polymerase to form RNA, and can comprise, for example, a transcriptionally active element, as defined below.

Transcriptionally-activated ITRs provide both transcriptional activation and ITR functions to the nucleic acid molecule in a relatively limited nucleotide sequence length which effectively maximizes the length of a transgene which can be carried and expressed from the nucleic acid molecule. Incorporation of a transcriptionally active element into an ITR can be accomplished in a variety of ways. A comparison of the ITR sequence and the sequence requirements of the transcriptionally active element can provide insight into ways to encode the element within an ITR. For example, transcriptional activity can be added to an ITR through the introduction of specific changes in the ITR sequence that replicates the functional elements of the transcriptionally active element. A number of techniques exist in the art to efficiently add, delete, and/or change particular nucleotide sequences at specific sites (see, for example, Deng and Nickoloff (1992) Anal. Biochem. 200:81-88). Another way to create transcriptionally-activated ITRs involves the introduction of a restriction site at a desired location in the ITR. In addition, multiple transcriptionally activate elements can be incorporated into a transcriptionally-activated ITR, using methods known in the art. By way of illustration, transcriptionally-activated ITRs can be generated by inclusion of one or more transcriptionally active elements such as: TATA box, GC box, CCAAT box, Sp1 site, Inr region, CRE (cAMP regulatory element) site, ATF-1/CRE site, APBβ box, APBα box, CArG box, CCAC box, or any other element involved in transcription as known in the art.

5.5.1.4 Gene of Interest and Other Sequences

Certain aspects of the present disclosure are directed to methods of administering to a subject an AAV therapy. In some embodiments, the AAV comprises a gene of interest (GOI). In some embodiments, the GOI is a nucleic acid molecule comprising a nucleotide sequence as disclosed herein, which encodes a miniaturized dystrophin polypeptide as disclosed herein.

The GOI being expressed can be either a DNA segment encoding a protein, with any necessary control elements (e.g., promoters, operators) desired by the user, or a non-coding DNA segment, the transcription of which produces all or part of some RNA-containing molecule, such as a ribozyme or an anti-sense molecule.

In some embodiments, the AAV comprises more than one GOI. In AAVs with more than one GOI, some embodiments include elements such as IRES or 2A, to co-express them from one promoter. In some embodiments, the AAV comprises two genes of interest separated by an IRES element. In some embodiments, the AAV comprises two genes of interest separated by a 2A element. In some embodiments, the AAV comprises three genes of interest separated by an IRES element between the genes of interest (e.g., GOI-IRES-GOI-IRES-GOI). In some embodiments, the AAV comprises three genes of interest separated by 2A elements between the genes of interest.

In some embodiments, the AAV comprises a regulatory sequence. In some embodiments, the AAV comprises non-coding regulatory DNA. In some embodiments, the AAV genome comprises regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, CA (1990)). It will be appreciated by those skilled in the art that the design of the AAV, including the selection of regulatory sequences, can depend on such factors as the choice of the host cell to be transformed, the level of expression of protein desired, etc. In some embodiments, the AAV genome comprises mRNA splice donor/splice acceptor sites. Certain regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences can be used, such as the ubiquitin promoter or β-globin promoter. Still further, regulatory elements composed of sequences from different sources, such as the SRa promoter system, which contains sequences from the SV40 early promoter and the long terminal repeat of human T cell leukemia virus type 1 (Takebe, Y. et al. (1988) *Mol. Cell. Biol.* 8:466-472). In certain embodiments, the regulatory sequence comprises a tissue specific promoter. In some embodiments, the tissue specific promoter drives expression of the gene of interest in a tissue selected from the group consisting of heart, liver, lungs, eyes, nervous system, lymphatic system, muscle and stem cells.

5.5.1.5 AAV Formulations

In some embodiments, the AAV vector is formulated with a delivery agent. In some embodiments, the delivery agent comprises a lipid nanoparticle. In some embodiments, the delivery agent is selected from the group consisting of liposomes, non-lipid polymeric molecules, endosomes, and any combination thereof.

5.5.2 Non-AAV Vectors

A vector which comprises the above-described polynucleotides operably linked to a promoter is also provided herein. A nucleotide sequence is "operably linked" to an expression control sequence (e.g., a promoter) when the expression control sequence controls and regulates the transcription and translation of that sequence. The term "operably linked" when referring to a nucleotide sequence includes having an appropriate start signal (e.g., ATG) in front of the nucleotide sequence to be expressed and maintaining the correct reading frame to permit expression of the sequence under the control of the expression control sequence and production of the desired product encoded by the sequence. If a gene that one desires to insert into a recombinant nucleic acid molecule does not contain an appropriate start signal, such a start signal can be inserted in front of the gene. A "vector" is a replicon, such as plasmid, phage or cosmid, to which another nucleic acid segment can be attached so as to bring about the replication of the attached segment. The promoter can be, or is identical to, a bacterial, yeast, insect or mammalian promoter.

In some embodiments, the vector can be a plasmid, cosmid, yeast artificial chromosome (YAC), bacteriophage or eukaryotic viral DNA. Other numerous vector backbones known in the art as useful for expressing protein can be employed. Such vectors include, but are not limited to:

adenoviral vector, a retroviral vector, poxvirus vector, a baculovirus vector, a herpes viral vector, simian virus 40 (SV40), cytomegalovirus (CMV), mouse mammary tumor virus (MMTV), and Moloney murine leukemia virus. Further, one class of vectors comprises DNA elements derived from viruses such as bovine papilloma virus, polyoma virus, baculovirus, retroviruses, or Semliki Forest virus. Such vectors can be obtained commercially or assembled from the sequences described by methods well-known in the art.

In some embodiments, the vector described herein is formulated with a delivery agent. In some embodiments, the delivery agent comprises a lipid nanoparticle. In some embodiments, the delivery agent is selected from the group consisting of liposomes, non-lipid polymeric molecules, endosomes, and any combination thereof.

5.6 Pharmaceutical Compositions

The various polypeptides and polynucleotides disclosed herein (also referred to herein as "active compounds") can be incorporated into pharmaceutical compositions suitable for administration. Such compositions typically comprise the polypeptide, or polynucleotides, and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active compounds is well known in the art. Except insofar as any conventional media or agent is incompatible with the active compound, use thereof in the compositions is contemplated. Supplementary active compounds can also be incorporated into the compositions.

In some embodiments, disclosed is a pharmaceutical composition comprising (a) a polypeptide as described herein and (b) a pharmaceutically acceptable excipient.

In some embodiments, disclosed is a pharmaceutical composition comprising (a) a composition comprising a polypeptide as described herein and (b) a pharmaceutically acceptable excipient.

In some embodiments, disclosed is a pharmaceutical composition comprising (a) a polynucleotide as described herein and (b) a pharmaceutically acceptable excipient.

In some embodiments, disclosed is a pharmaceutical composition comprising (a) a vector (e.g., rAAV) as described herein and (b) a pharmaceutically acceptable excipient.

In some embodiments, disclosed is a pharmaceutical composition comprising (a) a host cell as described herein and (b) a pharmaceutically acceptable excipient.

A pharmaceutical composition of the disclosure is formulated to be compatible with its intended route of administration. Examples of routes of administration include parenteral, e.g., intravenous, intradermal, subcutaneous, oral, transdermal (topical), and transmucosal, and any combination thereof. Another route of administration includes pulmonary administration. In addition, it can be desirable to administer a therapeutically effective amount of the pharmaceutical composition locally to an area in need of treatment. This can be achieved by, for example, local or regional infusion or perfusion during surgery, topical application, injection, catheter, suppository, or implant (for example, implants formed from porous, non-porous, or gelatinous materials, including membranes, such as sialastic membranes or fibers), and the like. In another embodiment, the therapeutically effective amount of the pharmaceutical composition is delivered in a vesicle, such as liposomes (see, e.g., Langer, Science 249:1527-33, 1990 and Treat et al., in Liposomes in the Therapy of Infectious Disease and Cancer, Lopez Berestein and Fidler (eds.), Liss, N.Y., pp. 353-65, 1989).

In yet another embodiment, the therapeutically effective amount of the pharmaceutical composition can be delivered in a controlled release system. In one example, a pump can be used (see, e.g., Langer, Science 249:1527-33, 1990; Sefton, Crit. Rev. Biomed. Eng. 14:201-40, 1987; Buchwald et al., Surgery 88:507-16, 1980; Saudek et al., N Engl. J Med. 321:574-79, 1989). In another example, polymeric materials can be used (see, e.g., Levy et al., Science 228: 190-92, 1985; During et al., Ann. Neural. 25:351-56, 1989; Howard et al., J Neurosurg. 71:105-12, 1989). Other controlled release systems, such as those discussed by Langer (Science 249:1527-33, 1990), can also be used.

Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances. Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations can be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions includes EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor ELS (BASF; Parsippany, NJ), or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride, in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the methods of preparation can be vacuum drying and freeze-drying, which yields a powder of the active ingredient plus any additional desired ingredient from a previously sterile-filtered solution thereof.

For administration by inhalation, the compounds are delivered in the form of an aerosol spray from a pressurized container or dispenser that contains a suitable propellant, e.g., a gas such as carbon dioxide, or a nebulizer. Systemic administration can also be by transmucosal or transdermal means.

For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated with each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved, and the limitations inherent in the art of compounding such a functional compound for the treatment of individuals. The pharmaceutical compositions can be included in a container, pack, or dispenser together with instructions for administration.

5.7 Uses and Methods

5.7.1 Methods of Producing Miniaturized Dystrophins

Also disclosed herein are methods of producing a miniaturized dystrophin polypeptide, comprising: culturing a host cell described herein under suitable conditions and recovering the miniaturized dystrophin polypeptide.

As used herein, an "isolated" polynucleotide or nucleic acid molecule is one which is separated from other nucleic acid molecules which are present in the natural source (e.g., in a mouse or a human) of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. For example, the language "substantially free" includes preparations of polynucleotide or nucleic acid molecule having less than about 15%, 10%, 5%, 2%, 1%, 0.5%, or 0.1% (in particular less than about 10%) of other material, e.g., cellular material, culture medium, other nucleic acid molecules, chemical precursors and/or other chemicals. In a specific embodiment, a nucleic acid molecule(s) encoding a polypeptide described herein is isolated or purified.

The polynucleotides can be obtained, and the nucleotide sequence of the polynucleotides determined, by any method known in the art. Nucleotide sequences encoding polypeptides described herein, e.g., the polypeptides described in Tables 3 and 4, and modified versions of these polypeptides can be determined using methods well known in the art, i.e., nucleotide codons known to encode particular amino acids are assembled in such a way to generate a nucleic acid that encodes the polypeptides. Such a polynucleotide encoding the polypeptide can be assembled from chemically synthesized oligonucleotides (e.g., as described in Kutmeier G et al., (1994), BioTechniques 17: 242-6), which, briefly, involves the synthesis of overlapping oligonucleotides containing portions of the sequence encoding the polypeptide, annealing and ligating of those oligonucleotides, and then amplification of the ligated oligonucleotides by PCR.

Alternatively, a polynucleotide encoding a polypeptide described herein can be generated from nucleic acid from a suitable source (e.g., a hybridoma) using methods well known in the art (e.g., PCR and other molecular cloning methods). For example, PCR amplification using synthetic primers hybridizable to the 3' and 5' ends of a known sequence can be performed using genomic DNA obtained from hybridoma cells producing the polypeptide of interest. Such PCR amplification methods can be used to obtain nucleic acids comprising the sequence encoding e.g., IL2, a linker sequence, or IL2-Ra. The amplified nucleic acids can be cloned into vectors for expression in host cells and for further cloning, for example, to generate polypeptides.

If a clone containing a nucleic acid encoding a particular polypeptide is not available, but the sequence of the polypeptide molecule is known, a nucleic acid encoding the polypeptide can be chemically synthesized or obtained from a suitable source (e.g., a cDNA library or a cDNA library generated from, or nucleic acid, preferably poly A+ RNA, isolated from, any tissue or cells expressing the proteins of interest, such as hybridoma cells selected to express a polypeptide described herein) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the polypeptides. Amplified nucleic acids generated by PCR can then be cloned into replicable cloning vectors using any method well known in the art.

DNA encoding polypeptides described herein can be readily isolated and sequenced using conventional procedures (e.g., by using oligonucleotide probes that are capable of binding specifically to genes encoding the polypeptides disclosed herein). Hybridoma cells can serve as a source of such DNA. Once isolated, the DNA can be placed into expression vectors, which are then transfected into host cells such as *E. coli* cells, simian COS cells, Chinese hamster ovary (CHO) cells (e.g., CHO cells from the CHO GS SYSTEM™ (Lonza)), or myeloma cells that do not otherwise produce immunoglobulin protein, to obtain the synthesis of polypeptides in the recombinant host cells.

5.7.1 Therapeutic Uses and Methods

The miniaturized dystrophin polypeptides, polynucleotides encoding miniaturized dystrophin polypeptides, vectors (e.g., rAAV) harboring polynucleotides encoding miniaturized dystrophin polypeptides and methods described herein have numerous in vitro and in vivo utilities. For example, the nucleotide sequence encoding a miniaturized dystrophin polypeptide, e.g., a vector, e.g., an AAV vector, or the polypeptides described herein can be administered to cells in culture, in vitro or ex vivo, or to human subjects, e.g., in vivo, to treat diseases.

Accordingly, disclosed herein are therapeutic methods using any of the miniaturized dystrophin nucleic acid molecules as disclosed herein, polypeptides as disclosed herein, host cells as disclosed herein, vectors as disclosed herein, or pharmaceutical compositions as disclosed herein, or any combination thereof.

In some embodiments, disclosed herein is a method of expressing a miniaturized dystrophin polypeptide in a subject in need thereof, comprising administering to the subject a nucleic acid as disclosed herein, a vector as disclosed herein, a host cell as disclosed herein, or a pharmaceutical composition as disclosed herein.

In some embodiments, disclosed herein is a method of treating a subject having a disease or condition comprising administering to the subject a nucleic acid as disclosed herein, a vector as disclosed herein, a polypeptide as disclosed herein, a host cell as disclosed herein, or a pharmaceutical composition as disclosed herein. In some embodiments, the disease or condition is caused by dystrophin deficiency. In some embodiments, the disease is Duchene muscular dystrophy (DMD), Becker muscular dystrophy (BMD), X-linked dilated cardiomyopathy (XLDC), facioscapulohumeral muscular dystrophy, myotonic muscular dystrophy, limb-girdle muscular dystrophy, oculopharyngeal muscular dystrophy, Emery-Dreifuss muscular dystrophy, distal muscular dystrophy, and/or congenital muscular dystrophy. In other embodiments, the disease to be treated is Sarcopenia, heart disease, cachexia.

In some embodiments, a nucleic acid molecule as disclosed herein, a polypeptide as disclosed herein, a vector (e.g., rAAV) as disclosed herein, a host cell as disclosed herein, or a pharmaceutical composition as disclosed herein is administered intravenously, transdermally, intradermally, subcutaneously, orally, or pulmonarily, or any combination thereof. In some embodiments, the nucleic acid molecule as disclosed herein, the polypeptide as disclosed herein, the vector as disclosed herein, the host cell as disclosed herein, or the pharmaceutical composition as disclosed herein is administered via a topical, epidermal mucosal, intranasal, oral, vaginal, rectal, sublingual, topical, intravenous, intraperitoneal, intramuscular, intraarterial, intrathecal, intralymphatic, intralesional, intracapsular, intraorbital, intracardiac, intradermal, transtracheal, subcutaneous, subcuticular, intraarticular, subcapsular, subarachnoid, intraspinal, epidural or intrasternal route. In some embodiments, the nucleic acid molecule, the vector (e.g., rAAV), the host cell as disclosed herein, or the polypeptide is administered intravenously.

In some embodiments, the method of treatment further comprises administering to the subject a second agent.

As used herein, the term “subject” includes any human or non-human animal. For example, the methods and compositions described herein can be used to treat a subject having cancer. The term “non-human animal” includes all vertebrates, e.g., mammals and non-mammals, such as non-human primates, sheep, dog, cow, chickens, amphibians, reptiles, etc. In some embodiments, the subject is a human.

In some embodiments, the administration of the nucleic acid molecule, the vector (e.g., rAAV), the polypeptide, the host cell, or the pharmaceutical composition to the subject results in an increased dystrophin protein expression, relative to dystrophin protein expression in the subject prior to the administration, wherein the dystrophin protein expression is increased by at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 20-fold, at least about 25-fold, at least about 30-fold, at least about 35-fold, at least about 40-fold, at least about 50-fold, at least about 60-fold, at least about 70-fold, at least about 80-fold, at least about 90-fold, or at least about 100-fold.

In certain aspects of the disclosure, the method comprises, or further comprises, administering an AAV therapy to the subject. In some embodiments, the AAV therapy comprises administering a recombinant AAV. Any recombinant AAV known in the art and/or disclosed herein can be used in the methods of the present disclosure. In some embodiments, the AAV therapy comprises administering an AAV selected from the group consisting of AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, snake AAV, avian AAV, bovine AAV, canine AAV, equine AAV, ovine AAV, goat AAV, shrimp AAV, and any combination thereof. In certain embodiments, the AAV therapy comprises administering an AAV type 1. In certain embodiments, the AAV therapy comprises administering an AAV type 2. In certain embodiments, the AAV therapy comprises administering an AAV type 3. In certain embodiments, the AAV therapy comprises administering an AAV type 4. In certain embodiments, the AAV therapy comprises administering an AAV type 5. In certain embodiments, the AAV therapy comprises administering an AAV type 6. In certain embodiments, the AAV therapy comprises administering an AAV type 7. In certain embodiments, the AAV therapy comprises administering an AAV type 8. In certain embodiments, the AAV therapy comprises administering an AAV type 9. In certain embodiments, the AAV therapy comprises administering an AAV type 10. In certain embodiments, the AAV therapy comprises administering an AAV type 11. In certain embodiments, the AAV therapy comprises administering an AAV type 12. In certain embodiments, the AAV therapy comprises administering an AAV type 13.

In some embodiments, treatment of a subject with the miniaturized dystrophin nucleic acid molecules as disclosed herein, polypeptides as disclosed herein, host cells as disclosed herein, vectors as disclosed herein, or pharmaceutical compositions as disclosed herein, or any combination thereof, does not cause significant inflammatory reactions, e.g., immune-mediated pneumonitis, immune-mediated colitis, immune mediated hepatitis, immune-mediated nephritis or renal dysfunction, immune-mediated hypophysitis, immune-mediated hypothyroidism and hyperthyroidism, or other immune-mediated adverse reactions. In some embodiments, treatment of a subject with the miniaturized dystrophin nucleic acid molecules as disclosed herein, polypeptides as disclosed herein, host cells as disclosed herein, vectors as disclosed herein, pharmaceutical compositions as disclosed herein, or any combination thereof does not cause significant cardiac disorders, e.g., ventricular arrhythmia; eye disorders, e.g., iridocyclitis; infusion-related reactions; increased amylase, increased lipase; nervous system disorders, e.g., dizziness, peripheral and sensory neuropathy; skin and subcutaneous tissue disorders, e.g., rash, pruritus, exfoliative dermatitis, erythema multiforme, vitiligo or psoriasis; respiratory, thoracic and mediastinal disorders, e.g., cough; fatigue; nausea; decreased appetite; constipation; arthralgia; or diarrhea.

5.8 Kits

Also disclosed herein are kits comprising one or more nucleic acid molecules disclosed herein, one or more vectors (e.g., rAAV) as disclosed herein, one or more polypeptides as disclosed herein, or one or more host cells as disclosed herein, or any combination thereof. In some embodiments, the kit also comprises instructions for administering any of the aforesaid, or a combination thereof, to a subject in need thereof.

The terms "kit" and "system," as used herein are intended to refer to at least one or more nucleic acid molecules disclosed herein, one or more vectors (e.g., rAAV) as disclosed herein, one or more polypeptides as disclosed herein, or one or more host cells as disclosed herein, or any combination thereof, which, in specific embodiments, are in combination with one or more other types of elements or components (e.g., other types of biochemical reagents, containers, packages, such as packaging intended for commercial sale, instructions of use, and the like).

In some embodiments, disclosed is a kit comprising (a) one or more of a miniaturized dystrophin polypeptide as described herein, a composition comprising a miniaturized dystrophin polypeptide as described herein, a nucleic acid encoding for a miniaturized dystrophin polypeptide as described herein, a vector (e.g., rAAV), and/or a host cell; and (b) and instructions for administering any of the aforesaid to a subject in need thereof. In some embodiments, disclosed is a kit comprising (a) a miniaturized dystrophin polypeptide as described herein and (b) and instructions for administering the miniaturized dystrophin polypeptide to a subject in need thereof. In some embodiments, disclosed is a kit comprising (a) a composition comprising a miniaturized dystrophin polypeptide as described herein and (b) and instructions for administering the composition to a subject in need thereof. In some embodiments, disclosed is a kit comprising (a) a nucleic acid encoding for a miniaturized dystrophin polypeptide as described herein and (b) and instructions for administering the nucleic to a subject in need thereof. In some embodiments, disclosed is a kit comprising (a) a vector as described herein and (b) and instructions for administering the vector to a subject in need thereof. In some embodiments, disclosed is a kit comprising (a) an AAV vector as described herein and (b) and instructions for administering the vector to a subject in need thereof. In some embodiments, disclosed is a kit comprising (a) a host cell as described herein and (b) and instructions for administering the host cell to a subject in need thereof.

In a specific embodiment, provided herein is a pharmaceutical pack or kit comprising one or more containers filled with one or more of the ingredients of the pharmaceutical compositions described herein, such as one or more miniaturized dystrophin peptides provided herein. In some embodiments, the kits contain a pharmaceutical composition described herein and any prophylactic or therapeutic agent, such as those described herein. In certain embodiments, the kits can contain a T cell mitogen, such as, e.g., phytohaemagglutinin (PHA) and/or phorbol myristate acetate (PMA), or a TCR complex stimulating antibody, such as an anti-CD3 antibody and anti-CD28 antibody. Optionally associated with such container(s) can be a notice in the form prescribed by a governmental agency regulating the manufacture, use or sale of pharmaceuticals or biological products, which notice reflects approval by the agency of manufacture, use or sale for human administration.

Also provided herein are kits that can be used in the above methods. In one embodiment, a kit comprises a miniaturized dystrophin polypeptide described herein, preferably a purified miniaturized dystrophin polypeptide, in one or more containers. In a specific embodiment, kits described herein contain a substantially isolated miniaturized dystrophin polypeptide as a control. In another specific embodiment, the kits described herein further comprise a control protein which does not react with a miniaturized dystrophin polypeptide antigen. In another specific embodiment, kits described herein contain one or more elements for detecting the binding of the miniaturized dystrophin polypeptide to a dystrophin antigen (e.g., the miniaturized dystrophin polypeptide can be conjugated to a detectable substrate such as a fluorescent compound, an enzymatic substrate, a radioactive compound or a luminescent compound, or a second antibody which recognizes the first antibody can be conjugated to a detectable substrate). In specific embodiments, a kit provided herein can include a recombinantly produced or chemically synthesized miniaturized dystrophin polypeptide. The antigen to a miniaturized dystrophin polypeptide disclosed herein as provided in the kit can also be attached to a solid support. In a more specific embodiment, the detecting means of the above described kit includes a solid support to which an antigen of the miniaturized dystrophin polypeptide is attached. Such a kit can also include a non-attached reporter-labeled anti-human antibody or anti-mouse/rat antibody. In this embodiment, binding of the miniaturized dystrophin polypeptide to an antigen can be detected by binding of the said reporter-labeled antibody.

The practice of the present disclosure will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press) (1986); Perbal (1984) A Practical Guide To Molecular Cloning; the treatise, Methods In Enzymology (Academic Press, Inc., N.Y.); Miller and Calos eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986)); Crooks, Antisense drug Technology: Principles, strategies and applications, $2^{nd}$ Ed. CRC Press (2007) and in Ausubel et al. (1989) Current Protocols in Molecular Biology (John Wiley and Sons, Baltimore, Md.).

All of the references cited above, as well as all references cited herein and the amino acid or nucleotide sequences (e.g., GenBank numbers and/or Uniprot numbers), are incorporated herein by reference in their entireties.

The following examples are offered by way of illustration and not by way of limitation.

6. EXAMPLES

6.1 Novel Miniaturized Dystrophins with Reduced Immunogenicity and Enhanced Stability Mutations in the dystrophin gene often result in an impairment of the stability of the corresponding dystrophin protein, which in turn leads to proteosomal degradation of the unstable dystrophin protein, and dystrophic pathophysiology. Similarly, miniaturizing dystrophin-encoding DNA to accommodate the limited packaging capacity of AAV can impair the stability of the corresponding miniaturized dystrophin protein.

The stability of various miniaturized dystrophin proteins was examined by comparing dystrophin protein:mRNA ratios in cells transfected with the corresponding dystrophin expression vectors. Male human isogenic induced-pluripotent stem cell (iPSC)-derived cardiac myocytes (iCMs) were generated that carry an E2035X premature stop codon in the dystrophin gene that prevented endogenous dystrophin expression. These cells were transfected with various miniaturized cassettes expressing miniaturized dystrophin proteins and the dystrophin protein:mRNA ratios were examined after the transfected cells had been cultured in vitro for 24 days. The protein levels were examined by a Meso Scale Discovery (MSD) ELISA assay, and the mRNA levels by qrtPCR.

Figure 1:
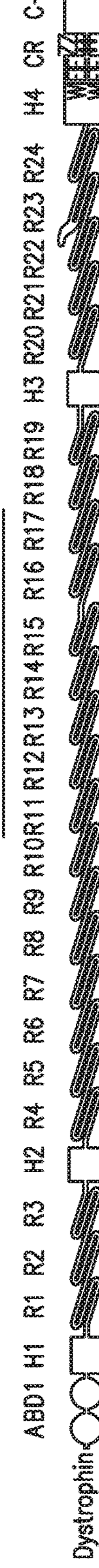
Figure 2:
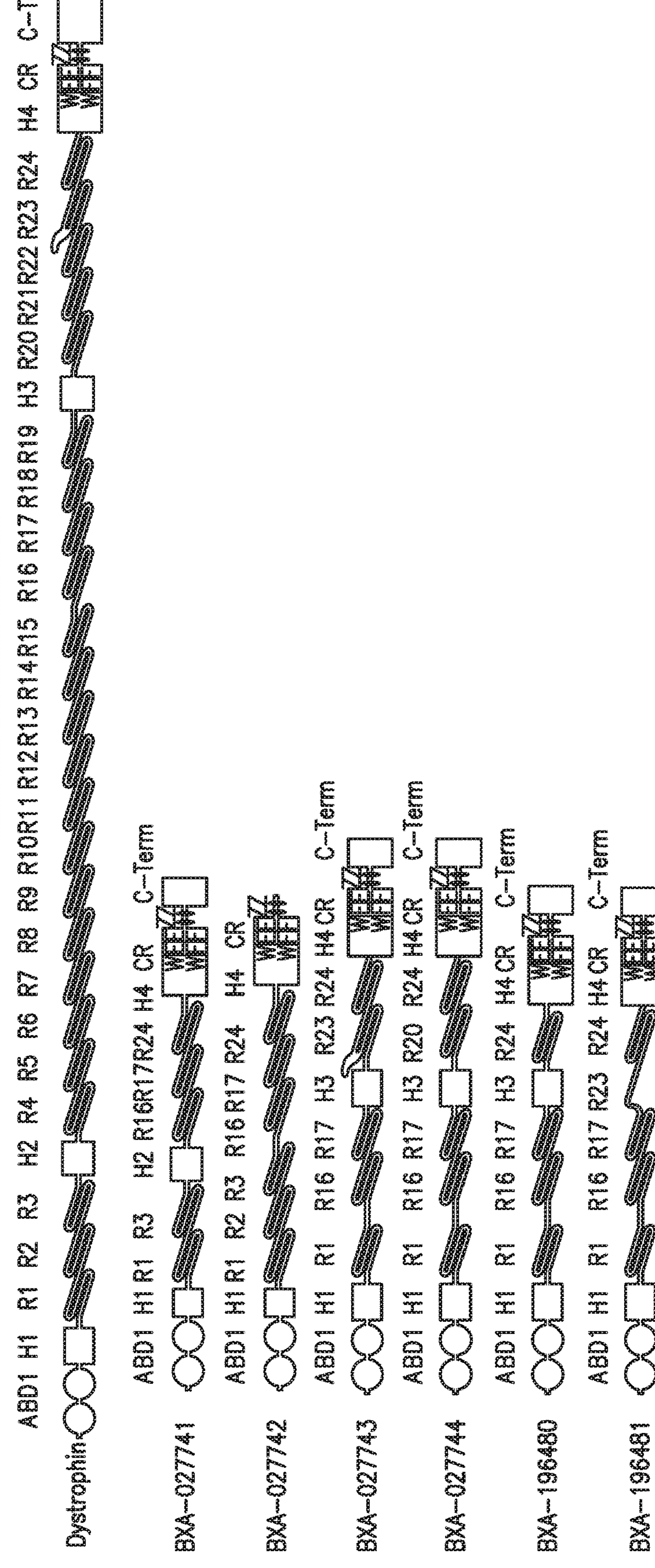
Figure 3:
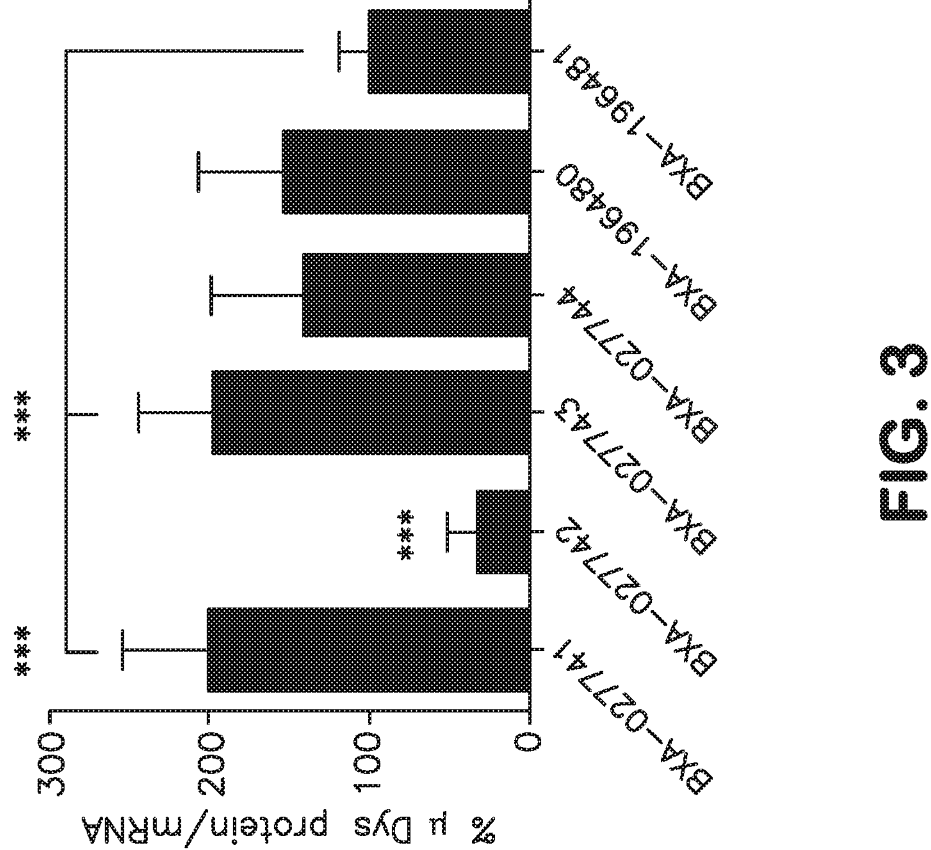

The miniaturized dystrophins tested and the test results are shown in FIG. 2 and FIG. 3, respectively. The data indicated that miniaturized dystrophin peptides BXA-027741 (SEQ ID NO:129) and BXA-027743 (SEQ ID NO:132) provide the best protein stability.

Figure 4:
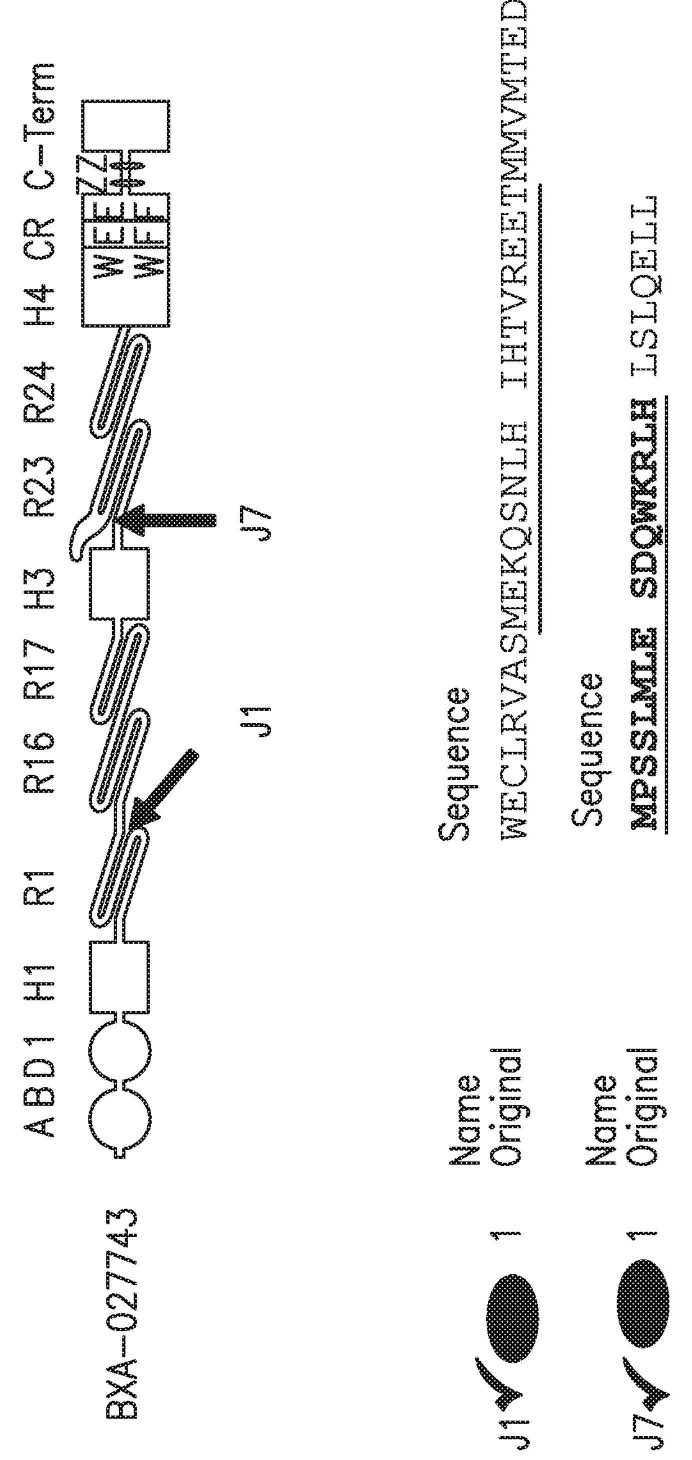
FIG. 4 shows a schematic diagram of the miniaturized dystrophin polypeptide of BXA-027743 (SEQ ID NO:132), as well as the amino acid sequence of its junctions J1 (SEQ ID NO: 167) and J7 (SEQ ID NO:168), which have relatively low immunogenicity, as indicated.

Subsequently, the immunogenicity of the novel junctions created within these two most stable designs were tested using an in silico immunogenicity prediction tool. The novel junctions of the BXA-027743 design (R1/linkerR16 (junction J1), R17/H3 and H3/R23 (junction J7)) (see FIG. 4 and not shown) were determined to have minimal immunogenic risk, based on the aforesaid in silico approach.

Figure 5:
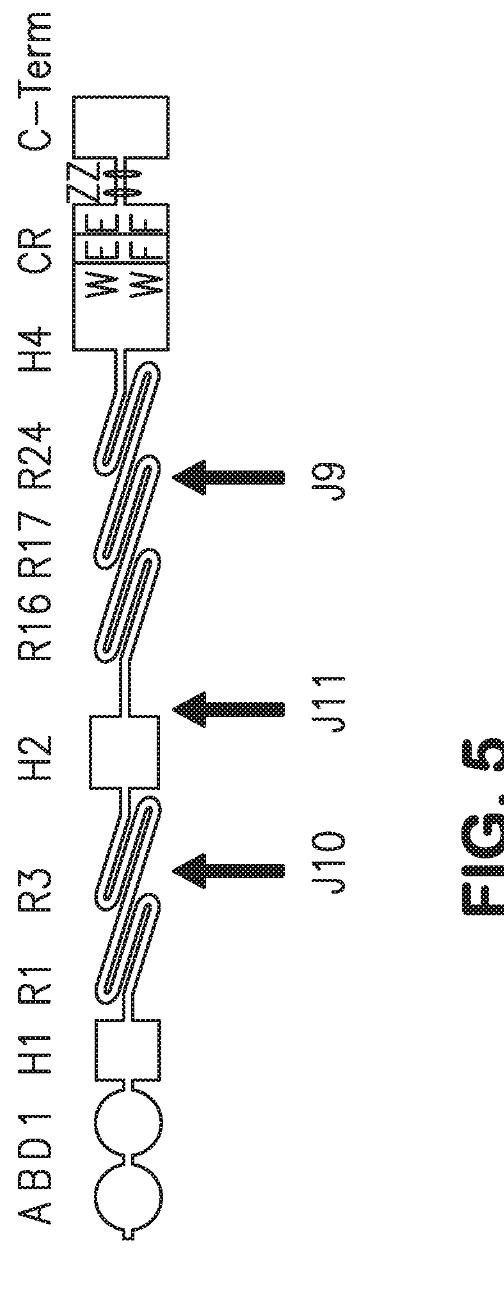
FIG. 5 shows a schematic diagram of the miniaturized dystrophin polypeptide of BXA-027741 (SEQ ID NO: 129) with arrows pointing to its junctions J10, J 11 and J9.

The novel junctions of the BXA-027741 design (R1/R3 (junction J10), H2/linkerR16 (junction J11) and R17/R24 (junction J9)) (see FIG. 5) were analyzed in a similar fashion. The junction J9 was determined to have minimal immunogenic risk, while junctions J10 and J11 could be improved.

The immunogenic potential of the aforesaid junctions of the BXA-027741 design, and junction variants thereof, were tested using an in vitro T cell proliferation assay as described below. Briefly, samples of peripheral blood mononuclear cells (PBMC) were isolated from healthy volunteer human subjects by Ficoll (GE Healthcare) gradient centrifugation and characterized, regarding human lymphocyte antigen (HLA) Class I and II expression, using a combination of polymerase chain reaction (PCR) amplification and hybridization with oligonucleotide probes (ProImmune, Sarasota, FL).

A panel of PBMC samples from 40 donors, having an HLA expression profile closely matching world population frequencies, was used for further analysis. PBMC samples were labeled with CF SE (Invitrogen, Carlsbad, CA) to monitor proliferation and plated in 96 well plates in six replicates at 200,000 cells per well in RPMI (Lonza, Basel, Switzerland) containing 10% human AB (Bioreclamation, Westbury, NY), non-essential amino acids and pen-strep (both Gibco/Fisher Scientific).

BXA-027741 junction peptides, variants thereof, and control peptides were each cultured with the panel of 40 PBMC samples at 1 μM for 7 days, after which the media was washed away and cells were labeled with an anti-CD4 and an anti CD8 APC monoclonal antibody (BD Biosciences, Franklin Lake, NJ). After removal of the unbound antibodies through washing, cells were fixed with 3.7% formalin (Sigma, St. Louis, MO) in PBS and analyzed by flow cytometry to determine the percentage of proliferating CD4+ cells or CD8+ cells. The percentage of samples (among the 40 donor samples) that showed a positive response after seven days in culture with the different BXA-027741 junction peptides and variants thereof—defined as a significant increase in the number of CD4+ or CD8+T proliferating cells compared to PBMC incubated in media without junction peptides or control peptides—is shown in FIG. 6A (CD4+) and FIG. 6B (CD8+). Control peptides used were: (1) Avastin Framework Peptide; (2) VL6-VL CDR3 Peptide; and (3) PADRE peptide-61309. It was found that version 3 of junction J10 (J10v3) was superior to junction J10, and other tested versions thereof, and that version 12 of junction J11 (J11v12) was overall superior with respect to immunogenic risk to junction J11.

The C-terminal domain of miniaturized dystrophin BXA-027741 was then deleted to generate miniaturized dystrophin BXA-196473 (SEQ ID NO:119) (FIG. 7) to better accommodate the limited packaging capacity of AAV. J10v3 was then used to replace J10, and J11v12 was used to replace J11, in miniaturized dystrophin BXA-196473, resulting in miniaturized dystrophin BXA-196477 (SEQ ID NO:118) (FIGS. 8A and 8B). To create J10v3 and J11v12, the amino acids RV were inserted between amino acids 446 and 447, and the amino acids SEAQ were inserted between amino acids 606 and 607, respectively, in BXA-196473 (SEQ ID NO:119) (FIGS. 8A and 8B).

BXA-196473 (SEQ ID NO:119) was additionally modified with the other junction versions tested as follows:

BXA-196474 (SEQ ID NO:120): Junction 9 Version 2 (J9v2) and Junction 11 Version 12 (J11v12)

BXA-196475 (SEQ ID NO:121): Junction 9 Version 5 (J9v5) and Junction 11 Version 12 (J11v12)

BXA-196476 (SEQ ID NO:122): Junction 9 Version 6 (J9v6) and Junction 11 Version 12 (J11v12)

BXA-196478 (SEQ ID NO:124): Junction 10 Version 6 (J10v6) and Junction 11 Version 12 (J11v12)

BXA-196479 (SEQ ID NO:125): Junction 11 Version 12 (J11v12)

J9v2 is a substitution of amino acids LER to KNI between the R17 domain and R24 domain, i.e., amino acids 843 to 845 in BXA-196473.

J9v5 is an insertion of K between the R17 domain and R24 domain, i.e., between amino acids 842 and 843 in BXA-196473.

J9v6 is an insertion of KNI between the R17 domain and R24 domain, i.e., between amino acids 842 and 843 in BXA-196473.

J10v3 is an insertion of RV between the R1 and R3 domain, i.e., between amino acids 446 and 447 in BXA-196473.

J10v6 is an insertion of RVLLQDI (SEQ ID NO: 169) between the R1 and R3 domain, i.e., between amino acids 446 and 447 in BXA-196473.

J11v12 is an insertion of SEAQ between the H2 domain and the linker before the R16 domain, i.e., between amino acids 606 and 607 in BXA-196473.

The resulting miniaturized dystrophins were then tested for stability as described before (FIG. 9). The results indicated that the BXA-196477 miniaturized dystrophin design (that contained J10V3 and J11V12) had not only the lowest immunogenic risk, but was also the most stable.

In addition, miniaturized dystrophin polypeptide design BXA-212371 was modified by deleting the last three C-terminal amino acids, and by inserting the amino acid junction variant sequence KNDL (J2V10; between spectrin repeat 17 (R17) domain and hinge 3 (H3) domain) after amino acid position 682 of BXA-212371 (resulting in miniaturized dystrophin BXA-213788, SEQ ID NO:152), which was found to have lower immunogenic risk.

6.2 In Vitro Physiology

DMD iCMs have lower Na+ channel amplitude, prolonged cFPD (Q-T interval), and greater beat rate variability, when compared to isogenic wild-type iCMs using multi-electrode arrays. DMD iCMs also have a higher Ca2+ transduction and lower impedance than wild-type iCMs, with each method confirming the beat rate variability in non-paced cells.

It is examined whether expression of miniaturized dystrophin BXA-196477 in DMD iCMs carrying the E2035X mutation can mitigate the DMD phenotype and improve the physiological traits of the cells. Multi-electrode arrays, impedance contraction assay, and Ca2+ transients are used to measure the effect of miniaturized dystrophin expression. We also deleted the C-terminal domain of BXA-027743 to generate BXA-212371 to better accommodate the limited packaging capacity of AAV. The functional capacity of BXA-212371 to mitigate the DMD phenotype and improve the physiological traits of the same cells is examined utilizing the same assays proposed for BXA196477.

The hiPSC CMs used in this study were DMD (E2035X) iCells purchased from Cellular Dynamics International, Madison, Wisconsin Human ventricular fibroblasts were purchased from Lonza, Walkersville, Maryland iCell hiPSC CMs have been reported to have electrophysiological properties close to primary adult cardiomyocytes and to respond similarly to a range of cardiac ion channel inhibitors as well as adrenergic and muscarinic receptor agonists and antagonists. Our own work showed that co-culturing hiPSC CMs with fibroblasts provided a more stable preparation for electrophysiologic studies on multi-electrode arrays (MEAs). hiPSC CMs are cultured with 7% $CO_2$ on 0.1% gelatin treated 6-well culture plates for 7 days, then trypsinized and diluted with human adult cardiac fibroblasts at about a 5:1 ratio. Suspensions of hiPSC CMs and fibroblasts were then co-cultured on laminin-coated 9-well multi-electrode array (MEA) plates (256-9wellMEA300/30iR-ITO-mq; Multichannel Systems). hiPSC CMs were infected with AAV9-mDys expression constructs (expressing miniaturized dystrophins BXA-196477 and BXA-213788, FIG. 15D) at MOI of $1\times10^6$ for 48 hrs, and the hiPSC CMs were then evaluated for effects on extracellular field potentials (FPs) 7 days and 9 days after infection. Both BXA-196477 and BXA-213788 significantly improved conduction velocity by ~80% compared to the DMD CMs (Two-way ANOVA *P<0.001 with Tukey post-test n=6)(FIG. 15E). A dystrophin ELISA confirmed dystrophin expression in the cells (FIG. 15**F).

MEA technology enables high content spatiotemporal analysis of excitable cells or tissues from an array of embedded substrate-integrated extracellular electrodes onto which cells can be cultured or tissues placed. Extracellular field potentials (FPs) are recorded by each electrode and correspond to cellular action potentials. Assessment of FP morphology, duration and conduction velocity provides a picture of ion channel activities of a treatment as well as effects on repolarization and conduction. After 7 days culture of hiPSC CMs on MEA plates, cells formed a spontaneously beating monolayer over recording electrodes imbedded in each well. Spontaneous FPs were recorded from 28 electrodes/well (30 um diameter, 300 um center to center spacing) at a sampling frequency of 10 kHz using an USB-MEA256-System and MC Rack acquisition software (Multi Channel Systems). Following a 20-minute equilibration period in a humidified environment at 37° C. with constant 5% $CO_2$ and 95% $O_2$ supply, each well was transfected with AAV9-mDys expression constructs in 300 μl maintenance medium. Effects of expression of miniaturized Dystrophins on inter-pulse intervals (IPIs) of FPs were monitored and recorded. Data were analyzed with custom software written in MatLab (Mathworks). Beat rate (beats/minute), a surrogate for heart rate, was calculated by using BR=60000/IPI, where the IPI is the averaged IPIs (msec) of 100 second recording at steady-state under each condition.

Electrophysiologic parameters to be measured are field potential duration, a surrogate for repolarization, and field potential conduction velocity. Field potential duration was corrected for beat rate changes (FPDc). All treatments had at least 3 replicates. Conduction velocity was quantified by measuring field potential activation times for each electrode imbedded in an MEA well during a synchronized single propagated beat. The digitized recordings of field potentials from each electrode were smoothed using a 21-point least squares smoothing polynomial (Savitsky & Golay, 1964) with a window of 2.1 ms. The activation time is the value for the peak in the negative derivative of each field potential waveform. The time between two of the earliest and latest activation times is the conduction time for field potential propagation across a monolayer of cardiomyocytes and the distance between these two electrodes is the conduction distance. The conduction time divided by the conduction distance of each propagation is the conduction velocity of each beat of the monolayer cardiomyocytes on an MEA well (FIG. 15).

The data show that both miniaturized Dystrophin design significantly improved conduction velocity (FIG. 15).

6.3 In Vivo Restoration of Skeletal Muscle Physiology

Dystrophin-deficient skeletal muscles produce less specific force (force per area) and are highly susceptible to contraction-induced injury. Restoration of dystrophin expression can mitigate these disorders. Dystrophic mdx mice are systemically treated with either 2e14vg/kg AAV9-05-12-BXA-196477 or AAV9-05-12-BXA-212371 at 2 weeks of age by retro-orbital injection. The limb muscle physiology are examined at 8 weeks of age. Briefly, the mouse knee is clamped and the foot is placed in a stirrup, and the stirrup is moved while the muscles are maximally contracted with a needle electrode. This assay measures the peak twitch and tetanic muscle force production and contraction-induced injury.

6.4 In Vivo Prevention of Dystrophic Pathology

The skeletal muscles in the mdx mouse model of DMD typically undergo necrosis and regeneration from ~3-4 weeks of age. The regenerated muscles are typically more variable in size and contain centrally located nuclei in frozen transverse sections. Also, fibrosis becomes more prevalent in regenerated muscles. The muscle fiber size, proportion of centrally located nuclei, and fibrosis in untreated mdx muscles and mdx muscles treated with either AAV9-05-12-BXA-196477 or AAV9-05-12-BXA-212371 is measured. The proportion of muscle fibers expressing the miniaturized dystrophins is also quantified. The diaphragm, gastrocnemius, tibialis anterior, and cardiac muscles is examined using the HALO and Columbus imaging computer programs.

6.5 In Vivo Study

Outline of Study $mdx^{4cv}$ mice were treated with 2e14vg/kg AAV9-BXA-196477 or AAV9-BXA-213788 at 2 weeks of age. Two-weeks after administration, n=3 mice were terminated to examine target engagement of miniaturized dystrophin (biodistribution and expression levels). At 2 months of age the right tibialis anterior muscle was examined for strength and resistance to contraction-induced injury (n=10) similar to previously described (Khairallah et. al., 2012). The mice were terminated at 3 months of age and examined for target engagement and prevention of dystrophy (FIG. 16).

Target Engagement

Immuno-fluorescence—Muscles were frozen in OCT in 2-methylbutaine in liquid $N_2$. 10 um frozen sections were immunostained with antibodies to dystrophin (Mandys106; DSHB; 1:200) and wheat-germ agglutinin conjugated to Alexa-647. Alexa-488 IgG2a antibody was used to label the dystrophin primary antibody. Sections were imaged using the Phoenix Opera High Content screening confocal microscope (Perkin-Elmer) and quantified using Columbus software. Briefly, the Alexa-647 images were inverted, M-mode was used to find the cells and calculate the morphology in a select population of cells in transverse sections <2000 $um^2$. Next, the intensity of the Alexa-488 was calculated and the population with intensity greater than $mdx^{4cv}$ control muscles was selected. Greater than 90% of the muscles were positive for miniaturized dystrophin in 4-weeks and 12-weeks mice (FIG. 17).

mRNA—For isolation of total RNA, tissue was homogenized using Qiagen Tissuelyzer and RNA was isolated using a Qiagen RNeasy 96 Universal tissue kit (Qiagen catalog number 74881). Tissue (~15) was placed in RNeasy kit collection microtubes containing 750 ul of Qiazol reagent and one 5 mm steel bead, homogenized using Tissuelyzer at 30 hz for 2 min and repeat this step until homogenized followed by a centrifugation at 6000×g for 1 min at 4° C. To each tube 150 ml of chloroform was added and samples vortexed vigorously for 15 sec. Following a 3 min incubation at room temperature, samples were spun at 6000×g for 15 min at 4° C. The aqueous phase was removed (~360 ul) and transferred to a new tube containing 1 volume of RNAse free 70% EtOH. All samples were transferred to a 96 well RNeasy 96 plate and plates were sealed with AirPore tape and centrifuge at 5600×g for 4 min at room temperature. 400 ul of RW1 buffer was added per well and plate resealed and spun for 4 min at 5600×g. During spin a DNaseI stock solution was prepared by adding 550 ul of RNAse free water per DNase vial. 670 ul of the DNase I stock solution was diluted into 7.3 mls RDD buffer, mixed and stored at 4° C. When centrifugation was completed the flow-through was discarded and 80 ul of DNase I mix was added directly to center of each well and the plate was incubated at room temperature for 15 min. Following incubation, 400 ul of RW1 was added to each well and the plate was sealed sand centrifuged for 4 min at 5600×g. Flow-through was discarded and 800 ul of RPE buffer was added per well the plate was re-sealed and spun for 4 min at 5600×g. This process was repeated and the plate was centrifuged for 10 min at 5600×g. Each sample was then eluted into a fresh tube by adding 60 ul of RNAse free water to center of each well and centrifuging for 4 min at 5600×g. To improve recovery the 60 uL was re-applied back onto plate and centrifuged for an additional 4 min at 5600×g. RNA yield was quantitated using nanodrop 8000.

RT-PCR—For cDNA synthesis and subsequent PCR, 1 µg of RNA was added to 1 well of a 96 well plate in 10 ul $H_2O$ (Plate-Axygen, PCR-96-C-S). To each well 10 ul of master mix (High Capacity cDNA Reverse Transcription Kit, Applied Biosystem) was added and plate was centrifuged at 1000 rpm. cDNA synthesis was carried out at 25° C. for 10 min, 37° C. for 120 min, 85° C. for 5 min followed by a hold at 4° C. For qPCR, each sample was run in duplicate with primer/probe sets (forward primer 5'-TGGAAGATTGCTACGAGCGC-3' (SEQ ID NO: 170); reverse primer 5'-CAGGTCGCTGAACAGGTTCT-3' (SEQ ID NO:171); probe-6FAM-GCAAGTTCGGCAAGCAGCACA-MGBNFG (SEQ ID NO:172)) in 384 well clear reaction plates (applied biosystem; catalog number 4483285). To each reaction 2 ul of cDNA and 8 ul of master mix (5 ul fast advanced master mix, 0.5 ul 20×FAM primer probe mix and 2.5 ul water) was added and plates were centrifuged for 1 min at 1000 rpm. Samples were incubated at 95° C. for 20 sec follow by 40 cycles at 95° C. for 1 sec and 60° C. for 20 sec using ViiA7 system and Quant Studio real-time PCR software for data analysis (Applied Biosystem).

Vector Genome/Genomic DNA isolation and qPCR—For genomic DNA isolation, tissue was homogenized using Qiagen Tissuelyzer and genomic DNA was isolated using a Qiagen DNeasy 96 blood and tissue kit (Qiagen catalog number 69581). Tissue (~10 mg) was placed in 96 well plate (costar assay block 1 ml, catalog number 3958) containing 200 ul of proteinase K-buffer ATL and one 5 mm steel bead, homogenized using Tissuelyzer 30 hz, 2 min, repeat until homogenized. Gnomic DNA isolation followed by manufactural instructions. For qPCR, each sample was run in duplicate with primer/probe sets (forward primer 5'-TGGAAGATTGCTACGAGCGC-3' (SEQ ID NO:170); reverse primer 5'-CAGGTCGCTGAACAGGTTCT-3' (SEQ ID NO:171); probe-6FAM-GCAAGTTCGGCAAGCAGCACA-MGBNFG (SEQ ID NO:172)) in 384 well clear reaction plates (applied biosystem; catalog number 4483285).

To each reaction 2 ul of genomic DNA (80 ng) and 8 uL of master mix (5 ul fast advanced master mix, 0.5 ul 20×FAM primer probe mix and 2.5 ul water) was added and plates were centrifuged for 1 min at 1000 rpm. Samples were incubated at 95° C. for 20 sec follow by 40 cycles at 95° C. for 1 sec and 60° C. for 20 sec using ViiA7 system and Quant Studio real-time PCR software for data analysis (Applied Biosystem).

MSD-ELISA—Protein expression was determined by Elisa assay. Multi-assay 384-well plates (Meso Scale Discovery, catalog number L21XB-4) were pre-coated with monoclonal antibody Manex 1011b at concentration of 2 ug/ml in bicarbonate buffer overnight. Plates were then blocked with blocking buffer (5% BSA in PBS) for 4 hrs with shaking at room temperature. Tissue (~20 mg) were homogenized in ripa buffer at concentration of 1 mg tissue/10 ul lysis buffer (Sigma, catalog number R0278) with protease inhibitor cocktail tablet (Roche, catalog number 04 693 159 001) using Qiagen Tissuelyzer at 30 hz for 5 min and repeat this step until homogenized. Tissue ripa lysate were diluted 1 to 3 in binding buffer (1% BSA, 0.05% tween 20, 20 mM Tris pH 7.5 in PBS). Tissue lysates and sulfo-conjugated Mandys 106 (0.2 ug/ml) were added to the pre-coated 384 well plates and incubate at 40° C. with shaking overnight. Plates were washed with PBS with 0.05% tween 20 and add 40 ul MSD read buffer T with surfactant (catalog number R92TC-1). Plates were then read on MSD Sector 6000 machine.

The data showed that sufficient virus was administered to achieve expression (mRNA and protein) in >90% striated muscle cells at 4-weeks of age (FIG. 18).

Creatine Kinase—Creatine kinase as an indicator of muscle damage was measured in serum using commercially available kits. The CK was measured at 4 weeks of age (2-weeks post delivery). Also, the CK was measured at 3 months of age, which was 1 month after the contraction-induced injury protocol (see below). **P<0.001 one-way ANOVA with Tukey post-test, n=10 compared to $mdx^{4cv}$. The data showed that in mice treated with BXA-196477 or BXA-213788, creatine kinase levels and thus muscle damage were significantly reduced (FIG. 19**).

Functional Studies

The tibialis anterior (TA) muscle contractile properties were tested by an in vivo (foot plate) apparatus as per manufacturers instructions (Aurora Scientific). Briefly, the peak tetanic contraction was achieved at 150 Hz in force frequency curve (force is measured in Torque as Newton Meters). The peak tetanic contraction was the same in wild-type, mdx4cv and mdx4cv mice treated with BXA-196477 or BXA-213788. However, the TA muscle mass is greater in mdx4cv **P<0.001 one-way ANOVA with Tukey post-test, n=10), such that normalization of peak tetanic force to TA mass was reduced in mdx4cv mice and at wild-type levels in the treated mice *P<0.001 compared to mdx4cv; one-way ANOVA with Tukey post-test, n=10) (FIG. 20).

The tibialis anterior (TA) muscle injury was measured by an in vivo (foot plate) apparatus as per manufacturers instructions (Aurora Scientific). During peak tetanic contraction at 150 Hz (maximum isometric torque), the foot plate was rotated from 90° to 135° degrees to strain the muscles. This contraction was repeated every minute for 20 contractions as previously described (Khairallah et. al., 2012). The maximum isometrique torque immediately prior to strain significantly reduced with each contraction in $mdx^{4cv}$ mice (P<0.0001 compared to wild-type; 2-way ANOVA; n=9-10). In contrast both BXA-196477 and BXA-213788 prevented the contraction-induced injury similar to wild-type levels (**P<0.0001 BXA-213788 and P<0.01 BXA-196477 compared to $mdx^{4cv}$ with Tukey post-test n=9-10). The data show that both miniaturized dystrophins designs protect the TA muscles from contraction-induced injury (FIG. 21).

In vitro an in vivo expression of miniaturized dystrophin constructs described in the Examples herein was under the control of a C5-12 promoter (see US 2004/0175727) wherein the first seven and last thirteen nucleotides were removed. The AAV used was AAV9, wherein the ITRs where AAV2.

6.6 Further Immunogenicity Studies

The immunogenicity of novel junctions (see Table 12: SEQ ID NOs: 156 to 166; SEQ ID NO:155 was original sequence) created between hinge 2 (H2) domain and R16 spectrin repeat 16 (R16) within miniaturized dystrophin polypeptide BXA-027741 were tested using an in silico immunogenicity prediction tool. The novel junction SEQ ID NO:157 (see FIG. 22) was determined to have minimal immunogenic risk, based on the aforesaid in silico approach. The tested junction sequences are numbered as follows: SEQ ID NO:155 (1), SEQ ID NO:156 (2), SEQ ID NO:157 (3), SEQ ID NO:158 (4), SEQ ID NO:159 (5), SEQ ID NO:160 (6), SEQ ID NO:161 (7), SEQ ID NO:162 (8), SEQ ID NO:163 (9), SEQ ID NO:164 (10), SEQ ID NO:165 (11), SEQ ID NO:166 (12) (see FIG. 22B).

The immunogenic potential of the aforesaid junctions of the BXA-027741 design, and junction variants thereof, were tested using an in vitro T cell proliferation assay as described above. The data indicate that junction J11v3 (SEQ ID NO:157, No. 3 in FIG. 22B) elicited significantly less CD8+(FIG. 23A) and CD4+T (FIG. 23B) cell proliferation compared to other tested junctions and is therefore superior (FIG. 23). Miniaturized dystrophin polypeptide BXA-196477 was modified to carry junction J11v3, the last three amino acids at the C-terminus were deleted, and the 3'UTR was shortened, resulting in miniaturized dystrophin polypeptide BXA-213780 (SEQ ID NO:153) and nucleotide sequence SEQ ID NO:154.

What is claimed is:

1. A nucleic acid molecule comprising a nucleotide sequence, which encodes a miniaturized dystrophin polypeptide comprising from N terminus to C terminus hinge 1 (H1) domain, spectrin repeat 1 (R1) domain, spectrin repeat 3 (R3) domain, hinge 2 (H2) domain, spectrin repeat 16 (R16) domain, spectrin repeat 17 (R17) domain, spectrin repeat 24 (R24) domain, and hinge 4 (H4) domain of dystrophin, wherein the miniaturized dystrophin polypeptide does not comprise spectrin repeat 2 (R2) of dystrophin, wherein the R1 domain and the R3 domain are fused by amino acids ARGVAL (RV) and wherein the H2 domain and the R16 domain are fused by the amino acid sequence set forth in SEQ ID NOs: 74 or 75, and wherein (i) the H1 domain and the R1 domain are fused directly, (ii) the R3 domain and the H2 domain are fused directly, (iii) the R16 and R17 domains are fused directly, (iv) the R17 and R24 domains are fused directly, and (v) the R24 and H4 domains are fused directly.

2. The nucleic acid molecule of claim 1, wherein the miniaturized dystrophin polypeptide further comprises an ABD1 domain and/or a CR domain.

3. The nucleic acid molecule of claim 2, wherein the miniaturized dystrophin polypeptide consists of, from N terminus to C terminus, the ABD1 domain, the H1 domain, the R1 domain, amino acids RV, the R3 domain, the H2 domain, the amino acid sequence as set forth in SEQ ID NOs: 74 or 75, the R16 domain, the R17 domain, the R24 domain, the H4 domain, and the CR domain of dystrophin.

4. The nucleic acid molecule of claim 3, wherein the miniaturized dystrophin polypeptide comprises an amino acid sequence at least 90%, at least 95%, at least 96%, at least 97%, at least 98%, at least 99%, or 100% identical to the amino acid sequence of SEQ ID NO: 118.

5. The nucleic acid molecule of claim 4, wherein the nucleotide sequence comprises a sequence at least 90%, at least 95%, at least 96%, at least 97%, at least 98%, at least 99%, or 100% identical to the nucleotide sequence of SEQ ID NO: 133.

6. The nucleic acid molecule of any one of claim 5, wherein the miniaturized dystrophin polypeptide comprises the amino acid sequence of SEQ ID NO: 118.

7. A vector comprising the nucleic acid molecule of claim 1.

8. The vector of claim 7, which is an adeno-associated virus (AAV) vector, wherein the AAV vector is selected from AAV1, AAV2, AAV3, AAV4, AAV5, AAV6, AAV7, AAV8, AAV9, AAV10, and AAV11.

9. The vector of claim 8, wherein the AAV vector is AAV9.

10. The vector of claim 8, wherein the AAV vector is AAV8.

11. A host cell comprising the vector of claim 7.

12. A pharmaceutical composition comprising the vector of claim 7 and a pharmaceutically acceptable excipient.

13. A polypeptide encoded by the nucleic acid molecule of claim 1.

14. A pharmaceutical composition comprising the polypeptide of claim 13 and a pharmaceutically acceptable excipient.

15. A host cell comprising the nucleic acid molecule of claim 1.

16. A pharmaceutical composition comprising the host cell of claim 15 and a pharmaceutically acceptable excipient.

17. A pharmaceutical composition comprising the nucleic acid molecule of claim 1 and a pharmaceutically acceptable excipient.

18. A recombinant adeno-associated virus (rAAV) vector particle comprising an AAV capsid and a nucleic acid molecule comprising a nucleotide sequence, which encodes a miniaturized dystrophin polypeptide comprising the amino acid sequence of SEQ ID NO: 118.

19. The rAAV vector particle of claim 18, comprising a nucleic acid molecule comprising the nucleotide sequence of SEQ ID NO: 133.

20. The rAAV vector particle of claim 19, wherein the nucleic acid molecule further comprises a first ITR and a second ITR both from AAV.

21. The rAAV vector particle of claim 20, wherein the first ITR and the second ITR are from the genome of AAV2.

22. The rAAV vector particle of claim 21, wherein the AAV capsid is from AAV9.

23. The rAAV vector particle of claim 21, wherein the AAV capsid is from AAV8.

24. The rAAV vector particle of claim 18, wherein the nucleic acid molecule further comprises a first inverted terminal repeat (ITR) and a second inverted terminal repeat (ITR) both from adeno-associated virus (AAV).

25. The rAAV vector particle of claim 24, wherein the first ITR and the second ITR are from the genome of AAV2.

26. The rAAV vector particle of claim 25, wherein the AAV capsid is from AAV9.

27. The rAAV vector particle of claim 25, wherein the AAV capsid is from AAV8.

* * * * *

SEQUENCE LISTING

```
<160> NUMBER OF SEQ ID NOS: 174

<210> SEQ ID NO 1
<211> LENGTH: 3685
<212> TYPE: PRT
<213> ORGANISM: Homo sapiens

<400> SEQUENCE: 1

Met Leu Trp Trp Glu Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
            20                  25                  30

Gly Lys Gln His Ile Glu Asn Leu Phe Ser Asp Leu Gln Asp Gly Arg
    35                  40                  45

Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Asn Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
    115                 120                 125

Ala Gly Leu Gln Gln Thr Asn Ser Glu Lys Ile Leu Leu Ser Trp Val
    130                 135                 140

Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His
                165                 170                 175

Arg Pro Asp Leu Phe Asp Trp Asn Ser Val Val Cys Gln Gln Ser Ala
            180                 185                 190

Thr Gln Arg Leu Glu His Ala Phe Asn Ile Ala Arg Tyr Gln Leu Gly
    195                 200                 205

Ile Glu Lys Leu Leu Asp Pro Glu Asp Val Asp Thr Thr Tyr Pro Asp
    210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu Met Leu Pro Arg
                245                 250                 255

Pro Pro Lys Val Thr Lys Glu Glu His Phe Gln Leu His His Gln Met
            260                 265                 270

His Tyr Ser Gln Gln Ile Thr Val Ser Leu Ala Gln Gly Tyr Glu Arg
    275                 280                 285

Thr Ser Ser Pro Lys Pro Arg Phe Lys Ser Tyr Ala Tyr Thr Gln Ala
    290                 295                 300

Ala Tyr Val Thr Thr Ser Asp Pro Thr Arg Ser Pro Phe Pro Ser Gln
```

```
305                 310                 315                 320

His Leu Glu Ala Pro Glu Asp Lys Ser Phe Gly Ser Ser Leu Met Glu
                325                 330                 335

Ser Glu Val Asn Leu Asp Arg Tyr Gln Thr Ala Leu Glu Glu Val Leu
            340                 345                 350

Ser Trp Leu Leu Ser Ala Glu Asp Thr Leu Gln Ala Gln Gly Glu Ile
        355                 360                 365

Ser Asn Asp Val Glu Val Val Lys Asp Gln Phe His Thr His Glu Gly
    370                 375                 380

Tyr Met Met Asp Leu Thr Ala His Gln Gly Arg Val Gly Asn Ile Leu
385                 390                 395                 400

Gln Leu Gly Ser Lys Leu Ile Gly Thr Gly Lys Leu Ser Glu Asp Glu
                405                 410                 415

Glu Thr Glu Val Gln Glu Gln Met Asn Leu Leu Asn Ser Arg Trp Glu
            420                 425                 430

Cys Leu Arg Val Ala Ser Met Glu Lys Gln Ser Asn Leu His Arg Val
        435                 440                 445

Leu Met Asp Leu Gln Asn Gln Lys Leu Lys Glu Leu Asn Asp Trp Leu
    450                 455                 460

Thr Lys Thr Glu Glu Arg Thr Arg Lys Met Glu Glu Glu Pro Leu Gly
465                 470                 475                 480

Pro Asp Leu Glu Asp Leu Lys Arg Gln Val Gln Gln His Lys Val Leu
                485                 490                 495

Gln Glu Asp Leu Glu Gln Glu Gln Val Arg Val Asn Ser Leu Thr His
            500                 505                 510

Met Val Val Val Val Asp Glu Ser Ser Gly Asp His Ala Thr Ala Ala
        515                 520                 525

Leu Glu Glu Gln Leu Lys Val Leu Gly Asp Arg Trp Ala Asn Ile Cys
    530                 535                 540

Arg Trp Thr Glu Asp Arg Trp Val Leu Leu Gln Asp Ile Leu Leu Lys
545                 550                 555                 560

Trp Gln Arg Leu Thr Glu Glu Gln Cys Leu Phe Ser Ala Trp Leu Ser
                565                 570                 575

Glu Lys Glu Asp Ala Val Asn Lys Ile His Thr Thr Gly Phe Lys Asp
            580                 585                 590

Gln Asn Glu Met Leu Ser Ser Leu Gln Lys Leu Ala Val Leu Lys Ala
        595                 600                 605

Asp Leu Glu Lys Lys Lys Gln Ser Met Gly Lys Leu Tyr Ser Leu Lys
    610                 615                 620

Gln Asp Leu Leu Ser Thr Leu Lys Asn Lys Ser Val Thr Gln Lys Thr
625                 630                 635                 640

Glu Ala Trp Leu Asp Asn Phe Ala Arg Cys Trp Asp Asn Leu Val Gln
                645                 650                 655

Lys Leu Glu Lys Ser Thr Ala Gln Ile Ser Gln Ala Val Thr Thr Thr
            660                 665                 670

Gln Pro Ser Leu Thr Gln Thr Thr Val Met Glu Thr Val Thr Thr Val
        675                 680                 685

Thr Thr Arg Glu Gln Ile Leu Val Lys His Ala Gln Glu Glu Leu Pro
    690                 695                 700

Pro Pro Pro Pro Gln Lys Lys Arg Gln Ile Thr Val Asp Ser Glu Ile
705                 710                 715                 720

Arg Lys Arg Leu Asp Val Asp Ile Thr Glu Leu His Ser Trp Ile Thr
                725                 730                 735
```

```
Arg Ser Glu Ala Val Leu Gln Ser Pro Glu Phe Ala Ile Phe Arg Lys
            740                 745                 750

Glu Gly Asn Phe Ser Asp Leu Lys Glu Lys Val Asn Ala Ile Glu Arg
        755                 760                 765

Glu Lys Ala Glu Lys Phe Arg Lys Leu Gln Asp Ala Ser Arg Ser Ala
    770                 775                 780

Gln Ala Leu Val Glu Gln Met Val Asn Glu Gly Val Asn Ala Asp Ser
785                 790                 795                 800

Ile Lys Gln Ala Ser Glu Gln Leu Asn Ser Arg Trp Ile Glu Phe Cys
                805                 810                 815

Gln Leu Leu Ser Glu Arg Leu Asn Trp Leu Glu Tyr Gln Asn Asn Ile
            820                 825                 830

Ile Ala Phe Tyr Asn Gln Leu Gln Gln Leu Glu Gln Met Thr Thr Thr
        835                 840                 845

Ala Glu Asn Trp Leu Lys Ile Gln Pro Thr Thr Pro Ser Glu Pro Thr
    850                 855                 860

Ala Ile Lys Ser Gln Leu Lys Ile Cys Lys Asp Glu Val Asn Arg Leu
865                 870                 875                 880

Ser Gly Leu Gln Pro Gln Ile Glu Arg Leu Lys Ile Gln Ser Ile Ala
                885                 890                 895

Leu Lys Glu Lys Gly Gln Gly Pro Met Phe Leu Asp Ala Asp Phe Val
            900                 905                 910

Ala Phe Thr Asn His Phe Lys Gln Val Phe Ser Asp Val Gln Ala Arg
        915                 920                 925

Glu Lys Glu Leu Gln Thr Ile Phe Asp Thr Leu Pro Pro Met Arg Tyr
    930                 935                 940

Gln Glu Thr Met Ser Ala Ile Arg Thr Trp Val Gln Gln Ser Glu Thr
945                 950                 955                 960

Lys Leu Ser Ile Pro Gln Leu Ser Val Thr Asp Tyr Glu Ile Met Glu
                965                 970                 975

Gln Arg Leu Gly Glu Leu Gln Ala Leu Gln Ser Ser Leu Gln Glu Gln
            980                 985                 990

Gln Ser Gly Leu Tyr Tyr Leu Ser  Thr Thr Val Lys Glu  Met Ser Lys
        995                 1000                1005

Lys Ala  Pro Ser Glu Ile Ser  Arg Lys Tyr Gln Ser  Glu Phe Glu
    1010                1015                1020

Glu Ile  Glu Gly Arg Trp Lys  Lys Leu Ser Ser Gln  Leu Val Glu
    1025                1030                1035

His Cys  Gln Lys Leu Glu Glu  Gln Met Asn Lys Leu  Arg Lys Ile
    1040                1045                1050

Gln Asn  His Ile Gln Thr Leu  Lys Lys Trp Met Ala  Glu Val Asp
    1055                1060                1065

Val Phe  Leu Lys Glu Glu Trp  Pro Ala Leu Gly Asp  Ser Glu Ile
    1070                1075                1080

Leu Lys  Lys Gln Leu Lys Gln  Cys Arg Leu Leu Val  Ser Asp Ile
    1085                1090                1095

Gln Thr  Ile Gln Pro Ser Leu  Asn Ser Val Asn Glu  Gly Gly Gln
    1100                1105                1110

Lys Ile  Lys Asn Glu Ala Glu  Pro Glu Phe Ala Ser  Arg Leu Glu
    1115                1120                1125

Thr Glu  Leu Lys Glu Leu Asn  Thr Gln Trp Asp His  Met Cys Gln
    1130                1135                1140
```

```
Gln Val  Tyr Ala Arg Lys Glu  Ala Leu Lys Gly Gly  Leu Glu Lys
    1145                 1150                 1155

Thr Val  Ser Leu Gln Lys Asp  Leu Ser Glu Met His  Glu Trp Met
    1160                 1165                 1170

Thr Gln  Ala Glu Glu Glu Tyr  Leu Glu Arg Asp Phe  Glu Tyr Lys
    1175                 1180                 1185

Thr Pro  Asp Glu Leu Gln Lys  Ala Val Glu Glu Met  Lys Arg Ala
    1190                 1195                 1200

Lys Glu  Glu Ala Gln Gln Lys  Glu Ala Lys Val Lys  Leu Leu Thr
    1205                 1210                 1215

Glu Ser  Val Asn Ser Val Ile  Ala Gln Ala Pro Pro  Val Ala Gln
    1220                 1225                 1230

Glu Ala  Leu Lys Lys Glu Leu  Glu Thr Leu Thr Thr  Asn Tyr Gln
    1235                 1240                 1245

Trp Leu  Cys Thr Arg Leu Asn  Gly Lys Cys Lys Thr  Leu Glu Glu
    1250                 1255                 1260

Val Trp  Ala Cys Trp His Glu  Leu Leu Ser Tyr Leu  Glu Lys Ala
    1265                 1270                 1275

Asn Lys  Trp Leu Asn Glu Val  Glu Phe Lys Leu Lys  Thr Thr Glu
    1280                 1285                 1290

Asn Ile  Pro Gly Gly Ala Glu  Glu Ile Ser Glu Val  Leu Asp Ser
    1295                 1300                 1305

Leu Glu  Asn Leu Met Arg His  Ser Glu Asp Asn Pro  Asn Gln Ile
    1310                 1315                 1320

Arg Ile  Leu Ala Gln Thr Leu  Thr Asp Gly Gly Val  Met Asp Glu
    1325                 1330                 1335

Leu Ile  Asn Glu Glu Leu Glu  Thr Phe Asn Ser Arg  Trp Arg Glu
    1340                 1345                 1350

Leu His  Glu Glu Ala Val Arg  Arg Gln Lys Leu Leu  Glu Gln Ser
    1355                 1360                 1365

Ile Gln  Ser Ala Gln Glu Thr  Glu Lys Ser Leu His  Leu Ile Gln
    1370                 1375                 1380

Glu Ser  Leu Thr Phe Ile Asp  Lys Gln Leu Ala Ala  Tyr Ile Ala
    1385                 1390                 1395

Asp Lys  Val Asp Ala Ala Gln  Met Pro Gln Glu Ala  Gln Lys Ile
    1400                 1405                 1410

Gln Ser  Asp Leu Thr Ser His  Glu Ile Ser Leu Glu  Glu Met Lys
    1415                 1420                 1425

Lys His  Asn Gln Gly Lys Glu  Ala Ala Gln Arg Val  Leu Ser Gln
    1430                 1435                 1440

Ile Asp  Val Ala Gln Lys Lys  Leu Gln Asp Val Ser  Met Lys Phe
    1445                 1450                 1455

Arg Leu  Phe Gln Lys Pro Ala  Asn Phe Glu Gln Arg  Leu Gln Glu
    1460                 1465                 1470

Ser Lys  Met Ile Leu Asp Glu  Val Lys Met His Leu  Pro Ala Leu
    1475                 1480                 1485

Glu Thr  Lys Ser Val Glu Gln  Glu Val Val Gln Ser  Gln Leu Asn
    1490                 1495                 1500

His Cys  Val Asn Leu Tyr Lys  Ser Leu Ser Glu Val  Lys Ser Glu
    1505                 1510                 1515

Val Glu  Met Val Ile Lys Thr  Gly Arg Gln Ile Val  Gln Lys Lys
    1520                 1525                 1530

Gln Thr  Glu Asn Pro Lys Glu  Leu Asp Glu Arg Val  Thr Ala Leu
```

```
    1535                1540                1545

Lys Leu His Tyr Asn Glu Leu Gly Ala Lys Val Thr Glu Arg Lys
    1550                1555                1560

Gln Gln Leu Glu Lys Cys Leu Lys Leu Ser Arg Lys Met Arg Lys
    1565                1570                1575

Glu Met Asn Val Leu Thr Glu Trp Leu Ala Ala Thr Asp Met Glu
    1580                1585                1590

Leu Thr Lys Arg Ser Ala Val Glu Gly Met Pro Ser Asn Leu Asp
    1595                1600                1605

Ser Glu Val Ala Trp Gly Lys Ala Thr Gln Lys Glu Ile Glu Lys
    1610                1615                1620

Gln Lys Val His Leu Lys Ser Ile Thr Glu Val Gly Glu Ala Leu
    1625                1630                1635

Lys Thr Val Leu Gly Lys Lys Glu Thr Leu Val Glu Asp Lys Leu
    1640                1645                1650

Ser Leu Leu Asn Ser Asn Trp Ile Ala Val Thr Ser Arg Ala Glu
    1655                1660                1665

Glu Trp Leu Asn Leu Leu Leu Glu Tyr Gln Lys His Met Glu Thr
    1670                1675                1680

Phe Asp Gln Asn Val Asp His Ile Thr Lys Trp Ile Ile Gln Ala
    1685                1690                1695

Asp Thr Leu Leu Asp Glu Ser Glu Lys Lys Lys Pro Gln Gln Lys
    1700                1705                1710

Glu Asp Val Leu Lys Arg Leu Lys Ala Glu Leu Asn Asp Ile Arg
    1715                1720                1725

Pro Lys Val Asp Ser Thr Arg Asp Gln Ala Ala Asn Leu Met Ala
    1730                1735                1740

Asn Arg Gly Asp His Cys Arg Lys Leu Val Glu Pro Gln Ile Ser
    1745                1750                1755

Glu Leu Asn His Arg Phe Ala Ala Ile Ser His Arg Ile Lys Thr
    1760                1765                1770

Gly Lys Ala Ser Ile Pro Leu Lys Glu Leu Glu Gln Phe Asn Ser
    1775                1780                1785

Asp Ile Gln Lys Leu Leu Glu Pro Leu Glu Ala Glu Ile Gln Gln
    1790                1795                1800

Gly Val Asn Leu Lys Glu Glu Asp Phe Asn Lys Asp Met Asn Glu
    1805                1810                1815

Asp Asn Glu Gly Thr Val Lys Glu Leu Leu Gln Arg Gly Asp Asn
    1820                1825                1830

Leu Gln Gln Arg Ile Thr Asp Glu Arg Lys Arg Glu Glu Ile Lys
    1835                1840                1845

Ile Lys Gln Gln Leu Leu Gln Thr Lys His Asn Ala Leu Lys Asp
    1850                1855                1860

Leu Arg Ser Gln Arg Arg Lys Lys Ala Leu Glu Ile Ser His Gln
    1865                1870                1875

Trp Tyr Gln Tyr Lys Arg Gln Ala Asp Asp Leu Leu Lys Cys Leu
    1880                1885                1890

Asp Asp Ile Glu Lys Lys Leu Ala Ser Leu Pro Glu Pro Arg Asp
    1895                1900                1905

Glu Arg Lys Ile Lys Glu Ile Asp Arg Glu Leu Gln Lys Lys Lys
    1910                1915                1920

Glu Glu Leu Asn Ala Val Arg Arg Gln Ala Glu Gly Leu Ser Glu
    1925                1930                1935
```

-continued

```
Asp Gly  Ala Ala Met Ala Val  Glu Pro Thr Gln Ile  Gln Leu Ser
    1940                 1945                 1950

Lys Arg  Trp Arg Glu Ile Glu  Ser Lys Phe Ala Gln  Phe Arg Arg
    1955                 1960                 1965

Leu Asn  Phe Ala Gln Ile His  Thr Val Arg Glu Glu  Thr Met Met
    1970                 1975                 1980

Val Met  Thr Glu Asp Met Pro  Leu Glu Ile Ser Tyr  Val Pro Ser
    1985                 1990                 1995

Thr Tyr  Leu Thr Glu Ile Thr  His Val Ser Gln Ala  Leu Leu Glu
    2000                 2005                 2010

Val Glu  Gln Leu Leu Asn Ala  Pro Asp Leu Cys Ala  Lys Asp Phe
    2015                 2020                 2025

Glu Asp  Leu Phe Lys Gln Glu  Glu Ser Leu Lys Asn  Ile Lys Asp
    2030                 2035                 2040

Ser Leu  Gln Gln Ser Ser Gly  Arg Ile Asp Ile Ile  His Ser Lys
    2045                 2050                 2055

Lys Thr  Ala Ala Leu Gln Ser  Ala Thr Pro Val Glu  Arg Val Lys
    2060                 2065                 2070

Leu Gln  Glu Ala Leu Ser Gln  Leu Asp Phe Gln Trp  Glu Lys Val
    2075                 2080                 2085

Asn Lys  Met Tyr Lys Asp Arg  Gln Gly Arg Phe Asp  Arg Ser Val
    2090                 2095                 2100

Glu Lys  Trp Arg Arg Phe His  Tyr Asp Ile Lys Ile  Phe Asn Gln
    2105                 2110                 2115

Trp Leu  Thr Glu Ala Glu Gln  Phe Leu Arg Lys Thr  Gln Ile Pro
    2120                 2125                 2130

Glu Asn  Trp Glu His Ala Lys  Tyr Lys Trp Tyr Leu  Lys Glu Leu
    2135                 2140                 2145

Gln Asp  Gly Ile Gly Gln Arg  Gln Thr Val Val Arg  Thr Leu Asn
    2150                 2155                 2160

Ala Thr  Gly Glu Glu Ile Ile  Gln Gln Ser Ser Lys  Thr Asp Ala
    2165                 2170                 2175

Ser Ile  Leu Gln Glu Lys Leu  Gly Ser Leu Asn Leu  Arg Trp Gln
    2180                 2185                 2190

Glu Val  Cys Lys Gln Leu Ser  Asp Arg Lys Lys Arg  Leu Glu Glu
    2195                 2200                 2205

Gln Lys  Asn Ile Leu Ser Glu  Phe Gln Arg Asp Leu  Asn Glu Phe
    2210                 2215                 2220

Val Leu  Trp Leu Glu Glu Ala  Asp Asn Ile Ala Ser  Ile Pro Leu
    2225                 2230                 2235

Glu Pro  Gly Lys Glu Gln Gln  Leu Lys Glu Lys Leu  Glu Gln Val
    2240                 2245                 2250

Lys Leu  Leu Val Glu Glu Leu  Pro Leu Arg Gln Gly  Ile Leu Lys
    2255                 2260                 2265

Gln Leu  Asn Glu Thr Gly Gly  Pro Val Leu Val Ser  Ala Pro Ile
    2270                 2275                 2280

Ser Pro  Glu Glu Gln Asp Lys  Leu Glu Asn Lys Leu  Lys Gln Thr
    2285                 2290                 2295

Asn Leu  Gln Trp Ile Lys Val  Ser Arg Ala Leu Pro  Glu Lys Gln
    2300                 2305                 2310

Gly Glu  Ile Glu Ala Gln Ile  Lys Asp Leu Gly Gln  Leu Glu Lys
    2315                 2320                 2325
```

```
Lys Leu  Glu Asp Leu Glu Glu  Gln Leu Asn His Leu  Leu Leu Trp
    2330                 2335                 2340

Leu Ser  Pro Ile Arg Asn Gln  Leu Glu Ile Tyr Asn  Gln Pro Asn
    2345                 2350                 2355

Gln Glu  Gly Pro Phe Asp Val  Gln Glu Thr Glu Ile  Ala Val Gln
    2360                 2365                 2370

Ala Lys  Gln Pro Asp Val Glu  Glu Ile Leu Ser Lys  Gly Gln His
    2375                 2380                 2385

Leu Tyr  Lys Glu Lys Pro Ala  Thr Gln Pro Val Lys  Arg Lys Leu
    2390                 2395                 2400

Glu Asp  Leu Ser Ser Glu Trp  Lys Ala Val Asn Arg  Leu Leu Gln
    2405                 2410                 2415

Glu Leu  Arg Ala Lys Gln Pro  Asp Leu Ala Pro Gly  Leu Thr Thr
    2420                 2425                 2430

Ile Gly  Ala Ser Pro Thr Gln  Thr Val Thr Leu Val  Thr Gln Pro
    2435                 2440                 2445

Val Val  Thr Lys Glu Thr Ala  Ile Ser Lys Leu Glu  Met Pro Ser
    2450                 2455                 2460

Ser Leu  Met Leu Glu Val Pro  Ala Leu Ala Asp Phe  Asn Arg Ala
    2465                 2470                 2475

Trp Thr  Glu Leu Thr Asp Trp  Leu Ser Leu Leu Asp  Gln Val Ile
    2480                 2485                 2490

Lys Ser  Gln Arg Val Met Val  Gly Asp Leu Glu Asp  Ile Asn Glu
    2495                 2500                 2505

Met Ile  Ile Lys Gln Lys Ala  Thr Met Gln Asp Leu  Glu Gln Arg
    2510                 2515                 2520

Arg Pro  Gln Leu Glu Glu Leu  Ile Thr Ala Ala Gln  Asn Leu Lys
    2525                 2530                 2535

Asn Lys  Thr Ser Asn Gln Glu  Ala Arg Thr Ile Ile  Thr Asp Arg
    2540                 2545                 2550

Ile Glu  Arg Ile Gln Asn Gln  Trp Asp Glu Val Gln  Glu His Leu
    2555                 2560                 2565

Gln Asn  Arg Arg Gln Gln Leu  Asn Glu Met Leu Lys  Asp Ser Thr
    2570                 2575                 2580

Gln Trp  Leu Glu Ala Lys Glu  Glu Ala Glu Gln Val  Leu Gly Gln
    2585                 2590                 2595

Ala Arg  Ala Lys Leu Glu Ser  Trp Lys Glu Gly Pro  Tyr Thr Val
    2600                 2605                 2610

Asp Ala  Ile Gln Lys Lys Ile  Thr Glu Thr Lys Gln  Leu Ala Lys
    2615                 2620                 2625

Asp Leu  Arg Gln Trp Gln Thr  Asn Val Asp Val Ala  Asn Asp Leu
    2630                 2635                 2640

Ala Leu  Lys Leu Leu Arg Asp  Tyr Ser Ala Asp Asp  Thr Arg Lys
    2645                 2650                 2655

Val His  Met Ile Thr Glu Asn  Ile Asn Ala Ser Trp  Arg Ser Ile
    2660                 2665                 2670

His Lys  Arg Val Ser Glu Arg  Glu Ala Ala Leu Glu  Glu Thr His
    2675                 2680                 2685

Arg Leu  Leu Gln Gln Phe Pro  Leu Asp Leu Glu Lys  Phe Leu Ala
    2690                 2695                 2700

Trp Leu  Thr Glu Ala Glu Thr  Thr Ala Asn Val Leu  Gln Asp Ala
    2705                 2710                 2715

Thr Arg  Lys Glu Arg Leu Leu  Glu Asp Ser Lys Gly  Val Lys Glu
```

```
    2720                2725                2730

Leu Met  Lys Gln Trp Gln Asp  Leu Gln Gly Glu Ile  Glu Ala His
    2735                2740                2745

Thr Asp  Val Tyr His Asn Leu  Asp Glu Asn Ser Gln  Lys Ile Leu
    2750                2755                2760

Arg Ser  Leu Glu Gly Ser Asp  Asp Ala Val Leu Leu  Gln Arg Arg
    2765                2770                2775

Leu Asp  Asn Met Asn Phe Lys  Trp Ser Glu Leu Arg  Lys Lys Ser
    2780                2785                2790

Leu Asn  Ile Arg Ser His Leu  Glu Ala Ser Ser Asp  Gln Trp Lys
    2795                2800                2805

Arg Leu  His Leu Ser Leu Gln  Glu Leu Leu Val Trp  Leu Gln Leu
    2810                2815                2820

Lys Asp  Asp Glu Leu Ser Arg  Gln Ala Pro Ile Gly  Gly Asp Phe
    2825                2830                2835

Pro Ala  Val Gln Lys Gln Asn  Asp Val His Arg Ala  Phe Lys Arg
    2840                2845                2850

Glu Leu  Lys Thr Lys Glu Pro  Val Ile Met Ser Thr  Leu Glu Thr
    2855                2860                2865

Val Arg  Ile Phe Leu Thr Glu  Gln Pro Leu Glu Gly  Leu Glu Lys
    2870                2875                2880

Leu Tyr  Gln Glu Pro Arg Glu  Leu Pro Pro Glu Glu  Arg Ala Gln
    2885                2890                2895

Asn Val  Thr Arg Leu Leu Arg  Lys Gln Ala Glu Glu  Val Asn Thr
    2900                2905                2910

Glu Trp  Glu Lys Leu Asn Leu  His Ser Ala Asp Trp  Gln Arg Lys
    2915                2920                2925

Ile Asp  Glu Thr Leu Glu Arg  Leu Gln Glu Leu Gln  Glu Ala Thr
    2930                2935                2940

Asp Glu  Leu Asp Leu Lys Leu  Arg Gln Ala Glu Val  Ile Lys Gly
    2945                2950                2955

Ser Trp  Gln Pro Val Gly Asp  Leu Leu Ile Asp Ser  Leu Gln Asp
    2960                2965                2970

His Leu  Glu Lys Val Lys Ala  Leu Arg Gly Glu Ile  Ala Pro Leu
    2975                2980                2985

Lys Glu  Asn Val Ser His Val  Asn Asp Leu Ala Arg  Gln Leu Thr
    2990                2995                3000

Thr Leu  Gly Ile Gln Leu Ser  Pro Tyr Asn Leu Ser  Thr Leu Glu
    3005                3010                3015

Asp Leu  Asn Thr Arg Trp Lys  Leu Leu Gln Val Ala  Val Glu Asp
    3020                3025                3030

Arg Val  Arg Gln Leu His Glu  Ala His Arg Asp Phe  Gly Pro Ala
    3035                3040                3045

Ser Gln  His Phe Leu Ser Thr  Ser Val Gln Gly Pro  Trp Glu Arg
    3050                3055                3060

Ala Ile  Ser Pro Asn Lys Val  Pro Tyr Tyr Ile Asn  His Glu Thr
    3065                3070                3075

Gln Thr  Thr Cys Trp Asp His  Pro Lys Met Thr Glu  Leu Tyr Gln
    3080                3085                3090

Ser Leu  Ala Asp Leu Asn Asn  Val Arg Phe Ser Ala  Tyr Arg Thr
    3095                3100                3105

Ala Met  Lys Leu Arg Arg Leu  Gln Lys Ala Leu Cys  Leu Asp Leu
    3110                3115                3120
```

```
Leu Ser  Leu Ser Ala Ala Cys  Asp Ala Leu Asp Gln  His Asn Leu
    3125                 3130                 3135

Lys Gln  Asn Asp Gln Pro Met  Asp Ile Leu Gln Ile  Ile Asn Cys
    3140                 3145                 3150

Leu Thr  Thr Ile Tyr Asp Arg  Leu Glu Gln Glu His  Asn Asn Leu
    3155                 3160                 3165

Val Asn  Val Pro Leu Cys Val  Asp Met Cys Leu Asn  Trp Leu Leu
    3170                 3175                 3180

Asn Val  Tyr Asp Thr Gly Arg  Thr Gly Arg Ile Arg  Val Leu Ser
    3185                 3190                 3195

Phe Lys  Thr Gly Ile Ile Ser  Leu Cys Lys Ala His  Leu Glu Asp
    3200                 3205                 3210

Lys Tyr  Arg Tyr Leu Phe Lys  Gln Val Ala Ser Ser  Thr Gly Phe
    3215                 3220                 3225

Cys Asp  Gln Arg Arg Leu Gly  Leu Leu Leu His Asp  Ser Ile Gln
    3230                 3235                 3240

Ile Pro  Arg Gln Leu Gly Glu  Val Ala Ser Phe Gly  Gly Ser Asn
    3245                 3250                 3255

Ile Glu  Pro Ser Val Arg Ser  Cys Phe Gln Phe Ala  Asn Asn Lys
    3260                 3265                 3270

Pro Glu  Ile Glu Ala Ala Leu  Phe Leu Asp Trp Met  Arg Leu Glu
    3275                 3280                 3285

Pro Gln  Ser Met Val Trp Leu  Pro Val Leu His Arg  Val Ala Ala
    3290                 3295                 3300

Ala Glu  Thr Ala Lys His Gln  Ala Lys Cys Asn Ile  Cys Lys Glu
    3305                 3310                 3315

Cys Pro  Ile Ile Gly Phe Arg  Tyr Arg Ser Leu Lys  His Phe Asn
    3320                 3325                 3330

Tyr Asp  Ile Cys Gln Ser Cys  Phe Phe Ser Gly Arg  Val Ala Lys
    3335                 3340                 3345

Gly His  Lys Met His Tyr Pro  Met Val Glu Tyr Cys  Thr Pro Thr
    3350                 3355                 3360

Thr Ser  Gly Glu Asp Val Arg  Asp Phe Ala Lys Val  Leu Lys Asn
    3365                 3370                 3375

Lys Phe  Arg Thr Lys Arg Tyr  Phe Ala Lys His Pro  Arg Met Gly
    3380                 3385                 3390

Tyr Leu  Pro Val Gln Thr Val  Leu Glu Gly Asp Asn  Met Glu Thr
    3395                 3400                 3405

Pro Val  Thr Leu Ile Asn Phe  Trp Pro Val Asp Ser  Ala Pro Ala
    3410                 3415                 3420

Ser Ser  Pro Gln Leu Ser His  Asp Asp Thr His Ser  Arg Ile Glu
    3425                 3430                 3435

His Tyr  Ala Ser Arg Leu Ala  Glu Met Glu Asn Ser  Asn Gly Ser
    3440                 3445                 3450

Tyr Leu  Asn Asp Ser Ile Ser  Pro Asn Glu Ser Ile  Asp Asp Glu
    3455                 3460                 3465

His Leu  Leu Ile Gln His Tyr  Cys Gln Ser Leu Asn  Gln Asp Ser
    3470                 3475                 3480

Pro Leu  Ser Gln Pro Arg Ser  Pro Ala Gln Ile Leu  Ile Ser Leu
    3485                 3490                 3495

Glu Ser  Glu Glu Arg Gly Glu  Leu Glu Arg Ile Leu  Ala Asp Leu
    3500                 3505                 3510
```

```
Glu Glu  Glu Asn Arg Asn Leu  Gln Ala Glu Tyr Asp  Arg Leu Lys
    3515                 3520                 3525

Gln Gln  His Glu His Lys Gly  Leu Ser Pro Leu Pro  Ser Pro Pro
    3530                 3535                 3540

Glu Met  Met Pro Thr Ser Pro  Gln Ser Pro Arg Asp  Ala Glu Leu
    3545                 3550                 3555

Ile Ala  Glu Ala Lys Leu Leu  Arg Gln His Lys Gly  Arg Leu Glu
    3560                 3565                 3570

Ala Arg  Met Gln Ile Leu Glu  Asp His Asn Lys Gln  Leu Glu Ser
    3575                 3580                 3585

Gln Leu  His Arg Leu Arg Gln  Leu Leu Glu Gln Pro  Gln Ala Glu
    3590                 3595                 3600

Ala Lys  Val Asn Gly Thr Thr  Val Ser Ser Pro Ser  Thr Ser Leu
    3605                 3610                 3615

Gln Arg  Ser Asp Ser Ser Gln  Pro Met Leu Leu Arg  Val Val Gly
    3620                 3625                 3630

Ser Gln  Thr Ser Asp Ser Met  Gly Glu Glu Asp Leu  Leu Ser Pro
    3635                 3640                 3645

Pro Gln  Asp Thr Ser Thr Gly  Leu Glu Glu Val Met  Glu Gln Leu
    3650                 3655                 3660

Asn Asn  Ser Phe Pro Ser Ser  Arg Gly Arg Asn Thr  Pro Gly Lys
    3665                 3670                 3675

Pro Met  Arg Glu Asp Thr Met
    3680                 3685


<210> SEQ ID NO 2
<211> LENGTH: 13957
<212> TYPE: DNA
<213> ORGANISM: Homo sapiens

<400> SEQUENCE: 2

gggattccct cactttcccc ctacaggact cagatctggg aggcaattac cttcggagaa      60

aaacgaatag gaaaaactga agtgttactt tttttaaagc tgctgaagtt tgttggtttc     120

tcattgtttt taagcctact ggagcaataa agtttgaaga acttttacca ggtttttttt     180

atcgctgcct tgatatacac ttttcaaaat gctttggtgg gaagaagtag aggactgtta     240

tgaaagagaa gatgttcaaa agaaaacatt cacaaaatgg gtaaatgcac aattttctaa     300

gtttgggaag cagcatattg agaacctctt cagtgaccta caggatggga ggcgcctcct     360

agacctcctc gaaggcctga cagggcaaaa actgccaaaa gaaaaaggat ccacaagagt     420

tcatgccctg aacaatgtca acaaggcact gcgggttttg cagaacaata atgttgattt     480

agtgaatatt ggaagtactg acatcgtaga tggaaatcat aaactgactc ttggtttgat     540

ttggaatata atcctccact ggcaggtcaa aaatgtaatg aaaaatatca tggctggatt     600

gcaacaaacc aacagtgaaa agattctcct gagctgggtc cgacaatcaa ctcgtaatta     660

tccacaggtt aatgtaatca acttcaccac cagctggtct gatggcctgg ctttgaatgc     720

tctcatccat agtcataggc cagacctatt tgactggaat agtgtggttt gccagcagtc     780

agccacacaa cgactggaac atgcattcaa catcgccaga tatcaattag gcatagagaa     840

actactcgat cctgaagatg ttgataccac ctatccagat aagaagtcca tcttaatgta     900

catcacatca ctcttccaag ttttgcctca acaagtgagc attgaagcca tccaggaagt     960

ggaaatgttg ccaaggccac ctaaagtgac taaagaagaa cattttcagt tacatcatca    1020

aatgcactat tctcaacaga tcacggtcag tctagcacag ggatatgaga gaacttcttc    1080
```

-continued

```
ccctaagcct cgattcaaga gctatgccta cacacaggct gcttatgtca ccacctctga   1140
ccctacacgg agcccatttc cttcacagca tttggaagct cctgaagaca agtcatttgg   1200
cagttcattg atggagagtg aagtaaacct ggaccgttat caaacagctt tagaagaagt   1260
attatcgtgg cttctttctg ctgaggacac attgcaagca caaggagaga tttctaatga   1320
tgtggaagtg gtgaaagacc agtttcatac tcatgagggg tacatgatgg atttgacagc   1380
ccatcagggc cgggttggta atattctaca attgggaagt aagctgattg gaacaggaaa   1440
attatcagaa gatgaagaaa ctgaagtaca agagcagatg aatctcctaa attcaagatg   1500
ggaatgcctc agggtagcta gcatggaaaa acaaagcaat ttacatagag ttttaatgga   1560
tctccagaat cagaaactga aagagttgaa tgactggcta acaaaaacag aagaaagaac   1620
aaggaaaatg gaggaagagc ctcttggacc tgatcttgaa gacctaaaac gccaagtaca   1680
acaacataag gtgcttcaag aagatctaga acaagaacaa gtcagggtca attctctcac   1740
tcacatggtg gtggtagttg atgaatctag tggagatcac gcaactgctg ctttggaaga   1800
acaacttaag gtattgggag atcgatgggc aaacatctgt agatggacag aagaccgctg   1860
ggttctttta caagacatcc ttctcaaatg gcaacgtctt actgaagaac agtgcctttt   1920
tagtgcatgg ctttcagaaa aagaagatgc agtgaacaag attcacacaa ctggctttaa   1980
agatcaaaat gaaatgttat caagtcttca aaaactggcc gttttaaaag cggatctaga   2040
aaagaaaaag caatccatgg gcaaactgta ttcactcaaa caagatcttc tttcaacact   2100
gaagaataag tcagtgaccc agaagacgga agcatggctg gataactttg cccggtgttg   2160
ggataattta gtccaaaaac ttgaaaagag tacagcacag atttcacagg ctgtcaccac   2220
cactcagcca tcactaacac agacaactgt aatggaaaca gtaactacgg tgaccacaag   2280
ggaacagatc ctggtaaagc atgctcaaga ggaacttcca ccaccacctc cccaaaagaa   2340
gaggcagatt actgtggatt ctgaaattag gaaaaggttg gatgttgata taactgaact   2400
tcacagctgg attactcgct cagaagctgt gttgcagagt cctgaatttg caatctttcg   2460
gaaggaaggc aacttctcag acttaaaaga aaaagtcaat gccatagagc gagaaaaagc   2520
tgagaagttc agaaaactgc aagatgccag cagatcagct caggccctgg tggaacagat   2580
ggtgaatgag ggtgttaatg cagatagcat caaacaagcc tcagaacaac tgaacagccg   2640
gtggatcgaa ttctgccagt tgctaagtga gagacttaac tggctggagt atcagaacaa   2700
catcatcgct ttctataatc agctacaaca attggagcag atgacaacta ctgctgaaaa   2760
ctggttgaaa atccaaccca ccaccccatc agagccaaca gcaattaaaa gtcagttaaa   2820
aatttgtaag gatgaagtca accggctatc aggtcttcaa cctcaaattg aacgattaaa   2880
aattcaaagc atagccctga aagagaaagg acaaggaccc atgttcctgg atgcagactt   2940
tgtggccttt acaaatcatt ttaagcaagt cttttctgat gtgcaggcca gagagaaaga   3000
gctacagaca atttttgaca ctttgccacc aatgcgctat caggagacca tgagtgccat   3060
caggacatgg gtccagcagt cagaaaccaa actctccata cctcaactta gtgtcaccga   3120
ctatgaaatc atggagcaga gactcgggga attgcaggct ttacaaagtt ctctgcaaga   3180
gcaacaaagt ggcctatact atctcagcac cactgtgaaa gagatgtcga agaaagcgcc   3240
ctctgaaatt agccggaaat atcaatcaga atttgaagaa attgagggac gctggaagaa   3300
gctctcctcc cagctggttg agcattgtca aaagctagag gagcaaatga ataaactccg   3360
aaaaattcag aatcacatac aaaccctgaa gaaatggatg gctgaagttg atgtttttct   3420
```

```
gaaggaggaa tggcctgccc ttggggattc agaaattcta aaaaagcagc tgaaacagtg   3480
cagactttta gtcagtgata ttcagacaat tcagcccagt ctaaacagtg tcaatgaagg   3540
tgggcagaag ataaagaatg aagcagagcc agagtttgct tcgagacttg agacagaact   3600
caaagaactt aacactcagt gggatcacat gtgccaacag gtctatgcca gaaaggaggc   3660
cttgaaggga ggtttggaga aaactgtaag cctccagaaa gatctatcag agatgcacga   3720
atggatgaca caagctgaag aagagtatct tgagagagat tttgaatata aaactccaga   3780
tgaattacag aaagcagttg aagagatgaa gagagctaaa gaagaggccc aacaaaaaga   3840
agcgaaagtg aaactcctta ctgagtctgt aaatagtgtc atagctcaag ctccacctgt   3900
agcacaagag gccttaaaaa aggaacttga aactctaacc accaactacc agtggctctg   3960
cactaggctg aatgggaaat gcaagacttt ggaagaagtt tgggcatgtt ggcatgagtt   4020
attgtcatac ttggagaaag caaacaagtg gctaaatgaa gtagaattta aacttaaaac   4080
cactgaaaac attcctggcg gagctgagga aatctctgag gtgctagatt cacttgaaaa   4140
tttgatgcga cattcagagg ataacccaaa tcagattcgc atattggcac agaccctaac   4200
agatggcgga gtcatggatg agctaatcaa tgaggaactt gagacattta attctcgttg   4260
gagggaacta catgaagagg ctgtaaggag gcaaaagttg cttgaacaga gcatccagtc   4320
tgcccaggag actgaaaaat ccttacactt aatccaggag tccctcacat tcattgacaa   4380
gcagttggca gcttatattg cagacaaggt ggacgcagct caaatgcctc aggaagccca   4440
gaaaatccaa tctgatttga caagtcatga gatcagttta gaagaaatga agaaacataa   4500
tcaggggaag gaggctgccc aaagagtcct gtctcagatt gatgttgcac agaaaaaatt   4560
acaagatgtc tccatgaagt ttcgattatt ccagaaacca gccaattttg agctgcgtct   4620
acaagaaagt aagatgattt tagatgaagt gaagatgcac ttgcctgcat tggaaacaaa   4680
gagtgtggaa caggaagtag tacagtcaca gctaaatcat tgtgtgaact tgtataaaag   4740
tctgagtgaa gtgaagtctg aagtggaaat ggtgataaag actggacgtc agattgtaca   4800
gaaaaagcag acggaaaatc ccaaagaact tgatgaaaga gtaacagctt tgaaattgca   4860
ttataatgag ctgggagcaa aggtaacaga aagaaagcaa cagttggaga aatgcttgaa   4920
attgtcccgt aagatgcgaa aggaaatgaa tgtcttgaca gaatggctgg cagctacaga   4980
tatggaattg acaaagagat cagcagttga aggaatgcct agtaatttgg attctgaagt   5040
tgcctgggga aaggctactc aaaaagagat tgagaaacag aaggtgcacc tgaagagtat   5100
cacagaggta ggagaggcct tgaaaacagt tttgggcaag aaggagacgt tggtggaaga   5160
taaactcagt cttctgaata gtaactggat agctgtcacc tcccgagcag aagagtggtt   5220
aaatcttttg ttggaatacc agaaacacat ggaaactttt gaccagaatg tggaccacat   5280
cacaaagtgg atcattcagg ctgacacact tttggatgaa tcagagaaaa agaaacccca   5340
gcaaaaagaa gacgtgctta agcgtttaaa ggcagaactg aatgacatac gcccaaaggt   5400
ggactctaca cgtgaccaag cagcaaactt gatggcaaac cgcggtgacc actgcaggaa   5460
attagtagag ccccaaatct cagagctcaa ccatcgattt gcagccattt cacacagaat   5520
taagactgga aaggcctcca ttcctttgaa ggaattggag cagtttaact cagatataca   5580
aaaattgctt gaaccactgg aggctgaaat tcagcagggg gtgaatctga aagaggaaga   5640
cttcaataaa gatatgaatg aagacaatga gggtactgta aaagaattgt tgcaaagagg   5700
agacaactta caacaaagaa tcacagatga gagaaagaga gaggaaataa agataaaaca   5760
gcagctgtta cagacaaaac ataatgctct caaggatttg aggtctcaaa gaagaaaaaa   5820
```

```
ggctctagaa atttctcatc agtggtatca gtacaagagg caggctgatg atctcctgaa   5880
atgcttggat gacattgaaa aaaaattagc cagcctacct gagcccagag atgaaaggaa   5940
aataaaggaa attgatcggg aattgcagaa gaagaaagag gagctgaatg cagtgcgtag   6000
gcaagctgag ggcttgtctg aggatggggc cgcaatggca gtggagccaa ctcagatcca   6060
gctcagcaag cgctggcggg aaattgagag caaatttgct cagtttcgaa gactcaactt   6120
tgcacaaatt cacactgtcc gtgaagaaac gatgatggtg atgactgaag acatgccttt   6180
ggaaatttct tatgtgcctt ctacttattt gactgaaatc actcatgtct cacaagccct   6240
attagaagtg gaacaacttc tcaatgctcc tgacctctgt gctaaggact ttgaagatct   6300
ctttaagcaa gaggagtctc tgaagaatat aaaagatagt ctacaacaaa gctcaggtcg   6360
gattgacatt attcatagca agaagacagc agcattgcaa agtgcaacgc ctgtggaaag   6420
ggtgaagcta caggaagctc tctcccagct tgatttccaa tgggaaaaag ttaacaaaat   6480
gtacaaggac cgacaagggc gatttgacag atctgttgag aaatggcggc gttttcatta   6540
tgatataaag atatttaatc agtggctaac agaagctgaa cagtttctca gaaagacaca   6600
aattcctgag aattgggaac atgctaaata caaatggtat cttaaggaac tccaggatgg   6660
cattgggcag cggcaaactg ttgtcagaac attgaatgca actggggaag aaataattca   6720
gcaatcctca aaaacagatg ccagtattct acaggaaaaa ttgggaagcc tgaatctgcg   6780
gtggcaggag gtctgcaaac agctgtcaga cagaaaaaag aggctagaag aacaaaagaa   6840
tatcttgtca gaatttcaaa gagatttaaa tgaatttgtt ttatggttgg aggaagcaga   6900
taacattgct agtatcccac ttgaacctgg aaaagagcag caactaaaag aaaagcttga   6960
gcaagtcaag ttactggtgg aagagttgcc cctgcgccag ggaattctca aacaattaaa   7020
tgaaactgga ggacccgtgc ttgtaagtgc tcccataagc ccagaagagc aagataaact   7080
tgaaaataag ctcaagcaga caaatctcca gtggataaag gtttccagag ctttacctga   7140
gaaacaagga gaaattgaag ctcaaataaa agaccttggg cagcttgaaa aaaagcttga   7200
agaccttgaa gagcagttaa atcatctgct gctgtggtta tctcctatta ggaatcagtt   7260
ggaaatttat aaccaaccaa accaagaagg accatttgac gttcaggaaa ctgaaatagc   7320
agttcaagct aaacaaccgg atgtggaaga gattttgtct aaagggcagc atttgtacaa   7380
ggaaaaacca gccactcagc cagtgaagag gaagttagaa gatctgagct ctgagtggaa   7440
ggcggtaaac cgtttacttc aagagctgag ggcaaagcag cctgacctag ctcctggact   7500
gaccactatt ggagcctctc ctactcagac tgttactctg gtgacacaac ctgtggttac   7560
taaggaaact gccatctcca aactagaaat gccatcttcc ttgatgttgg aggtacctgc   7620
tctggcagat ttcaaccggg cttggacaga acttaccgac tggctttctc tgcttgatca   7680
agttataaaa tcacagaggg tgatggtggg tgaccttgag gatatcaacg agatgatcat   7740
caagcagaag gcaacaatgc aggatttgga acagaggcgt ccccagttgg aagaactcat   7800
taccgctgcc caaaatttga aaaacaagac cagcaatcaa gaggctagaa caatcattac   7860
ggatcgaatt gaaagaattc agaatcagtg ggatgaagta caagaacacc ttcagaaccg   7920
gaggcaacag ttgaatgaaa tgttaaagga ttcaacacaa tggctggaag ctaaggaaga   7980
agctgagcag gtcttaggac aggccagagc caagcttgag tcatggaagg agggtcccta   8040
tacagtagat gcaatccaaa agaaaatcac agaaaccaag cagttggcca aagacctccg   8100
ccagtggcag acaaatgtag atgtggcaaa tgacttggcc ctgaaacttc tccgggatta   8160
```

```
ttctgcagat gataccagaa aagtccacat gataacagag aatatcaatg cctcttggag   8220
aagcattcat aaaagggtga gtgagcgaga ggctgctttg gaagaaactc atagattact   8280
gcaacagttc cccctggacc tggaaaagtt tcttgcctgg cttacagaag ctgaaacaac   8340
tgccaatgtc ctacaggatg ctacccgtaa ggaaaggctc ctagaagact ccaagggagt   8400
aaaagagctg atgaaacaat ggcaagacct ccaaggtgaa attgaagctc acacagatgt   8460
ttatcacaac ctggatgaaa acagccaaaa aatcctgaga tccctggaag gttccgatga   8520
tgcagtcctg ttacaaagac gtttggataa catgaacttc aagtggagtg aacttcggaa   8580
aaagtctctc aacattaggt cccatttgga agccagttct gaccagtgga agcgtctgca   8640
cctttctctg caggaacttc tggtgtggct acagctgaaa gatgatgaat taagccggca   8700
ggcacctatt ggaggcgact ttccagcagt tcagaagcag aacgatgtac atagggcctt   8760
caagagggaa ttgaaaacta aagaacctgt aatcatgagt actcttgaga ctgtacgaat   8820
atttctgaca gagcagcctt tggaaggact agagaaactc taccaggagc ccagagagct   8880
gcctcctgag gagagagccc agaatgtcac tcggcttcta cgaaagcagg ctgaggaggt   8940
caatactgag tgggaaaaat tgaacctgca ctccgctgac tggcagagaa aaatagatga   9000
gacccttgaa agactccagg aacttcaaga ggccacggat gagctggacc tcaagctgcg   9060
ccaagctgag gtgatcaagg gatcctggca gcccgtgggc gatctcctca ttgactctct   9120
ccaagatcac ctcgagaaag tcaaggcact tcgaggagaa attgcgcctc tgaaagagaa   9180
cgtgagccac gtcaatgacc ttgctcgcca gcttaccact ttgggcattc agctctcacc   9240
gtataacctc agcactctgg aagacctgaa caccagatgg aagcttctgc aggtggccgt   9300
cgaggaccga gtcaggcagc tgcatgaagc ccacagggac tttggtccag catctcagca   9360
ctttctttcc acgtctgtcc agggtccctg ggagagagcc atctcgccaa acaaagtgcc   9420
ctactatatc aaccacgaga ctcaaacaac ttgctgggac catcccaaaa tgacagagct   9480
ctaccagtct ttagctgacc tgaataatgt cagattctca gcttatagga ctgccatgaa   9540
actccgaaga ctgcagaagg ccctttgctt ggatctcttg agcctgtcag ctgcatgtga   9600
tgccttggac cagcacaacc tcaagcaaaa tgaccagccc atggatatcc tgcagattat   9660
taattgtttg accactattt atgaccgcct ggagcaagag cacaacaatt tggtcaacgt   9720
ccctctctgc gtggatatgt gtctgaactg gctgctgaat gtttatgata cgggacgaac   9780
agggaggatc cgtgtcctgt cttttaaaac tggcatcatt tccctgtgta aagcacattt   9840
ggaagacaag tacagatacc ttttcaagca agtggcaagt tcaacaggat tttgtgacca   9900
gcgcaggctg ggcctccttc tgcatgattc tatccaaatt ccaagacagt tgggtgaagt   9960
tgcatccttt gggggcagta acattgagcc aagtgtccgg agctgcttcc aatttgctaa  10020
taataagcca gagatcgaag cggccctctt cctagactgg atgagactgg aaccccagtc  10080
catggtgtgg ctgcccgtcc tgcacagagt ggctgctgca gaaactgcca agcatcaggc  10140
caaatgtaac atctgcaaag agtgtccaat cattggattc aggtacagga gtctaaagca  10200
ctttaattat gacatctgcc aaagctgctt tttttctggt cgagttgcaa aaggccataa  10260
aatgcactat cccatggtgg aatattgcac tccgactaca tcaggagaag atgttcgaga  10320
ctttgccaag gtactaaaaa acaaatttcg aaccaaaagg tattttgcga agcatccccg  10380
aatgggctac ctgccagtgc agactgtctt agagggggac aacatggaaa ctcccgttac  10440
tctgatcaac ttctggccag tagattctgc gcctgcctcg tcccctcagc tttcacacga  10500
tgatactcat tcacgcattg aacattatgc tagcaggcta gcagaaatgg aaaacagcaa  10560
```

```
tggatcttat ctaaatgata gcatctctcc taatgagagc atagatgatg aacatttgtt  10620
aatccagcat tactgccaaa gtttgaacca ggactccccc ctgagccagc ctcgtagtcc  10680
tgcccagatc ttgatttcct tagagagtga ggaaagaggg gagctagaga gaatcctagc  10740
agatcttgag gaagaaaaca ggaatctgca agcagaatat gaccgtctaa agcagcagca  10800
cgaacataaa ggcctgtccc cactgccgtc ccctcctgaa atgatgccca cctctcccca  10860
gagtccccgg gatgctgagc tcattgctga ggccaagcta ctgcgtcaac acaaaggccg  10920
cctggaagcc aggatgcaaa tcctggaaga ccacaataaa cagctggagt cacagttaca  10980
caggctaagg cagctgctgg agcaacccca ggcagaggcc aaagtgaatg gcacaacggt  11040
gtcctctcct tctacctctc tacagaggtc cgacagcagt cagcctatgc tgctccgagt  11100
ggttggcagt caaacttcgg actccatggg tgaggaagat cttctcagtc ctccccagga  11160
cacaagcaca gggttagagg aggtgatgga gcaactcaac aactccttcc ctagttcaag  11220
aggaagaaat accccctggaa agccaatgag agaggacaca atgtaggaag tcttttccac  11280
atggcagatg atttgggcag agcgatggag tccttagtat cagtcatgac agatgaagaa  11340
ggagcagaat aaatgtttta caactcctga ttcccgcatg gtttttataa tattcataca  11400
acaaagagga ttagacagta agagtttaca agaaataaat ctatattttt gtgaagggta  11460
gtggtattat actgtagatt tcagtagttt ctaagtctgt tattgttttg ttaacaatgg  11520
caggttttac acgtctatgc aattgtacaa aaaagttata agaaaactac atgtaaaatc  11580
ttgatagcta aataacttgc catttcttta tatggaacgc attttgggtt gtttaaaaat  11640
ttataacagt tataaagaaa gattgtaaac taaagtgtgc tttataaaaa aaagttgttt  11700
ataaaaaccc ctaaaaacaa aacaaacaca cacacacaca catacacaca cacacacaaa  11760
actttgaggc agcgcattgt tttgcatcct tttggcgtga tatccatatg aaattcatgg  11820
ctttttcttt ttttgcatat taaagataag acttcctcta ccaccacacc aaatgactac  11880
tacacactgc tcatttgaga actgtcagct gagtggggca ggcttgagtt ttcatttcat  11940
atatctatat gtctataagt atataaatac tatagttata tagataaaga gatacgaatt  12000
tctatagact gactttttcc attttttaaa tgttcatgtc acatcctaat agaaagaaat  12060
tacttctagt cagtcatcca ggcttacctg cttggtctag aatggatttt tcccggagcc  12120
ggaagccagg aggaaactac accacactaa aacattgtct acagctccag atgtttctca  12180
ttttaaacaa ctttccactg acaacgaaag taaagtaaag tattggattt ttttaaaggg  12240
aacatgtgaa tgaatacaca ggacttatta tatcagagtg agtaatcggt tggttggttg  12300
attgattgat tgattgatac attcagcttc ctgctgctag caatgccacg atttagattt  12360
aatgatgctt cagtggaaat caatcagaag gtattctgac cttgtgaaca tcagaaggta  12420
ttttttaact cccaagcagt agcaggacga tgatagggct ggagggctat ggattcccag  12480
cccatccctg tgaaggagta ggccactctt taagtgaagg attggatgat tgttcataat  12540
acataaagtt ctctgtaatt acaactaaat tattatgccc tcttctcaca gtcaaaagga  12600
actgggtggt ttggtttttg ttgctttttt agatttattg tcccatgtgg gatgagtttt  12660
taaatgccac aagacataat ttaaaataaa taaactttgg gaaaaggtgt aagacagtag  12720
ccccatcaca tttgtgatac tgacaggtat caacccagaa gcccatgaac tgtgtttcca  12780
tcctttgcat ttctctgcga gtagttccac acaggtttgt aagtaagtaa gaaagaaggc  12840
aaattgattc aaatgttaca aaaaaaccct tcttggtgga ttagacaggt taaatatata  12900
```

```
aacaaacaaa caaaaattgc tcaaaaaaga ggagaaaagc tcaagaggaa aagctaagga  12960

ctggtaggaa aaagctttac tctttcatgc cattttattt ctttttgatt tttaaatcat  13020

tcattcaata gataccaccg tgtgacctat aattttgcaa atctgttacc tctgacatca  13080

agtgtaatta gcttttggag agtgggctga catcaagtgt aattagcttt tggagagtgg  13140

gttttgtcca ttattaataa ttaattaatt aacatcaaac acggcttctc atgctatttc  13200

tacctcactt tggttttggg gtgttcctga taattgtgca cacctgagtt cacagcttca  13260

ccacttgtcc attgcgttat tttctttttc ctttataatt ctttcttttt ccttcataat  13320

tttcaaaaga aaacccaaag ctctaaggta acaaattacc aaattacatg aagatttggt  13380

ttttgtcttg catttttttc ctttatgtga cgctggacct tttctttacc caaggatttt  13440

taaaactcag atttaaaaca aggggttact ttacatccta ctaagaagtt taagtaagta  13500

agtttcattc taaaatcaga ggtaaataga gtgcataaat aattttgttt taatcttttt  13560

gtttttcttt tagacacatt agctctggag tgagtctgtc ataatatttg aacaaaaatt  13620

gagagcttta ttgctgcatt ttaagcataa ttaatttgga cattatttcg tgttgtgttc  13680

tttataacca ccgagtatta aactgtaaat cataatgtaa ctgaagcata aacatcacat  13740

ggcatgtttt gtcattgttt tcaggtactg agttcttact tgagtatcat aatatattgt  13800

gttttaacac caacactgta acatttacga attatttttt taaacttcag ttttactgca  13860

ttttcacaac atatcagact tcaccaaata tatgccttac tattgtatta tagtactgct  13920

ttactgtgta tctcaataaa gcacgcagtt atgttac                           13957
```

<210> SEQ ID NO 3
<211> LENGTH: 252
<212> TYPE: PRT
<213> ORGANISM: Homo sapiens

<400> SEQUENCE: 3

```
Met Leu Trp Trp Glu Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
            20                  25                  30

Gly Lys Gln His Ile Glu Asn Leu Phe Ser Asp Leu Gln Asp Gly Arg
        35                  40                  45

Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Asn Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
        115                 120                 125

Ala Gly Leu Gln Gln Thr Asn Ser Glu Lys Ile Leu Leu Ser Trp Val
    130                 135                 140

Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His
                165                 170                 175

Arg Pro Asp Leu Phe Asp Trp Asn Ser Val Val Cys Gln Gln Ser Ala
            180                 185                 190
```

```
Thr Gln Arg Leu Glu His Ala Phe Asn Ile Ala Arg Tyr Gln Leu Gly
        195                 200                 205

Ile Glu Lys Leu Leu Asp Pro Glu Asp Val Asp Thr Thr Tyr Pro Asp
    210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu
                245                 250


<210> SEQ ID NO 4
<211> LENGTH: 85
<212> TYPE: PRT
<213> ORGANISM: Homo sapiens

<400> SEQUENCE: 4

Met Leu Pro Arg Pro Pro Lys Val Thr Lys Glu Glu His Phe Gln Leu
1               5                   10                  15

His His Gln Met His Tyr Ser Gln Gln Ile Thr Val Ser Leu Ala Gln
            20                  25                  30

Gly Tyr Glu Arg Thr Ser Ser Pro Lys Pro Arg Phe Lys Ser Tyr Ala
        35                  40                  45

Tyr Thr Gln Ala Ala Tyr Val Thr Thr Ser Asp Pro Thr Arg Ser Pro
    50                  55                  60

Phe Pro Ser Gln His Leu Glu Ala Pro Glu Asp Lys Ser Phe Gly Ser
65                  70                  75                  80

Ser Leu Met Glu Ser
                85


<210> SEQ ID NO 5
<211> LENGTH: 109
<212> TYPE: PRT
<213> ORGANISM: Homo sapiens

<400> SEQUENCE: 5

Glu Val Asn Leu Asp Arg Tyr Gln Thr Ala Leu Glu Glu Val Leu Ser
1               5                   10                  15

Trp Leu Leu Ser Ala Glu Asp Thr Leu Gln Ala Gln Gly Glu Ile Ser
            20                  25                  30

Asn Asp Val Glu Val Val Lys Asp Gln Phe His Thr His Glu Gly Tyr
        35                  40                  45

Met Met Asp Leu Thr Ala His Gln Gly Arg Val Gly Asn Ile Leu Gln
    50                  55                  60

Leu Gly Ser Lys Leu Ile Gly Thr Gly Lys Leu Ser Glu Asp Glu Glu
65                  70                  75                  80

Thr Glu Val Gln Glu Gln Met Asn Leu Leu Asn Ser Arg Trp Glu Cys
                85                  90                  95

Leu Arg Val Ala Ser Met Glu Lys Gln Ser Asn Leu His
            100                 105


<210> SEQ ID NO 6
<211> LENGTH: 111
<212> TYPE: PRT
<213> ORGANISM: Homo sapiens

<400> SEQUENCE: 6

Arg Val Leu Met Asp Leu Gln Asn Gln Lys Leu Lys Glu Leu Asn Asp
1               5                   10                  15
```

```
Trp Leu Thr Lys Thr Glu Glu Arg Thr Arg Lys Met Glu Glu Glu Pro
            20                  25                  30

Leu Gly Pro Asp Leu Glu Asp Leu Lys Arg Gln Val Gln Gln His Lys
        35                  40                  45

Val Leu Gln Glu Asp Leu Glu Gln Glu Gln Val Arg Val Asn Ser Leu
    50                  55                  60

Thr His Met Val Val Val Val Asp Glu Ser Ser Gly Asp His Ala Thr
65                  70                  75                  80

Ala Ala Leu Glu Glu Gln Leu Lys Val Leu Gly Asp Arg Trp Ala Asn
                85                  90                  95

Ile Cys Arg Trp Thr Glu Asp Arg Trp Val Leu Leu Gln Asp Ile
            100                 105                 110


<210> SEQ ID NO 7
<211> LENGTH: 111
<212> TYPE: PRT
<213> ORGANISM: Homo sapiens

<400> SEQUENCE: 7

Leu Leu Lys Trp Gln Arg Leu Thr Glu Glu Gln Cys Leu Phe Ser Ala
1               5                   10                  15

Trp Leu Ser Glu Lys Glu Asp Ala Val Asn Lys Ile His Thr Thr Gly
            20                  25                  30

Phe Lys Asp Gln Asn Glu Met Leu Ser Ser Leu Gln Lys Leu Ala Val
        35                  40                  45

Leu Lys Ala Asp Leu Glu Lys Lys Lys Gln Ser Met Gly Lys Leu Tyr
    50                  55                  60

Ser Leu Lys Gln Asp Leu Leu Ser Thr Leu Lys Asn Lys Ser Val Thr
65                  70                  75                  80

Gln Lys Thr Glu Ala Trp Leu Asp Asn Phe Ala Arg Cys Trp Asp Asn
                85                  90                  95

Leu Val Gln Lys Leu Glu Lys Ser Thr Ala Gln Ile Ser Gln Ala
            100                 105                 110


<210> SEQ ID NO 8
<211> LENGTH: 49
<212> TYPE: PRT
<213> ORGANISM: Homo sapiens

<400> SEQUENCE: 8

Val Thr Thr Thr Gln Pro Ser Leu Thr Gln Thr Thr Val Met Glu Thr
1               5                   10                  15

Val Thr Thr Val Thr Thr Arg Glu Gln Ile Leu Val Lys His Ala Gln
            20                  25                  30

Glu Glu Leu Pro Pro Pro Pro Pro Gln Lys Lys Arg Gln Ile Thr Val
        35                  40                  45

Asp


<210> SEQ ID NO 9
<211> LENGTH: 111
<212> TYPE: PRT
<213> ORGANISM: Homo sapiens

<400> SEQUENCE: 9

Ser Glu Ile Arg Lys Arg Leu Asp Val Asp Ile Thr Glu Leu His Ser
1               5                   10                  15

Trp Ile Thr Arg Ser Glu Ala Val Leu Gln Ser Pro Glu Phe Ala Ile
            20                  25                  30
```

```
Phe Arg Lys Glu Gly Asn Phe Ser Asp Leu Lys Glu Lys Val Asn Ala
        35                  40                  45

Ile Glu Arg Glu Lys Ala Glu Lys Phe Arg Lys Leu Gln Asp Ala Ser
    50                  55                  60

Arg Ser Ala Gln Ala Leu Val Glu Gln Met Val Asn Glu Gly Val Asn
65                  70                  75                  80

Ala Asp Ser Ile Lys Gln Ala Ser Glu Gln Leu Asn Ser Arg Trp Ile
                85                  90                  95

Glu Phe Cys Gln Leu Leu Ser Glu Arg Leu Asn Trp Leu Glu Tyr
            100                 105                 110


<210> SEQ ID NO 10
<211> LENGTH: 109
<212> TYPE: PRT
<213> ORGANISM: Homo sapiens

<400> SEQUENCE: 10

Gln Asn Asn Ile Ile Ala Phe Tyr Asn Gln Leu Gln Gln Leu Glu Gln
1               5                   10                  15

Met Thr Thr Thr Ala Glu Asn Trp Leu Lys Ile Gln Pro Thr Thr Pro
            20                  25                  30

Ser Glu Pro Thr Ala Ile Lys Ser Gln Leu Lys Ile Cys Lys Asp Glu
        35                  40                  45

Val Asn Arg Leu Ser Gly Leu Gln Pro Gln Ile Glu Arg Leu Lys Ile
    50                  55                  60

Gln Ser Ile Ala Leu Lys Glu Lys Gly Gln Gly Pro Met Phe Leu Asp
65                  70                  75                  80

Ala Asp Phe Val Ala Phe Thr Asn His Phe Lys Gln Val Phe Ser Asp
                85                  90                  95

Val Gln Ala Arg Glu Lys Glu Leu Gln Thr Ile Phe Asp
            100                 105


<210> SEQ ID NO 11
<211> LENGTH: 109
<212> TYPE: PRT
<213> ORGANISM: Homo sapiens

<400> SEQUENCE: 11

Thr Leu Pro Pro Met Arg Tyr Gln Glu Thr Met Ser Ala Ile Arg Thr
1               5                   10                  15

Trp Val Gln Gln Ser Glu Thr Lys Leu Ser Ile Pro Gln Leu Ser Val
            20                  25                  30

Thr Asp Tyr Glu Ile Met Glu Gln Arg Leu Gly Glu Leu Gln Ala Leu
        35                  40                  45

Gln Ser Ser Leu Gln Glu Gln Gln Ser Gly Leu Tyr Tyr Leu Ser Thr
    50                  55                  60

Thr Val Lys Glu Met Ser Lys Lys Ala Pro Ser Glu Ile Ser Arg Lys
65                  70                  75                  80

Tyr Gln Ser Glu Phe Glu Glu Ile Glu Gly Arg Trp Lys Lys Leu Ser
                85                  90                  95

Ser Gln Leu Val Glu His Cys Gln Lys Leu Glu Glu Gln
            100                 105


<210> SEQ ID NO 12
<211> LENGTH: 109
<212> TYPE: PRT
<213> ORGANISM: Homo sapiens
```

<400> SEQUENCE: 12

```
Met Asn Lys Leu Arg Lys Ile Gln Asn His Ile Gln Thr Leu Lys Lys
1               5                   10                  15

Trp Met Ala Glu Val Asp Val Phe Leu Lys Glu Glu Trp Pro Ala Leu
            20                  25                  30

Gly Asp Ser Glu Ile Leu Lys Lys Gln Leu Lys Gln Cys Arg Leu Leu
        35                  40                  45

Val Ser Asp Ile Gln Thr Ile Gln Pro Ser Leu Asn Ser Val Asn Glu
    50                  55                  60

Gly Gly Gln Lys Ile Lys Asn Glu Ala Glu Pro Glu Phe Ala Ser Arg
65                  70                  75                  80

Leu Glu Thr Glu Leu Lys Glu Leu Asn Thr Gln Trp Asp His Met Cys
                85                  90                  95

Gln Gln Val Tyr Ala Arg Lys Glu Ala Leu Lys Gly Gly
            100                 105
```

<210> SEQ ID NO 13
<211> LENGTH: 109
<212> TYPE: PRT
<213> ORGANISM: Homo sapiens

<400> SEQUENCE: 13

```
Leu Glu Lys Thr Val Ser Leu Gln Lys Asp Leu Ser Glu Met His Glu
1               5                   10                  15

Trp Met Thr Gln Ala Glu Glu Glu Tyr Leu Glu Arg Asp Phe Glu Tyr
            20                  25                  30

Lys Thr Pro Asp Glu Leu Gln Lys Ala Val Glu Glu Met Lys Arg Ala
        35                  40                  45

Lys Glu Glu Ala Gln Gln Lys Glu Ala Lys Val Lys Leu Leu Thr Glu
    50                  55                  60

Ser Val Asn Ser Val Ile Ala Gln Ala Pro Pro Val Ala Gln Glu Ala
65                  70                  75                  80

Leu Lys Lys Glu Leu Glu Thr Leu Thr Thr Asn Tyr Gln Trp Leu Cys
                85                  90                  95

Thr Arg Leu Asn Gly Lys Cys Lys Thr Leu Glu Glu Val
            100                 105
```

<210> SEQ ID NO 14
<211> LENGTH: 104
<212> TYPE: PRT
<213> ORGANISM: Homo sapiens

<400> SEQUENCE: 14

```
Trp Ala Cys Trp His Glu Leu Leu Ser Tyr Leu Glu Lys Ala Asn Lys
1               5                   10                  15

Trp Leu Asn Glu Val Glu Phe Lys Leu Lys Thr Thr Glu Asn Ile Pro
            20                  25                  30

Gly Gly Ala Glu Glu Ile Ser Glu Val Leu Asp Ser Leu Glu Asn Leu
        35                  40                  45

Met Arg His Ser Glu Asp Asn Pro Asn Gln Ile Arg Ile Leu Ala Gln
    50                  55                  60

Thr Leu Thr Asp Gly Gly Val Met Asp Glu Leu Ile Asn Glu Glu Leu
65                  70                  75                  80

Glu Thr Phe Asn Ser Arg Trp Arg Glu Leu His Glu Glu Ala Val Arg
                85                  90                  95
```

Arg Gln Lys Leu Leu Glu Gln Ser
100

<210> SEQ ID NO 15
<211> LENGTH: 92
<212> TYPE: PRT
<213> ORGANISM: Homo sapiens

<400> SEQUENCE: 15

Ile Gln Ser Ala Gln Glu Thr Glu Lys Ser Leu His Leu Ile Gln Glu
1 5 10 15

Ser Leu Thr Phe Ile Asp Lys Gln Leu Ala Ala Tyr Ile Ala Asp Lys
20 25 30

Val Asp Ala Ala Gln Met Pro Gln Glu Ala Gln Lys Ile Gln Ser Asp
35 40 45

Leu Thr Ser His Glu Ile Ser Leu Glu Glu Met Lys Lys His Asn Gln
50 55 60

Gly Lys Glu Ala Ala Gln Arg Val Leu Ser Gln Ile Asp Val Ala Gln
65 70 75 80

Lys Lys Leu Gln Asp Val Ser Met Lys Phe Arg Leu
85 90

<210> SEQ ID NO 16
<211> LENGTH: 109
<212> TYPE: PRT
<213> ORGANISM: Homo sapiens

<400> SEQUENCE: 16

Phe Gln Lys Pro Ala Asn Phe Glu Gln Arg Leu Gln Glu Ser Lys Met
1 5 10 15

Ile Leu Asp Glu Val Lys Met His Leu Pro Ala Leu Glu Thr Lys Ser
20 25 30

Val Glu Gln Glu Val Val Gln Ser Gln Leu Asn His Cys Val Asn Leu
35 40 45

Tyr Lys Ser Leu Ser Glu Val Lys Ser Glu Val Glu Met Val Ile Lys
50 55 60

Thr Gly Arg Gln Ile Val Gln Lys Lys Gln Thr Glu Asn Pro Lys Glu
65 70 75 80

Leu Asp Glu Arg Val Thr Ala Leu Lys Leu His Tyr Asn Glu Leu Gly
85 90 95

Ala Lys Val Thr Glu Arg Lys Gln Gln Leu Glu Lys Cys
100 105

<210> SEQ ID NO 17
<211> LENGTH: 108
<212> TYPE: PRT
<213> ORGANISM: Homo sapiens

<400> SEQUENCE: 17

Leu Lys Leu Ser Arg Lys Met Arg Lys Glu Met Asn Val Leu Thr Glu
1 5 10 15

Trp Leu Ala Ala Thr Asp Met Glu Leu Thr Lys Arg Ser Ala Val Glu
20 25 30

Gly Met Pro Ser Asn Leu Asp Ser Glu Val Ala Trp Gly Lys Ala Thr
35 40 45

Gln Lys Glu Ile Glu Lys Gln Lys Val His Leu Lys Ser Ile Thr Glu
50 55 60

Val Gly Glu Ala Leu Lys Thr Val Leu Gly Lys Lys Glu Thr Leu Val 65 70 75 80

Glu Asp Lys Leu Ser Leu Leu Asn Ser Asn Trp Ile Ala Val Thr Ser
85 90 95

Arg Ala Glu Glu Trp Leu Asn Leu Leu Leu Glu Tyr
100 105

<210> SEQ ID NO 18
<211> LENGTH: 104
<212> TYPE: PRT
<213> ORGANISM: Homo sapiens

<400> SEQUENCE: 18

Gln Lys His Met Glu Thr Phe Asp Gln Asn Val Asp His Ile Thr Lys
1 5 10 15

Trp Ile Ile Gln Ala Asp Thr Leu Leu Asp Glu Ser Glu Lys Lys Lys
20 25 30

Pro Gln Gln Lys Glu Asp Val Leu Lys Arg Leu Lys Ala Glu Leu Asn
35 40 45

Asp Ile Arg Pro Lys Val Asp Ser Thr Arg Asp Gln Ala Ala Asn Leu
50 55 60

Met Ala Asn Arg Gly Asp His Cys Arg Lys Leu Val Glu Pro Gln Ile
65 70 75 80

Ser Glu Leu Asn His Arg Phe Ala Ala Ile Ser His Arg Ile Lys Thr
85 90 95

Gly Lys Ala Ser Ile Pro Leu Lys
100

<210> SEQ ID NO 19
<211> LENGTH: 94
<212> TYPE: PRT
<213> ORGANISM: Homo sapiens

<400> SEQUENCE: 19

Glu Leu Glu Gln Phe Asn Ser Asp Ile Gln Lys Leu Leu Glu Pro Leu
1 5 10 15

Glu Ala Glu Ile Gln Gln Gly Val Asn Leu Lys Glu Glu Asp Phe Asn
20 25 30

Lys Asp Met Asn Glu Asp Asn Glu Gly Thr Val Lys Glu Leu Leu Gln
35 40 45

Arg Gly Asp Asn Leu Gln Gln Arg Ile Thr Asp Glu Arg Lys Arg Glu
50 55 60

Glu Ile Lys Ile Lys Gln Gln Leu Leu Gln Thr Lys His Asn Ala Leu
65 70 75 80

Lys Asp Leu Arg Ser Gln Arg Arg Lys Lys Ala Leu Glu Ile
85 90

<210> SEQ ID NO 20
<211> LENGTH: 98
<212> TYPE: PRT
<213> ORGANISM: Homo sapiens

<400> SEQUENCE: 20

Ser His Gln Trp Tyr Gln Tyr Lys Arg Gln Ala Asp Asp Leu Leu Lys
1 5 10 15

Cys Leu Asp Asp Ile Glu Lys Lys Leu Ala Ser Leu Pro Glu Pro Arg
20 25 30

Asp Glu Arg Lys Ile Lys Glu Ile Asp Arg Glu Leu Gln Lys Lys Lys
35 40 45

```
Glu Glu Leu Asn Ala Val Arg Arg Gln Ala Glu Gly Leu Ser Glu Asp
    50                  55                  60

Gly Ala Ala Met Ala Val Glu Pro Thr Gln Ile Gln Leu Ser Lys Arg
65                  70                  75                  80

Trp Arg Glu Ile Glu Ser Lys Phe Ala Gln Phe Arg Arg Leu Asn Phe
                85                  90                  95

Ala Gln


<210> SEQ ID NO 21
<211> LENGTH: 20
<212> TYPE: PRT
<213> ORGANISM: Homo sapiens

<400> SEQUENCE: 21

Ile His Thr Val Arg Glu Glu Thr Met Met Val Met Thr Glu Asp Met
1               5                   10                  15

Pro Leu Glu Ile
            20


<210> SEQ ID NO 22
<211> LENGTH: 109
<212> TYPE: PRT
<213> ORGANISM: Homo sapiens

<400> SEQUENCE: 22

Ser Tyr Val Pro Ser Thr Tyr Leu Thr Glu Ile Thr His Val Ser Gln
1               5                   10                  15

Ala Leu Leu Glu Val Glu Gln Leu Leu Asn Ala Pro Asp Leu Cys Ala
            20                  25                  30

Lys Asp Phe Glu Asp Leu Phe Lys Gln Glu Glu Ser Leu Lys Asn Ile
        35                  40                  45

Lys Asp Ser Leu Gln Gln Ser Ser Gly Arg Ile Asp Ile Ile His Ser
    50                  55                  60

Lys Lys Thr Ala Ala Leu Gln Ser Ala Thr Pro Val Glu Arg Val Lys
65                  70                  75                  80

Leu Gln Glu Ala Leu Ser Gln Leu Asp Phe Gln Trp Glu Lys Val Asn
                85                  90                  95

Lys Met Tyr Lys Asp Arg Gln Gly Arg Phe Asp Arg Ser
            100                 105


<210> SEQ ID NO 23
<211> LENGTH: 107
<212> TYPE: PRT
<213> ORGANISM: Homo sapiens

<400> SEQUENCE: 23

Val Glu Lys Trp Arg Arg Phe His Tyr Asp Ile Lys Ile Phe Asn Gln
1               5                   10                  15

Trp Leu Thr Glu Ala Glu Gln Phe Leu Arg Lys Thr Gln Ile Pro Glu
            20                  25                  30

Asn Trp Glu His Ala Lys Tyr Lys Trp Tyr Leu Lys Glu Leu Gln Asp
        35                  40                  45

Gly Ile Gly Gln Arg Gln Thr Val Val Arg Thr Leu Asn Ala Thr Gly
    50                  55                  60

Glu Glu Ile Ile Gln Gln Ser Ser Lys Thr Asp Ala Ser Ile Leu Gln
65                  70                  75                  80

Glu Lys Leu Gly Ser Leu Asn Leu Arg Trp Gln Glu Val Cys Lys Gln
```

```
                85                  90                  95

Leu Ser Asp Arg Lys Lys Arg Leu Glu Glu Gln
            100                 105


<210> SEQ ID NO 24
<211> LENGTH: 117
<212> TYPE: PRT
<213> ORGANISM: Homo sapiens

<400> SEQUENCE: 24

Lys Asn Ile Leu Ser Glu Phe Gln Arg Asp Leu Asn Glu Phe Val Leu
1               5                   10                  15

Trp Leu Glu Glu Ala Asp Asn Ile Ala Ser Ile Pro Leu Glu Pro Gly
            20                  25                  30

Lys Glu Gln Gln Leu Lys Glu Lys Leu Glu Gln Val Lys Leu Leu Val
        35                  40                  45

Glu Glu Leu Pro Leu Arg Gln Gly Ile Leu Lys Gln Leu Asn Glu Thr
    50                  55                  60

Gly Gly Pro Val Leu Val Ser Ala Pro Ile Ser Pro Glu Glu Gln Asp
65                  70                  75                  80

Lys Leu Glu Asn Lys Leu Lys Gln Thr Asn Leu Gln Trp Ile Lys Val
                85                  90                  95

Ser Arg Ala Leu Pro Glu Lys Gln Gly Glu Ile Glu Ala Gln Ile Lys
            100                 105                 110

Asp Leu Gly Gln Leu
        115


<210> SEQ ID NO 25
<211> LENGTH: 101
<212> TYPE: PRT
<213> ORGANISM: Homo sapiens

<400> SEQUENCE: 25

Glu Lys Lys Leu Glu Asp Leu Glu Glu Gln Leu Asn His Leu Leu Leu
1               5                   10                  15

Trp Leu Ser Pro Ile Arg Asn Gln Leu Glu Ile Tyr Asn Gln Pro Asn
            20                  25                  30

Gln Glu Gly Pro Phe Asp Val Gln Glu Thr Glu Ile Ala Val Gln Ala
        35                  40                  45

Lys Gln Pro Asp Val Glu Glu Ile Leu Ser Lys Gly Gln His Leu Tyr
    50                  55                  60

Lys Glu Lys Pro Ala Thr Gln Pro Val Lys Arg Lys Leu Glu Asp Leu
65                  70                  75                  80

Ser Ser Glu Trp Lys Ala Val Asn Arg Leu Leu Gln Glu Leu Arg Ala
                85                  90                  95

Lys Gln Pro Asp Leu
            100


<210> SEQ ID NO 26
<211> LENGTH: 41
<212> TYPE: PRT
<213> ORGANISM: Homo sapiens

<400> SEQUENCE: 26

Ala Pro Gly Leu Thr Thr Ile Gly Ala Ser Pro Thr Gln Thr Val Thr
1               5                   10                  15

Leu Val Thr Gln Pro Val Val Thr Lys Glu Thr Ala Ile Ser Lys Leu
            20                  25                  30
```

```
Glu Met Pro Ser Ser Leu Met Leu Glu
        35                  40


<210> SEQ ID NO 27
<211> LENGTH: 110
<212> TYPE: PRT
<213> ORGANISM: Homo sapiens

<400> SEQUENCE: 27

Val Pro Ala Leu Ala Asp Phe Asn Arg Ala Trp Thr Glu Leu Thr Asp
1               5                   10                  15

Trp Leu Ser Leu Leu Asp Gln Val Ile Lys Ser Gln Arg Val Met Val
            20                  25                  30

Gly Asp Leu Glu Asp Ile Asn Glu Met Ile Ile Lys Gln Lys Ala Thr
        35                  40                  45

Met Gln Asp Leu Glu Gln Arg Arg Pro Gln Leu Glu Glu Leu Ile Thr
    50                  55                  60

Ala Ala Gln Asn Leu Lys Asn Lys Thr Ser Asn Gln Glu Ala Arg Thr
65                  70                  75                  80

Ile Ile Thr Asp Arg Ile Glu Arg Ile Gln Asn Gln Trp Asp Glu Val
                85                  90                  95

Gln Glu His Leu Gln Asn Arg Arg Gln Gln Leu Asn Glu Met
            100                 105                 110


<210> SEQ ID NO 28
<211> LENGTH: 109
<212> TYPE: PRT
<213> ORGANISM: Homo sapiens

<400> SEQUENCE: 28

Leu Lys Asp Ser Thr Gln Trp Leu Glu Ala Lys Glu Glu Ala Glu Gln
1               5                   10                  15

Val Leu Gly Gln Ala Arg Ala Lys Leu Glu Ser Trp Lys Glu Gly Pro
            20                  25                  30

Tyr Thr Val Asp Ala Ile Gln Lys Lys Ile Thr Glu Thr Lys Gln Leu
        35                  40                  45

Ala Lys Asp Leu Arg Gln Trp Gln Thr Asn Val Asp Val Ala Asn Asp
    50                  55                  60

Leu Ala Leu Lys Leu Leu Arg Asp Tyr Ser Ala Asp Asp Thr Arg Lys
65                  70                  75                  80

Val His Met Ile Thr Glu Asn Ile Asn Ala Ser Trp Arg Ser Ile His
                85                  90                  95

Lys Arg Val Ser Glu Arg Glu Ala Ala Leu Glu Glu Thr
            100                 105


<210> SEQ ID NO 29
<211> LENGTH: 116
<212> TYPE: PRT
<213> ORGANISM: Homo sapiens

<400> SEQUENCE: 29

His Arg Leu Leu Gln Gln Phe Pro Leu Asp Leu Glu Lys Phe Leu Ala
1               5                   10                  15

Trp Leu Thr Glu Ala Glu Thr Thr Ala Asn Val Leu Gln Asp Ala Thr
            20                  25                  30

Arg Lys Glu Arg Leu Leu Glu Asp Ser Lys Gly Val Lys Glu Leu Met
        35                  40                  45
```

```
Lys Gln Trp Gln Asp Leu Gln Gly Glu Ile Glu Ala His Thr Asp Val
    50                  55                  60

Tyr His Asn Leu Asp Glu Asn Ser Gln Lys Ile Leu Arg Ser Leu Glu
65                  70                  75                  80

Gly Ser Asp Asp Ala Val Leu Leu Gln Arg Arg Leu Asp Asn Met Asn
                85                  90                  95

Phe Lys Trp Ser Glu Leu Arg Lys Lys Ser Leu Asn Ile Arg Ser His
            100                 105                 110

Leu Glu Ala Ser
        115


<210> SEQ ID NO 30
<211> LENGTH: 129
<212> TYPE: PRT
<213> ORGANISM: Homo sapiens

<400> SEQUENCE: 30

Ser Asp Gln Trp Lys Arg Leu His Leu Ser Leu Gln Glu Leu Leu Val
1               5                   10                  15

Trp Leu Gln Leu Lys Asp Asp Glu Leu Ser Arg Gln Ala Pro Ile Gly
            20                  25                  30

Gly Asp Phe Pro Ala Val Gln Lys Gln Asn Asp Val His Arg Ala Phe
        35                  40                  45

Lys Arg Glu Leu Lys Thr Lys Glu Pro Val Ile Met Ser Thr Leu Glu
    50                  55                  60

Thr Val Arg Ile Phe Leu Thr Glu Gln Pro Leu Glu Gly Leu Glu Lys
65                  70                  75                  80

Leu Tyr Gln Glu Pro Arg Glu Leu Pro Pro Glu Glu Arg Ala Gln Asn
                85                  90                  95

Val Thr Arg Leu Leu Arg Lys Gln Ala Glu Glu Val Asn Thr Glu Trp
            100                 105                 110

Glu Lys Leu Asn Leu His Ser Ala Asp Trp Gln Arg Lys Ile Asp Glu
        115                 120                 125

Thr


<210> SEQ ID NO 31
<211> LENGTH: 108
<212> TYPE: PRT
<213> ORGANISM: Homo sapiens

<400> SEQUENCE: 31

Leu Glu Arg Leu Gln Glu Leu Gln Glu Ala Thr Asp Glu Leu Asp Leu
1               5                   10                  15

Lys Leu Arg Gln Ala Glu Val Ile Lys Gly Ser Trp Gln Pro Val Gly
            20                  25                  30

Asp Leu Leu Ile Asp Ser Leu Gln Asp His Leu Glu Lys Val Lys Ala
        35                  40                  45

Leu Arg Gly Glu Ile Ala Pro Leu Lys Glu Asn Val Ser His Val Asn
    50                  55                  60

Asp Leu Ala Arg Gln Leu Thr Thr Leu Gly Ile Gln Leu Ser Pro Tyr
65                  70                  75                  80

Asn Leu Ser Thr Leu Glu Asp Leu Asn Thr Arg Trp Lys Leu Leu Gln
                85                  90                  95

Val Ala Val Glu Asp Arg Val Arg Gln Leu His Glu
            100                 105
```

<210> SEQ ID NO 32
<211> LENGTH: 72
<212> TYPE: PRT
<213> ORGANISM: Homo sapiens

<400> SEQUENCE: 32

```
Ala His Arg Asp Phe Gly Pro Ala Ser Gln His Phe Leu Ser Thr Ser
1               5                   10                  15

Val Gln Gly Pro Trp Glu Arg Ala Ile Ser Pro Asn Lys Val Pro Tyr
            20                  25                  30

Tyr Ile Asn His Glu Thr Gln Thr Thr Cys Trp Asp His Pro Lys Met
        35                  40                  45

Thr Glu Leu Tyr Gln Ser Leu Ala Asp Leu Asn Asn Val Arg Phe Ser
    50                  55                  60

Ala Tyr Arg Thr Ala Met Lys Leu
65                  70
```

<210> SEQ ID NO 33
<211> LENGTH: 296
<212> TYPE: PRT
<213> ORGANISM: Homo sapiens

<400> SEQUENCE: 33

```
Arg Arg Leu Gln Lys Ala Leu Cys Leu Asp Leu Leu Ser Leu Ser Ala
1               5                   10                  15

Ala Cys Asp Ala Leu Asp Gln His Asn Leu Lys Gln Asn Asp Gln Pro
            20                  25                  30

Met Asp Ile Leu Gln Ile Ile Asn Cys Leu Thr Thr Ile Tyr Asp Arg
        35                  40                  45

Leu Glu Gln Glu His Asn Asn Leu Val Asn Val Pro Leu Cys Val Asp
    50                  55                  60

Met Cys Leu Asn Trp Leu Leu Asn Val Tyr Asp Thr Gly Arg Thr Gly
65                  70                  75                  80

Arg Ile Arg Val Leu Ser Phe Lys Thr Gly Ile Ile Ser Leu Cys Lys
                85                  90                  95

Ala His Leu Glu Asp Lys Tyr Arg Tyr Leu Phe Lys Gln Val Ala Ser
            100                 105                 110

Ser Thr Gly Phe Cys Asp Gln Arg Arg Leu Gly Leu Leu Leu His Asp
        115                 120                 125

Ser Ile Gln Ile Pro Arg Gln Leu Gly Glu Val Ala Ser Phe Gly Gly
    130                 135                 140

Ser Asn Ile Glu Pro Ser Val Arg Ser Cys Phe Gln Phe Ala Asn Asn
145                 150                 155                 160

Lys Pro Glu Ile Glu Ala Ala Leu Phe Leu Asp Trp Met Arg Leu Glu
                165                 170                 175

Pro Gln Ser Met Val Trp Leu Pro Val Leu His Arg Val Ala Ala Ala
            180                 185                 190

Glu Thr Ala Lys His Gln Ala Lys Cys Asn Ile Cys Lys Glu Cys Pro
        195                 200                 205

Ile Ile Gly Phe Arg Tyr Arg Ser Leu Lys His Phe Asn Tyr Asp Ile
    210                 215                 220

Cys Gln Ser Cys Phe Phe Ser Gly Arg Val Ala Lys Gly His Lys Met
225                 230                 235                 240

His Tyr Pro Met Val Glu Tyr Cys Thr Pro Thr Thr Ser Gly Glu Asp
                245                 250                 255

Val Arg Asp Phe Ala Lys Val Leu Lys Asn Lys Phe Arg Thr Lys Arg
```

```
            260                 265                 270

Tyr Phe Ala Lys His Pro Arg Met Gly Tyr Leu Pro Val Gln Thr Val
        275                 280                 285

Leu Glu Gly Asp Asn Met Glu Thr
    290                 295


<210> SEQ ID NO 34
<211> LENGTH: 277
<212> TYPE: PRT
<213> ORGANISM: Homo sapiens

<400> SEQUENCE: 34

Pro Val Thr Leu Ile Asn Phe Trp Pro Val Asp Ser Ala Pro Ala Ser
1               5                   10                  15

Ser Pro Gln Leu Ser His Asp Asp Thr His Ser Arg Ile Glu His Tyr
            20                  25                  30

Ala Ser Arg Leu Ala Glu Met Glu Asn Ser Asn Gly Ser Tyr Leu Asn
        35                  40                  45

Asp Ser Ile Ser Pro Asn Glu Ser Ile Asp Asp Glu His Leu Leu Ile
    50                  55                  60

Gln His Tyr Cys Gln Ser Leu Asn Gln Asp Ser Pro Leu Ser Gln Pro
65                  70                  75                  80

Arg Ser Pro Ala Gln Ile Leu Ile Ser Leu Glu Ser Glu Glu Arg Gly
                85                  90                  95

Glu Leu Glu Arg Ile Leu Ala Asp Leu Glu Glu Glu Asn Arg Asn Leu
            100                 105                 110

Gln Ala Glu Tyr Asp Arg Leu Lys Gln Gln His Glu His Lys Gly Leu
        115                 120                 125

Ser Pro Leu Pro Ser Pro Pro Glu Met Met Pro Thr Ser Pro Gln Ser
    130                 135                 140

Pro Arg Asp Ala Glu Leu Ile Ala Glu Ala Lys Leu Leu Arg Gln His
145                 150                 155                 160

Lys Gly Arg Leu Glu Ala Arg Met Gln Ile Leu Glu Asp His Asn Lys
                165                 170                 175

Gln Leu Glu Ser Gln Leu His Arg Leu Arg Gln Leu Leu Glu Gln Pro
            180                 185                 190

Gln Ala Glu Ala Lys Val Asn Gly Thr Thr Val Ser Ser Pro Ser Thr
        195                 200                 205

Ser Leu Gln Arg Ser Asp Ser Ser Gln Pro Met Leu Leu Arg Val Val
    210                 215                 220

Gly Ser Gln Thr Ser Asp Ser Met Gly Glu Glu Asp Leu Leu Ser Pro
225                 230                 235                 240

Pro Gln Asp Thr Ser Thr Gly Leu Glu Glu Val Met Glu Gln Leu Asn
                245                 250                 255

Asn Ser Phe Pro Ser Ser Arg Gly Arg Asn Thr Pro Gly Lys Pro Met
            260                 265                 270

Arg Glu Asp Thr Met
        275


<210> SEQ ID NO 35
<211> LENGTH: 208
<212> TYPE: DNA
<213> ORGANISM: Homo sapiens

<400> SEQUENCE: 35

gggattccct cactttcccc ctacaggact cagatctggg aggcaattac cttcggagaa     60
```

```
aaacgaatag gaaaaactga agtgttactt tttttaaagc tgctgaagtt tgttggtttc    120

tcattgtttt taagcctact ggagcaataa agtttgaaga acttttacca ggtttttttt    180

atcgctgcct tgatatacac ttttcaaa                                       208
```

<210> SEQ ID NO 36
<211> LENGTH: 756
<212> TYPE: DNA
<213> ORGANISM: Homo sapiens

<400> SEQUENCE: 36

```
atgctttggt gggaagaagt agaggactgt tatgaaagag aagatgttca aaagaaaaca     60

ttcacaaaat gggtaaatgc acaattttct aagtttggga agcagcatat tgagaacctc    120

ttcagtgacc tacaggatgg gaggcgcctc ctagacctcc tcgaaggcct gacagggcaa    180

aaactgccaa aagaaaaagg atccacaaga gttcatgccc tgaacaatgt caacaaggca    240

ctgcgggttt tgcagaacaa taatgttgat ttagtgaata ttggaagtac tgacatcgta    300

gatggaaatc ataaactgac tcttggtttg atttggaata taatcctcca ctggcaggtc    360

aaaaatgtaa tgaaaaatat catggctgga ttgcaacaaa ccaacagtga aaagattctc    420

ctgagctggg tccgacaatc aactcgtaat tatccacagg ttaatgtaat caacttcacc    480

accagctggt ctgatggcct ggctttgaat gctctcatcc atagtcatag gccagaccta    540

tttgactgga atagtgtggt ttgccagcag tcagccacac aacgactgga acatgcattc    600

aacatcgcca gatatcaatt aggcatagag aaactactcg atcctgaaga tgttgatacc    660

acctatccag ataagaagtc catcttaatg tacatcacat cactcttcca agttttgcct    720

caacaagtga gcattgaagc catccaggaa gtggaa                              756
```

<210> SEQ ID NO 37
<211> LENGTH: 255
<212> TYPE: DNA
<213> ORGANISM: Homo sapiens

<400> SEQUENCE: 37

```
atgttgccaa ggccacctaa agtgactaaa gaagaacatt ttcagttaca tcatcaaatg     60

cactattctc aacagatcac ggtcagtcta gcacagggat atgagagaac ttcttcccct    120

aagcctcgat tcaagagcta tgcctacaca caggctgctt atgtcaccac ctctgaccct    180

acacggagcc catttccttc acagcatttg gaagctcctg aagacaagtc atttggcagt    240

tcattgatgg agagt                                                     255
```

<210> SEQ ID NO 38
<211> LENGTH: 327
<212> TYPE: DNA
<213> ORGANISM: Homo sapiens

<400> SEQUENCE: 38

```
gaagtaaacc tggaccgtta tcaaacagct ttagaagaag tattatcgtg gcttcttttct     60

gctgaggaca cattgcaagc acaaggagag atttctaatg atgtggaagt ggtgaaagac    120

cagtttcata ctcatgaggg gtacatgatg gatttgacag cccatcaggg ccgggttggt    180

aatattctac aattgggaag taagctgatt ggaacaggaa aattatcaga agatgaagaa    240

actgaagtac aagagcagat gaatctccta aattcaagat gggaatgcct cagggtagct    300

agcatggaaa aacaaagcaa tttacat                                        327
```

<210> SEQ ID NO 39
<211> LENGTH: 333
<212> TYPE: DNA
<213> ORGANISM: Homo sapiens

<400> SEQUENCE: 39

```
agagttttaa tggatctcca gaatcagaaa ctgaaagagt tgaatgactg gctaacaaaa     60

acagaagaaa gaacaaggaa aatggaggaa gagcctcttg gacctgatct tgaagaccta    120

aaacgccaag tacaacaaca taaggtgctt caagaagatc tagaacaaga acaagtcagg    180

gtcaattctc tcactcacat ggtggtggta gttgatgaat ctagtggaga tcacgcaact    240

gctgctttgg aagaacaact taaggtattg ggagatcgat gggcaaacat ctgtagatgg    300

acagaagacc gctgggttct tttacaagac atc                                 333
```

<210> SEQ ID NO 40
<211> LENGTH: 333
<212> TYPE: DNA
<213> ORGANISM: Homo sapiens

<400> SEQUENCE: 40

```
cttctcaaat ggcaacgtct tactgaagaa cagtgccttt ttagtgcatg gctttcagaa     60

aaagaagatg cagtgaacaa gattcacaca actggcttta aagatcaaaa tgaaatgtta    120

tcaagtcttc aaaaactggc cgttttaaaa gcggatctag aaaagaaaaa gcaatccatg    180

ggcaaactgt attcactcaa acaagatctt ctttcaacac tgaagaataa gtcagtgacc    240

cagaagacgg aagcatggct ggataacttt gcccggtgtt gggataattt agtccaaaaa    300

cttgaaaaga gtacagcaca gatttcacag gct                                 333
```

<210> SEQ ID NO 41
<211> LENGTH: 147
<212> TYPE: DNA
<213> ORGANISM: Homo sapiens

<400> SEQUENCE: 41

```
gtcaccacca ctcagccatc actaacacag acaactgtaa tggaaacagt aactacggtg     60

accacaaggg aacagatcct ggtaaagcat gctcaagagg aacttccacc accacctccc    120

caaaagaaga ggcagattac tgtggat                                        147
```

<210> SEQ ID NO 42
<211> LENGTH: 333
<212> TYPE: DNA
<213> ORGANISM: Homo sapiens

<400> SEQUENCE: 42

```
tctgaaatta ggaaaaggtt ggatgttgat ataactgaac ttcacagctg gattactcgc     60

tcagaagctg tgttgcagag tcctgaattt gcaatctttc ggaaggaagg caacttctca    120

gacttaaaag aaaaagtcaa tgccatagag cgagaaaaag ctgagaagtt cagaaaactg    180

caagatgcca gcagatcagc tcaggccctg gtggaacaga tggtgaatga gggtgttaat    240

gcagatagca tcaaacaagc ctcagaacaa ctgaacagcc ggtggatcga attctgccag    300

ttgctaagtg agagacttaa ctggctggag tat                                 333
```

<210> SEQ ID NO 43
<211> LENGTH: 327
<212> TYPE: DNA
<213> ORGANISM: Homo sapiens

<400> SEQUENCE: 43

```
cagaacaaca tcatcgcttt ctataatcag ctacaacaat tggagcagat gacaactact     60
gctgaaaact ggttgaaaat ccaacccacc accccatcag agccaacagc aattaaaagt    120
cagttaaaaa tttgtaagga tgaagtcaac cggctatcag gtcttcaacc tcaaattgaa    180
cgattaaaaa ttcaaagcat agccctgaaa gagaaaggac aaggacccat gttcctggat    240
gcagactttg tggcctttac aaatcatttt aagcaagtct tttctgatgt gcaggccaga    300
gagaaagagc tacagacaat ttttgac                                        327
```

<210> SEQ ID NO 44
<211> LENGTH: 327
<212> TYPE: DNA
<213> ORGANISM: Homo sapiens

<400> SEQUENCE: 44

```
actttgccac caatgcgcta tcaggagacc atgagtgcca tcaggacatg ggtccagcag     60
tcagaaacca aactctccat acctcaactt agtgtcaccg actatgaaat catggagcag    120
agactcgggg aattgcaggc tttacaaagt tctctgcaag agcaacaaag tggcctatac    180
tatctcagca ccactgtgaa agagatgtcg aagaaagcgc cctctgaaat tagccggaaa    240
tatcaatcag aatttgaaga aattgaggga cgctggaaga agctctcctc ccagctggtt    300
gagcattgtc aaaagctaga ggagcaa                                        327
```

<210> SEQ ID NO 45
<211> LENGTH: 327
<212> TYPE: DNA
<213> ORGANISM: Homo sapiens

<400> SEQUENCE: 45

```
atgaataaac tccgaaaaat tcagaatcac atacaaaccc tgaagaaatg gatggctgaa     60
gttgatgttt ttctgaagga ggaatggcct gcccttgggg attcagaaat tctaaaaaag    120
cagctgaaac agtgcagact tttagtcagt gatattcaga caattcagcc cagtctaaac    180
agtgtcaatg aaggtgggca gaagataaag aatgaagcag agccagagtt tgcttcgaga    240
cttgagacag aactcaaaga acttaacact cagtgggatc acatgtgcca acaggtctat    300
gccagaaagg aggccttgaa gggaggt                                        327
```

<210> SEQ ID NO 46
<211> LENGTH: 327
<212> TYPE: DNA
<213> ORGANISM: Homo sapiens

<400> SEQUENCE: 46

```
ttggagaaaa ctgtaagcct ccagaaagat ctatcagaga tgcacgaatg gatgacacaa     60
gctgaagaag agtatcttga gagagatttt gaatataaaa ctccagatga attacagaaa    120
gcagttgaag agatgaagag agctaaagaa gaggcccaac aaaaagaagc gaaagtgaaa    180
ctccttactg agtctgtaaa tagtgtcata gctcaagctc cacctgtagc acaagaggcc    240
ttaaaaaagg aacttgaaac tctaaccacc aactaccagt ggctctgcac taggctgaat    300
gggaaatgca agactttgga agaagtt                                        327
```

<210> SEQ ID NO 47
<211> LENGTH: 312
<212> TYPE: DNA

<213> ORGANISM: Homo sapiens

<400> SEQUENCE: 47

```
tgggcatgtt ggcatgagtt attgtcatac ttggagaaag caaacaagtg gctaaatgaa     60

gtagaattta aacttaaaac cactgaaaac attcctggcg gagctgagga aatctctgag    120

gtgctagatt cacttgaaaa tttgatgcga cattcagagg ataacccaaa tcagattcgc    180

atattggcac agaccctaac agatggcgga gtcatggatg agctaatcaa tgaggaactt    240

gagacattta attctcgttg gagggaacta catgaagagg ctgtaaggag gcaaaagttg    300

cttgaacaga gc                                                        312
```

<210> SEQ ID NO 48
<211> LENGTH: 276
<212> TYPE: DNA
<213> ORGANISM: Homo sapiens

<400> SEQUENCE: 48

```
atccagtctg cccaggagac tgaaaaatcc ttacacttaa tccaggagtc cctcacattc     60

attgacaagc agttggcagc ttatattgca gacaaggtgg acgcagctca aatgcctcag    120

gaagcccaga aaatccaatc tgatttgaca agtcatgaga tcagtttaga agaaatgaag    180

aaacataatc aggggaagga ggctgcccaa agagtcctgt ctcagattga tgttgcacag    240

aaaaaattac aagatgtctc catgaagttt cgatta                              276
```

<210> SEQ ID NO 49
<211> LENGTH: 327
<212> TYPE: DNA
<213> ORGANISM: Homo sapiens

<400> SEQUENCE: 49

```
ttccagaaac cagccaattt tgagctgcgt ctacaagaaa gtaagatgat tttagatgaa     60

gtgaagatgc acttgcctgc attggaaaca aagagtgtgg aacaggaagt agtacagtca    120

cagctaaatc attgtgtgaa cttgtataaa agtctgagtg aagtgaagtc tgaagtggaa    180

atggtgataa agactggacg tcagattgta cagaaaaagc agacggaaaa tcccaaagaa    240

cttgatgaaa gagtaacagc tttgaaattg cattataatg agctgggagc aaaggtaaca    300

gaaagaaagc aacagttgga gaaatgc                                        327
```

<210> SEQ ID NO 50
<211> LENGTH: 324
<212> TYPE: DNA
<213> ORGANISM: Homo sapiens

<400> SEQUENCE: 50

```
ttgaaattgt cccgtaagat gcgaaaggaa atgaatgtct tgacagaatg gctggcagct     60

acagatatgg aattgacaaa gagatcagca gttgaaggaa tgcctagtaa tttggattct    120

gaagttgcct ggggaaaggc tactcaaaaa gagattgaga aacagaaggt gcacctgaag    180

agtatcacag aggtaggaga ggccttgaaa acagttttgg gcaagaagga gacgttggtg    240

gaagataaac tcagtcttct gaatagtaac tggatagctg tcacctcccg agcagaagag    300

tggttaaatc ttttgttgga atac                                           324
```

<210> SEQ ID NO 51
<211> LENGTH: 312
<212> TYPE: DNA
<213> ORGANISM: Homo sapiens

<400> SEQUENCE: 51
cagaaacaca tggaaacttt tgaccagaat gtggaccaca tcacaaagtg gatcattcag 60
gctgacacac ttttggatga atcagagaaa aagaaacccc agcaaaaaga agacgtgctt 120
aagcgtttaa aggcagaact gaatgacata cgcccaaagg tggactctac acgtgaccaa 180
gcagcaaact tgatggcaaa ccgcggtgac cactgcagga aattagtaga gccccaaatc 240
tcagagctca accatcgatt tgcagccatt tcacacagaa ttaagactgg aaaggcctcc 300
attcctttga ag 312

<210> SEQ ID NO 52
<211> LENGTH: 282
<212> TYPE: DNA
<213> ORGANISM: Homo sapiens

<400> SEQUENCE: 52
gaattggagc agtttaactc agatatacaa aaattgcttg aaccactgga ggctgaaatt 60
cagcaggggg tgaatctgaa agaggaagac ttcaataaag atatgaatga agacaatgag 120
ggtactgtaa aagaattgtt gcaaagagga gacaacttac aacaaagaat cacagatgag 180
agaaagagag aggaaataaa gataaaacag cagctgttac agacaaaaca taatgctctc 240
aaggatttga ggtctcaaag aagaaaaaag gctctagaaa tt 282

<210> SEQ ID NO 53
<211> LENGTH: 294
<212> TYPE: DNA
<213> ORGANISM: Homo sapiens

<400> SEQUENCE: 53
tctcatcagt ggtatcagta caagaggcag gctgatgatc tcctgaaatg cttggatgac 60
attgaaaaaa aattagccag cctacctgag cccagagatg aaaggaaaat aaaggaaatt 120
gatcgggaat tgcagaagaa gaaagaggag ctgaatgcag tgcgtaggca agctgagggc 180
ttgtctgagg atggggccgc aatggcagtg gagccaactc agatccagct cagcaagcgc 240
tggcgggaaa ttgagagcaa atttgctcag tttcgaagac tcaactttgc acaa 294

<210> SEQ ID NO 54
<211> LENGTH: 60
<212> TYPE: DNA
<213> ORGANISM: Homo sapiens

<400> SEQUENCE: 54
attcacactg tccgtgaaga aacgatgatg gtgatgactg aagacatgcc tttggaaatt 60

<210> SEQ ID NO 55
<211> LENGTH: 327
<212> TYPE: DNA
<213> ORGANISM: Homo sapiens

<400> SEQUENCE: 55
tcttatgtgc cttctactta tttgactgaa atcactcatg tctcacaagc cctattagaa 60
gtggaacaac ttctcaatgc tcctgacctc tgtgctaagg actttgaaga tctctttaag 120
caagaggagt ctctgaagaa tataaaagat agtctacaac aaagctcagg tcggattgac 180
attattcata gcaagaagac agcagcattg caaagtgcaa cgcctgtgga aagggtgaag 240
ctacaggaag ctctctccca gcttgatttc caatgggaaa aagttaacaa aatgtacaag 300
gaccgacaag ggcgatttga cagatct 327

<210> SEQ ID NO 56
<211> LENGTH: 321
<212> TYPE: DNA
<213> ORGANISM: Homo sapiens

<400> SEQUENCE: 56
gttgagaaat ggcggcgttt tcattatgat ataaagatat ttaatcagtg gctaacagaa 60
gctgaacagt ttctcagaaa gacacaaatt cctgagaatt gggaacatgc taaatacaaa 120
tggtatctta aggaactcca ggatggcatt gggcagcggc aaactgttgt cagaacattg 180
aatgcaactg gggaagaaat aattcagcaa tcctcaaaaa cagatgccag tattctacag 240
gaaaaattgg gaagcctgaa tctgcggtgg caggaggtct gcaaacagct gtcagacaga 300
aaaaagaggc tagaagaaca a 321

<210> SEQ ID NO 57
<211> LENGTH: 351
<212> TYPE: DNA
<213> ORGANISM: Homo sapiens

<400> SEQUENCE: 57
aagaatatct tgtcagaatt tcaaagagat ttaaatgaat ttgttttatg gttggaggaa 60
gcagataaca ttgctagtat cccacttgaa cctggaaaag agcagcaact aaaagaaaag 120
cttgagcaag tcaagttact ggtggaagag ttgcccctgc gccagggaat tctcaaacaa 180
ttaaatgaaa ctggaggacc cgtgcttgta agtgctccca taagcccaga agagcaagat 240
aaacttgaaa ataagctcaa gcagacaaat ctccagtgga taaaggtttc cagagcttta 300
cctgagaaac aaggagaaat tgaagctcaa ataaaagacc ttgggcagct t 351

<210> SEQ ID NO 58
<211> LENGTH: 303
<212> TYPE: DNA
<213> ORGANISM: Homo sapiens

<400> SEQUENCE: 58
gaaaaaaagc ttgaagacct tgaagagcag ttaaatcatc tgctgctgtg gttatctcct 60
attaggaatc agttggaaat ttataaccaa ccaaaccaag aaggaccatt tgacgttcag 120
gaaactgaaa tagcagttca agctaaacaa ccggatgtgg aagagatttt gtctaaaggg 180
cagcatttgt acaaggaaaa accagccact cagccagtga agaggaagtt agaagatctg 240
agctctgagt ggaaggcggt aaaccgttta cttcaagagc tgagggcaaa gcagcctgac 300
cta 303

<210> SEQ ID NO 59
<211> LENGTH: 123
<212> TYPE: DNA
<213> ORGANISM: Homo sapiens

<400> SEQUENCE: 59
gctcctggac tgaccactat tggagcctct cctactcaga ctgttactct ggtgacacaa 60
cctgtggtta ctaaggaaac tgccatctcc aaactagaaa tgccatcttc cttgatgttg 120
gag 123

<210> SEQ ID NO 60
<211> LENGTH: 330

<212> TYPE: DNA
<213> ORGANISM: Homo sapiens

<400> SEQUENCE: 60
gtacctgctc tggcagattt caaccgggct tggacagaac ttaccgactg gctttctctg 60
cttgatcaag ttataaaatc acagagggtg atggtgggtg accttgagga tatcaacgag 120
atgatcatca agcagaaggc aacaatgcag gatttggaac agaggcgtcc ccagttggaa 180
gaactcatta ccgctgccca aaatttgaaa aacaagacca gcaatcaaga ggctagaaca 240
atcattacgg atcgaattga aagaattcag aatcagtggg atgaagtaca agaacacctt 300
cagaaccgga ggcaacagtt gaatgaaatg 330

<210> SEQ ID NO 61
<211> LENGTH: 327
<212> TYPE: DNA
<213> ORGANISM: Homo sapiens

<400> SEQUENCE: 61
ttaaaggatt caacacaatg gctggaagct aaggaagaag ctgagcaggt cttaggacag 60
gccagagcca agcttgagtc atggaaggag ggtccctata cagtagatgc aatccaaaag 120
aaaatcacag aaaccaagca gttggccaaa gacctccgcc agtggcagac aaatgtagat 180
gtggcaaatg acttggccct gaaacttctc cgggattatt ctgcagatga taccagaaaa 240
gtccacatga taacagagaa tatcaatgcc tcttggagaa gcattcataa aagggtgagt 300
gagcgagagg ctgctttgga agaaact 327

<210> SEQ ID NO 62
<211> LENGTH: 348
<212> TYPE: DNA
<213> ORGANISM: Homo sapiens

<400> SEQUENCE: 62
catagattac tgcaacagtt ccccctggac ctggaaaagt ttcttgcctg gcttacagaa 60
gctgaaacaa ctgccaatgt cctacaggat gctacccgta aggaaaggct cctagaagac 120
tccaagggag taaaagagct gatgaaacaa tggcaagacc tccaaggtga aattgaagct 180
cacacagatg tttatcacaa cctggatgaa aacagccaaa aaatcctgag atccctggaa 240
ggttccgatg atgcagtcct gttacaaaga cgtttggata acatgaactt caagtggagt 300
gaacttcgga aaaagtctct caacattagg tcccatttgg aagccagt 348

<210> SEQ ID NO 63
<211> LENGTH: 387
<212> TYPE: DNA
<213> ORGANISM: Homo sapiens

<400> SEQUENCE: 63
tctgaccagt ggaagcgtct gcacctttct ctgcaggaac ttctggtgtg gctacagctg 60
aaagatgatg aattaagccg gcaggcacct attggaggcg actttccagc agttcagaag 120
cagaacgatg tacatagggc cttcaagagg gaattgaaaa ctaaagaacc tgtaatcatg 180
agtactcttg agactgtacg aatatttctg acagagcagc ctttggaagg actagagaaa 240
ctctaccagg agcccagaga gctgcctcct gaggagagag cccagaatgt cactcggctt 300
ctacgaaagc aggctgagga ggtcaatact gagtgggaaa aattgaacct gcactccgct 360
gactggcaga gaaaaataga tgagacc 387

<210> SEQ ID NO 64
<211> LENGTH: 324
<212> TYPE: DNA
<213> ORGANISM: Homo sapiens

<400> SEQUENCE: 64

```
cttgaaagac tccaggaact tcaagaggcc acggatgagc tggacctcaa gctgcgccaa     60

gctgaggtga tcaagggatc ctggcagccc gtgggcgatc tcctcattga ctctctccaa    120

gatcacctcg agaaagtcaa ggcacttcga ggagaaattg cgcctctgaa agagaacgtg    180

agccacgtca atgaccttgc tcgccagctt accactttgg gcattcagct ctcaccgtat    240

aacctcagca ctctggaaga cctgaacacc agatggaagc ttctgcaggt ggccgtcgag    300

gaccgagtca ggcagctgca tgaa                                           324
```

<210> SEQ ID NO 65
<211> LENGTH: 216
<212> TYPE: DNA
<213> ORGANISM: Homo sapiens

<400> SEQUENCE: 65

```
gcccacaggg actttggtcc agcatctcag cactttcttt ccacgtctgt ccagggtccc     60

tgggagagag ccatctcgcc aaacaaagtg ccctactata tcaaccacga gactcaaaca    120

acttgctggg accatcccaa aatgacagag ctctaccagt ctttagctga cctgaataat    180

gtcagattct cagcttatag gactgccatg aaactc                              216
```

<210> SEQ ID NO 66
<211> LENGTH: 888
<212> TYPE: DNA
<213> ORGANISM: Homo sapiens

<400> SEQUENCE: 66

```
cgaagactgc agaaggccct ttgcttggat ctcttgagcc tgtcagctgc atgtgatgcc     60

ttggaccagc acaacctcaa gcaaaatgac cagcccatgg atatcctgca gattattaat    120

tgtttgacca ctatttatga ccgcctggag caagagcaca acaatttggt caacgtccct    180

ctctgcgtgg atatgtgtct gaactggctg ctgaatgttt atgatacggg acgaacaggg    240

aggatccgtg tcctgtcttt taaaactggc atcatttccc tgtgtaaagc acatttggaa    300

gacaagtaca gataccttt caagcaagtg gcaagttcaa caggattttg tgaccagcgc    360

aggctgggcc tccttctgca tgattctatc caaattccaa gacagttggg tgaagttgca    420

tcctttgggg gcagtaacat tgagccaagt gtccggagct gcttccaatt tgctaataat    480

aagccagaga tcgaagcggc cctcttccta gactggatga gactggaacc ccagtccatg    540

gtgtggctgc ccgtcctgca cagagtggct gctgcagaaa ctgccaagca tcaggccaaa    600

tgtaacatct gcaaagagtg tccaatcatt ggattcaggt acaggagtct aaagcacttt    660

aattatgaca tctgccaaag ctgctttttt tctggtcgag ttgcaaaagg ccataaaatg    720

cactatccca tggtggaata ttgcactccg actacatcag gagaagatgt tcgagacttt    780

gccaaggtac taaaaaacaa atttcgaacc aaaaggtatt ttgcgaagca tccccgaatg    840

ggctacctgc cagtgcagac tgtcttagag gggacaaca tggaaact                 888
```

<210> SEQ ID NO 67
<211> LENGTH: 834
<212> TYPE: DNA
<213> ORGANISM: Homo sapiens

<400> SEQUENCE: 67

```
cccgttactc tgatcaactt ctggccagta gattctgcgc ctgcctcgtc ccctcagctt     60
tcacacgatg atactcattc acgcattgaa cattatgcta gcaggctagc agaaatggaa    120
aacagcaatg gatcttatct aaatgatagc atctctccta atgagagcat agatgatgaa    180
catttgttaa tccagcatta ctgccaaagt ttgaaccagg actccccccct gagccagcct    240
cgtagtcctg cccagatctt gatttcctta gagagtgagg aaagagggga gctagagaga    300
atcctagcag atcttgagga agaaaacagg aatctgcaag cagaatatga ccgtctaaag    360
cagcagcacg aacataaagg cctgtcccca ctgccgtccc ctcctgaaat gatgcccacc    420
tctccccaga gtccccggga tgctgagctc attgctgagg ccaagctact gcgtcaacac    480
aaaggccgcc tggaagccag gatgcaaatc ctggaagacc acaataaaca gctggagtca    540
cagttacaca ggctaaggca gctgctggag caaccccagg cagaggccaa agtgaatggc    600
acaacggtgt cctctccttc tacctctcta cagaggtccg acagcagtca gcctatgctg    660
ctccgagtgg ttggcagtca aacttcggac tccatgggtg aggaagatct tctcagtcct    720
ccccaggaca caagcacagg gttagaggag gtgatggagc aactcaacaa ctccttccct    780
agttcaagag gaagaaatac ccctggaaag ccaatgagag aggacacaat gtag          834
```

<210> SEQ ID NO 68
<211> LENGTH: 252
<212> TYPE: PRT
<213> ORGANISM: Homo sapiens

<400> SEQUENCE: 68

```
Met Leu Trp Trp Glu Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
            20                  25                  30

Gly Lys Gln His Ile Glu Asn Leu Phe Ser Asp Leu Gln Asp Gly Arg
        35                  40                  45

Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Asn Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
        115                 120                 125

Ala Gly Leu Gln Gln Thr Asn Ser Glu Lys Ile Leu Leu Ser Trp Val
    130                 135                 140

Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His
                165                 170                 175

Arg Pro Asp Leu Phe Asp Trp Asn Ser Val Val Cys Gln Gln Ser Ala
            180                 185                 190

Thr Gln Arg Leu Glu His Ala Phe Asn Ile Ala Arg Tyr Gln Leu Gly
        195                 200                 205

Ile Glu Lys Leu Leu Asp Pro Glu Asp Val Asp Thr Thr Tyr Pro Asp
```

```
    210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu
                245                 250


<210> SEQ ID NO 69
<211> LENGTH: 85
<212> TYPE: PRT
<213> ORGANISM: Homo sapiens

<400> SEQUENCE: 69

Met Leu Pro Arg Pro Pro Lys Val Thr Lys Glu Glu His Phe Gln Leu
1               5                   10                  15

His His Gln Met His Tyr Ser Gln Gln Ile Thr Val Ser Leu Ala Gln
            20                  25                  30

Gly Tyr Glu Arg Thr Ser Ser Pro Lys Pro Arg Phe Lys Ser Tyr Ala
        35                  40                  45

Tyr Thr Gln Ala Ala Tyr Val Thr Thr Ser Asp Pro Thr Arg Ser Pro
    50                  55                  60

Phe Pro Ser Gln His Leu Glu Ala Pro Glu Asp Lys Ser Phe Gly Ser
65                  70                  75                  80

Ser Leu Met Glu Ser
                85


<210> SEQ ID NO 70
<211> LENGTH: 109
<212> TYPE: PRT
<213> ORGANISM: Homo sapiens

<400> SEQUENCE: 70

Glu Val Asn Leu Asp Arg Tyr Gln Thr Ala Leu Glu Glu Val Leu Ser
1               5                   10                  15

Trp Leu Leu Ser Ala Glu Asp Thr Leu Gln Ala Gln Gly Glu Ile Ser
            20                  25                  30

Asn Asp Val Glu Val Val Lys Asp Gln Phe His Thr His Glu Gly Tyr
        35                  40                  45

Met Met Asp Leu Thr Ala His Gln Gly Arg Val Gly Asn Ile Leu Gln
    50                  55                  60

Leu Gly Ser Lys Leu Ile Gly Thr Gly Lys Leu Ser Glu Asp Glu Glu
65                  70                  75                  80

Thr Glu Val Gln Glu Gln Met Asn Leu Leu Asn Ser Arg Trp Glu Cys
                85                  90                  95

Leu Arg Val Ala Ser Met Glu Lys Gln Ser Asn Leu His
            100                 105


<210> SEQ ID NO 71
<211> LENGTH: 2
<212> TYPE: PRT
<213> ORGANISM: Homo sapiens
<220> FEATURE:
<221> NAME/KEY: MISC_FEATURE
<223> OTHER INFORMATION: RV-Linker

<400> SEQUENCE: 71

Arg Val
1


<210> SEQ ID NO 72
```

<211> LENGTH: 111
<212> TYPE: PRT
<213> ORGANISM: Homo sapiens

<400> SEQUENCE: 72

```
Leu Leu Lys Trp Gln Arg Leu Thr Glu Glu Gln Cys Leu Phe Ser Ala
1               5                   10                  15

Trp Leu Ser Glu Lys Glu Asp Ala Val Asn Lys Ile His Thr Thr Gly
            20                  25                  30

Phe Lys Asp Gln Asn Glu Met Leu Ser Ser Leu Gln Lys Leu Ala Val
        35                  40                  45

Leu Lys Ala Asp Leu Glu Lys Lys Lys Gln Ser Met Gly Lys Leu Tyr
    50                  55                  60

Ser Leu Lys Gln Asp Leu Leu Ser Thr Leu Lys Asn Lys Ser Val Thr
65                  70                  75                  80

Gln Lys Thr Glu Ala Trp Leu Asp Asn Phe Ala Arg Cys Trp Asp Asn
                85                  90                  95

Leu Val Gln Lys Leu Glu Lys Ser Thr Ala Gln Ile Ser Gln Ala
            100                 105                 110
```

<210> SEQ ID NO 73
<211> LENGTH: 49
<212> TYPE: PRT
<213> ORGANISM: Homo sapiens

<400> SEQUENCE: 73

```
Val Thr Thr Thr Gln Pro Ser Leu Thr Gln Thr Thr Val Met Glu Thr
1               5                   10                  15

Val Thr Thr Val Thr Thr Arg Glu Gln Ile Leu Val Lys His Ala Gln
            20                  25                  30

Glu Glu Leu Pro Pro Pro Pro Pro Gln Lys Lys Arg Gln Ile Thr Val
        35                  40                  45

Asp
```

<210> SEQ ID NO 74
<211> LENGTH: 4
<212> TYPE: PRT
<213> ORGANISM: Homo sapiens
<220> FEATURE:
<221> NAME/KEY: MISC_FEATURE
<223> OTHER INFORMATION: SEAQ linker

<400> SEQUENCE: 74

```
Ser Glu Ala Gln
1
```

<210> SEQ ID NO 75
<211> LENGTH: 20
<212> TYPE: PRT
<213> ORGANISM: Homo sapiens

<400> SEQUENCE: 75

```
Ile His Thr Val Arg Glu Glu Thr Met Met Val Met Thr Glu Asp Met
1               5                   10                  15

Pro Leu Glu Ile
            20
```

<210> SEQ ID NO 76
<211> LENGTH: 109
<212> TYPE: PRT
<213> ORGANISM: Homo sapiens

<400> SEQUENCE: 76

```
Ser Tyr Val Pro Ser Thr Tyr Leu Thr Glu Ile Thr His Val Ser Gln
1               5                   10                  15

Ala Leu Leu Glu Val Glu Gln Leu Leu Asn Ala Pro Asp Leu Cys Ala
            20                  25                  30

Lys Asp Phe Glu Asp Leu Phe Lys Gln Glu Glu Ser Leu Lys Asn Ile
        35                  40                  45

Lys Asp Ser Leu Gln Gln Ser Ser Gly Arg Ile Asp Ile Ile His Ser
    50                  55                  60

Lys Lys Thr Ala Ala Leu Gln Ser Ala Thr Pro Val Glu Arg Val Lys
65                  70                  75                  80

Leu Gln Glu Ala Leu Ser Gln Leu Asp Phe Gln Trp Glu Lys Val Asn
                85                  90                  95

Lys Met Tyr Lys Asp Arg Gln Gly Arg Phe Asp Arg Ser
            100                 105
```

<210> SEQ ID NO 77
<211> LENGTH: 107
<212> TYPE: PRT
<213> ORGANISM: Homo sapiens

<400> SEQUENCE: 77

```
Val Glu Lys Trp Arg Arg Phe His Tyr Asp Ile Lys Ile Phe Asn Gln
1               5                   10                  15

Trp Leu Thr Glu Ala Glu Gln Phe Leu Arg Lys Thr Gln Ile Pro Glu
            20                  25                  30

Asn Trp Glu His Ala Lys Tyr Lys Trp Tyr Leu Lys Glu Leu Gln Asp
        35                  40                  45

Gly Ile Gly Gln Arg Gln Thr Val Val Arg Thr Leu Asn Ala Thr Gly
    50                  55                  60

Glu Glu Ile Ile Gln Gln Ser Ser Lys Thr Asp Ala Ser Ile Leu Gln
65                  70                  75                  80

Glu Lys Leu Gly Ser Leu Asn Leu Arg Trp Gln Glu Val Cys Lys Gln
                85                  90                  95

Leu Ser Asp Arg Lys Lys Arg Leu Glu Glu Gln
            100                 105
```

<210> SEQ ID NO 78
<211> LENGTH: 108
<212> TYPE: PRT
<213> ORGANISM: Homo sapiens

<400> SEQUENCE: 78

```
Leu Glu Arg Leu Gln Glu Leu Gln Glu Ala Thr Asp Glu Leu Asp Leu
1               5                   10                  15

Lys Leu Arg Gln Ala Glu Val Ile Lys Gly Ser Trp Gln Pro Val Gly
            20                  25                  30

Asp Leu Leu Ile Asp Ser Leu Gln Asp His Leu Glu Lys Val Lys Ala
        35                  40                  45

Leu Arg Gly Glu Ile Ala Pro Leu Lys Glu Asn Val Ser His Val Asn
    50                  55                  60

Asp Leu Ala Arg Gln Leu Thr Thr Leu Gly Ile Gln Leu Ser Pro Tyr
65                  70                  75                  80

Asn Leu Ser Thr Leu Glu Asp Leu Asn Thr Arg Trp Lys Leu Leu Gln
                85                  90                  95
```

```
Val Ala Val Glu Asp Arg Val Arg Gln Leu His Glu
            100                 105


<210> SEQ ID NO 79
<211> LENGTH: 72
<212> TYPE: PRT
<213> ORGANISM: Homo sapiens

<400> SEQUENCE: 79

Ala His Arg Asp Phe Gly Pro Ala Ser Gln His Phe Leu Ser Thr Ser
1               5                   10                  15

Val Gln Gly Pro Trp Glu Arg Ala Ile Ser Pro Asn Lys Val Pro Tyr
            20                  25                  30

Tyr Ile Asn His Glu Thr Gln Thr Thr Cys Trp Asp His Pro Lys Met
        35                  40                  45

Thr Glu Leu Tyr Gln Ser Leu Ala Asp Leu Asn Asn Val Arg Phe Ser
    50                  55                  60

Ala Tyr Arg Thr Ala Met Lys Leu
65                  70


<210> SEQ ID NO 80
<211> LENGTH: 299
<212> TYPE: PRT
<213> ORGANISM: Homo sapiens

<400> SEQUENCE: 80

Arg Arg Leu Gln Lys Ala Leu Cys Leu Asp Leu Leu Ser Leu Ser Ala
1               5                   10                  15

Ala Cys Asp Ala Leu Asp Gln His Asn Leu Lys Gln Asn Asp Gln Pro
            20                  25                  30

Met Asp Ile Leu Gln Ile Ile Asn Cys Leu Thr Thr Ile Tyr Asp Arg
        35                  40                  45

Leu Glu Gln Glu His Asn Asn Leu Val Asn Val Pro Leu Cys Val Asp
    50                  55                  60

Met Cys Leu Asn Trp Leu Leu Asn Val Tyr Asp Thr Gly Arg Thr Gly
65                  70                  75                  80

Arg Ile Arg Val Leu Ser Phe Lys Thr Gly Ile Ile Ser Leu Cys Lys
                85                  90                  95

Ala His Leu Glu Asp Lys Tyr Arg Tyr Leu Phe Lys Gln Val Ala Ser
            100                 105                 110

Ser Thr Gly Phe Cys Asp Gln Arg Arg Leu Gly Leu Leu Leu His Asp
        115                 120                 125

Ser Ile Gln Ile Pro Arg Gln Leu Gly Glu Val Ala Ser Phe Gly Gly
    130                 135                 140

Ser Asn Ile Glu Pro Ser Val Arg Ser Cys Phe Gln Phe Ala Asn Asn
145                 150                 155                 160

Lys Pro Glu Ile Glu Ala Ala Leu Phe Leu Asp Trp Met Arg Leu Glu
                165                 170                 175

Pro Gln Ser Met Val Trp Leu Pro Val Leu His Arg Val Ala Ala Ala
            180                 185                 190

Glu Thr Ala Lys His Gln Ala Lys Cys Asn Ile Cys Lys Glu Cys Pro
        195                 200                 205

Ile Ile Gly Phe Arg Tyr Arg Ser Leu Lys His Phe Asn Tyr Asp Ile
    210                 215                 220

Cys Gln Ser Cys Phe Phe Ser Gly Arg Val Ala Lys Gly His Lys Met
225                 230                 235                 240
```

```
His Tyr Pro Met Val Glu Tyr Cys Thr Pro Thr Thr Ser Gly Glu Asp
                245                 250                 255

Val Arg Asp Phe Ala Lys Val Leu Lys Asn Lys Phe Arg Thr Lys Arg
            260                 265                 270

Tyr Phe Ala Lys His Pro Arg Met Gly Tyr Leu Pro Val Gln Thr Val
        275                 280                 285

Leu Glu Gly Asp Asn Met Glu Thr Asp Thr Met
    290                 295


<210> SEQ ID NO 81
<211> LENGTH: 252
<212> TYPE: PRT
<213> ORGANISM: Homo sapiens

<400> SEQUENCE: 81

Met Leu Trp Trp Glu Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
            20                  25                  30

Gly Lys Gln His Ile Glu Asn Leu Phe Ser Asp Leu Gln Asp Gly Arg
        35                  40                  45

Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Asn Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
        115                 120                 125

Ala Gly Leu Gln Gln Thr Asn Ser Glu Lys Ile Leu Leu Ser Trp Val
    130                 135                 140

Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His
                165                 170                 175

Arg Pro Asp Leu Phe Asp Trp Asn Ser Val Val Cys Gln Gln Ser Ala
            180                 185                 190

Thr Gln Arg Leu Glu His Ala Phe Asn Ile Ala Arg Tyr Gln Leu Gly
        195                 200                 205

Ile Glu Lys Leu Leu Asp Pro Glu Asp Val Asp Thr Thr Tyr Pro Asp
    210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu
                245                 250


<210> SEQ ID NO 82
<211> LENGTH: 85
<212> TYPE: PRT
<213> ORGANISM: Homo sapiens

<400> SEQUENCE: 82

Met Leu Pro Arg Pro Pro Lys Val Thr Lys Glu Glu His Phe Gln Leu
1               5                   10                  15
```

```
His His Gln Met His Tyr Ser Gln Gln Ile Thr Val Ser Leu Ala Gln
            20                  25                  30

Gly Tyr Glu Arg Thr Ser Ser Pro Lys Pro Arg Phe Lys Ser Tyr Ala
        35                  40                  45

Tyr Thr Gln Ala Ala Tyr Val Thr Thr Ser Asp Pro Thr Arg Ser Pro
    50                  55                  60

Phe Pro Ser Gln His Leu Glu Ala Pro Glu Asp Lys Ser Phe Gly Ser
65                  70                  75                  80

Ser Leu Met Glu Ser
                85


<210> SEQ ID NO 83
<211> LENGTH: 109
<212> TYPE: PRT
<213> ORGANISM: Homo sapiens

<400> SEQUENCE: 83

Glu Val Asn Leu Asp Arg Tyr Gln Thr Ala Leu Glu Glu Val Leu Ser
1               5                   10                  15

Trp Leu Leu Ser Ala Glu Asp Thr Leu Gln Ala Gln Gly Glu Ile Ser
            20                  25                  30

Asn Asp Val Glu Val Val Lys Asp Gln Phe His Thr His Glu Gly Tyr
        35                  40                  45

Met Met Asp Leu Thr Ala His Gln Gly Arg Val Gly Asn Ile Leu Gln
    50                  55                  60

Leu Gly Ser Lys Leu Ile Gly Thr Gly Lys Leu Ser Glu Asp Glu Glu
65                  70                  75                  80

Thr Glu Val Gln Glu Gln Met Asn Leu Leu Asn Ser Arg Trp Glu Cys
                85                  90                  95

Leu Arg Val Ala Ser Met Glu Lys Gln Ser Asn Leu His
            100                 105


<210> SEQ ID NO 84
<211> LENGTH: 20
<212> TYPE: PRT
<213> ORGANISM: Homo sapiens

<400> SEQUENCE: 84

Ile His Thr Val Arg Glu Glu Thr Met Met Val Met Thr Glu Asp Met
1               5                   10                  15

Pro Leu Glu Ile
            20


<210> SEQ ID NO 85
<211> LENGTH: 109
<212> TYPE: PRT
<213> ORGANISM: Homo sapiens

<400> SEQUENCE: 85

Ser Tyr Val Pro Ser Thr Tyr Leu Thr Glu Ile Thr His Val Ser Gln
1               5                   10                  15

Ala Leu Leu Glu Val Glu Gln Leu Leu Asn Ala Pro Asp Leu Cys Ala
            20                  25                  30

Lys Asp Phe Glu Asp Leu Phe Lys Gln Glu Glu Ser Leu Lys Asn Ile
        35                  40                  45

Lys Asp Ser Leu Gln Gln Ser Ser Gly Arg Ile Asp Ile Ile His Ser
    50                  55                  60

Lys Lys Thr Ala Ala Leu Gln Ser Ala Thr Pro Val Glu Arg Val Lys
```

```
65                  70                  75                  80

Leu Gln Glu Ala Leu Ser Gln Leu Asp Phe Gln Trp Glu Lys Val Asn
                85                  90                  95

Lys Met Tyr Lys Asp Arg Gln Gly Arg Phe Asp Arg Ser
            100                 105


<210> SEQ ID NO 86
<211> LENGTH: 107
<212> TYPE: PRT
<213> ORGANISM: Homo sapiens

<400> SEQUENCE: 86

Val Glu Lys Trp Arg Arg Phe His Tyr Asp Ile Lys Ile Phe Asn Gln
1               5                   10                  15

Trp Leu Thr Glu Ala Glu Gln Phe Leu Arg Lys Thr Gln Ile Pro Glu
            20                  25                  30

Asn Trp Glu His Ala Lys Tyr Lys Trp Tyr Leu Lys Glu Leu Gln Asp
        35                  40                  45

Gly Ile Gly Gln Arg Gln Thr Val Val Arg Thr Leu Asn Ala Thr Gly
    50                  55                  60

Glu Glu Ile Ile Gln Gln Ser Ser Lys Thr Asp Ala Ser Ile Leu Gln
65                  70                  75                  80

Glu Lys Leu Gly Ser Leu Asn Leu Arg Trp Gln Glu Val Cys Lys Gln
                85                  90                  95

Leu Ser Asp Arg Lys Lys Arg Leu Glu Glu Gln
            100                 105


<210> SEQ ID NO 87
<211> LENGTH: 41
<212> TYPE: PRT
<213> ORGANISM: Homo sapiens

<400> SEQUENCE: 87

Ala Pro Gly Leu Thr Thr Ile Gly Ala Ser Pro Thr Gln Thr Val Thr
1               5                   10                  15

Leu Val Thr Gln Pro Val Val Thr Lys Glu Thr Ala Ile Ser Lys Leu
            20                  25                  30

Glu Met Pro Ser Ser Leu Met Leu Glu
        35                  40


<210> SEQ ID NO 88
<211> LENGTH: 129
<212> TYPE: PRT
<213> ORGANISM: Homo sapiens

<400> SEQUENCE: 88

Ser Asp Gln Trp Lys Arg Leu His Leu Ser Leu Gln Glu Leu Leu Val
1               5                   10                  15

Trp Leu Gln Leu Lys Asp Asp Glu Leu Ser Arg Gln Ala Pro Ile Gly
            20                  25                  30

Gly Asp Phe Pro Ala Val Gln Lys Gln Asn Asp Val His Arg Ala Phe
        35                  40                  45

Lys Arg Glu Leu Lys Thr Lys Glu Pro Val Ile Met Ser Thr Leu Glu
    50                  55                  60

Thr Val Arg Ile Phe Leu Thr Glu Gln Pro Leu Glu Gly Leu Glu Lys
65                  70                  75                  80

Leu Tyr Gln Glu Pro Arg Glu Leu Pro Pro Glu Glu Arg Ala Gln Asn
                85                  90                  95
```

Val Thr Arg Leu Leu Arg Lys Gln Ala Glu Glu Val Asn Thr Glu Trp
100 105 110

Glu Lys Leu Asn Leu His Ser Ala Asp Trp Gln Arg Lys Ile Asp Glu
115 120 125

Thr

<210> SEQ ID NO 89
<211> LENGTH: 108
<212> TYPE: PRT
<213> ORGANISM: Homo sapiens

<400> SEQUENCE: 89

Leu Glu Arg Leu Gln Glu Leu Gln Glu Ala Thr Asp Glu Leu Asp Leu
1 5 10 15

Lys Leu Arg Gln Ala Glu Val Ile Lys Gly Ser Trp Gln Pro Val Gly
20 25 30

Asp Leu Leu Ile Asp Ser Leu Gln Asp His Leu Glu Lys Val Lys Ala
35 40 45

Leu Arg Gly Glu Ile Ala Pro Leu Lys Glu Asn Val Ser His Val Asn
50 55 60

Asp Leu Ala Arg Gln Leu Thr Thr Leu Gly Ile Gln Leu Ser Pro Tyr
65 70 75 80

Asn Leu Ser Thr Leu Glu Asp Leu Asn Thr Arg Trp Lys Leu Leu Gln
85 90 95

Val Ala Val Glu Asp Arg Val Arg Gln Leu His Glu
100 105

<210> SEQ ID NO 90
<211> LENGTH: 72
<212> TYPE: PRT
<213> ORGANISM: Homo sapiens

<400> SEQUENCE: 90

Ala His Arg Asp Phe Gly Pro Ala Ser Gln His Phe Leu Ser Thr Ser
1 5 10 15

Val Gln Gly Pro Trp Glu Arg Ala Ile Ser Pro Asn Lys Val Pro Tyr
20 25 30

Tyr Ile Asn His Glu Thr Gln Thr Thr Cys Trp Asp His Pro Lys Met
35 40 45

Thr Glu Leu Tyr Gln Ser Leu Ala Asp Leu Asn Asn Val Arg Phe Ser
50 55 60

Ala Tyr Arg Thr Ala Met Lys Leu
65 70

<210> SEQ ID NO 91
<211> LENGTH: 352
<212> TYPE: PRT
<213> ORGANISM: Homo sapiens

<400> SEQUENCE: 91

Arg Arg Leu Gln Lys Ala Leu Cys Leu Asp Leu Leu Ser Leu Ser Ala
1 5 10 15

Ala Cys Asp Ala Leu Asp Gln His Asn Leu Lys Gln Asn Asp Gln Pro
20 25 30

Met Asp Ile Leu Gln Ile Ile Asn Cys Leu Thr Thr Ile Tyr Asp Arg
35 40 45

Leu Glu Gln Glu His Asn Asn Leu Val Asn Val Pro Leu Cys Val Asp

```
    50                  55                  60

Met Cys Leu Asn Trp Leu Leu Asn Val Tyr Asp Thr Gly Arg Thr Gly
65                  70                  75                  80

Arg Ile Arg Val Leu Ser Phe Lys Thr Gly Ile Ile Ser Leu Cys Lys
                85                  90                  95

Ala His Leu Glu Asp Lys Tyr Arg Tyr Leu Phe Lys Gln Val Ala Ser
            100                 105                 110

Ser Thr Gly Phe Cys Asp Gln Arg Arg Leu Gly Leu Leu Leu His Asp
        115                 120                 125

Ser Ile Gln Ile Pro Arg Gln Leu Gly Glu Val Ala Ser Phe Gly Gly
    130                 135                 140

Ser Asn Ile Glu Pro Ser Val Arg Ser Cys Phe Gln Phe Ala Asn Asn
145                 150                 155                 160

Lys Pro Glu Ile Glu Ala Ala Leu Phe Leu Asp Trp Met Arg Leu Glu
                165                 170                 175

Pro Gln Ser Met Val Trp Leu Pro Val Leu His Arg Val Ala Ala Ala
            180                 185                 190

Glu Thr Ala Lys His Gln Ala Lys Cys Asn Ile Cys Lys Glu Cys Pro
        195                 200                 205

Ile Ile Gly Phe Arg Tyr Arg Ser Leu Lys His Phe Asn Tyr Asp Ile
    210                 215                 220

Cys Gln Ser Cys Phe Phe Ser Gly Arg Val Ala Lys Gly His Lys Met
225                 230                 235                 240

His Tyr Pro Met Val Glu Tyr Cys Thr Pro Thr Thr Ser Gly Glu Asp
                245                 250                 255

Val Arg Asp Phe Ala Lys Val Leu Lys Asn Lys Phe Arg Thr Lys Arg
            260                 265                 270

Tyr Phe Ala Lys His Pro Arg Met Gly Tyr Leu Pro Val Gln Thr Val
        275                 280                 285

Leu Glu Gly Asp Asn Met Glu Thr Pro Ala Gln Ile Leu Ile Ser Leu
    290                 295                 300

Glu Ser Glu Glu Arg Gly Glu Leu Glu Arg Ile Leu Ala Asp Leu Glu
305                 310                 315                 320

Glu Glu Asn Arg Asn Leu Gln Ala Glu Tyr Asp Arg Leu Lys Gln Gln
                325                 330                 335

His Glu His Lys Gly Leu Ser Pro Leu Pro Ser Pro Pro Asp Thr Met
            340                 345                 350
```

<210> SEQ ID NO 92
<211> LENGTH: 322
<212> TYPE: DNA
<213> ORGANISM: Homo sapiens

<400> SEQUENCE: 92

```
ccgccttcgg caccattcct cacgacaccc aaatatggca cgggtgagga atggtgggga     60

gttattttag agcggtgagg aaggtgggca ggcagcaggt gttggcgctc taaaaataac    120

tcccgggagt tattttagag cggaggaatg gtggacaccc aaataggcga cggttcctca    180

cccgtcgcca tatttgggtg tccgccctcg gccggggccg cattcctggg gccgggcggt    240

gctcccgccc gcctcgataa aaggctccgg ggccggcggc ggcccacgag ctacccggag    300

gagcgggagg ctctagacca cc                                             322
```

<210> SEQ ID NO 93
<211> LENGTH: 756

<212> TYPE: DNA
<213> ORGANISM: Homo sapiens

<400> SEQUENCE: 93
atgctgtggt gggaggaagt ggaagattgc tacgagcgcg aggacgtgca gaagaaaacc 60
ttcaccaaat gggtgaacgc ccagttcagc aagttcggca agcagcacat cgagaacctg 120
ttcagcgacc tgcaggacgg cagacggctg ctggacctgc tggaaggcct gaccggccag 180
aagctgccca aagagaaggg cagcaccaga gtgcacgccc tgaacaacgt gaacaaggcc 240
ctgcgggtgc tgcagaacaa caacgtggac ctggtgaaca tcggcagcac cgacatcgtg 300
gacggcaacc acaagctgac cctgggcctg atctggaaca tcatcctgca ctggcaggtc 360
aaaaacgtga tgaagaacat catggccggc ctgcagcaga ccaacagcga gaagatcctg 420
ctgagctggg tgcgccagag cacccggaac tacccccagg tcaacgtgat caacttcacc 480
acctcttgga gcgacggcct ggccctgaac gccctgatcc acagccaccg gcccgacctg 540
ttcgactgga acagcgtggt ctgccagcag agcgccaccc agcggctgga acacgccttc 600
aatatcgcca gataccagct gggcatcgag aagctgctgg atcccgagga cgtggacacc 660
acctaccccg acaagaaatc catcctgatg tatatcacca gcctgttcca ggtgctgccc 720
cagcaggtgt ccatcgaggc catccaggaa gtggaa 756

<210> SEQ ID NO 94
<211> LENGTH: 255
<212> TYPE: DNA
<213> ORGANISM: Homo sapiens

<400> SEQUENCE: 94
atgctgccca gacccccccaa agtgaccaaa gaggaacact tccagctgca ccaccagatg 60
cactacagcc agcagatcac cgtgtccctg gcccagggct acgagagaac cagcagcccc 120
aagccccggt tcaagagcta cgcctatacc caggccgcct acgtgaccac cagcgaccct 180
accagaagcc cattccccag ccagcatctg gaagcccccg aggacaagag cttcggcagc 240
agcctgatgg aaagc 255

<210> SEQ ID NO 95
<211> LENGTH: 327
<212> TYPE: DNA
<213> ORGANISM: Homo sapiens

<400> SEQUENCE: 95
gaagtgaacc tggacagata ccagaccgcc ctggaagagg tgctgagctg gctgctgagc 60
gccgaggata cactgcaggc tcagggcgag atcagcaacg acgtggaagt cgtgaaggac 120
cagttccaca cccacgaggg ctacatgatg gacctgacag cccaccaggg cagagtgggc 180
aacatcctgc agctgggctc caagctgatc ggcaccggca agctgagcga ggacgaagag 240
acagaggtgc aggaacagat gaacctgctg aacagcagat gggagtgcct gcgggtggcc 300
agcatggaaa agcagagcaa cctgcat 327

<210> SEQ ID NO 96
<211> LENGTH: 6
<212> TYPE: DNA
<213> ORGANISM: Homo sapiens

<400> SEQUENCE: 96 agggtc 6

<210> SEQ ID NO 97
<211> LENGTH: 333
<212> TYPE: DNA
<213> ORGANISM: Homo sapiens

<400> SEQUENCE: 97
ctgctgaagt ggcagcggct gaccgaggaa cagtgcctgt ttagcgcctg gctgtccgag 60
aaagaggacg ccgtgaacaa gatccacacc accggcttca aggaccagaa cgagatgctg 120
agcagcctgc agaaactggc cgtgctgaag gccgacctgg aaaagaaaaa gcagtccatg 180
ggcaagctgt actccctgaa gcaggacctg ctgtccaccc tgaagaacaa gagcgtgacc 240
cagaaaaccg aggcctggct ggacaacttc gcccggtgct gggacaacct ggtgcagaag 300
ctggaaaagt ccaccgccca gatctcccag gcc 333

<210> SEQ ID NO 98
<211> LENGTH: 147
<212> TYPE: DNA
<213> ORGANISM: Homo sapiens

<400> SEQUENCE: 98
gtgaccacaa cacagcccag cctgacccag accaccgtga tggaaaccgt gacaacagtg 60
accacccggg aacagatcct cgtgaagcac gcccaggaag aactgccccc tccacccccc 120
cagaagaaac ggcagatcac agtggac 147

<210> SEQ ID NO 99
<211> LENGTH: 12
<212> TYPE: DNA
<213> ORGANISM: Homo sapiens

<400> SEQUENCE: 99
agtgaagctc ag 12

<210> SEQ ID NO 100
<211> LENGTH: 60
<212> TYPE: DNA
<213> ORGANISM: Homo sapiens

<400> SEQUENCE: 100
atccacaccg tgcgggaaga gacaatgatg gtcatgacag aggacatgcc cctggaaatc 60

<210> SEQ ID NO 101
<211> LENGTH: 327
<212> TYPE: DNA
<213> ORGANISM: Homo sapiens

<400> SEQUENCE: 101
agctacgtgc ccagcaccta cctgaccgag atcacccatg tgtcccaggc cctgctggaa 60
gtggaacagc tgctgaacgc ccccgacctg tgcgccaagg atttcgagga cctgttcaag 120
caggaagaga gcctgaagaa tatcaaggat agcctgcagc agagcagcgg ccggatcgac 180
atcatccaca gcaagaaaac agccgccctg cagagcgcca cccccgtgga aagagtgaaa 240
ctgcaggaag ccctgtccca gctggacttc cagtgggaga aagtgaacaa aatgtacaag 300
gaccggcagg gcagattcga ccgcagc 327

<210> SEQ ID NO 102
<211> LENGTH: 321
<212> TYPE: DNA
<213> ORGANISM: Homo sapiens

<400> SEQUENCE: 102
gtggaaaagt ggcggcggtt ccactacgac atcaagatct tcaaccagtg gctgacagag 60
gccgagcagt tcctgagaaa gacccagatc cccgagaact gggagcacgc caagtacaag 120
tggtatctga aagagctgca ggacggcatc ggccagagac agacagtcgt gcggaccctg 180
aatgccaccg gcgaggaaat catccagcag tccagcaaga ccgacgccag cattctgcag 240
gaaaagctgg gcagcctgaa cctgcggtgg caggaagtgt gcaagcagct gtccgaccgg 300
aagaagcggc tggaagaaca g 321

<210> SEQ ID NO 103
<211> LENGTH: 324
<212> TYPE: DNA
<213> ORGANISM: Homo sapiens

<400> SEQUENCE: 103
ctggaacggc tgcaggaact gcaggaggcc accgacgagc tggacctgaa actgagacag 60
gccgaagtga tcaagggcag ctggcagcca gtgggcgacc tgctgatcga ctccctgcag 120
gaccatctgg aaaaagtgaa ggccctgaga ggcgagatcg ccccccctgaa agaaaacgtg 180
tcccacgtga acgacctggc ccggcagctg acaacactgg gcattcagct gagcccctac 240
aacctgagca cactggaaga tctgaacacc cggtggaagc tgctgcaggt ggccgtggaa 300
gatagagtgc ggcagctgca cgag 324

<210> SEQ ID NO 104
<211> LENGTH: 215
<212> TYPE: DNA
<213> ORGANISM: Homo sapiens

<400> SEQUENCE: 104
gcccacagag attttggccc tgcctcccag cacttcctga gcaccagtgt gcagggccct 60
tgggagagag ccatctcccc taacaaggtg ccctactaca tcaaccacga gacacagacc 120
acctgttggg accaccccaa gatgaccgag ctgtaccaga gcctggctga cctgaacaac 180
gtgcggttca ggcctaccgg accgccatga agctg 215

<210> SEQ ID NO 105
<211> LENGTH: 1068
<212> TYPE: DNA
<213> ORGANISM: Homo sapiens

<400> SEQUENCE: 105
cggagactgc agaaagctct gtgcctggat ctgctgtccc tgtccgccgc ctgtgatgcc 60
ctggaccagc acaatctgaa gcagaacgac cagcccatgg atatcctgca gatcatcaac 120
tgcctgacca ccatctacga ccggctggaa caggaacaca acaatctcgt gaacgtgccc 180
ctgtgcgtgg acatgtgcct gaattggctg ctgaatgtgt acgacaccgg ccggacaggc 240
cggatcagag tgctgtcctt caagaccggc atcatcagcc tgtgcaaagc ccacctggaa 300
gataagtacc ggtatctgtt caaacaggtg gcctctagca ccggcttttg cgaccagaga 360
aggctgggcc tgctgctgca cgacagcatc cagatcccta gacagctggg cgaagtggcc 420
agctttggcg gcagcaacat cgagcctagc gtgcggagct gcttccagtt cgccaacaac 480
aagcccgaga tcgaggccgc cctgttcctg gactggatga gactggaacc ccagagcatg 540
gtgtggctgc ccgtgctgca tagagtggcc gctgccgaga cagccaagca ccaggccaag 600

```
tgcaacatct gcaaagagtg ccccatcatc ggcttccggt acagaagcct gaagcacttc    660

aactacgata tctgccagag ctgtttcttc agcggcaggg tggccaaggg ccacaaaatg    720

cactacccca tggtggaata ctgcaccccc accacaagcg gcgaggatgt gcgggatttc    780

gccaaggtgc tgaaaaacaa gttccggacc aagcggtact tcgccaaaca cccccggatg    840

ggctacctgc ctgtgcagac agtgctggaa ggcgacaaca tggaaaccga caccatgtga    900

tgatgatttg ggcagagcga tggagtcctt agtatcagtc atgacagatg aagaaggagc    960

agaataaatg ttttacaact cctgattccc gcatgcggcc agcttatcga taccgtcgaa   1020

ataaaagatc cttattttca ttggatctgt gtgttggttt tttgtgtg                1068
```

<210> SEQ ID NO 106
<211> LENGTH: 334
<212> TYPE: DNA
<213> ORGANISM: Homo sapiens

<400> SEQUENCE: 106

```
cctgcggccg ccttcggcac cattcctcac gacacccaaa tatggcgacg ggtgaggaat     60

ggtggggagt tatttttaga gcggtgagga aggtgggcag gcagcaggtg ttggcgctct    120

aaaaataact cccgggagtt atttttagag cggaggaatg gtggacaccc aaatatggcg    180

acggttcctc acccgtcgcc atatttgggt gtccgccctc ggccggggcc gcattcctgg    240

gggccgggcg gtgctcccgc ccgcctcgat aaaaggctcc ggggccggcg gcggcccacg    300

agctacccgg aggagcggga ggctctagac cacc                                334
```

<210> SEQ ID NO 107
<211> LENGTH: 756
<212> TYPE: DNA
<213> ORGANISM: Homo sapiens

<400> SEQUENCE: 107

```
atgctgtggt gggaggaagt ggaagattgc tacgagcgcg aggacgtgca gaagaaaacc     60

ttcaccaaat gggtgaacgc ccagttcagc aagttcggca agcagcacat cgagaacctg    120

ttcagcgacc tgcaggacgg cagacggctg ctggacctgc tggaaggcct gaccggccag    180

aagctgccca aagagaaggg cagcaccaga gtgcacgccc tgaacaacgt gaacaaggcc    240

ctgcgggtgc tgcagaacaa caacgtggac ctggtgaaca tcggcagcac cgacatcgtg    300

gacggcaacc acaagctgac cctgggcctg atctggaaca tcatcctgca ctggcaggtc    360

aaaaacgtga tgaagaacat catggccggc ctgcagcaga ccaacagcga gaagatcctg    420

ctgagctggg tgcgccagag cacccggaac tacccccagg tcaacgtgat caacttcacc    480

acctcttgga gcgacggcct ggccctgaac gccctgatcc acagccaccg gcccgacctg    540

ttcgactgga acagcgtggt ctgccagcag agcgccaccc agcggctgga acacgccttc    600

aatatcgcca gataccagct gggcatcgag aagctgctgg atcccgagga cgtggacacc    660

acctaccccg acaagaaatc catcctgatg tatatcacca gcctgttcca ggtgctgccc    720

cagcaggtgt ccatcgaggc catccaggaa gtggaa                              756
```

<210> SEQ ID NO 108
<211> LENGTH: 255
<212> TYPE: DNA
<213> ORGANISM: Homo sapiens

<400> SEQUENCE: 108

```
atgctgccca gaccccccaa agtgaccaaa gaggaacact tccagctgca ccaccagatg     60
```

```
cactacagcc agcagatcac cgtgtccctg gctcagggct acgagcggac cagcagcccc    120

aagccccggt tcaagagcta cgcctacacc caggccgcct acgtgaccac cagcgacccc    180

accagaagcc cattccccag ccagcatctg gaagcccccg aggacaagag cttcggcagc    240

agcctgatgg aaagc                                                     255


<210> SEQ ID NO 109
<211> LENGTH: 327
<212> TYPE: DNA
<213> ORGANISM: Homo sapiens

<400> SEQUENCE: 109

gaagtgaacc tggacagata ccagaccgcc ctggaagagg tgctgtcctg gctgctgagc     60

gccgaggata cactgcaggc ccagggcgag atcagcaacg acgtggaagt ggtgaaagac    120

cagttccaca cccacgaggg ctacatgatg gacctgaccg cccaccaggg cagagtgggc    180

aacatcctgc agctgggcag caagctgatc ggcaccggca agctgagcga ggacgaagag    240

acagaggtgc aggaacagat gaacctgctg aacagcagat gggagtgcct gcgggtggcc    300

agcatggaaa agcagagcaa cctgcac                                        327


<210> SEQ ID NO 110
<211> LENGTH: 60
<212> TYPE: DNA
<213> ORGANISM: Homo sapiens

<400> SEQUENCE: 110

atccacaccg tgcgggaaga gacaatgatg gtgatgaccg aggacatgcc cctggaaatc     60


<210> SEQ ID NO 111
<211> LENGTH: 327
<212> TYPE: DNA
<213> ORGANISM: Homo sapiens

<400> SEQUENCE: 111

agctacgtgc ccagcaccta cctgaccgag atcacccacg tgtcccaggc tctgctggaa     60

gtggaacagc tgctgaacgc ccccgacctg tgcgccaagg acttcgagga tctgttcaag    120

caggaagaga gcctgaagaa tatcaaggac tccctgcagc agtccagcgg ccggatcgac    180

atcatccaca gcaagaaaac agccgccctg cagtccgcca cccccgtgga aagagtgaag    240

ctgcaggaag ccctgagcca gctggacttc cagtgggaga aagtgaacaa gatgtacaag    300

gaccggcagg gcagattcga ccgcagc                                        327


<210> SEQ ID NO 112
<211> LENGTH: 321
<212> TYPE: DNA
<213> ORGANISM: Homo sapiens

<400> SEQUENCE: 112

gtggaaaagt ggcggcggtt ccactacgac atcaagatct tcaaccagtg gctgaccgag     60

gccgagcagt tcctgagaaa gacccagatc cccgagaact gggagcacgc caagtacaag    120

tggtatctga aagaactgca ggatggcatc ggccagcggc agaccgtggt gcgcacactg    180

aatgccaccg gcgaggaaat catccagcag agcagcaaga ccgacgccag catcctgcag    240

gaaaagctgg gctccctgaa cctgcggtgg caggaagtgt gcaagcagct gagcgaccgg    300

aagaagaggc tggaagaaca g                                              321
```

<210> SEQ ID NO 113
<211> LENGTH: 123
<212> TYPE: DNA
<213> ORGANISM: Homo sapiens

<400> SEQUENCE: 113
gcccctggcc tgaccaccat cggcgccagc cctacccaga ccgtgaccct ggtgacacag 60
cccgtggtga caaaagagac agccatctcc aagctggaaa tgcccagctc cctgatgctg 120
gaa 123

<210> SEQ ID NO 114
<211> LENGTH: 387
<212> TYPE: DNA
<213> ORGANISM: Homo sapiens

<400> SEQUENCE: 114
tctgaccagt ggaagcgtct gcacctttct ctgcaggaac ttctggtgtg gctacagctg 60
aaagatgatg aattaagccg gcaggcacct attggaggcg actttccagc agttcagaag 120
cagaacgatg tacatagggc cttcaagagg gaattgaaaa ctaaagaacc tgtaatcatg 180
agtactcttg agactgtacg aatatttctg acagagcagc ctttggaagg actagagaaa 240
ctctaccagg agcccagaga gctgcctcct gaggagagag cccagaatgt cactcggctt 300
ctacgaaagc aggctgagga ggtcaatact gagtgggaaa aattgaacct gcactccgct 360
gactggcaga gaaaaataga tgagacc 387

<210> SEQ ID NO 115
<211> LENGTH: 324
<212> TYPE: DNA
<213> ORGANISM: Homo sapiens

<400> SEQUENCE: 115
ctggaaaggc tgcaggaact gcaggaggcc accgacgagc tggacctgaa gctgcggcag 60
gccgaagtga tcaagggcag ctggcagccc gtgggcgacc tgctgatcga cagcctgcag 120
gaccacctgg aaaaagtgaa ggccctgaga ggcgagatcg ccccccctgaa agaaaacgtg 180 tcccacgtga acgacctggc ccggcagctg accaccctgg gcatccagct gagcccctac 240
aacctgagca ccctggaaga tctgaacacc cggtggaagc tgctgcaggt ggccgtggaa 300
gatagagtgc ggcagctgca cgag 324

<210> SEQ ID NO 116
<211> LENGTH: 216
<212> TYPE: DNA
<213> ORGANISM: Homo sapiens

<400> SEQUENCE: 116
gcccacagag actttggccc tgccagccag cacttcctga gcacctctgt gcagggaccc 60
tgggagagag ccatcagccc caacaaggtg ccctactaca tcaaccacga gacacagacc 120
acctgttggg accaccccaa gatgaccgag ctgtaccaga gcctggccga cctgaacaat 180
gtgcggttca gcgcctaccg gaccgccatg aagctg 216

<210> SEQ ID NO 117
<211> LENGTH: 1059
<212> TYPE: DNA
<213> ORGANISM: Homo sapiens

<400> SEQUENCE: 117

```
aggcggctgc agaaagctct gtgcctggat ctgctgagcc tgagcgccgc ctgcgacgcc      60
ctggaccagc acaacctgaa gcagaacgac cagcccatgg atatcctgca gatcatcaac     120
tgcctgacca caatctacga caggctggaa caggaacaca acaatctggt caacgtgccc     180
ctgtgcgtgg acatgtgcct gaattggctg ctgaatgtgt acgacaccgg ccggaccggc     240
agaatccggg tgctgagctt caagaccggc atcatcagcc tgtgcaaggc ccacctggaa     300
gataagtacc gctacctgtt caaacaggtg gccagctcca ccggcttttg cgaccagcgg     360
agactgggcc tgctgctgca cgacagcatc cagatcccca gacagctggg cgaggtggcc     420
tccttcggcg gcagcaacat tgagcccagc gtgcggagct gcttccagtt cgccaacaac     480
aagcccgaga tcgaggccgc cctgttcctg gactggatga gactggaacc ccagagcatg     540
gtgtggctgc ccgtgctgca tcgggtggcc gctgccgaga cagccaagca ccaggccaag     600
tgcaacatct gcaaagagtg ccccatcatc ggcttccggt acagaagcct gaagcacttc     660
aactacgata tctgccagag ctgcttcttc agcggcagag tggccaaggg ccacaaaatg     720
cactacccca tggtggaata ctgcaccccc accaccagcg gcgaggatgt gcgggacttc     780
gccaaggtgc tgaaaaacaa gttccggacc aagcggtact ttgccaagca cccccggatg     840
ggctacctgc ccgtgcagac agtgctggaa ggcgacaaca tggaaacccc tgcccagatc     900
ctgatcagcc tggaaagcga ggaacggggc gagctggaac ggatcctggc cgatctggaa     960
gaggaaaacc ggaacctgca ggccgagtac gaccggctga agcagcagca cgagcacaag    1020
ggcctgagcc ccctgcctag ccccccctgac accatgtga                          1059
```

<210> SEQ ID NO 118
<211> LENGTH: 1327
<212> TYPE: PRT
<213> ORGANISM: Homo sapiens

<400> SEQUENCE: 118

```
Met Leu Trp Trp Glu Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
            20                  25                  30

Gly Lys Gln His Ile Glu Asn Leu Phe Ser Asp Leu Gln Asp Gly Arg
        35                  40                  45

Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Asn Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
        115                 120                 125

Ala Gly Leu Gln Gln Thr Asn Ser Glu Lys Ile Leu Leu Ser Trp Val
    130                 135                 140

Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His
                165                 170                 175

Arg Pro Asp Leu Phe Asp Trp Asn Ser Val Val Cys Gln Gln Ser Ala
```

```
            180                 185                 190

Thr Gln Arg Leu Glu His Ala Phe Asn Ile Ala Arg Tyr Gln Leu Gly
        195                 200                 205

Ile Glu Lys Leu Leu Asp Pro Glu Asp Val Asp Thr Thr Tyr Pro Asp
    210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu Met Leu Pro Arg
                245                 250                 255

Pro Pro Lys Val Thr Lys Glu Glu His Phe Gln Leu His His Gln Met
            260                 265                 270

His Tyr Ser Gln Gln Ile Thr Val Ser Leu Ala Gln Gly Tyr Glu Arg
        275                 280                 285

Thr Ser Ser Pro Lys Pro Arg Phe Lys Ser Tyr Ala Tyr Thr Gln Ala
    290                 295                 300

Ala Tyr Val Thr Thr Ser Asp Pro Thr Arg Ser Pro Phe Pro Ser Gln
305                 310                 315                 320

His Leu Glu Ala Pro Glu Asp Lys Ser Phe Gly Ser Ser Leu Met Glu
                325                 330                 335

Ser Glu Val Asn Leu Asp Arg Tyr Gln Thr Ala Leu Glu Glu Val Leu
            340                 345                 350

Ser Trp Leu Leu Ser Ala Glu Asp Thr Leu Gln Ala Gln Gly Glu Ile
        355                 360                 365

Ser Asn Asp Val Glu Val Val Lys Asp Gln Phe His Thr His Glu Gly
    370                 375                 380

Tyr Met Met Asp Leu Thr Ala His Gln Gly Arg Val Gly Asn Ile Leu
385                 390                 395                 400

Gln Leu Gly Ser Lys Leu Ile Gly Thr Gly Lys Leu Ser Glu Asp Glu
                405                 410                 415

Glu Thr Glu Val Gln Glu Gln Met Asn Leu Leu Asn Ser Arg Trp Glu
            420                 425                 430

Cys Leu Arg Val Ala Ser Met Glu Lys Gln Ser Asn Leu His Arg Val
        435                 440                 445

Leu Leu Lys Trp Gln Arg Leu Thr Glu Glu Gln Cys Leu Phe Ser Ala
    450                 455                 460

Trp Leu Ser Glu Lys Glu Asp Ala Val Asn Lys Ile His Thr Thr Gly
465                 470                 475                 480

Phe Lys Asp Gln Asn Glu Met Leu Ser Ser Leu Gln Lys Leu Ala Val
                485                 490                 495

Leu Lys Ala Asp Leu Glu Lys Lys Lys Gln Ser Met Gly Lys Leu Tyr
            500                 505                 510

Ser Leu Lys Gln Asp Leu Leu Ser Thr Leu Lys Asn Lys Ser Val Thr
        515                 520                 525

Gln Lys Thr Glu Ala Trp Leu Asp Asn Phe Ala Arg Cys Trp Asp Asn
    530                 535                 540

Leu Val Gln Lys Leu Glu Lys Ser Thr Ala Gln Ile Ser Gln Ala Val
545                 550                 555                 560

Thr Thr Thr Gln Pro Ser Leu Thr Gln Thr Thr Val Met Glu Thr Val
                565                 570                 575

Thr Thr Val Thr Thr Arg Glu Gln Ile Leu Val Lys His Ala Gln Glu
            580                 585                 590

Glu Leu Pro Pro Pro Pro Pro Gln Lys Lys Arg Gln Ile Thr Val Asp
        595                 600                 605
```

```
Ser Glu Ala Gln Ile His Thr Val Arg Glu Glu Thr Met Met Val Met
    610                 615                 620

Thr Glu Asp Met Pro Leu Glu Ile Ser Tyr Val Pro Ser Thr Tyr Leu
625                 630                 635                 640

Thr Glu Ile Thr His Val Ser Gln Ala Leu Leu Glu Val Glu Gln Leu
                645                 650                 655

Leu Asn Ala Pro Asp Leu Cys Ala Lys Asp Phe Glu Asp Leu Phe Lys
            660                 665                 670

Gln Glu Glu Ser Leu Lys Asn Ile Lys Asp Ser Leu Gln Gln Ser Ser
        675                 680                 685

Gly Arg Ile Asp Ile Ile His Ser Lys Lys Thr Ala Ala Leu Gln Ser
    690                 695                 700

Ala Thr Pro Val Glu Arg Val Lys Leu Gln Glu Ala Leu Ser Gln Leu
705                 710                 715                 720

Asp Phe Gln Trp Glu Lys Val Asn Lys Met Tyr Lys Asp Arg Gln Gly
                725                 730                 735

Arg Phe Asp Arg Ser Val Glu Lys Trp Arg Arg Phe His Tyr Asp Ile
            740                 745                 750

Lys Ile Phe Asn Gln Trp Leu Thr Glu Ala Glu Gln Phe Leu Arg Lys
        755                 760                 765

Thr Gln Ile Pro Glu Asn Trp Glu His Ala Lys Tyr Lys Trp Tyr Leu
    770                 775                 780

Lys Glu Leu Gln Asp Gly Ile Gly Gln Arg Gln Thr Val Val Arg Thr
785                 790                 795                 800

Leu Asn Ala Thr Gly Glu Glu Ile Ile Gln Gln Ser Ser Lys Thr Asp
                805                 810                 815

Ala Ser Ile Leu Gln Glu Lys Leu Gly Ser Leu Asn Leu Arg Trp Gln
            820                 825                 830

Glu Val Cys Lys Gln Leu Ser Asp Arg Lys Lys Arg Leu Glu Glu Gln
        835                 840                 845

Leu Glu Arg Leu Gln Glu Leu Gln Glu Ala Thr Asp Glu Leu Asp Leu
    850                 855                 860

Lys Leu Arg Gln Ala Glu Val Ile Lys Gly Ser Trp Gln Pro Val Gly
865                 870                 875                 880

Asp Leu Leu Ile Asp Ser Leu Gln Asp His Leu Glu Lys Val Lys Ala
                885                 890                 895

Leu Arg Gly Glu Ile Ala Pro Leu Lys Glu Asn Val Ser His Val Asn
            900                 905                 910

Asp Leu Ala Arg Gln Leu Thr Thr Leu Gly Ile Gln Leu Ser Pro Tyr
        915                 920                 925

Asn Leu Ser Thr Leu Glu Asp Leu Asn Thr Arg Trp Lys Leu Leu Gln
    930                 935                 940

Val Ala Val Glu Asp Arg Val Arg Gln Leu His Glu Ala His Arg Asp
945                 950                 955                 960

Phe Gly Pro Ala Ser Gln His Phe Leu Ser Thr Ser Val Gln Gly Pro
                965                 970                 975

Trp Glu Arg Ala Ile Ser Pro Asn Lys Val Pro Tyr Tyr Ile Asn His
            980                 985                 990

Glu Thr Gln Thr Thr Cys Trp Asp  His Pro Lys Met Thr  Glu Leu Tyr
        995                 1000                1005

Gln Ser  Leu Ala Asp Leu Asn  Asn Val Arg Phe Ser  Ala Tyr Arg
    1010                1015                1020
```

```
Thr Ala  Met Lys Leu Arg Arg  Leu Gln Lys Ala Leu  Cys Leu Asp
    1025                 1030                 1035

Leu Leu  Ser Leu Ser Ala Ala  Cys Asp Ala Leu Asp  Gln His Asn
    1040                 1045                 1050

Leu Lys  Gln Asn Asp Gln Pro  Met Asp Ile Leu Gln  Ile Ile Asn
    1055                 1060                 1065

Cys Leu  Thr Thr Ile Tyr Asp  Arg Leu Glu Gln Glu  His Asn Asn
    1070                 1075                 1080

Leu Val  Asn Val Pro Leu Cys  Val Asp Met Cys Leu  Asn Trp Leu
    1085                 1090                 1095

Leu Asn  Val Tyr Asp Thr Gly  Arg Thr Gly Arg Ile  Arg Val Leu
    1100                 1105                 1110

Ser Phe  Lys Thr Gly Ile Ile  Ser Leu Cys Lys Ala  His Leu Glu
    1115                 1120                 1125

Asp Lys  Tyr Arg Tyr Leu Phe  Lys Gln Val Ala Ser  Ser Thr Gly
    1130                 1135                 1140

Phe Cys  Asp Gln Arg Arg Leu  Gly Leu Leu Leu His  Asp Ser Ile
    1145                 1150                 1155

Gln Ile  Pro Arg Gln Leu Gly  Glu Val Ala Ser Phe  Gly Gly Ser
    1160                 1165                 1170

Asn Ile  Glu Pro Ser Val Arg  Ser Cys Phe Gln Phe  Ala Asn Asn
    1175                 1180                 1185

Lys Pro  Glu Ile Glu Ala Ala  Leu Phe Leu Asp Trp  Met Arg Leu
    1190                 1195                 1200

Glu Pro  Gln Ser Met Val Trp  Leu Pro Val Leu His  Arg Val Ala
    1205                 1210                 1215

Ala Ala  Glu Thr Ala Lys His  Gln Ala Lys Cys Asn  Ile Cys Lys
    1220                 1225                 1230

Glu Cys  Pro Ile Ile Gly Phe  Arg Tyr Arg Ser Leu  Lys His Phe
    1235                 1240                 1245

Asn Tyr  Asp Ile Cys Gln Ser  Cys Phe Phe Ser Gly  Arg Val Ala
    1250                 1255                 1260

Lys Gly  His Lys Met His Tyr  Pro Met Val Glu Tyr  Cys Thr Pro
    1265                 1270                 1275

Thr Thr  Ser Gly Glu Asp Val  Arg Asp Phe Ala Lys  Val Leu Lys
    1280                 1285                 1290

Asn Lys  Phe Arg Thr Lys Arg  Tyr Phe Ala Lys His  Pro Arg Met
    1295                 1300                 1305

Gly Tyr  Leu Pro Val Gln Thr  Val Leu Glu Gly Asp  Asn Met Glu
    1310                 1315                 1320

Thr Asp  Thr Met
    1325
```

<210> SEQ ID NO 119
<211> LENGTH: 1321
<212> TYPE: PRT
<213> ORGANISM: Homo sapiens

<400> SEQUENCE: 119

```
Met Leu Trp Trp Glu Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
            20                  25                  30

Gly Lys Gln His Ile Glu Asn Leu Phe Ser Asp Leu Gln Asp Gly Arg
        35                  40                  45
```

```
Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Asn Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
        115                 120                 125

Ala Gly Leu Gln Gln Thr Asn Ser Glu Lys Ile Leu Leu Ser Trp Val
    130                 135                 140

Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His
                165                 170                 175

Arg Pro Asp Leu Phe Asp Trp Asn Ser Val Val Cys Gln Gln Ser Ala
            180                 185                 190

Thr Gln Arg Leu Glu His Ala Phe Asn Ile Ala Arg Tyr Gln Leu Gly
        195                 200                 205

Ile Glu Lys Leu Leu Asp Pro Glu Asp Val Asp Thr Thr Tyr Pro Asp
    210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu Met Leu Pro Arg
                245                 250                 255

Pro Pro Lys Val Thr Lys Glu Glu His Phe Gln Leu His His Gln Met
            260                 265                 270

His Tyr Ser Gln Gln Ile Thr Val Ser Leu Ala Gln Gly Tyr Glu Arg
        275                 280                 285

Thr Ser Ser Pro Lys Pro Arg Phe Lys Ser Tyr Ala Tyr Thr Gln Ala
    290                 295                 300

Ala Tyr Val Thr Thr Ser Asp Pro Thr Arg Ser Pro Phe Pro Ser Gln
305                 310                 315                 320

His Leu Glu Ala Pro Glu Asp Lys Ser Phe Gly Ser Ser Leu Met Glu
                325                 330                 335

Ser Glu Val Asn Leu Asp Arg Tyr Gln Thr Ala Leu Glu Glu Val Leu
            340                 345                 350

Ser Trp Leu Leu Ser Ala Glu Asp Thr Leu Gln Ala Gln Gly Glu Ile
        355                 360                 365

Ser Asn Asp Val Glu Val Val Lys Asp Gln Phe His Thr His Glu Gly
    370                 375                 380

Tyr Met Met Asp Leu Thr Ala His Gln Gly Arg Val Gly Asn Ile Leu
385                 390                 395                 400

Gln Leu Gly Ser Lys Leu Ile Gly Thr Gly Lys Leu Ser Glu Asp Glu
                405                 410                 415

Glu Thr Glu Val Gln Glu Gln Met Asn Leu Leu Asn Ser Arg Trp Glu
            420                 425                 430

Cys Leu Arg Val Ala Ser Met Glu Lys Gln Ser Asn Leu His Leu Leu
        435                 440                 445

Lys Trp Gln Arg Leu Thr Glu Glu Gln Cys Leu Phe Ser Ala Trp Leu
    450                 455                 460
```

```
Ser Glu Lys Glu Asp Ala Val Asn Lys Ile His Thr Thr Gly Phe Lys
465                 470                 475                 480

Asp Gln Asn Glu Met Leu Ser Ser Leu Gln Lys Leu Ala Val Leu Lys
                485                 490                 495

Ala Asp Leu Glu Lys Lys Lys Gln Ser Met Gly Lys Leu Tyr Ser Leu
            500                 505                 510

Lys Gln Asp Leu Leu Ser Thr Leu Lys Asn Lys Ser Val Thr Gln Lys
        515                 520                 525

Thr Glu Ala Trp Leu Asp Asn Phe Ala Arg Cys Trp Asp Asn Leu Val
    530                 535                 540

Gln Lys Leu Glu Lys Ser Thr Ala Gln Ile Ser Gln Ala Val Thr Thr
545                 550                 555                 560

Thr Gln Pro Ser Leu Thr Gln Thr Thr Val Met Glu Thr Val Thr Thr
                565                 570                 575

Val Thr Thr Arg Glu Gln Ile Leu Val Lys His Ala Gln Glu Glu Leu
            580                 585                 590

Pro Pro Pro Pro Pro Gln Lys Lys Arg Gln Ile Thr Val Asp Ile His
        595                 600                 605

Thr Val Arg Glu Glu Thr Met Met Val Met Thr Glu Asp Met Pro Leu
    610                 615                 620

Glu Ile Ser Tyr Val Pro Ser Thr Tyr Leu Thr Glu Ile Thr His Val
625                 630                 635                 640

Ser Gln Ala Leu Leu Glu Val Glu Gln Leu Leu Asn Ala Pro Asp Leu
                645                 650                 655

Cys Ala Lys Asp Phe Glu Asp Leu Phe Lys Gln Glu Glu Ser Leu Lys
            660                 665                 670

Asn Ile Lys Asp Ser Leu Gln Gln Ser Ser Gly Arg Ile Asp Ile Ile
        675                 680                 685

His Ser Lys Lys Thr Ala Ala Leu Gln Ser Ala Thr Pro Val Glu Arg
    690                 695                 700

Val Lys Leu Gln Glu Ala Leu Ser Gln Leu Asp Phe Gln Trp Glu Lys
705                 710                 715                 720

Val Asn Lys Met Tyr Lys Asp Arg Gln Gly Arg Phe Asp Arg Ser Val
                725                 730                 735

Glu Lys Trp Arg Arg Phe His Tyr Asp Ile Lys Ile Phe Asn Gln Trp
            740                 745                 750

Leu Thr Glu Ala Glu Gln Phe Leu Arg Lys Thr Gln Ile Pro Glu Asn
        755                 760                 765

Trp Glu His Ala Lys Tyr Lys Trp Tyr Leu Lys Glu Leu Gln Asp Gly
    770                 775                 780

Ile Gly Gln Arg Gln Thr Val Val Arg Thr Leu Asn Ala Thr Gly Glu
785                 790                 795                 800

Glu Ile Ile Gln Gln Ser Ser Lys Thr Asp Ala Ser Ile Leu Gln Glu
                805                 810                 815

Lys Leu Gly Ser Leu Asn Leu Arg Trp Gln Glu Val Cys Lys Gln Leu
            820                 825                 830

Ser Asp Arg Lys Lys Arg Leu Glu Glu Gln Leu Glu Arg Leu Gln Glu
        835                 840                 845

Leu Gln Glu Ala Thr Asp Glu Leu Asp Leu Lys Leu Arg Gln Ala Glu
    850                 855                 860

Val Ile Lys Gly Ser Trp Gln Pro Val Gly Asp Leu Leu Ile Asp Ser
865                 870                 875                 880

Leu Gln Asp His Leu Glu Lys Val Lys Ala Leu Arg Gly Glu Ile Ala
```

```
                885                 890                 895

Pro Leu Lys Glu Asn Val Ser His Val Asn Asp Leu Ala Arg Gln Leu
            900                 905                 910

Thr Thr Leu Gly Ile Gln Leu Ser Pro Tyr Asn Leu Ser Thr Leu Glu
        915                 920                 925

Asp Leu Asn Thr Arg Trp Lys Leu Leu Gln Val Ala Val Glu Asp Arg
    930                 935                 940

Val Arg Gln Leu His Glu Ala His Arg Asp Phe Gly Pro Ala Ser Gln
945                 950                 955                 960

His Phe Leu Ser Thr Ser Val Gln Gly Pro Trp Glu Arg Ala Ile Ser
                965                 970                 975

Pro Asn Lys Val Pro Tyr Tyr Ile Asn His Glu Thr Gln Thr Thr Cys
            980                 985                 990

Trp Asp His Pro Lys Met Thr Glu  Leu Tyr Gln Ser Leu  Ala Asp Leu
        995                 1000                1005

Asn Asn  Val Arg Phe Ser Ala  Tyr Arg Thr Ala Met  Lys Leu Arg
    1010                1015                1020

Arg Leu  Gln Lys Ala Leu Cys  Leu Asp Leu Leu Ser  Leu Ser Ala
    1025                1030                1035

Ala Cys  Asp Ala Leu Asp Gln  His Asn Leu Lys Gln  Asn Asp Gln
    1040                1045                1050

Pro Met  Asp Ile Leu Gln Ile  Ile Asn Cys Leu Thr  Thr Ile Tyr
    1055                1060                1065

Asp Arg  Leu Glu Gln Glu His  Asn Asn Leu Val Asn  Val Pro Leu
    1070                1075                1080

Cys Val  Asp Met Cys Leu Asn  Trp Leu Leu Asn Val  Tyr Asp Thr
    1085                1090                1095

Gly Arg  Thr Gly Arg Ile Arg  Val Leu Ser Phe Lys  Thr Gly Ile
    1100                1105                1110

Ile Ser  Leu Cys Lys Ala His  Leu Glu Asp Lys Tyr  Arg Tyr Leu
    1115                1120                1125

Phe Lys  Gln Val Ala Ser Ser  Thr Gly Phe Cys Asp  Gln Arg Arg
    1130                1135                1140

Leu Gly  Leu Leu Leu His Asp  Ser Ile Gln Ile Pro  Arg Gln Leu
    1145                1150                1155

Gly Glu  Val Ala Ser Phe Gly  Gly Ser Asn Ile Glu  Pro Ser Val
    1160                1165                1170

Arg Ser  Cys Phe Gln Phe Ala  Asn Asn Lys Pro Glu  Ile Glu Ala
    1175                1180                1185

Ala Leu  Phe Leu Asp Trp Met  Arg Leu Glu Pro Gln  Ser Met Val
    1190                1195                1200

Trp Leu  Pro Val Leu His Arg  Val Ala Ala Ala Glu  Thr Ala Lys
    1205                1210                1215

His Gln  Ala Lys Cys Asn Ile  Cys Lys Glu Cys Pro  Ile Ile Gly
    1220                1225                1230

Phe Arg  Tyr Arg Ser Leu Lys  His Phe Asn Tyr Asp  Ile Cys Gln
    1235                1240                1245

Ser Cys  Phe Phe Ser Gly Arg  Val Ala Lys Gly His  Lys Met His
    1250                1255                1260

Tyr Pro  Met Val Glu Tyr Cys  Thr Pro Thr Thr Ser  Gly Glu Asp
    1265                1270                1275

Val Arg  Asp Phe Ala Lys Val  Leu Lys Asn Lys Phe  Arg Thr Lys
    1280                1285                1290
```

```
Arg Tyr  Phe Ala Lys His Pro  Arg Met Gly Tyr Leu  Pro Val Gln
    1295                 1300                 1305

Thr Val  Leu Glu Gly Asp Asn  Met Glu Thr Asp Thr  Met
    1310                 1315                 1320


<210> SEQ ID NO 120
<211> LENGTH: 1347
<212> TYPE: PRT
<213> ORGANISM: Homo sapiens

<400> SEQUENCE: 120

Met Leu Trp Trp Glu Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
            20                  25                  30

Gly Lys Gln His Ile Glu Asn Leu Phe Ser Asp Leu Gln Asp Gly Arg
        35                  40                  45

Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Asn Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
        115                 120                 125

Ala Gly Leu Gln Gln Thr Asn Ser Glu Lys Ile Leu Leu Ser Trp Val
    130                 135                 140

Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His
                165                 170                 175

Arg Pro Asp Leu Phe Asp Trp Asn Ser Val Val Cys Gln Gln Ser Ala
            180                 185                 190

Thr Gln Arg Leu Glu His Ala Phe Asn Ile Ala Arg Tyr Gln Leu Gly
        195                 200                 205

Ile Glu Lys Leu Leu Asp Pro Glu Asp Val Asp Thr Thr Tyr Pro Asp
    210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu Met Leu Pro Arg
                245                 250                 255

Pro Pro Lys Val Thr Lys Glu Glu His Phe Gln Leu His His Gln Met
            260                 265                 270

His Tyr Ser Gln Gln Ile Thr Val Ser Leu Ala Gln Gly Tyr Glu Arg
        275                 280                 285

Thr Ser Ser Pro Lys Pro Arg Phe Lys Ser Tyr Ala Tyr Thr Gln Ala
    290                 295                 300

Ala Tyr Val Thr Thr Ser Asp Pro Thr Arg Ser Pro Phe Pro Ser Gln
305                 310                 315                 320

His Leu Glu Ala Pro Glu Asp Lys Ser Phe Gly Ser Ser Leu Met Glu
                325                 330                 335

Ser Glu Val Asn Leu Asp Arg Tyr Gln Thr Ala Leu Glu Glu Val Leu
```

```
            340                 345                 350

Ser Trp Leu Leu Ser Ala Glu Asp Thr Leu Gln Ala Gln Gly Glu Ile
        355                 360                 365

Ser Asn Asp Val Glu Val Val Lys Asp Gln Phe His Thr His Glu Gly
    370                 375                 380

Tyr Met Met Asp Leu Thr Ala His Gln Gly Arg Val Gly Asn Ile Leu
385                 390                 395                 400

Gln Leu Gly Ser Lys Leu Ile Gly Thr Gly Lys Leu Ser Glu Asp Glu
                405                 410                 415

Glu Thr Glu Val Gln Glu Gln Met Asn Leu Leu Asn Ser Arg Trp Glu
            420                 425                 430

Cys Leu Arg Val Ala Ser Met Glu Lys Gln Ser Asn Leu His Leu Leu
        435                 440                 445

Lys Trp Gln Arg Leu Thr Glu Glu Gln Cys Leu Phe Ser Ala Trp Leu
    450                 455                 460

Ser Glu Lys Glu Asp Ala Val Asn Lys Ile His Thr Thr Gly Phe Lys
465                 470                 475                 480

Asp Gln Asn Glu Met Leu Ser Ser Leu Gln Lys Leu Ala Val Leu Lys
                485                 490                 495

Ala Asp Leu Glu Lys Lys Lys Gln Ser Met Gly Lys Leu Tyr Ser Leu
            500                 505                 510

Lys Gln Asp Leu Leu Ser Thr Leu Lys Asn Lys Ser Val Thr Gln Lys
        515                 520                 525

Thr Glu Ala Trp Leu Asp Asn Phe Ala Arg Cys Trp Asp Asn Leu Val
    530                 535                 540

Gln Lys Leu Glu Lys Ser Thr Ala Gln Ile Ser Gln Ala Val Thr Thr
545                 550                 555                 560

Thr Gln Pro Ser Leu Thr Gln Thr Thr Val Met Glu Thr Val Thr Thr
                565                 570                 575

Val Thr Thr Arg Glu Gln Ile Leu Val Lys His Ala Gln Glu Glu Leu
            580                 585                 590

Pro Pro Pro Pro Pro Gln Lys Lys Arg Gln Ile Thr Val Asp Ser Glu
        595                 600                 605

Ala Gln Ile His Thr Val Arg Glu Glu Thr Met Met Val Met Thr Glu
    610                 615                 620

Asp Met Pro Leu Glu Ile Ser Tyr Val Pro Ser Thr Tyr Leu Thr Glu
625                 630                 635                 640

Ile Thr His Val Ser Gln Ala Leu Leu Glu Val Glu Gln Leu Leu Asn
                645                 650                 655

Ala Pro Asp Leu Cys Ala Lys Asp Phe Glu Asp Leu Phe Lys Gln Glu
            660                 665                 670

Glu Ser Leu Lys Asn Ile Lys Asp Ser Leu Gln Gln Ser Ser Gly Arg
        675                 680                 685

Ile Asp Ile Ile His Ser Lys Lys Thr Ala Ala Leu Gln Ser Ala Thr
    690                 695                 700

Pro Val Glu Arg Val Lys Leu Gln Glu Ala Leu Ser Gln Leu Asp Phe
705                 710                 715                 720

Gln Trp Glu Lys Val Asn Lys Met Tyr Lys Asp Arg Gln Gly Arg Phe
                725                 730                 735

Asp Arg Ser Val Glu Lys Trp Arg Arg Phe His Tyr Asp Ile Lys Ile
            740                 745                 750

Phe Asn Gln Trp Leu Thr Glu Ala Glu Gln Phe Leu Arg Lys Thr Gln
        755                 760                 765
```

```
Ile Pro Glu Asn Trp Glu His Ala Lys Tyr Lys Trp Tyr Leu Lys Glu
    770                 775                 780

Leu Gln Asp Gly Ile Gly Gln Arg Gln Thr Val Val Arg Thr Leu Asn
785                 790                 795                 800

Ala Thr Gly Glu Glu Ile Ile Gln Gln Ser Ser Lys Thr Asp Ala Ser
                805                 810                 815

Ile Leu Gln Glu Lys Leu Gly Ser Leu Asn Leu Arg Trp Gln Glu Val
            820                 825                 830

Cys Lys Gln Leu Ser Asp Arg Lys Lys Arg Leu Glu Glu Gln Lys Asn
        835                 840                 845

Ile Leu Gln Glu Leu Gln Glu Ala Thr Asp Glu Leu Asp Leu Lys Leu
    850                 855                 860

Arg Gln Ala Glu Val Ile Lys Gly Ser Trp Gln Pro Val Gly Asp Leu
865                 870                 875                 880

Leu Ile Asp Ser Leu Gln Asp His Leu Glu Lys Val Lys Ala Leu Arg
                885                 890                 895

Gly Glu Ile Ala Pro Leu Lys Glu Asn Val Ser His Val Asn Asp Leu
            900                 905                 910

Ala Arg Gln Leu Thr Thr Leu Gly Ile Gln Leu Ser Pro Tyr Asn Leu
        915                 920                 925

Ser Thr Leu Glu Asp Leu Asn Thr Arg Trp Lys Leu Leu Gln Val Ala
    930                 935                 940

Val Glu Asp Arg Val Arg Gln Leu His Glu Ala His Arg Asp Phe Gly
945                 950                 955                 960

Pro Ala Ser Gln His Phe Leu Ser Thr Ser Val Gln Gly Pro Trp Glu
                965                 970                 975

Arg Ala Ile Ser Pro Asn Lys Val Pro Tyr Tyr Ile Asn His Glu Thr
            980                 985                 990

Gln Thr Thr Cys Trp Asp His Pro  Lys Met Thr Glu Leu  Tyr Gln Ser
        995                 1000                1005

Leu Ala  Asp Leu Asn Asn Val  Arg Phe Ser Ala Tyr  Arg Thr Ala
    1010                1015                1020

Met Lys  Leu Arg Arg Leu Gln  Lys Ala Leu Cys Leu  Asp Leu Leu
    1025                1030                1035

Ser Leu  Ser Ala Ala Cys Asp  Ala Leu Asp Gln His  Asn Leu Lys
    1040                1045                1050

Gln Asn  Asp Gln Pro Met Asp  Ile Leu Gln Ile Ile  Asn Cys Leu
    1055                1060                1065

Thr Thr  Ile Tyr Asp Arg Leu  Glu Gln Glu His Asn  Asn Leu Val
    1070                1075                1080

Asn Val  Pro Leu Cys Val Asp  Met Cys Leu Asn Trp  Leu Leu Asn
    1085                1090                1095

Val Tyr  Asp Thr Gly Arg Thr  Gly Arg Ile Arg Val  Leu Ser Phe
    1100                1105                1110

Lys Thr  Gly Ile Ile Ser Leu  Cys Lys Ala His Leu  Glu Asp Lys
    1115                1120                1125

Tyr Arg  Tyr Leu Phe Lys Gln  Val Ala Ser Ser Thr  Gly Phe Cys
    1130                1135                1140

Asp Gln  Arg Arg Leu Gly Leu  Leu Leu His Asp Ser  Ile Gln Ile
    1145                1150                1155

Pro Arg  Gln Leu Gly Glu Val  Ala Ser Phe Gly Gly  Ser Asn Ile
    1160                1165                1170
```

```
Glu Pro  Ser Val Arg Ser Cys  Phe Gln Phe Ala Asn  Asn Lys Pro
    1175                 1180                 1185

Glu Ile  Glu Ala Ala Leu Phe  Leu Asp Trp Met Arg  Leu Glu Pro
    1190                 1195                 1200

Gln Ser  Met Val Trp Leu Pro  Val Leu His Arg Val  Ala Ala Ala
    1205                 1210                 1215

Glu Thr  Ala Lys His Gln Ala  Lys Cys Asn Ile Cys  Lys Glu Cys
    1220                 1225                 1230

Pro Ile  Ile Gly Phe Arg Tyr  Arg Ser Leu Lys His  Phe Asn Tyr
    1235                 1240                 1245

Asp Ile  Cys Gln Ser Cys Phe  Phe Ser Gly Arg Val  Ala Lys Gly
    1250                 1255                 1260

His Lys  Met His Tyr Pro Met  Val Glu Tyr Cys Thr  Pro Thr Thr
    1265                 1270                 1275

Ser Gly  Glu Asp Val Arg Asp  Phe Ala Lys Val Leu  Lys Asn Lys
    1280                 1285                 1290

Phe Arg  Thr Lys Arg Tyr Phe  Ala Lys His Pro Arg  Met Gly Tyr
    1295                 1300                 1305

Leu Pro  Val Gln Thr Val Leu  Glu Gly Asp Asn Met  Glu Thr Thr
    1310                 1315                 1320

Pro Cys  Asp Asp Asp Leu Gly  Arg Ala Met Glu Ser  Leu Val Ser
    1325                 1330                 1335

Val Met  Thr Asp Glu Glu Gly  Ala Glu
    1340                 1345
```

<210> SEQ ID NO 121
<211> LENGTH: 1326
<212> TYPE: PRT
<213> ORGANISM: Homo sapiens

<400> SEQUENCE: 121

```
Met Leu Trp Trp Glu Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
            20                  25                  30

Gly Lys Gln His Ile Glu Asn Leu Phe Ser Asp Leu Gln Asp Gly Arg
        35                  40                  45

Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Asn Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
        115                 120                 125

Ala Gly Leu Gln Gln Thr Asn Ser Glu Lys Ile Leu Leu Ser Trp Val
    130                 135                 140

Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His
                165                 170                 175

Arg Pro Asp Leu Phe Asp Trp Asn Ser Val Val Cys Gln Gln Ser Ala
            180                 185                 190
```

```
Thr Gln Arg Leu Glu His Ala Phe Asn Ile Ala Arg Tyr Gln Leu Gly
        195                 200                 205

Ile Glu Lys Leu Leu Asp Pro Glu Asp Val Asp Thr Thr Tyr Pro Asp
    210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu Met Leu Pro Arg
                245                 250                 255

Pro Pro Lys Val Thr Lys Glu Glu His Phe Gln Leu His His Gln Met
            260                 265                 270

His Tyr Ser Gln Gln Ile Thr Val Ser Leu Ala Gln Gly Tyr Glu Arg
        275                 280                 285

Thr Ser Ser Pro Lys Pro Arg Phe Lys Ser Tyr Ala Tyr Thr Gln Ala
    290                 295                 300

Ala Tyr Val Thr Thr Ser Asp Pro Thr Arg Ser Pro Phe Pro Ser Gln
305                 310                 315                 320

His Leu Glu Ala Pro Glu Asp Lys Ser Phe Gly Ser Ser Leu Met Glu
                325                 330                 335

Ser Glu Val Asn Leu Asp Arg Tyr Gln Thr Ala Leu Glu Glu Val Leu
            340                 345                 350

Ser Trp Leu Leu Ser Ala Glu Asp Thr Leu Gln Ala Gln Gly Glu Ile
        355                 360                 365

Ser Asn Asp Val Glu Val Val Lys Asp Gln Phe His Thr His Glu Gly
    370                 375                 380

Tyr Met Met Asp Leu Thr Ala His Gln Gly Arg Val Gly Asn Ile Leu
385                 390                 395                 400

Gln Leu Gly Ser Lys Leu Ile Gly Thr Gly Lys Leu Ser Glu Asp Glu
                405                 410                 415

Glu Thr Glu Val Gln Glu Gln Met Asn Leu Leu Asn Ser Arg Trp Glu
            420                 425                 430

Cys Leu Arg Val Ala Ser Met Glu Lys Gln Ser Asn Leu His Leu Leu
        435                 440                 445

Lys Trp Gln Arg Leu Thr Glu Glu Gln Cys Leu Phe Ser Ala Trp Leu
    450                 455                 460

Ser Glu Lys Glu Asp Ala Val Asn Lys Ile His Thr Thr Gly Phe Lys
465                 470                 475                 480

Asp Gln Asn Glu Met Leu Ser Ser Leu Gln Lys Leu Ala Val Leu Lys
                485                 490                 495

Ala Asp Leu Glu Lys Lys Lys Gln Ser Met Gly Lys Leu Tyr Ser Leu
            500                 505                 510

Lys Gln Asp Leu Leu Ser Thr Leu Lys Asn Lys Ser Val Thr Gln Lys
        515                 520                 525

Thr Glu Ala Trp Leu Asp Asn Phe Ala Arg Cys Trp Asp Asn Leu Val
    530                 535                 540

Gln Lys Leu Glu Lys Ser Thr Ala Gln Ile Ser Gln Ala Val Thr Thr
545                 550                 555                 560

Thr Gln Pro Ser Leu Thr Gln Thr Thr Val Met Glu Thr Val Thr Thr
                565                 570                 575

Val Thr Thr Arg Glu Gln Ile Leu Val Lys His Ala Gln Glu Glu Leu
            580                 585                 590

Pro Pro Pro Pro Pro Gln Lys Lys Arg Gln Ile Thr Val Asp Ser Glu
        595                 600                 605
```

```
Ala Gln Ile His Thr Val Arg Glu Glu Thr Met Met Val Met Thr Glu
    610                 615                 620

Asp Met Pro Leu Glu Ile Ser Tyr Val Pro Ser Thr Tyr Leu Thr Glu
625                 630                 635                 640

Ile Thr His Val Ser Gln Ala Leu Leu Glu Val Glu Gln Leu Leu Asn
                645                 650                 655

Ala Pro Asp Leu Cys Ala Lys Asp Phe Glu Asp Leu Phe Lys Gln Glu
            660                 665                 670

Glu Ser Leu Lys Asn Ile Lys Asp Ser Leu Gln Gln Ser Ser Gly Arg
        675                 680                 685

Ile Asp Ile Ile His Ser Lys Lys Thr Ala Ala Leu Gln Ser Ala Thr
    690                 695                 700

Pro Val Glu Arg Val Lys Leu Gln Glu Ala Leu Ser Gln Leu Asp Phe
705                 710                 715                 720

Gln Trp Glu Lys Val Asn Lys Met Tyr Lys Asp Arg Gln Gly Arg Phe
                725                 730                 735

Asp Arg Ser Val Glu Lys Trp Arg Arg Phe His Tyr Asp Ile Lys Ile
            740                 745                 750

Phe Asn Gln Trp Leu Thr Glu Ala Glu Gln Phe Leu Arg Lys Thr Gln
        755                 760                 765

Ile Pro Glu Asn Trp Glu His Ala Lys Tyr Lys Trp Tyr Leu Lys Glu
    770                 775                 780

Leu Gln Asp Gly Ile Gly Gln Arg Gln Thr Val Val Arg Thr Leu Asn
785                 790                 795                 800

Ala Thr Gly Glu Glu Ile Ile Gln Gln Ser Ser Lys Thr Asp Ala Ser
                805                 810                 815

Ile Leu Gln Glu Lys Leu Gly Ser Leu Asn Leu Arg Trp Gln Glu Val
            820                 825                 830

Cys Lys Gln Leu Ser Asp Arg Lys Lys Arg Leu Glu Glu Gln Lys Leu
        835                 840                 845

Glu Arg Leu Gln Glu Leu Gln Glu Ala Thr Asp Glu Leu Asp Leu Lys
    850                 855                 860

Leu Arg Gln Ala Glu Val Ile Lys Gly Ser Trp Gln Pro Val Gly Asp
865                 870                 875                 880

Leu Leu Ile Asp Ser Leu Gln Asp His Leu Glu Lys Val Lys Ala Leu
                885                 890                 895

Arg Gly Glu Ile Ala Pro Leu Lys Glu Asn Val Ser His Val Asn Asp
            900                 905                 910

Leu Ala Arg Gln Leu Thr Thr Leu Gly Ile Gln Leu Ser Pro Tyr Asn
        915                 920                 925

Leu Ser Thr Leu Glu Asp Leu Asn Thr Arg Trp Lys Leu Leu Gln Val
    930                 935                 940

Ala Val Glu Asp Arg Val Arg Gln Leu His Glu Ala His Arg Asp Phe
945                 950                 955                 960

Gly Pro Ala Ser Gln His Phe Leu Ser Thr Ser Val Gln Gly Pro Trp
                965                 970                 975

Glu Arg Ala Ile Ser Pro Asn Lys Val Pro Tyr Tyr Ile Asn His Glu
            980                 985                 990

Thr Gln Thr Thr Cys Trp Asp His  Pro Lys Met Thr Glu  Leu Tyr Gln
        995                 1000                 1005

Ser Leu  Ala Asp Leu Asn Asn  Val Arg Phe Ser Ala  Tyr Arg Thr
    1010                 1015                 1020

Ala Met  Lys Leu Arg Arg Leu  Gln Lys Ala Leu Cys  Leu Asp Leu
```

1025 1030 1035

Leu Ser Leu Ser Ala Ala Cys Asp Ala Leu Asp Gln His Asn Leu
1040 1045 1050

Lys Gln Asn Asp Gln Pro Met Asp Ile Leu Gln Ile Ile Asn Cys
1055 1060 1065

Leu Thr Thr Ile Tyr Asp Arg Leu Glu Gln Glu His Asn Asn Leu
1070 1075 1080

Val Asn Val Pro Leu Cys Val Asp Met Cys Leu Asn Trp Leu Leu
1085 1090 1095

Asn Val Tyr Asp Thr Gly Arg Thr Gly Arg Ile Arg Val Leu Ser
1100 1105 1110

Phe Lys Thr Gly Ile Ile Ser Leu Cys Lys Ala His Leu Glu Asp
1115 1120 1125

Lys Tyr Arg Tyr Leu Phe Lys Gln Val Ala Ser Ser Thr Gly Phe
1130 1135 1140

Cys Asp Gln Arg Arg Leu Gly Leu Leu Leu His Asp Ser Ile Gln
1145 1150 1155

Ile Pro Arg Gln Leu Gly Glu Val Ala Ser Phe Gly Gly Ser Asn
1160 1165 1170

Ile Glu Pro Ser Val Arg Ser Cys Phe Gln Phe Ala Asn Asn Lys
1175 1180 1185

Pro Glu Ile Glu Ala Ala Leu Phe Leu Asp Trp Met Arg Leu Glu
1190 1195 1200

Pro Gln Ser Met Val Trp Leu Pro Val Leu His Arg Val Ala Ala
1205 1210 1215

Ala Glu Thr Ala Lys His Gln Ala Lys Cys Asn Ile Cys Lys Glu
1220 1225 1230

Cys Pro Ile Ile Gly Phe Arg Tyr Arg Ser Leu Lys His Phe Asn
1235 1240 1245

Tyr Asp Ile Cys Gln Ser Cys Phe Phe Ser Gly Arg Val Ala Lys
1250 1255 1260

Gly His Lys Met His Tyr Pro Met Val Glu Tyr Cys Thr Pro Thr
1265 1270 1275

Thr Ser Gly Glu Asp Val Arg Asp Phe Ala Lys Val Leu Lys Asn
1280 1285 1290

Lys Phe Arg Thr Lys Arg Tyr Phe Ala Lys His Pro Arg Met Gly
1295 1300 1305

Tyr Leu Pro Val Gln Thr Val Leu Glu Gly Asp Asn Met Glu Thr
1310 1315 1320

Asp Thr Met
1325

<210> SEQ ID NO 122
<211> LENGTH: 1328
<212> TYPE: PRT
<213> ORGANISM: Homo sapiens

<400> SEQUENCE: 122

Met Leu Trp Trp Glu Glu Val Glu Asp Cys Tyr Glu Arg Glu Asp Val
1 5 10 15

Gln Lys Lys Thr Phe Thr Lys Trp Val Asn Ala Gln Phe Ser Lys Phe
20 25 30

Gly Lys Gln His Ile Glu Asn Leu Phe Ser Asp Leu Gln Asp Gly Arg
35 40 45

```
Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Asn Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
        115                 120                 125

Ala Gly Leu Gln Gln Thr Asn Ser Glu Lys Ile Leu Leu Ser Trp Val
    130                 135                 140

Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His
                165                 170                 175

Arg Pro Asp Leu Phe Asp Trp Asn Ser Val Val Cys Gln Gln Ser Ala
            180                 185                 190

Thr Gln Arg Leu Glu His Ala Phe Asn Ile Ala Arg Tyr Gln Leu Gly
        195                 200                 205

Ile Glu Lys Leu Leu Asp Pro Glu Asp Val Asp Thr Thr Tyr Pro Asp
    210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu Met Leu Pro Arg
                245                 250                 255

Pro Pro Lys Val Thr Lys Glu Glu His Phe Gln Leu His His Gln Met
            260                 265                 270

His Tyr Ser Gln Gln Ile Thr Val Ser Leu Ala Gln Gly Tyr Glu Arg
        275                 280                 285

Thr Ser Ser Pro Lys Pro Arg Phe Lys Ser Tyr Ala Tyr Thr Gln Ala
    290                 295                 300

Ala Tyr Val Thr Thr Ser Asp Pro Thr Arg Ser Pro Phe Pro Ser Gln
305                 310                 315                 320

His Leu Glu Ala Pro Glu Asp Lys Ser Phe Gly Ser Ser Leu Met Glu
                325                 330                 335

Ser Glu Val Asn Leu Asp Arg Tyr Gln Thr Ala Leu Glu Glu Val Leu
            340                 345                 350

Ser Trp Leu Leu Ser Ala Glu Asp Thr Leu Gln Ala Gln Gly Glu Ile
        355                 360                 365

Ser Asn Asp Val Glu Val Val Lys Asp Gln Phe His Thr His Glu Gly
    370                 375                 380

Tyr Met Met Asp Leu Thr Ala His Gln Gly Arg Val Gly Asn Ile Leu
385                 390                 395                 400

Gln Leu Gly Ser Lys Leu Ile Gly Thr Gly Lys Leu Ser Glu Asp Glu
                405                 410                 415

Glu Thr Glu Val Gln Glu Gln Met Asn Leu Leu Asn Ser Arg Trp Glu
            420                 425                 430

Cys Leu Arg Val Ala Ser Met Glu Lys Gln Ser Asn Leu His Leu Leu
        435                 440                 445

Lys Trp Gln Arg Leu Thr Glu Glu Gln Cys Leu Phe Ser Ala Trp Leu
    450                 455                 460

Ser Glu Lys Glu Asp Ala Val Asn Lys Ile His Thr Thr Gly Phe Lys
```

```
465                 470                 475                 480

Asp Gln Asn Glu Met Leu Ser Ser Leu Gln Lys Leu Ala Val Leu Lys
                485                 490                 495

Ala Asp Leu Glu Lys Lys Lys Gln Ser Met Gly Lys Leu Tyr Ser Leu
            500                 505                 510

Lys Gln Asp Leu Leu Ser Thr Leu Lys Asn Lys Ser Val Thr Gln Lys
        515                 520                 525

Thr Glu Ala Trp Leu Asp Asn Phe Ala Arg Cys Trp Asp Asn Leu Val
    530                 535                 540

Gln Lys Leu Glu Lys Ser Thr Ala Gln Ile Ser Gln Ala Val Thr Thr
545                 550                 555                 560

Thr Gln Pro Ser Leu Thr Gln Thr Thr Val Met Glu Thr Val Thr Thr
                565                 570                 575

Val Thr Thr Arg Glu Gln Ile Leu Val Lys His Ala Gln Glu Glu Leu
            580                 585                 590

Pro Pro Pro Pro Pro Gln Lys Lys Arg Gln Ile Thr Val Asp Ser Glu
        595                 600                 605

Ala Gln Ile His Thr Val Arg Glu Glu Thr Met Met Val Met Thr Glu
    610                 615                 620

Asp Met Pro Leu Glu Ile Ser Tyr Val Pro Ser Thr Tyr Leu Thr Glu
625                 630                 635                 640

Ile Thr His Val Ser Gln Ala Leu Leu Glu Val Glu Gln Leu Leu Asn
                645                 650                 655

Ala Pro Asp Leu Cys Ala Lys Asp Phe Glu Asp Leu Phe Lys Gln Glu
            660                 665                 670

Glu Ser Leu Lys Asn Ile Lys Asp Ser Leu Gln Gln Ser Ser Gly Arg
        675                 680                 685

Ile Asp Ile Ile His Ser Lys Lys Thr Ala Ala Leu Gln Ser Ala Thr
    690                 695                 700

Pro Val Glu Arg Val Lys Leu Gln Glu Ala Leu Ser Gln Leu Asp Phe
705                 710                 715                 720

Gln Trp Glu Lys Val Asn Lys Met Tyr Lys Asp Arg Gln Gly Arg Phe
                725                 730                 735

Asp Arg Ser Val Glu Lys Trp Arg Arg Phe His Tyr Asp Ile Lys Ile
            740                 745                 750

Phe Asn Gln Trp Leu Thr Glu Ala Glu Gln Phe Leu Arg Lys Thr Gln
        755                 760                 765

Ile Pro Glu Asn Trp Glu His Ala Lys Tyr Lys Trp Tyr Leu Lys Glu
    770                 775                 780

Leu Gln Asp Gly Ile Gly Gln Arg Gln Thr Val Val Arg Thr Leu Asn
785                 790                 795                 800

Ala Thr Gly Glu Glu Ile Ile Gln Gln Ser Ser Lys Thr Asp Ala Ser
                805                 810                 815

Ile Leu Gln Glu Lys Leu Gly Ser Leu Asn Leu Arg Trp Gln Glu Val
            820                 825                 830

Cys Lys Gln Leu Ser Asp Arg Lys Lys Arg Leu Glu Glu Gln Lys Asn
        835                 840                 845

Ile Leu Glu Arg Leu Gln Glu Leu Gln Glu Ala Thr Asp Glu Leu Asp
    850                 855                 860

Leu Lys Leu Arg Gln Ala Glu Val Ile Lys Gly Ser Trp Gln Pro Val
865                 870                 875                 880

Gly Asp Leu Leu Ile Asp Ser Leu Gln Asp His Leu Glu Lys Val Lys
                885                 890                 895
```

```
Ala Leu Arg Gly Glu Ile Ala Pro Leu Lys Glu Asn Val Ser His Val
        900                 905                 910

Asn Asp Leu Ala Arg Gln Leu Thr Thr Leu Gly Ile Gln Leu Ser Pro
    915                 920                 925

Tyr Asn Leu Ser Thr Leu Glu Asp Leu Asn Thr Arg Trp Lys Leu Leu
    930                 935                 940

Gln Val Ala Val Glu Asp Arg Val Arg Gln Leu His Glu Ala His Arg
945                 950                 955                 960

Asp Phe Gly Pro Ala Ser Gln His Phe Leu Ser Thr Ser Val Gln Gly
                965                 970                 975

Pro Trp Glu Arg Ala Ile Ser Pro Asn Lys Val Pro Tyr Tyr Ile Asn
        980                 985                 990

His Glu Thr Gln Thr Thr Cys Trp  Asp His Pro Lys Met  Thr Glu Leu
    995                 1000                1005

Tyr Gln  Ser Leu Ala Asp Leu  Asn Asn Val Arg Phe  Ser Ala Tyr
    1010                1015                1020

Arg Thr  Ala Met Lys Leu Arg  Arg Leu Gln Lys Ala  Leu Cys Leu
    1025                1030                1035

Asp Leu  Leu Ser Leu Ser Ala  Ala Cys Asp Ala Leu  Asp Gln His
    1040                1045                1050

Asn Leu  Lys Gln Asn Asp Gln  Pro Met Asp Ile Leu  Gln Ile Ile
    1055                1060                1065

Asn Cys  Leu Thr Thr Ile Tyr  Asp Arg Leu Glu Gln  Glu His Asn
    1070                1075                1080

Asn Leu  Val Asn Val Pro Leu  Cys Val Asp Met Cys  Leu Asn Trp
    1085                1090                1095

Leu Leu  Asn Val Tyr Asp Thr  Gly Arg Thr Gly Arg  Ile Arg Val
    1100                1105                1110

Leu Ser  Phe Lys Thr Gly Ile  Ile Ser Leu Cys Lys  Ala His Leu
    1115                1120                1125

Glu Asp  Lys Tyr Arg Tyr Leu  Phe Lys Gln Val Ala  Ser Ser Thr
    1130                1135                1140

Gly Phe  Cys Asp Gln Arg Arg  Leu Gly Leu Leu Leu  His Asp Ser
    1145                1150                1155

Ile Gln  Ile Pro Arg Gln Leu  Gly Glu Val Ala Ser  Phe Gly Gly
    1160                1165                1170

Ser Asn  Ile Glu Pro Ser Val  Arg Ser Cys Phe Gln  Phe Ala Asn
    1175                1180                1185

Asn Lys  Pro Glu Ile Glu Ala  Ala Leu Phe Leu Asp  Trp Met Arg
    1190                1195                1200

Leu Glu  Pro Gln Ser Met Val  Trp Leu Pro Val Leu  His Arg Val
    1205                1210                1215

Ala Ala  Ala Glu Thr Ala Lys  His Gln Ala Lys Cys  Asn Ile Cys
    1220                1225                1230

Lys Glu  Cys Pro Ile Ile Gly  Phe Arg Tyr Arg Ser  Leu Lys His
    1235                1240                1245

Phe Asn  Tyr Asp Ile Cys Gln  Ser Cys Phe Phe Ser  Gly Arg Val
    1250                1255                1260

Ala Lys  Gly His Lys Met His  Tyr Pro Met Val Glu  Tyr Cys Thr
    1265                1270                1275

Pro Thr  Thr Ser Gly Glu Asp  Val Arg Asp Phe Ala  Lys Val Leu
    1280                1285                1290
```

```
Lys Asn  Lys Phe Arg Thr Lys  Arg Tyr Phe Ala Lys  His Pro Arg
    1295                 1300                 1305

Met Gly  Tyr Leu Pro Val Gln  Thr Val Leu Glu Gly  Asp Asn Met
    1310                 1315                 1320

Glu Thr  Asp Thr Met
    1325


<210> SEQ ID NO 123
<211> LENGTH: 1327
<212> TYPE: PRT
<213> ORGANISM: Homo sapiens

<400> SEQUENCE: 123

Met Leu Trp Trp Glu Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
            20                  25                  30

Gly Lys Gln His Ile Glu Asn Leu Phe Ser Asp Leu Gln Asp Gly Arg
        35                  40                  45

Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Asn Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
        115                 120                 125

Ala Gly Leu Gln Gln Thr Asn Ser Glu Lys Ile Leu Leu Ser Trp Val
    130                 135                 140

Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His
                165                 170                 175

Arg Pro Asp Leu Phe Asp Trp Asn Ser Val Val Cys Gln Gln Ser Ala
            180                 185                 190

Thr Gln Arg Leu Glu His Ala Phe Asn Ile Ala Arg Tyr Gln Leu Gly
        195                 200                 205

Ile Glu Lys Leu Leu Asp Pro Glu Asp Val Asp Thr Thr Tyr Pro Asp
    210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu Met Leu Pro Arg
                245                 250                 255

Pro Pro Lys Val Thr Lys Glu Glu His Phe Gln Leu His His Gln Met
            260                 265                 270

His Tyr Ser Gln Gln Ile Thr Val Ser Leu Ala Gln Gly Tyr Glu Arg
        275                 280                 285

Thr Ser Ser Pro Lys Pro Arg Phe Lys Ser Tyr Ala Tyr Thr Gln Ala
    290                 295                 300

Ala Tyr Val Thr Thr Ser Asp Pro Thr Arg Ser Pro Phe Pro Ser Gln
305                 310                 315                 320

His Leu Glu Ala Pro Glu Asp Lys Ser Phe Gly Ser Ser Leu Met Glu
                325                 330                 335
```

```
Ser Glu Val Asn Leu Asp Arg Tyr Gln Thr Ala Leu Glu Glu Val Leu
            340                 345                 350

Ser Trp Leu Leu Ser Ala Glu Asp Thr Leu Gln Ala Gln Gly Glu Ile
        355                 360                 365

Ser Asn Asp Val Glu Val Val Lys Asp Gln Phe His Thr His Glu Gly
    370                 375                 380

Tyr Met Met Asp Leu Thr Ala His Gln Gly Arg Val Gly Asn Ile Leu
385                 390                 395                 400

Gln Leu Gly Ser Lys Leu Ile Gly Thr Gly Lys Leu Ser Glu Asp Glu
                405                 410                 415

Glu Thr Glu Val Gln Glu Gln Met Asn Leu Leu Asn Ser Arg Trp Glu
            420                 425                 430

Cys Leu Arg Val Ala Ser Met Glu Lys Gln Ser Asn Leu His Arg Val
        435                 440                 445

Leu Leu Lys Trp Gln Arg Leu Thr Glu Glu Gln Cys Leu Phe Ser Ala
    450                 455                 460

Trp Leu Ser Glu Lys Glu Asp Ala Val Asn Lys Ile His Thr Thr Gly
465                 470                 475                 480

Phe Lys Asp Gln Asn Glu Met Leu Ser Ser Leu Gln Lys Leu Ala Val
                485                 490                 495

Leu Lys Ala Asp Leu Glu Lys Lys Lys Gln Ser Met Gly Lys Leu Tyr
            500                 505                 510

Ser Leu Lys Gln Asp Leu Leu Ser Thr Leu Lys Asn Lys Ser Val Thr
        515                 520                 525

Gln Lys Thr Glu Ala Trp Leu Asp Asn Phe Ala Arg Cys Trp Asp Asn
    530                 535                 540

Leu Val Gln Lys Leu Glu Lys Ser Thr Ala Gln Ile Ser Gln Ala Val
545                 550                 555                 560

Thr Thr Thr Gln Pro Ser Leu Thr Gln Thr Thr Val Met Glu Thr Val
                565                 570                 575

Thr Thr Val Thr Thr Arg Glu Gln Ile Leu Val Lys His Ala Gln Glu
            580                 585                 590

Glu Leu Pro Pro Pro Pro Pro Gln Lys Lys Arg Gln Ile Thr Val Asp
        595                 600                 605

Ser Glu Ala Gln Ile His Thr Val Arg Glu Glu Thr Met Met Val Met
    610                 615                 620

Thr Glu Asp Met Pro Leu Glu Ile Ser Tyr Val Pro Ser Thr Tyr Leu
625                 630                 635                 640

Thr Glu Ile Thr His Val Ser Gln Ala Leu Leu Glu Val Glu Gln Leu
                645                 650                 655

Leu Asn Ala Pro Asp Leu Cys Ala Lys Asp Phe Glu Asp Leu Phe Lys
            660                 665                 670

Gln Glu Glu Ser Leu Lys Asn Ile Lys Asp Ser Leu Gln Gln Ser Ser
        675                 680                 685

Gly Arg Ile Asp Ile Ile His Ser Lys Lys Thr Ala Ala Leu Gln Ser
    690                 695                 700

Ala Thr Pro Val Glu Arg Val Lys Leu Gln Glu Ala Leu Ser Gln Leu
705                 710                 715                 720

Asp Phe Gln Trp Glu Lys Val Asn Lys Met Tyr Lys Asp Arg Gln Gly
                725                 730                 735

Arg Phe Asp Arg Ser Val Glu Lys Trp Arg Arg Phe His Tyr Asp Ile
            740                 745                 750
```

```
Lys Ile Phe Asn Gln Trp Leu Thr Glu Ala Glu Gln Phe Leu Arg Lys
        755                 760                 765

Thr Gln Ile Pro Glu Asn Trp Glu His Ala Lys Tyr Lys Trp Tyr Leu
    770                 775                 780

Lys Glu Leu Gln Asp Gly Ile Gly Gln Arg Gln Thr Val Val Arg Thr
785                 790                 795                 800

Leu Asn Ala Thr Gly Glu Glu Ile Ile Gln Gln Ser Ser Lys Thr Asp
                805                 810                 815

Ala Ser Ile Leu Gln Glu Lys Leu Gly Ser Leu Asn Leu Arg Trp Gln
            820                 825                 830

Glu Val Cys Lys Gln Leu Ser Asp Arg Lys Lys Arg Leu Glu Glu Gln
        835                 840                 845

Leu Glu Arg Leu Gln Glu Leu Gln Glu Ala Thr Asp Glu Leu Asp Leu
    850                 855                 860

Lys Leu Arg Gln Ala Glu Val Ile Lys Gly Ser Trp Gln Pro Val Gly
865                 870                 875                 880

Asp Leu Leu Ile Asp Ser Leu Gln Asp His Leu Glu Lys Val Lys Ala
                885                 890                 895

Leu Arg Gly Glu Ile Ala Pro Leu Lys Glu Asn Val Ser His Val Asn
            900                 905                 910

Asp Leu Ala Arg Gln Leu Thr Thr Leu Gly Ile Gln Leu Ser Pro Tyr
        915                 920                 925

Asn Leu Ser Thr Leu Glu Asp Leu Asn Thr Arg Trp Lys Leu Leu Gln
    930                 935                 940

Val Ala Val Glu Asp Arg Val Arg Gln Leu His Glu Ala His Arg Asp
945                 950                 955                 960

Phe Gly Pro Ala Ser Gln His Phe Leu Ser Thr Ser Val Gln Gly Pro
                965                 970                 975

Trp Glu Arg Ala Ile Ser Pro Asn Lys Val Pro Tyr Tyr Ile Asn His
            980                 985                 990

Glu Thr Gln Thr Thr Cys Trp Asp  His Pro Lys Met Thr  Glu Leu Tyr
        995                 1000                1005

Gln Ser  Leu Ala Asp Leu Asn  Asn Val Arg Phe Ser  Ala Tyr Arg
    1010                 1015                 1020

Thr Ala  Met Lys Leu Arg Arg  Leu Gln Lys Ala Leu  Cys Leu Asp
    1025                 1030                 1035

Leu Leu  Ser Leu Ser Ala Ala  Cys Asp Ala Leu Asp  Gln His Asn
    1040                 1045                 1050

Leu Lys  Gln Asn Asp Gln Pro  Met Asp Ile Leu Gln  Ile Ile Asn
    1055                 1060                 1065

Cys Leu  Thr Thr Ile Tyr Asp  Arg Leu Glu Gln Glu  His Asn Asn
    1070                 1075                 1080

Leu Val  Asn Val Pro Leu Cys  Val Asp Met Cys Leu  Asn Trp Leu
    1085                 1090                 1095

Leu Asn  Val Tyr Asp Thr Gly  Arg Thr Gly Arg Ile  Arg Val Leu
    1100                 1105                 1110

Ser Phe  Lys Thr Gly Ile Ile  Ser Leu Cys Lys Ala  His Leu Glu
    1115                 1120                 1125

Asp Lys  Tyr Arg Tyr Leu Phe  Lys Gln Val Ala Ser  Ser Thr Gly
    1130                 1135                 1140

Phe Cys  Asp Gln Arg Arg Leu  Gly Leu Leu Leu His  Asp Ser Ile
    1145                 1150                 1155

Gln Ile  Pro Arg Gln Leu Gly  Glu Val Ala Ser Phe  Gly Gly Ser
```

```
    1160                1165                1170

Asn Ile  Glu Pro Ser Val Arg  Ser Cys Phe Gln Phe  Ala Asn Asn
    1175                1180                1185

Lys Pro  Glu Ile Glu Ala Ala  Leu Phe Leu Asp Trp  Met Arg Leu
    1190                1195                1200

Glu Pro  Gln Ser Met Val Trp  Leu Pro Val Leu His  Arg Val Ala
    1205                1210                1215

Ala Ala  Glu Thr Ala Lys His  Gln Ala Lys Cys Asn  Ile Cys Lys
    1220                1225                1230

Glu Cys  Pro Ile Ile Gly Phe  Arg Tyr Arg Ser Leu  Lys His Phe
    1235                1240                1245

Asn Tyr  Asp Ile Cys Gln Ser  Cys Phe Phe Ser Gly  Arg Val Ala
    1250                1255                1260

Lys Gly  His Lys Met His Tyr  Pro Met Val Glu Tyr  Cys Thr Pro
    1265                1270                1275

Thr Thr  Ser Gly Glu Asp Val  Arg Asp Phe Ala Lys  Val Leu Lys
    1280                1285                1290

Asn Lys  Phe Arg Thr Lys Arg  Tyr Phe Ala Lys His  Pro Arg Met
    1295                1300                1305

Gly Tyr  Leu Pro Val Gln Thr  Val Leu Glu Gly Asp  Asn Met Glu
    1310                1315                1320

Thr Asp  Thr Met
    1325


<210> SEQ ID NO 124
<211> LENGTH: 1332
<212> TYPE: PRT
<213> ORGANISM: Homo sapiens

<400> SEQUENCE: 124

Met Leu Trp Trp Glu Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
            20                  25                  30

Gly Lys Gln His Ile Glu Asn Leu Phe Ser Asp Leu Gln Asp Gly Arg
        35                  40                  45

Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Asn Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
        115                 120                 125

Ala Gly Leu Gln Gln Thr Asn Ser Glu Lys Ile Leu Leu Ser Trp Val
    130                 135                 140

Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His
                165                 170                 175

Arg Pro Asp Leu Phe Asp Trp Asn Ser Val Val Cys Gln Gln Ser Ala
            180                 185                 190
```

```
Thr Gln Arg Leu Glu His Ala Phe Asn Ile Ala Arg Tyr Gln Leu Gly
        195                 200                 205

Ile Glu Lys Leu Leu Asp Pro Glu Asp Val Asp Thr Thr Tyr Pro Asp
    210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu Met Leu Pro Arg
                245                 250                 255

Pro Pro Lys Val Thr Lys Glu Glu His Phe Gln Leu His His Gln Met
            260                 265                 270

His Tyr Ser Gln Gln Ile Thr Val Ser Leu Ala Gln Gly Tyr Glu Arg
        275                 280                 285

Thr Ser Ser Pro Lys Pro Arg Phe Lys Ser Tyr Ala Tyr Thr Gln Ala
    290                 295                 300

Ala Tyr Val Thr Thr Ser Asp Pro Thr Arg Ser Pro Phe Pro Ser Gln
305                 310                 315                 320

His Leu Glu Ala Pro Glu Asp Lys Ser Phe Gly Ser Ser Leu Met Glu
                325                 330                 335

Ser Glu Val Asn Leu Asp Arg Tyr Gln Thr Ala Leu Glu Glu Val Leu
            340                 345                 350

Ser Trp Leu Leu Ser Ala Glu Asp Thr Leu Gln Ala Gln Gly Glu Ile
        355                 360                 365

Ser Asn Asp Val Glu Val Val Lys Asp Gln Phe His Thr His Glu Gly
    370                 375                 380

Tyr Met Met Asp Leu Thr Ala His Gln Gly Arg Val Gly Asn Ile Leu
385                 390                 395                 400

Gln Leu Gly Ser Lys Leu Ile Gly Thr Gly Lys Leu Ser Glu Asp Glu
                405                 410                 415

Glu Thr Glu Val Gln Glu Gln Met Asn Leu Leu Asn Ser Arg Trp Glu
            420                 425                 430

Cys Leu Arg Val Ala Ser Met Glu Lys Gln Ser Asn Leu His Arg Val
        435                 440                 445

Leu Leu Gln Asp Ile Leu Leu Lys Trp Gln Arg Leu Thr Glu Glu Gln
    450                 455                 460

Cys Leu Phe Ser Ala Trp Leu Ser Glu Lys Glu Asp Ala Val Asn Lys
465                 470                 475                 480

Ile His Thr Thr Gly Phe Lys Asp Gln Asn Glu Met Leu Ser Ser Leu
                485                 490                 495

Gln Lys Leu Ala Val Leu Lys Ala Asp Leu Glu Lys Lys Lys Gln Ser
            500                 505                 510

Met Gly Lys Leu Tyr Ser Leu Lys Gln Asp Leu Leu Ser Thr Leu Lys
        515                 520                 525

Asn Lys Ser Val Thr Gln Lys Thr Glu Ala Trp Leu Asp Asn Phe Ala
    530                 535                 540

Arg Cys Trp Asp Asn Leu Val Gln Lys Leu Glu Lys Ser Thr Ala Gln
545                 550                 555                 560

Ile Ser Gln Ala Val Thr Thr Thr Gln Pro Ser Leu Thr Gln Thr Thr
                565                 570                 575

Val Met Glu Thr Val Thr Thr Val Thr Thr Arg Glu Gln Ile Leu Val
            580                 585                 590

Lys His Ala Gln Glu Glu Leu Pro Pro Pro Pro Pro Gln Lys Lys Arg
        595                 600                 605

Gln Ile Thr Val Asp Ser Glu Ala Gln Ile His Thr Val Arg Glu Glu
```

```
    610                 615                 620

Thr Met Met Val Met Thr Glu Asp Met Pro Leu Glu Ile Ser Tyr Val
625                 630                 635                 640

Pro Ser Thr Tyr Leu Thr Glu Ile Thr His Val Ser Gln Ala Leu Leu
                645                 650                 655

Glu Val Glu Gln Leu Leu Asn Ala Pro Asp Leu Cys Ala Lys Asp Phe
            660                 665                 670

Glu Asp Leu Phe Lys Gln Glu Glu Ser Leu Lys Asn Ile Lys Asp Ser
        675                 680                 685

Leu Gln Gln Ser Ser Gly Arg Ile Asp Ile Ile His Ser Lys Lys Thr
    690                 695                 700

Ala Ala Leu Gln Ser Ala Thr Pro Val Glu Arg Val Lys Leu Gln Glu
705                 710                 715                 720

Ala Leu Ser Gln Leu Asp Phe Gln Trp Glu Lys Val Asn Lys Met Tyr
                725                 730                 735

Lys Asp Arg Gln Gly Arg Phe Asp Arg Ser Val Glu Lys Trp Arg Arg
            740                 745                 750

Phe His Tyr Asp Ile Lys Ile Phe Asn Gln Trp Leu Thr Glu Ala Glu
        755                 760                 765

Gln Phe Leu Arg Lys Thr Gln Ile Pro Glu Asn Trp Glu His Ala Lys
    770                 775                 780

Tyr Lys Trp Tyr Leu Lys Glu Leu Gln Asp Gly Ile Gly Gln Arg Gln
785                 790                 795                 800

Thr Val Val Arg Thr Leu Asn Ala Thr Gly Glu Glu Ile Ile Gln Gln
                805                 810                 815

Ser Ser Lys Thr Asp Ala Ser Ile Leu Gln Glu Lys Leu Gly Ser Leu
            820                 825                 830

Asn Leu Arg Trp Gln Glu Val Cys Lys Gln Leu Ser Asp Arg Lys Lys
        835                 840                 845

Arg Leu Glu Glu Gln Leu Glu Arg Leu Gln Glu Leu Gln Glu Ala Thr
    850                 855                 860

Asp Glu Leu Asp Leu Lys Leu Arg Gln Ala Glu Val Ile Lys Gly Ser
865                 870                 875                 880

Trp Gln Pro Val Gly Asp Leu Leu Ile Asp Ser Leu Gln Asp His Leu
                885                 890                 895

Glu Lys Val Lys Ala Leu Arg Gly Glu Ile Ala Pro Leu Lys Glu Asn
            900                 905                 910

Val Ser His Val Asn Asp Leu Ala Arg Gln Leu Thr Thr Leu Gly Ile
        915                 920                 925

Gln Leu Ser Pro Tyr Asn Leu Ser Thr Leu Glu Asp Leu Asn Thr Arg
    930                 935                 940

Trp Lys Leu Leu Gln Val Ala Val Glu Asp Arg Val Arg Gln Leu His
945                 950                 955                 960

Glu Ala His Arg Asp Phe Gly Pro Ala Ser Gln His Phe Leu Ser Thr
                965                 970                 975

Ser Val Gln Gly Pro Trp Glu Arg Ala Ile Ser Pro Asn Lys Val Pro
            980                 985                 990

Tyr Tyr Ile Asn His Glu Thr Gln  Thr Thr Cys Trp Asp  His Pro Lys
        995                 1000                1005

Met Thr  Glu Leu Tyr Gln Ser  Leu Ala Asp Leu Asn  Asn Val Arg
    1010                1015                1020

Phe Ser  Ala Tyr Arg Thr Ala  Met Lys Leu Arg Arg  Leu Gln Lys
    1025                1030                1035
```

```
Ala Leu  Cys Leu Asp Leu Leu  Ser Leu Ser Ala Ala  Cys Asp Ala
    1040                 1045                 1050

Leu Asp  Gln His Asn Leu Lys  Gln Asn Asp Gln Pro  Met Asp Ile
    1055                 1060                 1065

Leu Gln  Ile Ile Asn Cys Leu  Thr Thr Ile Tyr Asp  Arg Leu Glu
    1070                 1075                 1080

Gln Glu  His Asn Asn Leu Val  Asn Val Pro Leu Cys  Val Asp Met
    1085                 1090                 1095

Cys Leu  Asn Trp Leu Leu Asn  Val Tyr Asp Thr Gly  Arg Thr Gly
    1100                 1105                 1110

Arg Ile  Arg Val Leu Ser Phe  Lys Thr Gly Ile Ile  Ser Leu Cys
    1115                 1120                 1125

Lys Ala  His Leu Glu Asp Lys  Tyr Arg Tyr Leu Phe  Lys Gln Val
    1130                 1135                 1140

Ala Ser  Ser Thr Gly Phe Cys  Asp Gln Arg Arg Leu  Gly Leu Leu
    1145                 1150                 1155

Leu His  Asp Ser Ile Gln Ile  Pro Arg Gln Leu Gly  Glu Val Ala
    1160                 1165                 1170

Ser Phe  Gly Gly Ser Asn Ile  Glu Pro Ser Val Arg  Ser Cys Phe
    1175                 1180                 1185

Gln Phe  Ala Asn Asn Lys Pro  Glu Ile Glu Ala Ala  Leu Phe Leu
    1190                 1195                 1200

Asp Trp  Met Arg Leu Glu Pro  Gln Ser Met Val Trp  Leu Pro Val
    1205                 1210                 1215

Leu His  Arg Val Ala Ala Ala  Glu Thr Ala Lys His  Gln Ala Lys
    1220                 1225                 1230

Cys Asn  Ile Cys Lys Glu Cys  Pro Ile Ile Gly Phe  Arg Tyr Arg
    1235                 1240                 1245

Ser Leu  Lys His Phe Asn Tyr  Asp Ile Cys Gln Ser  Cys Phe Phe
    1250                 1255                 1260

Ser Gly  Arg Val Ala Lys Gly  His Lys Met His Tyr  Pro Met Val
    1265                 1270                 1275

Glu Tyr  Cys Thr Pro Thr Thr  Ser Gly Glu Asp Val  Arg Asp Phe
    1280                 1285                 1290

Ala Lys  Val Leu Lys Asn Lys  Phe Arg Thr Lys Arg  Tyr Phe Ala
    1295                 1300                 1305

Lys His  Pro Arg Met Gly Tyr  Leu Pro Val Gln Thr  Val Leu Glu
    1310                 1315                 1320

Gly Asp  Asn Met Glu Thr Asp  Thr Met
    1325                 1330
```

<210> SEQ ID NO 125
<211> LENGTH: 1325
<212> TYPE: PRT
<213> ORGANISM: Homo sapiens

<400> SEQUENCE: 125

```
Met Leu Trp Trp Glu Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
            20                  25                  30

Gly Lys Gln His Ile Glu Asn Leu Phe Ser Asp Leu Gln Asp Gly Arg
        35                  40                  45

Arg Leu Leu Asp Leu Leu Glu Gly Leu Thr Gly Gln Lys Leu Pro Lys
```

```
    50                  55                  60

Glu Lys Gly Ser Thr Arg Val His Ala Leu Asn Asn Val Asn Lys Ala
65                  70                  75                  80

Leu Arg Val Leu Gln Asn Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
        115                 120                 125

Ala Gly Leu Gln Gln Thr Asn Ser Glu Lys Ile Leu Leu Ser Trp Val
    130                 135                 140

Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His
                165                 170                 175

Arg Pro Asp Leu Phe Asp Trp Asn Ser Val Val Cys Gln Gln Ser Ala
            180                 185                 190

Thr Gln Arg Leu Glu His Ala Phe Asn Ile Ala Arg Tyr Gln Leu Gly
        195                 200                 205

Ile Glu Lys Leu Leu Asp Pro Glu Asp Val Asp Thr Thr Tyr Pro Asp
    210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu Met Leu Pro Arg
                245                 250                 255

Pro Pro Lys Val Thr Lys Glu Glu His Phe Gln Leu His His Gln Met
            260                 265                 270

His Tyr Ser Gln Gln Ile Thr Val Ser Leu Ala Gln Gly Tyr Glu Arg
        275                 280                 285

Thr Ser Ser Pro Lys Pro Arg Phe Lys Ser Tyr Ala Tyr Thr Gln Ala
    290                 295                 300

Ala Tyr Val Thr Thr Ser Asp Pro Thr Arg Ser Pro Phe Pro Ser Gln
305                 310                 315                 320

His Leu Glu Ala Pro Glu Asp Lys Ser Phe Gly Ser Ser Leu Met Glu
                325                 330                 335

Ser Glu Val Asn Leu Asp Arg Tyr Gln Thr Ala Leu Glu Glu Val Leu
            340                 345                 350

Ser Trp Leu Leu Ser Ala Glu Asp Thr Leu Gln Ala Gln Gly Glu Ile
        355                 360                 365

Ser Asn Asp Val Glu Val Val Lys Asp Gln Phe His Thr His Glu Gly
    370                 375                 380

Tyr Met Met Asp Leu Thr Ala His Gln Gly Arg Val Gly Asn Ile Leu
385                 390                 395                 400

Gln Leu Gly Ser Lys Leu Ile Gly Thr Gly Lys Leu Ser Glu Asp Glu
                405                 410                 415

Glu Thr Glu Val Gln Glu Gln Met Asn Leu Leu Asn Ser Arg Trp Glu
            420                 425                 430

Cys Leu Arg Val Ala Ser Met Glu Lys Gln Ser Asn Leu His Leu Leu
        435                 440                 445

Lys Trp Gln Arg Leu Thr Glu Glu Gln Cys Leu Phe Ser Ala Trp Leu
    450                 455                 460

Ser Glu Lys Glu Asp Ala Val Asn Lys Ile His Thr Thr Gly Phe Lys
465                 470                 475                 480
```

```
Asp Gln Asn Glu Met Leu Ser Ser Leu Gln Lys Leu Ala Val Leu Lys
                485                 490                 495

Ala Asp Leu Glu Lys Lys Lys Gln Ser Met Gly Lys Leu Tyr Ser Leu
            500                 505                 510

Lys Gln Asp Leu Leu Ser Thr Leu Lys Asn Lys Ser Val Thr Gln Lys
        515                 520                 525

Thr Glu Ala Trp Leu Asp Asn Phe Ala Arg Cys Trp Asp Asn Leu Val
    530                 535                 540

Gln Lys Leu Glu Lys Ser Thr Ala Gln Ile Ser Gln Ala Val Thr Thr
545                 550                 555                 560

Thr Gln Pro Ser Leu Thr Gln Thr Thr Val Met Glu Thr Val Thr Thr
                565                 570                 575

Val Thr Thr Arg Glu Gln Ile Leu Val Lys His Ala Gln Glu Glu Leu
            580                 585                 590

Pro Pro Pro Pro Pro Gln Lys Lys Arg Gln Ile Thr Val Asp Ser Glu
        595                 600                 605

Ala Gln Ile His Thr Val Arg Glu Glu Thr Met Met Val Met Thr Glu
    610                 615                 620

Asp Met Pro Leu Glu Ile Ser Tyr Val Pro Ser Thr Tyr Leu Thr Glu
625                 630                 635                 640

Ile Thr His Val Ser Gln Ala Leu Leu Glu Val Glu Gln Leu Leu Asn
                645                 650                 655

Ala Pro Asp Leu Cys Ala Lys Asp Phe Glu Asp Leu Phe Lys Gln Glu
            660                 665                 670

Glu Ser Leu Lys Asn Ile Lys Asp Ser Leu Gln Gln Ser Ser Gly Arg
        675                 680                 685

Ile Asp Ile Ile His Ser Lys Lys Thr Ala Ala Leu Gln Ser Ala Thr
    690                 695                 700

Pro Val Glu Arg Val Lys Leu Gln Glu Ala Leu Ser Gln Leu Asp Phe
705                 710                 715                 720

Gln Trp Glu Lys Val Asn Lys Met Tyr Lys Asp Arg Gln Gly Arg Phe
                725                 730                 735

Asp Arg Ser Val Glu Lys Trp Arg Arg Phe His Tyr Asp Ile Lys Ile
            740                 745                 750

Phe Asn Gln Trp Leu Thr Glu Ala Glu Gln Phe Leu Arg Lys Thr Gln
        755                 760                 765

Ile Pro Glu Asn Trp Glu His Ala Lys Tyr Lys Trp Tyr Leu Lys Glu
    770                 775                 780

Leu Gln Asp Gly Ile Gly Gln Arg Gln Thr Val Val Arg Thr Leu Asn
785                 790                 795                 800

Ala Thr Gly Glu Glu Ile Ile Gln Gln Ser Ser Lys Thr Asp Ala Ser
                805                 810                 815

Ile Leu Gln Glu Lys Leu Gly Ser Leu Asn Leu Arg Trp Gln Glu Val
            820                 825                 830

Cys Lys Gln Leu Ser Asp Arg Lys Lys Arg Leu Glu Glu Gln Leu Glu
        835                 840                 845

Arg Leu Gln Glu Leu Gln Glu Ala Thr Asp Glu Leu Asp Leu Lys Leu
    850                 855                 860

Arg Gln Ala Glu Val Ile Lys Gly Ser Trp Gln Pro Val Gly Asp Leu
865                 870                 875                 880

Leu Ile Asp Ser Leu Gln Asp His Leu Glu Lys Val Lys Ala Leu Arg
                885                 890                 895
```

```
Gly Glu Ile Ala Pro Leu Lys Glu Asn Val Ser His Val Asn Asp Leu
            900                 905                 910

Ala Arg Gln Leu Thr Thr Leu Gly Ile Gln Leu Ser Pro Tyr Asn Leu
        915                 920                 925

Ser Thr Leu Glu Asp Leu Asn Thr Arg Trp Lys Leu Leu Gln Val Ala
    930                 935                 940

Val Glu Asp Arg Val Arg Gln Leu His Glu Ala His Arg Asp Phe Gly
945                 950                 955                 960

Pro Ala Ser Gln His Phe Leu Ser Thr Ser Val Gln Gly Pro Trp Glu
                965                 970                 975

Arg Ala Ile Ser Pro Asn Lys Val Pro Tyr Tyr Ile Asn His Glu Thr
            980                 985                 990

Gln Thr Thr Cys Trp Asp His Pro  Lys Met Thr Glu Leu  Tyr Gln Ser
        995                 1000                1005

Leu Ala  Asp Leu Asn Asn Val  Arg Phe Ser Ala Tyr  Arg Thr Ala
    1010                1015                1020

Met Lys  Leu Arg Arg Leu Gln  Lys Ala Leu Cys Leu  Asp Leu Leu
    1025                1030                1035

Ser Leu  Ser Ala Ala Cys Asp  Ala Leu Asp Gln His  Asn Leu Lys
    1040                1045                1050

Gln Asn  Asp Gln Pro Met Asp  Ile Leu Gln Ile Ile  Asn Cys Leu
    1055                1060                1065

Thr Thr  Ile Tyr Asp Arg Leu  Glu Gln Glu His Asn  Asn Leu Val
    1070                1075                1080

Asn Val  Pro Leu Cys Val Asp  Met Cys Leu Asn Trp  Leu Leu Asn
    1085                1090                1095

Val Tyr  Asp Thr Gly Arg Thr  Gly Arg Ile Arg Val  Leu Ser Phe
    1100                1105                1110

Lys Thr  Gly Ile Ile Ser Leu  Cys Lys Ala His Leu  Glu Asp Lys
    1115                1120                1125

Tyr Arg  Tyr Leu Phe Lys Gln  Val Ala Ser Ser Thr  Gly Phe Cys
    1130                1135                1140

Asp Gln  Arg Arg Leu Gly Leu  Leu Leu His Asp Ser  Ile Gln Ile
    1145                1150                1155

Pro Arg  Gln Leu Gly Glu Val  Ala Ser Phe Gly Gly  Ser Asn Ile
    1160                1165                1170

Glu Pro  Ser Val Arg Ser Cys  Phe Gln Phe Ala Asn  Asn Lys Pro
    1175                1180                1185

Glu Ile  Glu Ala Ala Leu Phe  Leu Asp Trp Met Arg  Leu Glu Pro
    1190                1195                1200

Gln Ser  Met Val Trp Leu Pro  Val Leu His Arg Val  Ala Ala Ala
    1205                1210                1215

Glu Thr  Ala Lys His Gln Ala  Lys Cys Asn Ile Cys  Lys Glu Cys
    1220                1225                1230

Pro Ile  Ile Gly Phe Arg Tyr  Arg Ser Leu Lys His  Phe Asn Tyr
    1235                1240                1245

Asp Ile  Cys Gln Ser Cys Phe  Phe Ser Gly Arg Val  Ala Lys Gly
    1250                1255                1260

His Lys  Met His Tyr Pro Met  Val Glu Tyr Cys Thr  Pro Thr Thr
    1265                1270                1275

Ser Gly  Glu Asp Val Arg Asp  Phe Ala Lys Val Leu  Lys Asn Lys
    1280                1285                1290

Phe Arg  Thr Lys Arg Tyr Phe  Ala Lys His Pro Arg  Met Gly Tyr
```

```
    1295                1300                1305

Leu Pro  Val Gln Thr Val Leu  Glu Gly Asp Asn Met  Glu Thr Asp
    1310                1315                1320

Thr Met
    1325
```

<210> SEQ ID NO 126
<211> LENGTH: 1255
<212> TYPE: PRT
<213> ORGANISM: Homo sapiens

<400> SEQUENCE: 126

```
Met Leu Trp Trp Glu Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
            20                  25                  30

Gly Lys Gln His Ile Glu Asn Leu Phe Ser Asp Leu Gln Asp Gly Arg
        35                  40                  45

Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Asn Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
        115                 120                 125

Ala Gly Leu Gln Gln Thr Asn Ser Glu Lys Ile Leu Leu Ser Trp Val
    130                 135                 140

Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His
                165                 170                 175

Arg Pro Asp Leu Phe Asp Trp Asn Ser Val Val Cys Gln Gln Ser Ala
            180                 185                 190

Thr Gln Arg Leu Glu His Ala Phe Asn Ile Ala Arg Tyr Gln Leu Gly
        195                 200                 205

Ile Glu Lys Leu Leu Asp Pro Glu Asp Val Asp Thr Thr Tyr Pro Asp
    210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu Met Leu Pro Arg
                245                 250                 255

Pro Pro Lys Val Thr Lys Glu Glu His Phe Gln Leu His His Gln Met
            260                 265                 270

His Tyr Ser Gln Gln Ile Thr Val Ser Leu Ala Gln Gly Tyr Glu Arg
        275                 280                 285

Thr Ser Ser Pro Lys Pro Arg Phe Lys Ser Tyr Ala Tyr Thr Gln Ala
    290                 295                 300

Ala Tyr Val Thr Thr Ser Asp Pro Thr Arg Ser Pro Phe Pro Ser Gln
305                 310                 315                 320

His Leu Glu Ala Pro Glu Asp Lys Ser Phe Gly Ser Ser Leu Met Glu
                325                 330                 335
```

```
Ser Glu Val Asn Leu Asp Arg Tyr Gln Thr Ala Leu Glu Glu Val Leu
            340                 345                 350

Ser Trp Leu Leu Ser Ala Glu Asp Thr Leu Gln Ala Gln Gly Glu Ile
        355                 360                 365

Ser Asn Asp Val Glu Val Val Lys Asp Gln Phe His Thr His Glu Gly
    370                 375                 380

Tyr Met Met Asp Leu Thr Ala His Gln Gly Arg Val Gly Asn Ile Leu
385                 390                 395                 400

Gln Leu Gly Ser Lys Leu Ile Gly Thr Gly Lys Leu Ser Glu Asp Glu
                405                 410                 415

Glu Thr Glu Val Gln Glu Gln Met Asn Leu Leu Asn Ser Arg Trp Glu
            420                 425                 430

Cys Leu Arg Val Ala Ser Met Glu Lys Gln Ser Asn Leu His Ile His
        435                 440                 445

Thr Val Arg Glu Glu Thr Met Met Val Met Thr Glu Asp Met Pro Leu
    450                 455                 460

Glu Ile Ser Tyr Val Pro Ser Thr Tyr Leu Thr Glu Ile Thr His Val
465                 470                 475                 480

Ser Gln Ala Leu Leu Glu Val Glu Gln Leu Leu Asn Ala Pro Asp Leu
                485                 490                 495

Cys Ala Lys Asp Phe Glu Asp Leu Phe Lys Gln Glu Glu Ser Leu Lys
            500                 505                 510

Asn Ile Lys Asp Ser Leu Gln Gln Ser Ser Gly Arg Ile Asp Ile Ile
        515                 520                 525

His Ser Lys Lys Thr Ala Ala Leu Gln Ser Ala Thr Pro Val Glu Arg
    530                 535                 540

Val Lys Leu Gln Glu Ala Leu Ser Gln Leu Asp Phe Gln Trp Glu Lys
545                 550                 555                 560

Val Asn Lys Met Tyr Lys Asp Arg Gln Gly Arg Phe Asp Arg Ser Val
                565                 570                 575

Glu Lys Trp Arg Arg Phe His Tyr Asp Ile Lys Ile Phe Asn Gln Trp
            580                 585                 590

Leu Thr Glu Ala Glu Gln Phe Leu Arg Lys Thr Gln Ile Pro Glu Asn
        595                 600                 605

Trp Glu His Ala Lys Tyr Lys Trp Tyr Leu Lys Glu Leu Gln Asp Gly
    610                 615                 620

Ile Gly Gln Arg Gln Thr Val Val Arg Thr Leu Asn Ala Thr Gly Glu
625                 630                 635                 640

Glu Ile Ile Gln Gln Ser Ser Lys Thr Asp Ala Ser Ile Leu Gln Glu
                645                 650                 655

Lys Leu Gly Ser Leu Asn Leu Arg Trp Gln Glu Val Cys Lys Gln Leu
            660                 665                 670

Ser Asp Arg Lys Lys Arg Leu Glu Glu Gln Ala Pro Gly Leu Thr Thr
        675                 680                 685

Ile Gly Ala Ser Pro Thr Gln Thr Val Thr Leu Val Thr Gln Pro Val
    690                 695                 700

Val Thr Lys Glu Thr Ala Ile Ser Lys Leu Glu Met Pro Ser Ser Leu
705                 710                 715                 720

Met Leu Glu Leu Glu Arg Leu Gln Glu Leu Gln Glu Ala Thr Asp Glu
                725                 730                 735

Leu Asp Leu Lys Leu Arg Gln Ala Glu Val Ile Lys Gly Ser Trp Gln
            740                 745                 750

Pro Val Gly Asp Leu Leu Ile Asp Ser Leu Gln Asp His Leu Glu Lys
```

```
        755                 760                 765

Val Lys Ala Leu Arg Gly Glu Ile Ala Pro Leu Lys Glu Asn Val Ser
    770                 775                 780

His Val Asn Asp Leu Ala Arg Gln Leu Thr Thr Leu Gly Ile Gln Leu
785                 790                 795                 800

Ser Pro Tyr Asn Leu Ser Thr Leu Glu Asp Leu Asn Thr Arg Trp Lys
                805                 810                 815

Leu Leu Gln Val Ala Val Glu Asp Arg Val Arg Gln Leu His Glu Ala
            820                 825                 830

His Arg Asp Phe Gly Pro Ala Ser Gln His Phe Leu Ser Thr Ser Val
        835                 840                 845

Gln Gly Pro Trp Glu Arg Ala Ile Ser Pro Asn Lys Val Pro Tyr Tyr
    850                 855                 860

Ile Asn His Glu Thr Gln Thr Thr Cys Trp Asp His Pro Lys Met Thr
865                 870                 875                 880

Glu Leu Tyr Gln Ser Leu Ala Asp Leu Asn Asn Val Arg Phe Ser Ala
                885                 890                 895

Tyr Arg Thr Ala Met Lys Leu Arg Arg Leu Gln Lys Ala Leu Cys Leu
            900                 905                 910

Asp Leu Leu Ser Leu Ser Ala Ala Cys Asp Ala Leu Asp Gln His Asn
        915                 920                 925

Leu Lys Gln Asn Asp Gln Pro Met Asp Ile Leu Gln Ile Ile Asn Cys
    930                 935                 940

Leu Thr Thr Ile Tyr Asp Arg Leu Glu Gln Glu His Asn Asn Leu Val
945                 950                 955                 960

Asn Val Pro Leu Cys Val Asp Met Cys Leu Asn Trp Leu Leu Asn Val
                965                 970                 975

Tyr Asp Thr Gly Arg Thr Gly Arg Ile Arg Val Leu Ser Phe Lys Thr
            980                 985                 990

Gly Ile Ile Ser Leu Cys Lys Ala  His Leu Glu Asp Lys  Tyr Arg Tyr
        995                 1000                1005

Leu Phe  Lys Gln Val Ala Ser  Ser Thr Gly Phe Cys  Asp Gln Arg
    1010                1015                1020

Arg Leu  Gly Leu Leu Leu His  Asp Ser Ile Gln Ile  Pro Arg Gln
    1025                1030                1035

Leu Gly  Glu Val Ala Ser Phe  Gly Gly Ser Asn Ile  Glu Pro Ser
    1040                1045                1050

Val Arg  Ser Cys Phe Gln Phe  Ala Asn Asn Lys Pro  Glu Ile Glu
    1055                1060                1065

Ala Ala  Leu Phe Leu Asp Trp  Met Arg Leu Glu Pro  Gln Ser Met
    1070                1075                1080

Val Trp  Leu Pro Val Leu His  Arg Val Ala Ala Ala  Glu Thr Ala
    1085                1090                1095

Lys His  Gln Ala Lys Cys Asn  Ile Cys Lys Glu Cys  Pro Ile Ile
    1100                1105                1110

Gly Phe  Arg Tyr Arg Ser Leu  Lys His Phe Asn Tyr  Asp Ile Cys
    1115                1120                1125

Gln Ser  Cys Phe Phe Ser Gly  Arg Val Ala Lys Gly  His Lys Met
    1130                1135                1140

His Tyr  Pro Met Val Glu Tyr  Cys Thr Pro Thr Thr  Ser Gly Glu
    1145                1150                1155

Asp Val  Arg Asp Phe Ala Lys  Val Leu Lys Asn Lys  Phe Arg Thr
    1160                1165                1170
```

Lys Arg Tyr Phe Ala Lys His Pro Arg Met Gly Tyr Leu Pro Val
1175 1180 1185

Gln Thr Val Leu Glu Gly Asp Asn Met Glu Thr Pro Ala Gln Ile
1190 1195 1200

Leu Ile Ser Leu Glu Ser Glu Glu Arg Gly Glu Leu Glu Arg Ile
1205 1210 1215

Leu Ala Asp Leu Glu Glu Glu Asn Arg Asn Leu Gln Ala Glu Tyr
1220 1225 1230

Asp Arg Leu Lys Gln Gln His Glu His Lys Gly Leu Ser Pro Leu
1235 1240 1245

Pro Ser Pro Pro Asp Thr Met
1250 1255

<210> SEQ ID NO 127
<211> LENGTH: 1262
<212> TYPE: PRT
<213> ORGANISM: Homo sapiens

<400> SEQUENCE: 127

Met Leu Trp Trp Glu Glu Val Glu Asp Cys Tyr Glu Arg Glu Asp Val
1 5 10 15

Gln Lys Lys Thr Phe Thr Lys Trp Val Asn Ala Gln Phe Ser Lys Phe
20 25 30

Gly Lys Gln His Ile Glu Asn Leu Phe Ser Asp Leu Gln Asp Gly Arg
35 40 45

Arg Leu Leu Asp Leu Leu Glu Gly Leu Thr Gly Gln Lys Leu Pro Lys
50 55 60

Glu Lys Gly Ser Thr Arg Val His Ala Leu Asn Asn Val Asn Lys Ala
65 70 75 80

Leu Arg Val Leu Gln Asn Asn Asn Val Asp Leu Val Asn Ile Gly Ser
85 90 95

Thr Asp Ile Val Asp Gly Asn His Lys Leu Thr Leu Gly Leu Ile Trp
100 105 110

Asn Ile Ile Leu His Trp Gln Val Lys Asn Val Met Lys Asn Ile Met
115 120 125

Ala Gly Leu Gln Gln Thr Asn Ser Glu Lys Ile Leu Leu Ser Trp Val
130 135 140

Arg Gln Ser Thr Arg Asn Tyr Pro Gln Val Asn Val Ile Asn Phe Thr
145 150 155 160

Thr Ser Trp Ser Asp Gly Leu Ala Leu Asn Ala Leu Ile His Ser His
165 170 175

Arg Pro Asp Leu Phe Asp Trp Asn Ser Val Val Cys Gln Gln Ser Ala
180 185 190

Thr Gln Arg Leu Glu His Ala Phe Asn Ile Ala Arg Tyr Gln Leu Gly
195 200 205

Ile Glu Lys Leu Leu Asp Pro Glu Asp Val Asp Thr Thr Tyr Pro Asp
210 215 220

Lys Lys Ser Ile Leu Met Tyr Ile Thr Ser Leu Phe Gln Val Leu Pro
225 230 235 240

Gln Gln Val Ser Ile Glu Ala Ile Gln Glu Val Glu Met Leu Pro Arg
245 250 255

Pro Pro Lys Val Thr Lys Glu Glu His Phe Gln Leu His His Gln Met
260 265 270

His Tyr Ser Gln Gln Ile Thr Val Ser Leu Ala Gln Gly Tyr Glu Arg

```
        275                 280                 285

Thr Ser Ser Pro Lys Pro Arg Phe Lys Ser Tyr Ala Tyr Thr Gln Ala
    290                 295                 300

Ala Tyr Val Thr Thr Ser Asp Pro Thr Arg Ser Pro Phe Pro Ser Gln
305                 310                 315                 320

His Leu Glu Ala Pro Glu Asp Lys Ser Phe Gly Ser Ser Leu Met Glu
                325                 330                 335

Ser Glu Val Asn Leu Asp Arg Tyr Gln Thr Ala Leu Glu Glu Val Leu
            340                 345                 350

Ser Trp Leu Leu Ser Ala Glu Asp Thr Leu Gln Ala Gln Gly Glu Ile
        355                 360                 365

Ser Asn Asp Val Glu Val Val Lys Asp Gln Phe His Thr His Glu Gly
    370                 375                 380

Tyr Met Met Asp Leu Thr Ala His Gln Gly Arg Val Gly Asn Ile Leu
385                 390                 395                 400

Gln Leu Gly Ser Lys Leu Ile Gly Thr Gly Lys Leu Ser Glu Asp Glu
                405                 410                 415

Glu Thr Glu Val Gln Glu Gln Met Asn Leu Leu Asn Ser Arg Trp Glu
            420                 425                 430

Cys Leu Arg Val Ala Ser Met Glu Lys Gln Ser Asn Leu His Arg Val
        435                 440                 445

Leu Ile His Thr Val Arg Glu Glu Thr Met Met Val Met Thr Glu Asp
    450                 455                 460

Met Pro Leu Glu Ile Ser Tyr Val Pro Ser Thr Tyr Leu Thr Glu Ile
465                 470                 475                 480

Thr His Val Ser Gln Ala Leu Leu Glu Val Glu Gln Leu Leu Asn Ala
                485                 490                 495

Pro Asp Leu Cys Ala Lys Asp Phe Glu Asp Leu Phe Lys Gln Glu Glu
            500                 505                 510

Ser Leu Lys Asn Ile Lys Asp Ser Leu Gln Gln Ser Ser Gly Arg Ile
        515                 520                 525

Asp Ile Ile His Ser Lys Lys Thr Ala Ala Leu Gln Ser Ala Thr Pro
    530                 535                 540

Val Glu Arg Val Lys Leu Gln Glu Ala Leu Ser Gln Leu Asp Phe Gln
545                 550                 555                 560

Trp Glu Lys Val Asn Lys Met Tyr Lys Asp Arg Gln Gly Arg Phe Asp
                565                 570                 575

Arg Ser Val Glu Lys Trp Arg Arg Phe His Tyr Asp Ile Lys Ile Phe
            580                 585                 590

Asn Gln Trp Leu Thr Glu Ala Glu Gln Phe Leu Arg Lys Thr Gln Ile
        595                 600                 605

Pro Glu Asn Trp Glu His Ala Lys Tyr Lys Trp Tyr Leu Lys Glu Leu
    610                 615                 620

Gln Asp Gly Ile Gly Gln Arg Gln Thr Val Val Arg Thr Leu Asn Ala
625                 630                 635                 640

Thr Gly Glu Glu Ile Ile Gln Gln Ser Ser Lys Thr Asp Ala Ser Ile
                645                 650                 655

Leu Gln Glu Lys Leu Gly Ser Leu Asn Leu Arg Trp Gln Glu Val Cys
            660                 665                 670

Lys Gln Leu Ser Asp Arg Lys Lys Arg Leu Glu Glu Gln Lys Asn Asp
        675                 680                 685

Leu Ala Pro Gly Leu Thr Thr Ile Gly Ala Ser Pro Thr Gln Thr Val
    690                 695                 700
```

```
Thr Leu Val Thr Gln Pro Val Val Thr Lys Glu Thr Ala Ile Ser Lys
705                 710                 715                 720

Leu Glu Met Pro Ser Ser Leu Met Leu Glu Val Glu Arg Leu Gln Glu
                725                 730                 735

Leu Gln Glu Ala Thr Asp Glu Leu Asp Leu Lys Leu Arg Gln Ala Glu
            740                 745                 750

Val Ile Lys Gly Ser Trp Gln Pro Val Gly Asp Leu Leu Ile Asp Ser
        755                 760                 765

Leu Gln Asp His Leu Glu Lys Val Lys Ala Leu Arg Gly Glu Ile Ala
    770                 775                 780

Pro Leu Lys Glu Asn Val Ser His Val Asn Asp Leu Ala Arg Gln Leu
785                 790                 795                 800

Thr Thr Leu Gly Ile Gln Leu Ser Pro Tyr Asn Leu Ser Thr Leu Glu
                805                 810                 815

Asp Leu Asn Thr Arg Trp Lys Leu Leu Gln Val Ala Val Glu Asp Arg
            820                 825                 830

Val Arg Gln Leu His Glu Ala His Arg Asp Phe Gly Pro Ala Ser Gln
        835                 840                 845

His Phe Leu Ser Thr Ser Val Gln Gly Pro Trp Glu Arg Ala Ile Ser
    850                 855                 860

Pro Asn Lys Val Pro Tyr Tyr Ile Asn His Glu Thr Gln Thr Thr Cys
865                 870                 875                 880

Trp Asp His Pro Lys Met Thr Glu Leu Tyr Gln Ser Leu Ala Asp Leu
                885                 890                 895

Asn Asn Val Arg Phe Ser Ala Tyr Arg Thr Ala Met Lys Leu Arg Arg
            900                 905                 910

Leu Gln Lys Ala Leu Cys Leu Asp Leu Leu Ser Leu Ser Ala Ala Cys
        915                 920                 925

Asp Ala Leu Asp Gln His Asn Leu Lys Gln Asn Asp Gln Pro Met Asp
    930                 935                 940

Ile Leu Gln Ile Ile Asn Cys Leu Thr Thr Ile Tyr Asp Arg Leu Glu
945                 950                 955                 960

Gln Glu His Asn Asn Leu Val Asn Val Pro Leu Cys Val Asp Met Cys
                965                 970                 975

Leu Asn Trp Leu Leu Asn Val Tyr Asp Thr Gly Arg Thr Gly Arg Ile
            980                 985                 990

Arg Val Leu Ser Phe Lys Thr Gly  Ile Ile Ser Leu Cys  Lys Ala His
        995                 1000                1005

Leu Glu  Asp Lys Tyr Arg Tyr  Leu Phe Lys Gln Val  Ala Ser Ser
    1010                1015                1020

Thr Gly  Phe Cys Asp Gln Arg  Arg Leu Gly Leu Leu  Leu His Asp
    1025                1030                1035

Ser Ile  Gln Ile Pro Arg Gln  Leu Gly Glu Val Ala  Ser Phe Gly
    1040                1045                1050

Gly Ser  Asn Ile Glu Pro Ser  Val Arg Ser Cys Phe  Gln Phe Ala
    1055                1060                1065

Asn Asn  Lys Pro Glu Ile Glu  Ala Ala Leu Phe Leu  Asp Trp Met
    1070                1075                1080

Arg Leu  Glu Pro Gln Ser Met  Val Trp Leu Pro Val  Leu His Arg
    1085                1090                1095

Val Ala  Ala Ala Glu Thr Ala  Lys His Gln Ala Lys  Cys Asn Ile
    1100                1105                1110
```

```
Cys Lys  Glu Cys Pro Ile Ile  Gly Phe Arg Tyr Arg  Ser Leu Lys
    1115                 1120                 1125

His Phe  Asn Tyr Asp Ile Cys  Gln Ser Cys Phe Phe  Ser Gly Arg
    1130                 1135                 1140

Val Ala  Lys Gly His Lys Met  His Tyr Pro Met Val  Glu Tyr Cys
    1145                 1150                 1155

Thr Pro  Thr Thr Ser Gly Glu  Asp Val Arg Asp Phe  Ala Lys Val
    1160                 1165                 1170

Leu Lys  Asn Lys Phe Arg Thr  Lys Arg Tyr Phe Ala  Lys His Pro
    1175                 1180                 1185

Arg Met  Gly Tyr Leu Pro Val  Gln Thr Val Leu Glu  Gly Asp Asn
    1190                 1195                 1200

Met Glu  Thr Pro Ala Gln Ile  Leu Ile Ser Leu Glu  Ser Glu Glu
    1205                 1210                 1215

Arg Gly  Glu Leu Glu Arg Ile  Leu Ala Asp Leu Glu  Glu Glu Asn
    1220                 1225                 1230

Arg Asn  Leu Gln Ala Glu Tyr  Asp Arg Leu Lys Gln  Gln His Glu
    1235                 1240                 1245

His Lys  Gly Leu Ser Pro Leu  Pro Ser Pro Pro Asp  Thr Met
    1250                 1255                 1260


<210> SEQ ID NO 128
<211> LENGTH: 1249
<212> TYPE: PRT
<213> ORGANISM: Homo sapiens

<400> SEQUENCE: 128

Met Leu Trp Trp Glu Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
            20                  25                  30

Gly Lys Gln His Ile Glu Asn Leu Phe Ser Asp Leu Gln Asp Gly Arg
        35                  40                  45

Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Asn Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
        115                 120                 125

Ala Gly Leu Gln Gln Thr Asn Ser Glu Lys Ile Leu Leu Ser Trp Val
    130                 135                 140

Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His
                165                 170                 175

Arg Pro Asp Leu Phe Asp Trp Asn Ser Val Val Cys Gln Gln Ser Ala
            180                 185                 190

Thr Gln Arg Leu Glu His Ala Phe Asn Ile Ala Arg Tyr Gln Leu Gly
        195                 200                 205

Ile Glu Lys Leu Leu Asp Pro Glu Asp Val Asp Thr Thr Tyr Pro Asp
    210                 215                 220
```

```
Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu Met Leu Pro Arg
                245                 250                 255

Pro Pro Lys Val Thr Lys Glu Glu His Phe Gln Leu His His Gln Met
            260                 265                 270

His Tyr Ser Gln Gln Ile Thr Val Ser Leu Ala Gln Gly Tyr Glu Arg
        275                 280                 285

Thr Ser Ser Pro Lys Pro Arg Phe Lys Ser Tyr Ala Tyr Thr Gln Ala
    290                 295                 300

Ala Tyr Val Thr Thr Ser Asp Pro Thr Arg Ser Pro Phe Pro Ser Gln
305                 310                 315                 320

His Leu Glu Ala Pro Glu Asp Lys Ser Phe Gly Ser Ser Leu Met Glu
                325                 330                 335

Ser Glu Val Asn Leu Asp Arg Tyr Gln Thr Ala Leu Glu Glu Val Leu
            340                 345                 350

Ser Trp Leu Leu Ser Ala Glu Asp Thr Leu Gln Ala Gln Gly Glu Ile
        355                 360                 365

Ser Asn Asp Val Glu Val Val Lys Asp Gln Phe His Thr His Glu Gly
    370                 375                 380

Tyr Met Met Asp Leu Thr Ala His Gln Gly Arg Val Gly Asn Ile Leu
385                 390                 395                 400

Gln Leu Gly Ser Lys Leu Ile Gly Thr Gly Lys Leu Ser Glu Asp Glu
                405                 410                 415

Glu Thr Glu Val Gln Glu Gln Met Asn Leu Leu Asn Ser Arg Trp Glu
            420                 425                 430

Cys Leu Arg Val Ala Ser Met Glu Lys Gln Ser Asn Leu His Ser Tyr
        435                 440                 445

Val Pro Ser Thr Tyr Leu Thr Glu Ile Thr His Val Ser Gln Ala Leu
    450                 455                 460

Leu Glu Val Glu Gln Leu Leu Asn Ala Pro Asp Leu Cys Ala Lys Asp
465                 470                 475                 480

Phe Glu Asp Leu Phe Lys Gln Glu Glu Ser Leu Lys Asn Ile Lys Asp
                485                 490                 495

Ser Leu Gln Gln Ser Ser Gly Arg Ile Asp Ile Ile His Ser Lys Lys
            500                 505                 510

Thr Ala Ala Leu Gln Ser Ala Thr Pro Val Glu Arg Val Lys Leu Gln
        515                 520                 525

Glu Ala Leu Ser Gln Leu Asp Phe Gln Trp Glu Lys Val Asn Lys Met
    530                 535                 540

Tyr Lys Asp Arg Gln Gly Arg Phe Asp Arg Ser Val Glu Lys Trp Arg
545                 550                 555                 560

Arg Phe His Tyr Asp Ile Lys Ile Phe Asn Gln Trp Leu Thr Glu Ala
                565                 570                 575

Glu Gln Phe Leu Arg Lys Thr Gln Ile Pro Glu Asn Trp Glu His Ala
            580                 585                 590

Lys Tyr Lys Trp Tyr Leu Lys Glu Leu Gln Asp Gly Ile Gly Gln Arg
        595                 600                 605

Gln Thr Val Val Arg Thr Leu Asn Ala Thr Gly Glu Glu Ile Ile Gln
    610                 615                 620

Gln Ser Ser Lys Thr Asp Ala Ser Ile Leu Gln Glu Lys Leu Gly Ser
625                 630                 635                 640
```

```
Leu Asn Leu Arg Trp Gln Glu Val Cys Lys Gln Leu Ser Asp Arg Lys
                645                 650                 655

Lys Arg Leu Glu Glu Gln Leu Glu Gly Leu Glu Lys Leu Tyr Gln Glu
            660                 665                 670

Pro Arg Glu Leu Pro Pro Glu Glu Arg Ala Gln Asn Val Thr Arg Leu
        675                 680                 685

Leu Arg Lys Gln Ala Glu Glu Val Asn Thr Glu Trp Glu Lys Leu Asn
    690                 695                 700

Leu His Ser Ala Asp Trp Gln Arg Lys Ile Asp Glu Thr Leu Glu Arg
705                 710                 715                 720

Leu Gln Glu Leu Gln Glu Ala Thr Asp Glu Leu Asp Leu Lys Leu Arg
                725                 730                 735

Gln Ala Glu Val Ile Lys Gly Ser Trp Gln Pro Val Gly Asp Leu Leu
            740                 745                 750

Ile Asp Ser Leu Gln Asp His Leu Glu Lys Val Lys Ala Leu Arg Gly
        755                 760                 765

Glu Ile Ala Pro Leu Lys Glu Asn Val Ser His Val Asn Asp Leu Ala
    770                 775                 780

Arg Gln Leu Thr Thr Leu Gly Ile Gln Leu Ser Pro Tyr Asn Leu Ser
785                 790                 795                 800

Thr Leu Glu Asp Leu Asn Thr Arg Trp Lys Leu Leu Gln Val Ala Val
                805                 810                 815

Glu Asp Arg Val Arg Gln Leu His Glu Ala His Arg Asp Phe Gly Pro
            820                 825                 830

Ala Ser Gln His Phe Leu Ser Thr Ser Val Gln Gly Pro Trp Glu Arg
        835                 840                 845

Ala Ile Ser Pro Asn Lys Val Pro Tyr Tyr Ile Asn His Glu Thr Gln
    850                 855                 860

Thr Thr Cys Trp Asp His Pro Lys Met Thr Glu Leu Tyr Gln Ser Leu
865                 870                 875                 880

Ala Asp Leu Asn Asn Val Arg Phe Ser Ala Tyr Arg Thr Ala Met Lys
                885                 890                 895

Leu Arg Arg Leu Gln Lys Ala Leu Cys Leu Asp Leu Leu Ser Leu Ser
            900                 905                 910

Ala Ala Cys Asp Ala Leu Asp Gln His Asn Leu Lys Gln Asn Asp Gln
        915                 920                 925

Pro Met Asp Ile Leu Gln Ile Ile Asn Cys Leu Thr Thr Ile Tyr Asp
    930                 935                 940

Arg Leu Glu Gln Glu His Asn Asn Leu Val Asn Val Pro Leu Cys Val
945                 950                 955                 960

Asp Met Cys Leu Asn Trp Leu Leu Asn Val Tyr Asp Thr Gly Arg Thr
                965                 970                 975

Gly Arg Ile Arg Val Leu Ser Phe Lys Thr Gly Ile Ile Ser Leu Cys
            980                 985                 990

Lys Ala His Leu Glu Asp Lys Tyr  Arg Tyr Leu Phe Lys  Gln Val Ala
        995                 1000                1005

Ser Ser  Thr Gly Phe Cys Asp  Gln Arg Arg Leu Gly  Leu Leu Leu
    1010                1015                1020

His Asp  Ser Ile Gln Ile Pro  Arg Gln Leu Gly Glu  Val Ala Ser
    1025                1030                1035

Phe Gly  Gly Ser Asn Ile Glu  Pro Ser Val Arg Ser  Cys Phe Gln
    1040                1045                1050

Phe Ala  Asn Asn Lys Pro Glu  Ile Glu Ala Ala Leu  Phe Leu Asp
```

```
    1055                1060                1065

Trp Met  Arg Leu Glu Pro Gln  Ser Met Val Trp Leu  Pro Val Leu
    1070                1075                1080

His Arg  Val Ala Ala Ala Glu  Thr Ala Lys His Gln  Ala Lys Cys
    1085                1090                1095

Asn Ile  Cys Lys Glu Cys Pro  Ile Ile Gly Phe Arg  Tyr Arg Ser
    1100                1105                1110

Leu Lys  His Phe Asn Tyr Asp  Ile Cys Gln Ser Cys  Phe Phe Ser
    1115                1120                1125

Gly Arg  Val Ala Lys Gly His  Lys Met His Tyr Pro  Met Val Glu
    1130                1135                1140

Tyr Cys  Thr Pro Thr Thr Ser  Gly Glu Asp Val Arg  Asp Phe Ala
    1145                1150                1155

Lys Val  Leu Lys Asn Lys Phe  Arg Thr Lys Arg Tyr  Phe Ala Lys
    1160                1165                1170

His Pro  Arg Met Gly Tyr Leu  Pro Val Gln Thr Val  Leu Glu Gly
    1175                1180                1185

Asp Asn  Met Glu Thr Pro Ala  Gln Ile Leu Ile Ser  Leu Glu Ser
    1190                1195                1200

Glu Glu  Arg Gly Glu Leu Glu  Arg Ile Leu Ala Asp  Leu Glu Glu
    1205                1210                1215

Glu Asn  Arg Asn Leu Gln Ala  Glu Tyr Asp Arg Leu  Lys Gln Gln
    1220                1225                1230

His Glu  His Lys Gly Leu Ser  Pro Leu Pro Ser Pro  Pro Asp Thr
    1235                1240                1245

Met


<210> SEQ ID NO 129
<211> LENGTH: 1374
<212> TYPE: PRT
<213> ORGANISM: Homo sapiens

<400> SEQUENCE: 129

Met Leu Trp Trp Glu Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
            20                  25                  30

Gly Lys Gln His Ile Glu Asn Leu Phe Ser Asp Leu Gln Asp Gly Arg
        35                  40                  45

Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Asn Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
        115                 120                 125

Ala Gly Leu Gln Gln Thr Asn Ser Glu Lys Ile Leu Leu Ser Trp Val
    130                 135                 140

Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His
```

```
                165                 170                 175

Arg Pro Asp Leu Phe Asp Trp Asn Ser Val Val Cys Gln Gln Ser Ala
            180                 185                 190

Thr Gln Arg Leu Glu His Ala Phe Asn Ile Ala Arg Tyr Gln Leu Gly
        195                 200                 205

Ile Glu Lys Leu Leu Asp Pro Glu Asp Val Asp Thr Thr Tyr Pro Asp
    210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu Met Leu Pro Arg
                245                 250                 255

Pro Pro Lys Val Thr Lys Glu Glu His Phe Gln Leu His His Gln Met
            260                 265                 270

His Tyr Ser Gln Gln Ile Thr Val Ser Leu Ala Gln Gly Tyr Glu Arg
        275                 280                 285

Thr Ser Ser Pro Lys Pro Arg Phe Lys Ser Tyr Ala Tyr Thr Gln Ala
    290                 295                 300

Ala Tyr Val Thr Thr Ser Asp Pro Thr Arg Ser Pro Phe Pro Ser Gln
305                 310                 315                 320

His Leu Glu Ala Pro Glu Asp Lys Ser Phe Gly Ser Ser Leu Met Glu
                325                 330                 335

Ser Glu Val Asn Leu Asp Arg Tyr Gln Thr Ala Leu Glu Glu Val Leu
            340                 345                 350

Ser Trp Leu Leu Ser Ala Glu Asp Thr Leu Gln Ala Gln Gly Glu Ile
        355                 360                 365

Ser Asn Asp Val Glu Val Val Lys Asp Gln Phe His Thr His Glu Gly
    370                 375                 380

Tyr Met Met Asp Leu Thr Ala His Gln Gly Arg Val Gly Asn Ile Leu
385                 390                 395                 400

Gln Leu Gly Ser Lys Leu Ile Gly Thr Gly Lys Leu Ser Glu Asp Glu
                405                 410                 415

Glu Thr Glu Val Gln Glu Gln Met Asn Leu Leu Asn Ser Arg Trp Glu
            420                 425                 430

Cys Leu Arg Val Ala Ser Met Glu Lys Gln Ser Asn Leu His Leu Leu
        435                 440                 445

Lys Trp Gln Arg Leu Thr Glu Glu Gln Cys Leu Phe Ser Ala Trp Leu
    450                 455                 460

Ser Glu Lys Glu Asp Ala Val Asn Lys Ile His Thr Thr Gly Phe Lys
465                 470                 475                 480

Asp Gln Asn Glu Met Leu Ser Ser Leu Gln Lys Leu Ala Val Leu Lys
                485                 490                 495

Ala Asp Leu Glu Lys Lys Lys Gln Ser Met Gly Lys Leu Tyr Ser Leu
            500                 505                 510

Lys Gln Asp Leu Leu Ser Thr Leu Lys Asn Lys Ser Val Thr Gln Lys
        515                 520                 525

Thr Glu Ala Trp Leu Asp Asn Phe Ala Arg Cys Trp Asp Asn Leu Val
    530                 535                 540

Gln Lys Leu Glu Lys Ser Thr Ala Gln Ile Ser Gln Ala Val Thr Thr
545                 550                 555                 560

Thr Gln Pro Ser Leu Thr Gln Thr Thr Val Met Glu Thr Val Thr Thr
                565                 570                 575

Val Thr Thr Arg Glu Gln Ile Leu Val Lys His Ala Gln Glu Glu Leu
            580                 585                 590
```

```
Pro Pro Pro Pro Pro Gln Lys Lys Arg Gln Ile Thr Val Asp Ile His
        595                 600                 605

Thr Val Arg Glu Glu Thr Met Met Val Met Thr Glu Asp Met Pro Leu
    610                 615                 620

Glu Ile Ser Tyr Val Pro Ser Thr Tyr Leu Thr Glu Ile Thr His Val
625                 630                 635                 640

Ser Gln Ala Leu Leu Glu Val Glu Gln Leu Leu Asn Ala Pro Asp Leu
                645                 650                 655

Cys Ala Lys Asp Phe Glu Asp Leu Phe Lys Gln Glu Glu Ser Leu Lys
            660                 665                 670

Asn Ile Lys Asp Ser Leu Gln Gln Ser Ser Gly Arg Ile Asp Ile Ile
        675                 680                 685

His Ser Lys Lys Thr Ala Ala Leu Gln Ser Ala Thr Pro Val Glu Arg
    690                 695                 700

Val Lys Leu Gln Glu Ala Leu Ser Gln Leu Asp Phe Gln Trp Glu Lys
705                 710                 715                 720

Val Asn Lys Met Tyr Lys Asp Arg Gln Gly Arg Phe Asp Arg Ser Val
                725                 730                 735

Glu Lys Trp Arg Arg Phe His Tyr Asp Ile Lys Ile Phe Asn Gln Trp
            740                 745                 750

Leu Thr Glu Ala Glu Gln Phe Leu Arg Lys Thr Gln Ile Pro Glu Asn
        755                 760                 765

Trp Glu His Ala Lys Tyr Lys Trp Tyr Leu Lys Glu Leu Gln Asp Gly
    770                 775                 780

Ile Gly Gln Arg Gln Thr Val Val Arg Thr Leu Asn Ala Thr Gly Glu
785                 790                 795                 800

Glu Ile Ile Gln Gln Ser Ser Lys Thr Asp Ala Ser Ile Leu Gln Glu
                805                 810                 815

Lys Leu Gly Ser Leu Asn Leu Arg Trp Gln Glu Val Cys Lys Gln Leu
            820                 825                 830

Ser Asp Arg Lys Lys Arg Leu Glu Glu Gln Leu Glu Arg Leu Gln Glu
        835                 840                 845

Leu Gln Glu Ala Thr Asp Glu Leu Asp Leu Lys Leu Arg Gln Ala Glu
    850                 855                 860

Val Ile Lys Gly Ser Trp Gln Pro Val Gly Asp Leu Leu Ile Asp Ser
865                 870                 875                 880

Leu Gln Asp His Leu Glu Lys Val Lys Ala Leu Arg Gly Glu Ile Ala
                885                 890                 895

Pro Leu Lys Glu Asn Val Ser His Val Asn Asp Leu Ala Arg Gln Leu
            900                 905                 910

Thr Thr Leu Gly Ile Gln Leu Ser Pro Tyr Asn Leu Ser Thr Leu Glu
        915                 920                 925

Asp Leu Asn Thr Arg Trp Lys Leu Leu Gln Val Ala Val Glu Asp Arg
    930                 935                 940

Val Arg Gln Leu His Glu Ala His Arg Asp Phe Gly Pro Ala Ser Gln
945                 950                 955                 960

His Phe Leu Ser Thr Ser Val Gln Gly Pro Trp Glu Arg Ala Ile Ser
                965                 970                 975

Pro Asn Lys Val Pro Tyr Tyr Ile Asn His Glu Thr Gln Thr Thr Cys
            980                 985                 990

Trp Asp His Pro Lys Met Thr Glu  Leu Tyr Gln Ser Leu  Ala Asp Leu
        995                 1000                1005
```

```
Asn Asn  Val Arg Phe Ser Ala  Tyr Arg Thr Ala Met  Lys Leu Arg
    1010                 1015                 1020

Arg Leu  Gln Lys Ala Leu Cys  Leu Asp Leu Leu Ser  Leu Ser Ala
    1025                 1030                 1035

Ala Cys  Asp Ala Leu Asp Gln  His Asn Leu Lys Gln  Asn Asp Gln
    1040                 1045                 1050

Pro Met  Asp Ile Leu Gln Ile  Ile Asn Cys Leu Thr  Thr Ile Tyr
    1055                 1060                 1065

Asp Arg  Leu Glu Gln Glu His  Asn Asn Leu Val Asn  Val Pro Leu
    1070                 1075                 1080

Cys Val  Asp Met Cys Leu Asn  Trp Leu Leu Asn Val  Tyr Asp Thr
    1085                 1090                 1095

Gly Arg  Thr Gly Arg Ile Arg  Val Leu Ser Phe Lys  Thr Gly Ile
    1100                 1105                 1110

Ile Ser  Leu Cys Lys Ala His  Leu Glu Asp Lys Tyr  Arg Tyr Leu
    1115                 1120                 1125

Phe Lys  Gln Val Ala Ser Ser  Thr Gly Phe Cys Asp  Gln Arg Arg
    1130                 1135                 1140

Leu Gly  Leu Leu Leu His Asp  Ser Ile Gln Ile Pro  Arg Gln Leu
    1145                 1150                 1155

Gly Glu  Val Ala Ser Phe Gly  Gly Ser Asn Ile Glu  Pro Ser Val
    1160                 1165                 1170

Arg Ser  Cys Phe Gln Phe Ala  Asn Asn Lys Pro Glu  Ile Glu Ala
    1175                 1180                 1185

Ala Leu  Phe Leu Asp Trp Met  Arg Leu Glu Pro Gln  Ser Met Val
    1190                 1195                 1200

Trp Leu  Pro Val Leu His Arg  Val Ala Ala Ala Glu  Thr Ala Lys
    1205                 1210                 1215

His Gln  Ala Lys Cys Asn Ile  Cys Lys Glu Cys Pro  Ile Ile Gly
    1220                 1225                 1230

Phe Arg  Tyr Arg Ser Leu Lys  His Phe Asn Tyr Asp  Ile Cys Gln
    1235                 1240                 1245

Ser Cys  Phe Phe Ser Gly Arg  Val Ala Lys Gly His  Lys Met His
    1250                 1255                 1260

Tyr Pro  Met Val Glu Tyr Cys  Thr Pro Thr Thr Ser  Gly Glu Asp
    1265                 1270                 1275

Val Arg  Asp Phe Ala Lys Val  Leu Lys Asn Lys Phe  Arg Thr Lys
    1280                 1285                 1290

Arg Tyr  Phe Ala Lys His Pro  Arg Met Gly Tyr Leu  Pro Val Gln
    1295                 1300                 1305

Thr Val  Leu Glu Gly Asp Asn  Met Glu Thr Pro Ala  Gln Ile Leu
    1310                 1315                 1320

Ile Ser  Leu Glu Ser Glu Glu  Arg Gly Glu Leu Glu  Arg Ile Leu
    1325                 1330                 1335

Ala Asp  Leu Glu Glu Glu Asn  Arg Asn Leu Gln Ala  Glu Tyr Asp
    1340                 1345                 1350

Arg Leu  Lys Gln Gln His Glu  His Lys Gly Leu Ser  Pro Leu Pro
    1355                 1360                 1365

Ser Pro  Pro Asp Thr Met
    1370
```

<210> SEQ ID NO 130
<211> LENGTH: 1365
<212> TYPE: PRT

<213> ORGANISM: Homo sapiens

<400> SEQUENCE: 130

```
Met Leu Trp Trp Glu Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
            20                  25                  30

Gly Lys Gln His Ile Glu Asn Leu Phe Ser Asp Leu Gln Asp Gly Arg
        35                  40                  45

Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Asn Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
        115                 120                 125

Ala Gly Leu Gln Gln Thr Asn Ser Glu Lys Ile Leu Leu Ser Trp Val
    130                 135                 140

Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His
                165                 170                 175

Arg Pro Asp Leu Phe Asp Trp Asn Ser Val Val Cys Gln Gln Ser Ala
            180                 185                 190

Thr Gln Arg Leu Glu His Ala Phe Asn Ile Ala Arg Tyr Gln Leu Gly
        195                 200                 205

Ile Glu Lys Leu Leu Asp Pro Glu Asp Val Asp Thr Thr Tyr Pro Asp
    210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu Met Leu Pro Arg
                245                 250                 255

Pro Pro Lys Val Thr Lys Glu Glu His Phe Gln Leu His His Gln Met
            260                 265                 270

His Tyr Ser Gln Gln Ile Thr Val Ser Leu Ala Gln Gly Tyr Glu Arg
        275                 280                 285

Thr Ser Ser Pro Lys Pro Arg Phe Lys Ser Tyr Ala Tyr Thr Gln Ala
    290                 295                 300

Ala Tyr Val Thr Thr Ser Asp Pro Thr Arg Ser Pro Phe Pro Ser Gln
305                 310                 315                 320

His Leu Glu Ala Pro Glu Asp Lys Ser Phe Gly Ser Ser Leu Met Glu
                325                 330                 335

Ser Glu Val Asn Leu Asp Arg Tyr Gln Thr Ala Leu Glu Glu Val Leu
            340                 345                 350

Ser Trp Leu Leu Ser Ala Glu Asp Thr Leu Gln Ala Gln Gly Glu Ile
        355                 360                 365

Ser Asn Asp Val Glu Val Val Lys Asp Gln Phe His Thr His Glu Gly
    370                 375                 380

Tyr Met Met Asp Leu Thr Ala His Gln Gly Arg Val Gly Asn Ile Leu
385                 390                 395                 400
```

```
Gln Leu Gly Ser Lys Leu Ile Gly Thr Gly Lys Leu Ser Glu Asp Glu
                405                 410                 415

Glu Thr Glu Val Gln Glu Gln Met Asn Leu Leu Asn Ser Arg Trp Glu
            420                 425                 430

Cys Leu Arg Val Ala Ser Met Glu Lys Gln Ser Asn Leu His Ile His
        435                 440                 445

Thr Val Arg Glu Glu Thr Met Met Val Met Thr Glu Asp Met Pro Leu
    450                 455                 460

Glu Ile Ser Tyr Val Pro Ser Thr Tyr Leu Thr Glu Ile Thr His Val
465                 470                 475                 480

Ser Gln Ala Leu Leu Glu Val Glu Gln Leu Leu Asn Ala Pro Asp Leu
                485                 490                 495

Cys Ala Lys Asp Phe Glu Asp Leu Phe Lys Gln Glu Glu Ser Leu Lys
            500                 505                 510

Asn Ile Lys Asp Ser Leu Gln Gln Ser Ser Gly Arg Ile Asp Ile Ile
        515                 520                 525

His Ser Lys Lys Thr Ala Ala Leu Gln Ser Ala Thr Pro Val Glu Arg
    530                 535                 540

Val Lys Leu Gln Glu Ala Leu Ser Gln Leu Asp Phe Gln Trp Glu Lys
545                 550                 555                 560

Val Asn Lys Met Tyr Lys Asp Arg Gln Gly Arg Phe Asp Arg Ser Val
                565                 570                 575

Glu Lys Trp Arg Arg Phe His Tyr Asp Ile Lys Ile Phe Asn Gln Trp
            580                 585                 590

Leu Thr Glu Ala Glu Gln Phe Leu Arg Lys Thr Gln Ile Pro Glu Asn
        595                 600                 605

Trp Glu His Ala Lys Tyr Lys Trp Tyr Leu Lys Glu Leu Gln Asp Gly
    610                 615                 620

Ile Gly Gln Arg Gln Thr Val Val Arg Thr Leu Asn Ala Thr Gly Glu
625                 630                 635                 640

Glu Ile Ile Gln Gln Ser Ser Lys Thr Asp Ala Ser Ile Leu Gln Glu
                645                 650                 655

Lys Leu Gly Ser Leu Asn Leu Arg Trp Gln Glu Val Cys Lys Gln Leu
            660                 665                 670

Ser Asp Arg Lys Lys Arg Leu Glu Glu Gln Ala Pro Gly Leu Thr Thr
        675                 680                 685

Ile Gly Ala Ser Pro Thr Gln Thr Val Thr Leu Val Thr Gln Pro Val
    690                 695                 700

Val Thr Lys Glu Thr Ala Ile Ser Lys Leu Glu Met Pro Ser Ser Leu
705                 710                 715                 720

Met Leu Glu Val Pro Ala Leu Ala Asp Phe Asn Arg Ala Trp Thr Glu
                725                 730                 735

Leu Thr Asp Trp Leu Ser Leu Leu Asp Gln Val Ile Lys Ser Gln Arg
            740                 745                 750

Val Met Val Gly Asp Leu Glu Asp Ile Asn Glu Met Ile Ile Lys Gln
        755                 760                 765

Lys Ala Thr Met Gln Asp Leu Glu Gln Arg Arg Pro Gln Leu Glu Glu
    770                 775                 780

Leu Ile Thr Ala Ala Gln Asn Leu Lys Asn Lys Thr Ser Asn Gln Glu
785                 790                 795                 800

Ala Arg Thr Ile Ile Thr Asp Arg Ile Glu Arg Ile Gln Asn Gln Trp
                805                 810                 815

Asp Glu Val Gln Glu His Leu Gln Asn Arg Arg Gln Gln Leu Asn Glu
```

```
            820                 825                 830

Met Leu Glu Arg Leu Gln Glu Leu Gln Glu Ala Thr Asp Glu Leu Asp
        835                 840                 845

Leu Lys Leu Arg Gln Ala Glu Val Ile Lys Gly Ser Trp Gln Pro Val
    850                 855                 860

Gly Asp Leu Leu Ile Asp Ser Leu Gln Asp His Leu Glu Lys Val Lys
865                 870                 875                 880

Ala Leu Arg Gly Glu Ile Ala Pro Leu Lys Glu Asn Val Ser His Val
                885                 890                 895

Asn Asp Leu Ala Arg Gln Leu Thr Thr Leu Gly Ile Gln Leu Ser Pro
            900                 905                 910

Tyr Asn Leu Ser Thr Leu Glu Asp Leu Asn Thr Arg Trp Lys Leu Leu
        915                 920                 925

Gln Val Ala Val Glu Asp Arg Val Arg Gln Leu His Glu Ala His Arg
    930                 935                 940

Asp Phe Gly Pro Ala Ser Gln His Phe Leu Ser Thr Ser Val Gln Gly
945                 950                 955                 960

Pro Trp Glu Arg Ala Ile Ser Pro Asn Lys Val Pro Tyr Tyr Ile Asn
                965                 970                 975

His Glu Thr Gln Thr Thr Cys Trp Asp His Pro Lys Met Thr Glu Leu
            980                 985                 990

Tyr Gln Ser Leu Ala Asp Leu Asn  Asn Val Arg Phe Ser  Ala Tyr Arg
        995                 1000                1005

Thr Ala  Met Lys Leu Arg Arg  Leu Gln Lys Ala Leu  Cys Leu Asp
    1010                1015                1020

Leu Leu  Ser Leu Ser Ala Ala  Cys Asp Ala Leu Asp  Gln His Asn
    1025                1030                1035

Leu Lys  Gln Asn Asp Gln Pro  Met Asp Ile Leu Gln  Ile Ile Asn
    1040                1045                1050

Cys Leu  Thr Thr Ile Tyr Asp  Arg Leu Glu Gln Glu  His Asn Asn
    1055                1060                1065

Leu Val  Asn Val Pro Leu Cys  Val Asp Met Cys Leu  Asn Trp Leu
    1070                1075                1080

Leu Asn  Val Tyr Asp Thr Gly  Arg Thr Gly Arg Ile  Arg Val Leu
    1085                1090                1095

Ser Phe  Lys Thr Gly Ile Ile  Ser Leu Cys Lys Ala  His Leu Glu
    1100                1105                1110

Asp Lys  Tyr Arg Tyr Leu Phe  Lys Gln Val Ala Ser  Ser Thr Gly
    1115                1120                1125

Phe Cys  Asp Gln Arg Arg Leu  Gly Leu Leu Leu His  Asp Ser Ile
    1130                1135                1140

Gln Ile  Pro Arg Gln Leu Gly  Glu Val Ala Ser Phe  Gly Gly Ser
    1145                1150                1155

Asn Ile  Glu Pro Ser Val Arg  Ser Cys Phe Gln Phe  Ala Asn Asn
    1160                1165                1170

Lys Pro  Glu Ile Glu Ala Ala  Leu Phe Leu Asp Trp  Met Arg Leu
    1175                1180                1185

Glu Pro  Gln Ser Met Val Trp  Leu Pro Val Leu His  Arg Val Ala
    1190                1195                1200

Ala Ala  Glu Thr Ala Lys His  Gln Ala Lys Cys Asn  Ile Cys Lys
    1205                1210                1215

Glu Cys  Pro Ile Ile Gly Phe  Arg Tyr Arg Ser Leu  Lys His Phe
    1220                1225                1230
```

```
Asn Tyr  Asp Ile Cys Gln Ser  Cys Phe Phe Ser Gly  Arg Val Ala
    1235                 1240                 1245

Lys Gly  His Lys Met His Tyr  Pro Met Val Glu Tyr  Cys Thr Pro
    1250                 1255                 1260

Thr Thr  Ser Gly Glu Asp Val  Arg Asp Phe Ala Lys  Val Leu Lys
    1265                 1270                 1275

Asn Lys  Phe Arg Thr Lys Arg  Tyr Phe Ala Lys His  Pro Arg Met
    1280                 1285                 1290

Gly Tyr  Leu Pro Val Gln Thr  Val Leu Glu Gly Asp  Asn Met Glu
    1295                 1300                 1305

Thr Pro  Ala Gln Ile Leu Ile  Ser Leu Glu Ser Glu  Glu Arg Gly
    1310                 1315                 1320

Glu Leu  Glu Arg Ile Leu Ala  Asp Leu Glu Glu Glu  Asn Arg Asn
    1325                 1330                 1335

Leu Gln  Ala Glu Tyr Asp Arg  Leu Lys Gln Gln His  Glu His Lys
    1340                 1345                 1350

Gly Leu  Ser Pro Leu Pro Ser  Pro Pro Asp Thr Met
    1355                 1360                 1365


<210> SEQ ID NO 131
<211> LENGTH: 1383
<212> TYPE: PRT
<213> ORGANISM: Homo sapiens

<400> SEQUENCE: 131

Met Leu Trp Trp Glu Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
            20                  25                  30

Gly Lys Gln His Ile Glu Asn Leu Phe Ser Asp Leu Gln Asp Gly Arg
        35                  40                  45

Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Asn Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
        115                 120                 125

Ala Gly Leu Gln Gln Thr Asn Ser Glu Lys Ile Leu Leu Ser Trp Val
    130                 135                 140

Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His
                165                 170                 175

Arg Pro Asp Leu Phe Asp Trp Asn Ser Val Val Cys Gln Gln Ser Ala
            180                 185                 190

Thr Gln Arg Leu Glu His Ala Phe Asn Ile Ala Arg Tyr Gln Leu Gly
        195                 200                 205

Ile Glu Lys Leu Leu Asp Pro Glu Asp Val Asp Thr Thr Tyr Pro Asp
    210                 215                 220

Lys Lys Ser Ile Leu Met Tyr Ile Thr Ser Leu Phe Gln Val Leu Pro
```

```
225                 230                 235                 240

Gln Gln Val Ser Ile Glu Ala Ile Gln Glu Val Glu Met Leu Pro Arg
                245                 250                 255

Pro Pro Lys Val Thr Lys Glu Glu His Phe Gln Leu His His Gln Met
            260                 265                 270

His Tyr Ser Gln Gln Ile Thr Val Ser Leu Ala Gln Gly Tyr Glu Arg
        275                 280                 285

Thr Ser Ser Pro Lys Pro Arg Phe Lys Ser Tyr Ala Tyr Thr Gln Ala
    290                 295                 300

Ala Tyr Val Thr Thr Ser Asp Pro Thr Arg Ser Pro Phe Pro Ser Gln
305                 310                 315                 320

His Leu Glu Ala Pro Glu Asp Lys Ser Phe Gly Ser Ser Leu Met Glu
                325                 330                 335

Ser Glu Val Asn Leu Asp Arg Tyr Gln Thr Ala Leu Glu Glu Val Leu
            340                 345                 350

Ser Trp Leu Leu Ser Ala Glu Asp Thr Leu Gln Ala Gln Gly Glu Ile
        355                 360                 365

Ser Asn Asp Val Glu Val Val Lys Asp Gln Phe His Thr His Glu Gly
    370                 375                 380

Tyr Met Met Asp Leu Thr Ala His Gln Gly Arg Val Gly Asn Ile Leu
385                 390                 395                 400

Gln Leu Gly Ser Lys Leu Ile Gly Thr Gly Lys Leu Ser Glu Asp Glu
                405                 410                 415

Glu Thr Glu Val Gln Glu Gln Met Asn Leu Leu Asn Ser Arg Trp Glu
            420                 425                 430

Cys Leu Arg Val Ala Ser Met Glu Lys Gln Ser Asn Leu His Arg Val
        435                 440                 445

Leu Met Asp Leu Gln Asn Gln Lys Leu Lys Glu Leu Asn Asp Trp Leu
    450                 455                 460

Thr Lys Thr Glu Glu Arg Thr Arg Lys Met Glu Glu Glu Pro Leu Gly
465                 470                 475                 480

Pro Asp Leu Glu Asp Leu Lys Arg Gln Val Gln Gln His Lys Val Leu
                485                 490                 495

Gln Glu Asp Leu Glu Gln Glu Gln Val Arg Val Asn Ser Leu Thr His
            500                 505                 510

Met Val Val Val Val Asp Glu Ser Ser Gly Asp His Ala Thr Ala Ala
        515                 520                 525

Leu Glu Glu Gln Leu Lys Val Leu Gly Asp Arg Trp Ala Asn Ile Cys
    530                 535                 540

Arg Trp Thr Glu Asp Arg Trp Val Leu Leu Gln Asp Ile Leu Leu Lys
545                 550                 555                 560

Trp Gln Arg Leu Thr Glu Glu Gln Cys Leu Phe Ser Ala Trp Leu Ser
                565                 570                 575

Glu Lys Glu Asp Ala Val Asn Lys Ile His Thr Thr Gly Phe Lys Asp
            580                 585                 590

Gln Asn Glu Met Leu Ser Ser Leu Gln Lys Leu Ala Val Leu Lys Ala
        595                 600                 605

Asp Leu Glu Lys Lys Lys Gln Ser Met Gly Lys Leu Tyr Ser Leu Lys
    610                 615                 620

Gln Asp Leu Leu Ser Thr Leu Lys Asn Lys Ser Val Thr Gln Lys Thr
625                 630                 635                 640

Glu Ala Trp Leu Asp Asn Phe Ala Arg Cys Trp Asp Asn Leu Val Gln
                645                 650                 655
```

```
Lys Leu Glu Lys Ser Thr Ala Gln Ile Ser Gln Ala Ile His Thr Val
            660                 665                 670

Arg Glu Glu Thr Met Met Val Met Thr Glu Asp Met Pro Leu Glu Ile
        675                 680                 685

Ser Tyr Val Pro Ser Thr Tyr Leu Thr Glu Ile Thr His Val Ser Gln
    690                 695                 700

Ala Leu Leu Glu Val Glu Gln Leu Leu Asn Ala Pro Asp Leu Cys Ala
705                 710                 715                 720

Lys Asp Phe Glu Asp Leu Phe Lys Gln Glu Glu Ser Leu Lys Asn Ile
                725                 730                 735

Lys Asp Ser Leu Gln Gln Ser Ser Gly Arg Ile Asp Ile Ile His Ser
            740                 745                 750

Lys Lys Thr Ala Ala Leu Gln Ser Ala Thr Pro Val Glu Arg Val Lys
        755                 760                 765

Leu Gln Glu Ala Leu Ser Gln Leu Asp Phe Gln Trp Glu Lys Val Asn
    770                 775                 780

Lys Met Tyr Lys Asp Arg Gln Gly Arg Phe Asp Arg Ser Val Glu Lys
785                 790                 795                 800

Trp Arg Arg Phe His Tyr Asp Ile Lys Ile Phe Asn Gln Trp Leu Thr
                805                 810                 815

Glu Ala Glu Gln Phe Leu Arg Lys Thr Gln Ile Pro Glu Asn Trp Glu
            820                 825                 830

His Ala Lys Tyr Lys Trp Tyr Leu Lys Glu Leu Gln Asp Gly Ile Gly
        835                 840                 845

Gln Arg Gln Thr Val Val Arg Thr Leu Asn Ala Thr Gly Glu Glu Ile
    850                 855                 860

Ile Gln Gln Ser Ser Lys Thr Asp Ala Ser Ile Leu Gln Glu Lys Leu
865                 870                 875                 880

Gly Ser Leu Asn Leu Arg Trp Gln Glu Val Cys Lys Gln Leu Ser Asp
                885                 890                 895

Arg Lys Lys Arg Leu Glu Glu Gln Leu Glu Arg Leu Gln Glu Leu Gln
            900                 905                 910

Glu Ala Thr Asp Glu Leu Asp Leu Lys Leu Arg Gln Ala Glu Val Ile
        915                 920                 925

Lys Gly Ser Trp Gln Pro Val Gly Asp Leu Leu Ile Asp Ser Leu Gln
    930                 935                 940

Asp His Leu Glu Lys Val Lys Ala Leu Arg Gly Glu Ile Ala Pro Leu
945                 950                 955                 960

Lys Glu Asn Val Ser His Val Asn Asp Leu Ala Arg Gln Leu Thr Thr
                965                 970                 975

Leu Gly Ile Gln Leu Ser Pro Tyr Asn Leu Ser Thr Leu Glu Asp Leu
            980                 985                 990

Asn Thr Arg Trp Lys Leu Leu Gln  Val Ala Val Glu Asp  Arg Val Arg
        995                 1000                 1005

Gln Leu  His Glu Ala His Arg  Asp Phe Gly Pro Ala  Ser Gln His
    1010                 1015                 1020

Phe Leu  Ser Thr Ser Val Gln  Gly Pro Trp Glu Arg  Ala Ile Ser
    1025                 1030                 1035

Pro Asn  Lys Val Pro Tyr Tyr  Ile Asn His Glu Thr  Gln Thr Thr
    1040                 1045                 1050

Cys Trp  Asp His Pro Lys Met  Thr Glu Leu Tyr Gln  Ser Leu Ala
    1055                 1060                 1065
```

```
Asp Leu  Asn Asn Val Arg Phe  Ser Ala Tyr Arg Thr  Ala Met Lys
    1070                 1075                 1080

Leu Arg  Arg Leu Gln Lys Ala  Leu Cys Leu Asp Leu  Leu Ser Leu
    1085                 1090                 1095

Ser Ala  Ala Cys Asp Ala Leu  Asp Gln His Asn Leu  Lys Gln Asn
    1100                 1105                 1110

Asp Gln  Pro Met Asp Ile Leu  Gln Ile Ile Asn Cys  Leu Thr Thr
    1115                 1120                 1125

Ile Tyr  Asp Arg Leu Glu Gln  Glu His Asn Asn Leu  Val Asn Val
    1130                 1135                 1140

Pro Leu  Cys Val Asp Met Cys  Leu Asn Trp Leu Leu  Asn Val Tyr
    1145                 1150                 1155

Asp Thr  Gly Arg Thr Gly Arg  Ile Arg Val Leu Ser  Phe Lys Thr
    1160                 1165                 1170

Gly Ile  Ile Ser Leu Cys Lys  Ala His Leu Glu Asp  Lys Tyr Arg
    1175                 1180                 1185

Tyr Leu  Phe Lys Gln Val Ala  Ser Ser Thr Gly Phe  Cys Asp Gln
    1190                 1195                 1200

Arg Arg  Leu Gly Leu Leu Leu  His Asp Ser Ile Gln  Ile Pro Arg
    1205                 1210                 1215

Gln Leu  Gly Glu Val Ala Ser  Phe Gly Gly Ser Asn  Ile Glu Pro
    1220                 1225                 1230

Ser Val  Arg Ser Cys Phe Gln  Phe Ala Asn Asn Lys  Pro Glu Ile
    1235                 1240                 1245

Glu Ala  Ala Leu Phe Leu Asp  Trp Met Arg Leu Glu  Pro Gln Ser
    1250                 1255                 1260

Met Val  Trp Leu Pro Val Leu  His Arg Val Ala Ala  Ala Glu Thr
    1265                 1270                 1275

Ala Lys  His Gln Ala Lys Cys  Asn Ile Cys Lys Glu  Cys Pro Ile
    1280                 1285                 1290

Ile Gly  Phe Arg Tyr Arg Ser  Leu Lys His Phe Asn  Tyr Asp Ile
    1295                 1300                 1305

Cys Gln  Ser Cys Phe Phe Ser  Gly Arg Val Ala Lys  Gly His Lys
    1310                 1315                 1320

Met His  Tyr Pro Met Val Glu  Tyr Cys Thr Pro Thr  Thr Ser Gly
    1325                 1330                 1335

Glu Asp  Val Arg Asp Phe Ala  Lys Val Leu Lys Asn  Lys Phe Arg
    1340                 1345                 1350

Thr Lys  Arg Tyr Phe Ala Lys  His Pro Arg Met Gly  Tyr Leu Pro
    1355                 1360                 1365

Val Gln  Thr Val Leu Glu Gly  Asp Asn Met Glu Thr  Asp Thr Met
    1370                 1375                 1380
```

<210> SEQ ID NO 132
<211> LENGTH: 1384
<212> TYPE: PRT
<213> ORGANISM: Homo sapiens

<400> SEQUENCE: 132

```
Met Leu Trp Trp Glu Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
            20                  25                  30

Gly Lys Gln His Ile Glu Asn Leu Phe Ser Asp Leu Gln Asp Gly Arg
        35                  40                  45
```

```
Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Asn Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
        115                 120                 125

Ala Gly Leu Gln Gln Thr Asn Ser Glu Lys Ile Leu Leu Ser Trp Val
    130                 135                 140

Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His
                165                 170                 175

Arg Pro Asp Leu Phe Asp Trp Asn Ser Val Val Cys Gln Gln Ser Ala
            180                 185                 190

Thr Gln Arg Leu Glu His Ala Phe Asn Ile Ala Arg Tyr Gln Leu Gly
        195                 200                 205

Ile Glu Lys Leu Leu Asp Pro Glu Asp Val Asp Thr Thr Tyr Pro Asp
    210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu Met Leu Pro Arg
                245                 250                 255

Pro Pro Lys Val Thr Lys Glu Glu His Phe Gln Leu His His Gln Met
            260                 265                 270

His Tyr Ser Gln Gln Ile Thr Val Ser Leu Ala Gln Gly Tyr Glu Arg
        275                 280                 285

Thr Ser Ser Pro Lys Pro Arg Phe Lys Ser Tyr Ala Tyr Thr Gln Ala
    290                 295                 300

Ala Tyr Val Thr Thr Ser Asp Pro Thr Arg Ser Pro Phe Pro Ser Gln
305                 310                 315                 320

His Leu Glu Ala Pro Glu Asp Lys Ser Phe Gly Ser Ser Leu Met Glu
                325                 330                 335

Ser Glu Val Asn Leu Asp Arg Tyr Gln Thr Ala Leu Glu Glu Val Leu
            340                 345                 350

Ser Trp Leu Leu Ser Ala Glu Asp Thr Leu Gln Ala Gln Gly Glu Ile
        355                 360                 365

Ser Asn Asp Val Glu Val Val Lys Asp Gln Phe His Thr His Glu Gly
    370                 375                 380

Tyr Met Met Asp Leu Thr Ala His Gln Gly Arg Val Gly Asn Ile Leu
385                 390                 395                 400

Gln Leu Gly Ser Lys Leu Ile Gly Thr Gly Lys Leu Ser Glu Asp Glu
                405                 410                 415

Glu Thr Glu Val Gln Glu Gln Met Asn Leu Leu Asn Ser Arg Trp Glu
            420                 425                 430

Cys Leu Arg Val Ala Ser Met Glu Lys Gln Ser Asn Leu His Ile His
        435                 440                 445

Thr Val Arg Glu Glu Thr Met Met Val Met Thr Glu Asp Met Pro Leu
    450                 455                 460
```

-continued

```
Glu Ile Ser Tyr Val Pro Ser Thr Tyr Leu Thr Glu Ile Thr His Val
465                 470                 475                 480

Ser Gln Ala Leu Leu Glu Val Glu Gln Leu Leu Asn Ala Pro Asp Leu
                485                 490                 495

Cys Ala Lys Asp Phe Glu Asp Leu Phe Lys Gln Glu Glu Ser Leu Lys
            500                 505                 510

Asn Ile Lys Asp Ser Leu Gln Gln Ser Ser Gly Arg Ile Asp Ile Ile
        515                 520                 525

His Ser Lys Lys Thr Ala Ala Leu Gln Ser Ala Thr Pro Val Glu Arg
    530                 535                 540

Val Lys Leu Gln Glu Ala Leu Ser Gln Leu Asp Phe Gln Trp Glu Lys
545                 550                 555                 560

Val Asn Lys Met Tyr Lys Asp Arg Gln Gly Arg Phe Asp Arg Ser Val
                565                 570                 575

Glu Lys Trp Arg Arg Phe His Tyr Asp Ile Lys Ile Phe Asn Gln Trp
            580                 585                 590

Leu Thr Glu Ala Glu Gln Phe Leu Arg Lys Thr Gln Ile Pro Glu Asn
        595                 600                 605

Trp Glu His Ala Lys Tyr Lys Trp Tyr Leu Lys Glu Leu Gln Asp Gly
    610                 615                 620

Ile Gly Gln Arg Gln Thr Val Val Arg Thr Leu Asn Ala Thr Gly Glu
625                 630                 635                 640

Glu Ile Ile Gln Gln Ser Ser Lys Thr Asp Ala Ser Ile Leu Gln Glu
                645                 650                 655

Lys Leu Gly Ser Leu Asn Leu Arg Trp Gln Glu Val Cys Lys Gln Leu
            660                 665                 670

Ser Asp Arg Lys Lys Arg Leu Glu Glu Gln Ala Pro Gly Leu Thr Thr
        675                 680                 685

Ile Gly Ala Ser Pro Thr Gln Thr Val Thr Leu Val Thr Gln Pro Val
    690                 695                 700

Val Thr Lys Glu Thr Ala Ile Ser Lys Leu Glu Met Pro Ser Ser Leu
705                 710                 715                 720

Met Leu Glu Ser Asp Gln Trp Lys Arg Leu His Leu Ser Leu Gln Glu
                725                 730                 735

Leu Leu Val Trp Leu Gln Leu Lys Asp Asp Glu Leu Ser Arg Gln Ala
            740                 745                 750

Pro Ile Gly Gly Asp Phe Pro Ala Val Gln Lys Gln Asn Asp Val His
        755                 760                 765

Arg Ala Phe Lys Arg Glu Leu Lys Thr Lys Glu Pro Val Ile Met Ser
    770                 775                 780

Thr Leu Glu Thr Val Arg Ile Phe Leu Thr Glu Gln Pro Leu Glu Gly
785                 790                 795                 800

Leu Glu Lys Leu Tyr Gln Glu Pro Arg Glu Leu Pro Pro Glu Glu Arg
                805                 810                 815

Ala Gln Asn Val Thr Arg Leu Leu Arg Lys Gln Ala Glu Glu Val Asn
            820                 825                 830

Thr Glu Trp Glu Lys Leu Asn Leu His Ser Ala Asp Trp Gln Arg Lys
        835                 840                 845

Ile Asp Glu Thr Leu Glu Arg Leu Gln Glu Leu Gln Glu Ala Thr Asp
    850                 855                 860

Glu Leu Asp Leu Lys Leu Arg Gln Ala Glu Val Ile Lys Gly Ser Trp
865                 870                 875                 880

Gln Pro Val Gly Asp Leu Leu Ile Asp Ser Leu Gln Asp His Leu Glu
```

```
                885                 890                 895

Lys Val Lys Ala Leu Arg Gly Glu Ile Ala Pro Leu Lys Glu Asn Val
            900                 905                 910

Ser His Val Asn Asp Leu Ala Arg Gln Leu Thr Thr Leu Gly Ile Gln
        915                 920                 925

Leu Ser Pro Tyr Asn Leu Ser Thr Leu Glu Asp Leu Asn Thr Arg Trp
    930                 935                 940

Lys Leu Leu Gln Val Ala Val Glu Asp Arg Val Arg Gln Leu His Glu
945                 950                 955                 960

Ala His Arg Asp Phe Gly Pro Ala Ser Gln His Phe Leu Ser Thr Ser
                965                 970                 975

Val Gln Gly Pro Trp Glu Arg Ala Ile Ser Pro Asn Lys Val Pro Tyr
            980                 985                 990

Tyr Ile Asn His Glu Thr Gln Thr  Thr Cys Trp Asp His  Pro Lys Met
        995                 1000                 1005

Thr Glu  Leu Tyr Gln Ser Leu  Ala Asp Leu Asn Asn  Val Arg Phe
    1010                 1015                 1020

Ser Ala  Tyr Arg Thr Ala Met  Lys Leu Arg Arg Leu  Gln Lys Ala
    1025                 1030                 1035

Leu Cys  Leu Asp Leu Leu Ser  Leu Ser Ala Ala Cys  Asp Ala Leu
    1040                 1045                 1050

Asp Gln  His Asn Leu Lys Gln  Asn Asp Gln Pro Met  Asp Ile Leu
    1055                 1060                 1065

Gln Ile  Ile Asn Cys Leu Thr  Thr Ile Tyr Asp Arg  Leu Glu Gln
    1070                 1075                 1080

Glu His  Asn Asn Leu Val Asn  Val Pro Leu Cys Val  Asp Met Cys
    1085                 1090                 1095

Leu Asn  Trp Leu Leu Asn Val  Tyr Asp Thr Gly Arg  Thr Gly Arg
    1100                 1105                 1110

Ile Arg  Val Leu Ser Phe Lys  Thr Gly Ile Ile Ser  Leu Cys Lys
    1115                 1120                 1125

Ala His  Leu Glu Asp Lys Tyr  Arg Tyr Leu Phe Lys  Gln Val Ala
    1130                 1135                 1140

Ser Ser  Thr Gly Phe Cys Asp  Gln Arg Arg Leu Gly  Leu Leu Leu
    1145                 1150                 1155

His Asp  Ser Ile Gln Ile Pro  Arg Gln Leu Gly Glu  Val Ala Ser
    1160                 1165                 1170

Phe Gly  Gly Ser Asn Ile Glu  Pro Ser Val Arg Ser  Cys Phe Gln
    1175                 1180                 1185

Phe Ala  Asn Asn Lys Pro Glu  Ile Glu Ala Ala Leu  Phe Leu Asp
    1190                 1195                 1200

Trp Met  Arg Leu Glu Pro Gln  Ser Met Val Trp Leu  Pro Val Leu
    1205                 1210                 1215

His Arg  Val Ala Ala Ala Glu  Thr Ala Lys His Gln  Ala Lys Cys
    1220                 1225                 1230

Asn Ile  Cys Lys Glu Cys Pro  Ile Ile Gly Phe Arg  Tyr Arg Ser
    1235                 1240                 1245

Leu Lys  His Phe Asn Tyr Asp  Ile Cys Gln Ser Cys  Phe Phe Ser
    1250                 1255                 1260

Gly Arg  Val Ala Lys Gly His  Lys Met His Tyr Pro  Met Val Glu
    1265                 1270                 1275

Tyr Cys  Thr Pro Thr Thr Ser  Gly Glu Asp Val Arg  Asp Phe Ala
    1280                 1285                 1290
```

```
Lys Val  Leu Lys Asn Lys Phe  Arg Thr Lys Arg Tyr  Phe Ala Lys
    1295                 1300                 1305

His Pro  Arg Met Gly Tyr Leu  Pro Val Gln Thr Val  Leu Glu Gly
    1310                 1315                 1320

Asp Asn  Met Glu Thr Pro Ala  Gln Ile Leu Ile Ser  Leu Glu Ser
    1325                 1330                 1335

Glu Glu  Arg Gly Glu Leu Glu  Arg Ile Leu Ala Asp  Leu Glu Glu
    1340                 1345                 1350

Glu Asn  Arg Asn Leu Gln Ala  Glu Tyr Asp Arg Leu  Lys Gln Gln
    1355                 1360                 1365

His Glu  His Lys Gly Leu Ser  Pro Leu Pro Ser Pro  Pro Asp Thr
    1370                 1375                 1380

Met
```

<210> SEQ ID NO 133
<211> LENGTH: 4152
<212> TYPE: DNA
<213> ORGANISM: Homo sapiens

<400> SEQUENCE: 133

```
atgctgtggt gggaggaagt ggaagattgc tacgagcgcg aggacgtgca gaagaaaacc     60

ttcaccaaat gggtgaacgc ccagttcagc aagttcggca agcagcacat cgagaacctg    120

ttcagcgacc tgcaggacgg cagacggctg ctggacctgc tggaaggcct gaccggccag    180

aagctgccca aagagaaggg cagcaccaga gtgcacgccc tgaacaacgt gaacaaggcc    240

ctgcgggtgc tgcagaacaa caacgtggac ctggtgaaca tcggcagcac cgacatcgtg    300

gacggcaacc acaagctgac cctgggcctg atctggaaca tcatcctgca ctggcaggtc    360

aaaaacgtga tgaagaacat catggccggc ctgcagcaga ccaacagcga gaagatcctg    420

ctgagctggg tgcgccagag cacccggaac tacccccagg tcaacgtgat caacttcacc    480

acctcttgga gcgacggcct ggccctgaac gccctgatcc acagccaccg gcccgacctg    540

ttcgactgga acagcgtggt ctgccagcag agcgccaccc agcggctgga acacgccttc    600

aatatcgcca gataccagct gggcatcgag aagctgctgg atcccgagga cgtggacacc    660

acctaccccg acaagaaatc catcctgatg tatatcacca gcctgttcca ggtgctgccc    720

cagcaggtgt ccatcgaggc catccaggaa gtggaaatgc tgcccagacc ccccaaagtg    780

accaaagagg aacacttcca gctgcaccac cagatgcact acagccagca gatcaccgtg    840

tccctggccc agggctacga gagaaccagc agccccaagc cccggttcaa gagctacgcc    900

tatacccagg ccgcctacgt gaccaccagc gaccctacca gaagcccatt ccccagccag    960

catctggaag cccccgagga caagagcttc ggcagcagcc tgatggaaag cgaagtgaac   1020

ctggacagat accagaccgc cctggaagag gtgctgagct ggctgctgag cgccgaggat   1080

acactgcagg ctcagggcga gatcagcaac gacgtggaag tcgtgaagga ccagttccac   1140

acccacgagg gctacatgat ggacctgaca gcccaccagg gcagagtggg caacatcctg   1200

cagctgggct ccaagctgat cggcaccggc aagctgagcg aggacgaaga gacagaggtg   1260

caggaacaga tgaacctgct gaacagcaga tgggagtgcc tgcgggtggc cagcatggaa   1320

aagcagagca acctgcatag ggtcctgctg aagtggcagc ggctgaccga ggaacagtgc   1380

ctgtttagcg cctggctgtc cgagaaagag gacgccgtga acaagatcca caccaccggc   1440

ttcaaggacc agaacgagat gctgagcagc ctgcagaaac tggccgtgct gaaggccgac   1500
```

-continued

```
ctggaaaaga aaaagcagtc catgggcaag ctgtactccc tgaagcagga cctgctgtcc   1560
accctgaaga acaagagcgt gacccagaaa accgaggcct ggctggacaa cttcgcccgg   1620
tgctgggaca acctggtgca gaagctggaa aagtccaccg cccagatctc ccaggccgtg   1680
accacaacac agcccagcct gacccagacc accgtgatgg aaaccgtgac aacagtgacc   1740
acccgggaac agatcctcgt gaagcacgcc caggaagaac tgccccctcc acccccccag   1800
aagaaacggc agatcacagt ggacagtgaa gctcagatcc acaccgtgcg ggaagagaca   1860
atgatggtca tgacagagga catgcccctg gaaatcagct acgtgcccag cacctacctg   1920
accgagatca cccatgtgtc ccaggccctg ctggaagtgg aacagctgct gaacgccccc   1980
gacctgtgcg ccaaggattt cgaggacctg ttcaagcagg aagagagcct gaagaatatc   2040
aaggatagcc tgcagcagag cagcggccgg atcgacatca tccacagcaa gaaaacagcc   2100
gccctgcaga gcgccacccc cgtggaaaga gtgaaactgc aggaagccct gtcccagctg   2160
gacttccagt gggagaaagt gaacaaaatg tacaaggacc ggcagggcag attcgaccgc   2220
agcgtggaaa agtggcggcg gttccactac gacatcaaga tcttcaacca gtggctgaca   2280
gaggccgagc agttcctgag aaagacccag atccccgaga actgggagca cgccaagtac   2340
aagtggtatc tgaaagagct gcaggacggc atcggccaga gacagacagt cgtgcggacc   2400
ctgaatgcca ccggcgagga aatcatccag cagtccagca agaccgacgc cagcattctg   2460
caggaaaagc tgggcagcct gaacctgcgg tggcaggaag tgtgcaagca gctgtccgac   2520
cggaagaagc ggctggaaga acagctggaa cggctgcagg aactgcagga ggccaccgac   2580
gagctggacc tgaaactgag acaggccgaa gtgatcaagg gcagctggca gccagtgggc   2640
gacctgctga tcgactccct gcaggaccat ctggaaaaag tgaaggccct gagaggcgag   2700
atcgcccccc tgaaagaaaa cgtgtcccac gtgaacgacc tggcccggca gctgacaaca   2760
ctgggcattc agctgagccc ctacaacctg agcacactgg aagatctgaa cacccggtgg   2820
aagctgctgc aggtggccgt ggaagataga gtgcggcagc tgcacgaggc ccacagagat   2880
tttggccctg cctcccagca cttcctgagc accagtgtgc agggcccttg ggagagagcc   2940
atctccccta acaaggtgcc ctactacatc aaccacgaga cacagaccac ctgttgggac   3000
caccccaaga tgaccgagct gtaccagagc ctggctgacc tgaacaacgt gcggttcagc   3060
gcctaccgga ccgccatgaa gctgcggaga ctgcagaaag ctctgtgcct ggatctgctg   3120
tccctgtccg ccgcctgtga tgccctggac cagcacaatc tgaagcagaa cgaccagccc   3180
atggatatcc tgcagatcat caactgcctg accaccatct acgaccggct ggaacaggaa   3240
cacaacaatc tcgtgaacgt gcccctgtgc gtggacatgt gcctgaattg gctgctgaat   3300
gtgtacgaca ccggccggac aggccggatc agagtgctgt ccttcaagac cggcatcatc   3360
agcctgtgca aagcccacct ggaagataag taccggtatc tgttcaaaca ggtggcctct   3420
agcaccggct tttgcgacca gagaaggctg ggcctgctgc tgcacgacag catccagatc   3480
cctagacagc tgggcgaagt ggccagcttt ggcggcagca acatcgagcc tagcgtgcgg   3540
agctgcttcc agttcgccaa caacaagccc gagatcgagg ccgccctgtt cctggactgg   3600
atgagactgg aaccccagag catggtgtgg ctgcccgtgc tgcatagagt ggccgctgcc   3660
gagacagcca agcaccaggc caagtgcaac atctgcaaag agtgccccat catcggcttc   3720
cggtacagaa gcctgaagca cttcaactac gatatctgcc agagctgttt cttcagcggc   3780
agggtggcca agggccacaa aatgcactac cccatggtgg aatactgcac ccccaccaca   3840
agcggcgagg atgtgcggga tttcgccaag gtgctgaaaa acaagttccg gaccaagcgg   3900
```

```
tacttcgcca aacacccccg gatgggctac ctgcctgtgc agacagtgct ggaaggcgac   3960

aacatggaaa ccgacaccat gtgatgatga tttgggcaga gcgatggagt ccttagtatc   4020

agtcatgaca gatgaagaag gagcagaata aatgttttac aactcctgat tcccgcatgc   4080

ggccagctta tcgataccgt cgaaataaaa gatccttatt ttcattggat ctgtgtgttg   4140

gtttttgtg tg                                                        4152
```

<210> SEQ ID NO 134
<211> LENGTH: 4134
<212> TYPE: DNA
<213> ORGANISM: Homo sapiens

<400> SEQUENCE: 134

```
atgctgtggt gggaggaagt ggaagattgc tacgagcgcg aggacgtgca gaagaaaacc     60

ttcaccaaat gggtgaacgc ccagttcagc aagttcggca agcagcacat cgagaacctg    120

ttcagcgacc tgcaggacgg cagacggctg ctggacctgc tggaaggcct gaccggccag    180

aagctgccca aagagaaggg cagcaccaga gtgcacgccc tgaacaacgt gaacaaggcc    240

ctgcgggtgc tgcagaacaa caacgtggac ctggtgaaca tcggcagcac cgacatcgtg    300

gacggcaacc acaagctgac cctgggcctg atctggaaca tcatcctgca ctggcaggtc    360

aaaaacgtga tgaagaacat catggccggc ctgcagcaga ccaacagcga gaagatcctg    420

ctgagctggg tgcgccagag cacccggaac tacccccagg tcaacgtgat caacttcacc    480

acctcttgga gcgacggcct ggccctgaac gccctgatcc acagccaccg gcccgacctg    540

ttcgactgga acagcgtggt ctgccagcag agcgccaccc agcggctgga acacgccttc    600

aatatcgcca gataccagct gggcatcgag aagctgctgg atcccgagga cgtggacacc    660

acctaccccg acaagaaatc catcctgatg tatatcacca gcctgttcca ggtgctgccc    720

cagcaggtgt ccatcgaggc catccaggaa gtggaaatgc tgcccagacc ccccaaagtg    780

accaaagagg aacacttcca gctgcaccac cagatgcact acagccagca gatcaccgtg    840

tccctggccc agggctacga gagaaccagc agccccaagc cccggttcaa gagctacgcc    900

tatacccagg ccgcctacgt gaccaccagc gaccctacca gaagcccatt ccccagccag    960

catctggaag cccccgagga caagagcttc ggcagcagcc tgatggaaag cgaagtgaac   1020

ctggacagat accagaccgc cctggaagag gtgctgagct ggctgctgag cgccgaggat   1080

acactgcagg ctcagggcga gatcagcaac gacgtggaag tcgtgaagga ccagttccac   1140

acccacgagg gctacatgat ggacctgaca gcccaccagg gcagagtggg caacatcctg   1200

cagctgggct ccaagctgat cggcaccggc aagctgagcg aggacgaaga gacagaggtg   1260

caggaacaga tgaacctgct gaacagcaga tgggagtgcc tgcgggtggc cagcatggaa   1320

aagcagagca acctgcatct gctgaagtgg cagcggctga ccgaggaaca gtgcctgttt   1380

agcgcctggc tgtccgagaa agaggacgcc gtgaacaaga tccacaccac cggcttcaag   1440

gaccagaacg agatgctgag cagcctgcag aaactggccg tgctgaaggc cgacctggaa   1500

aagaaaaagc agtccatggg caagctgtac tccctgaagc aggacctgct gtccaccctg   1560

aagaacaaga gcgtgaccca gaaaaccgag gcctggctgg acaacttcgc ccggtgctgg   1620

gacaacctgg tgcagaagct ggaaaagtcc accgcccaga tctcccaggc cgtgaccaca   1680

acacagccca gcctgaccca gaccaccgtg atggaaaccg tgacaacagt gaccacccgg   1740

gaacagatcc tcgtgaagca cgcccaggaa gaactgcccc ctccaccccc ccagaagaaa   1800
```

-continued

```
cggcagatca cagtggacat ccacaccgtg cgggaagaga caatgatggt catgacagag   1860
gacatgcccc tggaaatcag ctacgtgccc agcacctacc tgaccgagat cacccatgtg   1920
tcccaggccc tgctggaagt ggaacagctg ctgaacgccc ccgacctgtg cgccaaggat   1980
ttcgaggacc tgttcaagca ggaagagagc ctgaagaata tcaaggatag cctgcagcag   2040
agcagcggcc ggatcgacat catccacagc aagaaaacag ccgccctgca gagcgccacc   2100
cccgtggaaa gagtgaaact gcaggaagcc ctgtcccagc tggacttcca gtgggagaaa   2160
gtgaacaaaa tgtacaagga ccggcagggc agattcgacc gcagcgtgga aaagtggcgg   2220
cggttccact acgacatcaa gatcttcaac cagtggctga cagaggccga gcagttcctg   2280
agaaagaccc agatccccga gaactgggag cacgccaagt acaagtggta tctgaaagag   2340
ctgcaggacg gcatcggcca gagacagaca gtcgtgcgga ccctgaatgc caccggcgag   2400
gaaatcatcc agcagtccag caagaccgac gccagcattc tgcaggaaaa gctgggcagc   2460
ctgaacctgc ggtggcagga agtgtgcaag cagctgtccg accggaagaa gcggctggaa   2520
gaacagctgg aacggctgca ggaactgcag gaggccaccg acgagctgga cctgaaactg   2580
agacaggccg aagtgatcaa gggcagctgg cagccagtgg gcgacctgct gatcgactcc   2640
ctgcaggacc atctggaaaa agtgaaggcc ctgagaggcg agatcgcccc cctgaaagaa   2700
aacgtgtccc acgtgaacga cctggcccgg cagctgacaa cactgggcat tcagctgagc   2760
ccctacaacc tgagcacact ggaagatctg aacacccggt ggaagctgct gcaggtggcc   2820
gtggaagata gagtgcggca gctgcacgag gcccacagag attttggccc tgcctcccag   2880
cacttcctga gcaccagtgt gcagggccct tgggagagag ccatctcccc taacaaggtg   2940
ccctactaca tcaaccacga gacacagacc acctgttggg accaccccaa gatgaccgag   3000
ctgtaccaga gcctggctga cctgaacaac gtgcggttca gcgcctaccg gaccgccatg   3060
aagctgcgga gactgcagaa agctctgtgc ctggatctgc tgtccctgtc cgccgcctgt   3120
gatgccctgg accagcacaa tctgaagcag aacgaccagc ccatggatat cctgcagatc   3180
atcaactgcc tgaccaccat ctacgaccgg ctggaacagg aacacaacaa tctcgtgaac   3240
gtgcccctgt gcgtggacat gtgcctgaat tggctgctga atgtgtacga caccggccgg   3300
acaggccgga tcagagtgct gtccttcaag accggcatca tcagcctgtg caaagcccac   3360
ctggaagata agtaccggta tctgttcaaa caggtggcct ctagcaccgg cttttgcgac   3420
cagagaaggc tgggcctgct gctgcacgac agcatccaga tccctagaca gctgggcgaa   3480
gtggccagct ttggcggcag caacatcgag cctagcgtgc ggagctgctt ccagttcgcc   3540
aacaacaagc ccgagatcga ggccgccctg ttcctggact ggatgagact ggaaccccag   3600
agcatggtgt ggctgcccgt gctgcataga gtggccgctg ccgagacagc caagcaccag   3660
gccaagtgca acatctgcaa agagtgcccc atcatcggct tccggtacag aagcctgaag   3720
cacttcaact acgatatctg ccagagctgt ttcttcagcg gcagggtggc caagggccac   3780
aaaatgcact accccatggt ggaatactgc acccccacca caagcggcga ggatgtgcgg   3840
gatttcgcca aggtgctgaa aaacaagttc cggaccaagc ggtacttcgc caaacacccc   3900
cggatgggct acctgcctgt gcagacagtg ctggaaggcg acaacatgga aaccgacacc   3960
atgtgatgat gatttgggca gagcgatgga gtccttagta tcagtcatga cagatgaaga   4020
aggagcagaa taaatgtttt acaactcctg attcccgcat gcggccagct tatcgatacc   4080
gtcgaaataa aagatcctta ttttcattgg atctgtgtgt tggttttttg tgtg         4134
```

<210> SEQ ID NO 135
<211> LENGTH: 4145
<212> TYPE: DNA
<213> ORGANISM: Homo sapiens

<400> SEQUENCE: 135

```
atgctgtggt gggaggaagt ggaagattgc tacgagcgcg aggacgtgca gaagaaaacc     60
ttcaccaaat gggtgaacgc ccagttcagc aagttcggca agcagcacat cgagaacctg    120
ttcagcgacc tgcaggacgg cagacggctg ctggacctgc tggaaggcct gaccggccag    180
aagctgccca aagagaaggg cagcaccaga gtgcacgccc tgaacaacgt gaacaaggcc    240
ctgcgggtgc tgcagaacaa caacgtggac ctggtgaaca tcggcagcac cgacatcgtg    300
gacggcaacc acaagctgac cctgggcctg atctggaaca tcatcctgca ctggcaggtc    360
aaaaacgtga tgaagaacat catggccggc ctgcagcaga ccaacagcga gaagatcctg    420
ctgagctggg tgcgccagag cacccggaac tacccccagg tcaacgtgat caacttcacc    480
acctcttgga gcgacggcct ggccctgaac gccctgatcc acagccaccg gcccgacctg    540
ttcgactgga acagcgtggt ctgccagcag agcgccaccc agcggctgga acacgccttc    600
aatatcgcca gataccagct gggcatcgag aagctgctgg atcccgagga cgtggacacc    660
acctaccccg acaagaaatc catcctgatg tatatcacca gcctgttcca ggtgctgccc    720
cagcaggtgt ccatcgaggc catccaggaa gtggaaatgc tgcccagacc ccccaaagtg    780
accaaagagg aacacttcca gctgcaccac cagatgcact acagccagca gatcaccgtg    840
tccctggccc agggctacga gagaaccagc agccccaagc cccggttcaa gagctacgcc    900
tatacccagg ccgcctacgt gaccaccagc gaccctacca gaagcccatt ccccagccag    960
catctggaag cccccgagga caagagcttc ggcagcagcc tgatggaaag cgaagtgaac   1020
ctggacagat accagaccgc cctggaagag gtgctgagct ggctgctgag cgccgaggat   1080
acactgcagg ctcagggcga gatcagcaac gacgtggaag tcgtgaagga ccagttccac   1140
acccacgagg gctacatgat ggacctgaca gcccaccagg gcagagtggg caacatcctg   1200
cagctgggct ccaagctgat cggcaccggc aagctgagcg aggacgaaga gacagaggtg   1260
caggaacaga tgaacctgct gaacagcaga tgggagtgcc tgcgggtggc cagcatggaa   1320
aagcagagca acctgcatct gctgaagtgg cagcggctga ccgaggaaca gtgcctgttt   1380
agcgcctggc tgtccgagaa agaggacgcc gtgaacaaga tccacaccac cggcttcaag   1440
gaccagaacg agatgctgag cagcctgcag aaactggccg tgctgaaggc cgacctggaa   1500
aagaaaaagc agtccatggg caagctgtac tccctgaagc aggacctgct gtccaccctg   1560
aagaacaaga gcgtgaccca gaaaaccgag gcctggctgg acaacttcgc ccggtgctgg   1620
gacaacctgg tgcagaagct ggaaaagtcc accgcccaga tctcccaggc cgtgaccaca   1680
acacagccca gcctgaccca gaccaccgtg atggaaaccg tgacaacagt gaccacccgg   1740
gaacagatcc tcgtgaagca cgcccaggaa gaactgcccc ctccaccccc ccagaagaaa   1800
cggcagatca cagtggacag tgaagctcag atccacaccg tgcgggaaga gacaatgatg   1860
gtcatgacag aggacatgcc cctggaaatc agctacgtgc ccagcaccta cctgaccgag   1920
atcacccatg tgtcccaggc cctgctggaa gtggaacagc tgctgaacgc ccccgacctg   1980
tgcgccaagg atttcgagga cctgttcaag caggaagaga gcctgaagaa tatcaaggat   2040
agcctgcagc agagcagcgg ccggatcgac atcatccaca gcaagaaaac agccgccctg   2100
cagagcgcca cccccgtgga aagagtgaaa ctgcaggaag ccctgtccca gctggacttc   2160
```

```
cagtgggaga aagtgaacaa aatgtacaag gaccggcagg gcagattcga ccgcagcgtg   2220
gaaaagtggc ggcggttcca ctacgacatc aagatcttca accagtggct gacagaggcc   2280
gagcagttcc tgagaaagac ccagatcccc gagaactggg agcacgccaa gtacaagtgg   2340
tatctgaaag agctgcagga cggcatcggc cagagacaga cagtcgtgcg gaccctgaat   2400
gccaccggcg aggaaatcat ccagcagtcc agcaagaccg acgccagcat tctgcaggaa   2460
aagctgggca gcctgaacct gcggtggcag gaagtgtgca agcagctgtc cgaccggaag   2520
aagcggctgg aagaacagaa gaacatcctg caggaactgc aggaggccac cgacgagctg   2580
gacctgaaac tgagacaggc cgaagtgatc aagggcagct ggcagccagt gggcgacctg   2640
ctgatcgact ccctgcagga ccatctggaa aaagtgaagg ccctgagagg cgagatcgcc   2700
cccctgaaag aaaacgtgtc ccacgtgaac gacctggccc ggcagctgac aacactgggc   2760
attcagctga gcccctacaa cctgagcaca ctggaagatc tgaacacccg gtggaagctg   2820
ctgcaggtgg ccgtggaaga tagagtgcgg cagctgcacg aggcccacag agattttggc   2880
cctgcctccc agcacttcct gagcaccagt gtgcagggcc cttgggagag agccatctcc   2940
cctaacaagg tgccctacta catcaaccac gagacacaga ccacctgttg ggaccacccc   3000
aagatgaccg agctgtacca gagcctggct gacctgaaca acgtgcggtt cagcgcctac   3060
cggaccgcca tgaagctgcg gagactgcag aaagctctgt gcctggatct gctgtccctg   3120
tccgccgcct gtgatgccct ggaccagcac aatctgaagc agaacgacca gcccatggat   3180
atcctgcaga tcatcaactg cctgaccacc atctacgacc ggctggaaca ggaacacaac   3240
aatctcgtga acgtgcccct gtgcgtggac atgtgcctga attggctgct gaatgtgtac   3300
gacaccggcc ggacaggccg gatcagagtg ctgtccttca agaccggcat catcagcctg   3360
tgcaaagccc acctggaaga taagtaccgg tatctgttca aacaggtggc ctctagcacc   3420
ggcttttgcg accagagaag gctgggcctg ctgctgcacg acagcatcca gatccctaga   3480
cagctgggcg aagtggccag ctttggcggc agcaacatcg agcctagcgt gcggagctgc   3540
ttccagttcg ccaacaacaa gcccgagatc gaggccgccc tgttcctgga ctggatgaga   3600
ctggaacccc agagcatggt gtggctgccc gtgctgcata gagtggccgc tgccgagaca   3660
gccaagcacc aggccaagtg caacatctgc aaagagtgcc ccatcatcgg cttccggtac   3720
agaagcctga agcacttcaa ctacgatatc tgccagagct gtttcttcag cggcagggtg   3780
gccaagggcc acaaaatgca ctaccccatg gtggaatact gcacccccac cacaagcggc   3840
gaggatgtgc gggatttcgc caaggtgctg aaaaacaagt tccggaccaa gcggtacttc   3900
gccaaacacc cccggatggg ctacctgcct gtgcagacag tgctggaagg cgacaacatg   3960
gaaaccacac catgtgatga tgatttgggc agagcgatgg agtccttagt atcagtcatg   4020
acagatgaag aaggagcaga ataaatgttt tacaactcct gattcccgca tgcggccagc   4080
ttatcgatac cgtcgaaata aaagatcctt attttcattg gatctgtgtg ttggtttttt   4140
gtgtg                                                               4145
```

<210> SEQ ID NO 136
<211> LENGTH: 4149
<212> TYPE: DNA
<213> ORGANISM: Homo sapiens

<400> SEQUENCE: 136

```
atgctgtggt gggaggaagt ggaagattgc tacgagcgcg aggacgtgca gaagaaaacc     60
ttcaccaaat gggtgaacgc ccagttcagc aagttcggca agcagcacat cgagaacctg    120
```

```
ttcagcgacc tgcaggacgg cagacggctg ctggacctgc tggaaggcct gaccggccag    180
aagctgccca aagagaaggg cagcaccaga gtgcacgccc tgaacaacgt gaacaaggcc    240
ctgcgggtgc tgcagaacaa caacgtggac ctggtgaaca tcggcagcac cgacatcgtg    300
gacggcaacc acaagctgac cctgggcctg atctggaaca tcatcctgca ctggcaggtc    360
aaaaacgtga tgaagaacat catggccggc ctgcagcaga ccaacagcga gaagatcctg    420
ctgagctggg tgcgccagag cacccggaac tacccccagg tcaacgtgat caacttcacc    480
acctcttgga gcgacggcct ggccctgaac gccctgatcc acagccaccg gcccgacctg    540
ttcgactgga acagcgtggt ctgccagcag agcgccaccc agcggctgga acacgccttc    600
aatatcgcca gataccagct gggcatcgag aagctgctgg atcccgagga cgtggacacc    660
acctaccccg acaagaaatc catcctgatg tatatcacca gcctgttcca ggtgctgccc    720
cagcaggtgt ccatcgaggc catccaggaa gtggaaatgc tgcccagacc ccccaaagtg    780
accaaagagg aacacttcca gctgcaccac cagatgcact acagccagca gatcaccgtg    840
tccctggccc agggctacga gagaaccagc agccccaagc cccggttcaa gagctacgcc    900
tatacccagg ccgcctacgt gaccaccagc gaccctacca gaagcccatt ccccagccag    960
catctggaag cccccgagga caagagcttc ggcagcagcc tgatggaaag cgaagtgaac   1020
ctggacagat accagaccgc cctggaagag gtgctgagct ggctgctgag cgccgaggat   1080
acactgcagg ctcagggcga gatcagcaac gacgtggaag tcgtgaagga ccagttccac   1140
acccacgagg gctacatgat ggacctgaca gcccaccagg gcagagtggg caacatcctg   1200
cagctgggct ccaagctgat cggcaccggc aagctgagcg aggacgaaga gacagaggtg   1260
caggaacaga tgaacctgct gaacagcaga tgggagtgcc tgcgggtggc cagcatggaa   1320
aagcagagca acctgcatct gctgaagtgg cagcggctga ccgaggaaca gtgcctgttt   1380
agcgcctggc tgtccgagaa agaggacgcc gtgaacaaga tccacaccac cggcttcaag   1440
gaccagaacg agatgctgag cagcctgcag aaactggccg tgctgaaggc cgacctggaa   1500
aagaaaaagc agtccatggg caagctgtac tccctgaagc aggacctgct gtccaccctg   1560
aagaacaaga gcgtgaccca gaaaaccgag gcctggctgg acaacttcgc ccggtgctgg   1620
gacaacctgg tgcagaagct ggaaaagtcc accgcccaga tctcccaggc cgtgaccaca   1680
acacagccca gcctgaccca gaccaccgtg atggaaaccg tgacaacagt gaccacccgg   1740
gaacagatcc tcgtgaagca cgcccaggaa gaactgcccc ctccaccccc ccagaagaaa   1800
cggcagatca cagtggacag tgaagctcag atccacaccg tgcgggaaga gacaatgatg   1860
gtcatgacag aggacatgcc cctggaaatc agctacgtgc ccagcaccta cctgaccgag   1920
atcacccatg tgtcccaggc cctgctggaa gtggaacagc tgctgaacgc ccccgacctg   1980
tgcgccaagg atttcgagga cctgttcaag caggaagaga gcctgaagaa tatcaaggat   2040
agcctgcagc agagcagcgg ccggatcgac atcatccaca gcaagaaaac agccgccctg   2100
cagagcgcca cccccgtgga aagagtgaaa ctgcaggaag ccctgtccca gctggacttc   2160
cagtgggaga aagtgaacaa aatgtacaag gaccggcagg gcagattcga ccgcagcgtg   2220
gaaaagtggc ggcggttcca ctacgacatc aagatcttca accagtggct gacagaggcc   2280
gagcagttcc tgagaaagac ccagatcccc gagaactggg agcacgccaa gtacaagtgg   2340
tatctgaaag agctgcagga cggcatcggc cagagacaga cagtcgtgcg gaccctgaat   2400
gccaccggcg aggaaatcat ccagcagtcc agcaagaccg acgccagcat tctgcaggaa   2460
```

```
aagctgggca gcctgaacct gcggtggcag gaagtgtgca agcagctgtc cgaccggaag   2520
aagcggctgg aagaacagaa gctggaacgg ctgcaggaac tgcaggaggc caccgacgag   2580
ctggacctga aactgagaca ggccgaagtg atcaagggca gctggcagcc agtgggcgac   2640
ctgctgatcg actccctgca ggaccatctg gaaaaagtga aggccctgag aggcgagatc   2700
gccccccctga aagaaaacgt gtcccacgtg aacgacctgg cccggcagct gacaacactg   2760
ggcattcagc tgagccccta caacctgagc acactggaag atctgaacac ccggtggaag   2820
ctgctgcagg tggccgtgga agatagagtg cggcagctgc acgaggccca cagagatttt   2880
ggccctgcct cccagcactt cctgagcacc agtgtgcagg gcccttggga gagagccatc   2940
tcccctaaca aggtgcccta ctacatcaac cacgagacac agaccacctg ttgggaccac   3000
cccaagatga ccgagctgta ccagagcctg gctgacctga acaacgtgcg gttcagcgcc   3060
taccggaccg ccatgaagct gcggagactg cagaaagctc tgtgcctgga tctgctgtcc   3120
ctgtccgccg cctgtgatgc cctggaccag cacaatctga agcagaacga ccagcccatg   3180
gatatcctgc agatcatcaa ctgcctgacc accatctacg accggctgga acaggaacac   3240
aacaatctcg tgaacgtgcc cctgtgcgtg gacatgtgcc tgaattggct gctgaatgtg   3300
tacgacaccg gccggacagg ccggatcaga gtgctgtcct tcaagaccgg catcatcagc   3360
ctgtgcaaag cccacctgga agataagtac cggtatctgt tcaaacaggt ggcctctagc   3420
accggctttt gcgaccagag aaggctgggc ctgctgctgc acgacagcat ccagatccct   3480
agacagctgg gcgaagtggc cagctttggc ggcagcaaca tcgagcctag cgtgcggagc   3540
tgcttccagt tcgccaacaa caagcccgag atcgaggccg ccctgttcct ggactggatg   3600
agactggaac cccagagcat ggtgtggctg cccgtgctgc atagagtggc cgctgccgag   3660
acagccaagc accaggccaa gtgcaacatc tgcaaagagt gccccatcat cggcttccgg   3720
tacagaagcc tgaagcactt caactacgat atctgccaga gctgtttctt cagcggcagg   3780
gtggccaagg gccacaaaat gcactacccc atggtggaat actgcacccc caccacaagc   3840
ggcgaggatg tgcgggattt cgccaaggtg ctgaaaaaca agttccggac caagcggtac   3900
ttcgccaaac acccccggat gggctacctg cctgtgcaga cagtgctgga aggcgacaac   3960
atggaaaccg acaccatgtg atgatgattt gggcagagcg atggagtcct tagtatcagt   4020
catgacagat gaagaaggag cagaataaat gttttacaac tcctgattcc cgcatgcggc   4080
cagcttatcg ataccgtcga aataaaagat ccttattttc attggatctg tgtgttggtt   4140
ttttgtgtg                                                           4149
```

```
<210> SEQ ID NO 137
<211> LENGTH: 4155
<212> TYPE: DNA
<213> ORGANISM: Homo sapiens

<400> SEQUENCE: 137
```

```
atgctgtggt gggaggaagt ggaagattgc tacgagcgcg aggacgtgca gaagaaaacc     60
ttcaccaaat gggtgaacgc ccagttcagc aagttcggca agcagcacat cgagaacctg    120
ttcagcgacc tgcaggacgg cagacggctg ctggacctgc tggaaggcct gaccggccag    180
aagctgccca aagagaaggg cagcaccaga gtgcacgccc tgaacaacgt gaacaaggcc    240
ctgcgggtgc tgcagaacaa caacgtggac ctggtgaaca tcggcagcac cgacatcgtg    300
gacggcaacc acaagctgac cctgggcctg atctggaaca tcatcctgca ctggcaggtc    360
aaaaacgtga tgaagaacat catggccggc ctgcagcaga ccaacagcga gaagatcctg    420
```

```
ctgagctggg tgcgccagag cacccggaac tacccccagg tcaacgtgat caacttcacc    480
acctcttgga gcgacggcct ggccctgaac gccctgatcc acagccaccg gcccgacctg    540
ttcgactgga acagcgtggt ctgccagcag agcgccaccc agcggctgga acacgccttc    600
aatatcgcca gataccagct gggcatcgag aagctgctgg atcccgagga cgtggacacc    660
acctaccccg acaagaaatc catcctgatg tatatcacca gcctgttcca ggtgctgccc    720
cagcaggtgt ccatcgaggc catccaggaa gtggaaatgc tgcccagacc ccccaaagtg    780
accaaagagg aacacttcca gctgcaccac cagatgcact acagccagca gatcaccgtg    840
tccctggccc agggctacga gagaaccagc agccccaagc cccggttcaa gagctacgcc    900
tatacccagg ccgcctacgt gaccaccagc gaccctacca gaagcccatt ccccagccag    960
catctggaag cccccgagga caagagcttc ggcagcagcc tgatggaaag cgaagtgaac   1020
ctggacagat accagaccgc cctggaagag gtgctgagct ggctgctgag cgccgaggat   1080
acactgcagg ctcagggcga gatcagcaac gacgtggaag tcgtgaagga ccagttccac   1140
acccacgagg gctacatgat ggacctgaca gcccaccagg gcagagtggg caacatcctg   1200
cagctgggct ccaagctgat cggcaccggc aagctgagcg aggacgaaga gacagaggtg   1260
caggaacaga tgaacctgct gaacagcaga tgggagtgcc tgcgggtggc cagcatggaa   1320
aagcagagca acctgcatct gctgaagtgg cagcggctga ccgaggaaca gtgcctgttt   1380
agcgcctggc tgtccgagaa agaggacgcc gtgaacaaga tccacaccac cggcttcaag   1440
gaccagaacg agatgctgag cagcctgcag aaactggccg tgctgaaggc cgacctggaa   1500
aagaaaaagc agtccatggg caagctgtac tccctgaagc aggacctgct gtccaccctg   1560
aagaacaaga gcgtgaccca gaaaaccgag gcctggctgg acaacttcgc ccggtgctgg   1620
gacaacctgg tgcagaagct ggaaaagtcc accgcccaga tctcccaggc cgtgaccaca   1680
acacagccca gcctgaccca gaccaccgtg atggaaaccg tgacaacagt gaccacccgg   1740
gaacagatcc tcgtgaagca cgcccaggaa gaactgcccc ctccaccccc ccagaagaaa   1800
cggcagatca cagtggacag tgaagctcag atccacaccg tgcgggaaga gacaatgatg   1860
gtcatgacag aggacatgcc cctggaaatc agctacgtgc ccagcaccta cctgaccgag   1920
atcacccatg tgtcccaggc cctgctggaa gtggaacagc tgctgaacgc ccccgacctg   1980
tgcgccaagg atttcgagga cctgttcaag caggaagaga gcctgaagaa tatcaaggat   2040
agcctgcagc agagcagcgg ccggatcgac atcatccaca gcaagaaaac agccgccctg   2100
cagagcgcca cccccgtgga aagagtgaaa ctgcaggaag ccctgtccca gctggacttc   2160
cagtgggaga aagtgaacaa aatgtacaag gaccggcagg gcagattcga ccgcagcgtg   2220
gaaaagtggc ggcggttcca ctacgacatc aagatcttca accagtggct gacagaggcc   2280
gagcagttcc tgagaaagac ccagatcccc gagaactggg agcacgccaa gtacaagtgg   2340
tatctgaaag agctgcagga cggcatcggc cagagacaga cagtcgtgcg gaccctgaat   2400
gccaccggcg aggaaatcat ccagcagtcc agcaagaccg acgccagcat tctgcaggaa   2460
aagctgggca gcctgaacct gcggtggcag gaagtgtgca agcagctgtc cgaccggaag   2520
aagcggctgg aagaacagaa gaacatcctg gaacggctgc aggaactgca ggaggccacc   2580
gacgagctgg acctgaaact gagacaggcc gaagtgatca agggcagctg gcagccagtg   2640
ggcgacctgc tgatcgactc cctgcaggac catctggaaa aagtgaaggc cctgagaggc   2700
gagatcgccc ccctgaaaga aaacgtgtcc cacgtgaacg acctggcccg gcagctgaca   2760
```

```
acactgggca ttcagctgag cccctacaac ctgagcacac tggaagatct gaacacccgg   2820

tggaagctgc tgcaggtggc cgtggaagat agagtgcggc agctgcacga ggcccacaga   2880

gattttggcc ctgcctccca gcacttcctg agcaccagtg tgcagggccc ttgggagaga   2940

gccatctccc ctaacaaggt gccctactac atcaaccacg agacacagac cacctgttgg   3000

gaccacccca agatgaccga gctgtaccag agcctggctg acctgaacaa cgtgcggttc   3060

agcgcctacc ggaccgccat gaagctgcgg agactgcaga aagctctgtg cctggatctg   3120

ctgtccctgt ccgccgcctg tgatgccctg gaccagcaca atctgaagca gaacgaccag   3180

cccatggata tcctgcagat catcaactgc ctgaccacca tctacgaccg gctggaacag   3240

gaacacaaca atctcgtgaa cgtgcccctg tgcgtggaca tgtgcctgaa ttggctgctg   3300

aatgtgtacg acaccggccg gacaggccgg atcagagtgc tgtccttcaa gaccggcatc   3360

atcagcctgt gcaaagccca cctggaagat aagtaccggt atctgttcaa acaggtggcc   3420

tctagcaccg gcttttgcga ccagagaagg ctgggcctgc tgctgcacga cagcatccag   3480

atccctagac agctgggcga agtggccagc tttggcggca gcaacatcga gcctagcgtg   3540

cggagctgct tccagttcgc caacaacaag cccgagatcg aggccgccct gttcctggac   3600

tggatgagac tggaacccca gagcatggtg tggctgcccg tgctgcatag agtggccgct   3660

gccgagacag ccaagcacca ggccaagtgc aacatctgca aagagtgccc catcatcggc   3720

ttccggtaca gaagcctgaa gcacttcaac tacgatatct gccagagctg tttcttcagc   3780

ggcagggtgg ccaagggcca caaaatgcac taccccatgg tggaatactg cacccccacc   3840

acaagcggcg aggatgtgcg ggatttcgcc aaggtgctga aaaacaagtt ccggaccaag   3900

cggtacttcg ccaaacaccc ccggatgggc tacctgcctg tgcagacagt gctggaaggc   3960

gacaacatgg aaaccgacac catgtgatga tgatttgggc agagcgatgg agtccttagt   4020

atcagtcatg acagatgaag aaggagcaga ataaatgttt tacaactcct gattcccgca   4080

tgcggccagc ttatcgatac cgtcgaaata aaagatcctt attttcattg gatctgtgtg   4140

ttggtttttt gtgtg                                                    4155
```

<210> SEQ ID NO 138
<211> LENGTH: 4152
<212> TYPE: DNA
<213> ORGANISM: Homo sapiens

<400> SEQUENCE: 138

```
atgctgtggt gggaggaagt ggaagattgc tacgagcgcg aggacgtgca gaagaaaacc     60

ttcaccaaat gggtgaacgc ccagttcagc aagttcggca agcagcacat cgagaacctg    120

ttcagcgacc tgcaggacgg cagacggctg ctggacctgc tggaaggcct gaccggccag    180

aagctgccca aagagaaggg cagcaccaga gtgcacgccc tgaacaacgt gaacaaggcc    240

ctgcgggtgc tgcagaacaa caacgtggac ctggtgaaca tcggcagcac cgacatcgtg    300

gacggcaacc acaagctgac cctgggcctg atctggaaca tcatcctgca ctggcaggtc    360

aaaaacgtga tgaagaacat catggccggc ctgcagcaga ccaacagcga gaagatcctg    420

ctgagctggg tgcgccagag cacccggaac tacccccagg tcaacgtgat caacttcacc    480

acctcttgga gcgacggcct ggccctgaac gccctgatcc acagccaccg gcccgacctg    540

ttcgactgga acagcgtggt ctgccagcag agcgccaccc agcggctgga acacgccttc    600

aatatcgcca gataccagct gggcatcgag aagctgctgg atcccgagga cgtggacacc    660

acctaccccg acaagaaatc catcctgatg tatatcacca gcctgttcca ggtgctgccc    720
```

```
cagcaggtgt ccatcgaggc catccaggaa gtggaaatgc tgcccagacc ccccaaagtg    780
accaaagagg aacacttcca gctgcaccac cagatgcact acagccagca gatcaccgtg    840
tccctggccc agggctacga gagaaccagc agccccaagc cccggttcaa gagctacgcc    900
tatacccagg ccgcctacgt gaccaccagc gaccctacca gaagcccatt ccccagccag    960
catctggaag cccccgagga caagagcttc ggcagcagcc tgatggaaag cgaagtgaac   1020
ctggacagat accagaccgc cctggaagag gtgctgagct ggctgctgag cgccgaggat   1080
acactgcagg ctcagggcga gatcagcaac gacgtggaag tcgtgaagga ccagttccac   1140
acccacgagg gctacatgat ggacctgaca gcccaccagg gcagagtggg caacatcctg   1200
cagctgggct ccaagctgat cggcaccggc aagctgagcg aggacgaaga gacagaggtg   1260
caggaacaga tgaacctgct gaacagcaga tgggagtgcc tgcgggtggc cagcatggaa   1320
aagcagagca acctgcatag ggtcctgctg aagtggcagc ggctgaccga ggaacagtgc   1380
ctgtttagcg cctggctgtc cgagaaagag gacgccgtga acaagatcca caccaccggc   1440
ttcaaggacc agaacgagat gctgagcagc ctgcagaaac tggccgtgct gaaggccgac   1500
ctggaaaaga aaaagcagtc catgggcaag ctgtactccc tgaagcagga cctgctgtcc   1560
accctgaaga acaagagcgt gacccagaaa accgaggcct ggctggacaa cttcgcccgg   1620
tgctgggaca acctggtgca gaagctggaa aagtccaccg cccagatctc ccaggccgtg   1680
accacaacac agcccagcct gacccagacc accgtgatgg aaaccgtgac aacagtgacc   1740
acccgggaac agatcctcgt gaagcacgcc caggaagaac tgccccctcc accccccag    1800
aagaaacggc agatcacagt ggacagtgaa gctcagatcc acaccgtgcg ggaagagaca   1860
atgatggtca tgacagagga catgcccctg gaaatcagct acgtgcccag cacctacctg   1920
accgagatca cccatgtgtc ccaggccctg ctggaagtgg aacagctgct gaacgccccc   1980
gacctgtgcg ccaaggattt cgaggacctg ttcaagcagg aagagagcct gaagaatatc   2040
aaggatagcc tgcagcagag cagcggccgg atcgacatca tccacagcaa gaaaacagcc   2100
gccctgcaga gcgccacccc cgtggaaaga gtgaaactgc aggaagccct gtcccagctg   2160
gacttccagt gggagaaagt gaacaaaatg tacaaggacc ggcagggcag attcgaccgc   2220
agcgtggaaa agtggcggcg gttccactac gacatcaaga tcttcaacca gtggctgaca   2280
gaggccgagc agttcctgag aaagacccag atccccgaga actgggagca cgccaagtac   2340
aagtggtatc tgaaagagct gcaggacggc atcggccaga gacagacagt cgtgcggacc   2400
ctgaatgcca ccggcgagga aatcatccag cagtccagca agaccgacgc cagcattctg   2460
caggaaaagc tgggcagcct gaacctgcgg tggcaggaag tgtgcaagca gctgtccgac   2520
cggaagaagc ggctggaaga acagctggaa cggctgcagg aactgcagga ggccaccgac   2580
gagctggacc tgaaactgag acaggccgaa gtgatcaagg gcagctggca gccagtgggc   2640
gacctgctga tcgactccct gcaggaccat ctggaaaaag tgaaggccct gagaggcgag   2700
atcgcccccc tgaaagaaaa cgtgtcccac gtgaacgacc tggcccggca gctgacaaca   2760
ctgggcattc agctgagccc ctacaacctg agcacactgg aagatctgaa cacccggtgg   2820
aagctgctgc aggtggccgt ggaagataga gtgcggcagc tgcacgaggc ccacagagat   2880
tttggccctg cctcccagca cttcctgagc accagtgtgc agggcccttg ggagagagcc   2940
atctccccta acaaggtgcc ctactacatc aaccacgaga cacagaccac ctgttgggac   3000
caccccaaga tgaccgagct gtaccagagc ctggctgacc tgaacaacgt gcggttcagc   3060
```

gcctaccgga ccgccatgaa gctgcggaga ctgcagaaag ctctgtgcct ggatctgctg 3120
tccctgtccg ccgcctgtga tgccctggac cagcacaatc tgaagcagaa cgaccagccc 3180
atggatatcc tgcagatcat caactgcctg accaccatct acgaccggct ggaacaggaa 3240
cacaacaatc tcgtgaacgt gcccctgtgc gtggacatgt gcctgaattg gctgctgaat 3300
gtgtacgaca ccggccggac aggccggatc agagtgctgt ccttcaagac cggcatcatc 3360
agcctgtgca aagcccacct ggaagataag taccggtatc tgttcaaaca ggtggcctct 3420
agcaccggct tttgcgacca gagaaggctg ggcctgctgc tgcacgacag catccagatc 3480
cctagacagc tgggcgaagt ggccagcttt ggcggcagca acatcgagcc tagcgtgcgg 3540
agctgcttcc agttcgccaa caacaagccc gagatcgagg ccgccctgtt cctggactgg 3600
atgagactgg aaccccagag catggtgtgg ctgcccgtgc tgcatagagt ggccgctgcc 3660
gagacagcca agcaccaggc caagtgcaac atctgcaaag agtgccccat catcggcttc 3720
cggtacagaa gcctgaagca cttcaactac gatatctgcc agagctgttt cttcagcggc 3780
agggtggcca agggccacaa aatgcactac cccatggtgg aatactgcac ccccaccaca 3840
agcggcgagg atgtgcggga tttcgccaag gtgctgaaaa acaagttccg gaccaagcgg 3900
tacttcgcca aacacccccg gatgggctac ctgcctgtgc agacagtgct ggaaggcgac 3960
aacatggaaa ccgacaccat gtgatgatga tttgggcaga gcgatggagt ccttagtatc 4020
agtcatgaca gatgaagaag gagcagaata aatgttttac aactcctgat tcccgcatgc 4080
ggccagctta tcgataccgt cgaaataaaa gatccttatt ttcattggat ctgtgtgttg 4140 gtttttgtg tg 4152

<210> SEQ ID NO 139
<211> LENGTH: 4167
<212> TYPE: DNA
<213> ORGANISM: Homo sapiens

<400> SEQUENCE: 139
atgctgtggt gggaggaagt ggaagattgc tacgagcgcg aggacgtgca gaagaaaacc 60
ttcaccaaat gggtgaacgc ccagttcagc aagttcggca agcagcacat cgagaacctg 120
ttcagcgacc tgcaggacgg cagacggctg ctggacctgc tggaaggcct gaccggccag 180
aagctgccca aagagaaggg cagcaccaga gtgcacgccc tgaacaacgt gaacaaggcc 240
ctgcgggtgc tgcagaacaa caacgtggac ctggtgaaca tcggcagcac cgacatcgtg 300
gacggcaacc acaagctgac cctgggcctg atctggaaca tcatcctgca ctggcaggtc 360
aaaaacgtga tgaagaacat catggccggc ctgcagcaga ccaacagcga gaagatcctg 420
ctgagctggg tgcgccagag cacccggaac taccccccagg tcaacgtgat caacttcacc 480
acctcttgga gcgacggcct ggccctgaac gccctgatcc acagccaccg gcccgacctg 540
ttcgactgga acagcgtggt ctgccagcag agcgccaccc agcggctgga acacgccttc 600
aatatcgcca gataccagct gggcatcgag aagctgctgg atcccgagga cgtggacacc 660
acctaccccg acaagaaatc catcctgatg tatatcacca gcctgttcca ggtgctgccc 720
cagcaggtgt ccatcgaggc catccaggaa gtggaaatgc tgcccagacc ccccaaagtg 780
accaaagagg aacacttcca gctgcaccac cagatgcact acagccagca gatcaccgtg 840
tccctggccc agggctacga gagaaccagc agccccaagc cccggttcaa gagctacgcc 900
tatacccagg ccgcctacgt gaccaccagc gaccctacca gaagcccatt ccccagccag 960
catctggaag cccccgagga caagagcttc ggcagcagcc tgatggaaag cgaagtgaac 1020

```
ctggacagat accagaccgc cctggaagag gtgctgagct ggctgctgag cgccgaggat   1080
acactgcagg ctcagggcga gatcagcaac gacgtggaag tcgtgaagga ccagttccac   1140
acccacgagg gctacatgat ggacctgaca gcccaccagg gcagagtggg caacatcctg   1200
cagctgggct ccaagctgat cggcaccggc aagctgagcg aggacgaaga gacagaggtg   1260
caggaacaga tgaacctgct gaacagcaga tgggagtgcc tgcgggtggc cagcatggaa   1320
aagcagagca acctgcatag agtactgctc caagacatcc tgctgaagtg gcagcggctg   1380
accgaggaac agtgcctgtt tagcgcctgg ctgtccgaga aagaggacgc cgtgaacaag   1440
atccacacca ccggcttcaa ggaccagaac gagatgctga gcagcctgca gaaactggcc   1500
gtgctgaagg ccgacctgga aaagaaaaag cagtccatgg gcaagctgta ctccctgaag   1560
caggacctgc tgtccaccct gaagaacaag agcgtgaccc agaaaaccga ggcctggctg   1620
gacaacttcg cccggtgctg ggacaacctg gtgcagaagc tggaaaagtc caccgcccag   1680
atctcccagg ccgtgaccac aacacagccc agcctgaccc agaccaccgt gatggaaacc   1740
gtgacaacag tgaccacccg ggaacagatc ctcgtgaagc acgcccagga agaactgccc   1800
cctccacccc cccagaagaa acggcagatc acagtggaca gtgaagctca gatccacacc   1860
gtgcgggaag agacaatgat ggtcatgaca gaggacatgc ccctggaaat cagctacgtg   1920
cccagcacct acctgaccga gatcacccat gtgtcccagg ccctgctgga agtggaacag   1980
ctgctgaacg cccccgacct gtgcgccaag gatttcgagg acctgttcaa gcaggaagag   2040
agcctgaaga atatcaagga tagcctgcag cagagcagcg gccggatcga catcatccac   2100
agcaagaaaa cagccgccct gcagagcgcc acccccgtgg aaagagtgaa actgcaggaa   2160
gccctgtccc agctggactt ccagtgggag aaagtgaaca aaatgtacaa ggaccggcag   2220
ggcagattcg accgcagcgt ggaaaagtgg cggcggttcc actacgacat caagatcttc   2280
aaccagtggc tgacagaggc cgagcagttc ctgagaaaga cccagatccc cgagaactgg   2340
gagcacgcca agtacaagtg gtatctgaaa gagctgcagg acggcatcgg ccagagacag   2400
acagtcgtgc ggaccctgaa tgccaccggc gaggaaatca tccagcagtc cagcaagacc   2460
gacgccagca ttctgcagga aaagctgggc agcctgaacc tgcggtggca ggaagtgtgc   2520
aagcagctgt ccgaccggaa gaagcggctg gaagaacagc tggaacggct gcaggaactg   2580
caggaggcca ccgacgagct ggacctgaaa ctgagacagg ccgaagtgat caagggcagc   2640
tggcagccag tgggcgacct gctgatcgac tccctgcagg accatctgga aaaagtgaag   2700
gccctgagag gcgagatcgc ccccctgaaa gaaaacgtgt cccacgtgaa cgacctggcc   2760
cggcagctga caacactggg cattcagctg agcccctaca acctgagcac actggaagat   2820
ctgaacaccc ggtggaagct gctgcaggtg gccgtggaag atagagtgcg gcagctgcac   2880
gaggcccaca gagattttgg ccctgcctcc cagcacttcc tgagcaccag tgtgcagggc   2940
ccttgggaga gagccatctc ccctaacaag gtgccctact acatcaacca cgagacacag   3000
accacctgtt gggaccaccc caagatgacc gagctgtacc agagcctggc tgacctgaac   3060
aacgtgcggt tcagcgccta ccggaccgcc atgaagctgc ggagactgca gaaagctctg   3120
tgcctggatc tgctgtccct gtccgccgcc tgtgatgccc tggaccagca caatctgaag   3180
cagaacgacc agcccatgga tatcctgcag atcatcaact gcctgaccac catctacgac   3240
cggctggaac aggaacacaa caatctcgtg aacgtgcccc tgtgcgtgga catgtgcctg   3300
aattggctgc tgaatgtgta cgacaccggc cggacaggcc ggatcagagt gctgtccttc   3360
```

```
aagaccggca tcatcagcct gtgcaaagcc cacctggaag ataagtaccg gtatctgttc   3420

aaacaggtgg cctctagcac cggcttttgc gaccagagaa ggctgggcct gctgctgcac   3480

gacagcatcc agatccctag acagctgggc gaagtggcca gctttggcgg cagcaacatc   3540

gagcctagcg tgcggagctg cttccagttc gccaacaaca agcccgagat cgaggccgcc   3600

ctgttcctgg actggatgag actggaaccc cagagcatgg tgtggctgcc cgtgctgcat   3660

agagtggccg ctgccgagac agccaagcac caggccaagt gcaacatctg caaagagtgc   3720

cccatcatcg gcttccggta cagaagcctg aagcacttca actacgatat ctgccagagc   3780

tgtttcttca gcggcagggt ggccaagggc cacaaaatgc actaccccat ggtggaatac   3840

tgcaccccca ccacaagcgg cgaggatgtg cgggatttcg ccaaggtgct gaaaaacaag   3900

ttccggacca agcggtactt cgccaaacac cccccggatgg gctacctgcc tgtgcagaca   3960

gtgctggaag gcgacaacat ggaaaccgac accatgtgat gatgatttgg gcagagcgat   4020

ggagtcctta gtatcagtca tgacagatga agaaggagca gaataaatgt tttacaactc   4080

ctgattcccg catgcggcca gcttatcgat accgtcgaaa taaaagatcc ttattttcat   4140

tggatctgtg tgttggtttt ttgtgtg                                       4167
```

<210> SEQ ID NO 140
<211> LENGTH: 4146
<212> TYPE: DNA
<213> ORGANISM: Homo sapiens

<400> SEQUENCE: 140

```
atgctgtggt gggaggaagt ggaagattgc tacgagcgcg aggacgtgca gaagaaaacc     60

ttcaccaaat gggtgaacgc ccagttcagc aagttcggca agcagcacat cgagaacctg    120

ttcagcgacc tgcaggacgg cagacggctg ctggacctgc tggaaggcct gaccggccag    180

aagctgccca aagagaaggg cagcaccaga gtgcacgccc tgaacaacgt gaacaaggcc    240

ctgcgggtgc tgcagaacaa caacgtggac ctggtgaaca tcggcagcac cgacatcgtg    300

gacggcaacc acaagctgac cctgggcctg atctggaaca tcatcctgca ctggcaggtc    360

aaaaacgtga tgaagaacat catggccggc ctgcagcaga ccaacagcga gaagatcctg    420

ctgagctggg tgcgccagag cacccggaac tacccccagg tcaacgtgat caacttcacc    480

acctcttgga gcgacggcct ggccctgaac gccctgatcc acagccaccg gcccgacctg    540

ttcgactgga acagcgtggt ctgccagcag agcgccaccc agcggctgga acacgccttc    600

aatatcgcca gataccagct gggcatcgag aagctgctgg atcccgagga cgtggacacc    660

acctaccccg acaagaaatc catcctgatg tatatcacca gcctgttcca ggtgctgccc    720

cagcaggtgt ccatcgaggc catccaggaa gtggaaatgc tgcccagacc ccccaaagtg    780

accaaagagg aacacttcca gctgcaccac cagatgcact acagccagca gatcaccgtg    840

tccctggccc agggctacga gagaaccagc agccccaagc cccggttcaa gagctacgcc    900

tatacccagg ccgcctacgt gaccaccagc gaccctacca gaagcccatt ccccagccag    960

catctggaag cccccgagga caagagcttc ggcagcagcc tgatggaaag cgaagtgaac   1020

ctggacagat accagaccgc cctggaagag gtgctgagct ggctgctgag cgccgaggat   1080

acactgcagg ctcagggcga gatcagcaac gacgtggaag tcgtgaagga ccagttccac   1140

acccacgagg gctacatgat ggacctgaca gcccaccagg gcagagtggg caacatcctg   1200

cagctgggct ccaagctgat cggcaccggc aagctgagcg aggacgaaga gacagaggtg   1260

caggaacaga tgaacctgct gaacagcaga tgggagtgcc tgcgggtggc cagcatggaa   1320
```

```
aagcagagca acctgcatct gctgaagtgg cagcggctga ccgaggaaca gtgcctgttt   1380
agcgcctggc tgtccgagaa agaggacgcc gtgaacaaga tccacaccac cggcttcaag   1440
gaccagaacg agatgctgag cagcctgcag aaactggccg tgctgaaggc cgacctggaa   1500
aagaaaaagc agtccatggg caagctgtac tccctgaagc aggacctgct gtccaccctg   1560
aagaacaaga gcgtgaccca gaaaaccgag gcctggctgg acaacttcgc ccggtgctgg   1620
gacaacctgg tgcagaagct ggaaaagtcc accgcccaga tctcccaggc cgtgaccaca   1680
acacagccca gcctgaccca gaccaccgtg atggaaaccg tgacaacagt gaccacccgg   1740
gaacagatcc tcgtgaagca cgcccaggaa gaactgcccc ctccaccccc ccagaagaaa   1800
cggcagatca cagtggacag tgaagctcag atccacaccg tgcgggaaga gacaatgatg   1860
gtcatgacag aggacatgcc cctggaaatc agctacgtgc ccagcaccta cctgaccgag   1920
atcacccatg tgtcccaggc cctgctggaa gtggaacagc tgctgaacgc ccccgacctg   1980
tgcgccaagg atttcgagga cctgttcaag caggaagaga gcctgaagaa tatcaaggat   2040
agcctgcagc agagcagcgg ccggatcgac atcatccaca gcaagaaaac agccgccctg   2100
cagagcgcca cccccgtgga aagagtgaaa ctgcaggaag ccctgtccca gctggacttc   2160
cagtgggaga aagtgaacaa aatgtacaag gaccggcagg gcagattcga ccgcagcgtg   2220
gaaaagtggc ggcggttcca ctacgacatc aagatcttca accagtggct gacagaggcc   2280
gagcagttcc tgagaaagac ccagatcccc gagaactggg agcacgccaa gtacaagtgg   2340
tatctgaaag agctgcagga cggcatcggc cagagacaga cagtcgtgcg gaccctgaat   2400
gccaccggcg aggaaatcat ccagcagtcc agcaagaccg acgccagcat tctgcaggaa   2460
aagctgggca gcctgaacct gcggtggcag gaagtgtgca agcagctgtc cgaccggaag   2520
aagcggctgg aagaacagct ggaacggctg caggaactgc aggaggccac cgacgagctg   2580
gacctgaaac tgagacaggc cgaagtgatc aagggcagct ggcagccagt gggcgacctg   2640
ctgatcgact ccctgcagga ccatctggaa aaagtgaagg ccctgagagg cgagatcgcc   2700
cccctgaaag aaaacgtgtc ccacgtgaac gacctggccc ggcagctgac aacactgggc   2760
attcagctga gcccctacaa cctgagcaca ctggaagatc tgaacacccg gtggaagctg   2820
ctgcaggtgg ccgtggaaga tagagtgcgg cagctgcacg aggcccacag agattttggc   2880
cctgcctccc agcacttcct gagcaccagt gtgcagggcc cttgggagag agccatctcc   2940
cctaacaagg tgccctacta catcaaccac gagacacaga ccacctgttg ggaccacccc   3000
aagatgaccg agctgtacca gagcctggct gacctgaaca acgtgcggtt cagcgcctac   3060
cggaccgcca tgaagctgcg gagactgcag aaagctctgt gcctggatct gctgtccctg   3120
tccgccgcct gtgatgccct ggaccagcac aatctgaagc agaacgacca gcccatggat   3180
atcctgcaga tcatcaactg cctgaccacc atctacgacc ggctggaaca ggaacacaac   3240
aatctcgtga acgtgcccct gtgcgtggac atgtgcctga attggctgct gaatgtgtac   3300
gacaccggcc ggacaggccg gatcagagtg ctgtccttca agaccggcat catcagcctg   3360
tgcaaagccc acctggaaga taagtaccgg tatctgttca aacaggtggc ctctagcacc   3420
ggcttttgcg accagagaag gctgggcctg ctgctgcacg acagcatcca gatccctaga   3480
cagctgggcg aagtggccag ctttggcggc agcaacatcg agcctagcgt gcggagctgc   3540
ttccagttcg ccaacaacaa gcccgagatc gaggccgccc tgttcctgga ctggatgaga   3600
ctggaacccc agagcatggt gtggctgccc gtgctgcata gagtggccgc tgccgagaca   3660
```

gccaagcacc aggccaagtg caacatctgc aaagagtgcc ccatcatcgg cttccggtac 3720
agaagcctga agcacttcaa ctacgatatc tgccagagct gtttcttcag cggcagggtg 3780
gccaagggcc acaaaatgca ctaccccatg gtggaatact gcacccccac cacaagcggc 3840
gaggatgtgc gggatttcgc caaggtgctg aaaaacaagt tccggaccaa gcggtacttc 3900
gccaaacacc cccggatggg ctacctgcct gtgcagacag tgctggaagg cgacaacatg 3960
gaaaccgaca ccatgtgatg atgatttggg cagagcgatg gagtccttag tatcagtcat 4020
gacagatgaa gaaggagcag aataaatgtt ttacaactcc tgattcccgc atgcggccag 4080
cttatcgata ccgtcgaaat aaaagatcct tattttcatt ggatctgtgt gttggttttt 4140
tgtgtg 4146

<210> SEQ ID NO 141
<211> LENGTH: 3936
<212> TYPE: DNA
<213> ORGANISM: Homo sapiens

<400> SEQUENCE: 141
atgctgtggt gggaggaagt ggaagattgc tacgagcgcg aggacgtgca gaagaaaacc 60
ttcaccaaat gggtgaacgc ccagttcagc aagttcggca agcagcacat cgagaacctg 120
ttcagcgacc tgcaggacgg cagacggctg ctggacctgc tggaaggcct gaccggccag 180
aagctgccca aagagaaggg cagcaccaga gtgcacgccc tgaacaacgt gaacaaggcc 240
ctgcgggtgc tgcagaacaa caacgtggac ctggtgaaca tcggcagcac cgacatcgtg 300
gacggcaacc acaagctgac cctgggcctg atctggaaca tcatcctgca ctggcaggtc 360
aaaaacgtga tgaagaacat catggccggc ctgcagcaga ccaacagcga gaagatcctg 420
ctgagctggg tgcgccagag cacccggaac taccccccagg tcaacgtgat caacttcacc 480
acctcttgga gcgacggcct ggccctgaac gccctgatcc acagccaccg gcccgacctg 540
ttcgactgga acagcgtggt ctgccagcag agcgccaccc agcggctgga acacgccttc 600
aatatcgcca gataccagct gggcatcgag aagctgctgg atcccgagga cgtggacacc 660
acctaccccg acaagaaatc catcctgatg tatatcacca gcctgttcca ggtgctgccc 720
cagcaggtgt ccatcgaggc catccaggaa gtggaaatgc tgcccagacc ccccaaagtg 780
accaaagagg aacacttcca gctgcaccac cagatgcact acagccagca gatcaccgtg 840
tccctggctc agggctacga gcggaccagc agccccaagc cccggttcaa gagctacgcc 900
tacacccagg ccgcctacgt gaccaccagc gaccccacca gaagcccatt ccccagccag 960
catctggaag cccccgagga caagagcttc ggcagcagcc tgatggaaag cgaagtgaac 1020
ctggacagat accagaccgc cctggaagag gtgctgtcct ggctgctgag cgccgaggat 1080
acactgcagg cccagggcga gatcagcaac gacgtggaag tggtgaaaga ccagttccac 1140
acccacgagg gctacatgat ggacctgacc gcccaccagg gcagagtggg caacatcctg 1200
cagctgggca gcaagctgat cggcaccggc aagctgagcg aggacgaaga gacagaggtg 1260
caggaacaga tgaacctgct gaacagcaga tgggagtgcc tgcgggtggc cagcatggaa 1320
aagcagagca acctgcacat ccacaccgtg cgggaagaga caatgatggt gatgaccgag 1380
gacatgcccc tggaaatcag ctacgtgccc agcacctacc tgaccgagat cacccacgtg 1440
tcccaggctc tgctggaagt ggaacagctg ctgaacgccc ccgacctgtg cgccaaggac 1500
ttcgaggatc tgttcaagca ggaagagagc ctgaagaata tcaaggactc cctgcagcag 1560
tccagcggcc ggatcgacat catccacagc aagaaaacag ccgccctgca gtccgccacc 1620

```
cccgtggaaa gagtgaagct gcaggaagcc ctgagccagc tggacttcca gtgggagaaa   1680
gtgaacaaga tgtacaagga ccggcagggc agattcgacc gcagcgtgga aaagtggcgg   1740
cggttccact acgacatcaa gatcttcaac cagtggctga ccgaggccga gcagttcctg   1800
agaaagaccc agatccccga gaactgggag cacgccaagt acaagtggta tctgaaagaa   1860
ctgcaggatg gcatcggcca gcggcagacc gtggtgcgca cactgaatgc caccggcgag   1920
gaaatcatcc agcagagcag caagaccgac gccagcatcc tgcaggaaaa gctgggctcc   1980
ctgaacctgc ggtggcagga agtgtgcaag cagctgagcg accggaagaa gaggctggaa   2040
gaacaggccc ctggcctgac caccatcggc gccagcccta cccagaccgt gaccctggtg   2100
acacagcccg tggtgacaaa agagacagcc atctccaagc tggaaatgcc cagctccctg   2160
atgctggaac tggaaaggct gcaggaactg caggaggcca ccgacgagct ggacctgaag   2220
ctgcggcagg ccgaagtgat caagggcagc tggcagcccg tgggcgacct gctgatcgac   2280
agcctgcagg accacctgga aaaagtgaag gccctgagag gcgagatcgc ccccctgaaa   2340
gaaaacgtgt cccacgtgaa cgacctggcc cggcagctga ccaccctggg catccagctg   2400
agcccctaca acctgagcac cctggaagat ctgaacaccc ggtggaagct gctgcaggtg   2460
gccgtggaag atagagtgcg gcagctgcac gaggcccaca gagactttgg ccctgccagc   2520
cagcacttcc tgagcacctc tgtgcaggga ccctgggaga gagccatcag ccccaacaag   2580
gtgccctact acatcaacca cgagacacag accacctgtt gggaccaccc caagatgacc   2640
gagctgtacc agagcctggc cgacctgaac aatgtgcggt tcagcgccta ccggaccgcc   2700
atgaagctga ggcggctgca gaaagctctg tgcctggatc tgctgagcct gagcgccgcc   2760
tgcgacgccc tggaccagca caacctgaag cagaacgacc agcccatgga tatcctgcag   2820
atcatcaact gcctgaccac aatctacgac aggctggaac aggaacacaa caatctggtc   2880
aacgtgcccc tgtgcgtgga catgtgcctg aattggctgc tgaatgtgta cgacaccggc   2940
cggaccggca gaatccgggt gctgagcttc aagaccggca tcatcagcct gtgcaaggcc   3000
cacctggaag ataagtaccg ctacctgttc aaacaggtgg ccagctccac cggcttttgc   3060
gaccagcgga gactgggcct gctgctgcac gacagcatcc agatccccag acagctgggc   3120
gaggtggcct ccttcggcgg cagcaacatt gagcccagcg tgcggagctg cttccagttc   3180
gccaacaaca agcccgagat cgaggccgcc ctgttcctgg actggatgag actggaaccc   3240
cagagcatgg tgtggctgcc cgtgctgcat cgggtggccg ctgccgagac agccaagcac   3300
caggccaagt gcaacatctg caaagagtgc cccatcatcg gcttccggta cagaagcctg   3360
aagcacttca actacgatat ctgccagagc tgcttcttca gcggcagagt ggccaagggc   3420
cacaaaatgc actaccccat ggtggaatac tgcacccccca ccaccagcgg cgaggatgtg   3480
cgggacttcg ccaaggtgct gaaaaacaag ttccggacca agcggtactt tgccaagcac   3540
ccccggatgg gctacctgcc cgtgcagaca gtgctggaag gcgacaacat ggaaacccct   3600
gcccagatcc tgatcagcct ggaaagcgag gaacggggcg agctggaacg gatcctggcc   3660
gatctggaag aggaaaaccg gaacctgcag gccgagtacg accggctgaa gcagcagcac   3720
gagcacaagg gcctgagccc cctgcctagc ccccctgaca ccatgtgatg atgatttggg   3780
cagagcgatg gagtccttag tatcagtcat gacagatgaa gaaggagcag aataaatgtt   3840
ttacaactcc tgattcccgc atgcggccag cttatcgata ccgtcgaaat aaaagatcct   3900
tattttcatt ggatctgtgt gttggttttt tgtgtg                              3936
```

<210> SEQ ID NO 142
<211> LENGTH: 3957
<212> TYPE: DNA
<213> ORGANISM: Homo sapiens

<400> SEQUENCE: 142

```
atgctgtggt gggaggaagt ggaagattgc tacgagcgcg aggacgtgca gaagaaaacc     60
ttcaccaaat gggtgaacgc ccagttcagc aagttcggca agcagcacat cgagaacctg    120
ttcagcgacc tgcaggacgg cagacggctg ctggacctgc tggaaggcct gaccggccag    180
aagctgccca aagagaaggg cagcaccaga gtgcacgccc tgaacaacgt gaacaaggcc    240
ctgcgggtgc tgcagaacaa caacgtggac ctggtgaaca tcggcagcac cgacatcgtg    300
gacggcaacc acaagctgac cctgggcctg atctggaaca tcatcctgca ctggcaggtc    360
aaaaacgtga tgaagaacat catggccggc ctgcagcaga ccaacagcga gaagatcctg    420
ctgagctggg tgcgccagag cacccggaac taccccccagg tcaacgtgat caacttcacc   480
acctcttgga gcgacggcct ggccctgaac gccctgatcc acagccaccg gcccgacctg    540
ttcgactgga acagcgtggt ctgccagcag agcgccaccc agcggctgga acacgccttc    600
aatatcgcca gataccagct gggcatcgag aagctgctgg atcccgagga cgtggacacc    660
acctaccccg acaagaaatc catcctgatg tatatcacca gcctgttcca ggtgctgccc    720
cagcaggtgt ccatcgaggc catccaggaa gtggaaatgc tgcccagacc ccccaaagtg    780
accaaagagg aacacttcca gctgcaccac cagatgcact acagccagca gatcaccgtg    840
tccctggctc agggctacga gcggaccagc agccccaagc cccggttcaa gagctacgcc    900
tacacccagg ccgcctacgt gaccaccagc gaccccacca gaagcccatt ccccagccag    960
catctggaag cccccgagga caagagcttc ggcagcagcc tgatggaaag cgaagtgaac   1020
ctggacagat accagaccgc cctggaagag gtgctgtcct ggctgctgag cgccgaggat   1080
acactgcagg cccagggcga gatcagcaac gacgtggaag tggtgaaaga ccagttccac   1140
acccacgagg gctacatgat ggacctgacc gcccaccagg gcagagtggg caacatcctg   1200
cagctgggca gcaagctgat cggcaccggc aagctgagcg aggacgaaga gacagaggtg   1260
caggaacaga tgaacctgct gaacagcaga tgggagtgcc tgcgggtggc cagcatggaa   1320
aagcagagca acctgcaccg ggtgctgatc cacaccgtgc gggaagagac aatgatggtg   1380
atgaccgagg acatgcccct ggaaatcagc tacgtgccca gcacctacct gaccgagatc   1440
acccacgtgt cccaggctct gctggaagtg gaacagctgc tgaacgcccc cgacctgtgc   1500
gccaaggact tcgaggatct gttcaagcag gaagagagcc tgaagaatat caaggactcc   1560
ctgcagcagt ccagcggccg gatcgacatc atccacagca agaaaaacagc cgccctgcag  1620
tccgccaccc ccgtggaaag agtgaagctg caggaagccc tgagccagct ggacttccag   1680
tgggagaaag tgaacaagat gtacaaggac cggcagggca gattcgaccg cagcgtggaa   1740
aagtggcggc ggttccacta cgacatcaag atcttcaacc agtggctgac cgaggccgag   1800
cagttcctga gaaagaccca gatccccgag aactgggagc acgccaagta caagtggtat   1860
ctgaaagaac tgcaggatgg catcggccag cggcagaccg tggtgcgcac actgaatgcc   1920
accggcgagg aaatcatcca gcagagcagc aagaccgacg ccagcatcct gcaggaaaag   1980
ctgggctccc tgaacctgcg gtggcaggaa gtgtgcaagc agctgagcga ccggaagaag   2040
aggctggaag aacagaagaa cgacctggcc cctggcctga ccaccatcgg cgccagccct   2100
acccagaccg tgaccctggt gacacagccc gtggtgacaa aagagacagc catctccaag   2160
```

```
ctggaaatgc ccagctccct gatgctggaa gtggaaaggc tgcaggaact gcaggaggcc   2220

accgacgagc tggacctgaa gctgcggcag gccgaagtga tcaagggcag ctggcagccc   2280

gtgggcgacc tgctgatcga cagcctgcag gaccacctgg aaaaagtgaa ggccctgaga   2340

ggcgagatcg ccccctgaa agaaaacgtg tcccacgtga acgacctggc ccggcagctg   2400

accaccctgg gcatccagct gagcccctac aacctgagca ccctggaaga tctgaacacc   2460

cggtggaagc tgctgcaggt ggccgtggaa gatagagtgc ggcagctgca cgaggcccac   2520

agagactttg gccctgccag ccagcacttc ctgagcacct ctgtgcaggg accctgggag   2580

agagccatca gccccaacaa ggtgccctac tacatcaacc acgagacaca gaccacctgt   2640

tgggaccacc ccaagatgac cgagctgtac cagagcctgg ccgacctgaa caatgtgcgg   2700

ttcagcgcct accggaccgc catgaagctg aggcggctgc agaaagctct gtgcctggat   2760

ctgctgagcc tgagcgccgc ctgcgacgcc ctggaccagc acaacctgaa gcagaacgac   2820

cagcccatgg atatcctgca gatcatcaac tgcctgacca caatctacga caggctggaa   2880

caggaacaca acaatctggt caacgtgccc ctgtgcgtgg acatgtgcct gaattggctg   2940

ctgaatgtgt acgacaccgg ccggaccggc agaatccggg tgctgagctt caagaccggc   3000

atcatcagcc tgtgcaaggc ccacctggaa gataagtacc gctacctgtt caaacaggtg   3060

gccagctcca ccggcttttg cgaccagcgg agactgggcc tgctgctgca cgacagcatc   3120

cagatcccca gacagctggg cgaggtggcc tccttcggcg gcagcaacat tgagcccagc   3180

gtgcggagct gcttccagtt cgccaacaac aagcccgaga tcgaggccgc cctgttcctg   3240

gactggatga gactggaacc ccagagcatg gtgtggctgc ccgtgctgca tcgggtggcc   3300

gctgccgaga cagccaagca ccaggccaag tgcaacatct gcaaagagtg ccccatcatc   3360

ggcttccggt acagaagcct gaagcacttc aactacgata tctgccagag ctgcttcttc   3420

agcggcagag tggccaaggg ccacaaaatg cactacccca tggtggaata ctgcaccccc   3480

accaccagcg gcgaggatgt gcgggacttc gccaaggtgc tgaaaaacaa gttccggacc   3540

aagcggtact ttgccaagca cccccggatg ggctacctgc ccgtgcagac agtgctggaa   3600

ggcgacaaca tggaaacccc tgcccagatc ctgatcagcc tggaaagcga ggaacggggc   3660

gagctggaac ggatcctggc cgatctggaa gaggaaaacc ggaacctgca ggccgagtac   3720

gaccggctga agcagcagca cgagcacaag ggcctgagcc ccctgcctag ccccccctgac   3780

accatgtgat gatgatttgg gcagagcgat ggagtcctta gtatcagtca tgacagatga   3840

agaaggagca gaataaatgt tttacaactc ctgattcccg catgcggcca gcttatcgat   3900

accgtcgaaa taaaagatcc ttattttcat tggatctgtg tgttggtttt ttgtgtg      3957
```

<210> SEQ ID NO 143
<211> LENGTH: 3918
<212> TYPE: DNA
<213> ORGANISM: Homo sapiens

<400> SEQUENCE: 143

```
atgctgtggt gggaggaagt ggaagattgc tacgagcgcg aggacgtgca gaagaaaacc     60

ttcaccaaat gggtgaacgc ccagttcagc aagttcggca agcagcacat cgagaacctg    120

ttcagcgacc tgcaggacgg cagacggctg ctggacctgc tggaaggcct gaccggccag    180

aagctgccca aagagaaggg cagcaccaga gtgcacgccc tgaacaacgt gaacaaggcc    240

ctgcgggtgc tgcagaacaa caacgtggac ctggtgaaca tcggcagcac cgacatcgtg    300
```

```
gacggcaacc acaagctgac cctgggcctg atctggaaca tcatcctgca ctggcaggtc    360
aaaaacgtga tgaagaacat catggccggc ctgcagcaga ccaacagcga gaagatcctg    420
ctgagctggg tgcgccagag cacccggaac tacccccagg tcaacgtgat caacttcacc    480
acctcttgga gcgacggcct ggccctgaac gccctgatcc acagccaccg gcccgacctg    540
ttcgactgga acagcgtggt ctgccagcag agcgccaccc agcggctgga acacgccttc    600
aatatcgcca gataccagct gggcatcgag aagctgctgg atcccgagga cgtggacacc    660
acctaccccg acaagaaatc catcctgatg tatatcacca gcctgttcca ggtgctgccc    720
cagcaggtgt ccatcgaggc catccaggaa gtggaaatgc tgcccagacc ccccaaagtg    780
accaaagagg aacacttcca gctgcaccac cagatgcact acagccagca gatcaccgtg    840
tccctggctc agggctacga gcggaccagc agccccaagc cccggttcaa gagctacgcc    900
tacacccagg ccgcctacgt gaccaccagc gaccccacca gaagcccatt ccccagccag    960
catctggaag cccccgagga caagagcttc ggcagcagcc tgatggaaag cgaagtgaac   1020
ctggacagat accagaccgc cctggaagag gtgctgtcct ggctgctgag cgccgaggat   1080
acactgcagg cccagggcga gatcagcaac gacgtggaag tggtgaaaga ccagttccac   1140
acccacgagg gctacatgat ggacctgacc gcccaccagg gcagagtggg caacatcctg   1200
cagctgggca gcaagctgat cggcaccggc aagctgagcg aggacgaaga gacagaggtg   1260
caggaacaga tgaacctgct gaacagcaga tgggagtgcc tgcgggtggc cagcatggaa   1320
aagcagagca acctgcacag ctacgtgccc agcacctacc tgaccgagat cacccacgtg   1380
tcccaggctc tgctggaagt ggaacagctg ctgaacgccc ccgacctgtg cgccaaggac   1440
ttcgaggatc tgttcaagca ggaagagagc ctgaagaata tcaaggactc cctgcagcag   1500
tccagcggcc ggatcgacat catccacagc aagaaaacag ccgccctgca gtccgccacc   1560
cccgtggaaa gagtgaagct gcaggaagcc ctgagccagc tggacttcca gtgggagaaa   1620
gtgaacaaga tgtacaagga ccggcagggc agattcgacc gcagcgtgga aaagtggcgg   1680
cggttccact acgacatcaa gatcttcaac cagtggctga ccgaggccga gcagttcctg   1740
agaaagaccc agatccccga gaactgggag cacgccaagt acaagtggta tctgaaagaa   1800
ctgcaggatg gcatcggcca gcggcagacc gtggtgcgca cactgaatgc caccggcgag   1860
gaaatcatcc agcagagcag caagaccgac gccagcatcc tgcaggaaaa gctgggctcc   1920
ctgaacctgc ggtggcagga agtgtgcaag cagctgagcg accggaagaa gaggctggaa   1980
gaacagctgg aaggactgga aaagctgtac caggaaccca gagagctgcc ccccgaggaa   2040
cgggcccaga acgtgacccg gctgctgcgg aaacaggccg aagaggtgaa caccgagtgg   2100
gagaagctga acctgcactc cgccgactgg cagcggaaga tcgacgagac actggaaagg   2160
ctgcaggaac tgcaggaggc caccgacgag ctggacctga agctgcggca ggccgaagtg   2220
atcaagggca gctggcagcc cgtgggcgac ctgctgatcg acagcctgca ggaccacctg   2280
gaaaaagtga aggccctgag aggcgagatc gccccccctga aagaaaacgt gtcccacgtg   2340
aacgacctgg cccggcagct gaccaccctg ggcatccagc tgagccccta caacctgagc   2400
accctggaag atctgaacac ccggtggaag ctgctgcagg tggccgtgga agatagagtg   2460
cggcagctgc acgaggccca cagagacttt ggccctgcca gccagcactt cctgagcacc   2520
tctgtgcagg gaccctggga gagagccatc agccccaaca aggtgcccta ctacatcaac   2580
cacgagacac agaccacctg ttgggaccac cccaagatga ccgagctgta ccagagcctg   2640
gccgacctga acaatgtgcg gttcagcgcc taccggaccg ccatgaagct gaggcggctg   2700
```

```
cagaaagctc tgtgcctgga tctgctgagc ctgagcgccg cctgcgacgc cctggaccag   2760

cacaacctga agcagaacga ccagcccatg gatatcctgc agatcatcaa ctgcctgacc   2820

acaatctacg acaggctgga acaggaacac aacaatctgg tcaacgtgcc cctgtgcgtg   2880

gacatgtgcc tgaattggct gctgaatgtg tacgacaccg gccggaccgg cagaatccgg   2940

gtgctgagct tcaagaccgg catcatcagc ctgtgcaagg cccacctgga agataagtac   3000

cgctacctgt tcaaacaggt ggccagctcc accggctttt gcgaccagcg gagactgggc   3060

ctgctgctgc acgacagcat ccagatcccc agacagctgg gcgaggtggc ctccttcggc   3120

ggcagcaaca ttgagcccag cgtgcggagc tgcttccagt tcgccaacaa caagcccgag   3180

atcgaggccg ccctgttcct ggactggatg agactggaac cccagagcat ggtgtggctg   3240

cccgtgctgc atcgggtggc cgctgccgag acagccaagc accaggccaa gtgcaacatc   3300

tgcaaagagt gccccatcat cggcttccgg tacagaagcc tgaagcactt caactacgat   3360

atctgccaga gctgcttctt cagcggcaga gtggccaagg gccacaaaat gcactacccc   3420

atggtggaat actgcacccc caccaccagc ggcgaggatg tgcgggactt cgccaaggtg   3480

ctgaaaaaca agttccggac caagcggtac tttgccaagc acccccggat gggctacctg   3540

cccgtgcaga cagtgctgga aggcgacaac atggaaaccc ctgcccagat cctgatcagc   3600

ctggaaagcg aggaacgggg cgagctggaa cggatcctgg ccgatctgga agaggaaaac   3660

cggaacctgc aggccgagta cgaccggctg aagcagcagc acgagcacaa gggcctgagc   3720

cccctgccta gcccccctga caccatgtga tgatgatttg ggcagagcga tggagtcctt   3780

agtatcagtc atgacagatg aagaaggagc agaataaatg ttttacaact cctgattccc   3840

gcatgcggcc agcttatcga taccgtcgaa ataaaagatc cttattttca ttggatctgt   3900

gtgttggttt tttgtgtg                                                 3918
```

```
<210> SEQ ID NO 144
<211> LENGTH: 4244
<212> TYPE: DNA
<213> ORGANISM: Homo sapiens

<400> SEQUENCE: 144

atgctgtggt gggaggaagt ggaagattgc tacgagcgcg aggacgtgca gaagaaaacc     60

ttcaccaaat gggtgaacgc ccagttcagc aagttcggca agcagcacat cgagaacctg    120

ttcagcgacc tgcaggacgg cagacggctg ctggacctgc tggaaggcct gaccggccag    180

aagctgccca aagagaaggg cagcaccaga gtgcacgccc tgaacaacgt gaacaaggcc    240

ctgcgggtgc tgcagaacaa caacgtggac ctggtgaaca tcggcagcac cgacatcgtg    300

gacggcaacc acaagctgac cctgggcctg atctggaaca tcatcctgca ctggcaggtc    360

aaaaacgtga tgaagaacat catggccggc ctgcagcaga ccaacagcga gaagatcctg    420

ctgagctggg tgcgccagag cacccggaac tacccccagg tcaacgtgat caacttcacc    480

acctcttgga gcgacggcct ggccctgaac gccctgatcc acagccaccg gcccgacctg    540

ttcgactgga acagcgtggt ctgccagcag agcgccaccc agcggctgga acacgccttc    600

aatatcgcca gataccagct gggcatcgag aagctgctgg atcccgagga cgtggacacc    660

acctaccccg acaagaaatc catcctgatg tatatcacca gcctgttcca ggtgctgccc    720

cagcaggtgt ccatcgaggc catccaggaa gtggaaatgc tgcccagacc ccccaaagtg    780

accaaagagg aacacttcca gctgcaccac cagatgcact acagccagca gatcaccgtg    840
```

```
tccctggccc agggctacga gagaaccagc agccccaagc cccggttcaa gagctacgcc    900
tatacccagg ccgcctacgt gaccaccagc gaccctacca gaagcccatt ccccagccag    960
catctggaag cccccgagga caagagcttc ggcagcagcc tgatggaaag cgaagtgaac   1020
ctggacagat accagaccgc cctggaagag gtgctgagct ggctgctgag cgccgaggat   1080
acactgcagg ctcagggcga gatcagcaac gacgtggaag tcgtgaagga ccagttccac   1140
acccacgagg gctacatgat ggacctgaca gcccaccagg gcagagtggg caacatcctg   1200
cagctgggct ccaagctgat cggcaccggc aagctgagcg aggacgaaga gacagaggtg   1260
caggaacaga tgaacctgct gaacagcaga tgggagtgcc tgcgggtggc cagcatggaa   1320
aagcagagca acctgcatct gctgaagtgg cagcggctga ccgaggaaca gtgcctgttt   1380
agcgcctggc tgtccgagaa agaggacgcc gtgaacaaga tccacaccac cggcttcaag   1440
gaccagaacg agatgctgag cagcctgcag aaactggccg tgctgaaggc cgacctggaa   1500
aagaaaaagc agtccatggg caagctgtac tccctgaagc aggacctgct gtccaccctg   1560
aagaacaaga gcgtgaccca gaaaaccgag gcctggctgg acaacttcgc ccggtgctgg   1620
gacaacctgg tgcagaagct ggaaaagtcc accgcccaga tctcccaggc cgtgaccaca   1680
acacagccca gcctgaccca gaccaccgtg atggaaaccg tgacaacagt gaccacccgg   1740
gaacagatcc tcgtgaagca cgcccaggaa gaactgcccc ctccaccccc ccagaagaaa   1800
cggcagatca cagtggacat ccacaccgtg cgggaagaga caatgatggt catgacagag   1860
gacatgcccc tggaaatcag ctacgtgccc agcacctacc tgaccgagat cacccatgtg   1920
tcccaggccc tgctggaagt ggaacagctg ctgaacgccc ccgacctgtg cgccaaggat   1980
ttcgaggacc tgttcaagca ggaagagagc ctgaagaata tcaaggatag cctgcagcag   2040
agcagcggcc ggatcgacat catccacagc aagaaaacag ccgccctgca gagcgccacc   2100
cccgtggaaa gagtgaaact gcaggaagcc ctgtcccagc tggacttcca gtgggagaaa   2160
gtgaacaaaa tgtacaagga ccggcagggc agattcgacc gcagcgtgga aaagtggcgg   2220
cggttccact acgacatcaa gatcttcaac cagtggctga cagaggccga gcagttcctg   2280
agaaagaccc agatccccga gaactgggag cacgccaagt acaagtggta tctgaaagag   2340
ctgcaggacg gcatcggcca gagacagaca gtcgtgcgga ccctgaatgc caccggcgag   2400
gaaatcatcc agcagtccag caagaccgac gccagcattc tgcaggaaaa gctgggcagc   2460
ctgaacctgc ggtggcagga agtgtgcaag cagctgtccg accggaagaa gcggctggaa   2520
gaacagctgg aacggctgca ggaactgcag gaggccaccg acgagctgga cctgaaactg   2580
agacaggccg aagtgatcaa gggcagctgg cagccagtgg gcgacctgct gatcgactcc   2640
ctgcaggacc atctggaaaa agtgaaggcc ctgagaggcg agatcgcccc cctgaaagaa   2700
aacgtgtccc acgtgaacga cctggcccgg cagctgacaa cactgggcat tcagctgagc   2760
ccctacaacc tgagcacact ggaagatctg aacacccggt ggaagctgct gcaggtggcc   2820
gtggaagata gagtgcggca gctgcacgag gcccacagag attttggccc tgcctcccag   2880
cacttcctga gcaccagtgt gcagggccct tgggagagag ccatctcccc taacaaggtg   2940
ccctactaca tcaaccacga gacacagacc acctgttggg accaccccaa gatgaccgag   3000
ctgtaccaga gcctggctga cctgaacaac gtgcggttca gcgcctaccg gaccgccatg   3060
aagctgcgga gactgcagaa agctctgtgc ctggatctgc tgtccctgtc cgccgcctgt   3120
gatgccctgg accagcacaa tctgaagcag aacgaccagc ccatggatat cctgcagatc   3180
atcaactgcc tgaccaccat ctacgaccgg ctggaacagg aacacaacaa tctcgtgaac   3240
```

```
gtgcccctgt gcgtggacat gtgcctgaat tggctgctga atgtgtacga caccggccgg   3300
acaggccgga tcagagtgct gtccttcaag accggcatca tcagcctgtg caaagcccac   3360
ctggaagata agtaccggta tctgttcaaa caggtggcct ctagcaccgg cttttgcgac   3420
cagagaaggc tgggcctgct gctgcacgac agcatccaga tccctagaca gctgggcgaa   3480
gtggccagct ttggcggcag caacatcgag cctagcgtgc ggagctgctt ccagttcgcc   3540
aacaacaagc ccgagatcga ggccgccctg ttcctggact ggatgagact ggaaccccag   3600
agcatggtgt ggctgcccgt gctgcataga gtggccgctg ccgagacagc caagcaccag   3660
gccaagtgca acatctgcaa agagtgcccc atcatcggct tccggtacag aagcctgaag   3720
cacttcaact acgatatctg ccagagctgt ttcttcagcg gcagggtggc caagggccac   3780
aaaatgcact accccatggt ggaatactgc acccccacca caagcggcga ggatgtgcgg   3840
gatttcgcca aggtgctgaa aaacaagttc cggaccaagc ggtacttcgc caaacacccc   3900
cggatgggct acctgcctgt gcagacagtg ctggaaggcg acaacatgga aacccctgcc   3960
cagatcctga tcagcctgga atccgaggaa cggggcgagc tggaacggat cctggccgat   4020
ctggaagagg aaaaccggaa cctgcaggcc gagtacgacc ggctgaagca gcagcacgag   4080
cacaagggcc tgagcccccct gcctagcccc cctgacacca tgtgatgatg atttgggcag   4140
agcgatggag tccttagtat cagtcatgac agatgaagaa ggagcagaat aaatgtttta   4200
caactcctga ttcccgcatg cggccagctt atcgataccg tcga                  4244
```

<210> SEQ ID NO 145
<211> LENGTH: 4266
<212> TYPE: DNA
<213> ORGANISM: Homo sapiens

<400> SEQUENCE: 145

```
atgctgtggt gggaggaagt ggaagattgc tacgagcgcg aggacgtgca gaagaaaacc     60
ttcaccaaat gggtgaacgc ccagttcagc aagttcggca agcagcacat cgagaacctg    120
ttcagcgacc tgcaggacgg cagacggctg ctggacctgc tggaaggcct gaccggccag    180
aagctgccca aagagaaggg cagcaccaga gtgcacgccc tgaacaacgt gaacaaggcc    240
ctgcgggtgc tgcagaacaa caacgtggac ctggtgaaca tcggcagcac cgacatcgtg    300
gacggcaacc acaagctgac cctgggcctg atctggaaca tcatcctgca ctggcaggtc    360
aaaaacgtga tgaagaacat catggccggc ctgcagcaga ccaacagcga gaagatcctg    420
ctgagctggg tgcgccagag cacccggaac tacccccagg tcaacgtgat caacttcacc    480
acctcttgga gcgacggcct ggccctgaac gccctgatcc acagccaccg gcccgacctg    540
ttcgactgga acagcgtggt ctgccagcag agcgccaccc agcggctgga acacgccttc    600
aatatcgcca gataccagct gggcatcgag aagctgctgg atcccgagga cgtggacacc    660
acctaccccg acaagaaatc catcctgatg tatatcacca gcctgttcca ggtgctgccc    720
cagcaggtgt ccatcgaggc catccaggaa gtggaaatgc tgcccagacc ccccaaagtg    780
accaaagagg aacacttcca gctgcaccac cagatgcact acagccagca gatcaccgtg    840
tccctggctc agggctacga gcggaccagc agccccaagc cccggttcaa gagctacgcc    900
tacacccagg ccgcctacgt gaccaccagc gaccccacca gaagcccatt ccccagccag    960
catctggaag cccccgagga caagagcttc ggcagcagcc tgatggaaag cgaagtgaac   1020
ctggacagat accagaccgc cctggaagag gtgctgtcct ggctgctgag cgccgaggat   1080
```

```
acactgcagg cccagggcga gatcagcaac gacgtggaag tggtgaaaga ccagttccac   1140
acccacgagg gctacatgat ggacctgacc gcccaccagg gcagagtggg caacatcctg   1200
cagctgggca gcaagctgat cggcaccggc aagctgagcg aggacgaaga gacagaggtg   1260
caggaacaga tgaacctgct gaacagcaga tgggagtgcc tgcgggtggc cagcatggaa   1320
aagcagagca acctgcacat ccacaccgtg cgggaagaga caatgatggt gatgaccgag   1380
gacatgcccc tggaaatcag ctacgtgccc agcacctacc tgaccgagat cacccacgtg   1440
tcccaggctc tgctggaagt ggaacagctg ctgaacgccc ccgacctgtg cgccaaggac   1500
ttcgaggatc tgttcaagca ggaagagagc ctgaagaata tcaaggactc cctgcagcag   1560
tccagcggcc ggatcgacat catccacagc aagaaaacag ccgccctgca gtccgccacc   1620
cccgtggaaa gagtgaagct gcaggaagcc ctgagccagc tggacttcca gtgggagaaa   1680
gtgaacaaga tgtacaagga ccggcagggc agattcgacc gcagcgtgga aaagtggcgg   1740
cggttccact acgacatcaa gatcttcaac cagtggctga ccgaggccga gcagttcctg   1800
agaaagaccc agatccccga gaactgggag cacgccaagt acaagtggta tctgaaagaa   1860
ctgcaggatg gcatcggcca gcggcagacc gtggtgcgca cactgaatgc caccggcgag   1920
gaaatcatcc agcagagcag caagaccgac gccagcatcc tgcaggaaaa gctgggctcc   1980
ctgaacctgc ggtggcagga agtgtgcaag cagctgagcg accggaagaa gaggctggaa   2040
gaacaggccc ctggcctgac caccatcggc gccagcccta cccagaccgt gaccctggtg   2100
acacagcccg tggtgacaaa agagacagcc atctccaagc tggaaatgcc cagctccctg   2160
atgctggaag tacctgctct ggcagatttc aaccgggctt ggacagaact taccgactgg   2220
ctttctctgc ttgatcaagt tataaaatca cagagggtga tggtgggtga ccttgaggat   2280
atcaacgaga tgatcatcaa gcagaaggca acaatgcagg atttggaaca gaggcgtccc   2340
cagttggaag aactcattac cgctgcccaa aatttgaaaa acaagaccag caatcaagag   2400
gctagaacaa tcattacgga tcgaattgaa agaattcaga atcagtggga tgaagtacaa   2460
gaacaccttc agaaccggag gcaacagttg aatgaaatgc tggaaaggct gcaggaactg   2520
caggaggcca ccgacgagct ggacctgaag ctgcggcagg ccgaagtgat caagggcagc   2580
tggcagcccg tgggcgacct gctgatcgac agcctgcagg accacctgga aaaagtgaag   2640
gccctgagag gcgagatcgc ccccctgaaa gaaaacgtgt cccacgtgaa cgacctggcc   2700
cggcagctga ccaccctggg catccagctg agcccctaca acctgagcac cctggaagat   2760
ctgaacaccc ggtggaagct gctgcaggtg gccgtggaag atagagtgcg gcagctgcac   2820
gaggcccaca gagactttgg ccctgccagc cagcacttcc tgagcacctc tgtgcaggga   2880
ccctgggaga gagccatcag ccccaacaag gtgccctact acatcaacca cgagacacag   2940
accacctgtt gggaccaccc caagatgacc gagctgtacc agagcctggc cgacctgaac   3000
aatgtgcggt tcagcgccta ccggaccgcc atgaagctga ggcggctgca gaaagctctg   3060
tgcctggatc tgctgagcct gagcgccgcc tgcgacgccc tggaccagca caacctgaag   3120
cagaacgacc agcccatgga tatcctgcag atcatcaact gcctgaccac aatctacgac   3180
aggctggaac aggaacacaa caatctggtc aacgtgcccc tgtgcgtgga catgtgcctg   3240
aattggctgc tgaatgtgta cgacaccggc cggaccggca gaatccgggt gctgagcttc   3300
aagaccggca tcatcagcct gtgcaaggcc cacctggaag ataagtaccg ctacctgttc   3360
aaacaggtgg ccagctccac cggcttttgc gaccagcgga gactgggcct gctgctgcac   3420
gacagcatcc agatccccag acagctgggc gaggtggcct ccttcggcgg cagcaacatt   3480
```

```
gagcccagcg tgcggagctg cttccagttc gccaacaaca agcccgagat cgaggccgcc   3540

ctgttcctgg actggatgag actggaaccc cagagcatgg tgtggctgcc cgtgctgcat   3600

cgggtggccg ctgccgagac agccaagcac caggccaagt gcaacatctg caaagagtgc   3660

cccatcatcg gcttccggta cagaagcctg aagcacttca actacgatat ctgccagagc   3720

tgcttcttca gcggcagagt ggccaagggc cacaaaatgc actaccccat ggtggaatac   3780

tgcaccccca ccaccagcgg cgaggatgtg cgggacttcg ccaaggtgct gaaaaacaag   3840

ttccggacca agcggtactt tgccaagcac ccccggatgg gctacctgcc cgtgcagaca   3900

gtgctggaag gcgacaacat ggaaacccct gcccagatcc tgatcagcct ggaaagcgag   3960

gaacggggcg agctggaacg gatcctggcc gatctggaag aggaaaaccg gaacctgcag   4020

gccgagtacg accggctgaa gcagcagcac gagcacaagg gcctgagccc cctgcctagc   4080

ccccctgaca ccatgtgatg atgatttggg cagagcgatg gagtccttag tatcagtcat   4140

gacagatgaa gaaggagcag aataaatgtt ttacaactcc tgattcccgc atgcggccag   4200

cttatcgata ccgtcgaaat aaaagatcct tattttcatt ggatctgtgt gttggttttt   4260

tgtgtg                                                              4266
```

<210> SEQ ID NO 146
<211> LENGTH: 4320
<212> TYPE: DNA
<213> ORGANISM: Homo sapiens

<400> SEQUENCE: 146

```
atgctgtggt gggaggaagt ggaagattgc tacgagcgcg aggacgtgca gaagaaaacc     60

ttcaccaaat gggtcaacgc ccagttcagc aagttcggca agcagcacat cgagaacctg    120

ttcagcgacc tgcaggacgg cagacggctg ctggatctgc tggaaggcct gaccggacag    180

aagctgccca aagagaaggg cagcaccaga gtgcacgccc tgaacaacgt gaacaaggcc    240

ctgcgggtgc tgcagaacaa caacgtggac ctcgtgaaca tcggcagcac cgacatcgtg    300

gacggcaacc acaagctgac cctgggcctg atctggaaca tcatcctgca ctggcaagtg    360

aagaacgtga tgaagaacat catggccggc ctgcagcaga ccaacagcga gaagatcctg    420

ctgagctggg tgcgccagag caccagaaac taccccaag tgaacgtgat caacttcacc     480

acctcttgga gcgacggcct ggccctgaat gccctgatcc acagccacag acccgacctg    540

ttcgactgga acagcgtcgt gtgtcagcag agcgccaccc agaggctgga acacgccttc    600

aatatcgcca gataccagct gggcatcgag aagctgctgg accccgagga tgtggacacc    660

acctaccccg acaagaaatc catcctgatg tatatcacca gcctgttcca ggtgctgcct    720

cagcaggtgt ccatcgaggc catccaggaa gtggaaatgc tgcccagacc ccccaaagtg    780

accaaagagg aacacttcca gctgcaccac cagatgcact actctcagca gatcaccgtg    840

tccctggccc agggctacga gagaaccagc agccccaagc cccggttcaa gagctacgcc    900

tatacccagg ccgcctacgt gaccaccagc gaccctacca gaagcccatt ccccagccag    960

catctggaag cccccgagga caagagcttc ggcagcagcc tgatggaaag cgaagtgaac   1020

ctggatagat accagaccgc cctggaagag gtgctgtcct ggctgctgag cgccgaggat   1080

acactgcagg ctcagggcga gatcagcaac gacgtggaag tcgtgaagga ccagttccac   1140

acccacgagg gctacatgat ggacctgaca gcccaccagg gcagagtggg caacattctg   1200

cagctgggct ccaagctgat cggcaccggc aagctgagcg aggacgaaga gacagaggtg   1260
```

-continued

```
caggaacaga tgaacctgct gaacagcaga tgggagtgcc tgagagtggc cagcatggaa   1320
aagcagagca acctgcaccg ggtgctgatg gatctgcaga accagaagct gaaagagctg   1380
aacgactggc tgaccaagac cgaggaacgg acccggaaga tggaagagga acccctggga   1440
ccagacctgg aagatctgaa aagacaggtg cagcagcaca aagtgctgca ggaagatctg   1500
gaacaggaac aggtgcgcgt gaacagcctg acccacatgg tcgtggtggt ggacgagagc   1560
agcggcgatc atgccacagc cgctctggaa gaacagctga aggtgctggg cgacagatgg   1620
gccaacatct gccggtggac cgaggataga tgggtgctgc tgcaggacat cctgctgaag   1680
tggcagcggc tgacagagga acagtgcctg ttctccgcct ggctgtccga gaaagaggac   1740
gccgtgaaca aaatccacac caccggcttc aaggaccaga acgagatgct gagcagcctg   1800
cagaaactgg ccgtgctgaa ggccgacctg gaaaagaaaa agcagtccat gggcaagctg   1860
tactccctga agcaggacct gctgtccacc ctgaagaaca agagcgtgac ccagaaaacc   1920
gaggcctggc tggacaactt cgcccggtgc tgggacaacc tggtgcagaa gctggaaaag   1980
tccaccgccc agatctccca ggccattcac accgtgcggg aagagacaat gatggtcatg   2040
actgaggaca tgcccctgga aatcagctac gtgccctcca cctacctgac cgagatcacc   2100
catgtgtccc aggccctgct ggaagtggaa cagctgctga acgcccccga tctgtgcgcc   2160
aaggacttcg aggatctgtt caagcaggaa gagagcctga agaatatcaa ggactctctg   2220
cagcagtcca gcggcagaat cgacatcatc cacagcaaga aaacagccgc cctgcagtcc   2280
gccacccccg tggaaagagt gaaactgcag gaagccctgt cccagctgga cttccagtgg   2340
gagaaagtga acaagatgta caaggaccgg cagggcagat tcgaccgcag cgtggaaaag   2400
tggcggcggt tccactacga catcaagatc ttcaaccagt ggctgaccga ggccgaacag   2460
ttcctgagaa agacccagat ccccgagaac tgggagcacg ccaagtacaa gtggtatctg   2520
aaagaactgc aggatggcat cggccagaga cagaccgtcg tgcggacact gaatgccacc   2580
ggcgaggaaa tcatccagca gagcagcaag accgacgcca gcatcctgca ggaaaagctg   2640
ggcagcctga acctgagatg gcaggaagtg tgcaagcagc tgtccgaccg gaagaagcgg   2700
ctggaagaac agctggaacg gctgcaggaa ctgcaggagg ccaccgacga gctggacctg   2760
aaactgagac aggccgaagt gatcaagggc agctggcagc cagtgggcga cctgctgatc   2820
gattctctgc aggaccacct ggaaaaagtg aaggccctga gaggcgagat cgccccccctg   2880
aaagaaaacg tgtcccacgt gaacgacctg gcccggcagc tgacaacact gggcatccag   2940
ctgagcccct acaacctgag cacactggaa gatctgaaca cccggtggaa gctgctgcag   3000
gtggccgtgg aagatagagt gcggcagctg cacgaggccc acagagattt tggccctgcc   3060
tcccagcact tcctgagcac ctcagtgcag ggcccttggg agagagccat ctcccctaac   3120
aaggtgccct actacatcaa ccacgagaca cagaccacct gttgggacca ccccaagatg   3180
accgagctgt accagagcct ggccgacctg aacaatgtgc ggttcagcgc ctaccggacc   3240
gccatgaagc tgcggagact gcagaaagct ctgtgcctgg atctgctgtc cctgagcgcc   3300
gcctgtgatg ccctggacca gcacaatctg aagcagaacg accagcccat ggatatcctg   3360
cagatcatta actgcctgac caccatctac gaccggctgg aacaggaaca caacaacctc   3420
gtgaacgtgc ccctgtgcgt ggacatgtgc ctgaattggc tgctgaatgt gtacgacacc   3480
ggccggacag gccggatcag agtgctgagc ttcaagaccg gcatcatcag cctgtgcaaa   3540
gcccatctgg aagataagta ccgctacctg ttcaaacagg tggccagctc taccggcttc   3600
tgcgatcaga gaaggctggg cctgctgctg catgactcca tccagatccc cagacagctg   3660
```

```
ggcgaggtgg cctctttcgg cggcagcaat atcgagccta gcgtgcggag ctgcttccag   3720

ttcgccaaca acaagcccga gatcgaggcc gccctgtttc tggactggat gagactggaa   3780

ccccagagca tggtgtggct gcccgtgctg catagagtgg ccgctgccga gacagccaag   3840

caccaggcca agtgcaatat ctgcaaagag tgccccatca tcggcttccg gtacagaagc   3900

ctgaagcact tcaactacga tatctgccag agctgtttct tcagcggcag ggtggccaag   3960

ggccacaaaa tgcactaccc catggtggaa tactgcaccc ccaccacaag cggagaggat   4020

gtgcgggact tcgccaaggt gctgaaaaac aagttccgga ccaagcggta tttcgccaaa   4080

cacccccgga tgggctacct gcctgtgcag acagtgctgg aaggcgacaa catggaaacc   4140

gacaccatgt gatgatgatt tgggcagagc gatggagtcc ttagtatcag tcatgacaga   4200

tgaagaagga gcagaataaa tgttttacaa ctcctgattc ccgcatgcgg ccagcttatc   4260

gataccgtcg aaataaaaga tccttatttt cattggatct gtgtgttggt tttttgtgtg   4320
```

<210> SEQ ID NO 147
<211> LENGTH: 4323
<212> TYPE: DNA
<213> ORGANISM: Homo sapiens

<400> SEQUENCE: 147

```
atgctgtggt gggaggaagt ggaagattgc tacgagcgcg aggacgtgca gaagaaaacc     60

ttcaccaaat gggtgaacgc ccagttcagc aagttcggca agcagcacat cgagaacctg    120

ttcagcgacc tgcaggacgg cagacggctg ctggacctgc tggaaggcct gaccggccag    180

aagctgccca aagagaaggg cagcaccaga gtgcacgccc tgaacaacgt gaacaaggcc    240

ctgcgggtgc tgcagaacaa caacgtggac ctggtgaaca tcggcagcac cgacatcgtg    300

gacggcaacc acaagctgac cctgggcctg atctggaaca tcatcctgca ctggcaggtc    360

aaaaacgtga tgaagaacat catggccggc ctgcagcaga ccaacagcga gaagatcctg    420

ctgagctggg tgcgccagag cacccggaac tacccccagg tcaacgtgat caacttcacc    480

acctcttgga gcgacggcct ggccctgaac gccctgatcc acagccaccg gcccgacctg    540

ttcgactgga acagcgtggt ctgccagcag agcgccaccc agcggctgga acacgccttc    600

aatatcgcca gataccagct gggcatcgag aagctgctgg atcccgagga cgtggacacc    660

acctaccccg acaagaaatc catcctgatg tatatcacca gcctgttcca ggtgctgccc    720

cagcaggtgt ccatcgaggc catccaggaa gtggaaatgc tgcccagacc ccccaaagtg    780

accaaagagg aacacttcca gctgcaccac cagatgcact acagccagca gatcaccgtg    840

tccctggctc agggctacga gcggaccagc agccccaagc cccggttcaa gagctacgcc    900

tacacccagg ccgcctacgt gaccaccagc gaccccacca gaagcccatt ccccagccag    960

catctggaag cccccgagga caagagcttc ggcagcagcc tgatggaaag cgaagtgaac   1020

ctggacagat accagaccgc cctggaagag gtgctgtcct ggctgctgag cgccgaggat   1080

acactgcagg cccagggcga gatcagcaac gacgtggaag tggtgaaaga ccagttccac   1140

acccacgagg gctacatgat ggacctgacc gcccaccagg gcagagtggg caacatcctg   1200

cagctgggca gcaagctgat cggcaccggc aagctgagcg aggacgaaga gacagaggtg   1260

caggaacaga tgaacctgct gaacagcaga tgggagtgcc tgcgggtggc cagcatggaa   1320

aagcagagca acctgcacat ccacaccgtg cgggaagaga caatgatggt gatgaccgag   1380

gacatgcccc tggaaatcag ctacgtgccc agcacctacc tgaccgagat cacccacgtg   1440
```

```
tcccaggctc tgctggaagt ggaacagctg ctgaacgccc ccgacctgtg cgccaaggac   1500
ttcgaggatc tgttcaagca ggaagagagc ctgaagaata tcaaggactc cctgcagcag   1560
tccagcggcc ggatcgacat catccacagc aagaaaacag ccgccctgca gtccgccacc   1620
cccgtggaaa gagtgaagct gcaggaagcc ctgagccagc tggacttcca gtgggagaaa   1680
gtgaacaaga tgtacaagga ccggcagggc agattcgacc gcagcgtgga aaagtggcgg   1740
cggttccact acgacatcaa gatcttcaac cagtggctga ccgaggccga gcagttcctg   1800
agaaagaccc agatccccga gaactgggag cacgccaagt acaagtggta tctgaaagaa   1860
ctgcaggatg gcatcggcca gcggcagacc gtggtgcgca cactgaatgc caccggcgag   1920
gaaatcatcc agcagagcag caagaccgac gccagcatcc tgcaggaaaa gctgggctcc   1980
ctgaacctgc ggtggcagga agtgtgcaag cagctgagcg accggaagaa gaggctggaa   2040
gaacaggccc ctggcctgac caccatcggc gccagcccta cccagaccgt gaccctggtg   2100
acacagcccg tggtgacaaa agagacagcc atctccaagc tggaaatgcc cagctccctg   2160
atgctggaat ctgaccagtg gaagcgtctg cacctttctc tgcaggaact tctggtgtgg   2220
ctacagctga aagatgatga attaagccgg caggcaccta ttggaggcga ctttccagca   2280
gttcagaagc agaacgatgt acatagggcc ttcaagaggg aattgaaaac taaagaacct   2340
gtaatcatga gtactcttga gactgtacga atatttctga cagagcagcc tttggaagga   2400
ctagagaaac tctaccagga gcccagagag ctgcctcctg aggagagagc ccagaatgtc   2460
actcggcttc tacgaaagca ggctgaggag gtcaatactg agtgggaaaa attgaacctg   2520
cactccgctg actggcagag aaaaatagat gagaccctgg aaaggctgca ggaactgcag   2580
gaggccaccg acgagctgga cctgaagctg cggcaggccg aagtgatcaa gggcagctgg   2640
cagcccgtgg gcgacctgct gatcgacagc ctgcaggacc acctggaaaa agtgaaggcc   2700
ctgagaggcg agatcgcccc cctgaaagaa aacgtgtccc acgtgaacga cctggcccgg   2760
cagctgacca ccctgggcat ccagctgagc ccctacaacc tgagcaccct ggaagatctg   2820
aacacccggt ggaagctgct gcaggtggcc gtggaagata gagtgcggca gctgcacgag   2880
gcccacagag actttggccc tgccagccag cacttcctga gcacctctgt gcagggaccc   2940
tgggagagag ccatcagccc caacaaggtg ccctactaca tcaaccacga gacacagacc   3000
acctgttggg accaccccaa gatgaccgag ctgtaccaga gcctggccga cctgaacaat   3060
gtgcggttca gcgcctaccg gaccgccatg aagctgaggc ggctgcagaa agctctgtgc   3120
ctggatctgc tgagcctgag cgccgcctgc gacgccctgg accagcacaa cctgaagcag   3180
aacgaccagc ccatggatat cctgcagatc atcaactgcc tgaccacaat ctacgacagg   3240
ctggaacagg aacacaacaa tctggtcaac gtgcccctgt gcgtggacat gtgcctgaat   3300
tggctgctga atgtgtacga caccggccgg accggcagaa tccgggtgct gagcttcaag   3360
accggcatca tcagcctgtg caaggcccac ctggaagata agtaccgcta cctgttcaaa   3420
caggtggcca gctccaccgg cttttgcgac cagcggagac tgggcctgct gctgcacgac   3480
agcatccaga tccccagaca gctgggcgag gtggcctcct tcggcggcag caacattgag   3540
cccagcgtgc ggagctgctt ccagttcgcc aacaacaagc ccgagatcga ggccgccctg   3600
ttcctggact ggatgagact ggaaccccag agcatggtgt ggctgcccgt gctgcatcgg   3660
gtggccgctg ccgagacagc caagcaccag gccaagtgca acatctgcaa agagtgcccc   3720
atcatcggct tccggtacag aagcctgaag cacttcaact acgatatctg ccagagctgc   3780
ttcttcagcg gcagagtggc caagggccac aaaatgcact accccatggt ggaatactgc   3840
```

```
acccccacca ccagcggcga ggatgtgcgg gacttcgcca aggtgctgaa aaacaagttc   3900

cggaccaagc ggtactttgc caagcacccc cggatgggct acctgcccgt gcagacagtg   3960

ctggaaggcg acaacatgga aacccctgcc cagatcctga tcagcctgga aagcgaggaa   4020

cggggcgagc tggaacggat cctggccgat ctggaagagg aaaaccggaa cctgcaggcc   4080

gagtacgacc ggctgaagca gcagcacgag cacaagggcc tgagccccct gcctagcccc   4140

cctgacacca tgtgatgatg atttgggcag agcgatggag tccttagtat cagtcatgac   4200

agatgaagaa ggagcagaat aaatgtttta caactcctga ttcccgcatg cggccagctt   4260

atcgataccg tcgaaataaa agatccttat tttcattgga tctgtgtgtt ggtttttttgt   4320

gtg                                                                 4323
```

<210> SEQ ID NO 148
<211> LENGTH: 4164
<212> TYPE: DNA
<213> ORGANISM: Homo sapiens

<400> SEQUENCE: 148

```
atgctgtggt gggaggaagt ggaagattgc tacgagcgcg aggacgtgca gaagaaaacc     60

ttcaccaaat gggtgaacgc ccagttcagc aagttcggca agcagcacat cgagaacctg    120

ttcagcgacc tgcaggacgg cagacggctg ctggacctgc tggaaggcct gaccggccag    180

aagctgccca aagagaaggg cagcaccaga gtgcacgccc tgaacaacgt gaacaaggcc    240

ctgcgggtgc tgcagaacaa caacgtggac ctggtgaaca tcggcagcac cgacatcgtg    300

gacggcaacc acaagctgac cctgggcctg atctggaaca tcatcctgca ctggcaggtc    360

aaaaacgtga tgaagaacat catggccggc ctgcagcaga ccaacagcga gaagatcctg    420

ctgagctggg tgcgccagag cacccggaac taccccaggg tcaacgtgat caacttcacc    480

acctcttgga gcgacggcct ggccctgaac gccctgatcc acagccaccg gcccgacctg    540

ttcgactgga acagcgtggt ctgccagcag agcgccaccc agcggctgga acacgccttc    600

aatatcgcca gataccagct gggcatcgag aagctgctgg atcccgagga cgtggacacc    660

acctaccccg acaagaaatc catcctgatg tatatcacca gcctgttcca ggtgctgccc    720

cagcaggtgt ccatcgaggc catccaggaa gtggaaatgc tgcccagacc ccccaaagtg    780

accaaagagg aacacttcca gctgcaccac cagatgcact acagccagca gatcaccgtg    840

tccctggctc agggctacga gcggaccagc agccccaagc cccggttcaa gagctacgcc    900

tacacccagg ccgcctacgt gaccaccagc gaccccacca gaagcccatt ccccagccag    960

catctggaag cccccgagga caagagcttc ggcagcagcc tgatggaaag cgaagtgaac   1020

ctggacagat accagaccgc cctggaagag gtgctgtcct ggctgctgag cgccgaggat   1080

acactgcagg cccagggcga gatcagcaac gacgtggaag tggtgaaaga ccagttccac   1140

acccacgagg gctacatgat ggacctgacc gcccaccagg gcagagtggg caacatcctg   1200

cagctgggca gcaagctgat cggcaccggc aagctgagcg aggacgaaga gacagaggtg   1260

caggaacaga tgaacctgct gaacagcaga tgggagtgcc tgcgggtggc cagcatggaa   1320

aagcagagca acctgcacat ccacaccgtg cgggaagaga caatgatggt gatgaccgag   1380

gacatgcccc tggaaatcag ctacgtgccc agcacctacc tgaccgagat cacccacgtg   1440

tcccaggctc tgctggaagt ggaacagctg ctgaacgccc ccgacctgtg cgccaaggac   1500

ttcgaggatc tgttcaagca ggaagagagc ctgaagaata tcaaggactc cctgcagcag   1560
```

```
tccagcggcc ggatcgacat catccacagc aagaaaacag ccgccctgca gtccgccacc   1620
cccgtggaaa gagtgaagct gcaggaagcc ctgagccagc tggacttcca gtgggagaaa   1680
gtgaacaaga tgtacaagga ccggcagggc agattcgacc gcagcgtgga aaagtggcgg   1740
cggttccact acgacatcaa gatcttcaac cagtggctga ccgaggccga gcagttcctg   1800
agaaagaccc agatccccga gaactgggag cacgccaagt acaagtggta tctgaaagag   1860
ctgcaggacg gcatcggcca gcggcagaca gtggtccgca ccctgaatgc caccggcgag   1920
gaaatcatcc agcagagcag caagaccgac gccagcatcc tgcaggaaaa gctgggcagc   1980
ctgaacctgc ggtggcagga agtgtgcaag cagctgagcg accggaagaa gcggctggaa   2040
gaacaggccc ctggcctgac cacaatcggc gccagcccta cccagaccgt gaccctggtg   2100
acacagcccg tggtgacaaa agagacagcc atcagcaagc tggaaatgcc cagcagcctg   2160
atgctggaaa gcgaccagtg gaagcggctg cacctgagcc tgcaggaact gctggtctgg   2220
ctgcagctga aggacgacga gctgagcaga caggccccca tcggcggcga tttccccgcc   2280
gtgcagaaac agaacgacgt gcaccgggcc ttcaagcgcg agctgaaaac aaaagaaccc   2340
gtgatcatga gcaccctgga aaccgtgcgg atcttcctga ccgagcagcc cctggaaggc   2400
ctggaaaagc tgtaccagga acccagagag ctgccccccg aggaacgggc ccagaacgtg   2460
accagactgc tgcggaagca ggccgaagag gtcaacaccg agtgggagaa gctgaacctg   2520
cacagcgccg actggcagcg gaagatcgac gagacactgg aacggctgca ggaactgcag   2580
gaggccaccg acgagctgga cctgaagctg agacaggccg aagtgatcaa gggcagctgg   2640
cagcccgtgg gcgacctgct gatcgactcc ctgcaggacc acctggaaaa agtgaaggcc   2700
ctgcggggcg agatcgcccc cctgaaagaa aacgtgtccc acgtgaacga cctggcccgg   2760
cagctgacca ccctgggcat ccagctgagc ccctacaacc tgtccaccct ggaagatctg   2820
aacacccggt ggaagctgct gcaggtggcc gtggaagata gagtgcggca gctgcacgag   2880
gcccacagag actttggccc tgccagccag cacttcctga gcacctctgt gcagggaccc   2940
tgggagagag ccatcagccc caacaaggtg ccctactaca tcaaccacga gacacagacc   3000
acctgttggg accaccccaa gatgaccgag ctgtaccaga gcctggccga cctgaacaat   3060
gtgcggttca gcgcctaccg gaccgccatg aagctgaggc ggctgcagaa agctctgtgc   3120
ctggatctgc tgagcctgag cgccgcctgc gacgccctgg accagcacaa cctgaagcag   3180
aacgaccagc ccatggatat cctgcagatc atcaactgcc tgaccacaat ctacgacagg   3240
ctggaacagg aacacaacaa tctggtcaac gtgcccctgt gcgtggacat gtgcctgaat   3300
tggctgctga atgtgtacga caccggccgg accggcagaa tccgggtgct gagcttcaag   3360
accggcatca tcagcctgtg caaggcccac ctggaagata agtaccgcta cctgttcaaa   3420
caggtggcca gctccaccgg cttttgcgac cagcggagac tgggcctgct gctgcacgac   3480
agcatccaga tccccagaca gctgggcgag gtggcctcct tcggcggcag caacattgag   3540
cccagcgtgc ggagctgctt ccagttcgcc aacaacaagc ccgagatcga ggccgccctg   3600
ttcctggact ggatgagact ggaaccccag agcatggtgt ggctgcccgt gctgcatcgg   3660
gtggccgctg ccgagacagc caagcaccag gccaagtgca acatctgcaa agagtgcccc   3720
atcatcggct tccggtacag aagcctgaag cacttcaact acgatatctg ccagagctgc   3780
ttcttcagcg gcagagtggc caagggccac aaaatgcact accccatggt ggaatactgc   3840
acccccacca ccagcggcga ggatgtgcgg gacttcgcca aggtgctgaa aaacaagttc   3900
cggaccaagc ggtactttgc caagcacccc cggatgggct acctgcccgt gcagacagtg   3960
```

```
ctggaaggcg acaacatgga aaccgacacc atgtgatgat gatttgggca gagcgatgga   4020

gtccttagta tcagtcatga cagatgaaga aggagcagaa taaatgtttt acaactcctg   4080

attcccgcat gcggccagct tatcgatacc gtcgaaataa aagatcctta ttttcattgg   4140

atctgtgtgt tggtttttttg tgtg                                          4164
```

<210> SEQ ID NO 149
<211> LENGTH: 4076
<212> TYPE: DNA
<213> ORGANISM: Homo sapiens

<400> SEQUENCE: 149

```
atgctgtggt gggaggaagt ggaagattgc tacgagcgcg aggacgtgca gaagaaaacc     60

ttcaccaaat gggtgaacgc ccagttcagc aagttcggca agcagcacat cgagaacctg    120

ttcagcgacc tgcaggacgg cagacggctg ctggacctgc tggaaggcct gaccggccag    180

aagctgccca aagagaaggg cagcaccaga gtgcacgccc tgaacaacgt gaacaaggcc    240

ctgcgggtgc tgcagaacaa caacgtggac ctggtgaaca tcggcagcac cgacatcgtg    300

gacggcaacc acaagctgac cctgggcctg atctggaaca tcatcctgca ctggcaggtc    360

aaaaacgtga tgaagaacat catggccggc ctgcagcaga ccaacagcga gaagatcctg    420

ctgagctggg tgcgccagag cacccggaac tacccccagg tcaacgtgat caacttcacc    480

acctcttgga gcgacggcct ggccctgaac gccctgatcc acagccaccg gcccgacctg    540

ttcgactgga acagcgtggt ctgccagcag agcgccaccc agcggctgga acacgccttc    600

aatatcgcca gataccagct gggcatcgag aagctgctgg atcccgagga cgtggacacc    660

acctaccccg acaagaaatc catcctgatg tatatcacca gcctgttcca ggtgctgccc    720

cagcaggtgt ccatcgaggc catccaggaa gtggaaatgc tgcccagacc ccccaaagtg    780

accaaagagg aacacttcca gctgcaccac cagatgcact acagccagca gatcaccgtg    840

tccctggctc agggctacga gcggaccagc agccccaagc cccggttcaa gagctacgcc    900

tacacccagg ccgcctacgt gaccaccagc gaccccacca gaagcccatt ccccagccag    960

catctggaag cccccgagga caagagcttc ggcagcagcc tgatggaaag cgaagtgaac   1020

ctggacagat accagaccgc cctggaagag gtgctgtcct ggctgctgag cgccgaggat   1080

acactgcagg cccagggcga gatcagcaac gacgtggaag tggtgaaaga ccagttccac   1140

acccacgagg gctacatgat ggacctgacc gcccaccagg gcagagtggg caacatcctg   1200

cagctgggca gcaagctgat cggcaccggc aagctgagcg aggacgaaga gacagaggtg   1260

caggaacaga tgaacctgct gaacagcaga tgggagtgcc tgcgggtggc cagcatggaa   1320

aagcagagca acctgcacat ccacaccgtg cgggaagaga caatgatggt gatgaccgag   1380

gacatgcccc tggaaatcag ctacgtgccc agcacctacc tgaccgagat cacccacgtg   1440

tcccaggctc tgctggaagt ggaacagctg ctgaacgccc ccgacctgtg cgccaaggac   1500

ttcgaggatc tgttcaagca ggaagagagc ctgaagaata tcaaggactc cctgcagcag   1560

tccagcggcc ggatcgacat catccacagc aagaaaacag ccgccctgca gtccgccacc   1620

cccgtggaaa gagtgaagct gcaggaagcc ctgagccagc tggacttcca gtgggagaaa   1680

gtgaacaaga tgtacaagga ccggcagggc agattcgacc gcagcgtgga aaagtggcgg   1740

cggttccact acgacatcaa gatcttcaac cagtggctga ccgaggccga gcagttcctg   1800

agaaagaccc agatccccga gaactgggag cacgccaagt acaagtggta tctgaaagag   1860
```

```
ctgcaggacg gcatcggcca gcggcagaca gtggtccgca ccctgaatgc caccggcgag   1920
gaaatcatcc agcagagcag caagaccgac gccagcatcc tgcaggaaaa gctgggcagc   1980
ctgaacctgc ggtggcagga agtgtgcaag cagctgagcg accggaagaa gcggctggaa   2040
gaacaggccc ctggcctgac cacaatcggc gccagcccta cccagaccgt gaccctggtg   2100
acacagcccg tggtgacaaa agagacagcc atcagcaagc tggaaatgcc cagcagcctg   2160
atgctggaaa gcgaccagtg gaagcggctg cacctgagcc tgcaggaact gctggtctgg   2220
ctgcagctga aggacgacga gctgagcaga caggccccca tcggcggcga tttccccgcc   2280
gtgcagaaac agaacgacgt gcaccgggcc ttcaagcgcg agctgaaaac aaaagaaccc   2340
gtgatcatga gcaccctgga aaccgtgcgg atcttcctga ccgagcagcc cctggaaggc   2400
ctggaaaagc tgtaccagga acccagagag ctgccccccg aggaacgggc ccagaacgtg   2460
accagactgc tgcggaagca ggccgaagag gtcaacaccg agtgggagaa gctgaacctg   2520
cacagcgccg actggcagcg gaagatcgac gagacactgg aacggctgca ggaactgcag   2580
gaggccaccg acgagctgga cctgaagctg agacaggccg aagtgatcaa gggcagctgg   2640
cagcccgtgg gcgacctgct gatcgactcc ctgcaggacc acctggaaaa agtgaaggcc   2700
ctgcggggcg agatcgcccc cctgaaagaa aacgtgtccc acgtgaacga cctggcccgg   2760
cagctgacca ccctgggcat ccagctgagc ccctacaacc tgtccaccct ggaagatctg   2820
aacacccggt ggaagctgct gcaggtggcc gtggaagata gagtgcggca gctgcacgag   2880
gcccacagag actttggccc tgccagccag cacttcctga gcacctctgt gcagggaccc   2940
tgggagagag ccatcagccc caacaaggtg ccctactaca tcaaccacga gacacagacc   3000
acctgttggg accaccccaa gatgaccgag ctgtaccaga gcctggccga cctgaacaat   3060
gtgcggttca gcgcctaccg gaccgccatg aagctgaggc ggctgcagaa agctctgtgc   3120
ctggatctgc tgagcctgag cgccgcctgc gacgccctgg accagcacaa cctgaagcag   3180
aacgaccagc ccatggatat cctgcagatc atcaactgcc tgaccacaat ctacgacagg   3240
ctggaacagg aacacaacaa tctggtcaac gtgcccctgt gcgtggacat gtgcctgaat   3300
tggctgctga atgtgtacga caccggccgg accggcagaa tccgggtgct gagcttcaag   3360
accggcatca tcagcctgtg caaggcccac ctggaagata agtaccgcta cctgttcaaa   3420
caggtggcca gctccaccgg cttttgcgac cagcggagac tgggcctgct gctgcacgac   3480
agcatccaga tccccagaca gctgggcgag gtggcctcct tcggcggcag caacattgag   3540
cccagcgtgc ggagctgctt ccagttcgcc aacaacaagc ccgagatcga ggccgccctg   3600
ttcctggact ggatgagact ggaaccccag agcatggtgt ggctgcccgt gctgcatcgg   3660
gtggccgctg ccgagacagc caagcaccag gccaagtgca acatctgcaa agagtgcccc   3720
atcatcggct tccggtacag aagcctgaag cacttcaact acgatatctg ccagagctgc   3780
ttcttcagcg gcagagtggc caagggccac aaaatgcact accccatggt ggaatactgc   3840
acccccacca ccagcggcga ggatgtgcgg gacttcgcca aggtgctgaa aaacaagttc   3900
cggaccaagc ggtactttgc caagcacccc cggatgggct acctgcccgt gcagacagtg   3960
ctggaaggcg acaacatgga aaccgacacc atgtgatgat gagaagtctt ttccacatgg   4020
cagatgaaat aaaagatcct tattttcatt ggatctgtgt gttggttttt tgtgtg       4076
```

<210> SEQ ID NO 150
<211> LENGTH: 10
<212> TYPE: DNA
<213> ORGANISM: Homo sapiens

<400> SEQUENCE: 150 gccrccaugg 10

<210> SEQ ID NO 151
<211> LENGTH: 10
<212> TYPE: DNA
<213> ORGANISM: Homo sapiens

<400> SEQUENCE: 151
gccaccatgg 10

<210> SEQ ID NO 152
<211> LENGTH: 1332
<212> TYPE: PRT
<213> ORGANISM: Homo sapiens

<400> SEQUENCE: 152

```
Met Leu Trp Trp Glu Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
            20                  25                  30

Gly Lys Gln His Ile Glu Asn Leu Phe Ser Asp Leu Gln Asp Gly Arg
        35                  40                  45

Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Asn Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
        115                 120                 125

Ala Gly Leu Gln Gln Thr Asn Ser Glu Lys Ile Leu Leu Ser Trp Val
    130                 135                 140

Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His
                165                 170                 175

Arg Pro Asp Leu Phe Asp Trp Asn Ser Val Val Cys Gln Gln Ser Ala
            180                 185                 190

Thr Gln Arg Leu Glu His Ala Phe Asn Ile Ala Arg Tyr Gln Leu Gly
        195                 200                 205

Ile Glu Lys Leu Leu Asp Pro Glu Asp Val Asp Thr Thr Tyr Pro Asp
    210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu Met Leu Pro Arg
                245                 250                 255

Pro Pro Lys Val Thr Lys Glu Glu His Phe Gln Leu His His Gln Met
            260                 265                 270

His Tyr Ser Gln Gln Ile Thr Val Ser Leu Ala Gln Gly Tyr Glu Arg
        275                 280                 285

Thr Ser Ser Pro Lys Pro Arg Phe Lys Ser Tyr Ala Tyr Thr Gln Ala
    290                 295                 300
```

```
Ala Tyr Val Thr Thr Ser Asp Pro Thr Arg Ser Pro Phe Pro Ser Gln
305                 310                 315                 320

His Leu Glu Ala Pro Glu Asp Lys Ser Phe Gly Ser Ser Leu Met Glu
                325                 330                 335

Ser Glu Val Asn Leu Asp Arg Tyr Gln Thr Ala Leu Glu Glu Val Leu
            340                 345                 350

Ser Trp Leu Leu Ser Ala Glu Asp Thr Leu Gln Ala Gln Gly Glu Ile
        355                 360                 365

Ser Asn Asp Val Glu Val Val Lys Asp Gln Phe His Thr His Glu Gly
    370                 375                 380

Tyr Met Met Asp Leu Thr Ala His Gln Gly Arg Val Gly Asn Ile Leu
385                 390                 395                 400

Gln Leu Gly Ser Lys Leu Ile Gly Thr Gly Lys Leu Ser Glu Asp Glu
                405                 410                 415

Glu Thr Glu Val Gln Glu Gln Met Asn Leu Leu Asn Ser Arg Trp Glu
            420                 425                 430

Cys Leu Arg Val Ala Ser Met Glu Lys Gln Ser Asn Leu His Ile His
        435                 440                 445

Thr Val Arg Glu Glu Thr Met Met Val Met Thr Glu Asp Met Pro Leu
    450                 455                 460

Glu Ile Ser Tyr Val Pro Ser Thr Tyr Leu Thr Glu Ile Thr His Val
465                 470                 475                 480

Ser Gln Ala Leu Leu Glu Val Glu Gln Leu Leu Asn Ala Pro Asp Leu
                485                 490                 495

Cys Ala Lys Asp Phe Glu Asp Leu Phe Lys Gln Glu Glu Ser Leu Lys
            500                 505                 510

Asn Ile Lys Asp Ser Leu Gln Gln Ser Ser Gly Arg Ile Asp Ile Ile
        515                 520                 525

His Ser Lys Lys Thr Ala Ala Leu Gln Ser Ala Thr Pro Val Glu Arg
    530                 535                 540

Val Lys Leu Gln Glu Ala Leu Ser Gln Leu Asp Phe Gln Trp Glu Lys
545                 550                 555                 560

Val Asn Lys Met Tyr Lys Asp Arg Gln Gly Arg Phe Asp Arg Ser Val
                565                 570                 575

Glu Lys Trp Arg Arg Phe His Tyr Asp Ile Lys Ile Phe Asn Gln Trp
            580                 585                 590

Leu Thr Glu Ala Glu Gln Phe Leu Arg Lys Thr Gln Ile Pro Glu Asn
        595                 600                 605

Trp Glu His Ala Lys Tyr Lys Trp Tyr Leu Lys Glu Leu Gln Asp Gly
    610                 615                 620

Ile Gly Gln Arg Gln Thr Val Val Arg Thr Leu Asn Ala Thr Gly Glu
625                 630                 635                 640

Glu Ile Ile Gln Gln Ser Ser Lys Thr Asp Ala Ser Ile Leu Gln Glu
                645                 650                 655

Lys Leu Gly Ser Leu Asn Leu Arg Trp Gln Glu Val Cys Lys Gln Leu
            660                 665                 670

Ser Asp Arg Lys Lys Arg Leu Glu Glu Gln Lys Asn Asp Leu Ala Pro
        675                 680                 685

Gly Leu Thr Thr Ile Gly Ala Ser Pro Thr Gln Thr Val Thr Leu Val
    690                 695                 700

Thr Gln Pro Val Val Thr Lys Glu Thr Ala Ile Ser Lys Leu Glu Met
705                 710                 715                 720
```

```
Pro Ser Ser Leu Met Leu Glu Ser Asp Gln Trp Lys Arg Leu His Leu
                725                 730                 735

Ser Leu Gln Glu Leu Leu Val Trp Leu Gln Leu Lys Asp Asp Glu Leu
            740                 745                 750

Ser Arg Gln Ala Pro Ile Gly Gly Asp Phe Pro Ala Val Gln Lys Gln
        755                 760                 765

Asn Asp Val His Arg Ala Phe Lys Arg Glu Leu Lys Thr Lys Glu Pro
    770                 775                 780

Val Ile Met Ser Thr Leu Glu Thr Val Arg Ile Phe Leu Thr Glu Gln
785                 790                 795                 800

Pro Leu Glu Gly Leu Glu Lys Leu Tyr Gln Glu Pro Arg Glu Leu Pro
                805                 810                 815

Pro Glu Glu Arg Ala Gln Asn Val Thr Arg Leu Leu Arg Lys Gln Ala
            820                 825                 830

Glu Glu Val Asn Thr Glu Trp Glu Lys Leu Asn Leu His Ser Ala Asp
        835                 840                 845

Trp Gln Arg Lys Ile Asp Glu Thr Leu Glu Arg Leu Gln Glu Leu Gln
    850                 855                 860

Glu Ala Thr Asp Glu Leu Asp Leu Lys Leu Arg Gln Ala Glu Val Ile
865                 870                 875                 880

Lys Gly Ser Trp Gln Pro Val Gly Asp Leu Leu Ile Asp Ser Leu Gln
                885                 890                 895

Asp His Leu Glu Lys Val Lys Ala Leu Arg Gly Glu Ile Ala Pro Leu
            900                 905                 910

Lys Glu Asn Val Ser His Val Asn Asp Leu Ala Arg Gln Leu Thr Thr
        915                 920                 925

Leu Gly Ile Gln Leu Ser Pro Tyr Asn Leu Ser Thr Leu Glu Asp Leu
    930                 935                 940

Asn Thr Arg Trp Lys Leu Leu Gln Val Ala Val Glu Asp Arg Val Arg
945                 950                 955                 960

Gln Leu His Glu Ala His Arg Asp Phe Gly Pro Ala Ser Gln His Phe
                965                 970                 975

Leu Ser Thr Ser Val Gln Gly Pro Trp Glu Arg Ala Ile Ser Pro Asn
            980                 985                 990

Lys Val Pro Tyr Tyr Ile Asn His  Glu Thr Gln Thr Thr  Cys Trp Asp
        995                 1000                1005

His Pro  Lys Met Thr Glu Leu  Tyr Gln Ser Leu Ala  Asp Leu Asn
    1010                1015                1020

Asn Val  Arg Phe Ser Ala Tyr  Arg Thr Ala Met Lys  Leu Arg Arg
    1025                1030                1035

Leu Gln  Lys Ala Leu Cys Leu  Asp Leu Leu Ser Leu  Ser Ala Ala
    1040                1045                1050

Cys Asp  Ala Leu Asp Gln His  Asn Leu Lys Gln Asn  Asp Gln Pro
    1055                1060                1065

Met Asp  Ile Leu Gln Ile Ile  Asn Cys Leu Thr Thr  Ile Tyr Asp
    1070                1075                1080

Arg Leu  Glu Gln Glu His Asn  Asn Leu Val Asn Val  Pro Leu Cys
    1085                1090                1095

Val Asp  Met Cys Leu Asn Trp  Leu Leu Asn Val Tyr  Asp Thr Gly
    1100                1105                1110

Arg Thr  Gly Arg Ile Arg Val  Leu Ser Phe Lys Thr  Gly Ile Ile
    1115                1120                1125

Ser Leu  Cys Lys Ala His Leu  Glu Asp Lys Tyr Arg  Tyr Leu Phe
```

```
    1130                1135                1140

Lys Gln  Val Ala Ser Ser Thr  Gly Phe Cys Asp Gln  Arg Arg Leu
    1145                1150                1155

Gly Leu  Leu Leu His Asp Ser  Ile Gln Ile Pro Arg  Gln Leu Gly
    1160                1165                1170

Glu Val  Ala Ser Phe Gly Gly  Ser Asn Ile Glu Pro  Ser Val Arg
    1175                1180                1185

Ser Cys  Phe Gln Phe Ala Asn  Asn Lys Pro Glu Ile  Glu Ala Ala
    1190                1195                1200

Leu Phe  Leu Asp Trp Met Arg  Leu Glu Pro Gln Ser  Met Val Trp
    1205                1210                1215

Leu Pro  Val Leu His Arg Val  Ala Ala Ala Glu Thr  Ala Lys His
    1220                1225                1230

Gln Ala  Lys Cys Asn Ile Cys  Lys Glu Cys Pro Ile  Ile Gly Phe
    1235                1240                1245

Arg Tyr  Arg Ser Leu Lys His  Phe Asn Tyr Asp Ile  Cys Gln Ser
    1250                1255                1260

Cys Phe  Phe Ser Gly Arg Val  Ala Lys Gly His Lys  Met His Tyr
    1265                1270                1275

Pro Met  Val Glu Tyr Cys Thr  Pro Thr Thr Ser Gly  Glu Asp Val
    1280                1285                1290

Arg Asp  Phe Ala Lys Val Leu  Lys Asn Lys Phe Arg  Thr Lys Arg
    1295                1300                1305

Tyr Phe  Ala Lys His Pro Arg  Met Gly Tyr Leu Pro  Val Gln Thr
    1310                1315                1320

Val Leu  Glu Gly Asp Asn Met  Glu Thr
    1325                1330


<210> SEQ ID NO 153
<211> LENGTH: 1322
<212> TYPE: PRT
<213> ORGANISM: Homo sapiens

<400> SEQUENCE: 153

Met Leu Trp Trp Glu Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
            20                  25                  30

Gly Lys Gln His Ile Glu Asn Leu Phe Ser Asp Leu Gln Asp Gly Arg
        35                  40                  45

Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Asn Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
        115                 120                 125

Ala Gly Leu Gln Gln Thr Asn Ser Glu Lys Ile Leu Leu Ser Trp Val
    130                 135                 140

Arg Gln Ser Thr Arg Asn Tyr Pro Gln Val Asn Val Ile Asn Phe Thr
145                 150                 155                 160
```

```
Thr Ser Trp Ser Asp Gly Leu Ala Leu Asn Ala Leu Ile His Ser His
                165                 170                 175

Arg Pro Asp Leu Phe Asp Trp Asn Ser Val Val Cys Gln Gln Ser Ala
            180                 185                 190

Thr Gln Arg Leu Glu His Ala Phe Asn Ile Ala Arg Tyr Gln Leu Gly
        195                 200                 205

Ile Glu Lys Leu Leu Asp Pro Glu Asp Val Asp Thr Thr Tyr Pro Asp
    210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu Met Leu Pro Arg
                245                 250                 255

Pro Pro Lys Val Thr Lys Glu Glu His Phe Gln Leu His His Gln Met
            260                 265                 270

His Tyr Ser Gln Gln Ile Thr Val Ser Leu Ala Gln Gly Tyr Glu Arg
        275                 280                 285

Thr Ser Ser Pro Lys Pro Arg Phe Lys Ser Tyr Ala Tyr Thr Gln Ala
    290                 295                 300

Ala Tyr Val Thr Thr Ser Asp Pro Thr Arg Ser Pro Phe Pro Ser Gln
305                 310                 315                 320

His Leu Glu Ala Pro Glu Asp Lys Ser Phe Gly Ser Ser Leu Met Glu
                325                 330                 335

Ser Glu Val Asn Leu Asp Arg Tyr Gln Thr Ala Leu Glu Glu Val Leu
            340                 345                 350

Ser Trp Leu Leu Ser Ala Glu Asp Thr Leu Gln Ala Gln Gly Glu Ile
        355                 360                 365

Ser Asn Asp Val Glu Val Val Lys Asp Gln Phe His Thr His Glu Gly
    370                 375                 380

Tyr Met Met Asp Leu Thr Ala His Gln Gly Arg Val Gly Asn Ile Leu
385                 390                 395                 400

Gln Leu Gly Ser Lys Leu Ile Gly Thr Gly Lys Leu Ser Glu Asp Glu
                405                 410                 415

Glu Thr Glu Val Gln Glu Gln Met Asn Leu Leu Asn Ser Arg Trp Glu
            420                 425                 430

Cys Leu Arg Val Ala Ser Met Glu Lys Gln Ser Asn Leu His Arg Val
        435                 440                 445

Leu Leu Lys Trp Gln Arg Leu Thr Glu Glu Gln Cys Leu Phe Ser Ala
    450                 455                 460

Trp Leu Ser Glu Lys Glu Asp Ala Val Asn Lys Ile His Thr Thr Gly
465                 470                 475                 480

Phe Lys Asp Gln Asn Glu Met Leu Ser Ser Leu Gln Lys Leu Ala Val
                485                 490                 495

Leu Lys Ala Asp Leu Glu Lys Lys Lys Gln Ser Met Gly Lys Leu Tyr
            500                 505                 510

Ser Leu Lys Gln Asp Leu Leu Ser Thr Leu Lys Asn Lys Ser Val Thr
        515                 520                 525

Gln Lys Thr Glu Ala Trp Leu Asp Asn Phe Ala Arg Cys Trp Asp Asn
    530                 535                 540

Leu Val Gln Lys Leu Glu Lys Ser Thr Ala Gln Ile Ser Gln Ala Val
545                 550                 555                 560

Thr Thr Thr Gln Pro Ser Leu Thr Gln Thr Thr Val Met Glu Thr Val
                565                 570                 575

Thr Thr Val Thr Thr Arg Glu Gln Ile Leu Val Lys His Ala Gln Glu
```

```
            580                 585                 590

Glu Leu Pro Pro Pro Pro Pro Gln Lys Lys Arg Gln Ile Thr Val Asp
        595                 600                 605

Ser Glu Ile His Thr Val Arg Glu Glu Thr Met Met Val Met Thr Glu
    610                 615                 620

Asp Met Pro Leu Glu Ile Ser Tyr Val Pro Ser Thr Tyr Leu Thr Glu
625                 630                 635                 640

Ile Thr His Val Ser Gln Ala Leu Leu Glu Val Glu Gln Leu Leu Asn
                645                 650                 655

Ala Pro Asp Leu Cys Ala Lys Asp Phe Glu Asp Leu Phe Lys Gln Glu
            660                 665                 670

Glu Ser Leu Lys Asn Ile Lys Asp Ser Leu Gln Gln Ser Ser Gly Arg
        675                 680                 685

Ile Asp Ile Ile His Ser Lys Lys Thr Ala Ala Leu Gln Ser Ala Thr
    690                 695                 700

Pro Val Glu Arg Val Lys Leu Gln Glu Ala Leu Ser Gln Leu Asp Phe
705                 710                 715                 720

Gln Trp Glu Lys Val Asn Lys Met Tyr Lys Asp Arg Gln Gly Arg Phe
                725                 730                 735

Asp Arg Ser Val Glu Lys Trp Arg Arg Phe His Tyr Asp Ile Lys Ile
            740                 745                 750

Phe Asn Gln Trp Leu Thr Glu Ala Glu Gln Phe Leu Arg Lys Thr Gln
        755                 760                 765

Ile Pro Glu Asn Trp Glu His Ala Lys Tyr Lys Trp Tyr Leu Lys Glu
    770                 775                 780

Leu Gln Asp Gly Ile Gly Gln Arg Gln Thr Val Val Arg Thr Leu Asn
785                 790                 795                 800

Ala Thr Gly Glu Glu Ile Ile Gln Gln Ser Ser Lys Thr Asp Ala Ser
                805                 810                 815

Ile Leu Gln Glu Lys Leu Gly Ser Leu Asn Leu Arg Trp Gln Glu Val
            820                 825                 830

Cys Lys Gln Leu Ser Asp Arg Lys Lys Arg Leu Glu Glu Gln Leu Glu
        835                 840                 845

Arg Leu Gln Glu Leu Gln Glu Ala Thr Asp Glu Leu Asp Leu Lys Leu
    850                 855                 860

Arg Gln Ala Glu Val Ile Lys Gly Ser Trp Gln Pro Val Gly Asp Leu
865                 870                 875                 880

Leu Ile Asp Ser Leu Gln Asp His Leu Glu Lys Val Lys Ala Leu Arg
                885                 890                 895

Gly Glu Ile Ala Pro Leu Lys Glu Asn Val Ser His Val Asn Asp Leu
            900                 905                 910

Ala Arg Gln Leu Thr Thr Leu Gly Ile Gln Leu Ser Pro Tyr Asn Leu
        915                 920                 925

Ser Thr Leu Glu Asp Leu Asn Thr Arg Trp Lys Leu Leu Gln Val Ala
    930                 935                 940

Val Glu Asp Arg Val Arg Gln Leu His Glu Ala His Arg Asp Phe Gly
945                 950                 955                 960

Pro Ala Ser Gln His Phe Leu Ser Thr Ser Val Gln Gly Pro Trp Glu
                965                 970                 975

Arg Ala Ile Ser Pro Asn Lys Val Pro Tyr Tyr Ile Asn His Glu Thr
            980                 985                 990

Gln Thr Thr Cys Trp Asp His Pro  Lys Met Thr Glu Leu  Tyr Gln Ser
        995                 1000                1005
```

```
Leu Ala  Asp Leu Asn Asn Val  Arg Phe Ser Ala Tyr  Arg Thr Ala
    1010                 1015                 1020

Met Lys  Leu Arg Arg Leu Gln  Lys Ala Leu Cys Leu  Asp Leu Leu
    1025                 1030                 1035

Ser Leu  Ser Ala Ala Cys Asp  Ala Leu Asp Gln His  Asn Leu Lys
    1040                 1045                 1050

Gln Asn  Asp Gln Pro Met Asp  Ile Leu Gln Ile Ile  Asn Cys Leu
    1055                 1060                 1065

Thr Thr  Ile Tyr Asp Arg Leu  Glu Gln Glu His Asn  Asn Leu Val
    1070                 1075                 1080

Asn Val  Pro Leu Cys Val Asp  Met Cys Leu Asn Trp  Leu Leu Asn
    1085                 1090                 1095

Val Tyr  Asp Thr Gly Arg Thr  Gly Arg Ile Arg Val  Leu Ser Phe
    1100                 1105                 1110

Lys Thr  Gly Ile Ile Ser Leu  Cys Lys Ala His Leu  Glu Asp Lys
    1115                 1120                 1125

Tyr Arg  Tyr Leu Phe Lys Gln  Val Ala Ser Ser Thr  Gly Phe Cys
    1130                 1135                 1140

Asp Gln  Arg Arg Leu Gly Leu  Leu Leu His Asp Ser  Ile Gln Ile
    1145                 1150                 1155

Pro Arg  Gln Leu Gly Glu Val  Ala Ser Phe Gly Gly  Ser Asn Ile
    1160                 1165                 1170

Glu Pro  Ser Val Arg Ser Cys  Phe Gln Phe Ala Asn  Asn Lys Pro
    1175                 1180                 1185

Glu Ile  Glu Ala Ala Leu Phe  Leu Asp Trp Met Arg  Leu Glu Pro
    1190                 1195                 1200

Gln Ser  Met Val Trp Leu Pro  Val Leu His Arg Val  Ala Ala Ala
    1205                 1210                 1215

Glu Thr  Ala Lys His Gln Ala  Lys Cys Asn Ile Cys  Lys Glu Cys
    1220                 1225                 1230

Pro Ile  Ile Gly Phe Arg Tyr  Arg Ser Leu Lys His  Phe Asn Tyr
    1235                 1240                 1245

Asp Ile  Cys Gln Ser Cys Phe  Phe Ser Gly Arg Val  Ala Lys Gly
    1250                 1255                 1260

His Lys  Met His Tyr Pro Met  Val Glu Tyr Cys Thr  Pro Thr Thr
    1265                 1270                 1275

Ser Gly  Glu Asp Val Arg Asp  Phe Ala Lys Val Leu  Lys Asn Lys
    1280                 1285                 1290

Phe Arg  Thr Lys Arg Tyr Phe  Ala Lys His Pro Arg  Met Gly Tyr
    1295                 1300                 1305

Leu Pro  Val Gln Thr Val Leu  Glu Gly Asp Asn Met  Glu Thr
    1310                 1315                 1320
```

<210> SEQ ID NO 154
<211> LENGTH: 4043
<212> TYPE: DNA
<213> ORGANISM: Homo sapiens

<400> SEQUENCE: 154

```
atgctgtggt gggaggaagt ggaagattgc tacgagcgcg aggacgtgca gaagaaaacc     60

ttcaccaaat gggtgaacgc ccagttcagc aagttcggca agcagcacat cgagaacctg    120

ttcagcgacc tgcaggacgg cagacggctg ctggacctgc tggaaggcct gaccggccag    180

aagctgccca aagagaaggg cagcaccaga gtgcacgccc tgaacaacgt gaacaaggcc    240
```

```
ctgcgggtgc tgcagaacaa caacgtggac ctggtgaaca tcggcagcac cgacatcgtg    300
gacggcaacc acaagctgac cctgggcctg atctggaaca tcatcctgca ctggcaggtc    360
aaaaacgtga tgaagaacat catggccggc ctgcagcaga ccaacagcga gaagatcctg    420
ctgagctggg tgcgccagag cacccggaac tacccccagg tcaacgtgat caacttcacc    480
acctcttgga gcgacggcct ggccctgaac gccctgatcc acagccaccg gcccgacctg    540
ttcgactgga acagcgtggt ctgccagcag agcgccaccc agcggctgga acacgccttc    600
aatatcgcca gataccagct gggcatcgag aagctgctgg atcccgagga cgtggacacc    660
acctaccccg acaagaaatc catcctgatg tatatcacca gcctgttcca ggtgctgccc    720
cagcaggtgt ccatcgaggc catccaggaa gtggaaatgc tgcccagacc ccccaaagtg    780
accaaagagg aacacttcca gctgcaccac cagatgcact acagccagca gatcaccgtg    840
tccctggccc agggctacga gagaaccagc agccccaagc cccggttcaa gagctacgcc    900
tatacccagg ccgcctacgt gaccaccagc gaccctacca gaagcccatt ccccagccag    960
catctggaag cccccgagga caagagcttc ggcagcagcc tgatggaaag cgaagtgaac   1020
ctggacagat accagaccgc cctggaagag gtgctgagct ggctgctgag cgccgaggat   1080
acactgcagg ctcagggcga gatcagcaac gacgtggaag tcgtgaagga ccagttccac   1140
acccacgagg gctacatgat ggacctgaca gcccaccagg gcagagtggg caacatcctg   1200
cagctgggct ccaagctgat cggcaccggc aagctgagcg aggacgaaga gacagaggtg   1260
caggaacaga tgaacctgct gaacagcaga tgggagtgcc tgcgggtggc cagcatggaa   1320
aagcagagca acctgcatag ggtcctgctg aagtggcagc ggctgaccga ggaacagtgc   1380
ctgtttagcg cctggctgtc cgagaaagag gacgccgtga acaagatcca caccaccggc   1440
ttcaaggacc agaacgagat gctgagcagc ctgcagaaac tggccgtgct gaaggccgac   1500
ctggaaaaga aaaagcagtc catgggcaag ctgtactccc tgaagcagga cctgctgtcc   1560
accctgaaga acaagagcgt gacccagaaa accgaggcct ggctggacaa cttcgcccgg   1620
tgctgggaca acctggtgca gaagctggaa aagtccaccg cccagatctc ccaggccgtg   1680
accacaacac agcccagcct gacccagacc accgtgatgg aaaccgtgac aacagtgacc   1740
acccgggaac agatcctcgt gaagcacgcc caggaagaac tgccccctcc accccccccag   1800
aagaaacggc agatcacagt ggacagtgaa atccacaccg tgcgggaaga gacaatgatg   1860
gtcatgacag aggacatgcc cctggaaatc agctacgtgc ccagcaccta cctgaccgag   1920
atcacccatg tgtcccaggc cctgctggaa gtggaacagc tgctgaacgc ccccgacctg   1980
tgcgccaagg atttcgagga cctgttcaag caggaagaga gcctgaagaa tatcaaggat   2040
agcctgcagc agagcagcgg ccggatcgac atcatccaca gcaagaaaac agccgccctg   2100
cagagcgcca cccccgtgga aagagtgaaa ctgcaggaag ccctgtccca gctggacttc   2160
cagtgggaga aagtgaacaa aatgtacaag gaccggcagg gcagattcga ccgcagcgtg   2220
gaaaagtggc ggcggttcca ctacgacatc aagatcttca accagtggct gacagaggcc   2280
gagcagttcc tgagaaagac ccagatcccc gagaactggg agcacgccaa gtacaagtgg   2340
tatctgaaag agctgcagga cggcatcggc cagagacaga cagtcgtgcg gaccctgaat   2400
gccaccggcg aggaaatcat ccagcagtcc agcaagaccg acgccagcat tctgcaggaa   2460
aagctgggca gcctgaacct gcggtggcag gaagtgtgca agcagctgtc cgaccggaag   2520
aagcggctgg aagaacagct ggaacggctg caggaactgc aggaggccac cgacgagctg   2580
```

```
gacctgaaac tgagacaggc cgaagtgatc aagggcagct ggcagccagt gggcgacctg   2640

ctgatcgact ccctgcagga ccatctggaa aaagtgaagg ccctgagagg cgagatcgcc   2700

cccctgaaag aaaacgtgtc ccacgtgaac gacctggccc ggcagctgac aacactgggc   2760

attcagctga gcccctacaa cctgagcaca ctggaagatc tgaacacccg gtggaagctg   2820

ctgcaggtgg ccgtggaaga tagagtgcgg cagctgcacg aggcccacag agattttggc   2880

cctgcctccc agcacttcct gagcaccagt gtgcagggcc cttgggagag agccatctcc   2940

cctaacaagg tgccctacta catcaaccac gagacacaga ccacctgttg ggaccacccc   3000

aagatgaccg agctgtacca gagcctggct gacctgaaca acgtgcggtt cagcgcctac   3060

cggaccgcca tgaagctgcg gagactgcag aaagctctgt gcctggatct gctgtccctg   3120

tccgccgcct gtgatgccct ggaccagcac aatctgaagc agaacgacca gcccatggat   3180

atcctgcaga tcatcaactg cctgaccacc atctacgacc ggctggaaca ggaacacaac   3240

aatctcgtga acgtgcccct gtgcgtggac atgtgcctga attggctgct gaatgtgtac   3300

gacaccggcc ggacaggccg gatcagagtg ctgtccttca agaccggcat catcagcctg   3360

tgcaaagccc acctggaaga taagtaccgg tatctgttca aacaggtggc ctctagcacc   3420

ggcttttgcg accagagaag gctgggcctg ctgctgcacg acagcatcca gatccctaga   3480

cagctgggcg aagtggccag ctttggcggc agcaacatcg agcctagcgt gcggagctgc   3540

ttccagttcg ccaacaacaa gcccgagatc gaggccgccc tgttcctgga ctggatgaga   3600

ctggaacccc agagcatggt gtggctgccc gtgctgcata gagtggccgc tgccgagaca   3660

gccaagcacc aggccaagtg caacatctgc aaagagtgcc ccatcatcgg cttccggtac   3720

agaagcctga agcacttcaa ctacgatatc tgccagagct gtttcttcag cggcagggtg   3780

gccaagggcc acaaaatgca ctaccccatg gtggaatact gcacccccac cacaagcggc   3840

gaggatgtgc gggatttcgc caaggtgctg aaaaacaagt tccggaccaa gcggtacttc   3900

gccaaacacc cccggatggg ctacctgcct gtgcagacag tgctggaagg cgacaacatg   3960

gaaacctgag aagtcttttc cacatggcag atgaaataaa agatccttat tttcattgga   4020

tctgtgtgtt ggtttttttgt gtg                                           4043
```

<210> SEQ ID NO 155
<211> LENGTH: 35
<212> TYPE: PRT
<213> ORGANISM: Homo sapiens

<400> SEQUENCE: 155

```
Leu Pro Pro Pro Pro Pro Gln Lys Lys Arg Gln Ile Thr Val Asp Ile
1               5                   10                  15

His Thr Val Arg Glu Glu Thr Met Met Val Met Thr Glu Asp Met Pro
            20                  25                  30

Leu Glu Ile
        35
```

<210> SEQ ID NO 156
<211> LENGTH: 36
<212> TYPE: PRT
<213> ORGANISM: Homo sapiens

<400> SEQUENCE: 156

```
Leu Pro Pro Pro Pro Pro Gln Lys Lys Arg Gln Ile Thr Val Asp Ser
1               5                   10                  15

Ile His Thr Val Arg Glu Glu Thr Met Met Val Met Thr Glu Asp Met
```

```
            20                  25                  30

Pro Leu Glu Ile
        35


<210> SEQ ID NO 157
<211> LENGTH: 37
<212> TYPE: PRT
<213> ORGANISM: Homo sapiens

<400> SEQUENCE: 157

Leu Pro Pro Pro Pro Pro Gln Lys Lys Arg Gln Ile Thr Val Asp Ser
1               5                   10                  15

Glu Ile His Thr Val Arg Glu Glu Thr Met Met Val Met Thr Glu Asp
            20                  25                  30

Met Pro Leu Glu Ile
        35


<210> SEQ ID NO 158
<211> LENGTH: 36
<212> TYPE: PRT
<213> ORGANISM: Homo sapiens

<400> SEQUENCE: 158

Leu Pro Pro Pro Pro Pro Gln Lys Lys Arg Gln Ile Thr Val Asp Gln
1               5                   10                  15

Ile His Thr Val Arg Glu Glu Thr Met Met Val Met Thr Glu Asp Met
            20                  25                  30

Pro Leu Glu Ile
        35


<210> SEQ ID NO 159
<211> LENGTH: 37
<212> TYPE: PRT
<213> ORGANISM: Homo sapiens

<400> SEQUENCE: 159

Leu Pro Pro Pro Pro Pro Gln Lys Lys Arg Gln Ile Thr Val Asp Ala
1               5                   10                  15

Gln Ile His Thr Val Arg Glu Glu Thr Met Met Val Met Thr Glu Asp
            20                  25                  30

Met Pro Leu Glu Ile
        35


<210> SEQ ID NO 160
<211> LENGTH: 34
<212> TYPE: PRT
<213> ORGANISM: Homo sapiens

<400> SEQUENCE: 160

Leu Pro Pro Pro Pro Pro Gln Lys Lys Arg Gln Ile Thr Val Ile His
1               5                   10                  15

Thr Val Arg Glu Glu Thr Met Met Val Met Thr Glu Asp Met Pro Leu
            20                  25                  30

Glu Ile


<210> SEQ ID NO 161
<211> LENGTH: 34
<212> TYPE: PRT
<213> ORGANISM: Homo sapiens

<400> SEQUENCE: 161
```

```
Leu Pro Pro Pro Pro Pro Gln Lys Lys Arg Gln Ile Thr Val Asp His
1               5                   10                  15

Thr Val Arg Glu Glu Thr Met Met Val Met Thr Glu Asp Met Pro Leu
            20                  25                  30

Glu Ile


<210> SEQ ID NO 162
<211> LENGTH: 33
<212> TYPE: PRT
<213> ORGANISM: Homo sapiens

<400> SEQUENCE: 162

Leu Pro Pro Pro Pro Pro Gln Lys Lys Arg Gln Ile Thr Val His Thr
1               5                   10                  15

Val Arg Glu Glu Thr Met Met Val Met Thr Glu Asp Met Pro Leu Glu
            20                  25                  30

Ile


<210> SEQ ID NO 163
<211> LENGTH: 37
<212> TYPE: PRT
<213> ORGANISM: Homo sapiens

<400> SEQUENCE: 163

Leu Pro Pro Pro Pro Pro Gln Lys Lys Arg Gln Ile Thr Val Asp Ser
1               5                   10                  15

Gln Ile His Thr Val Arg Glu Glu Thr Met Met Val Met Thr Glu Asp
            20                  25                  30

Met Pro Leu Glu Ile
        35


<210> SEQ ID NO 164
<211> LENGTH: 35
<212> TYPE: PRT
<213> ORGANISM: Homo sapiens

<400> SEQUENCE: 164

Leu Pro Pro Pro Pro Pro Gln Lys Lys Arg Gln Ile Thr Val Asp Ser
1               5                   10                  15

His Thr Val Arg Glu Glu Thr Met Met Val Met Thr Glu Asp Met Pro
            20                  25                  30

Leu Glu Ile
        35


<210> SEQ ID NO 165
<211> LENGTH: 35
<212> TYPE: PRT
<213> ORGANISM: Homo sapiens

<400> SEQUENCE: 165

Leu Pro Pro Pro Pro Pro Gln Lys Lys Arg Gln Ile Thr Val Gln Ile
1               5                   10                  15

His Thr Val Arg Glu Glu Thr Met Met Val Met Thr Glu Asp Met Pro
            20                  25                  30

Leu Glu Ile
        35


<210> SEQ ID NO 166
<211> LENGTH: 24
```

<212> TYPE: PRT
<213> ORGANISM: Homo sapiens

<400> SEQUENCE: 166

```
Gln Lys Lys Arg Gln Ile Thr Val Asp Ser Glu Ala Gln Ile His Thr
1               5                   10                  15

Val Arg Glu Glu Thr Met Met Val
            20
```

<210> SEQ ID NO 167
<211> LENGTH: 31
<212> TYPE: PRT
<213> ORGANISM: Artificial Sequence
<220> FEATURE:
<223> OTHER INFORMATION: Synthesized

<400> SEQUENCE: 167

```
Trp Glu Cys Leu Arg Val Ala Ser Met Glu Lys Gln Ser Asn Leu His
1               5                   10                  15

Ile His Thr Val Arg Glu Glu Thr Met Met Val Met Thr Glu Asp
            20                  25                  30
```

<210> SEQ ID NO 168
<211> LENGTH: 23
<212> TYPE: PRT
<213> ORGANISM: Artificial Sequence
<220> FEATURE:
<223> OTHER INFORMATION: Synthesized

<400> SEQUENCE: 168

```
Met Pro Ser Ser Leu Met Leu Glu Ser Asp Gln Trp Lys Arg Leu His
1               5                   10                  15

Leu Ser Leu Gln Glu Leu Leu
            20
```

<210> SEQ ID NO 169
<211> LENGTH: 7
<212> TYPE: PRT
<213> ORGANISM: Artificial Sequence
<220> FEATURE:
<223> OTHER INFORMATION: Synthesized

<400> SEQUENCE: 169

```
Arg Val Leu Leu Gln Asp Ile
1               5
```

<210> SEQ ID NO 170
<211> LENGTH: 20
<212> TYPE: DNA
<213> ORGANISM: Homo sapiens

<400> SEQUENCE: 170

```
tggaagattg ctacgagcgc                                                20
```

<210> SEQ ID NO 171
<211> LENGTH: 20
<212> TYPE: DNA
<213> ORGANISM: Homo sapiens

<400> SEQUENCE: 171

```
caggtcgctg aacaggttct                                                20
```

<210> SEQ ID NO 172
<211> LENGTH: 21

```
<212> TYPE: DNA
<213> ORGANISM: Homo sapiens

<400> SEQUENCE: 172

gcaagttcgg caagcagcac a                                              21


<210> SEQ ID NO 173
<211> LENGTH: 4
<212> TYPE: PRT
<213> ORGANISM: Artificial Sequence
<220> FEATURE:
<223> OTHER INFORMATION: Synthesized

<400> SEQUENCE: 173

Ser Glu Ala Gln
1


<210> SEQ ID NO 174
<211> LENGTH: 4
<212> TYPE: PRT
<213> ORGANISM: Artificial Sequence
<220> FEATURE:
<223> OTHER INFORMATION: Synthesized

<400> SEQUENCE: 174

Lys Asn Asp Leu
1
```